United States Patent
Iijima et al.

(10) Patent No.: US 9,556,159 B2
(45) Date of Patent: *Jan. 31, 2017

(54) RENIN INHIBITOR

(71) Applicants: MITSUBISHI TANABE PHARMA CORPORATION, Osaka-shi, Osaka (JP); Shanghai Pharmaceuticals Holding CO., LTD., Shanghai (CN)

(72) Inventors: Toru Iijima, Osaka (JP); Yoichi Takahashi, Osaka (JP); Miki Hirai, Osaka (JP); Hiroshi Sugama, Osaka (JP); Yuko Togashi, Osaka (JP); Jingkang Shen, Shanghai (CN); Guangxin Xia, Shanghai (CN); Huixin Wan, Shanghai (CN)

(73) Assignees: Mitsubishi Tanabe Pharma Corporation, Osaka-shi (JP); Shanghai Pharmaceuticals Holding Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/427,828

(22) PCT Filed: Sep. 13, 2013

(86) PCT No.: PCT/JP2013/074941
§ 371 (c)(1),
(2) Date: Mar. 12, 2015

(87) PCT Pub. No.: WO2014/042263
PCT Pub. Date: Mar. 20, 2014

(65) Prior Publication Data
US 2015/0232459 A1    Aug. 20, 2015

(30) Foreign Application Priority Data
Sep. 14, 2012  (JP) .................... 2012-203471

(51) Int. Cl.
| C07D 413/12 | (2006.01) |
| C07D 413/14 | (2006.01) |
| C07D 417/12 | (2006.01) |
| C07D 417/14 | (2006.01) |
| C07D 471/04 | (2006.01) |
| C07D 265/30 | (2006.01) |
| C07D 487/04 | (2006.01) |
| C07D 491/048 | (2006.01) |

(52) U.S. Cl.
CPC ........... *C07D 413/12* (2013.01); *C07D 265/30* (2013.01); *C07D 413/14* (2013.01); *C07D 417/12* (2013.01); *C07D 417/14* (2013.01); *C07D 471/04* (2013.01); *C07D 487/04* (2013.01); *C07D 491/048* (2013.01)

(58) Field of Classification Search
CPC ... C07D 413/12; C07D 413/14; C07D 417/12; C07D 417/14
See application file for complete search history.

(56) References Cited

U.S. PATENT DOCUMENTS

| 2009/0018103 A1 | 1/2009 | Baldwin et al. |
| 2009/0312304 A1 | 12/2009 | Breitenstein et al. |
| 2010/0240644 A1 | 9/2010 | Akatsuka et al. |

FOREIGN PATENT DOCUMENTS

| CA | 2 828 378 A1 | 9/2012 |
| EP | 2 168 952 A1 | 3/2010 |
| EP | 2 687 518 A1 | 1/2014 |
| JP | 2008-515916 A | 5/2008 |
| JP | 2008-526701 A | 7/2008 |
| WO | WO 2008/153182 A1 | 12/2008 |
| WO | WO 2012/124775 A1 | 9/2012 |

OTHER PUBLICATIONS

International Search Report, issued in PCT/JP2013/074941, dated Nov. 26, 2013.
English translation of the International Preliminary Report on Patentability and Written Opinion issued Mar. 26, 2015, in PCT International Application No. PCT/JP2013/074941.
Extended European Search Report for Application No. 13836321.3 dated Mar. 14, 2016.
STN on the Web, publication date of Apr. 19, 2011, File Registry, RN=1282600-96-7.
STN on the Web, publication date of Jun. 1, 2011, File Registry, RN=1304061-38-8, 1304060-57-8, 1304060-53-4.
(Continued)

*Primary Examiner* — Rebecca Anderson
(74) *Attorney, Agent, or Firm* — Birch, Stewart, Kolasch & Birch, LLP

(57) ABSTRACT

The present invention provides a nitrogen-containing saturated heterocyclic compound of the formula [I] which is useful as a renin inhibitor.

Formula[I]:

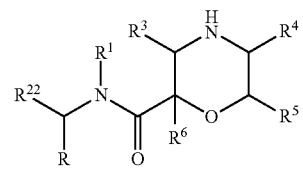

wherein $R^1$ is a cycloalkyl group or an alkyl, $R^{22}$ is an optionally substituted aryl and the like, R is a lower alkyl group, $R^3$, $R^4$, $R^5$ and $R^6$ are the same or different, and are a hydrogen atom, an optionally substituted carbamoyl, an optionally substituted alkyl, or alkoxycarbonyl, or a pharmaceutically acceptable salt thereof.

10 Claims, No Drawings

(56) References Cited

OTHER PUBLICATIONS

STN on the Web, publication date of Jun. 2, 2011, File Registry, RN=1304196-50-6.
STN on the Web, publication date of Jun. 5, 2011, File Registry, RN=1305533-03-2.
STN on the Web, publication date of Jun. 8, 2011, File Registry, RN=1307879-67-9.
STN on the Web, publication date of Jun. 9, 2011, File Registry, RN=1308143-41-0, 1308142-47-3.
STN on the Web, publication date of May 8, 2011, File Registry, RN=1291670-16-0, 1291669-94-7, 1291669-93-6, 1291669-90-3, 1291669-83-4, 1291669-80-1.
STN on the Web, publication date of May 9, 2011, File Registry, RN=1291958-82-1, 1291958-76-3, 1291897-95-4, 1291897-93-2.

RENIN INHIBITOR

TECHNICAL FIELD

The present invention relates to novel compounds which are useful as a medicine, especially as a renin inhibitor, or pharmaceutically acceptable salts thereof and to use, a process for preparation or intermediates thereof.

BACKGROUND ART

Renin inhibitors are expected as a medicine for the prevention and/or treatment of diseases such as hypertension, heart failure, diabetic nephropathy and the like, and 3,4-substituted piperidine derivatives are disclosed for example (Patent Literature 1). But a morpholine derivative is not described in the literature.

Also WO 2008/153182 discloses some morpholine derivatives but they are compounds having a formula I of the present invention wherein R is a hydrogen atom (Patent Literature 2).

CITATION LIST

Patent Literatures

Patent Literature 1: WO006/069788WO (US 2009/0312304A)
Patent Literature 2: WO2008/153182WO (US 2010/0240644A)

DISCLOSURE OF INVENTION

Technical Problem

The present invention provides novel compounds having an excellent activity to inhibit renin.

Solution to Problem

In order to solve the problem, the inventors have extensively studied to find novel compounds having an excellent activity to inhibit renin and finally completed the present invention.

The present invention is as follows;
(1) A compound of the formula [I];

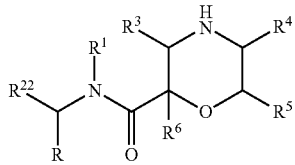

wherein $R^1$ is a cycloalkyl or an alkyl,
$R^{22}$ is 1) an optionally substituted aryl, 2) an optionally substituted pyridyl, 3) an optionally substituted pyrazolopyridyl, 4) an optionally substituted indolyl, 5) an optionally substituted benzofuranyl, 6) an optionally substituted quinolyl, 7) an optionally substituted chromanyl, 8) an optionally substituted dihydrobenzofuranyl, 9) an optionally substituted indazolyl, 10) an optionally substituted pyrrolopyridinyl, 11) an optionally substituted benzoisoxazolyl, 12) an optionally substituted indolinyl, 13) an optionally substituted quinazolinyl, 14) an optionally substituted dihydroquinazolinyl, 15) an optionally substituted furopyridyl, 16) an optionally substituted isoquinolyl, 17) an optionally substituted pyrrolopyrimidinyl, 18) an optionally substituted tetrahydroquinolyl, 19) an optionally substituted tetrahydroindazolyl, 20) an optionally substituted tetrahydrocyclopentapyrazolyl, 21) an optionally substituted pyrrolyl, 22) an optionally substituted imidazolyl, 23) an optionally substituted pyrazolyl, 24) an optionally substituted thienyl, 25) an optionally substituted thiazolyl, 26) an optionally substituted triazolyl, 27) an optionally substituted pyrimidinyl, 28) an optionally substituted pyrazyl, 29) an optionally substituted imidazopyridinyl, or, 30) an optionally substituted pyrrolopyrazyl,
R is a lower alkyl group,
$R^3$, $R^4$, $R^5$ and $R^6$ are the same or different, and are a hydrogen atom, an optionally substituted carbamoyl, an optionally substituted alkyl, or an alkoxycarbonyl;
or a pharmaceutically acceptable salt thereof.
(2) The compound of (1) above, wherein the substituents of 1) the optionally substituted aryl, 2) the optionally substituted pyridyl, 3) the optionally substituted pyrazolopyridyl, 4) the optionally substituted indolyl, 5) the optionally substituted benzofuranyl, 6) the optionally substituted quinolyl, 7) the optionally substituted chromanyl, 8) the optionally substituted dihydrobenzofuranyl, 9) the optionally substituted indazolyl, 10) the optionally substituted pyrrolopyridinyl, 11) the optionally substituted benzoisoxazolyl, 12) the optionally substituted indolinyl, 13) the optionally substituted quinazolinyl, 14) the optionally substituted dihydroquinazolinyl, 15) the optionally substituted furopyridyl, 16) the optionally substituted isoquinolyl, 17) the optionally substituted pyrrolopyrimidinyl, 18) the optionally substituted tetrahydroquinolyl, 19) the optionally substituted tetrahydroindazolyl, 20) the optionally substituted tetrahydrocyclopentapyrazolyl, 21) the optionally substituted pyrrolyl, 22) the optionally substituted imidazolyl, 23) the optionally substituted pyrazolyl, 24) the optionally substituted thienyl, 25) the optionally substituted thiazolyl, 26) the optionally substituted triazolyl, 27) the optionally substituted pyrimidinyl 28) the optionally substituted pyrazyl, 29) the optionally substituted imidazopyridinyl, or, 30) the optionally substituted pyrrolopyrazyl as $R^{22}$ are one to three groups selected from
1) an alkyl optionally substituted with same or different 1 or 2 groups selected from an alkanoylamino optionally substituted with a halogen, an alkoxycarbonylamino, an alkoxy, an aminocarbonylamino optionally substituted with 1 or 2 alkyl, an aryl optionally substituted with a halogen, an alkoxy, or a haloalkoxy, a hydroxyl, an heteroaryl, a halogen and an amino optionally substituted with 1 or 2 alkyl,
2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl, and a halogen,
3) an alkoxy optionally substituted with an alkoxy or an alkoxycarbonylamino,
4) a cycloalkyl,
5) a halogen,
6) a cyano,
7) an aliphatic heterocyclic group,
8) an aryl optionally substituted with same or different 1 or 2 groups selected from an alkyl optionally substituted with an alkylsulfonylamino optionally substituted with a halogen, and a halogen; a halogen; an alkoxycarbonyl; a methanesulfonylamino; a halomethanesulfonylamino; a methanesulfonylaminocarbonyl; a benzoylaminocarbonyl; a benzenesulfonylaminocarbonyl; a hydroxyoxazolyl; a hydroxyoxadiazolyl; a tetrazolyl; a hydroxyl; and, an alkoxy optionally substituted with an alkoxy, 9) a heteroaryl optionally substituted with same or different 1 or 2 groups selected from an alkyl, an amino, a halogen and an alkoxy, 10) an aryloxy, 11) an amino optionally substituted with 1 to 2 groups selected from an alkyl optionally substituted with an alkoxy, and alkylsulfonyl, 12) an alkynyl optionally substituted with a hydroxyl, 13) an aliphatic heterocyclic oxy, 14) an arylcarbamoyl optionally substituted with an alkoxy, 15) an alkanoyl, or a pharmaceutically acceptable salt thereof.

(3) The compound of (1) above, wherein the substituents of 1) the optionally substituted aryl, 2) the optionally substituted pyridyl, 3) the optionally substituted pyrazolopyridyl, 4) the optionally substituted indolyl, 5) the optionally substituted benzofuranyl, 6) the optionally substituted quinolyl, 7) the optionally substituted chromanyl, 8) the optionally substituted dihydrobenzofuranyl, 9) the optionally substituted indazolyl, 10) the optionally substituted pyrrolopyridinyl, 11) the optionally substituted benzoisoxazolyl, 12) the optionally substituted indolinyl, 13) the optionally substituted quinazolinyl, 14) the optionally substituted dihydroquinazolinyl, 5) the optionally substituted furopyridyl, 16) the optionally substituted isoquinolyl, 17) the optionally substituted pyrrolopyrimidinyl, 18) the optionally substituted tetrahydroquinolyl, 19) the optionally substituted tetrahydroindazolyl, 20) the optionally substituted tetrahydrocyclopentapyrazolyl, 21) the optionally substituted pyrrolyl, 22) the optionally substituted imidazolyl, 23) the optionally substituted pyrazolyl, 24) the optionally substituted thienyl, 25) the optionally substituted thiazolyl, 26) the optionally substituted triazolyl, 27) the optionally substituted pyrimidinyl, 28) the optionally substituted pyrazyl, 29) the optionally substituted imidazopyridinyl, or, 30) the optionally substituted pyrrolopyrazyl as $R^{22}$ are one to three groups selected from 1) an alkyl optionally substituted with same or different 1 or 2 groups selected from an alkanoylamino, an alkoxycarbonylamino, an alkoxy, an aminocarbonylamino optionally substituted with 1 or 2 alkyl, aryl, a hydroxyl, and a halogen, 2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl and a halogen, 3) an alkoxy optionally substituted with an alkoxy, 4) a cycloalkyl, 5) a halogen, 6) a cyano, 7) an aliphatic heterocyclic group, 8) an aryl optionally substituted with same or different 1 or 2 groups selected from an alkyl optionally substituted with an alkylsulfonylamino optionally substituted with a halogen, and a halogen; a halogen; an alkoxycarbonyl; a methanesulfonylamino; a benzoylaminocarbonyl; a hydroxyoxazolyl; a hydroxyl; and, an alkoxy optionally substituted with an alkoxy, 9) a heteroaryl optionally substituted with same or different 1 or 2 groups selected from an alkyl, and alkoxy, 10) an aryloxy, and 11) an amino optionally substituted with 1 to 2 groups selected from an alkyl and alkylsulfonyl, or a pharmaceutically acceptable salt thereof.

(4) The compound of (1) above, wherein the substituents of 1) the optionally substituted aryl, 2) the optionally substituted pyridyl, 3) the optionally substituted pyrazolopyridyl, 4) the optionally substituted indolyl, 5) the optionally substituted benzofuranyl, 6) the optionally substituted quinolyl, 7) the optionally substituted chromanyl, 8) the optionally substituted dihydrobenzofuranyl, 9) the optionally substituted indazolyl, 10) the optionally substituted pyrrolopyridinyl, 11) the optionally substituted benzoisoxazolyl, 12) the optionally substituted indolinyl, 13) the optionally substituted quinazolinyl, 14) the optionally substituted dihydroquinazolinyl, 15) the optionally substituted furopyridyl, 16) the optionally substituted isoquinolyl, 17) the optionally substituted pyrrolopyrimidinyl, 18) the optionally substituted tetrahydroquinolyl, 19) the optionally substituted tetrahydroindazolyl, 20) the optionally substituted tetrahydrocyclopentapyrazolyl, 21) the optionally substituted pyrrolyl, 22) the optionally substituted imidazolyl, 23) the optionally substituted pyrazolyl, 24) the optionally substituted thienyl, 25) the optionally substituted thiazolyl, 26) the optionally substituted triazolyl, 27) the optionally substituted pyrimidinyl, 28) the optionally substituted pyrazyl, 29) the optionally substituted imidazopyridinyl, or, 30) the optionally substituted pyrrolopyrazyl as $R^{22}$ are one group selected from 1) an alkyl optionally substituted with same or different 1 or 2 groups selected from an alkanoylamino optionally substituted with a halogen, an alkoxycarbonylamino, an alkoxy, an aminocarbonylamino optionally substituted with 1 or 2 alkyl, an aryl optionally substituted with a halogen, an alkoxy or a haloalkoxy, a hydroxyl, an heteroaryl, a halogen and an amino optionally substituted with 1 or 2 alkyl, 2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl, and a halogen, and 3) an alkoxy optionally substituted with an alkoxy or an alkoxycarbonylamino, or, a group selected from 1) an alkyl optionally substituted with same or different 1 or 2 groups selected from an alkanoylamino optionally substituted with a halogen, an alkoxycarbonylamino, an alkoxy, an aminocarbonylamino optionally substituted with 1 or 2 alkyl, an aryl optionally substituted with a halogen, an alkoxy, or a haloalkoxy, a hydroxyl, an heteroaryl, a halogen and an amino optionally substituted with 1 or 2 alkyl, 2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl, and a halogen, and 3) an alkoxy optionally substituted with an alkoxy or an alkoxycarbonylamino, and 1 to 2 groups selected from 1) an alkyl optionally substituted with same or different 1 or 2 groups selected from an alkanoylamino optionally substituted with a halogen, an alkoxycarbonylamino, an alkoxy, an aminocarbonylamino optionally substituted with 1 or 2 alkyl, an aryl optionally substituted with a halogen, an alkoxy, or a haloalkoxy, a hydroxyl, an heteroaryl, a halogen and an amino optionally substituted with 1 or 2 alkyl, 2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl and a halogen, 3) an alkoxy optionally substituted with an alkoxy or an alkoxycarbonylamino, 4) a cycloalkyl, 5) a halogen, 6) a cyano, 7) an aliphatic heterocyclic group, 8) an aryl optionally substituted with same or different 1 or 2 groups selected from an alkyl optionally substituted with an alkylsulfonylamino optionally substituted with a halogen, and a halogen; a halogen; an alkoxycarbonyl; a methanesulfonylamino; a halomethanesulfonylamino; a methanesulfonylaminocarbonyl; a benzoylaminocarbonyl; a benzenesulfonylaminocarbonyl; a hydroxyoxazolyl; a hydroxyoxadiazolyl; a tetrazolyl; a hydroxyl; and, an alkoxy optionally substituted with an alkoxy, 9) a heteroaryl optionally substituted with same or different 1 or 2 groups selected from an alkyl, an amino, a halogen and an alkoxy, 10) an aryloxy, 11) an amino optionally substituted with 1 to 2 groups selected from an alkyl optionally substituted with an alkoxy, and alkylsulfonyl group, 12) an alkynyl optionally substituted with a hydroxyl, 13) an aliphatic heterocyclic oxy, 14) an arylcarbamoyl optionally substituted with an alkoxy, 15) an alkanoyl, or a pharmaceutically acceptable salt thereof.

(5) The compound of (1) above, wherein the substituents of 1) the optionally substituted aryl, 2) the optionally substituted pyridyl, 3) the optionally substituted pyrazolopyridyl, 4) the optionally substituted indolyl, 5) the optionally substituted benzofuranyl, 6) the optionally substituted quinolyl, 7) the optionally substituted chromanyl, 8) the optionally substituted dihydrobenzofuranyl, 9) the optionally substituted indazolyl, 10) the optionally substituted pyrrolopyridinyl, 11) the optionally substituted benzoisoxazolyl, 12) the optionally substituted indolinyl, 13) the optionally substituted quinazolinyl, 14) the optionally substituted dihydroquinazolinyl, 15) the optionally substituted furopyridyl, 16) the optionally substituted isoquinolyl, 17) the optionally substituted pyrrolopyrimidinyl, 18) the optionally substituted tetrahydroquinolyl, 19) the optionally substituted tetrahydroindazolyl, 20) the optionally substituted tetrahydrocyclopentapyrazolyl, 21) the optionally substituted pyrrolyl, 22) the optionally substituted imidazolyl, 23) the optionally substituted pyrazolyl, 24) the optionally substituted thienyl, 25) the optionally substituted thiazolyl, 26) the optionally substituted triazolyl, 27) the optionally substituted pyrimidinyl, 28) the optionally substituted pyrazyl, 29) the optionally substituted imidazopyridinyl, or, 30) the optionally substituted pyrrolopyrazyl as $R^{22}$ are one group selected from 1) an alkyl optionally substituted with same or different 1 or 2 groups selected from an alkanoylamino, an alkoxycarbonylamino, an alkoxy, an aminocarbonylamino optionally substituted with 1 or 2 alkyl, aryl, a hydroxyl and a halogen, 2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl, and a halogen, and 3) an alkoxy optionally substituted with an alkoxy, or, a group selected from 1) an alkyl optionally substituted with same or different 1 or 2 groups selected from an alkanoylamino, an alkoxycarbonylamino, an alkoxy, an aminocarbonylamino optionally substituted with 1 or 2 alkyl, aryl, a hydroxyl, and a halogen, 2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl and a halogen, and 3) an alkoxy optionally substituted with an alkoxy, and 1 to 2 groups selected from 1) an alkyl optionally substituted with same or different 1 or 2 groups selected from an alkanoylamino, an alkoxycarbonylamino, an alkoxy, an aminocarbonylamino optionally substituted with 1 or 2 alkyl, aryl, a hydroxyl and a halogen, 2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl, and a halogen, 3) an alkoxy optionally substituted with an alkoxy, 4) a cycloalkyl, 5) a halogen, 6) a cyano, 7) an aliphatic heterocyclic group, 8) an aryl optionally substituted with same or different 1 or 2 groups selected from an alkyl optionally substituted with an alkylsulfonylamino optionally substituted with a halogen, and a halogen; a halogen; an alkoxycarbonyl; a methanesulfonylamino; a benzoylaminocarbonyl; a hydroxyoxazolyl; a hydroxyl; and an alkoxy optionally substituted with an alkoxy, 9) a heteroaryl optionally substituted with same or different 1 or 2 groups selected from an alkyl, and alkoxy, 10) an aryloxy, and 11) an amino optionally substituted with 1 to 2 groups selected from an alkyl, and alkylsulfonyl, or a pharmaceutically acceptable salt thereof.

(6) The compound of (1) above, wherein the substituents of 1) the optionally substituted aryl, 2) the optionally substituted pyridyl, 3) the optionally substituted pyrazolopyridyl, 4) the optionally substituted indolyl, 5) the optionally substituted benzofuranyl, 6) the optionally substituted quinolyl, 7) the optionally substituted chromanyl, 8) the optionally substituted dihydrobenzofuranyl, 9) the optionally substituted indazolyl, 10) the optionally substituted pyrrolopyridinyl, 11) the optionally substituted benzoisoxazolyl, 12) the optionally substituted indolinyl, 13) the optionally substituted quinazolinyl, 14) the optionally substituted dihydroquinazolinyl, 15) the optionally substituted furopyridyl, 16) the optionally substituted isoquinolyl, 17) the optionally substituted pyrrolopyrimidinyl, 18) the optionally substituted tetrahydroquinolyl, 19) the optionally substituted tetrahydroindazolyl, 20) the optionally substituted tetrahydrocyclopentapyrazolyl, 21) the optionally substituted pyrrolyl, 22) the optionally substituted imidazolyl, 23) the optionally substituted pyrazolyl, 24) the optionally substituted thienyl, 25) the optionally substituted thiazolyl, 26) the optionally substituted triazolyl, 27) the optionally substituted pyrimidinyl, 28) the optionally substituted pyrazyl, 29) the optionally substituted imidazopyridinyl, or, 30) the optionally substituted pyrrolopyrazyl as $R^{22}$ are one group selected from 1) an alkyl optionally substituted with same or different 1 or 2 groups selected from an alkanoylamino, an alkoxycarbonylamino, an alkoxy, an aminocarbonylamino optionally substituted with 1 or 2 alkyl, aryl, a hydroxyl, and a halogen, 2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl, and a halogen, and 3) an alkoxy optionally substituted with an alkoxy, and 1 to 2 groups selected from 1) an alkyl optionally substituted with same or different 1 or 2 groups selected from an aryl, an alkoxy, a halogen atom and a hydroxyl, 2) an alkoxy, 3) a cycloalkyl, 4) a halogen, 5) a cyano, 6) an aliphatic heterocyclic group, 7) an aryl optionally substituted with same or different 1 or 2 groups selected from an alkyl optionally substituted with an alkylsulfonylamino optionally substituted with a halogen, and a halogen; a halogen; an alkoxycarbonyl; a methanesulfonylamino; a benzoylaminocarbonyl; a hydroxyoxazolyl; a hydroxyl; and an alkoxy optionally substituted with an alkoxy, 8) a heteroaryl optionally substituted with same or different 1 or 2 groups selected from an alkyl, and alkoxy, 9) an aryloxy, and 10) an amino optionally substituted with 1 to 2 groups selected from an alkyl, and alkylsulfonyl, or a pharmaceutically acceptable salt thereof.

(7) The compound of (1) above, wherein the substituents of
1) the optionally substituted aryl, 2) the optionally substituted pyridyl, 3) the optionally substituted pyrazolopyridyl, 4) the optionally substituted indolyl, 5) the optionally substituted benzofuranyl, 6) the optionally substituted quinolyl, 7) the optionally substituted chromanyl, 8) the optionally substituted dihydrobenzofuranyl, 9) the optionally substituted indazolyl, 10) the optionally substituted pyrrolopyridinyl, 11) the optionally substituted benzoisoxazolyl, 12) the optionally substituted indolinyl, 13) the optionally substituted quinazolinyl, 14) the optionally substituted dihydroquinazolinyl, 15) the optionally substituted furopyridyl, 16) the optionally substituted isoquinolyl, 17) the optionally substituted pyrrolopyrimidinyl, 18) the optionally substituted tetrahydroquinolyl, 19) the optionally substituted tetrahydroindazolyl, 20) the optionally substituted tetrahydrocyclopentapyrazolyl, 21) the optionally substituted pyrrolyl, 22) the optionally substituted imidazolyl, 23) the optionally substituted pyrazolyl, 24) the optionally substituted thienyl, 25) the optionally substituted thiazolyl, 26) the optionally substituted triazolyl, 27) the optionally substituted pyrimidinyl, 28) the optionally substituted pyrazyl, 29) the optionally substituted imidazopyridinyl, or, 30) the optionally substituted pyrrolopyrazyl as $R^{22}$ are one group selected from 1) an alkyl optionally substituted with same or different 1 or 2 groups selected from an alkanoylamino optionally substituted with a halogen, an alkoxycarbonylamino, an alkoxy, an aminocarbonylamino optionally substituted with 1 or 2 alkyl, an aryl optionally substituted with a halogen, an alkoxy or a haloalkoxy, a hydroxyl, an heteroaryl, a halogen and an amino optionally substituted with 1 or 2 alkyl, 2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl, and a halogen, and 3) an alkoxy optionally substituted with an alkoxy or an alkoxycarbonylamino, and 1 group selected from 1) an aryl optionally substituted with same or different 1 or 2 groups selected from an alkyl optionally substituted with an alkylsulfonylamino optionally substituted with a halogen, and a halogen; a halogen; an alkoxycarbonyl; a methanesulfonylamino; a halomethanesulfonylamino; a methanesulfonylaminocarbonyl; a benzoylaminocarbonyl; a benzenesulfonylaminocarbonyl; a hydroxyoxazolyl; a hydroxyoxadiazolyl; a tetrazolyl; a hydroxyl; and, an alkoxy optionally substituted with an alkoxy, and 2) a heteroaryl optionally substituted with same or different 1 or 2 groups selected from an alkyl, an amino, a halogen and an alkoxy, or a pharmaceutically acceptable salt thereof.

(8) The compound of (1) above, wherein the substituents of
1) the optionally substituted aryl, 2) the optionally substituted pyridyl, 3) the optionally substituted pyrazolopyridyl, 4) the optionally substituted indolyl, 5) the optionally substituted benzofuranyl, 6) the optionally substituted quinolyl, 7) the optionally substituted chromanyl, 8) the optionally substituted dihydrobenzofuranyl, 9) the optionally substituted indazolyl, 10) the optionally substituted pyrrolopyridinyl, 11) the optionally substituted benzoisoxazolyl, 12) the optionally substituted indolinyl, 13) the optionally substituted quinazolinyl, 14) the optionally substituted dihydroquinazolinyl, 15) the optionally substituted furopyridyl, 16) the optionally substituted isoquinolyl, 17) the optionally substituted pyrrolopyrimidinyl, 18) the optionally substituted tetrahydroquinolyl, 19) the optionally substituted tetrahydroindazolyl, 20) the optionally substituted tetrahydrocyclopentapyrazolyl, 21) the optionally substituted pyrrolyl, 22) the optionally substituted imidazolyl, 23) the optionally substituted pyrazolyl, 24) the optionally substituted thienyl, 25) the optionally substituted thiazolyl, 26) the optionally substituted triazolyl, 27) the optionally substituted pyrimidinyl, 28) the optionally substituted pyrazyl, 29) the optionally substituted imidazopyridinyl, or, 30) the optionally substituted pyrrolopyrazyl as $R^{22}$ are one group selected from 1) an alkyl optionally substituted with same or different 1 or 2 groups selected from an alkanoylamino, an alkoxycarbonylamino, an alkoxy, an aminocarbonylamino optionally substituted with 1 or 2 alkyl, aryl, a hydroxyl, and a halogen, 2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl, and a halogen, and 3) an alkoxy optionally substituted with an alkoxy, and 1 group selected from 1) an aryl optionally substituted with same or different 1 or 2 groups selected from an alkyl optionally substituted with an alkylsulfonylamino optionally substituted with a halogen, and a halogen; a halogen; an alkoxycarbonyl; a methanesulfonylamino; a benzoylaminocarbonyl; a hydroxyoxazolyl; a hydroxyl; and, an alkoxy optionally substituted with an alkoxy, and 2) a heteroaryl optionally substituted with same or different 1 or 2 groups selected from an alkyl, and alkoxy, or a pharmaceutically acceptable salt thereof.

(9) The compound of any one of (1) to (8) above, wherein $R^{22}$ is a group selected from 1) the optionally substituted aryl, 2) the optionally substituted pyridyl, 3) the optionally substituted pyrazolopyridyl, 4) the optionally substituted indolyl, 6) the optionally substituted quinolyl, 7) the optionally substituted chromanyl, 9) the optionally substituted indazolyl, 10) the optionally substituted pyrrolopyridinyl, 12) the optionally substituted indolinyl, 14) the optionally substituted dihydroquinazolinyl, 15) the optionally substituted furopyridyl, 16) the optionally substituted isoquinolyl, 17) the optionally substituted pyrrolopyrimidinyl, 18) the optionally substituted tetrahydroquinolyl, 19) the optionally substituted tetrahydroindazolyl, 20) the optionally substituted tetrahydrocyclopentapyrazolyl, 21) the optionally substituted pyrrolyl, 22) the optionally substituted imidazolyl, 23) the optionally substituted pyrazolyl, 24) the optionally substituted thienyl, 25) the optionally substituted thiazolyl, 26) the optionally substituted triazolyl, 27) the optionally substituted pyrimidinyl, 28) the optionally substituted pyrazyl, 29) the optionally substituted imidazopyridinyl, and 30) the optionally substituted pyrrolopyrazyl, or a pharmaceutically acceptable salt thereof.

(10) The compound of any one of (1) to (8) above, wherein $R^{22}$ is a group selected from
2) the optionally substituted pyridyl,
3) the optionally substituted pyrazolopyridyl,
7) the optionally substituted chromanyl,
13) the optionally substituted quinazolinyl,
14) the optionally substituted dihydroquinazolinyl,
15) the optionally substituted furopyridyl,
16) the optionally substituted isoquinolyl,
17) the optionally substituted pyrrolopyrimidinyl,
18) the optionally substituted tetrahydroquinolyl,
19) the optionally substituted tetrahydroindazolyl,
20) the optionally substituted tetrahydrocyclopentapyrazolyl,
21) the optionally substituted pyrollyl,
22) the optionally substituted imidazolyl,
23) the optionally substituted pyrazolyl,
24) the optionally substituted thienyl,
25) the optionally substituted thiazolyl,
26) the optionally substituted triazolyl,
27) the optionally substituted pyrimidinyl,
28) the optionally substituted pyrazyl, and
29) the optionally substituted imidazopyridinyl,
30) the optionally substituted pyrrolopyrazyl,
or a pharmaceutically acceptable salt thereof.

(11) The compound of any one of (1) to (10) above, wherein $R^{22}$ is a group selected from
2) the optionally substituted pyridyl group,
3) the optionally substituted pyrazolopyridyl
7) the optionally substituted chromanyl group,
13) the optionally substituted quinazolinyl group,
14) the optionally substituted dihydroquinazolinyl group,
15) the optionally substituted furopyridyl group, and
29) the optionally substituted imidazopyridinyl,
or a pharmaceutically acceptable salt thereof.

(12) The compound of any one of (1) to (11) above, wherein $R^{22}$ is a group selected from
16) the optionally substituted isoquinolyl,
17) the optionally substituted pyrrolopyrimidinyl,
18) the optionally substituted tetrahydroquinolyl,
19) the optionally substituted tetrahydroindazolyl,
20) the optionally substituted tetrahydrocyclopentapyrazolyl,
21) the optionally substituted pyrrolyl,
22) the optionally substituted imidazolyl,
23) the optionally substituted pyrazolyl,
24) the optionally substituted thienyl,
25) the optionally substituted thiazolyl,
26) the optionally substituted triazolyl,
27) the optionally substituted pyrimidinyl,
28) the optionally substituted pyrazyl, and
30) the optionally substituted pyrrolopyrazyl,
or a pharmaceutically acceptable salt thereof.

(13) The compound of any one of (1) to (12) above, wherein $R^{22}$ is a group selected from
2) the optionally substituted pyridyl, 21) the optionally substituted pyrrolyl, 22) the optionally substituted imidazolyl, 23) the optionally substituted pyrazolyl, 24) the optionally substituted thienyl, 25) the optionally substituted thiazolyl, 26) the optionally substituted triazolyl, 27) the optionally substituted pyrimidinyl, and 28) the optionally substituted pyrazyl, or a pharmaceutically acceptable salt thereof.

(14) The compound of (13) above, wherein $R^{22}$ has a formula:

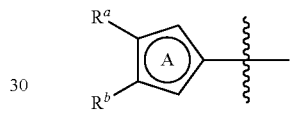

wherein, a Ring A is a pyrrolyl, an imidazolyl, a pyrazolyl, a thienyl, a thiazolyl, or a triazolyl,
$R^a$ is a group selected from
1) an alkyl optionally substituted with same or different 1 or 2 groups selected from an alkanoylamino, an alkoxycarbonylamino, an alkoxy, an aminocarbonylamino optionally substituted with 1 or 2 alkyl, aryl, a hydroxyl, and a halogen,
2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl, and a halogen, and
3) an alkoxy optionally substituted with an alkoxy, and
$R^b$ is
1) a phenyl optionally substituted with same or different 1 or 2 groups selected from an alkyl optionally substituted with an alkylsulfonylamino optionally substituted with a halogen, and a halogen; a halogen; an alkoxycarbonyl; a methanesulfonylamino; a benzoylaminocarbonyl; a hydroxyoxazolyl; a hydroxyl; and, an alkoxy optionally substituted with an alkoxy,
2) a heteroaryl optionally substituted with same or different 1 or 2 groups selected from an alkyl, and alkoxy (preferably said heteroaryl is a pyridyl, a pyrimidyl, or a pyrazolyl),
3) a cycloalkyl, or,
4) an aliphatic hetelocyclic ring (preferably said aliphatic hetelocyclic ring is a tetrahydropyranyl),
or a pharmaceutically acceptable salt thereof.

(15) The compound of any one of (1) to (14) above, wherein
$R^{22}$ is selected from 2) the optionally substituted pyridyl, 3) the optionally substituted pyrazolopyridyl, 4) the optionally substituted indolyl, 10) the optionally substituted pyrrolopyridinyl, 23) the optionally substituted pyrazolyl, 25) the optionally substituted thiazolyl, 26) the optionally substituted triazolyl, 27) the optionally substituted pyrimidinyl, 28) the optionally substituted pyrazyl, or 29) the optionally substituted imidazopyridinyl, or a pharmaceutically acceptable salt thereof.

(16) The compound of any one of (1) to (15) above, wherein $R^3$, $R^4$, $R^5$ and $R^6$ are the same or different, and are
  1) a hydrogen atom,
  2) a carbamoyl optionally substituted with an alkyl group which is optionally substituted with 1 or 2 phenyl,
  3) an alkyl optionally substituted with a group selected from an alkoxy optionally substituted with a halogen or a phenyl; a halogen; a hydroxyl; an amino optionally substituted with 1 or 2 alkyl; a cyano; and an aryloxy, and
  4) an alkoxycarbonyl,
or a pharmaceutically acceptable salt thereof.

(17) The compound of any one of (1) to (16) above, wherein $R^3$ and $R^6$ are hydrogen atoms, or a pharmaceutically acceptable salt thereof.

(18) The compound of any one of (1) to (17) above, wherein one of $R^4$ and $R^5$ is a hydrogen atom, and the other is
1) a carbamoyl optionally substituted with an alkyl which is optionally substituted with 1 or 2 phenyl,
2) an alkyl optionally substituted with an alkoxy optionally substituted with a halogen or a phenyl; a halogen; a hydroxyl; an amino optionally substituted with 1 or 2 alkyl; and a cyano; and
3) an alkoxycarbonyl,
or a pharmaceutically acceptable salt thereof.

(19) The compound of (18) above, wherein
one of $R^4$ and $R^5$ is a hydrogen atom, and
the other is
2) an alkyl optionally substituted with a group selected from an alkoxy optionally substituted with a halogen or a phenyl; a halogen; a hydroxyl; an amino optionally substituted with 1 or 2 alkyl; and a cyano, or a pharmaceutically acceptable salt thereof.

(20) The compound of (18) above, wherein
one of $R^4$, and $R^5$ is a hydrogen atom, and
the other is
2) an alkyl substituted with an alkoxy, or a pharmaceutically acceptable salt thereof.

(21) The compound of any one of (1) to (20) above, wherein $R^4$ is a hydrogen atom, or a pharmaceutically acceptable salt thereof.

(22) The compound of any one of (1) to (21) above, wherein $R^5$ is a hydrogen atom, or a pharmaceutically acceptable salt thereof.

(23) The compound of any one of (1) to (22) above, wherein $R^1$ is a cycloalkyl, or a pharmaceutically acceptable salt thereof.

(24) The compound of (1) above disclosed in the Examples, or a pharmaceutically acceptable salt thereof.

(25) The compound of (1) above selected from the compounds disclosed in Example 1, Example 2, Example 6, Example 116, Example 129, Example 136, Example 140, Example 183, Example 279, Example 282, Example 289, Example 290, Example 303, and Example 318, or a pharmaceutically acceptable salt thereof.

(26) A medicament comprising the compound of any one of (1) to (25) above or a pharmaceutically acceptable salt thereof.

(27) A renin inhibitor comprising the compound of any one of (1) to (25) above or a pharmaceutically acceptable salt thereof.

(28) A medicine for the treatment and/or prophylaxis of hypertension, cardiac failure, diabetic nephropathy and the like comprising the compound of any one of (1) to (25) above or a pharmaceutically acceptable salt thereof.

(29) The compound of any one of (1) to (25) above or a pharmaceutically acceptable salt thereof for the treatment and/or prophylaxis of hypertension, cardiac failure, diabetic nephropathy and the like.

(30) A method for the treatment and/or prophylaxis of hypertension, cardiac failure, diabetic nephropathy and the like, comprising administration of an effective amount of the compound the compound of any one of (1) to (25) above or a pharmaceutically acceptable salt thereof.

(31) Use of the compound of any one of (1) to (25) above or a pharmaceutically acceptable salt thereof for preparing a medicament for the treatment and/or prophylaxis of hypertension, cardiac failure, diabetic nephropathy and the like.

The term "alkyl" or "alkoxy" in the present invention is exemplified by a straight or branched chain group having 1 to 10 carbon atoms, and groups having 1 to 6 carbon atoms are preferable, and groups having 1 to 4 carbon atoms are especially preferable.

The term "alkenyl" is exemplified by a straight or branched chain group having 2 to 10 carbon atoms, and the group having 3 to 7 carbon atoms is preferable, and the group having 3 to 5 carbon atoms is especially preferable.

The term "alkynyl" is exemplified by a straight or branched chain group having 2 to 10 carbon atoms, and the group having 3 to 7 carbon atoms is preferable, and the group having 3 to 5 carbon atoms is especially preferable.

The term "alkanoyl" is exemplified by a straight or branched chain group having 1 to 7 carbon atoms, and the group having 2 to 5 carbon atoms is preferable.

The term "cycloalkyl" is exemplified by a cycloalkyl group having 3 to 8 carbon atoms, groups having 3 to 6 carbon atoms are preferable and groups having 3 to 4 carbon atoms are especially preferable.

The term "halogen" is exemplified by a fluorine, a chlorine, a bromine and an iodine, and a fluorine, a chlorine and a bromine are preferable, and a fluorine is especially preferable.

The term "aryl" is exemplified by a phenyl, a naphthyl and the like and a phenyl is preferable.

The term "heteroaryl" is, for example, an aromatic cyclic group comprising 1 to 4 heteroatoms selected from nitrogen atoms, oxygen atoms and sulfur atoms, including a monocyclic group having of 5- to 6-membered ring, a bicyclic group of 8- to 10-membered ring wherein same or different monocyclic heteroaromatic rings are fused to each other, and, a bicyclic group of 8- to 10-membered ring wherein a monocyclic heteroaromatic ring is fused to a benzene.

The aliphatic heterocyclic ring in "aliphatic heterocyclic group" and "aliphatic heterocyclic oxy" is exemplified by, for example, a non-aromatic heterocyclic ring comprising 1 to 4 heteroatoms selected from nitrogen atoms, oxygen atoms and sulfur atoms which have 5 to 12 ring members as a whole and which may be partially or fully saturated.

The lower alkyl in R is exemplified by, for example, a straight or branched chain group having 1 to 4 carbon atoms, and a methyl is especially preferable.

As the cycloalkyl of $R^1$, the cyclopropyl is preferable.

1) The optionally substituted aryl group, 2) the optionally substituted pyridyl, 3) the optionally substituted pyrazolopyridyl, 4) the optionally substituted indolyl, 5) the optionally substituted benzofuranyl, 6) the optionally substituted quinolyl, 7) the optionally substituted chromanyl, 8) the optionally substituted dihydrobenzofuranyl, 9) the optionally substituted indazolyl, 10) the optionally substituted pyrrolopyridinyl, 11) the optionally substituted benzoisoxazolyl, 12) the optionally substituted indolinyl, 13) the optionally substituted quinazolinyl, 14) the optionally substituted dihydroquinazolinyl, 15) the optionally substituted furopyridyl, 16) the optionally substituted isoquinolyl, 17) the optionally substituted pyrrolopyrimidinyl, 18) the optionally substituted tetrahydroquinolyl, 19) the optionally substituted tetrahydroindazolyl, 20) the optionally substituted tetrahydrocyclopentapyrazolyl, 21) the optionally substituted pyrrolyl, 22) the optionally substituted imidazolyl, 23) the optionally substituted pyrazolyl, 24) the optionally substituted thienyl, 25) the optionally substituted thiazolyl, 26) the optionally substituted triazolyl, 27) the optionally substituted pyrimidinyl, 28) the optionally substituted pyrazyl, 29) the optionally substituted imidazopyridinyl, or, 30) the optionally substituted pyrrolopyrazyl as $R^{22}$ is preferably a group substituted with 1 to 3 substituents. One of said 1 to 3 substituents is preferably selected from 1) an alkyl optionally substituted with same or different 1 or 2 groups selected from an alkanoylamino, an alkoxycarbonylamino, an alkoxy, an aminocarbonylamino optionally substituted with 1 or 2 alkyl, aryl, a hydroxyl, and a halogen, 2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl, and a halogen, and 3) an alkoxy optionally substituted with an alkoxy,
and, especially preferably, one of said 1 to 3 substituents is preferably selected from 1) a (C2-4) alkyl optionally substituted with same or different 1 or 2 groups selected from an alkanoylamino, an alkoxycarbonylamino, an alkoxy, an aminocarbonylamino optionally substituted with 1 or 2 alkyl, aryl, hydroxyl, and a halogen, 2) a (C2-4) alkenyl optionally substituted with same or different 1 or 2 groups selected from an alkanoylamino, an alkoxycarbonylamino, an alkoxy, an aminocarbonylamino optionally substituted with 1 or 2 alkyl, aryl, hydroxyl, and a halogen, and 3)a (C2-4) alkoxy optionally substituted with an alkoxy, especially, one of said 1 to 3 substituents is preferably a (C2-4) alkyl optionally substituted with same or different 1 or 2 groups selected from an alkanoylamino, an alkoxycarbonylamino, an alkoxy, an aminocarbonylamino optionally substituted with 1 or 2 alkyl, aryl, hydroxyl, and a halogen, specifically, one of said 1 to 3 substituents is an alkoxycarbonylamino (C2-4)alkyl.

For the substituents of 1) the optionally substituted aryl, 2) the optionally substituted pyridyl, 3) the optionally substituted pyrazolopyridyl, 4) the optionally substituted indolyl, 5) the optionally substituted benzofuranyl, 6) the optionally substituted quinolyl, 7) the optionally substituted chromanyl, 8) the optionally substituted dihydrobenzofuranyl, 9) the optionally substituted indazolyl, 10) the optionally substituted pyrrolopyridinyl, 11) the optionally substituted benzoisoxazolyl, 12) the optionally substituted indolinyl, 13) the optionally substituted quinazolinyl, 14) the optionally substituted dihydroquinazolinyl, 15) the optionally substituted furopyridyl, 16) the optionally substituted isoquinolyl, 17) the optionally substituted pyrrolopyrimidinyl, 18) the optionally substituted tetrahydroquinolyl, 19) the optionally substituted tetrahydroindazolyl, 20) the optionally substituted tetrahydrocyclopentapyrazolyl, 21) the optionally substituted pyrrolyl, 22) the optionally substituted imidazolyl, 23) the optionally substituted pyrazolyl, 24) the optionally substituted thienyl, 25) the optionally substituted thiazolyl, 26) the optionally substituted triazolyl, 27) the optionally substituted pyrimidinyl, 28) the optionally substituted pyrazyl, 29) the optionally substituted imidazopyridinyl, or, 30) the optionally substituted pyrrolopyrazyl as $R^{22}$, a heteroaryl in "a heteroaryl optionally substituted with same or different 1 or 2 selected from an alkyl, and alkoxy" is exemplified by, for example, a pyridyl, a pyrimidyl, or a pyrazolyl.

As the substituent of 1) the optionally substituted aryl, 2) the optionally substituted pyridyl, 3) the optionally substituted pyrazolopyridyl, 4) the optionally substituted indolyl, 5) the optionally substituted benzofuranyl, 6) the optionally substituted quinolyl, 7) the optionally substituted chromanyl, 8) the optionally substituted dihydrobenzofuranyl, 9) the optionally substituted indazolyl, 10) the optionally substituted pyrrolopyridinyl, 11) the optionally substituted benzoisoxazolyl, 12) the optionally substituted indolinyl, 13) the optionally substituted quinazolinyl, 14) the optionally substituted dihydroquinazolinyl, 15) the optionally substituted furopyridyl, 16) the optionally substituted isoquinolyl, 17) the optionally substituted pyrrolopyrimidinyl, 18) the optionally substituted tetrahydroquinolyl, 19) the optionally substituted tetrahydroindazolyl, 20) the optionally substituted tetrahydrocyclopentapyrazolyl, 21) the optionally substituted pyrrolyl, 22) the optionally substituted imidazolyl, 23) the optionally substituted pyrazolyl, 24) the optionally substituted thienyl, 25) the optionally substituted thiazolyl, 26) the optionally substituted triazolyl, 27) the optionally substituted pyrimidinyl, 28) the optionally substituted pyrazyl, 29) the optionally substituted imidazopyridinyl, or, 30) the optionally substituted pyrrolopyrazyl of $R^{22}$, the "aliphatic heterocyclic group" is exemplified by, for example, a tetrahydropyranyl.

The "indolinyl" in 12) the optionally substituted indolinyl as $R^{22}$ includes an oxoindolinyl.

The compound [I] of the present invention can be clinically used either in the free form or in the form of a pharmaceutically acceptable salt thereof. Examples of the pharmaceutically acceptable salt of the compound [I] include a salt with an inorganic acid such as hydrochloride, sulfate, phosphate or hydrobromide, or a salt with an organic acid such as acetate, fumarate, oxalate, citrate, methanesulfonate, benzenesulfonate, tosylate or maleate. Besides, when the compound [I] of the present invention has a substituent such as carboxyl group(s) and the like, examples of the pharmaceutically acceptable salt include, salts with a base (such as alkaline metal such as sodium salt and potassium salt or alkaline earth metal such as calcium salt).

"The compounds disclosed in Examples" comprise a free form of any compounds discloses as a salt form in Examples.

The compound [I] of the present invention also includes a mixture of a stereoisomer such as a geometrical isomer, a tautomer and an enantiomer, and an isolated stereoisomer thereof. In the compound [I] of the present invention, (R)-configuration is preferable for an asymmetric carbon atom of the morpholine ring having the substituent, $R^6$, from the view of renin-inhibition. From the view of renin-inhibition, (R)-configuration is also preferable for an asymmetric carbon atom which is substituted with R.

The present invention also includes an intramolecular salt, a hydrate, a pharmaceutically acceptable solvate and a crystal polymorph of the compound [I]. Additionally it should be understood that the compound [I] of the present invention is not limited to the compounds described in the examples below but includes whole the compounds of the formula [I] and pharmaceutically acceptable salts thereof.

Accordingly the compound of the present invention or the pharmaceutically acceptable salts thereof may be useful as an agent for prevention and/or treatment of hypertension, cardiac failure, diabetic nephropathy and the like, and can be advantageous as a medicine due to its low toxicity.

The compound [I] of the present invention or a pharmaceutically acceptable salt thereof can be either orally or parenterally administered, and can be formulated into a conventional pharmaceutical preparation such as tablets, granules, capsules, powders, injections or inhalants etc.

The dose of the compound [I] of the present invention or a pharmaceutically acceptable salt thereof may vary in accordance with the administration routes, and the ages, body weights and conditions of the patients, but usually it is in the range of about 0.001 to 500 mg/kg, preferably in the range of about 0.1 to 100 mg/kg.

The compound [I] of the present invention can be prepared by the following methods but should not be construed to be limited thereto.

Method for Preparing the Compound [I]

The compound [I] of the present invention or the pharmaceutically acceptable salt thereof can be prepared by deprotecting $P^1$ of the compound of the formula [II];

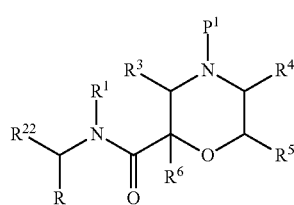

wherein, $P^1$ is a protecting group and the other symbols are the same as defined above, and converting the product to a pharmaceutically acceptable salt thereof, if necessary.

Method for Preparing the Compound [II]

The compound [II] can be prepared by reacting a carboxylic compound of the formula [III]:

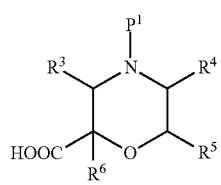

wherein the symbols are the same as defined above, or an activated derivative thereof with an amine compound of the formula [IV];

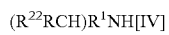

(R$^{22}$RCH)R$^1$NH[IV]

wherein the symbols are the same as defined above.

The compound of the present invention has two or more asymmetric carbons and the reaction product may be obtained as a mixture of diastereoisomers. Such a mixture of diastereoisomers can be separated and purified by a usual method, a silica gel column chromatography for example.

Reaction in the Method for Preparing the Compound [I]

Examples of the protecting group shown as $P^1$ include a usual amino-protecting group such as a t-butoxycarbonyl, a benzyloxycarbonyl, a 4-methoxybenzyloxycarbonyl, a benzyl, a 4-methoxybenzyl, an acetyl, a benzoyl, a tosyl and the like.

The protecting group $P^1$ of the compound [II] can be deprotected by treating with acid or base or catalytic reduction or a deprotecting agent in a suitable solvent or without solvent. As an acid, an inorganic acid such as hydrochloric acid, sulfuric acid and the like, and an organic acid such as acetic acid, trifluoroacetic acid, methanesulfonic acid, p-toluenesulfonic acid and the like can be preferably used. As a base, an inorganic base (e.g., an alkali metal hydride such as sodium hydride, an alkali metal carbonate such as sodium carbonates and potassium carbonates, an alkali metal amide such as sodium amides and lithium amide, an alkali metal alkoxide such as sodium methoxide, an alkali metal such as sodium, and an alkali metal hydroxide such as sodium hydroxide, potassium hydroxide etc.) and the like can be preferably used. As a deprotecting agent, zinc bromide and trimethylsilane trifluoromethanesulfonate etc. can be used. The catalytic reduction can be carried out by preferably using palladium carbon, palladium hydroxide carbon, platinum oxide and the like as a catalyst under hydrogen atmosphere. Examples of the solvent include any solvent which does not disturb the reaction, such as methanol, ethanol, isopropyl alcohol, 1,4-dioxane, diethyl ether, tetrahydrofuran, methylene chloride, chloroform, dichloroethane, ethyl acetate, toluene, and a mixture thereof. The acid or the base described above can be used as the solvent. The reaction can be suitably carried out at from −78° C. to a boiling temperature of the solvent.

Reaction in the Method for Preparing the Compound [II]

The compound [II] can be prepared by a condensation reaction of a carboxylic acid compound [III] and an amine compound [IV] in a suitable solvent or without a solvent.

The condensation reaction can be carried out by a conventional condensation reaction in the presence of a condensing agent, or reacting an activated derivative of the compound [III](e.g., an acid halide, a mixed acid anhydride, an activated ester and the like) with the compound [IV], after the compound [III] is converted to the reactive derivative thereof. Examples of the condensing agent include N,N-dicyclohexylcarbodiimide (DCC), 1-ethyl-3-(3-dimethylaminopropyl)carbodiimide (EDC) or hydrochloride thereof, carbonyldiimidazole (CDI), diphenylphosphoryl azide (DPPA), diethyl cyanophosphonate (DEPC) and the like, and among them DCC. EDC or its hydrochloride is preferable.

When the reactive derivative of the compound [III] is used, the reactive derivative can be reacted with the compound [IV] in a suitable solvent or without a solvent in presence of an acid scavenger if necessary, after the compound [III] is converted to an acid halide using a halogenating agent (e.g., thionyl chloride, thionyl bromide, oxalyl chloride and the like), a mixed acid anhydride using chlorocarbonate ester (e.g., methyl chlorocarbonate, ethyl chlorocarbonate, isobutyl chloroformate and the like) or acid chloride (2,4,6-trichlorobenzoyl chloride and the like), or an activated ester of N-hydroxylamine compound (1-hydroxysuccinimide, 1-hydroxybenzotriazole and the like) or of phenol compound (p-nitrophenol and the like) or a lower alcohol ester (methyl ester, ethyl ester and the like). In a method converting to an acid halide, an addition of catalyst such as dimethylformamide and the like can accelerate the reaction. As an acid scavenger, an inorganic base or an organic base is used when necessary, and examples of an inorganic base include sodium carbonate, potassium carbonate, cesium carbonate, sodium bicarbonate, sodium hydroxide, potassium hydroxide, lithium hydroxide and the like and examples of an organic base include triethylamine, tributylamine, diisopropylethylamine, 1,8-diazabicyclo[5,4,0]undeca-7-ene, N,N-diethylaniline, pyridine, lutidine, colidine and the like. In the present reaction, triethylamine, diisopropylethylamine, pyridine and the like are preferably used as an acid scavenger. When the acid scavenger is used in this reaction, acid scavenger is used as the solvent.

In the condensing reaction shown above, it can be conducted or accelerated by adding 4-aminopyridine and the like.

When using a solvent in the condensing reaction above, any inert solvent which does not disturb the reaction can be used and examples of the solvents include chloroform, dichloromethane, dichloroethane, toluene, diethyl ether, tetrahydrofuran, dioxane, 1,2-dimethoxyethane, ethyl acetate, amide-related solvent (N,N-dimethylformamide, N,N-dimethylacetamide, 1,3-dimethyl-2-imidazolidinon etc.), pyridine, 2,6-lutidine, water and the like, and a mixture thereof can be also used. Among them, chloroform, tetrahydrofuran, dioxane, N,N-dimethylformamide. N,N-dimethylacetamide, and a mixture of chloroform and N,N-dimethylformamide etc. are preferred.

Usually the condensation reaction above can be carried out at a temperature from −20° C. to a reflux temperature of the solvent and if necessary, it can be carried out at a lower temperature which is suitably selected.

Examples of the compounds [I] of the present invention prepared by the methods illustrated above are shown below, but the present invention should not be construed to be limited thereto.

EXAMPLES

Example 1

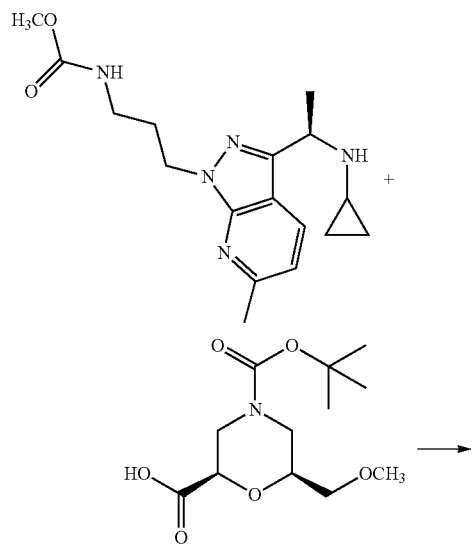

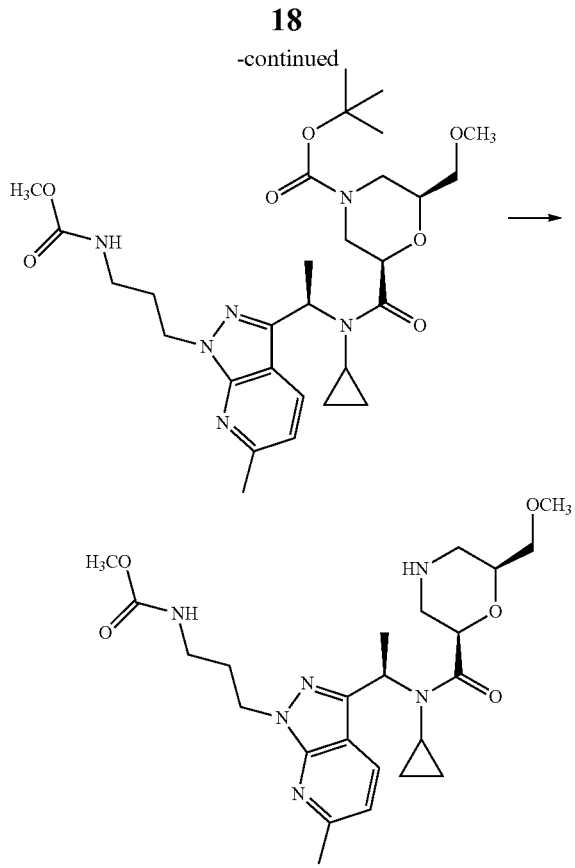

(1) To a solution of methyl (3-{3-[(1R)-1-(cyclopropylamino)ethyl]-6-methyl-1H-pyrazolo[3,4-b]pyridin-1-yl}propyl)carbamate (4.00 g) and (2R,6S)-4-(tert-butoxycarbonyl)-6-(methoxymethyl)morpholine-2-carboxylic acid (3.66 g) in N,N-dimethylformamide (80 mL) were added 1-ethyl-3-(3-dimethylaminopropyl)carbodiimide hydrochloride (3.45 g), 1-hydroxybenzotriazole (1.63 g) under ice-cooling, and then the mixture was stirred at room temperature for 5 hours. To the reaction mixture was added aqueous saturated sodium hydrogen carbonate solution, and the mixture was extracted with ethyl acetate. The organic layer was sequentially washed with water and saturated saline, dried over sodium sulfate, and then concentrated under reduced pressure. The resulting residue was purified by silica gel column chromatography (eluent: n-hexane/ethyl acetate=1/1→ethyl acetate) to give tert-butyl (2R,6S)-2-{cyclopropyl[(1R)-1-(1-{3-[(methoxycarbonyl)amino]propyl}-6-methyl-1H-pyrazolo[3,4-b]pyridin-3-yl)ethyl]carbamoyl}-6-(methoxymethyl)morpholine-4-carboxylate (5.57 g).

APCI-MS m/z: 589 [M+H]$^+$.

(2) To a solution of tert-butyl (2R,6S)-2-{cyclopropyl[(1R)-1-(1-{3-[(methoxycarbonyl)amino]propyl}-6-methyl-1H-pyrazolo[3,4-b]pyridin-3-yl)ethyl]carbamoyl}-6-(methoxymethyl)morpholine-4-carboxylate (5.28 g) in dichloromethane (30 mL) was added trifluoroacetic acid (15 mL) under ice-cooling and then the mixture was stirred at room temperature for 1 hour. The resulting reaction solution was concentrated under reduced pressure, and chloroform was added to the resulting residue, aqueous saturated sodium hydrogen carbonate solution was added to neutralize the mixture under ice-cooling, and then organic layer was separated. The organic layer was washed with saturated saline, dried over sodium sulfate, and then concentrated under reduced pressure. The resulting residue was purified by NH-silica gel column chromatography (eluent: ethyl acetate→ethyl acetate/methanol=20/1) to give methyl (3-{3-[(1R)-1-(cyclopropyl{[(2R,6S)-6-(methoxymethyl)morpholin-2-yl]carbonyl}amino)ethyl]-6-methyl-1H-pyrazolo[3,4-b]pyridin-1-yl}propyl)carbamate (3.72 g).

APCI-MS m/z: 489 [M+H]+.

Example 2

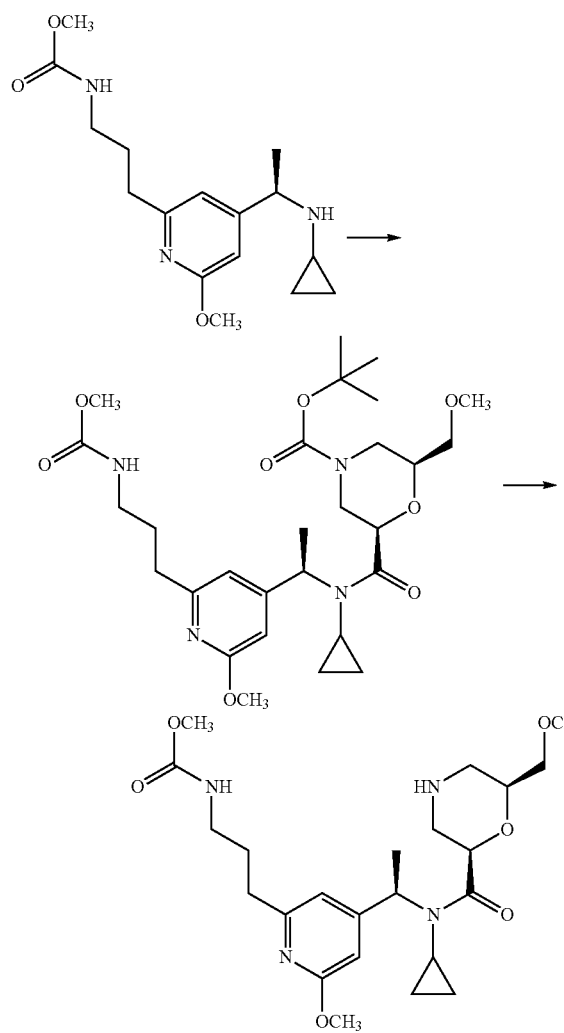

(1) To a solution of (2R,6S)-4-(tert-butoxycarbonyl)-6-(methoxymethyl)morpholine-2-carboxylic acid (7.59 g) in dichloromethane (70 mL) were added diisopropylethylamine (9.60 mL) and diphenyl chlorophosphate (5.71 mL) under ice-cooling, and the mixture was stirred at 15 minutes under ice-cooling. A solution of methyl (3-{4-[(1R)-1-(cyclopropylamino)ethyl]-6-methoxypyridin-2-yl}propyl)carbamate (5.65 g) in dichloromethane (20 mL) was added dropwise under ice-cooling, and then the mixture was stirred at room temperature for 20 hours. To the reaction mixture was added aqueous saturated sodium hydrogen carbonate solution under ice-cooling, and the mixture was extracted with chloroform. The organic layer was washed with saturated saline, dried over sodium sulfate, and then concentrated under reduced pressure. The resulting residue was purified by silica gel column chromatography (eluent: n-hexane/ethyl acetate=1/1→ethyl acetate) to give tert-butyl (2R,6S)-2-{cyclopropyl[(1R)-1-(2-methoxy-6-{3-[(methoxycarbonyl)amino]propyl}pyridin-4-yl)ethyl]carbamoyl}-6-(methoxymethyl)morpholine-4-carboxylate (7.13 g).

APCI-MS m/z: 565 [M+H]+.

(2) To a solution of tert-butyl (2R,6S)-2-{cyclopropyl[(1R)-1-(2-methoxy-6-{3-[(methoxycarbonyl)amino]propyl}pyridin-4-yl)ethyl]carbamoyl}-6-(methoxymethyl)morpholine-4-carboxylate (7.13 g) in dichloromethane (50 mL) was added trifluoroacetic acid (25 mL) under ice-cooling, and then the mixture was stirred at room temperature for 1 hour. The resulting reaction solution was concentrated under reduced pressure, and ethyl acetate was added to the resulting residue, aqueous saturated sodium hydrogen carbonate solution was added to neutralize the mixture under ice-cooling, and then organic layer was separated. The organic layer was washed with saturated saline, dried over sodium sulfate, and then concentrated under reduced pressure. The resulting residue was purified by NH-silica gel column chromatography (eluent: ethyl acetate→ethyl acetate/methanol=20/1) to give methyl (3-{4-[(1R)-1-(cyclopropyl{[(2R,6S)-6-(methoxymethyl)morpholin-2-yl]carbonyl}amino)ethyl]-6-methoxypyridin-2-yl}propyl)carbamate (5.40 g).

APCI-MS m/z: 465 [M+H]+.

Example 3

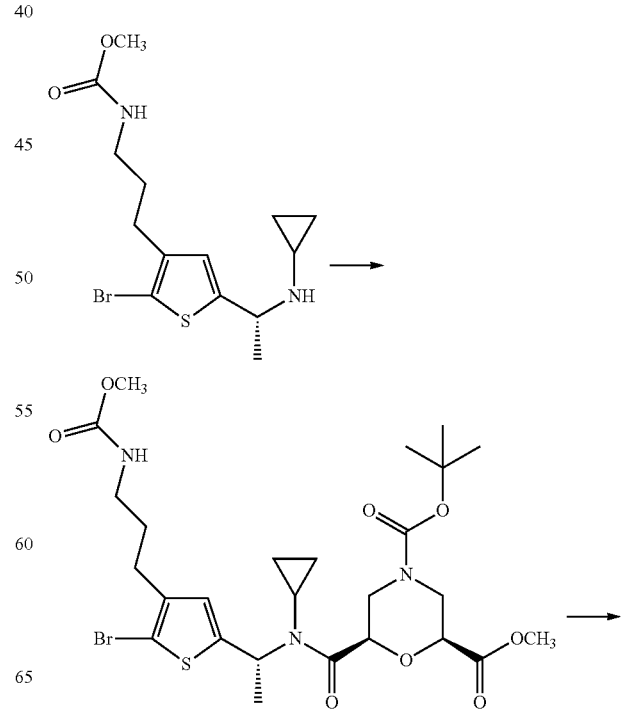

-continued

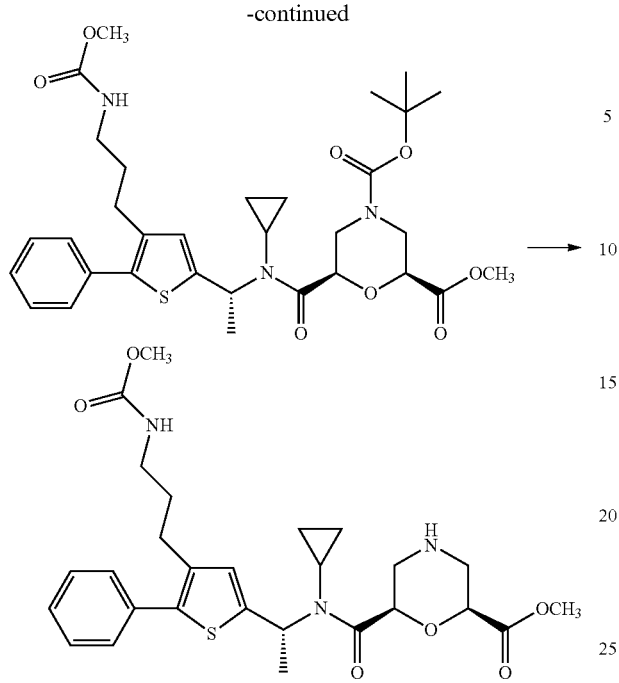

(1) To a solution of (2R,6S)-4-(tert-butoxycarbonyl)-6-(methoxycarbonyl)morpholine-2-carboxylic acid (289 mg) in dichloromethane (20 mL) were added diisopropylamine (523 µL) and diphenyl chlorophosphate (415 µL), under nitrogen stream and under ice-cooling, and the mixture was stirred for 30 minutes under ice-cooling, then a solution of methyl (3-{2-bromo-5-[(1R)-1-(cyclopropylamino)ethyl]thiophen-3-yl}propyl)carbamate (361 mg) in dichloromethane (3 mL) was added thereto, and the mixture was stirred at room temperature for 4 hours To the reaction solution was added aqueous saturated sodium hydrogen carbonate solution, and the mixture was extracted with chloroform. The organic layer was washed with saturated saline, and dried over anhydrous magnesium sulfate, and then the solvent was distilled under reduced pressure. The resulting residue was purified by silica gel column chromatography (eluent: n-hexane/ethyl acetate=75/25→40/60) to give 4-tert-butyl 2-methyl (2S, 6R)-6-{[(1R)-1-(5-bromo-4-{3-[(methoxycarbonyl)amino]propyl}thiophen-2-yl)ethyl](cyclopropyl)carbamoyl}morpholin-2,4-dicarboxylate (522 mg).
APCI-MS m/z: 632/634 [M+H]⁺.

(2) To a solution of 4-tert-butyl 2-methyl (2S,6R)-6-{[(1R)-1-(5-bromo-4-{3-[(methoxycarbonyl)amino]propyl}thiophen-2-yl)ethyl](cyclopropyl)carbamoyl}morpholin-2,4-dicarboxylate (504 mg) in 1,2-dimethoxyethane (12 mL) were added phenylboronic acid (195 mg), dichlorobis(triphenylphosphine)palladium (11) (56 mg), and 2-normal potassium carbonate aqueous solution (1.2 mL) at room temperature, and the mixture was heated to reflux for 3 hours under nitrogen stream. The reaction solution was cooled to room temperature, and then, aqueous saturated sodium hydrogen carbonate solution was added thereto, and the mixture was stirred for a while, and the mixture was extracted with ethyl acetate. The organic layer was washed with aqueous saturated sodium hydrogen carbonate solution and saturated saline, and then dried over anhydrous magnesium sulfate, and the solvent was distilled under reduced pressure. The resulting residue was purified by silica gel column chromatography (eluent: n-hexane/ethyl acetate=70/30→30/70) to give 4-tert-butyl 2-methyl (2S, 6R)-6-{cyclopropyl[(1R)-1-(4-{3-[(methoxycarbonyl)amino]propyl}-5-phenylthiophen-2-yl)ethyl]carbamoyl}morpholin-2,4-dicarboxylate (307 mg).
APCI-MS m/z: 630 [M+H]⁺.

(3) To a solution of 4-tert-butyl 2-methyl (2S,6R)-6-{cyclopropyl[(1R)-1-(4-{3-[(methoxycarbonyl)amino]propyl}-5-phenylthiophen-2-yl)ethyl]carbamoyl}morpholin-2,4-dicarboxylate (342 mg) in dichloromethane (10 mL) were added 2,6-lutidine (285 µL) and trimethylsilyl trifluoromethanesulfonate (344 µL) dropwise under ice-cooling, and under nitrogen stream, the mixture was stirred for 30 minutes under ice-cooling. To the reaction solution were added methanol and aqueous saturated sodium hydrogen carbonate solution under ice-cooling, and the mixture was stirred for 30 minutes, and then extracted with chloroform. The organic layer was washed with saturated saline, and then dried over anhydrous magnesium sulfate, and the solvent was distilled under reduced pressure. The resulting residue was redissolved to the solvent mixture of methanol (20 mL)-water (2 mL), and an appropriate amount of potassium fluoride was added to the mixture, and then the mixture was stirred for 1 hours at room temperature. After the reaction solvent was distilled under reduced pressure, the resulting residue was dissolved to ethyl acetate, dried over anhydrous magnesium sulfate, and the solvent was distilled under reduced pressure. The resulting residue was purified by silica gel column chromatography (eluent: chloroform/methanol=100/0→94/6) to give methyl (2S,6R)-6-{cyclopropyl[(1R)-1-(4-{3-[(methoxycarbonyl)amino]propyl}-5-phenylthiophen-2-yl)ethyl]carbamoyl}morpholine-2-carboxylate (214 mg).
APCI-MS m/z: 530 [M+H]⁺.

Example 4

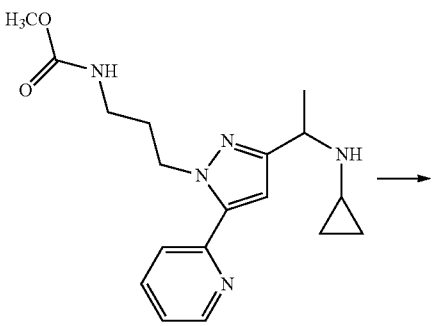

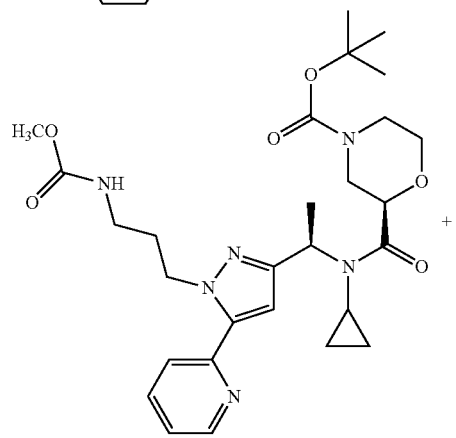

-continued

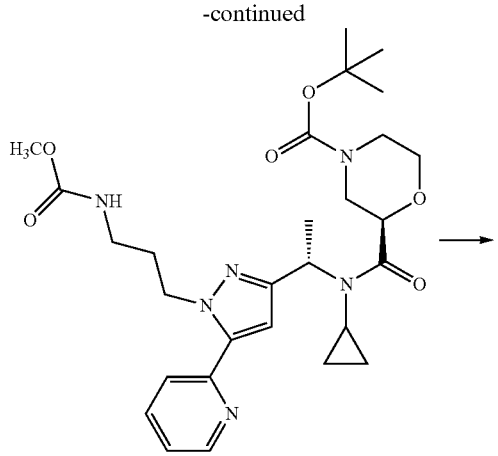

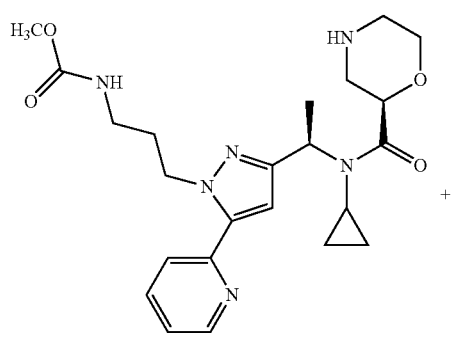

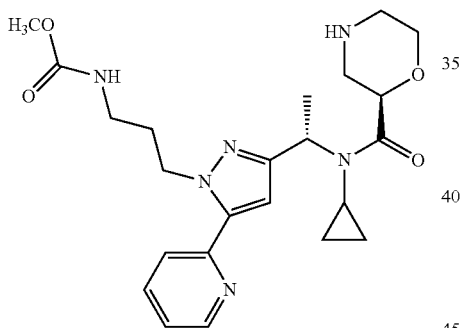

(1) To a solution of (2R)-4-(tert-butoxycarbonyl)morpholine-2-carboxylic acid (104 mg) and diisopropylethylamine (213 µL) in dichloromethane (2.5 mL) was added diphenyl chlorophosphate (131 mg) under ice-cooling, and the mixture was stirred for 15 minutes at the same temperature. To the reaction solution was added a solution of methyl (3-{3-[1-(cyclopropylamino)ethyl]-5-(pyridin-2-yl)-1H-pyrazol-1-yl}propyl)carbamate (140 mg) in dichloromethane (2.5 mL) under ice-cooling, and the mixture was stirred at room temperature for 15 hours. The mixture was concentrated under reduced pressure, and the resulting residue was purified by NH-silica gel column chromatography (eluent: n-hexane/ethyl acetate=1/1) to give tert-butyl (2R)-2-(cyclopropyl{(1R)-1-[1-{3-[(methoxycarbonyl)amino]propyl}-5-(pyridin-2-yl)-1H-pyrazol-3-yl]ethyl}carbamoyl)morpholine-4-carboxylate (104 mg) and tert-butyl (2R)-2-(cyclopropyl{(1S)-1-[1-{3-[(methoxycarbonyl)amino]propyl}-5-(pyridin-2-yl)-1H-pyrazole3-yl]ethyl}carbamoyl)morpholine-4-carboxylate (110 mg).

APCI-MS m/z: 557 [M+H]⁺.

(2) To a solution of tert-butyl (2R)-2-(cyclopropyl{(1R)-1-[1-{3-[(methoxycarbonyl)amino]propyl}-5-(pyridin-2-yl)-1H-pyrazol-3-yl]ethyl}carbamoyl)morpholine-4-carboxylate (100 mg) in dichloromethane (1.0 mL) was addedtrifluoroacetic acid (1.0 mL) at room temperature, and the mixture was stirred for 30 minutes at the same temperature. The mixture was concentrated under reduced pressure, then resulting residue was diluted with ethanol, and purified with Waters PoraPak™ Rxn CX (strong cation exchange packing material) cartridge (purification solvent: water→ethanol, eluent: 1-normal ammonia-methanol) to give methyl (3-{3-[(1R)-1-{cyclopropyl[(2R)-morpholin-2-ylcarbonyl]amino}ethyl]-5-(pyridin-2-yl)-1H-pyrazole1-yl}propyl)carbamate (77 mg).

APCI-MS m/z: 457 [M+H]⁺.

(3) Starting from tert-butyl (2R)-2-(cyclopropyl{(1S)-1-[1-{3-[(methoxycarbonyl)amino]propyl}-5-(pyridin-2-yl)-1H-pyrazol-3-yl]ethyl}carbamoyl)morpholine-4-carboxylate (105 mg) and a method analogy to the above was used to give methyl (3-{3-[(1S)-1-{cyclopropyl[(2R)-morpholin-2-ylcarbonyl]amino}ethyl]-5-(pyridin-2-yl)-1H-pyrazole1-yl}propyl)carbamate (81 mg).

APCI-MS m/z: 457 [M+H]⁺.

Example 5

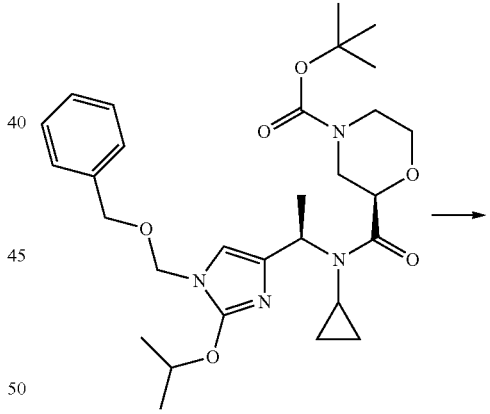

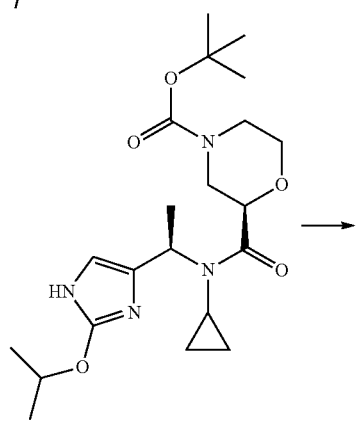

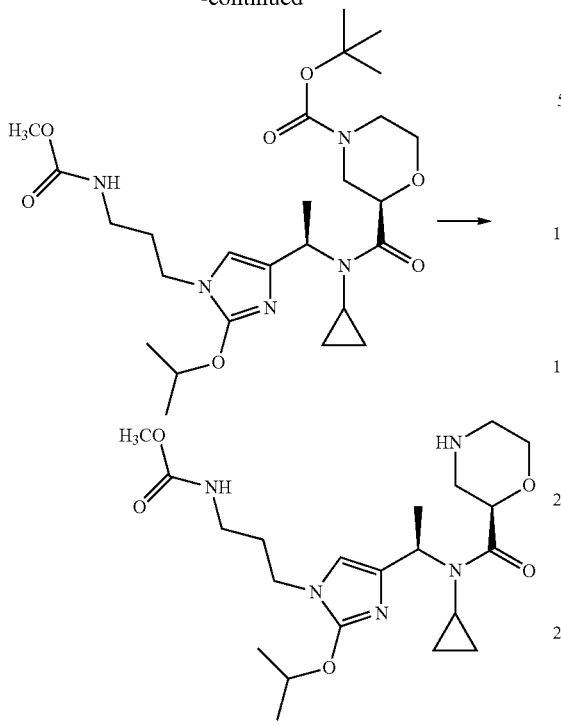

(1) To a solution of tert-butyl (2R)-2-{[(1R)-1-{1-[(benzyloxy)methyl]-2-(propan-2-yloxy)-1H-imidazol-4-yl}ethyl](cyclopropyl)carbamoyl}morpholine-4-carboxylate (215 mg) in methanol (6.0 mL) was added 20% palladium hydroxide on carbon (80 mg), and the mixture was stirred under hydrogen atmosphere for 6 hours. 20% Palladium hydroxide on carbon (80 mg) was added thereto, and the mixture was stirred under hydrogen atmosphere for 3 hours. An insoluble was filtered off through Celite, and the filtrate was concentrated under reduced pressure to give tert-butyl (2R)-2-(cyclopropyl{(1R)-1-[2-(propan-2-yloxy)-1H-imidazol-4-yl]ethyl}carbamoyl)morpholine-4-carboxylate (190 mg).
APCI-MS m/z: 423 [M+H]⁺.

(2) To a solution of tert-butyl (2R)-2-(cyclopropyl{(1R)-1-[2-(propan-2-yloxy)-1H-imidazol-4-yl]ethyl}carbamoyl)morpholine-4-carboxylate (185 mg) and methyl (3-bromopropyl)carbamate (215 mg) in N,N-dimethylformamide (4.0 mL) was added potassium carbonate (242 mg), and then the mixture was stirred at 60° C. for 17 hours. After cooling the reaction solution, water was added thereto, and the mixture was extracted with ethyl acetate. The organic layer was sequentially washed with water and saturated saline, dried over sodium sulfate, and then concentrated under reduced pressure. The resulting residue was purified by silica gel column chromatography (eluent: chloroform→chloroform/methanol=10/1) to give tert-butyl (2R)-2-(cyclopropyl{(1R)-1-[1-{3-[(methoxycarbonyl)amino]propyl}-2-(propan-2-yloxy)-1H-imidazol-4-yl]ethyl}carbamoyl)morpholine-4-carboxylate (143 mg).
APCI-MS m/z: 538 [M+H]⁺.

(3) To a solution of tert-butyl (2R)-2-(cyclopropyl{(1R)-1-[1-{3-[(methoxycarbonyl)amino]propyl}-2-(propan-2-yloxy)-1H-imidazol-4-yl]ethyl}carbamoyl)morpholine-4-carboxylate (140 mg) in dichloromethane (3.0 mL) was added trifluoroacetic acid (1.0 mL) under ice-cooling, and then the mixture was stirred at room temperature for 1 hour. The resulting reaction solution was concentrated under reduced pressure, chloroform was added to the resulting residue, and aqueous saturated sodium hydrogen carbonate solution was added to neutralize the mixture under ice-cooling, and then organic layer was separated. The organic layer was washed with saturated saline, dried over sodium sulfate, and then concentrated under reduced pressure. The resulting residue was purified by NH-silica gel column chromatography (eluent: ethyl acetate→ethyl acetate/methanol=8/1) to give methyl (3-{4-[(1R)-1-{cyclopropyl[(2R)-morpholin-2-ylcarbonyl]amino}ethyl]-2-(propan-2-yloxy)-1H-imidazol-1-yl}propyl)carbamate (81 mg).
APCI-MS m/z: 438 [M+H]⁺.

Example 6

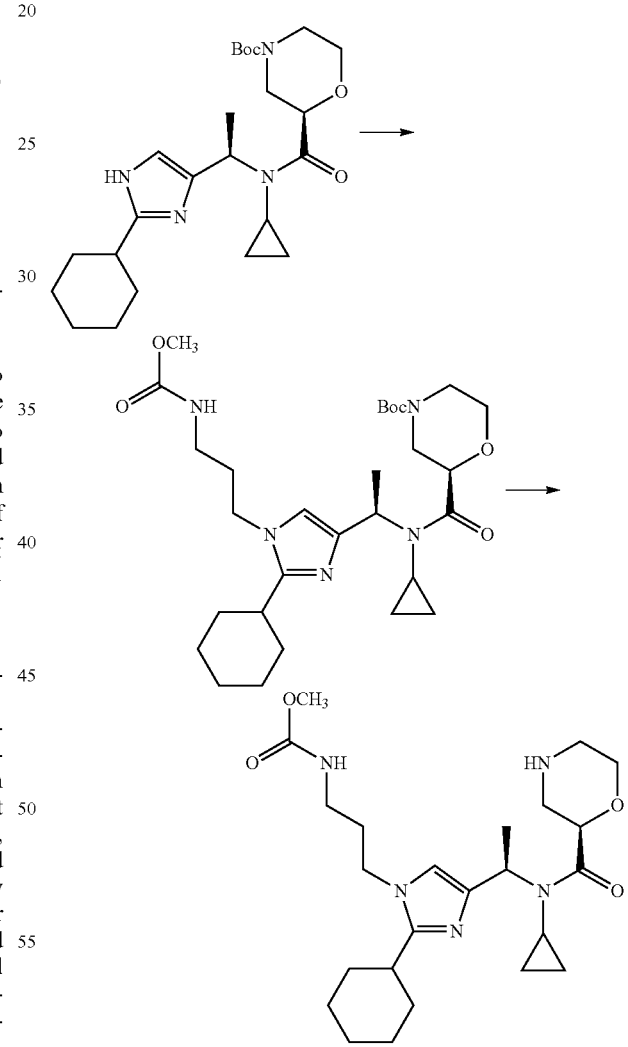

(1) To a solution of tert-butyl (2R)-2-{[(1R)-1-(2-cyclohexyl-1H-imidazol-4-yl)ethyl](cyclopropyl)carbamoyl}morpholine-4-carboxylate (735 mg) and methyl (3-bromopropyl)carbamate (482 mg) in N,N-dimethylformamide (10 mL) was added potassium carbonate (453 mg), and then the mixture was stirred at 60° C. for 17 hours. Additional methyl-(3-bromopropyl)carbamate (964 mg) was added thereto, and the mixture was stirred at 60° C. for 48 hours. To the reaction solution was added aqueous saturated sodium hydrogen carbonate solution, and then the mixture was extracted with chloroform. The organic layer was dried over sodium sulfate, and concentrated under reduced pressure. The resulting residue was briefly purified by silica gel column chromatography (eluent: chloroform/methanol=1/0→19/1), and then purified with gel permeation chromatography (eluent: chloroform) to give tert-butyl (2R)-2-{[(1R)-1-(2-cyclohexyl-1-{3-[(methoxycarbonyl)aminopropyl]-1H-imidazol-4-yl)ethyl](cyclopropyl)carbamoyl}morpholine-4-carboxylate (640 mg).
APCI-MS m/z: 562 [M+H]$^+$.

(2) To a solution of tert-butyl (2R)-2-{[(1R)-1-(2-cyclohexyl-1-{3-[(methoxycarbonyl)aminopropyl]-1H-imidazol-4-yl)ethyl](cyclopropyl)carbamoyl}morpholine-4-carboxylate (630 mg) in dichloromethane (10 mL) was added trifluoroacetic acid (1.5 mL) under ice-cooling, and the mixture was stirred for 1 hour at the same temperature. The mixture was concentrated under reduced pressure, and to the resulting residue was added saturated sodium hydrogen carbonate solution, and the mixture was extracted with chloroform. The organic layer was dried over sodium sulfate, and then concentrated under reduced pressure. The resulting residue was purified by NH-silica gel column chromatography (eluent: ethyl acetate/methanol=19/1→17/3) to give methyl (3-{2-cyclohexyl-4-[(1R)-1-{cyclopropyl[(2R)-morpholin-2-ylcarbonyl]amino}ethyl]-1H-imidazol-1-yl}propyl)carbamate (410 mg).
APCI-MS m/z: 462 [M+H]$^+$.

TABLE 1

| Example No. | Chemical Formula | MS Result | MS Method | Ion Species |
|---|---|---|---|---|
| Example 7 | 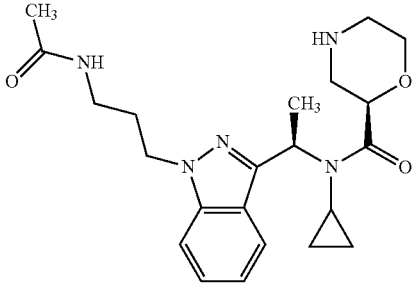 [SMILES: CC(=O)NCCCn1nc([C@@H](C)N(C(=O)[C@H]2CNCCO2)C2CC2)c2ccccc21] | 414 | APCI | [M + H]+ |
| Example 8 | 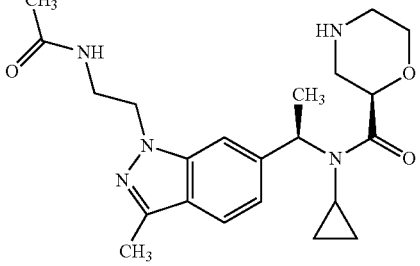 | 414 | APCI | [M + H]+ |
| Example 9 | 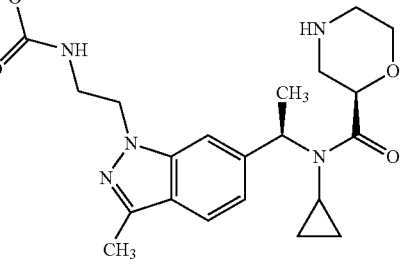 | 430 | APCI | [M + H]+ |
| Example 10 | 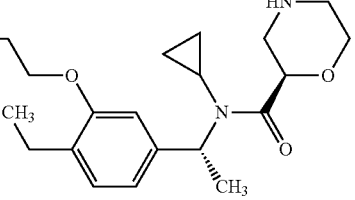 | 391 | APCI | [M + H]+ |

TABLE 1-continued
| Example No. | Chemical Formula | MS Result | MS Method | Ion Species |
|---|---|---|---|---|
| Example 11 | | 426 | APCI | [M + H]+ |
| Example 12 | | 401 | APCI | [M + H]+ |
| Example 13 | | 403 | APCI | [M + H]+ |
TABLE 2
| Example 14 | | 405 | APCI | [M + H]+ |
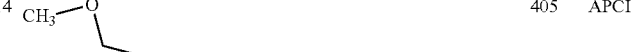

TABLE 2-continued
| Example 15 | 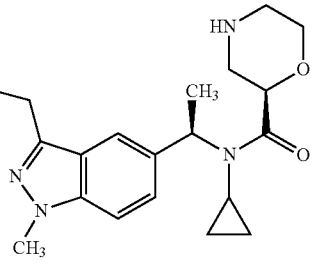 | 401 | APCI | [M + H]+ |
| Example 16 | 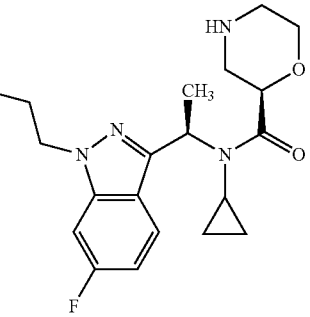 | 419 | APCI | [M + H]+ |
| Example 17 | 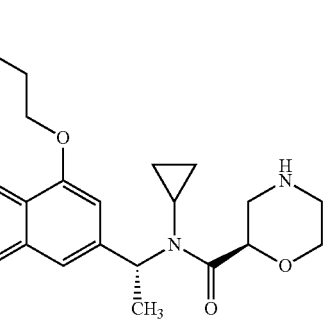 | 414 | APCI | [M + H]+ |
| Example 18 | 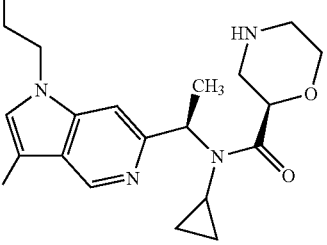 | 421/423 | APCI | [M + H]+ |
| Example 19 | 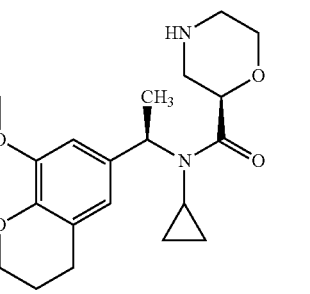 | 419 | APCI | [M + H]+ |

TABLE 2-continued
| Example 20 | 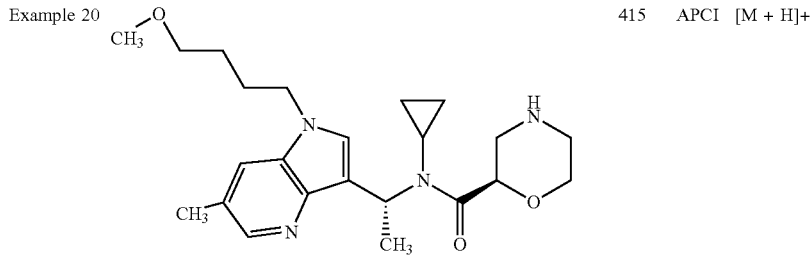 | 415 | APCI [M + H]+ |
TABLE 3
| Example 21 | 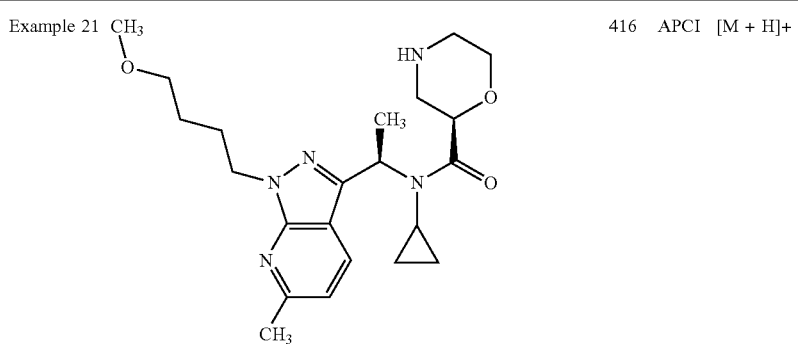 | 416 | APCI [M + H]+ |
| Example 22 | 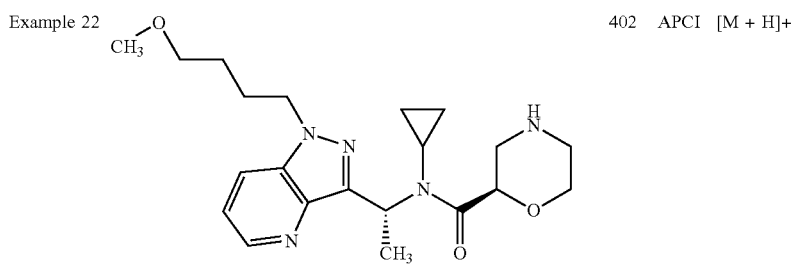 | 402 | APCI [M + H]+ |
| Example 23 | 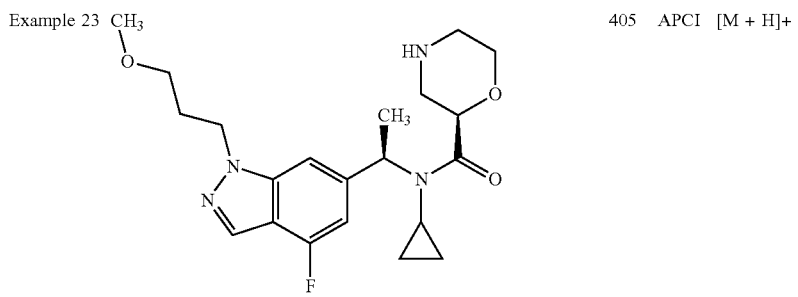 | 405 | APCI [M + H]+ |
| Example 24 | 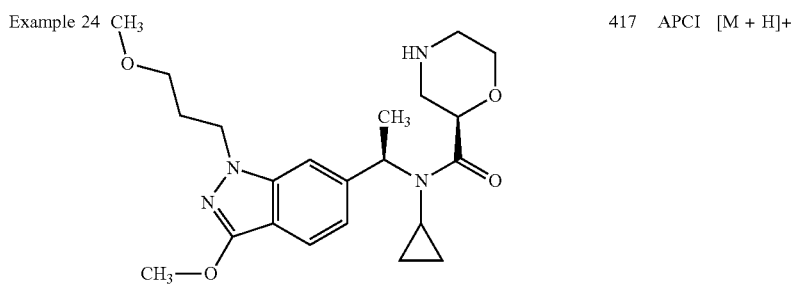 | 417 | APCI [M + H]+ |

TABLE 3-continued
| Example 25 | 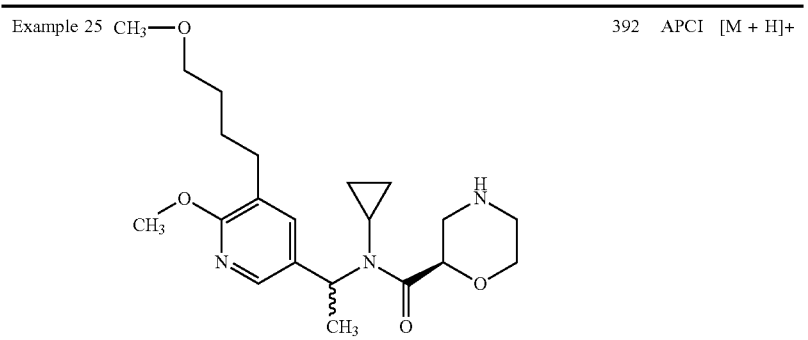 | 392 | APCI [M + H]+ |
| Example 26 | 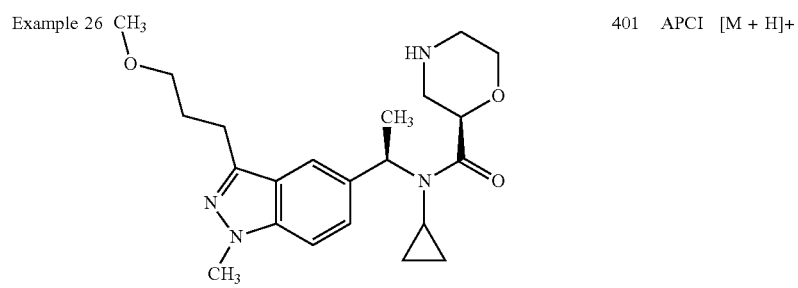 | 401 | APCI [M + H]+ |
| Example 27 | 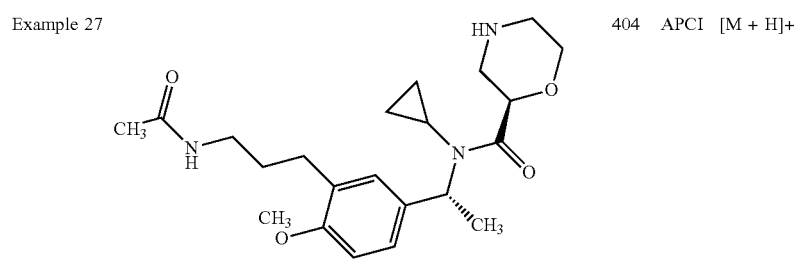 | 404 | APCI [M + H]+ |
TABLE 4
| Example 28 | 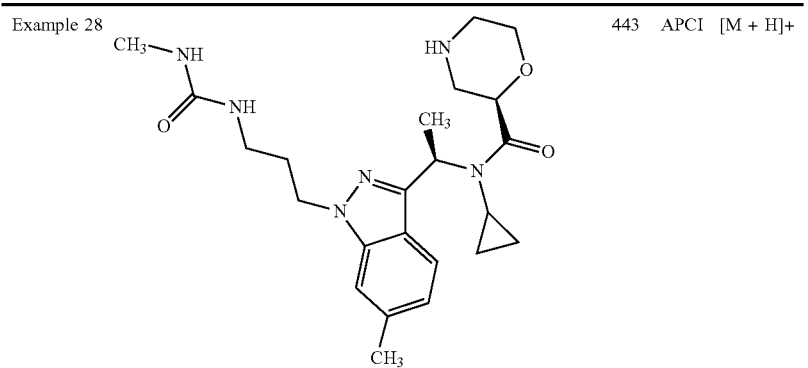 | 443 | APCI [M + H]+ |

TABLE 4-continued
| Example 29 | 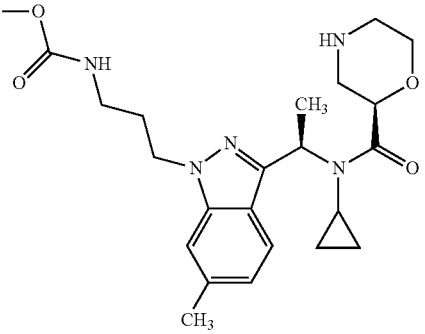 | 444 | APCI [M + H]+ |
| Example 30 | 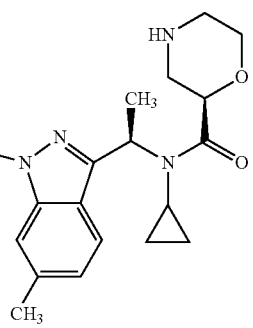 | 415 | APCI [M + H]+ |
| Example 31 | 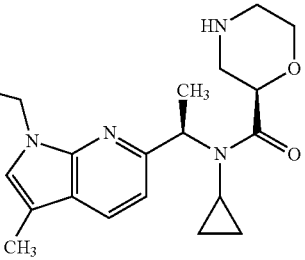 | 401 | APCI [M + H]+ |
| Example 32 | 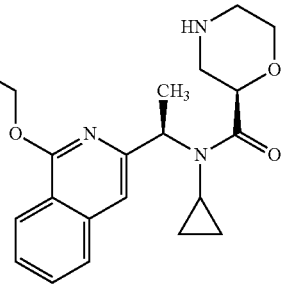 | 414 | APCI [M + H]+ |
| Example 33 | 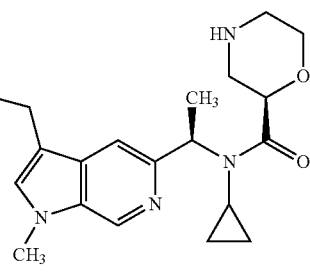 | 401 | APCI [M + H]+ |

TABLE 5
| Example 34 | 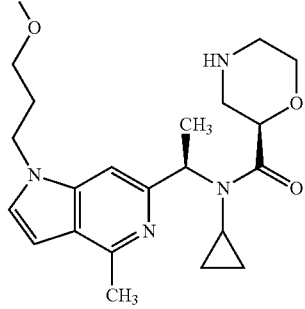 | 401 | APCI [M + H]+ |
| Example 35 | 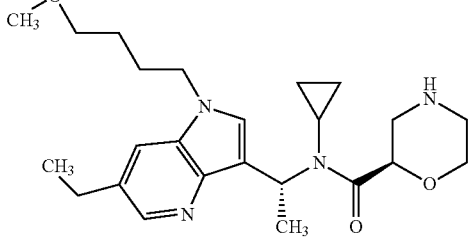 | 429 | APCI [M + H]+ |
| Example 36 | 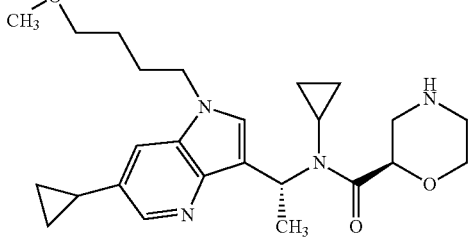 | 441 | APCI [M + H]+ |
| Example 37 | 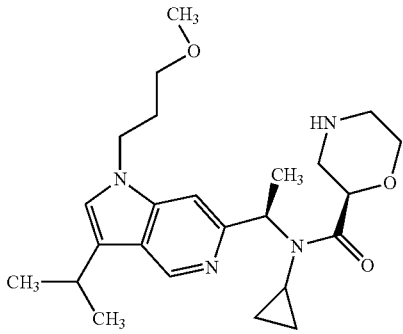 [SMILES: COCCCn1cc(C(C)C)c2cnc([C@@H](C)N(C(=O)[C@H]3CNCCO3)C3CC3)cc21] | 429 | APCI [M + H]+ |
| Example 38 | 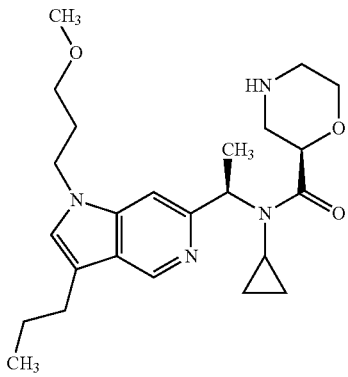 [SMILES: CCCc1cn(CCCOC)c2cc([C@@H](C)N(C(=O)[C@H]3CNCCO3)C3CC3)ncc12] | 429 | APCI [M + H]+ |

TABLE 5-continued
| Example 39 | 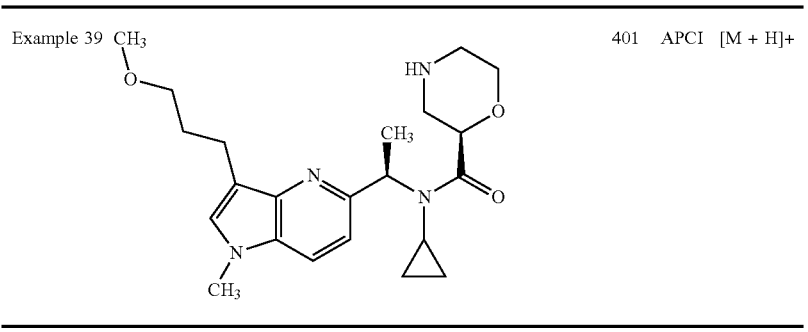 | 401 | APCI [M + H]+ |
TABLE 6
| Example 40 | 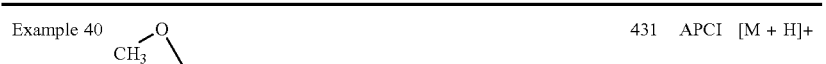 | 431 | APCI [M + H]+ |
| Example 41 | 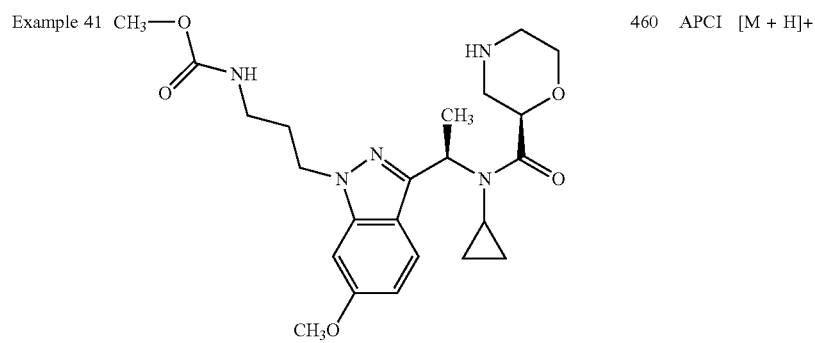 | 460 | APCI [M + H]+ |
| Example 42 | 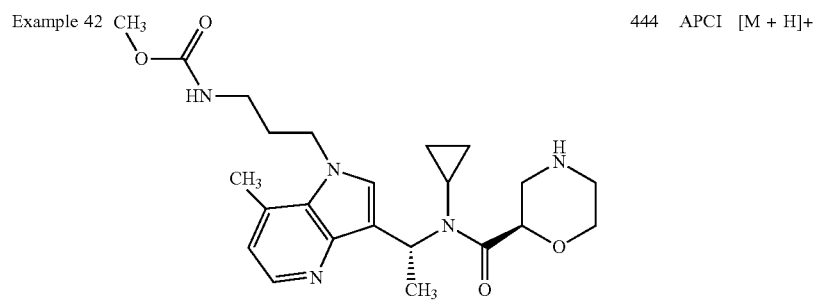 | 444 | APCI [M + H]+ |
| Example 43 | 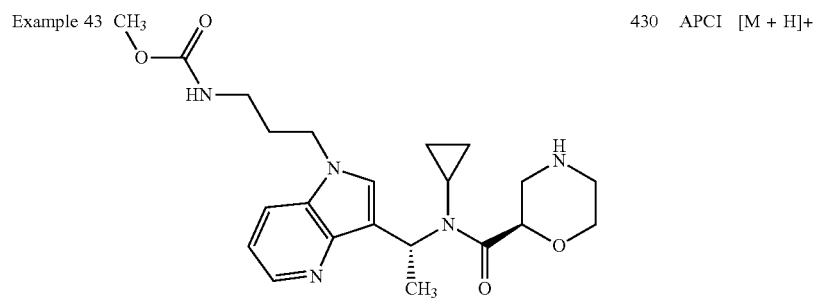 | 430 | APCI [M + H]+ |

TABLE 6-continued
| Example 44 | 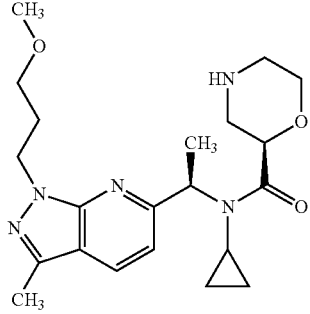 [SMILES: COCCCn1nc(C)c2ccc([C@@H](C)N(C(=O)[C@H]3CNCCO3)C3CC3)nc21] | 402 | APCI [M + H]+ |
| Example 45 | 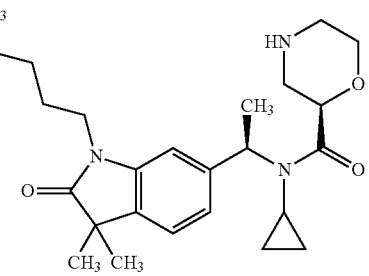 | 430 | APCI [M + H]+ |
TABLE 7
| Example 46 | 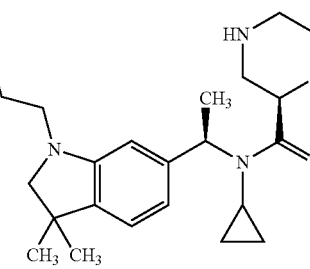 | 416 | APCI [M + H]+ |
| Example 47 | 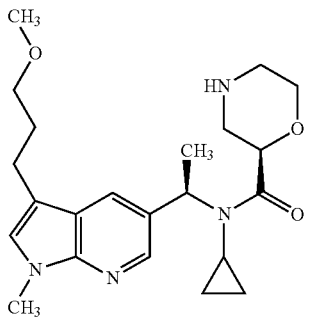 [SMILES: COCCCc1cn(C)c2ncc([C@@H](C)N(C(=O)[C@H]3CNCCO3)C3CC3)cc12] | 401 | APCI [M + H]+ |
| Example 48 | 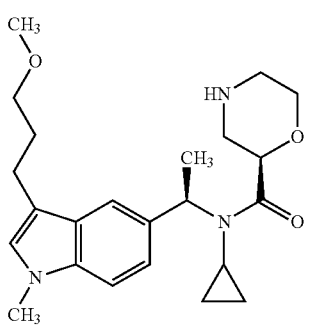 [SMILES: COCCCc1cn(C)c2ccc([C@@H](C)N(C(=O)[C@H]3CNCCO3)C3CC3)cc12] | 400 | APCI [M + H]+ |

TABLE 7-continued
| | | | | |
|---|---|---|---|---|
| Example 49 | 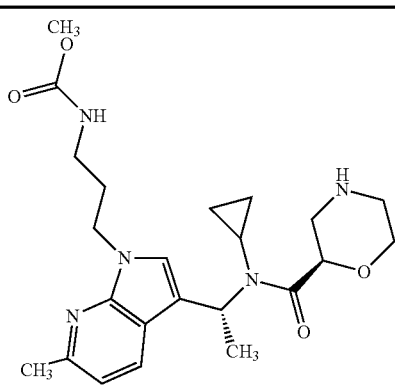 | 414 | APCI | [M + H]+ |
| Example 50 | 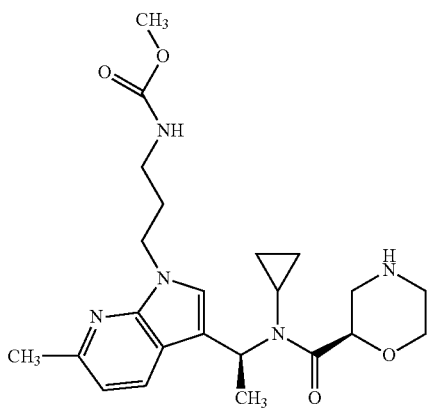 | 414 | APCI | [M + H]+ |
| Example 51 | 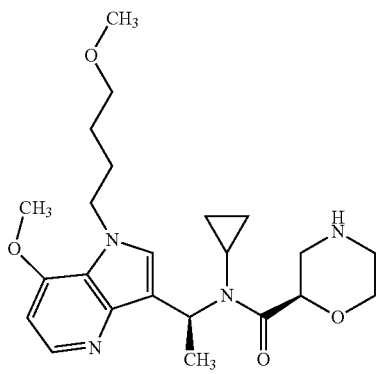 [SMILES: COCCCCn1cc([C@H](C)N(C(=O)[C@H]2CNCCO2)C2CC2)c2nccc(OC)c21] | 431 | APCI | [M + H]+ |
TABLE 8
| | | | | |
|---|---|---|---|---|
| Example 52 | 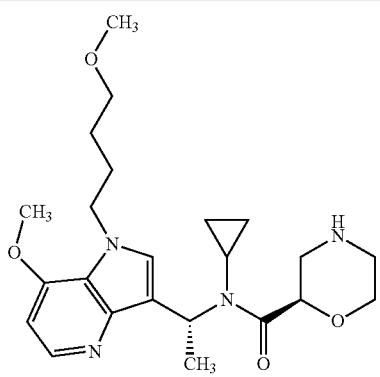 | 431 | APCI | [M + H]+ |

TABLE 8-continued
| Example 53 | 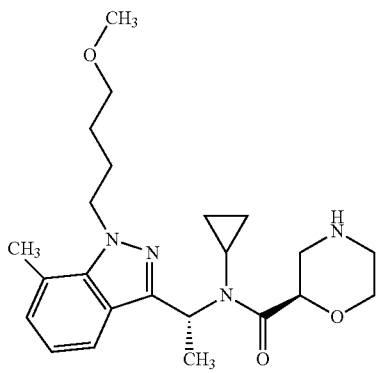 [SMILES: COCCCCn1nc([C@@H](C)N(C(=O)[C@H]2CNCCO2)C2CC2)c2cccc(C)c21] | 415 | APCI [M + H]+ |
| Example 54 | 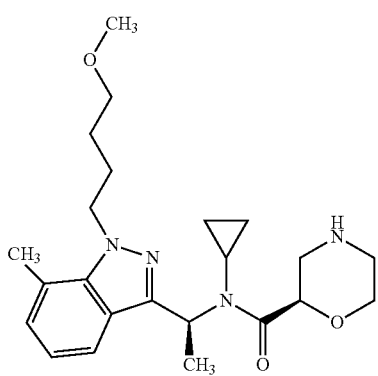 [SMILES: COCCCCn1nc([C@H](C)N(C(=O)[C@H]2CNCCO2)C2CC2)c2cccc(C)c21] | 415 | APCI [M + H]+ |
| Example 55 | 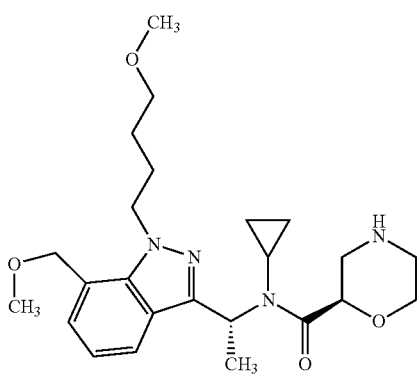 [SMILES: COCCCCn1nc([C@@H](C)N(C(=O)[C@H]2CNCCO2)C2CC2)c2cccc(COC)c21] | 445 | APCI [M + H]+ |
| Example 56 | 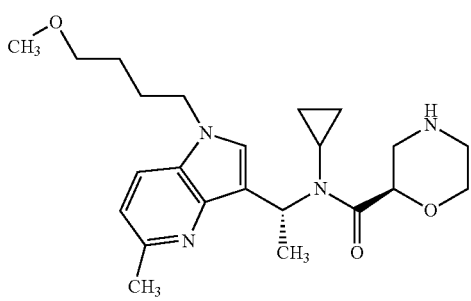 [SMILES: COCCCCn1cc([C@@H](C)N(C(=O)[C@H]2CNCCO2)C2CC2)c2nc(C)ccc21] | 415 | APCI [M + H]+ |

TABLE 8-continued
| Example 57 | 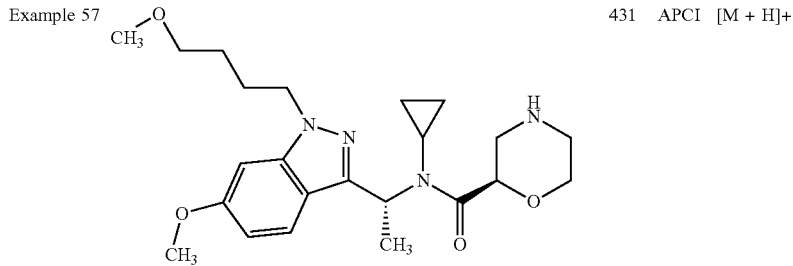 | 431 | APCI [M + H]+ |
TABLE 9
| Example 58 | 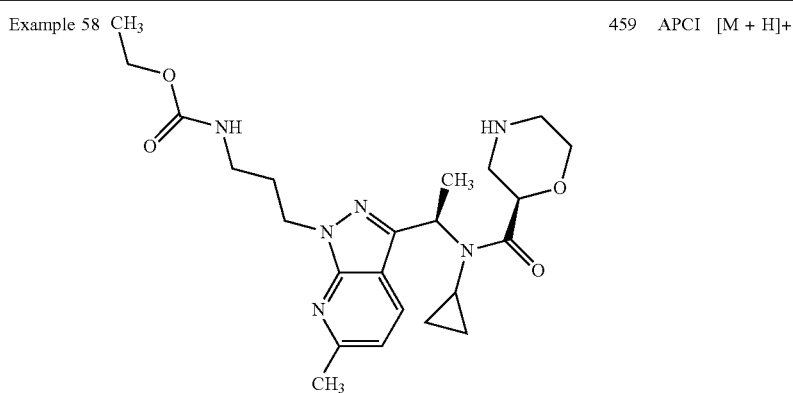 | 459 | APCI [M + H]+ |
| Example 59 | 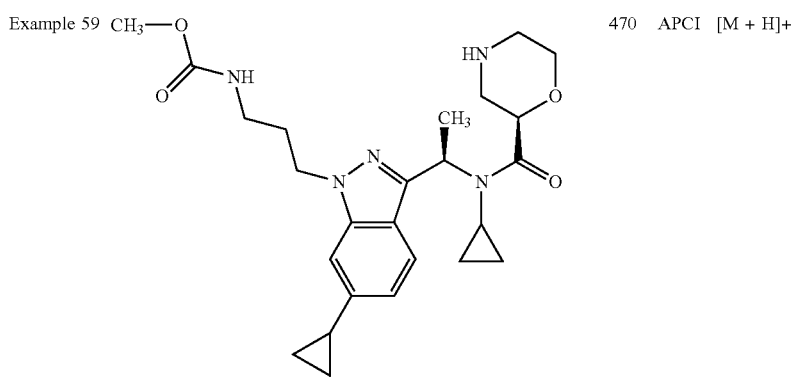 | 470 | APCI [M + H]+ |
| Example 60 | 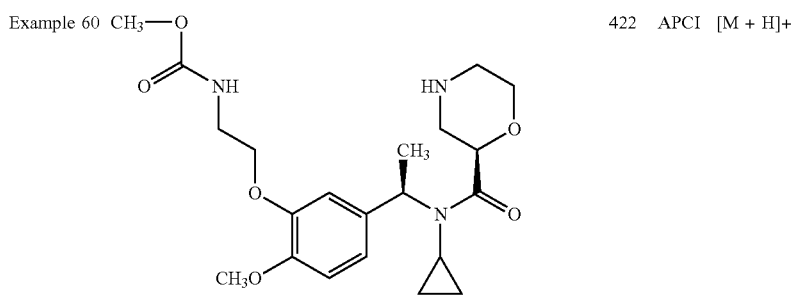 | 422 | APCI [M + H]+ |

TABLE 9-continued
| Example 61 | 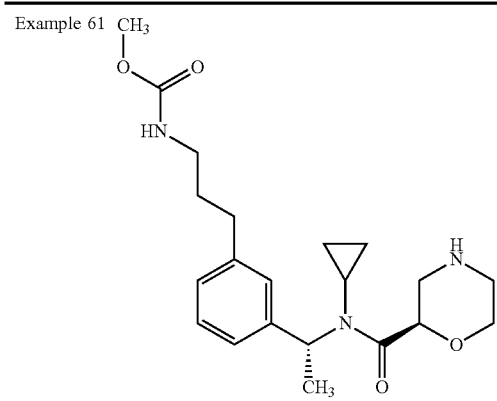 | 390 | APCI [M + H]+ |
| Example 62 | 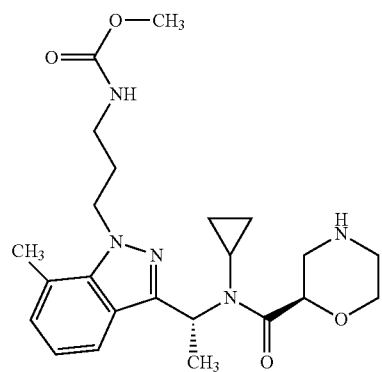 [SMILES: COC(=O)NCCCn1nc([C@@H](C)N(C(=O)[C@H]2CNCCO2)C2CC2)c2cccc(C)c21] | 444 | APCI [M + H]+ |
| Example 63 | 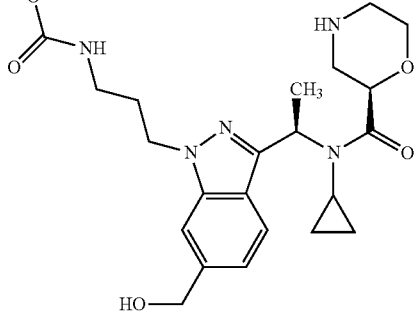 | 460 | APCI [M + H]+ |
TABLE 10
| Example 64 | 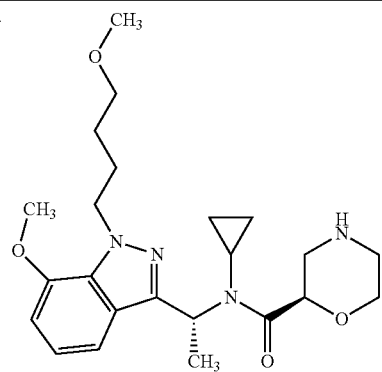 | 431 | APCI [M + H]+ |

TABLE 10-continued
| Example 65 | 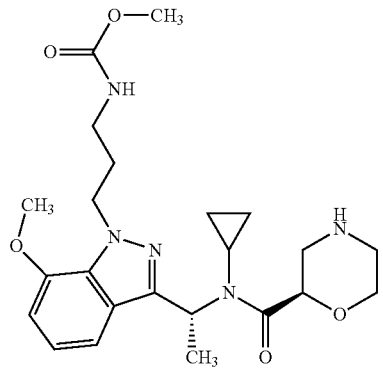 [SMILES: COC(=O)NCCCn1nc([C@@H](C)N(C(=O)[C@H]2CNCCO2)C2CC2)c2cccc(OC)c21] | 460 | APCI [M + H]+ |
| Example 66 | 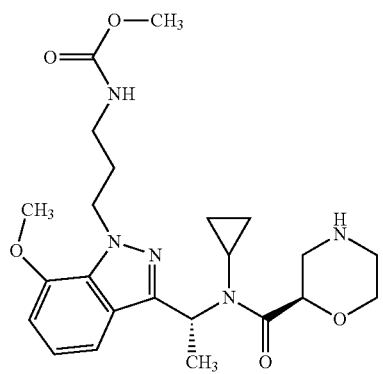 [SMILES: COC(=O)NCCCn1nc([C@@H](C)N(C(=O)[C@H]2CNCCO2)C2CC2)c2cccc(OC)c21] | 460 | APCI [M + H]+ |
| Example 67 | 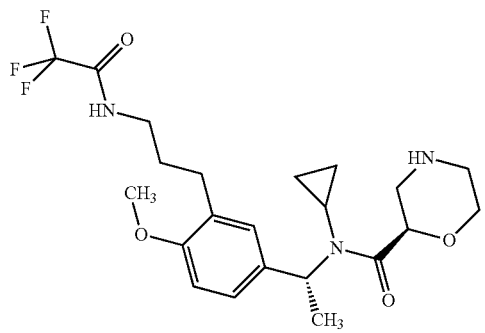 [SMILES: COc1ccc([C@@H](C)N(C(=O)[C@H]2CNCCO2)C2CC2)cc1CCCNC(=O)C(F)(F)F] | 458 | APCI [M + H]+ |
| Example 68 | 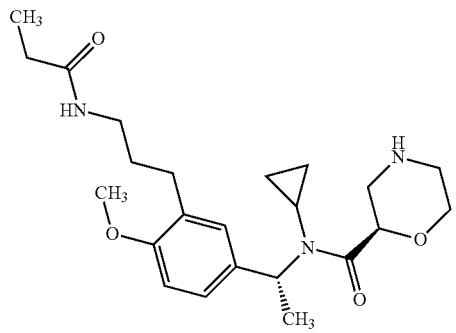 [SMILES: CCC(=O)NCCCc1cc([C@@H](C)N(C(=O)[C@H]2CNCCO2)C2CC2)ccc1OC] | 418 | APCI [M + H]+ |

TABLE 10-continued
| Example 69 | 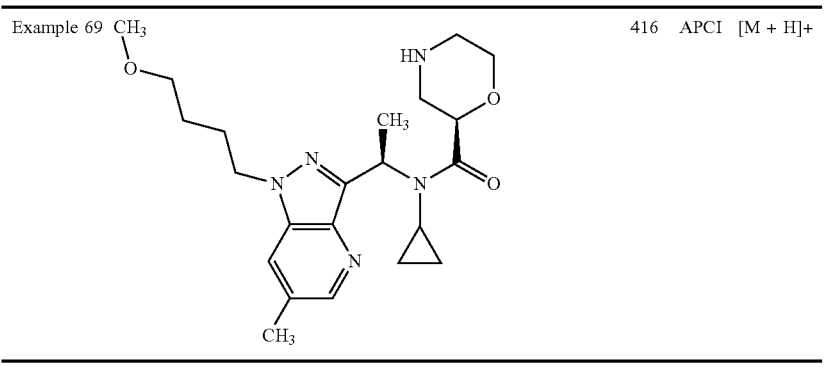 | 416 | APCI [M + H]+ |
TABLE 11
| Example 70 | 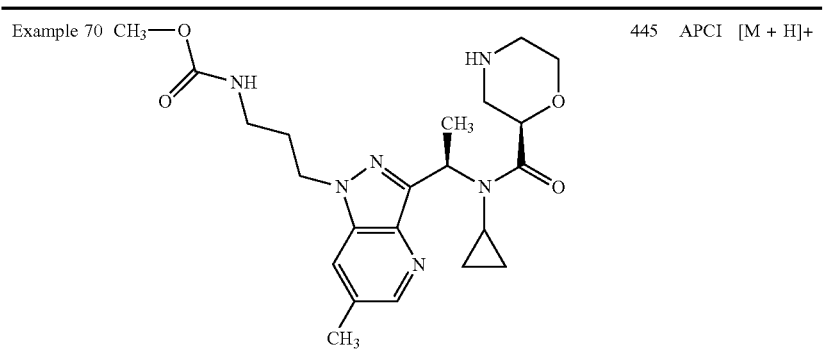 | 445 | APCI [M + H]+ |
| Example 71 | 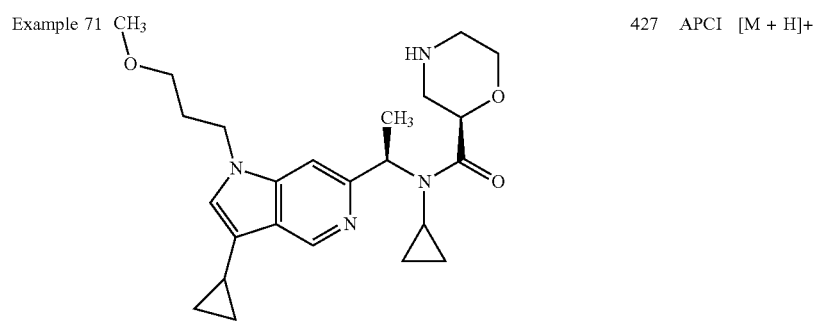 | 427 | APCI [M + H]+ |
| Example 72 | 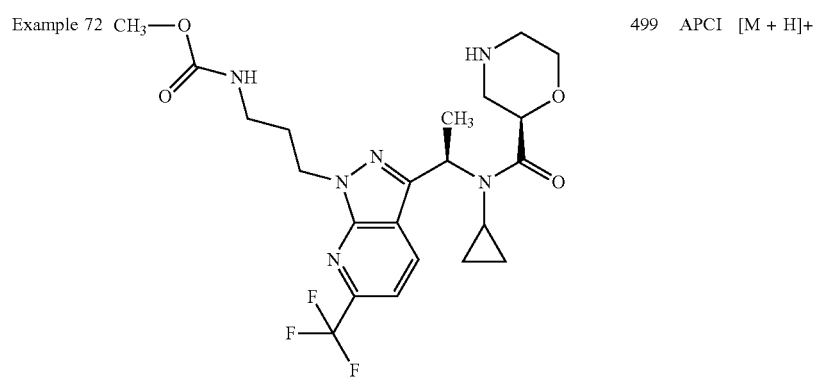 | 499 | APCI [M + H]+ |

TABLE 11-continued
| Example 73 | 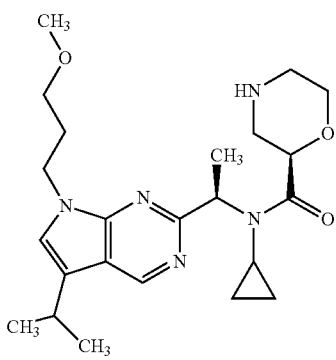 [SMILES: COCCCn1cc(C(C)C)c2cnc([C@@H](C)N(C(=O)[C@H]3CNCCO3)C3CC3)nc21] | 430 | APCI [M + H]+ |
| Example 74 | 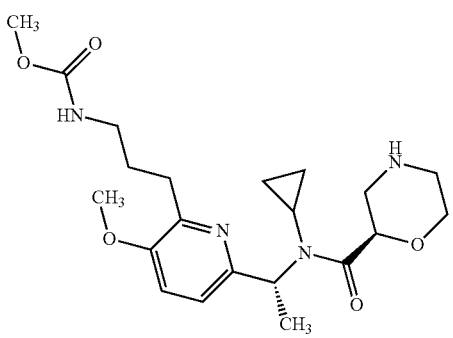 [SMILES: COC(=O)NCCCc1nc([C@@H](C)N(C(=O)[C@H]2CNCCO2)C2CC2)ccc1OC] | 421 | APCI [M + H]+ |
| Example 75 | 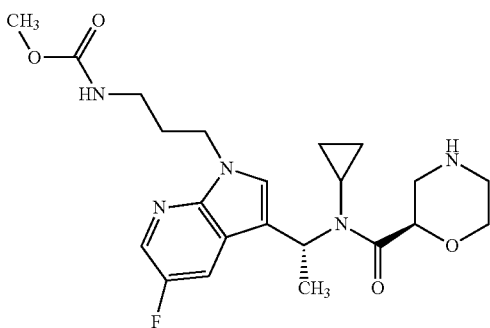 [SMILES: COC(=O)NCCCn1cc([C@@H](C)N(C(=O)[C@H]2CNCCO2)C2CC2)c2cc(F)cnc21] | 448 | APCI [M + H]+ |
TABLE 12
| Example 76 | 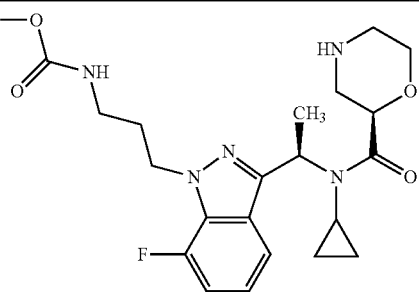 | 448 | APCI [M + H]+ |

TABLE 12-continued
| | | | |
|---|---|---|---|
| Example 77 | 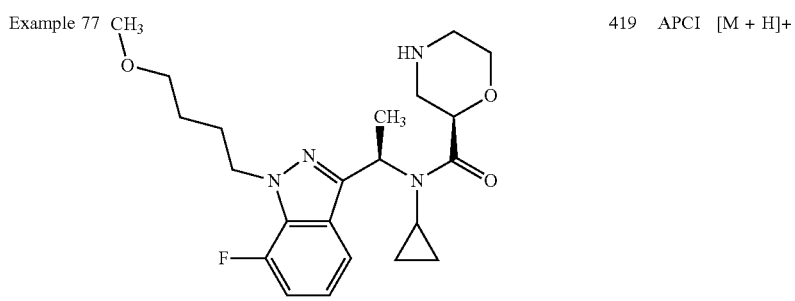 | 419 | APCI [M + H]+ |
| Example 78 | 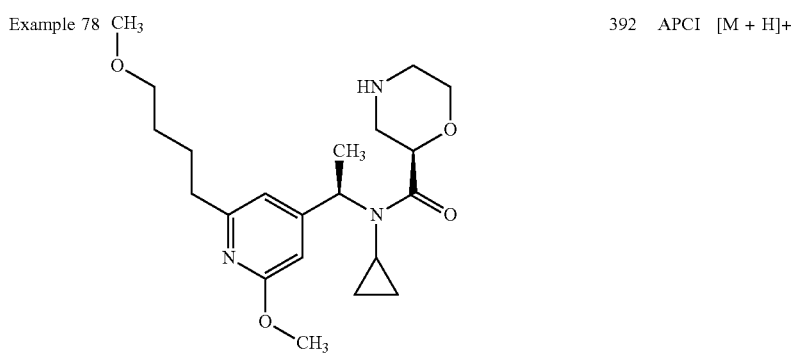 | 392 | APCI [M + H]+ |
| Example 79 |  | 429 | APCI [M + H]+ |
| Example 80 | 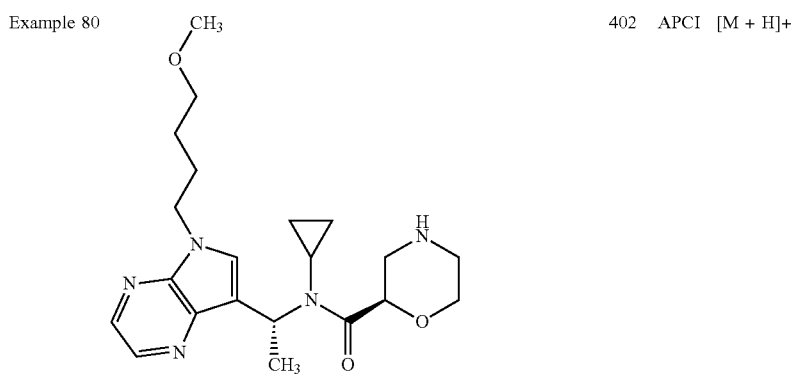 | 402 | APCI [M + H]+ |

TABLE 12-continued
| Example 81 | 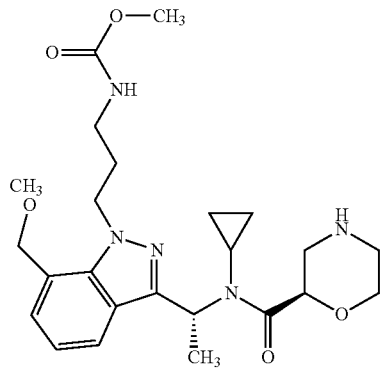 | 474 | APCI [M + H]+ |
TABLE 13
| Example 82 | 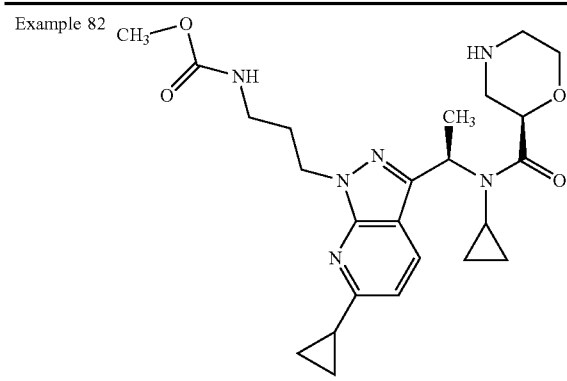 | 471 | APCI [M + H]+ |
| Example 83 | 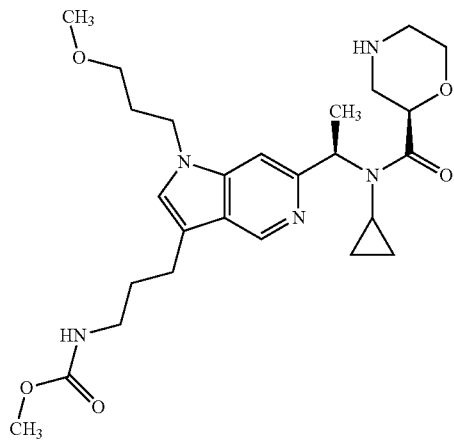 [SMILES: COCCCn1cc(CCCNC(=O)OC)c2cnc([C@@H](C)N(C(=O)[C@H]3CNCCO3)C3CC3)cc21] | 502 | APCI [M + H]+ |

TABLE 13-continued
| Example 84 | 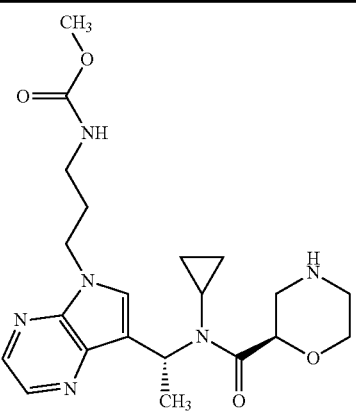 | 431 | APCI [M + H]+ |
| Example 85 | 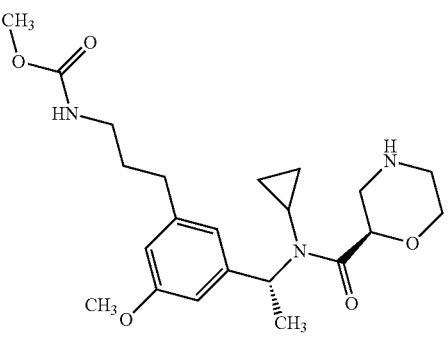 | 420 | APCI [M + H]+ |
| Example 86 | 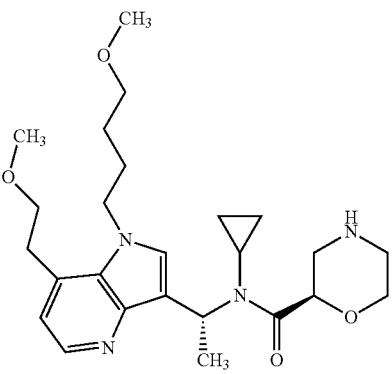 [SMILES: COCCCCn1cc([C@@H](C)N(C(=O)[C@H]2CNCCO2)C2CC2)c2nccc(CCOC)c21] | 459 | APCI [M + H]+ |
TABLE 14
| Example 87 | 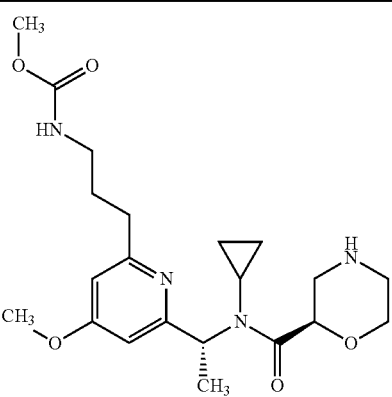 | 421 | APCI [M + H]+ |

TABLE 14-continued
| Example 88 | 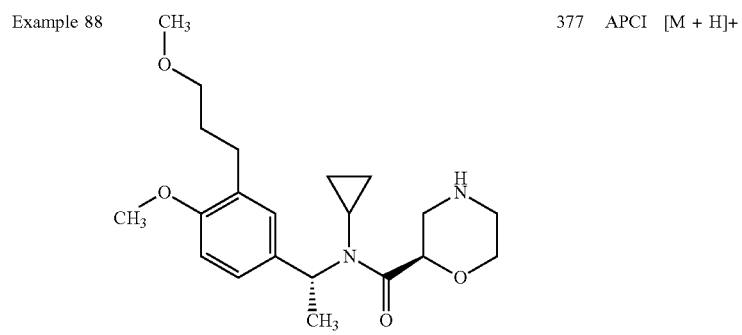 | 377 | APCI [M + H]+ |
| Example 89 | 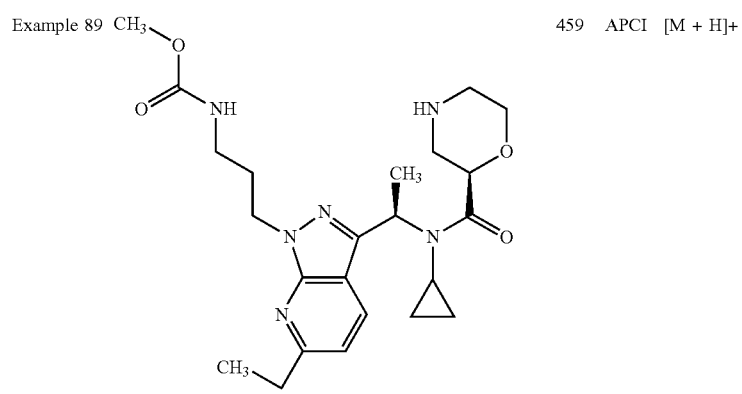 | 459 | APCI [M + H]+ |
| Example 90 | 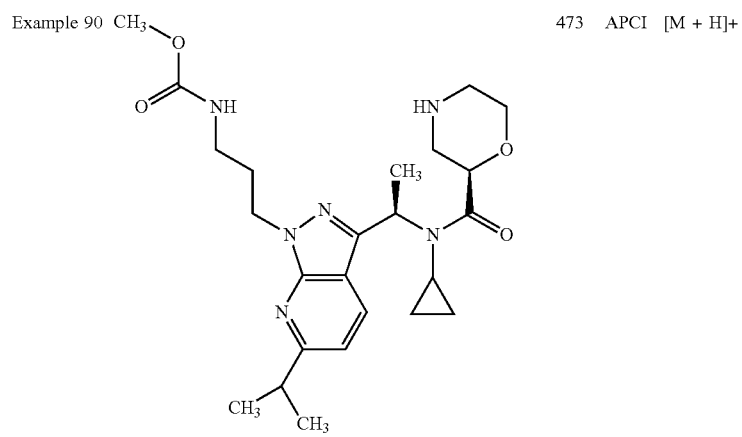 | 473 | APCI [M + H]+ |
| Example 91 | 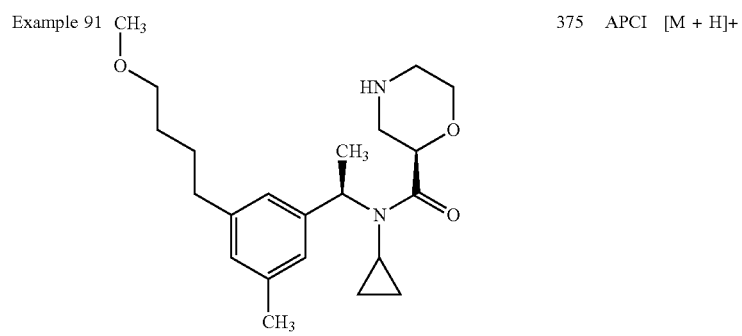 | 375 | APCI [M + H]+ |

TABLE 15
| Example 92 | 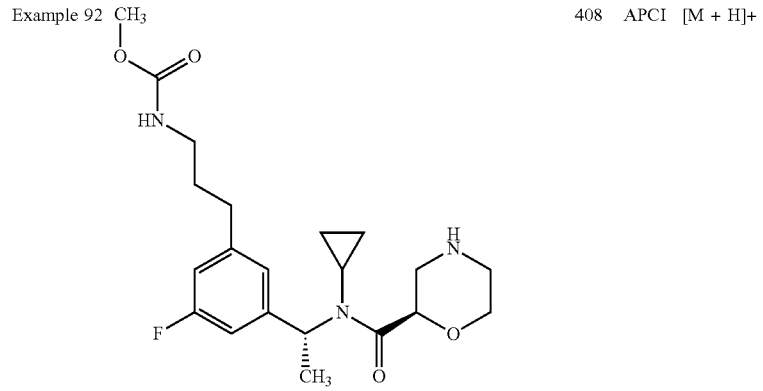 | 408 | APCI [M + H]+ |
| Example 93 | 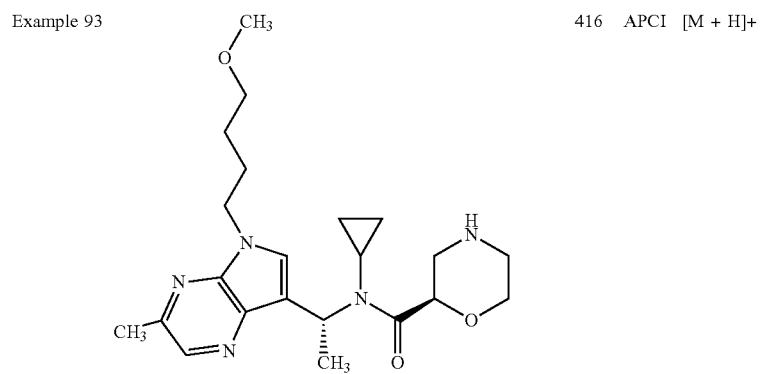 | 416 | APCI [M + H]+ |
| Example 94 | 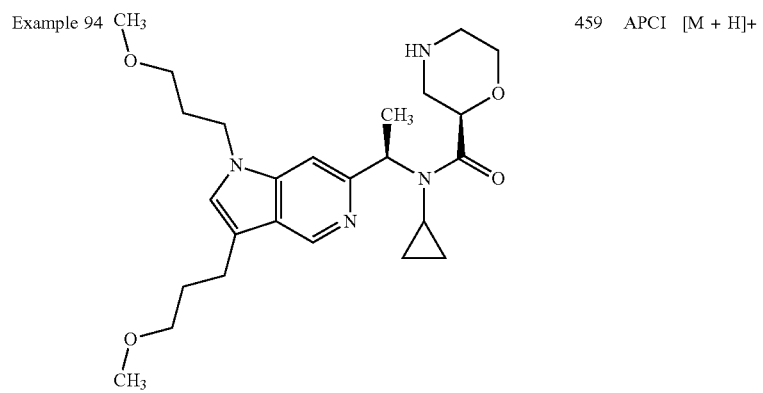 | 459 | APCI [M + H]+ |
| Example 95 | 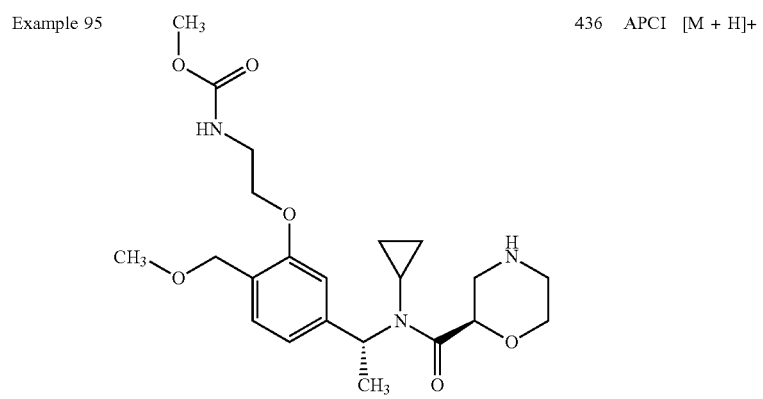 | 436 | APCI [M + H]+ |

TABLE 15-continued
| Example 96 | 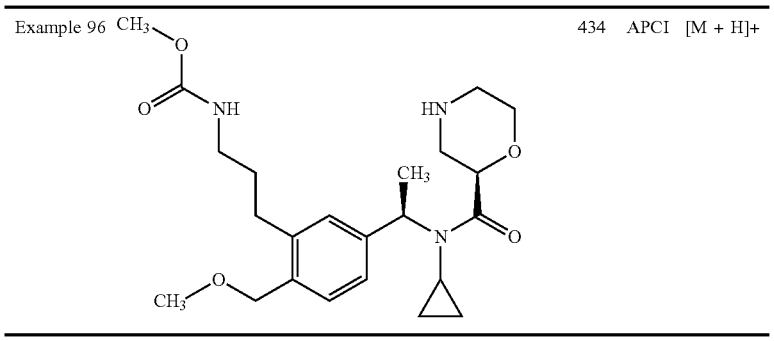 | 434 | APCI [M + H]+ |
TABLE 16
| Example 97 | 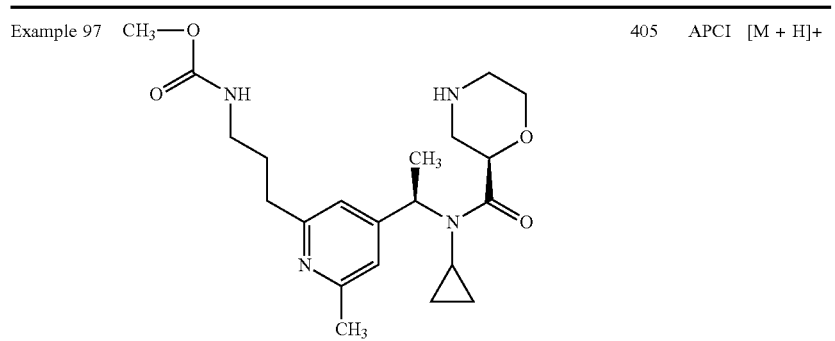 | 405 | APCI [M + H]+ |
| Example 98 | 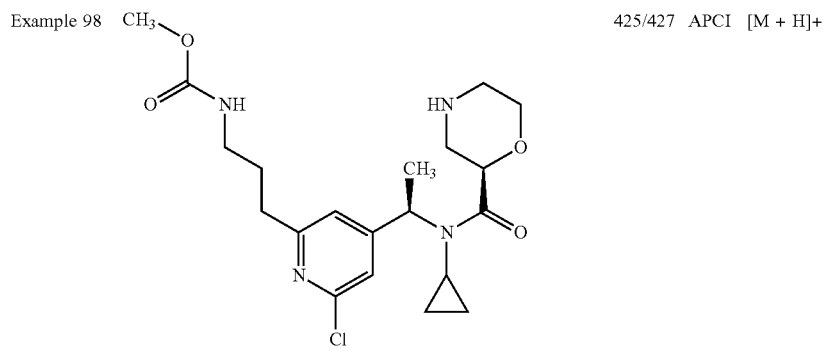 | 425/427 | APCI [M + H]+ |
| Example 99 | 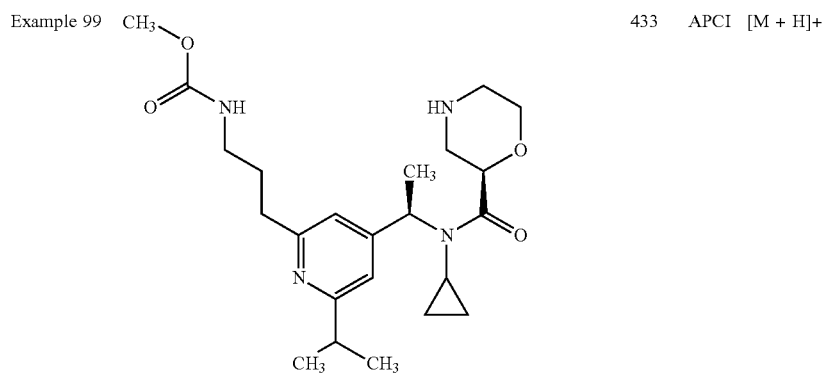 | 433 | APCI [M + H]+ |

TABLE 16-continued
| Example 100 | 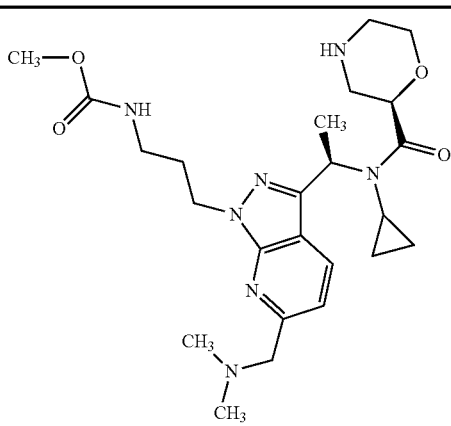 | 488 | APCI [M + H]+ |
| Example 101 | 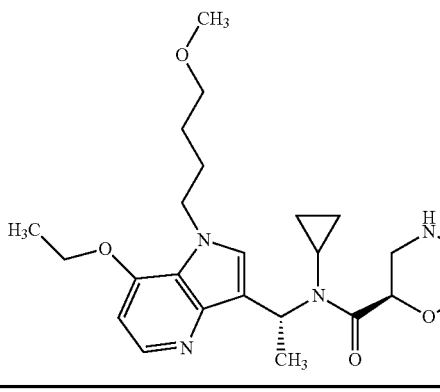 | 445 | APCI [M + H]+ |
TABLE 17
| Example 102 | 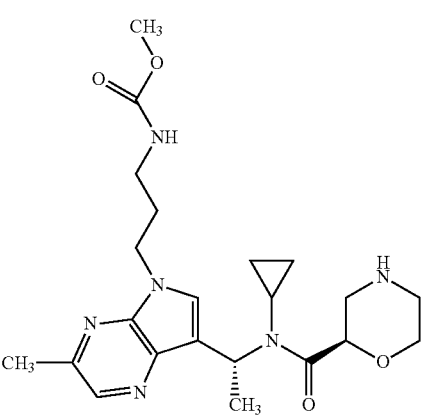 [SMILES: COC(=O)NCCCn1cc([C@@H](C)N(C(=O)[C@H]2CNCCO2)C2CC2)c2ncc(C)nc21] | 445 | APCI [M + H]+ |
| Example 103 | 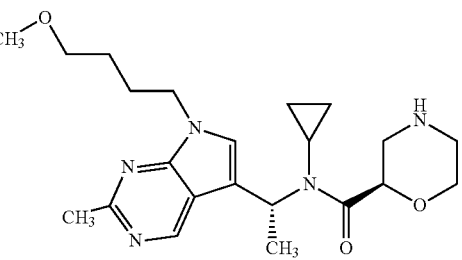 | 416 | APCI [M + H]+ |

US 9,556,159 B2
TABLE 17-continued
| | | | |
|---|---|---|---|
| Example 104 | 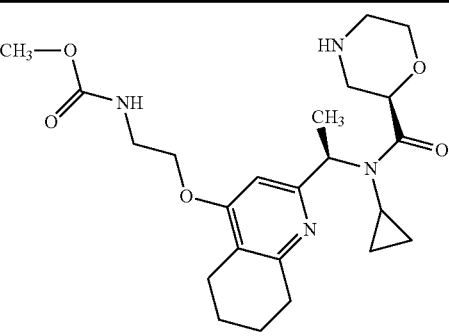 | 447 | APCI [M + H]+ |
| Example 105 | 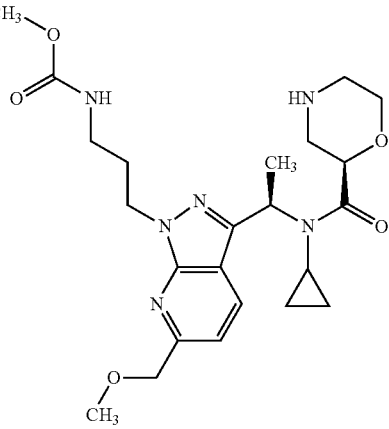 | 475 | APCI [M + H]+ |
| Example 106 | 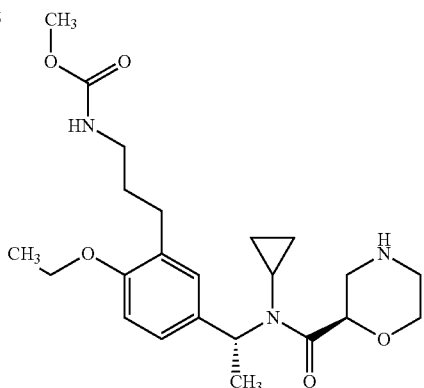 | 434 | APCI [M + H]+ |
TABLE 18
| | | | |
|---|---|---|---|
| Example 107 | 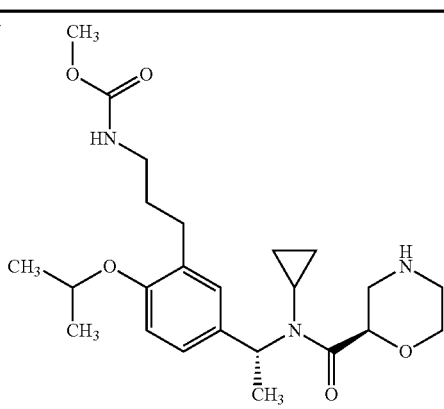 | 448 | APCI [M + H]+ |

TABLE 18-continued
| Example 108 | 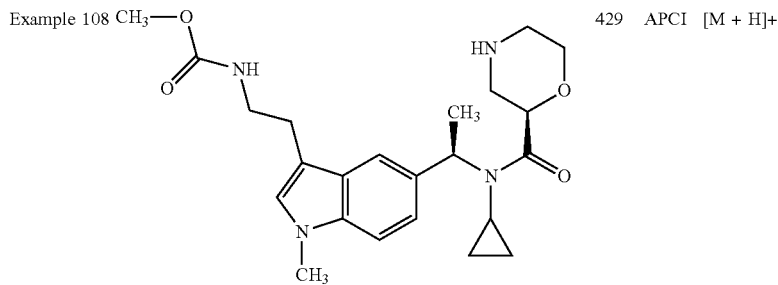 | 429 | APCI [M + H]+ |
| Example 109 | 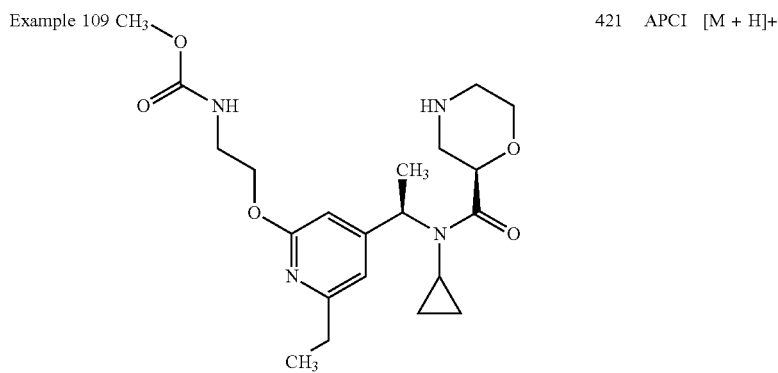 | 421 | APCI [M + H]+ |
| Example 110 | 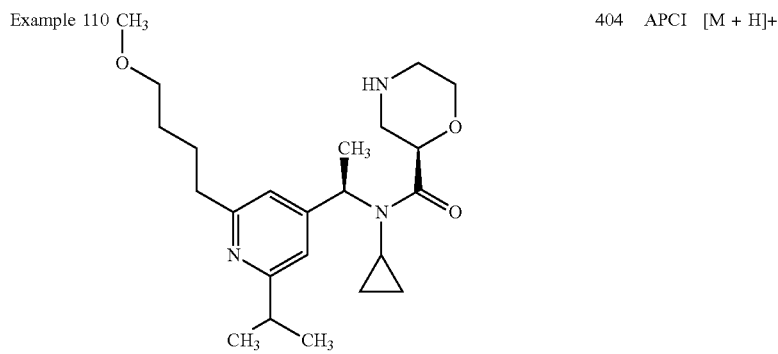 | 404 | APCI [M + H]+ |
| Example 111 | 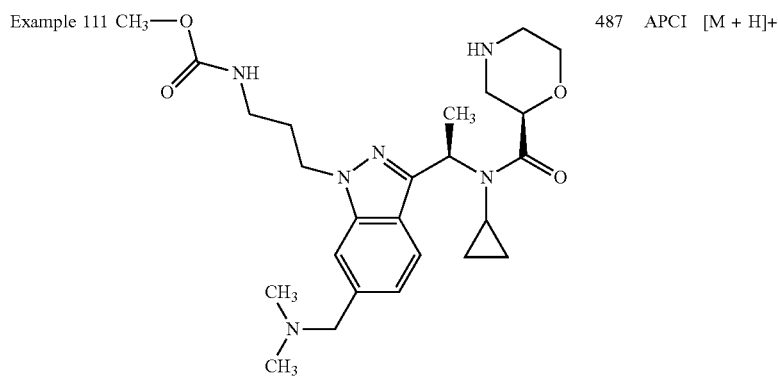 | 487 | APCI [M + H]+ |

TABLE 19
| Example | Structure | MS | Method |
|---|---|---|---|
| Example 112 | 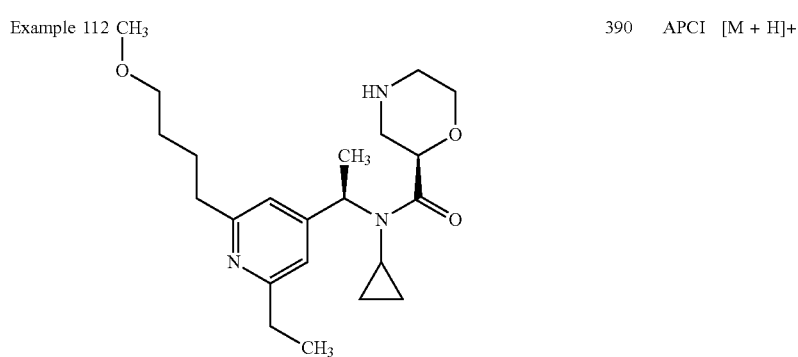 | 390 | APCI [M + H]+ |
| Example 113 | 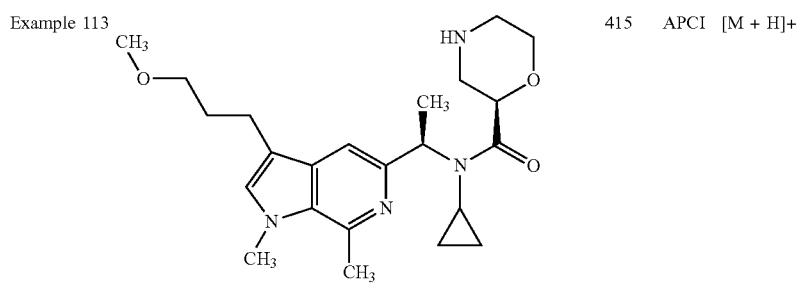 | 415 | APCI [M + H]+ |
| Example 114 | 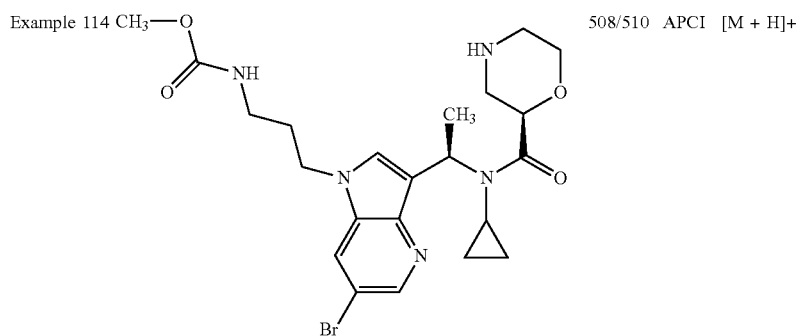 | 508/510 | APCI [M + H]+ |
| Example 115 | 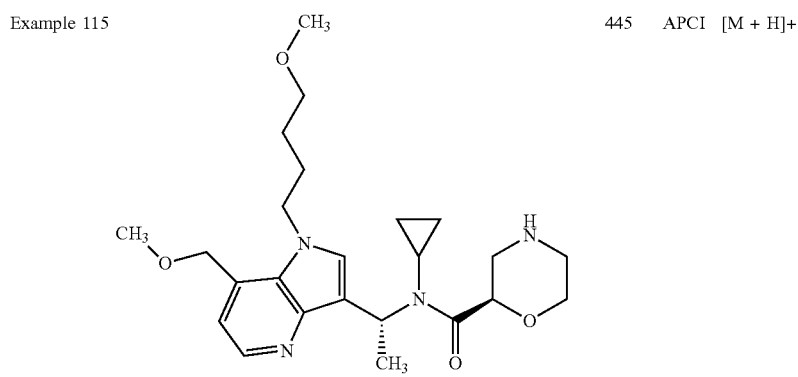 | 445 | APCI [M + H]+ |

TABLE 19-continued
| Example 116 | 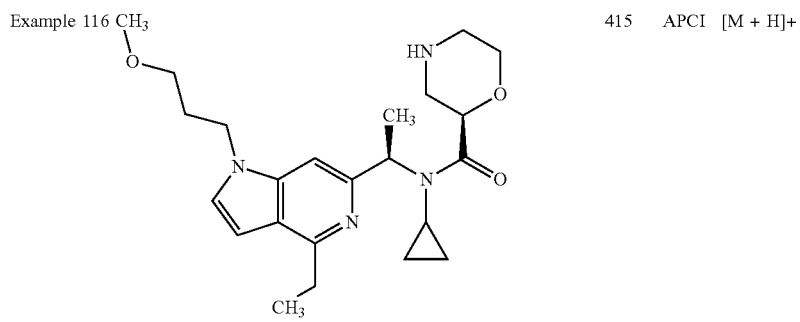 | 415 | APCI [M + H]+ |
| Example 117 | 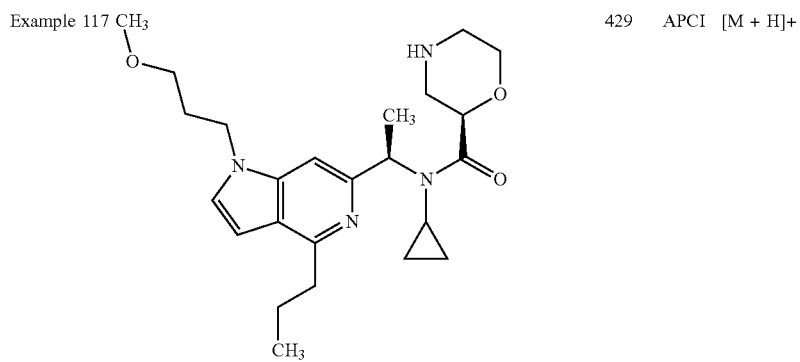 | 429 | APCI [M + H]+ |
TABLE 20
| Example 118 | 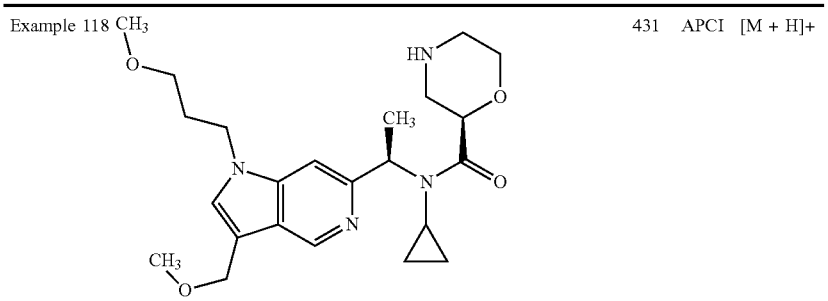 | 431 | APCI [M + H]+ |
| Example 119 | 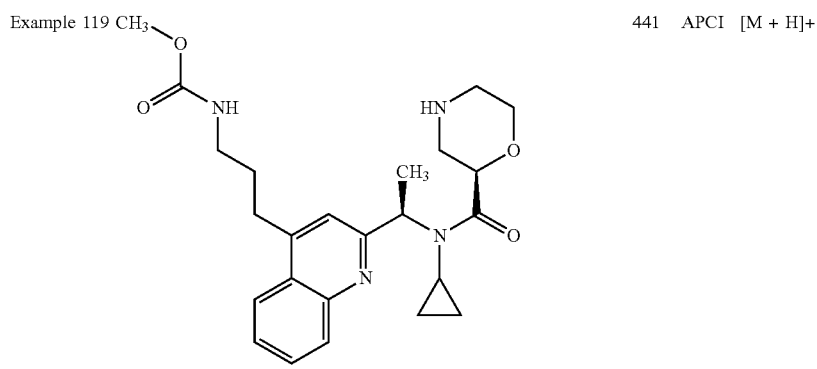 | 441 | APCI [M + H]+ |

TABLE 20-continued
| Example 120 | 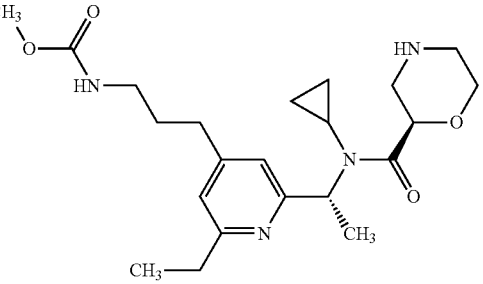 | 419 | APCI [M + H]+ |
| Example 121 | 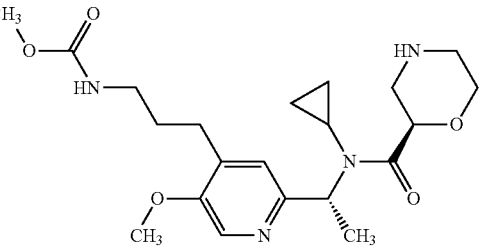 | 421 | APCI [M + H]+ |
| Example 122 | 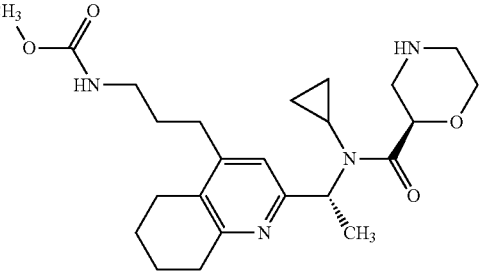 | 445 | APCI [M + H]+ |
| Example 123 | 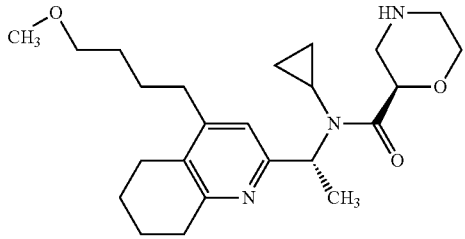 [SMILES: COCCCCc1cc([C@@H](C)N(C(=O)[C@H]2CNCCO2)C2CC2)nc2c1CCCC2] | 416 | APCI [M + H]+ |
| Example 124 | 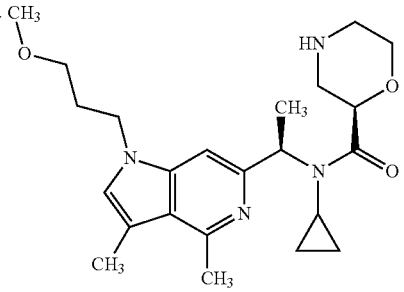 | 429 | APCI [M + H]+ |

TABLE 21
| | | | |
|---|---|---|---|
| Example 125 | 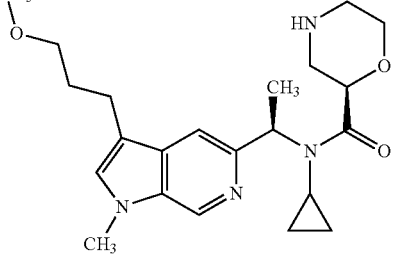 | 415 | APCI [M + H]+ |
| Example 126 | 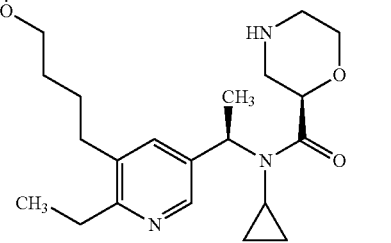 | 390 | APCI [M + H]+ |
| Example 127 | 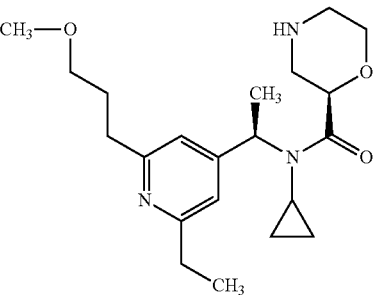 [SMILES: CCc1cc([C@@H](C)N(C(=O)[C@H]2CNCCO2)C2CC2)cc(CCCOC)n1] | 376 | APCI [M + H]+ |
| Example 128 | 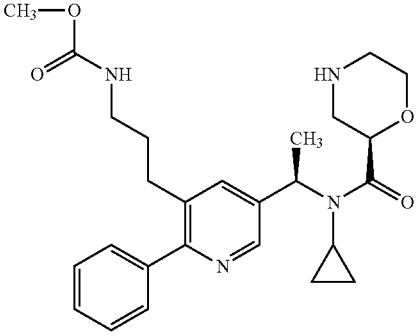 [SMILES: COC(=O)NCCCc1cc([C@@H](C)N(C(=O)[C@H]2CNCCO2)C2CC2)cnc1-c1ccccc1] | 467 | APCI [M + H]+ |
| Example 129 | 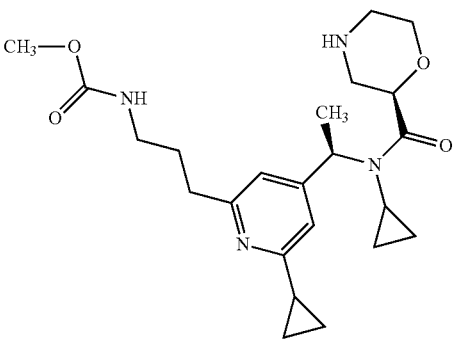 [SMILES: COC(=O)NCCCc1cc([C@@H](C)N(C(=O)[C@H]2CNCCO2)C2CC2)cc(C2CC2)n1] | 431 | APCI [M + H]+ |

TABLE 21-continued
| | | |
|---|---|---|
| Example 130 | 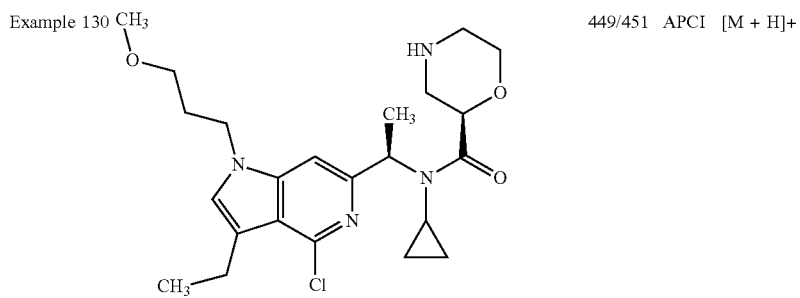 | 449/451 APCI [M + H]+ |
TABLE 22
| | | |
|---|---|---|
| Example 131 | 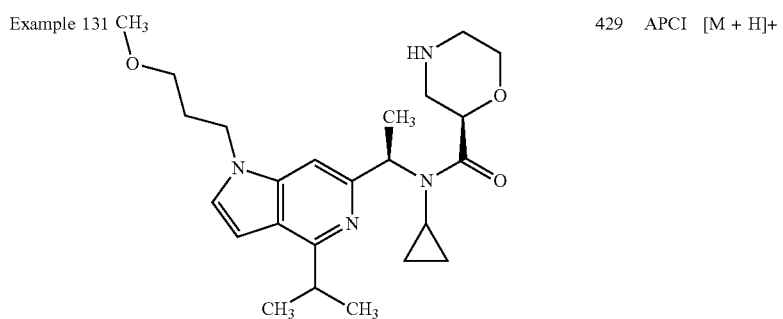 | 429 APCI [M + H]+ |
| Example 132 | 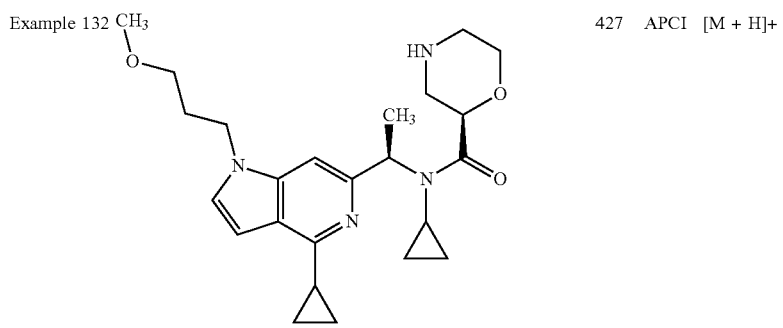 | 427 APCI [M + H]+ |
| Example 133 | 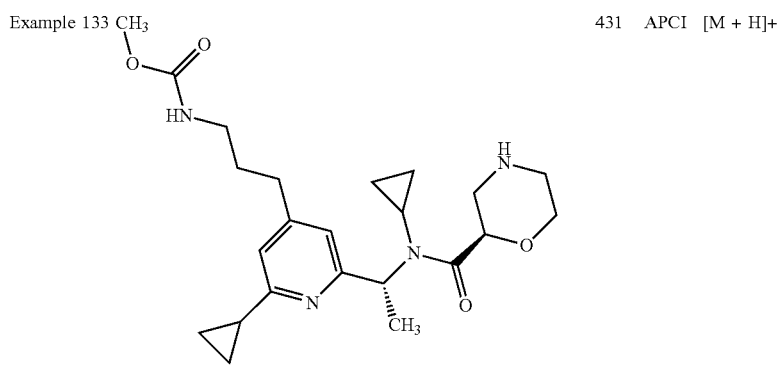 | 431 APCI [M + H]+ |

TABLE 22-continued
| Example 134 | 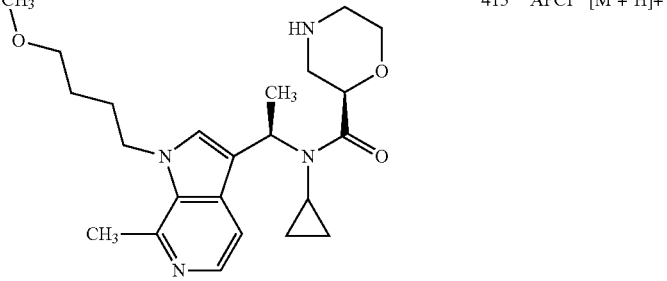 | 415 | APCI [M + H]+ |
| Example 135 | 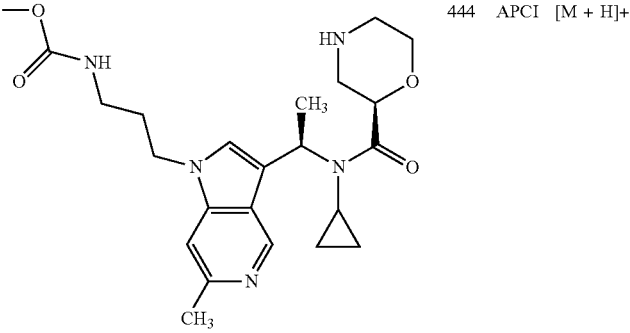 | 444 | APCI [M + H]+ |
| Example 136 | 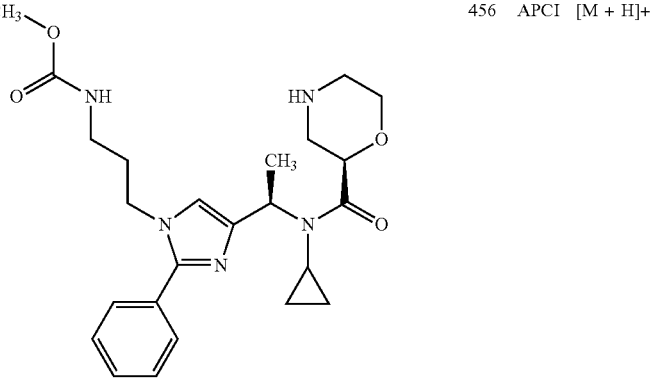 | 456 | APCI [M + H]+ |
TABLE 23
| Example 137 | 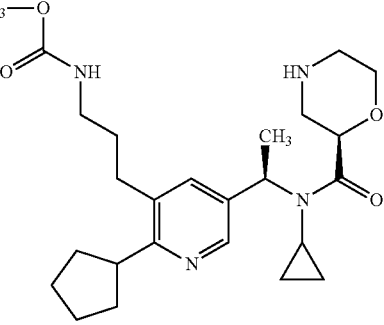 | 459 | APCI [M + H]+ |

TABLE 23-continued
| Example 138 | 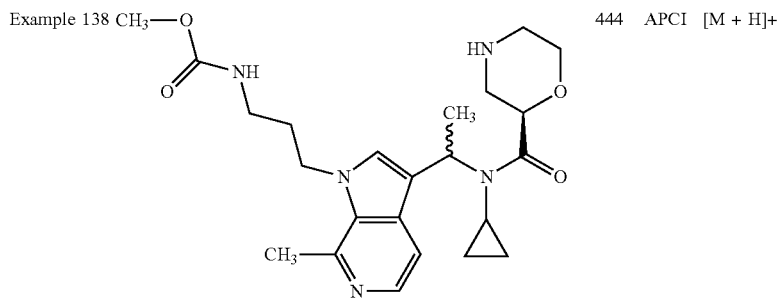 | 444 | APCI [M + H]+ |
| Example 139 | 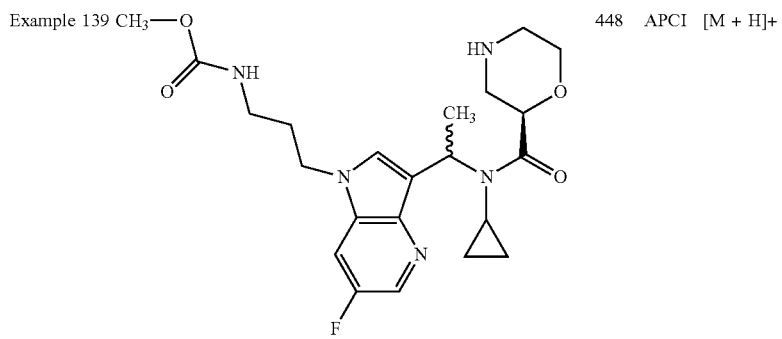 | 448 | APCI [M + H]+ |
| Example 140 | 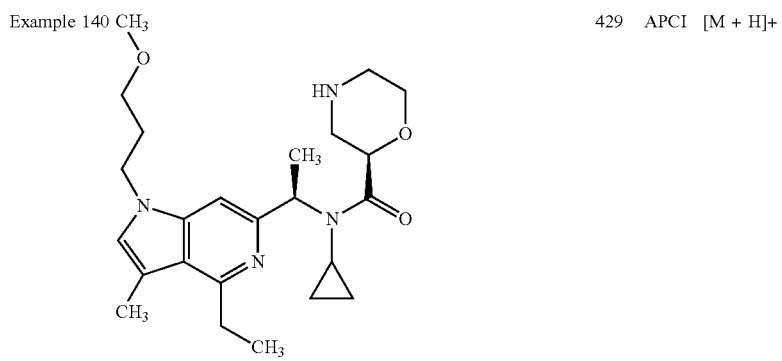 | 429 | APCI [M + H]+ |
| Example 141 | 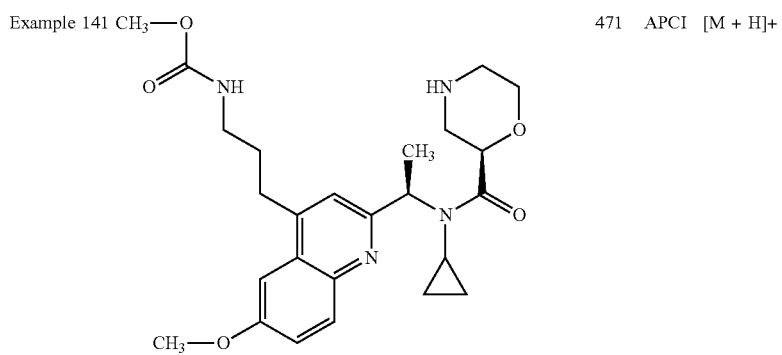 | 471 | APCI [M + H]+ |

TABLE 23-continued
| Example 142 | 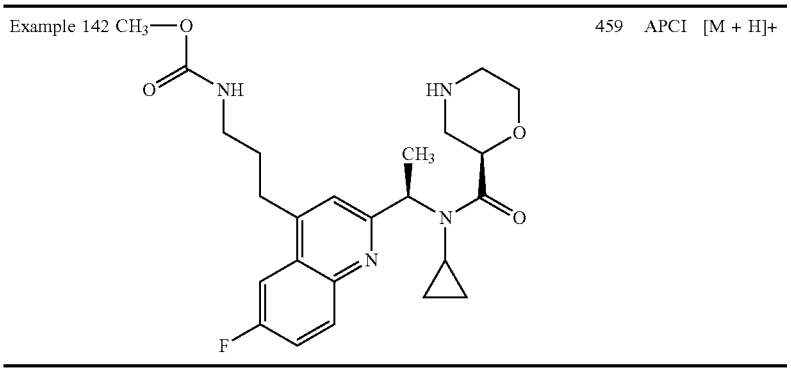 | 459 | APCI [M + H]+ |
TABLE 24
| Example 143 | 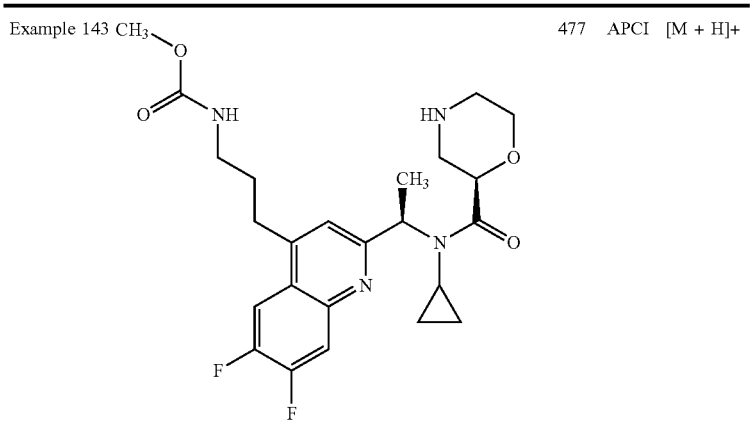 | 477 | APCI [M + H]+ |
| Example 144 | 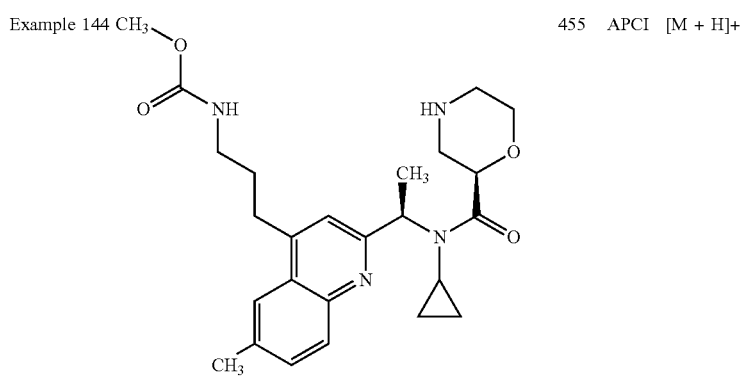 | 455 | APCI [M + H]+ |
| Example 145 | 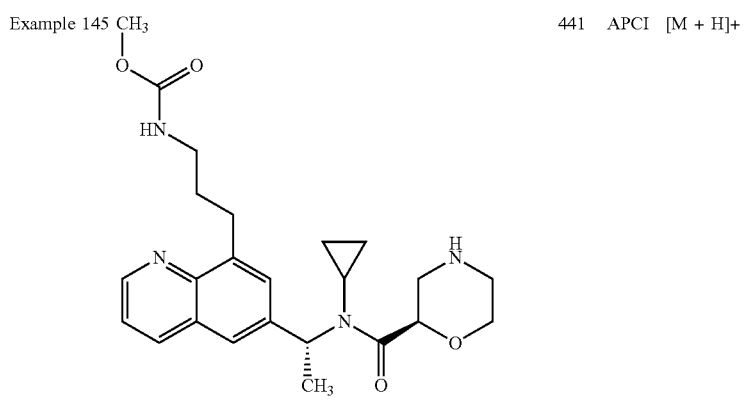 | 441 | APCI [M + H]+ |

TABLE 24-continued
| Example 146 | 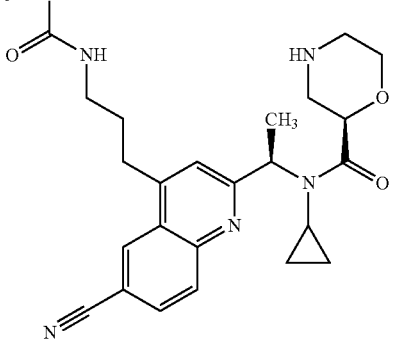 | 466 | APCI [M + H]+ |
| Example 147 | 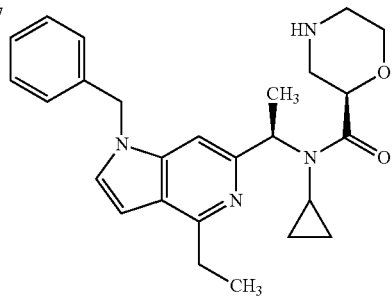 | 433 | APCI [M + H]+ |
TABLE 25
| Example 148 | 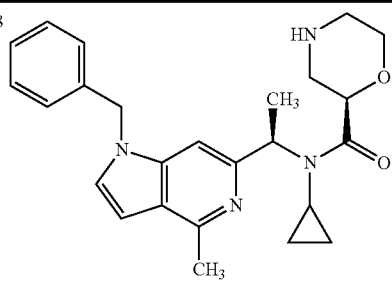 | 419 | APCI [M + H]+ |
| Example 149 | 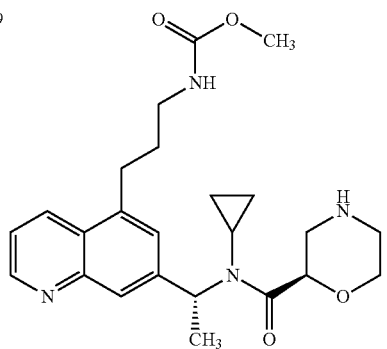 | 441 | APCI [M + H]+ |

TABLE 25-continued
| Example 150 | 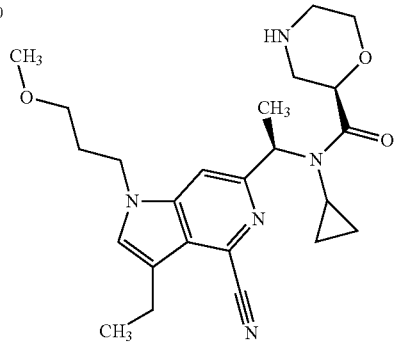 | 440 | APCI [M + H]+ |
| Example 151 | 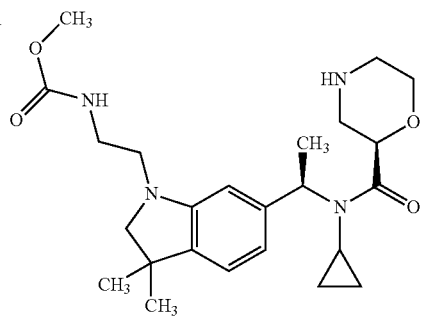 | 445 | APCI [M + H]+ |
| Example 152 | 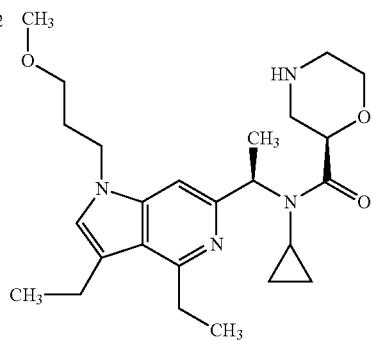 | 443 | APCI [M + H]+ |
| Example 153 | 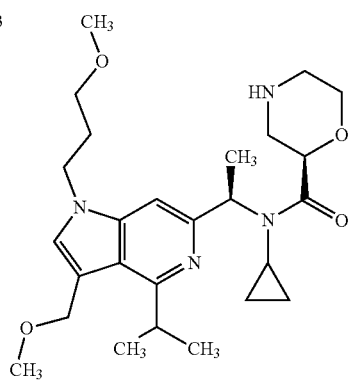 | 473 | APCI [M + H]+ |

TABLE 26
| Example 154 | 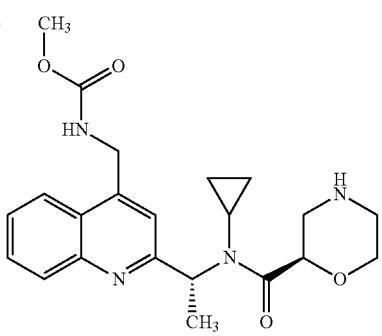 [SMILES: COC(=O)NCc1cc([C@@H](C)N(C(=O)[C@H]2CNCCO2)C2CC2)nc2ccccc12] | 413 | APCI [M + H]+ |
| Example 155 | 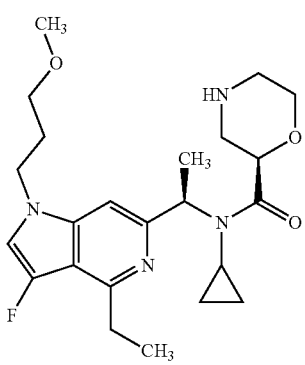 [SMILES: CCc1nc([C@@H](C)N(C(=O)[C@H]2CNCCO2)C2CC2)cc2c1c(F)cn2CCCOC] | 433 | APCI [M + H]+ |
| Example 156 | 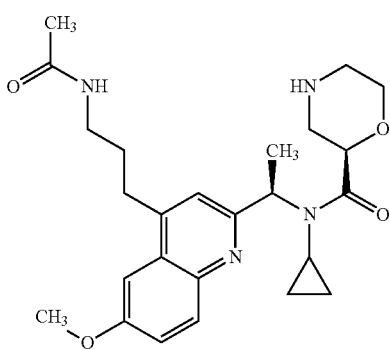 [SMILES: COc1ccc2nc([C@@H](C)N(C(=O)[C@H]3CNCCO3)C3CC3)cc(CCCNC(C)=O)c2c1] | 455 | APCI [M + H]+ |
| Example 157 | 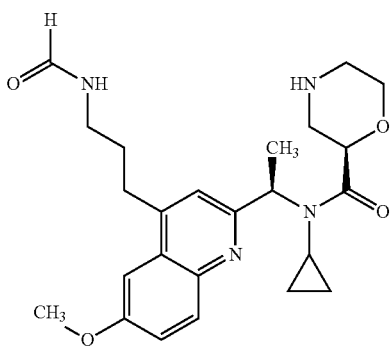 [SMILES: COc1ccc2nc([C@@H](C)N(C(=O)[C@H]3CNCCO3)C3CC3)cc(CCCNC=O)c2c1] | 441 | APCI [M + H]+ |

TABLE 26-continued
| Example 158 | 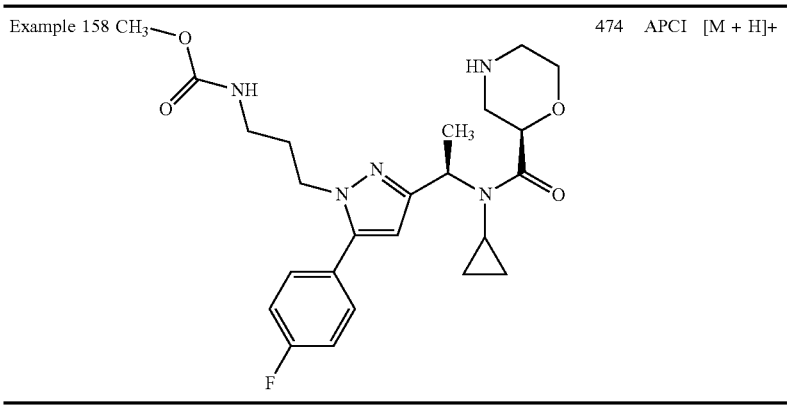 | 474 | APCI [M + H]+ |
TABLE 27
| Example 159 | 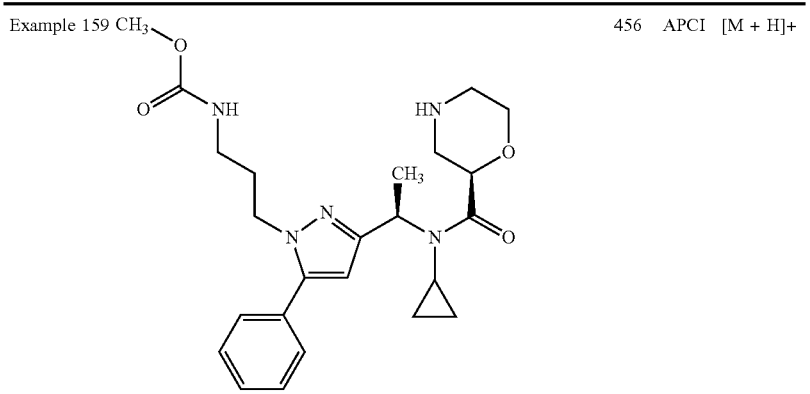 | 456 | APCI [M + H]+ |
| Example 160 | 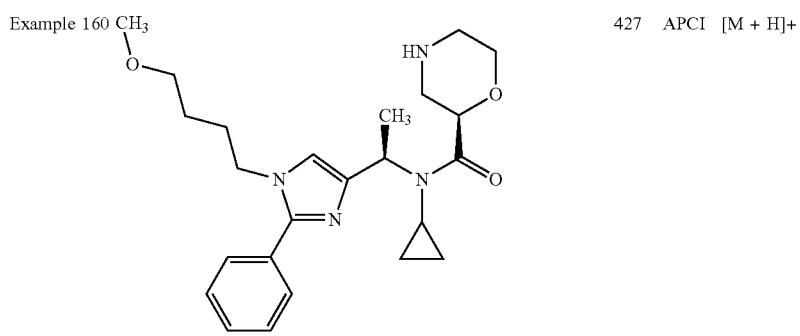 | 427 | APCI [M + H]+ |
| Example 161 | 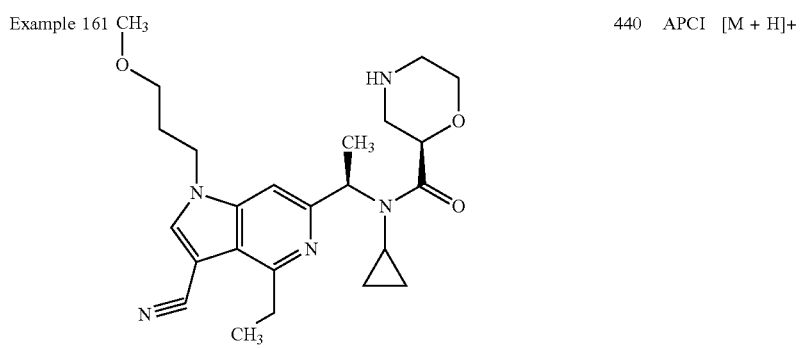 | 440 | APCI [M + H]+ |

TABLE 27-continued
| Example 162 | 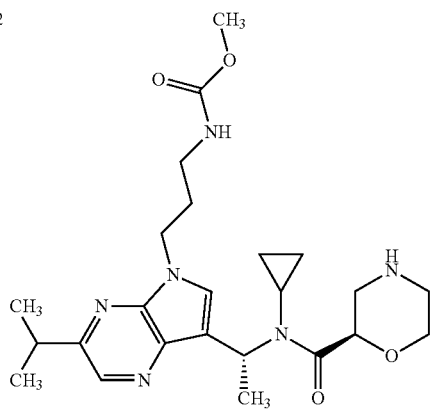 | 473 | APCI [M + H]+ |
| Example 163 | 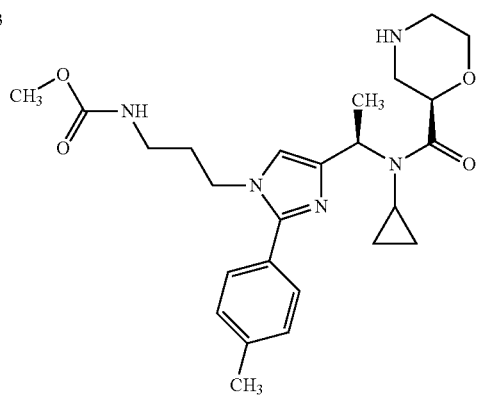 | 470 | APCI [M + H]+ |
TABLE 28
| Example 164 | 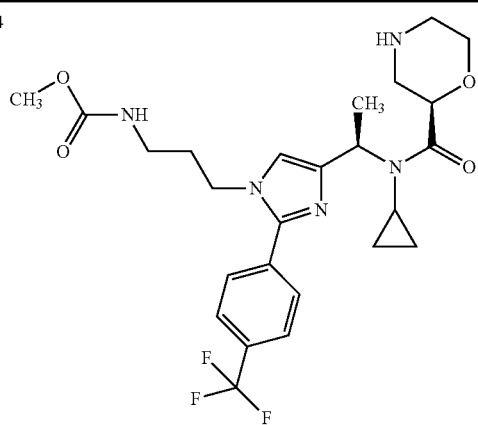 | 524 | APCI [M + H]+ |

TABLE 28-continued
| Example 165 | 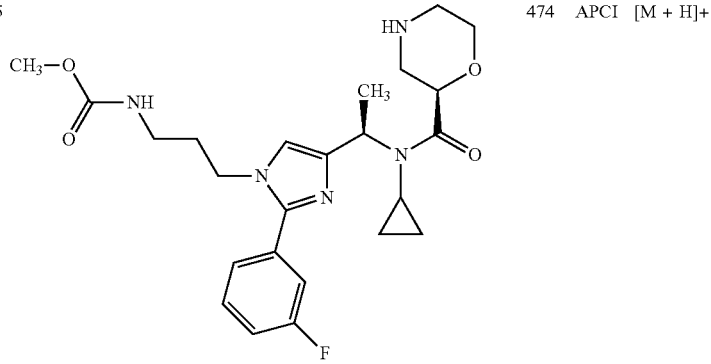 | 474 | APCI [M + H]+ |
| Example 166 | 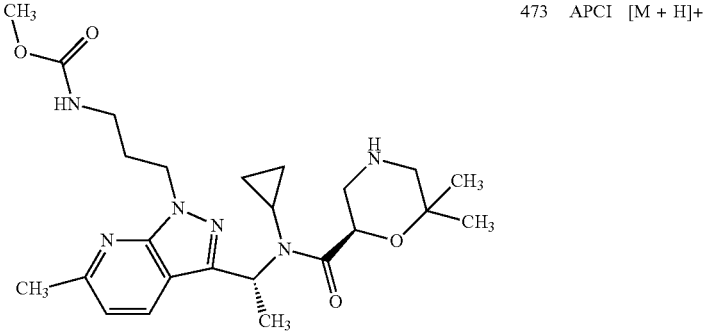 | 473 | APCI [M + H]+ |
| Example 167 | 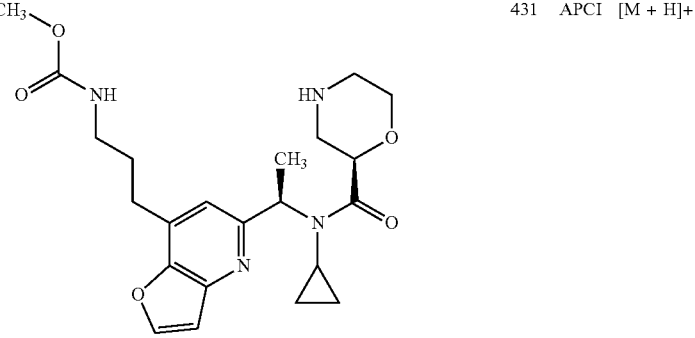 | 431 | APCI [M + H]+ |
| Example 168 | 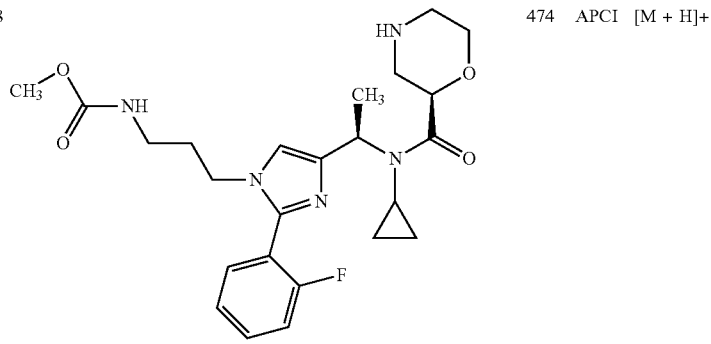 | 474 | APCI [M + H]+ |

TABLE 29
| Example 169 | 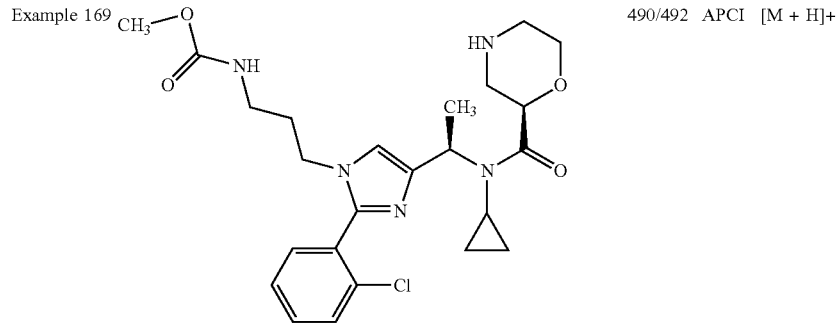 | 490/492 APCI [M + H]+ |
| Example 170 | 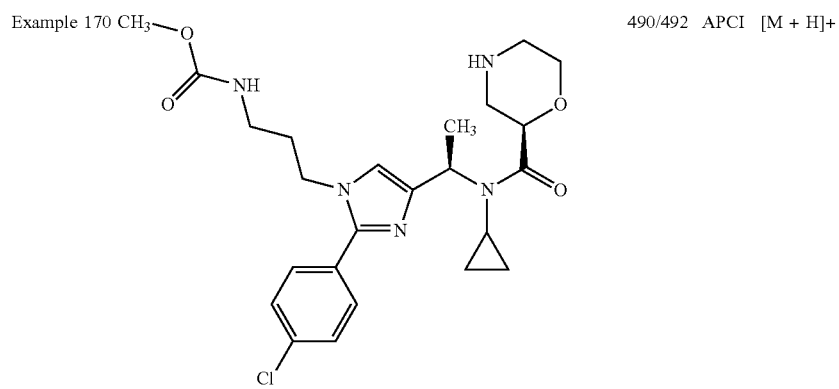 | 490/492 APCI [M + H]+ |
| Example 171 | 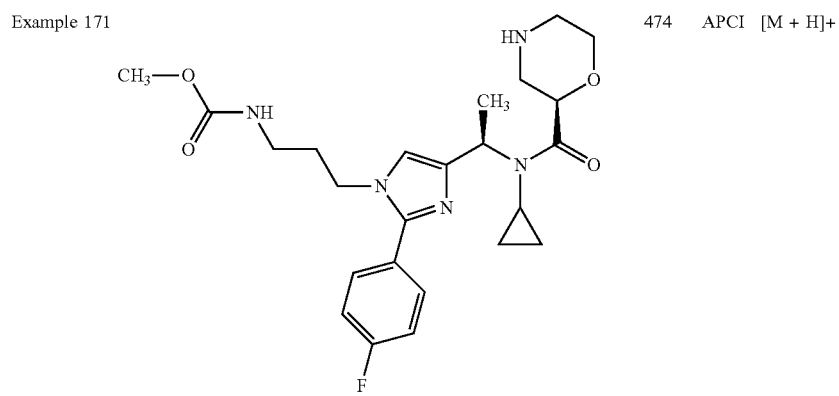 | 474 APCI [M + H]+ |
| Example 172 | 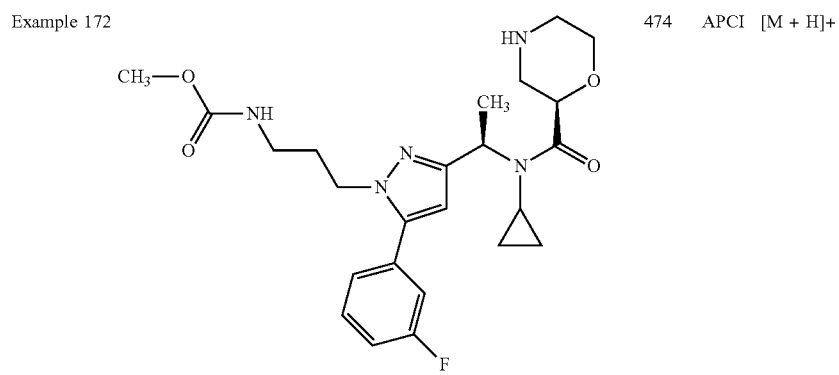 | 474 APCI [M + H]+ |

TABLE 29-continued
| Example 173 | 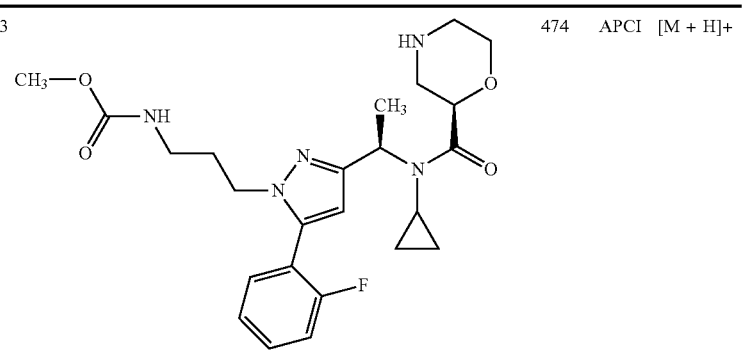 | 474 | APCI [M + H]+ |
TABLE 30
| Example 174 | 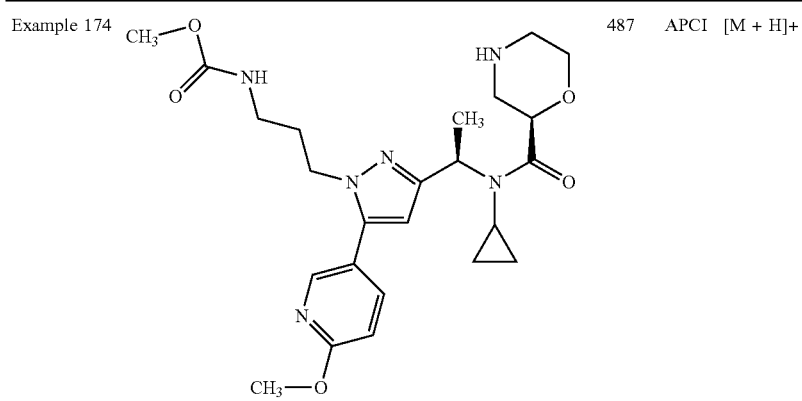 | 487 | APCI [M + H]+ |
| Example 175 | 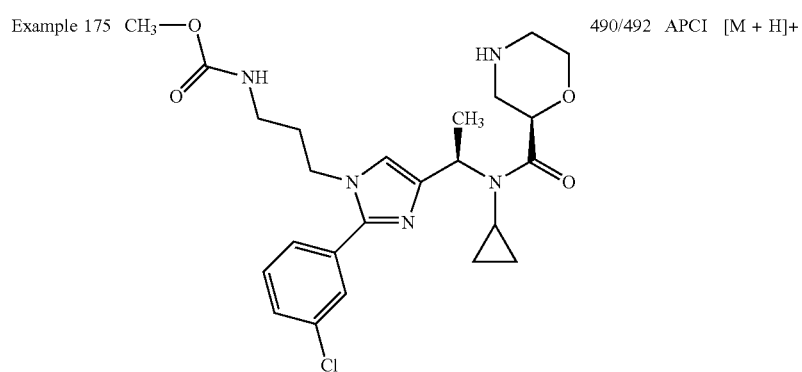 | 490/492 | APCI [M + H]+ |
| Example 176 | 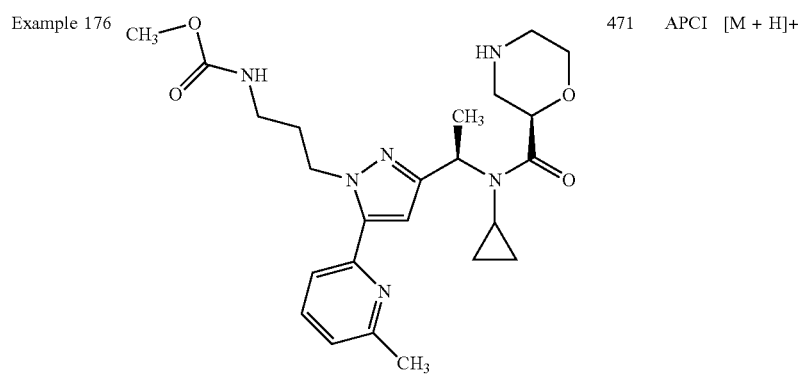 | 471 | APCI [M + H]+ |

TABLE 30-continued
Example 177 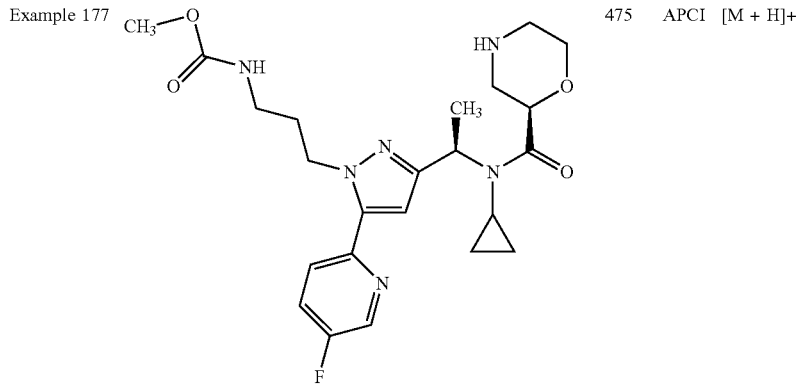 475 APCI [M + H]+
Example 178 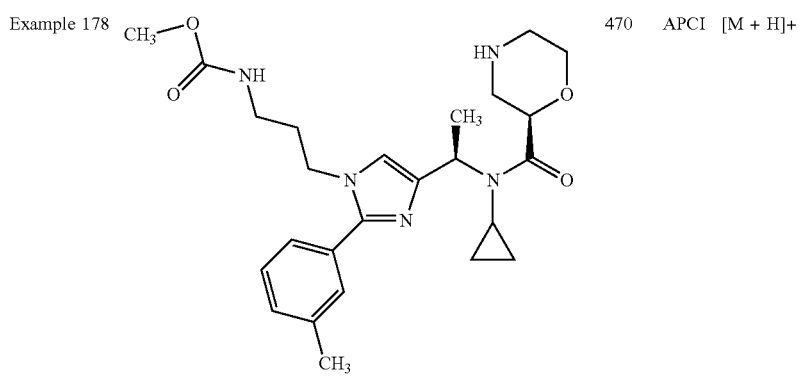 470 APCI [M + H]+
TABLE 31
Example 179 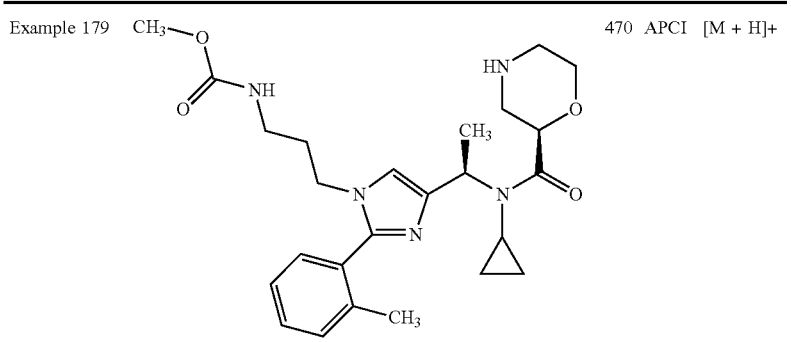 470 APCI [M + H]+
Example 180 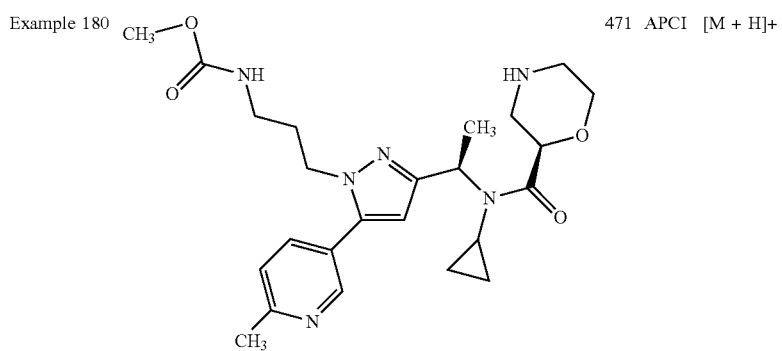 471 APCI [M + H]+

TABLE 31-continued
| Example 181 | 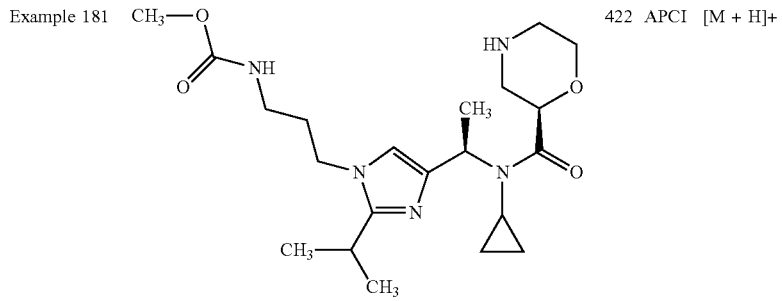 | 422 APCI [M + H]+ |
| Example 182 | 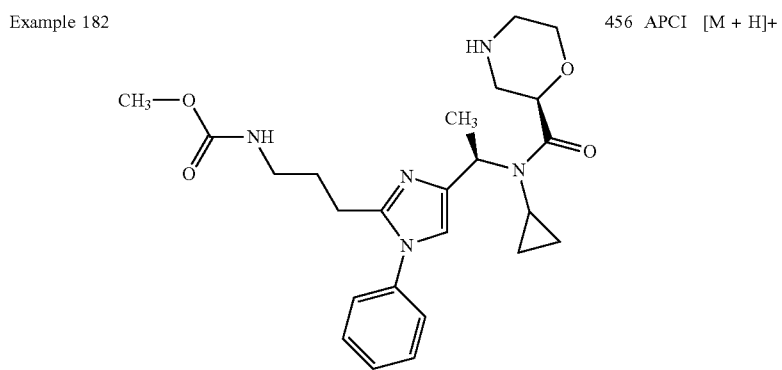 | 456 APCI [M + H]+ |
| Example 183 | 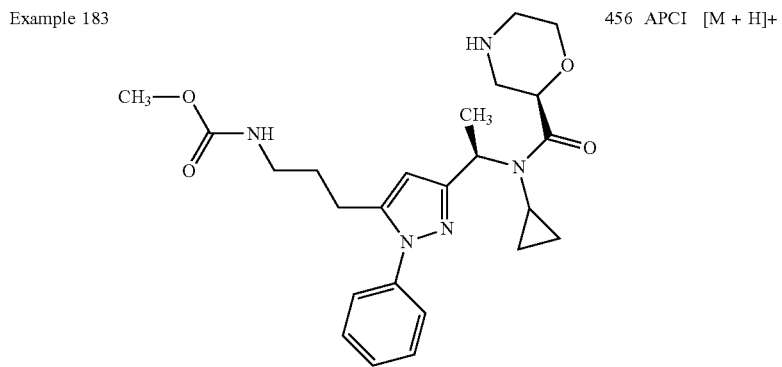 | 456 APCI [M + H]+ |
TABLE 32
| Example 184 | 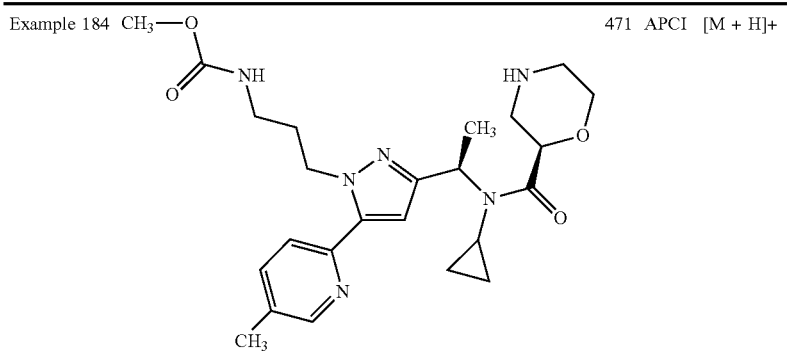 | 471 APCI [M + H]+ |

TABLE 32-continued
| Example 185 | 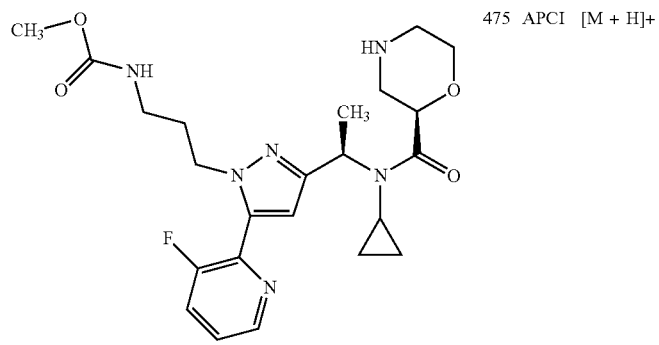 | 475 APCI [M + H]+ |
| Example 186 | 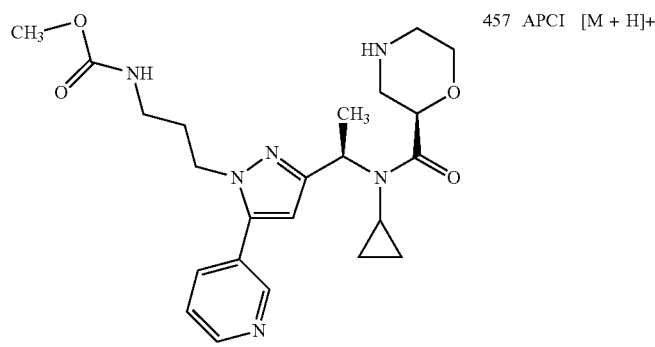 | 457 APCI [M + H]+ |
| Example 187 | 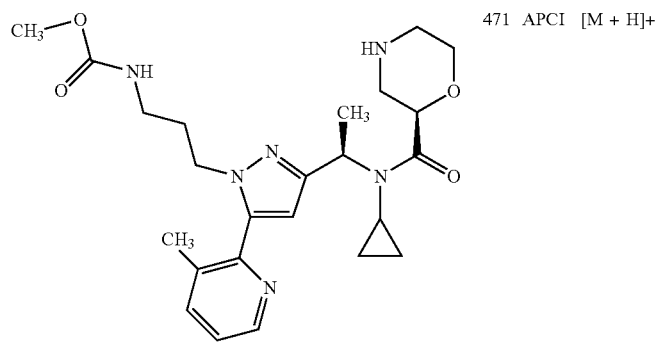 | 471 APCI [M + H]+ |
| Example 188 | 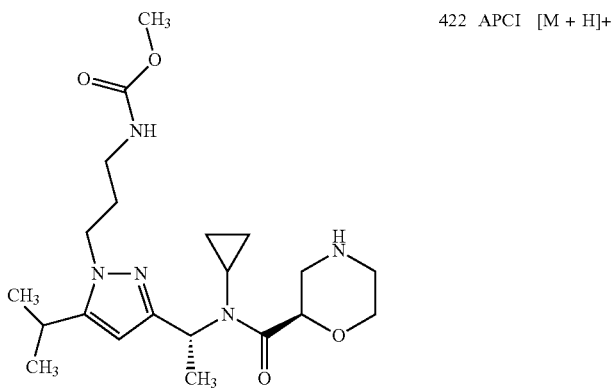 | 422 APCI [M + H]+ |

TABLE 33
| Example 189 | 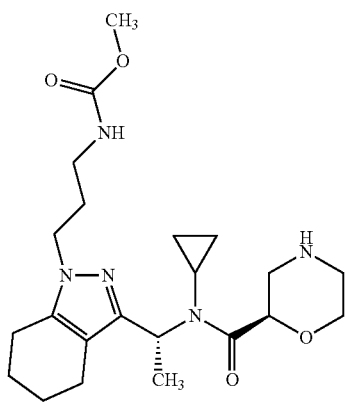 [SMILES: COC(=O)NCCCn1nc([C@@H](C)N(C(=O)[C@H]2CNCCO2)C2CC2)c2c1CCCC2] | 434 APCI [M + H]+ |
| Example 190 | 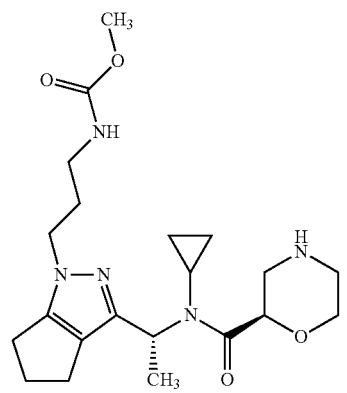 [SMILES: COC(=O)NCCCn1nc([C@@H](C)N(C(=O)[C@H]2CNCCO2)C2CC2)c2c1CCC2] | 420 APCI [M + H]+ |
| Example 191 | 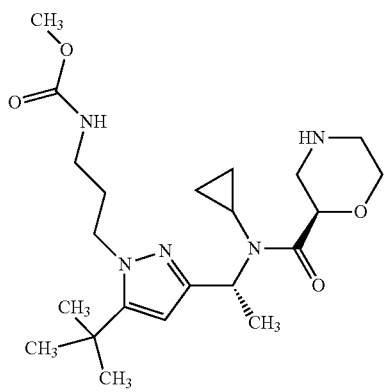 [SMILES: COC(=O)NCCCn1nc([C@@H](C)N(C(=O)[C@H]2CNCCO2)C2CC2)cc1C(C)(C)C] | 436 APCI [M + H]+ |
| Example 192 | 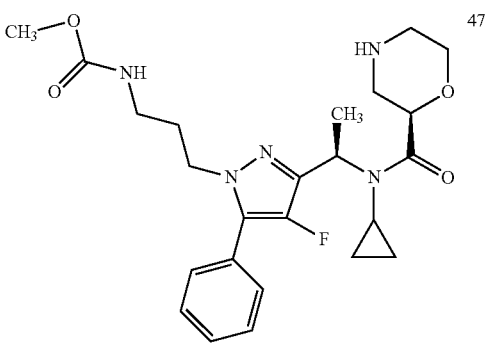 | 474 APCI [M + H]+ |

TABLE 33-continued
| Example 193 | 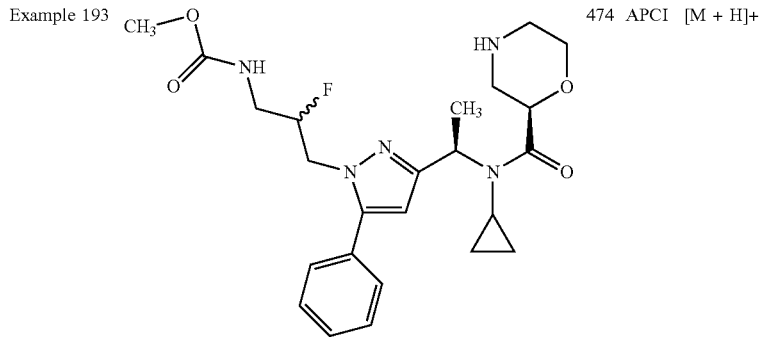 | 474 APCI [M + H]+ |
TABLE 34
| Example 194 | 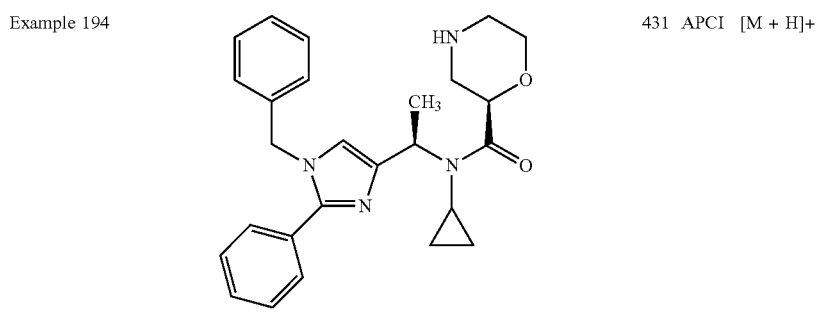 | 431 APCI [M + H]+ |
| Example 195 | 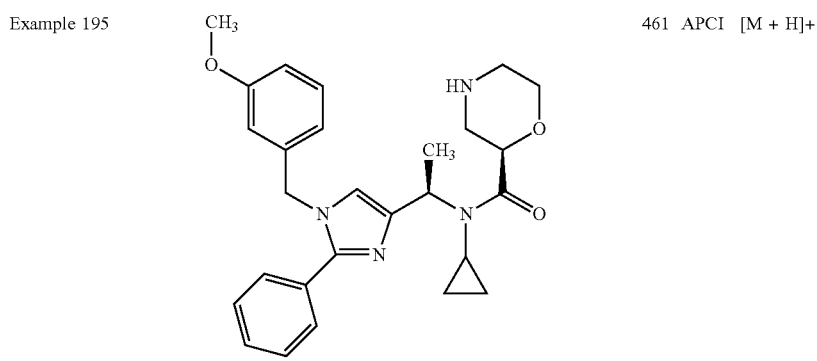 | 461 APCI [M + H]+ |
| Example 196 | 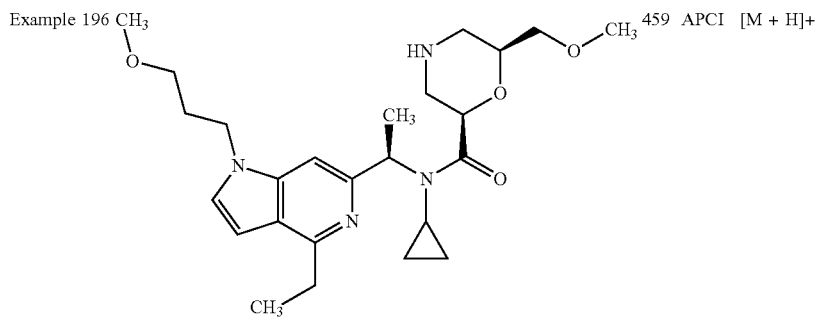 | 459 APCI [M + H]+ |

TABLE 34-continued
| Example 197 | 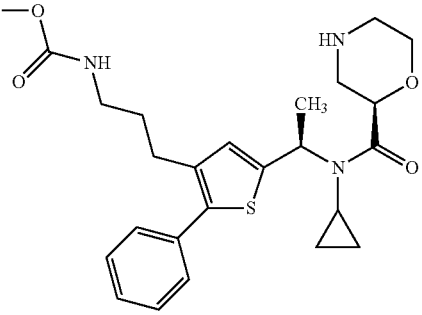 | 472 APCI [M + H]+ |
| Example 198 | 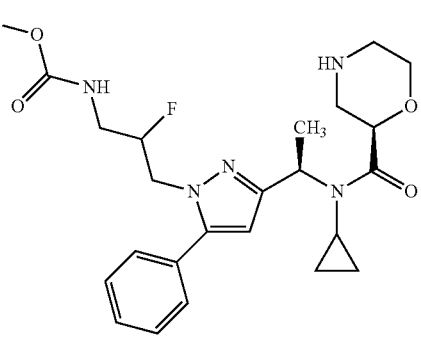 | 474 APCI [M + H]+ |
| Example 199 | 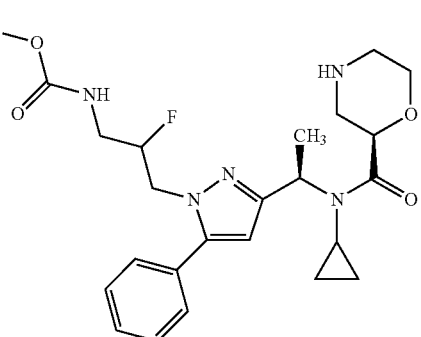 | 474 APCI [M + H]+ |
TABLE 35
| Example 200 | 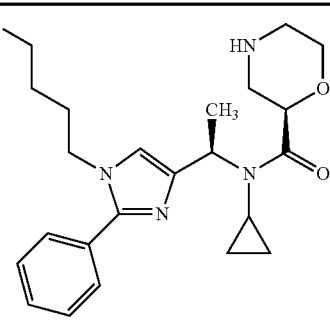 | 411 APCI [M + H]+ |
| Example 201 | 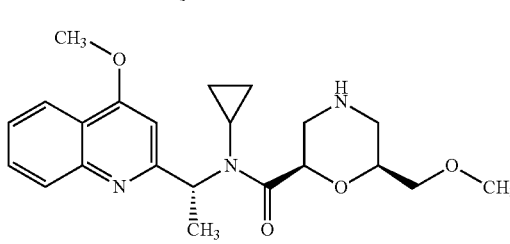 | 400 APCI [M + H]+ |

TABLE 35-continued
| Example 202 | 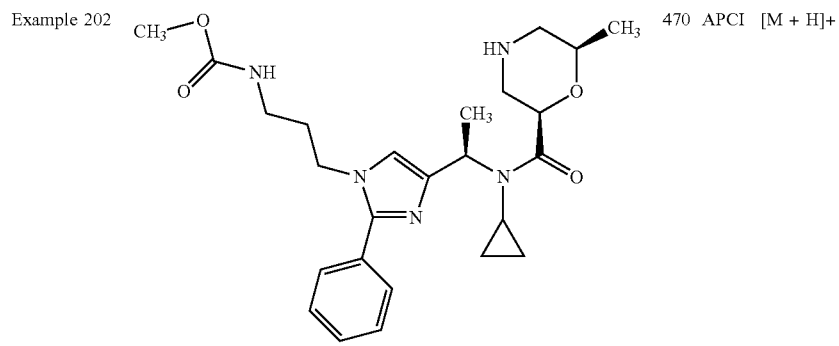 | 470 APCI [M + H]+ |
| Example 203 | 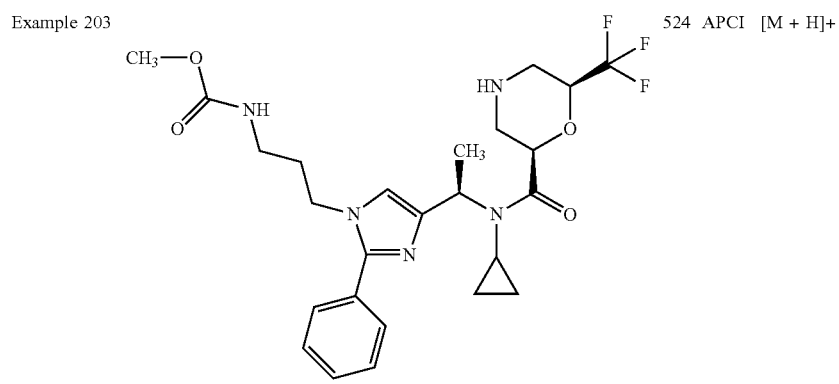 | 524 APCI [M + H]+ |
| Example 204 | 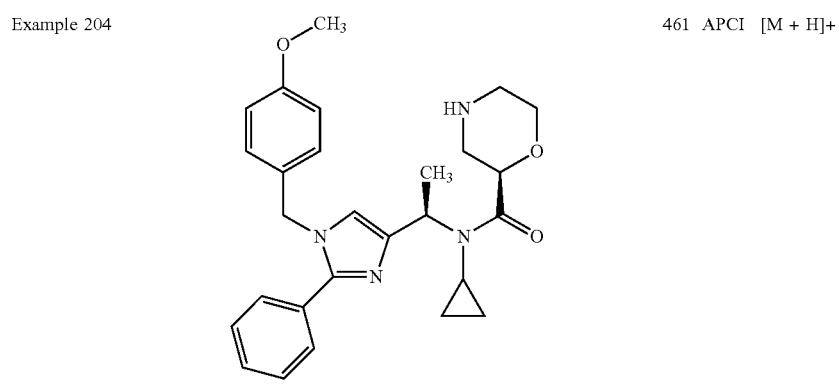 | 461 APCI [M + H]+ |
| Example 205 | 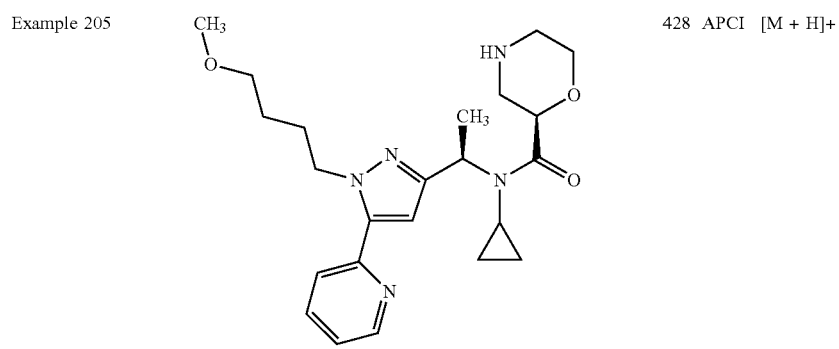 | 428 APCI [M + H]+ |

TABLE 36
Example 206 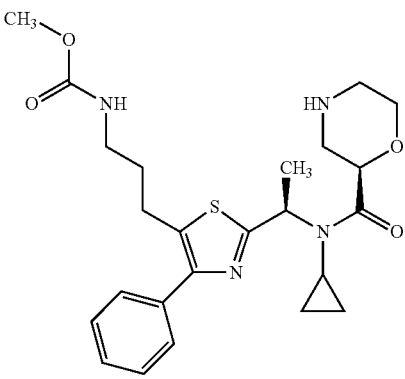 [SMILES: COC(=O)NCCCc1sc([C@@H](C)N(C(=O)[C@H]2CNCCO2)C2CC2)nc1-c1ccccc1] 473 APCI [M + H]+
Example 207 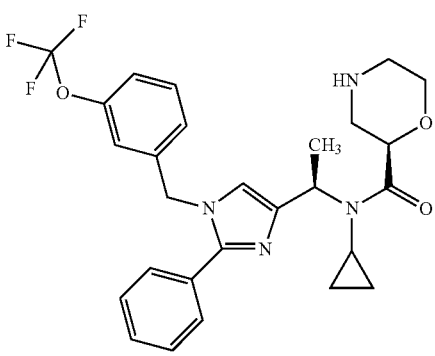 [SMILES: C[C@H](c1cn(Cc2cccc(OC(F)(F)F)c2)c(-c2ccccc2)n1)N(C(=O)[C@H]1CNCCO1)C1CC1] 515 APCI [M + H]+
Example 208 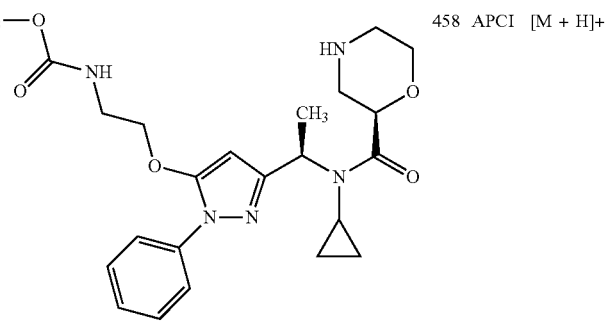 458 APCI [M + H]+
Example 209 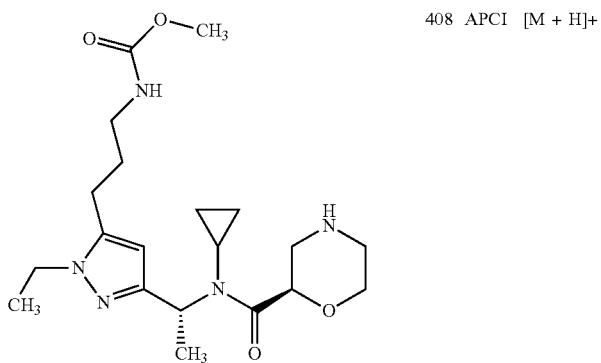 408 APCI [M + H]+

TABLE 36-continued
| | | | |
|---|---|---|---|
| Example 210 | 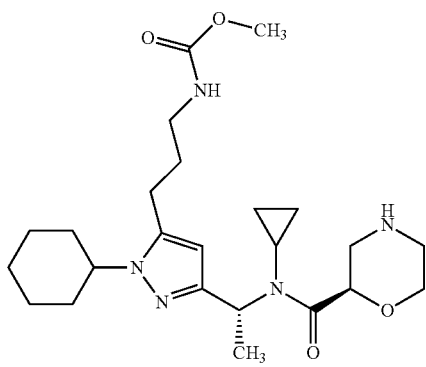 [SMILES: COC(=O)NCCCc1cc([C@@H](C)N(C(=O)[C@H]2CNCCO2)C2CC2)nn1C1CCCCC1] | 462 | APCI [M + H]+ |
TABLE 37
| | | | |
|---|---|---|---|
| Example 211 | 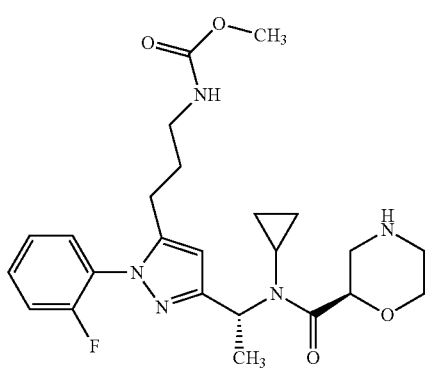 [SMILES: COC(=O)NCCCc1cc([C@@H](C)N(C(=O)[C@H]2CNCCO2)C2CC2)nn1-c1ccccc1F] | 474 | APCI [M + H]+ |
| Example 212 | 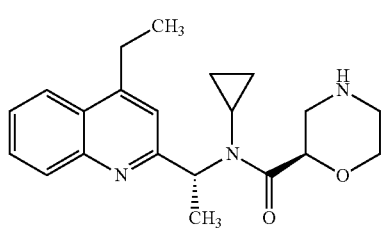 [SMILES: CCc1cc([C@@H](C)N(C(=O)[C@H]2CNCCO2)C2CC2)nc2ccccc12] | 354 | APCI [M + H]+ |
| Example 213 | 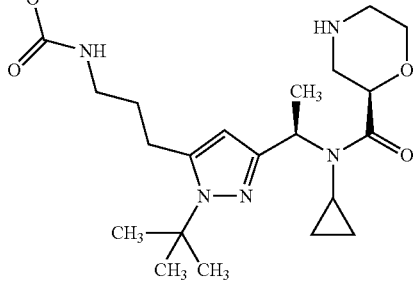 | 436 | APCI [M + H]+ |

TABLE 37-continued
| Example 214 | 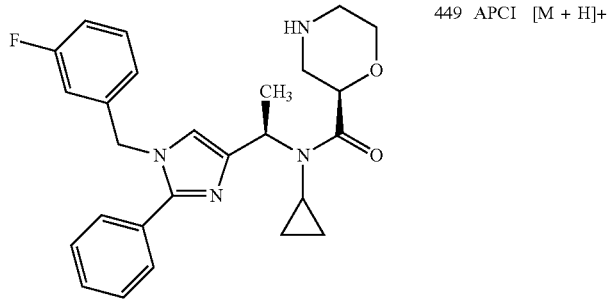 | 449 APCI [M + H]+ |
| Example 215 | 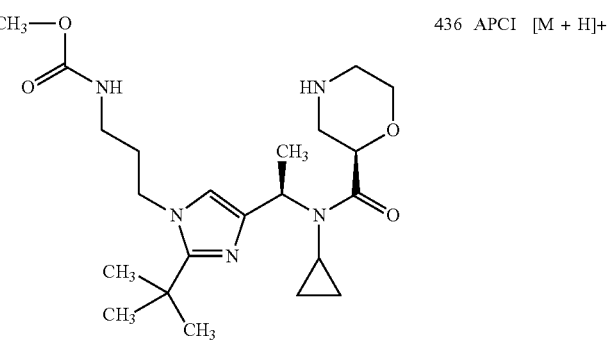 | 436 APCI [M + H]+ |
| Example 216 | 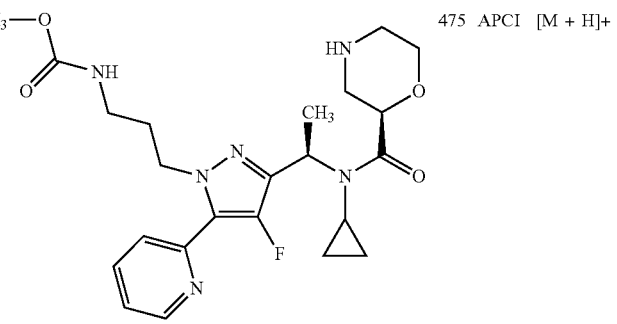 | 475 APCI [M + H]+ |
TABLE 38
| Example 217 | 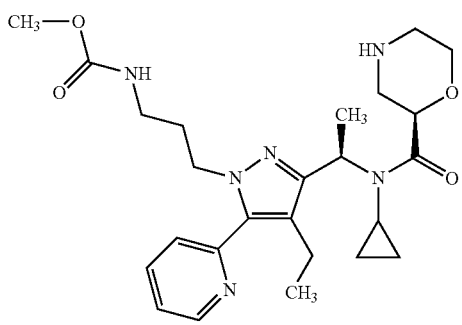 [SMILES: CCc1c([C@@H](C)N(C(=O)[C@H]2CNCCO2)C2CC2)nn(CCCNC(=O)OC)c1-c1ccccn1] | 485 APCI [M + H]+ |

TABLE 38-continued
Example 218 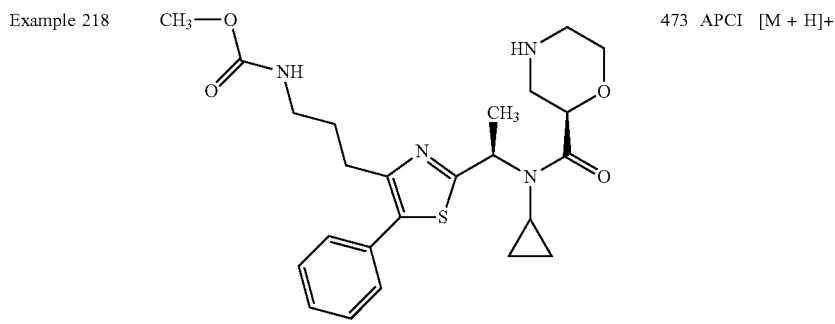 473 APCI [M + H]+
Example 219 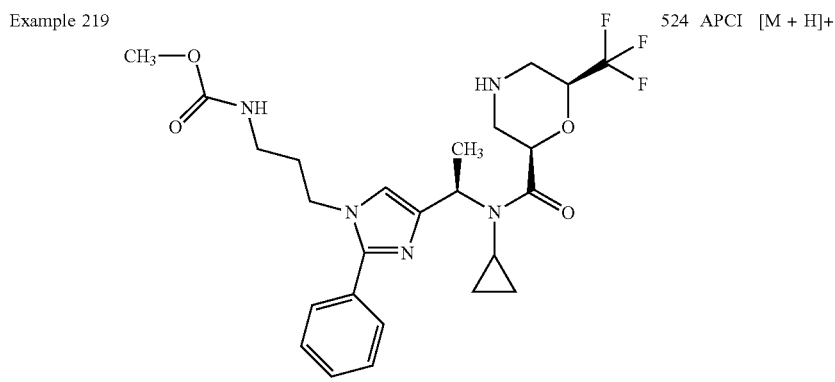 524 APCI [M + H]+
Example 220 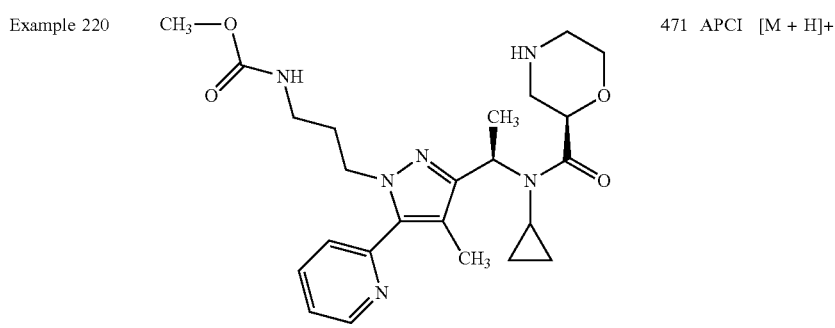 471 APCI [M + H]+
Example 221 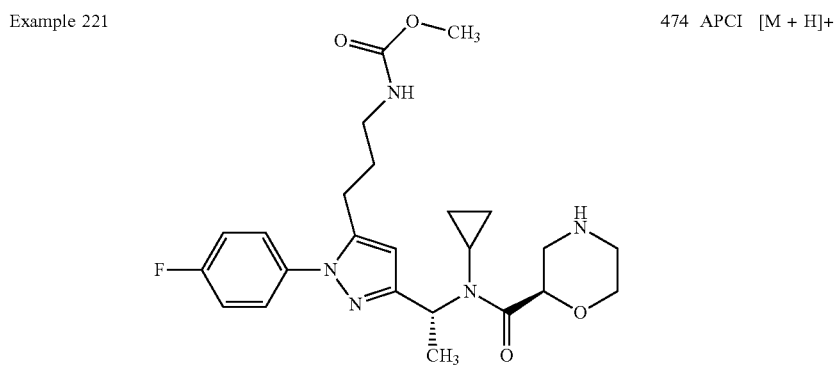 474 APCI [M + H]+

TABLE 39
| Example 222 | 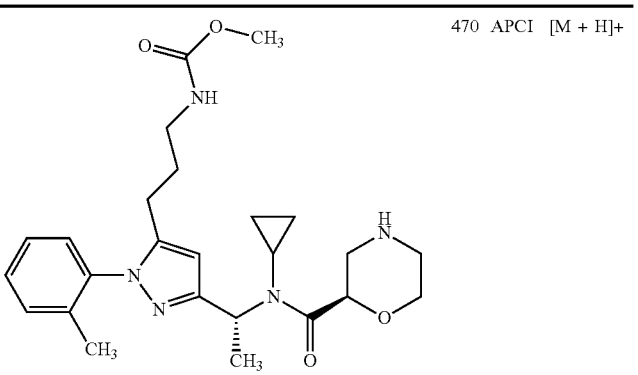 | 470 APCI [M + H]+ |
| Example 223 | 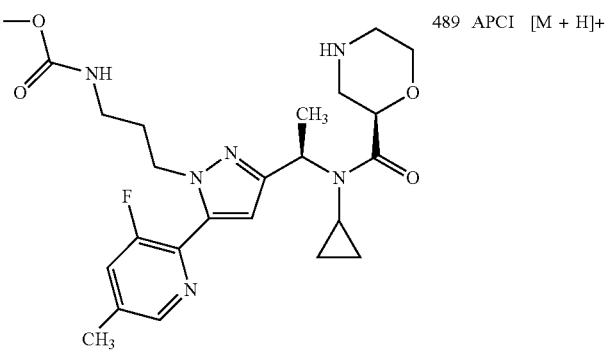 | 489 APCI [M + H]+ |
| Example 224 | 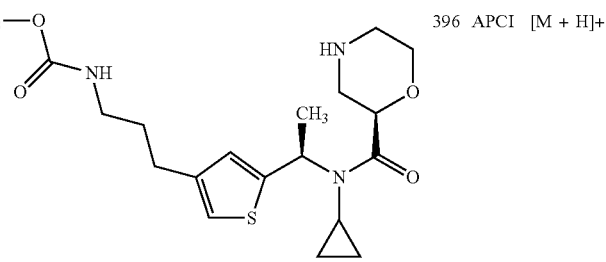 | 396 APCI [M + H]+ |
| Example 225 | 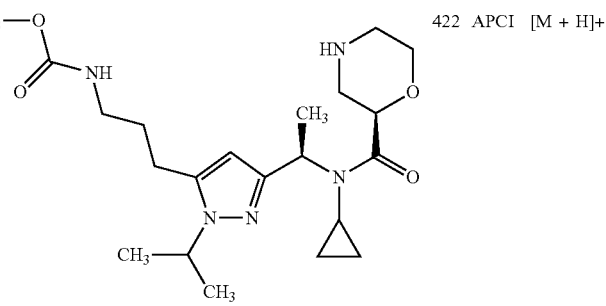 | 422 APCI [M + H]+ |
| Example 226 | 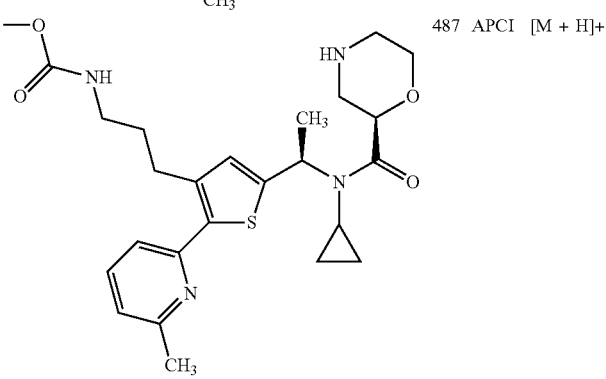 | 487 APCI [M + H]+ |

TABLE 40
Example 227 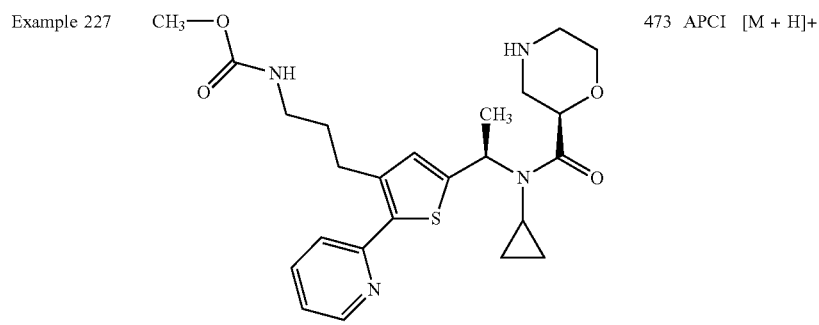 473 APCI [M + H]+
Example 228 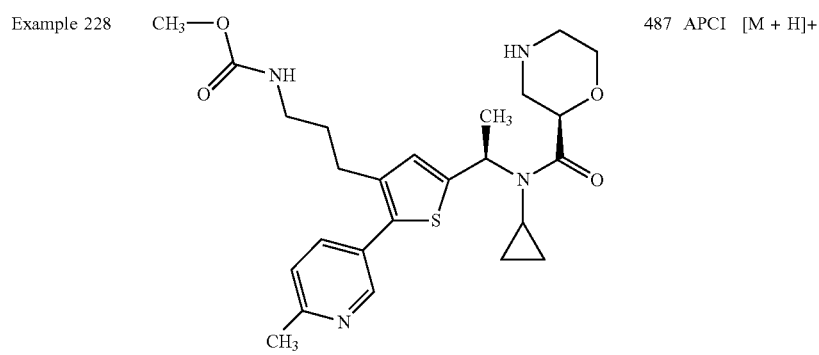 487 APCI [M + H]+
Example 229 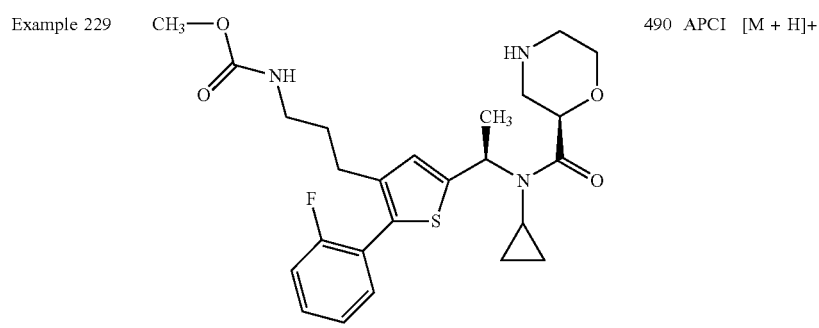 490 APCI [M + H]+
Example 230 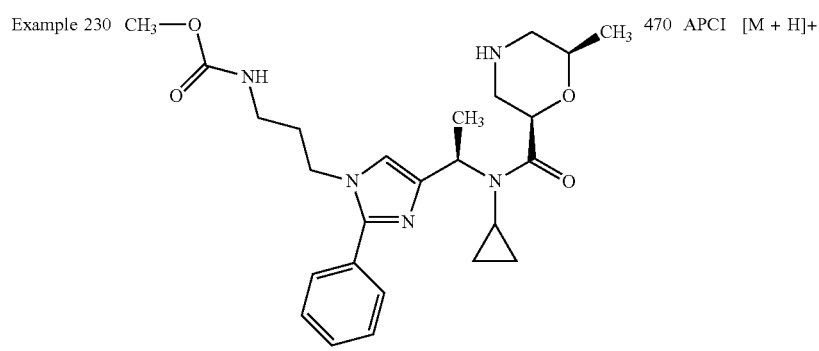 470 APCI [M + H]+

TABLE 40-continued
| Example 231 | 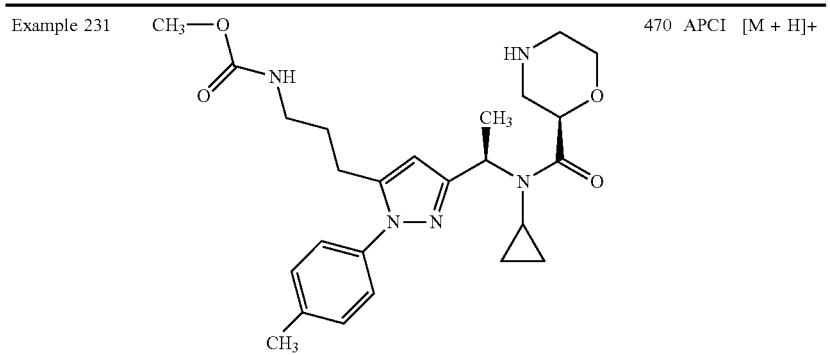 | 470 APCI [M + H]+ |
TABLE 41
| Example 232 | 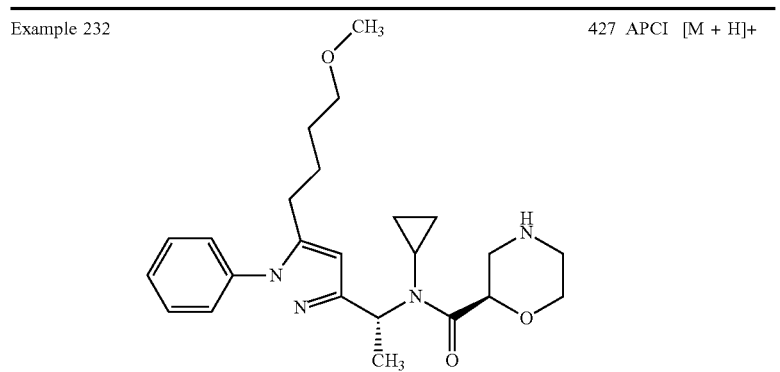 | 427 APCI [M + H]+ |
| Example 233 | 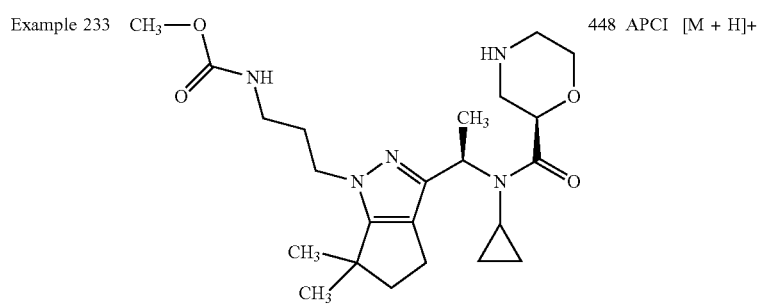 | 448 APCI [M + H]+ |
| Example 234 | 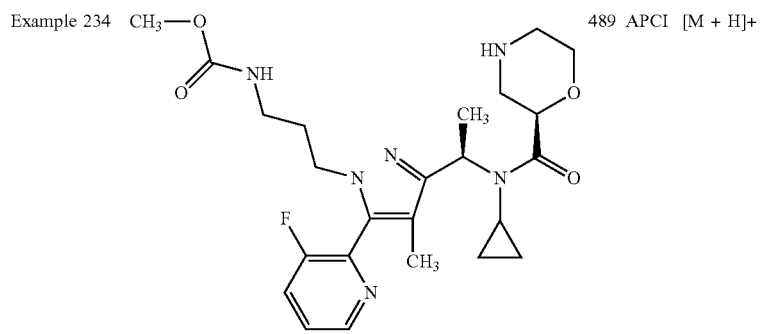 | 489 APCI [M + H]+ |

TABLE 41-continued
| Example 235 | 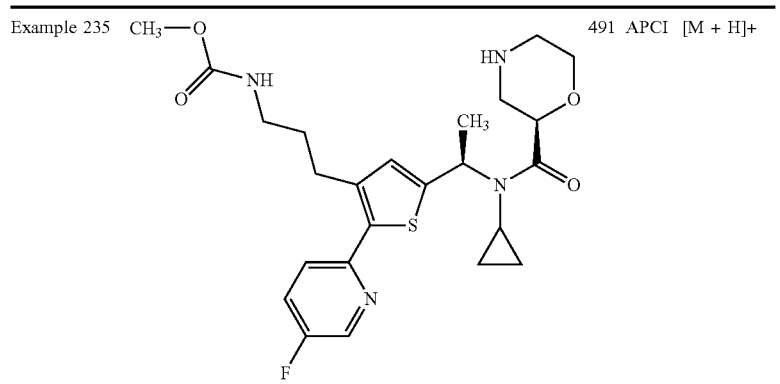 | 491 APCI [M + H]+ |
| Example 236 | 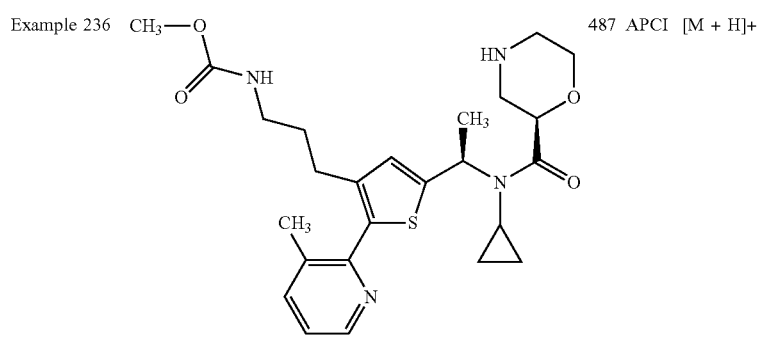 | 487 APCI [M + H]+ |
TABLE 42
| Example 237 | 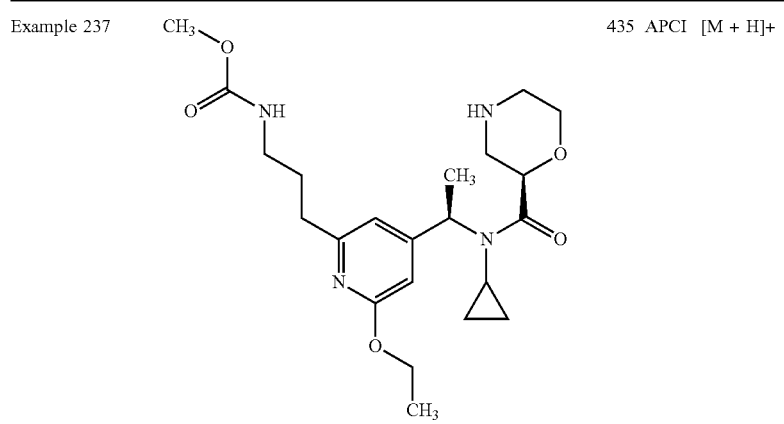 | 435 APCI [M + H]+ |
| Example 238 | 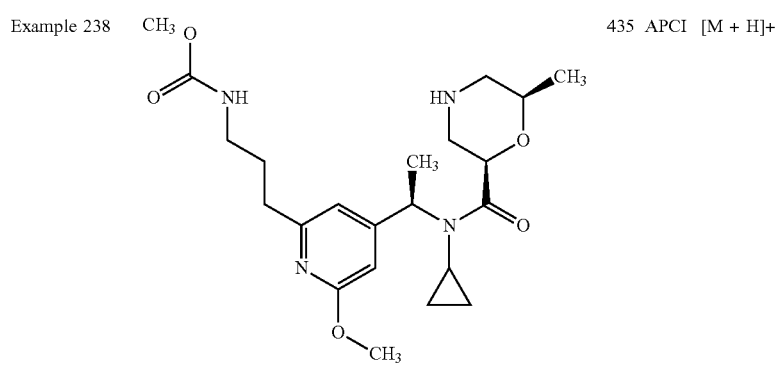 | 435 APCI [M + H]+ |

TABLE 42-continued
| Example 239 | 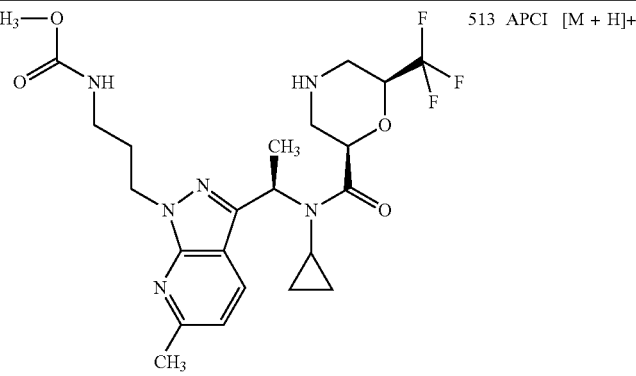 | 513 APCI [M + H]+ |
| Example 240 | 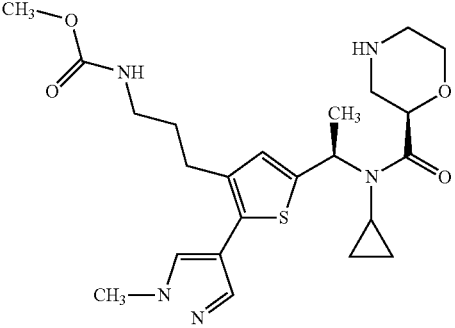 [SMILES: CN/C=C(\C=N)c1sc([C@@H](C)N(C(=O)[C@H]2CNCCO2)C2CC2)cc1CCCNC(=O)OC] | 476 APCI [M + H]+ |
| Example 241 | 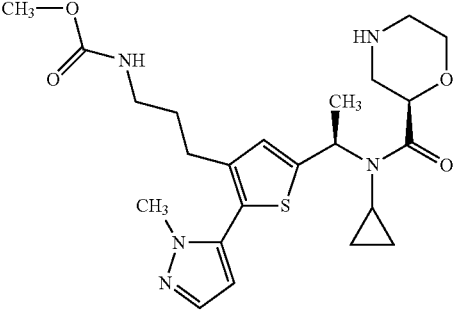 [SMILES: COC(=O)NCCCc1cc([C@@H](C)N(C(=O)[C@H]2CNCCO2)C2CC2)sc1-c1ccnn1C] | 476 APCI [M + H]+ |
TABLE 43
| Example 242 | 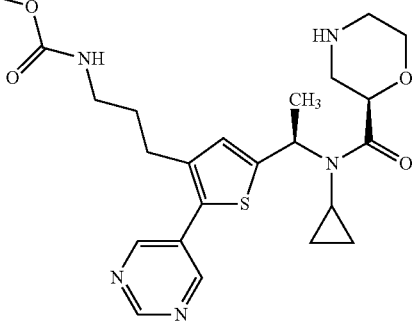 | 474 APCI [M + H]+ |

TABLE 43-continued
Example 243 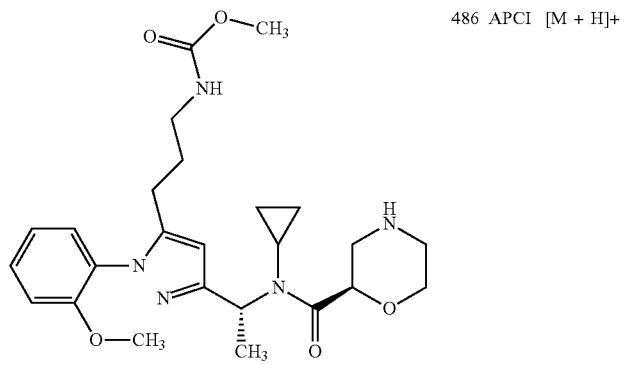 486 APCI [M + H]+
Example 244 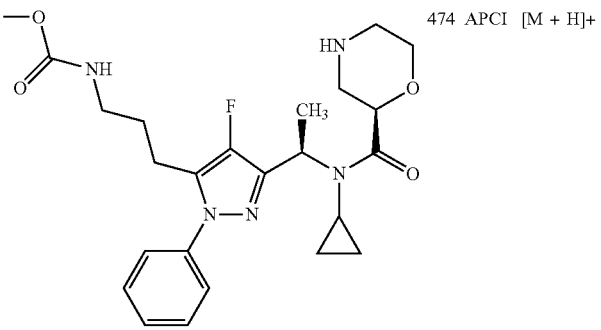 474 APCI [M + H]+
Example 245 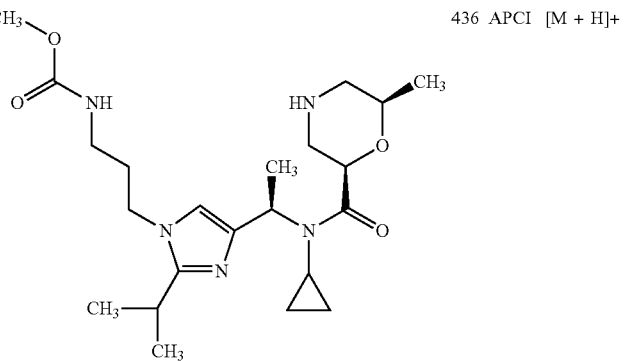 436 APCI [M + H]+
Example 246 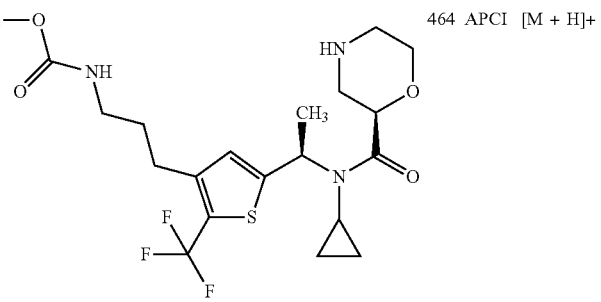 464 APCI [M + H]+

TABLE 44
| Example 247 | 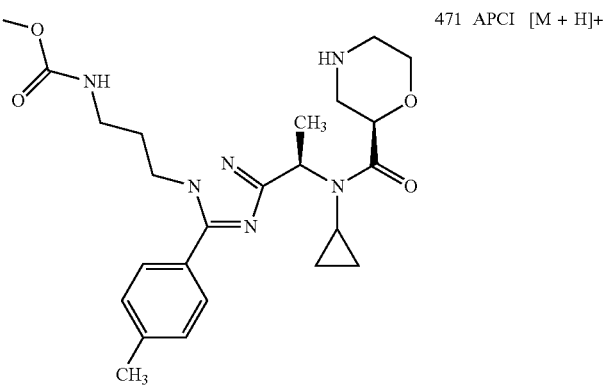 | 471 APCI [M + H]+ |
| --- | --- | --- |
| Example 248 | 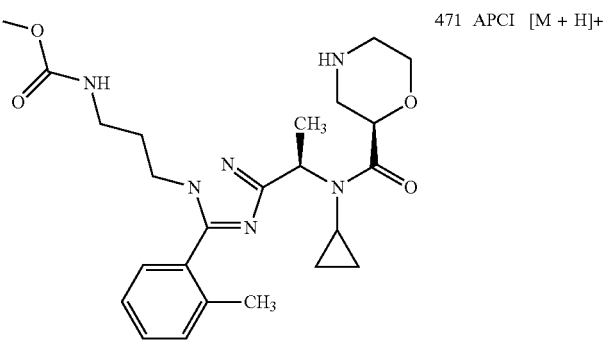 | 471 APCI [M + H]+ |
| Example 249 | 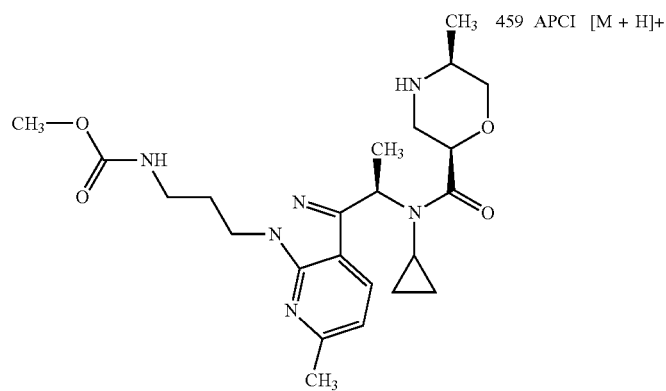 | 459 APCI [M + H]+ |
| Example 250 | 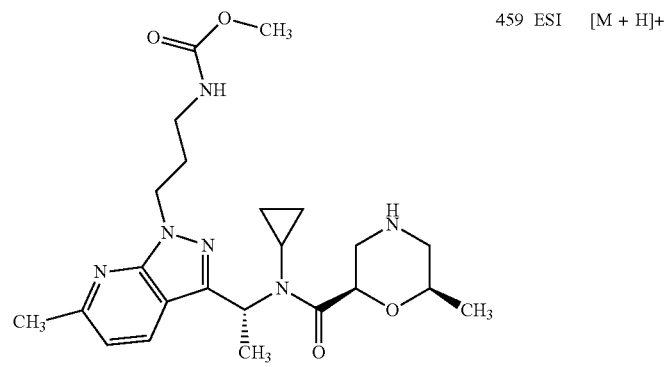 | 459 ESI [M + H]+ |

TABLE 44-continued
| Example 251 | 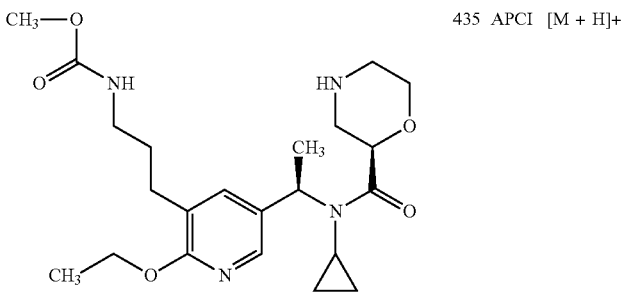 | 435 APCI [M + H]+ |
TABLE 45
| Example 252 | 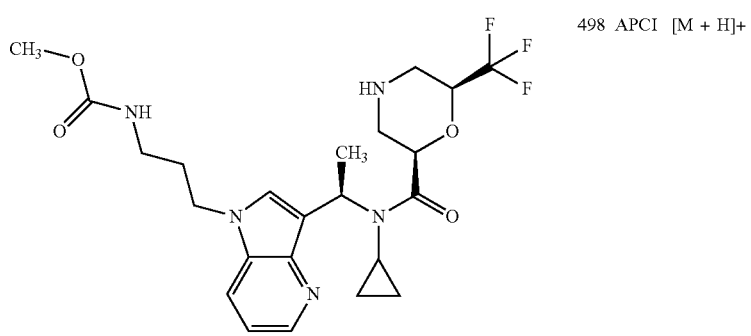 | 498 APCI [M + H]+ |
| Example 253 | 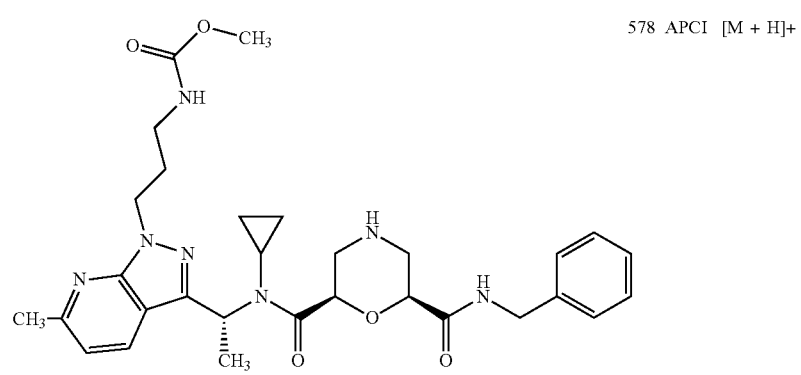 | 578 APCI [M + H]+ |
| Example 254 | 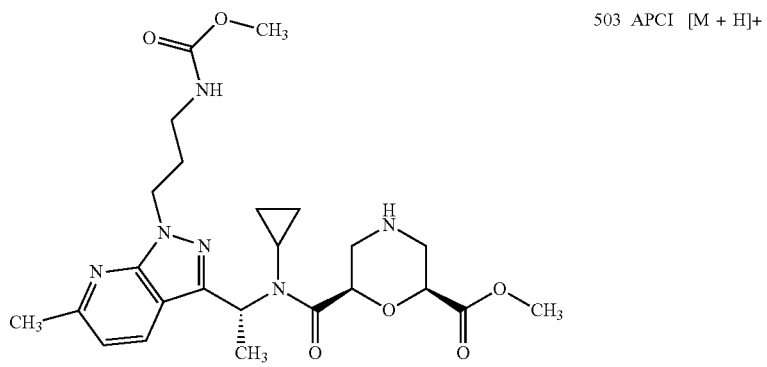 | 503 APCI [M + H]+ |

TABLE 45-continued
| Example 255 | 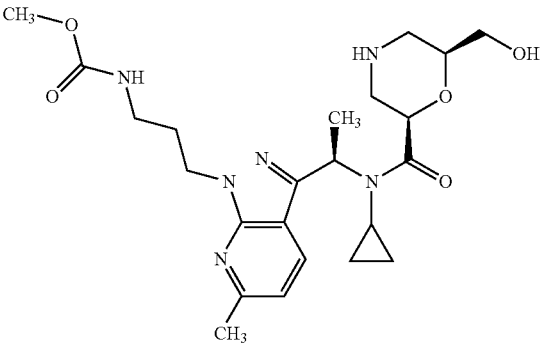 [SMILES: COC(=O)NCCCNc1nc(C)ccc1C(=N)[C@@H](C)N(C(=O)[C@H]1CNC[C@@H](CO)O1)C1CC1] | 475 APCI [M + H]+ |
| Example 256 | 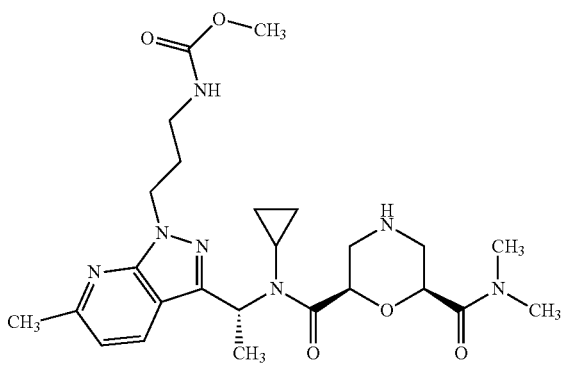 | 516 APCI [M + H]+ |
TABLE 46
| Example 257 | 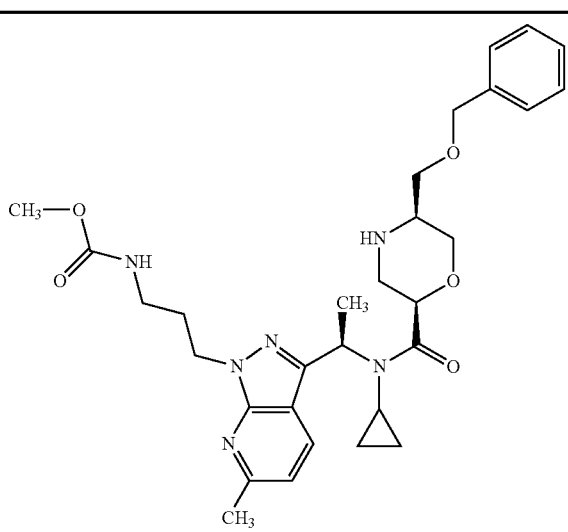 | 565 APCI [M + H]+ |

TABLE 46-continued
| Example 258 | 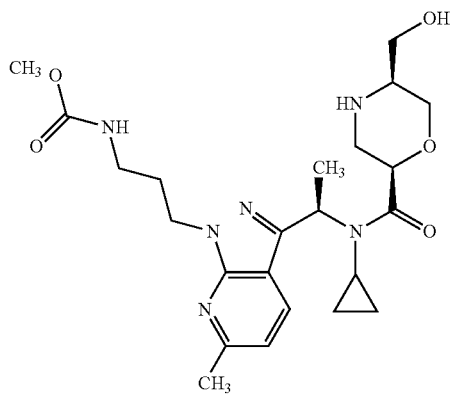 | 475 APCI [M + H]+ |
| Example 259 | 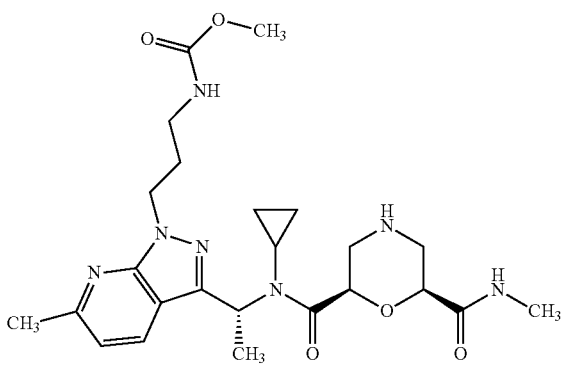 | 502 APCI [M + H]+ |
| Example 260 | 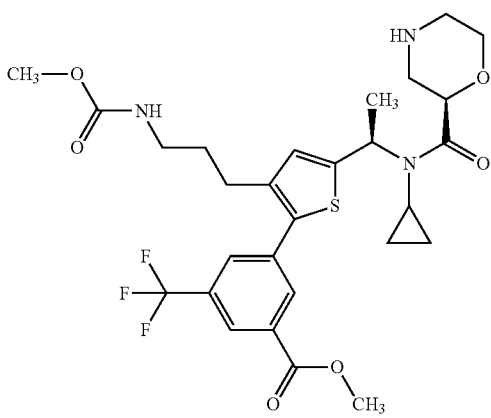 [SMILES: COC(=O)NCCCc1cc([C@@H](C)N(C(=O)[C@H]2CNCCO2)C2CC2)sc1-c1cc(C(=O)OC)cc(C(F)(F)F)c1] | 598 ESI [M + H]+ |
| Example 261 | 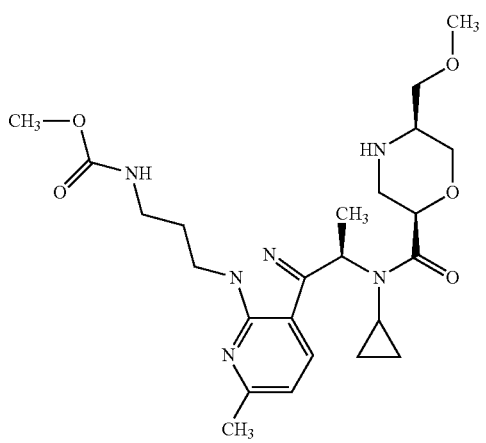 | 489 APCI [M + H]+ |

TABLE 47
Example 262 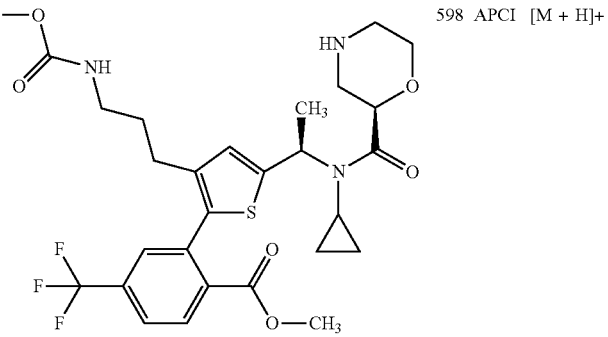 598 APCI [M + H]+
Example 263 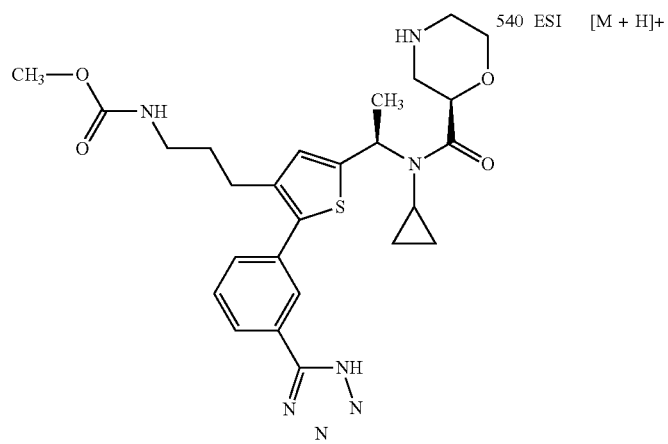 540 ESI [M + H]+
Example 264 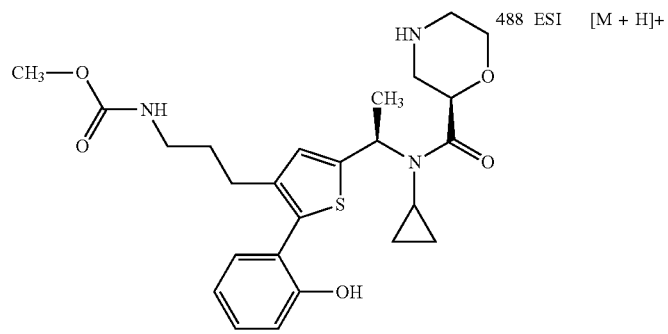 488 ESI [M + H]+
Example 265 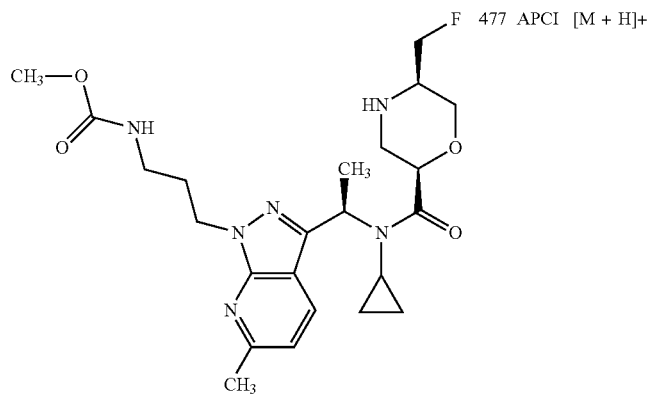 477 APCI [M + H]+

TABLE 47-continued
| Example 266 | 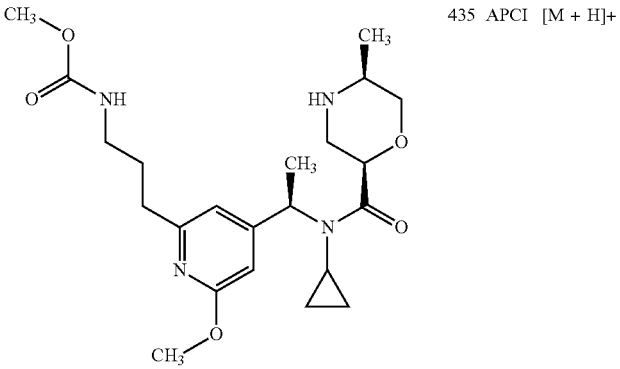 | 435 | APCI | [M + H]+ |
TABLE 48
| Example 267 | 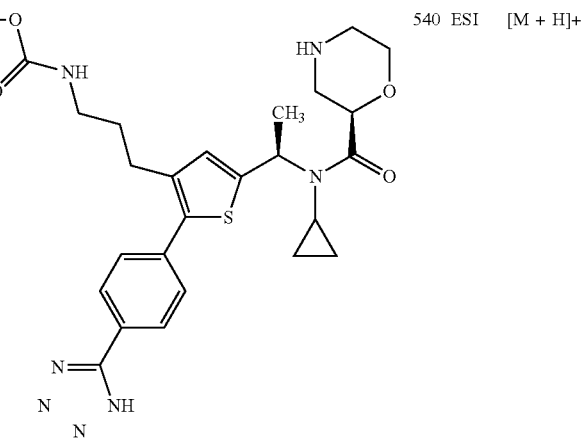 | 540 | ESI | [M + H]+ |
| Example 268 | 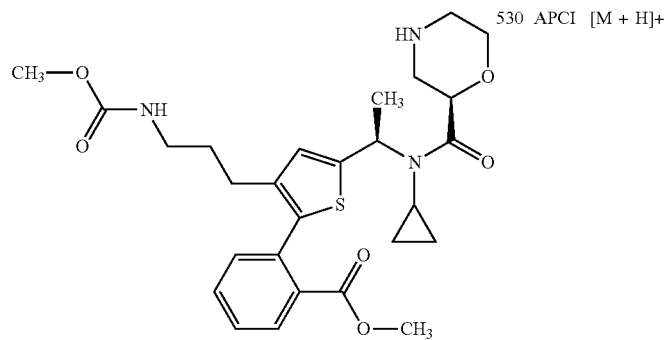 | 530 | APCI | [M + H]+ |

TABLE 48-continued
| Example 269 | 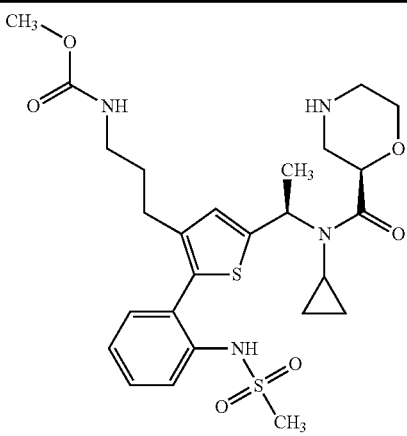 | 565 APCI [M + H]+ |
| Example 270 | 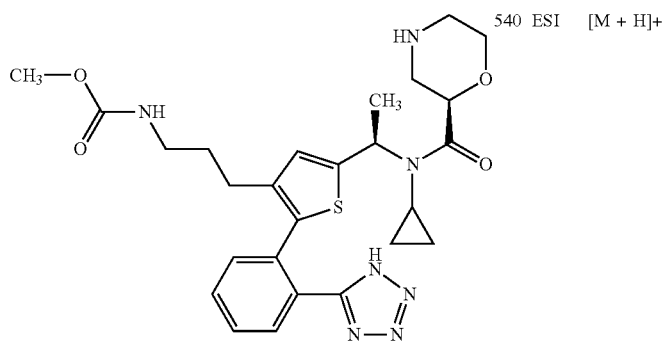 | 540 ESI [M + H]+ |
| Example 271 | 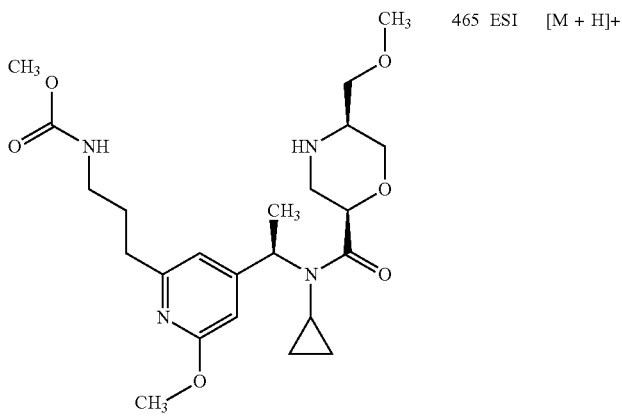 | 465 ESI [M + H]+ |
TABLE 49
| Example 272 | 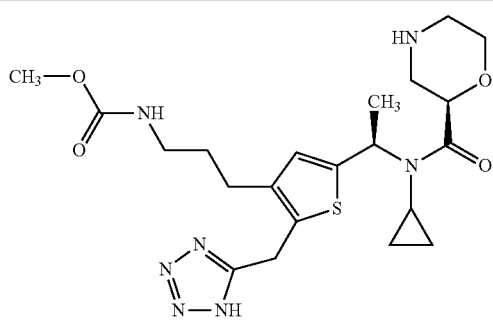 [SMILES: COC(=O)NCCCc1cc([C@@H](C)N(C(=O)[C@H]2CNCCO2)C2CC2)sc1Cc1nnn[nH]1] | 478 ESI [M + H]+ |

TABLE 49-continued
| Example 273 | 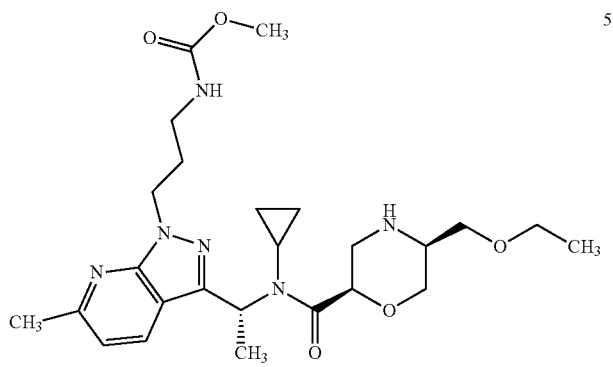 | 503 APCI [M + H]+ |
| Example 274 | 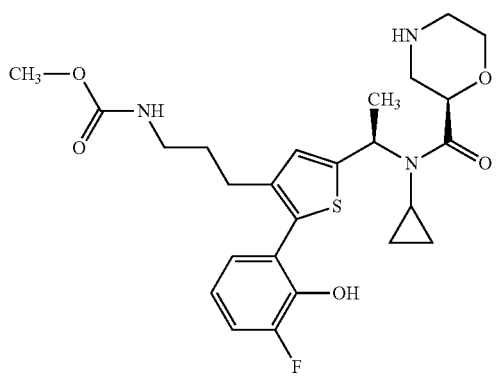 [SMILES: COC(=O)NCCCc1cc([C@@H](C)N(C(=O)[C@H]2CNCCO2)C2CC2)sc1-c1cccc(F)c1O] | 506 APCI [M + H]+ |
| Example 275 | 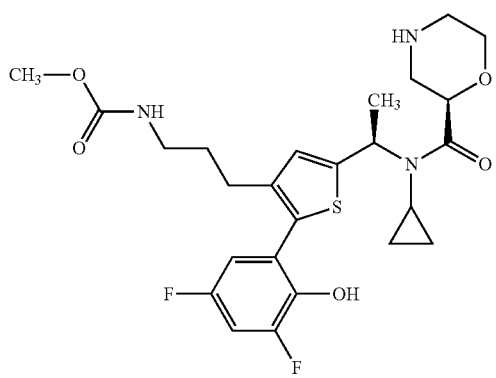 [SMILES: COC(=O)NCCCc1cc([C@@H](C)N(C(=O)[C@H]2CNCCO2)C2CC2)sc1-c1cc(F)cc(F)c1O] | 524 APCI [M + H]+ |
| Example 276 | 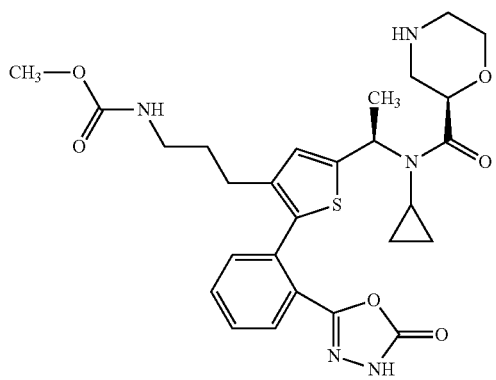 [SMILES: COC(=O)NCCCc1cc([C@@H](C)N(C(=O)[C@H]2CNCCO2)C2CC2)sc1-c1ccccc1-c1n[nH]c(=O)o1] | 556 ESI [M + H]+ |

TABLE 50
Example 277 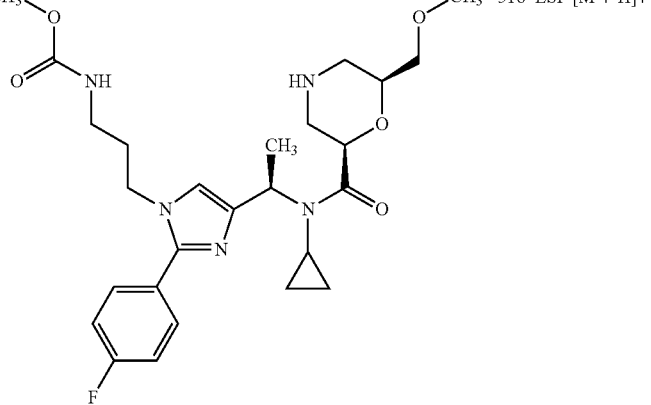 518 ESI [M + H]+
Example 278 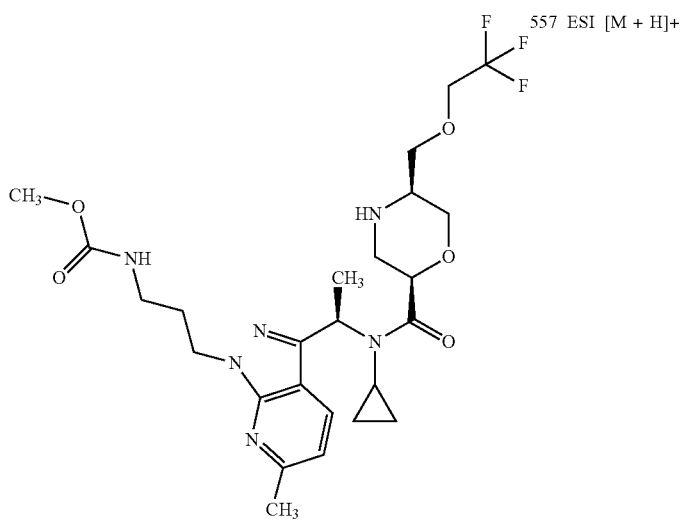 557 ESI [M + H]+
Example 279 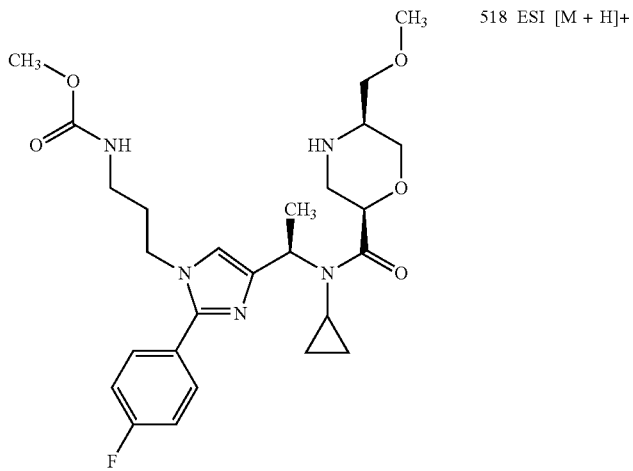 518 ESI [M + H]+

TABLE 50-continued
| Example 280 | 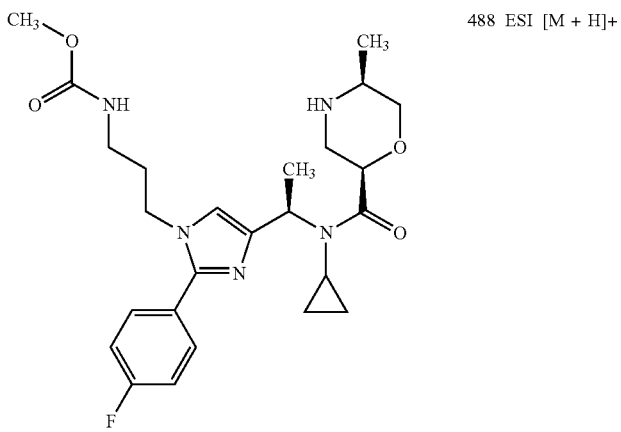 | 488 ESI [M + H]+ |
TABLE 51
| Example 281 | 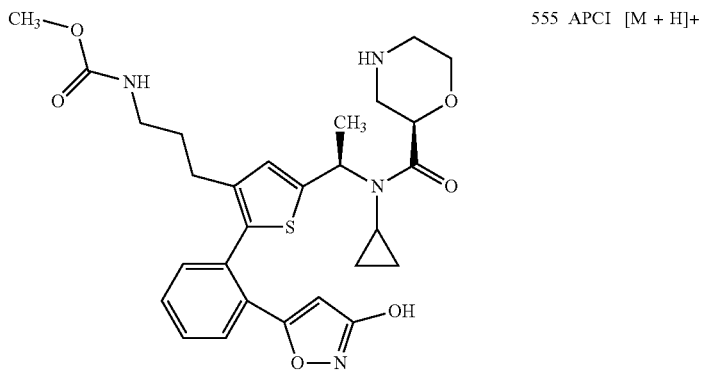 | 555 APCI [M + H]+ |
| Example 282 | 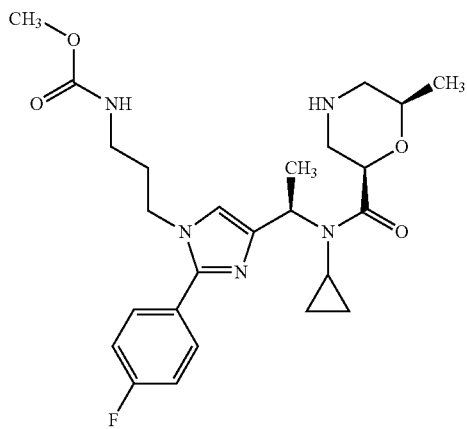 | 488 ESI [M + H]+ |

TABLE 51-continued
| Example 283 | 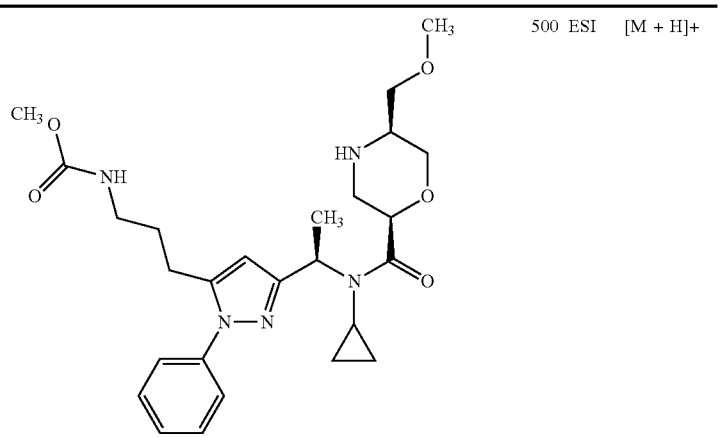 | 500 ESI [M + H]+ |
| Example 284 | 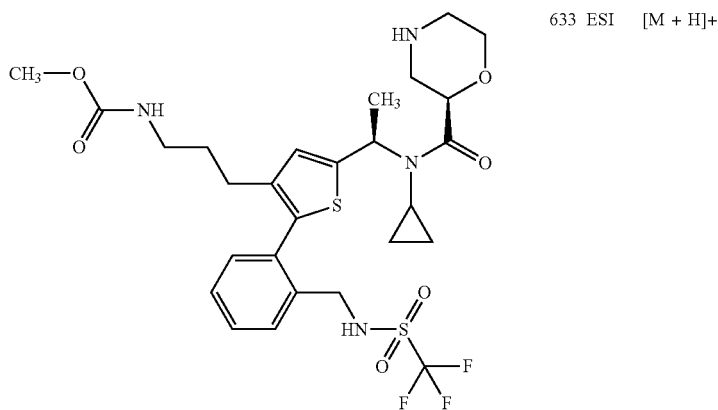 | 633 ESI [M + H]+ |
| Example 285 | 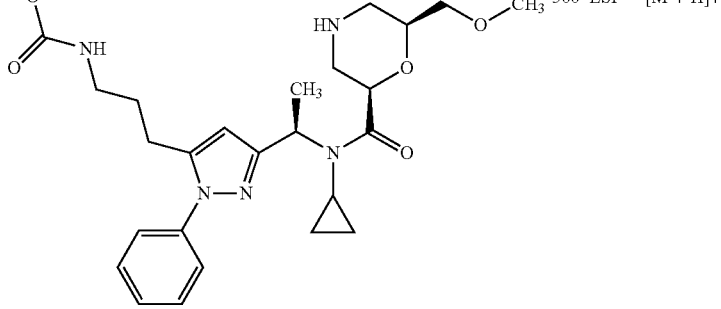 | 500 ESI [M + H]+ |
TABLE 52
| Example 286 | 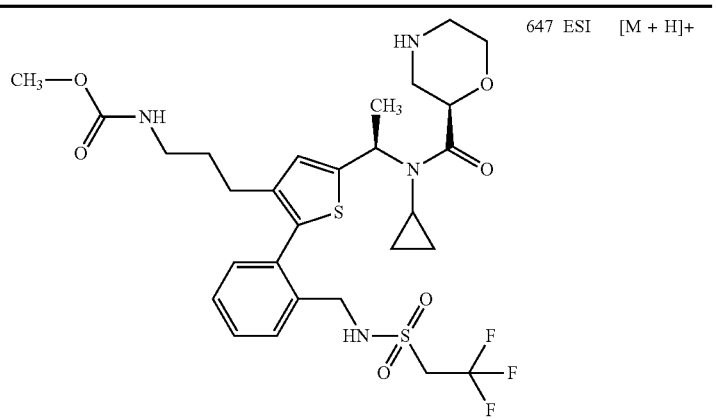 | 647 ESI [M + H]+ |

TABLE 52-continued
| Example 287 | 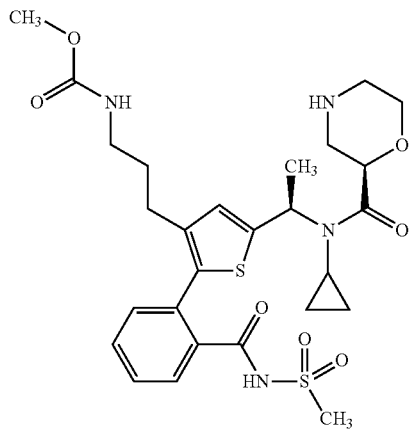 [SMILES: COC(=O)NCCCc1cc([C@@H](C)N(C(=O)[C@H]2CNCCO2)C2CC2)sc1-c1ccccc1C(=O)NS(C)(=O)=O] | 593 APCI [M + H]+ |
| Example 288 | 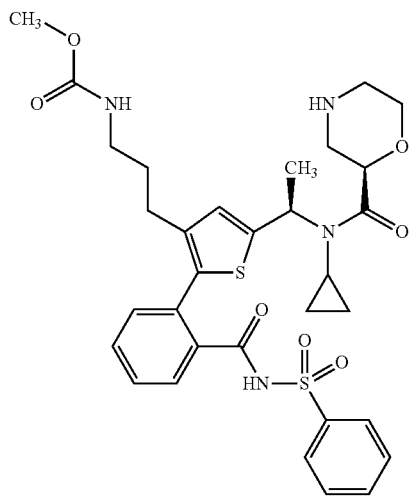 [SMILES: COC(=O)NCCCc1cc([C@@H](C)N(C(=O)[C@H]2CNCCO2)C2CC2)sc1-c1ccccc1C(=O)NS(=O)(=O)c1ccccc1] | 655 APCI [M + H]+ |
| Example 289 | 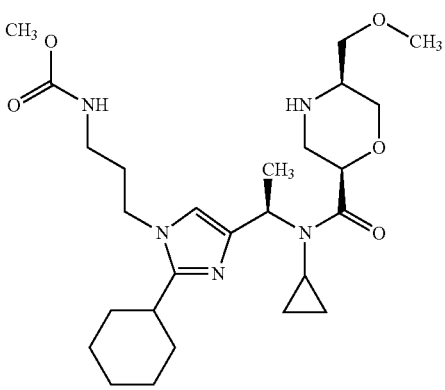 | 506 ESI [M + H]+ |

TABLE 53
| Example 290 | 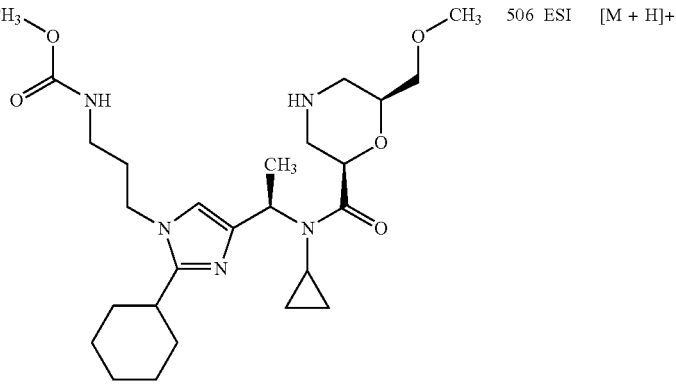 | 506 ESI [M + H]+ |
| Example 291 | 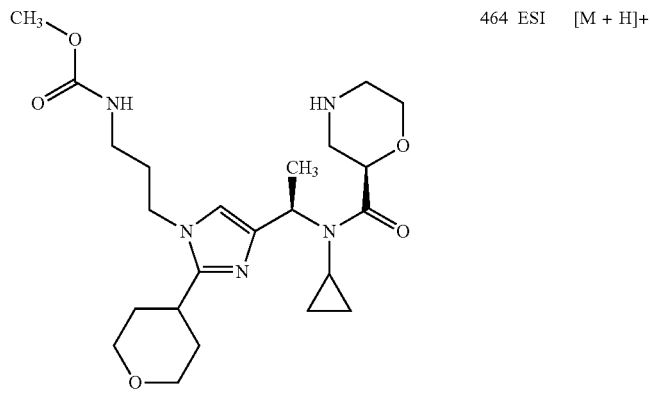 | 464 ESI [M + H]+ |
| Example 292 | 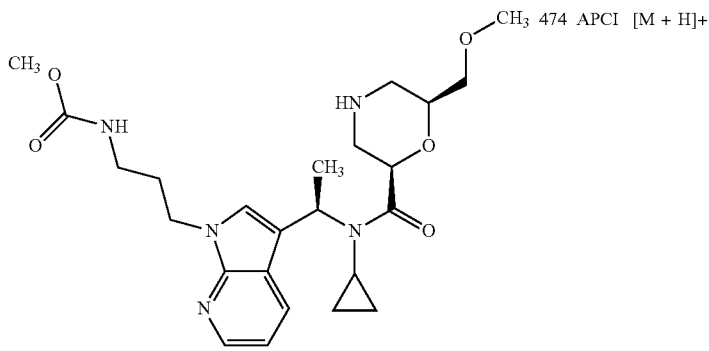 | 474 APCI [M + H]+ |
| Example 293 | 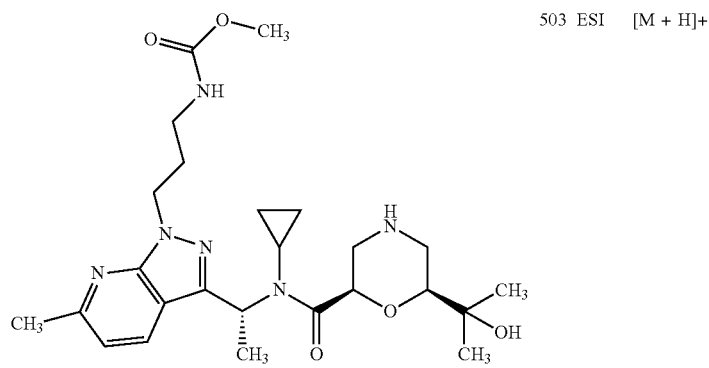 | 503 ESI [M + H]+ |

TABLE 53-continued
| Example 294 | 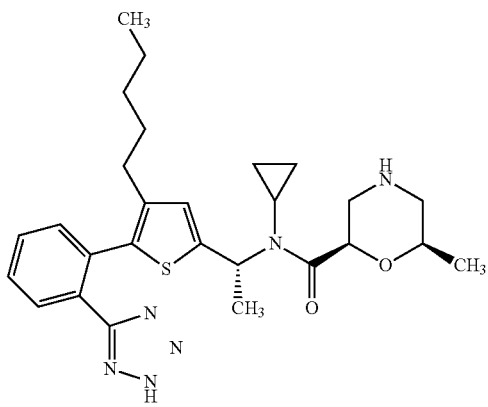 | 509 ESI [M + H]+ |
TABLE 54
| Example 295 | 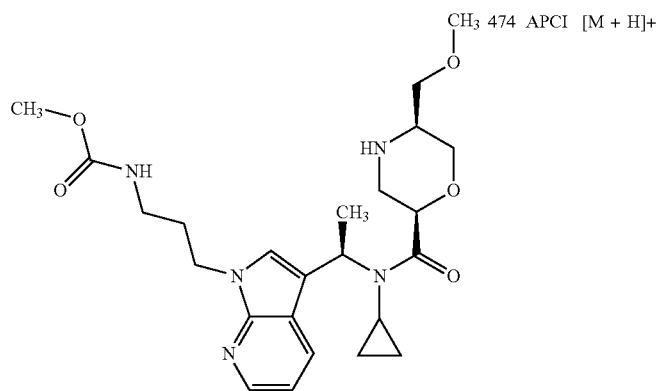 | 474 APCI [M + H]+ |
| Example 296 | 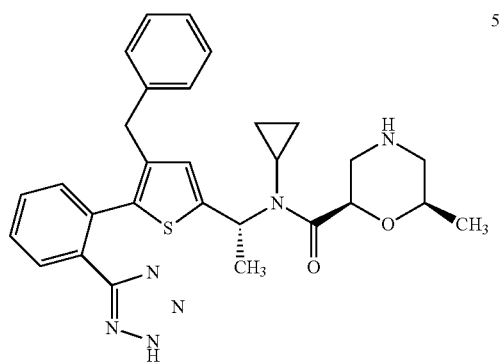 | 529 APCI [M + H]+ |

TABLE 54-continued
| Example 297 | 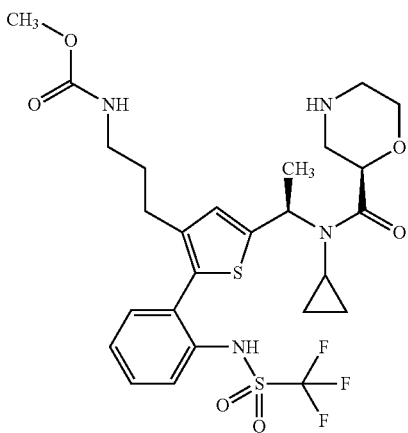 [SMILES: COC(=O)NCCCc1cc([C@@H](C)N(C(=O)[C@H]2CNCCO2)C2CC2)sc1-c1ccccc1NS(=O)(=O)C(F)(F)F] | 619 APCI [M + H]+ |
| Example 298 | 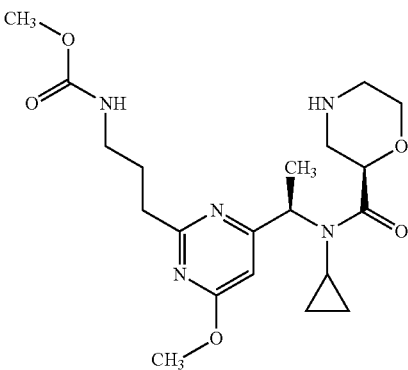 [SMILES: COC(=O)NCCCc1nc(OC)cc([C@@H](C)N(C(=O)[C@H]2CNCCO2)C2CC2)n1] | 422 APCI [M + H]+ |
TABLE 55
| Example 299 | 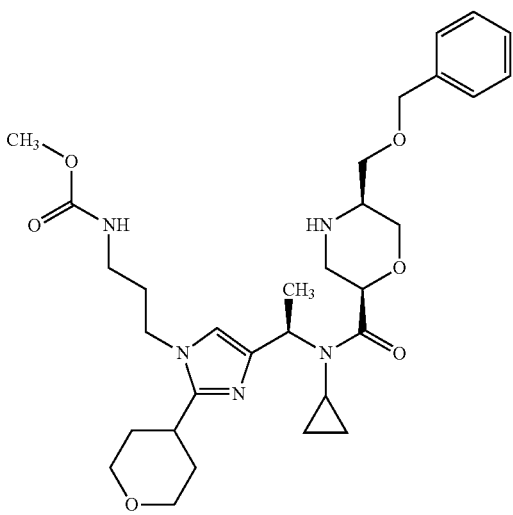 [SMILES: COC(=O)NCCCn1cc([C@@H](C)N(C(=O)[C@H]2CN[C@@H](COCc3ccccc3)CO2)C2CC2)nc1C1CCOCC1] | 584 ESI [M + H]+ |

TABLE 55-continued
| Example 300 | 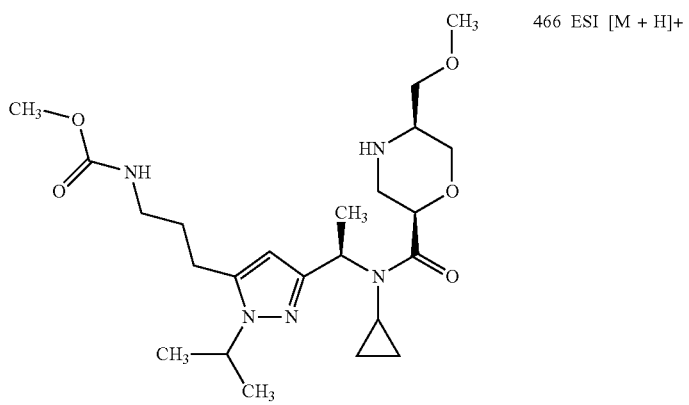 | 466 ESI [M + H]+ |
| Example 301 | 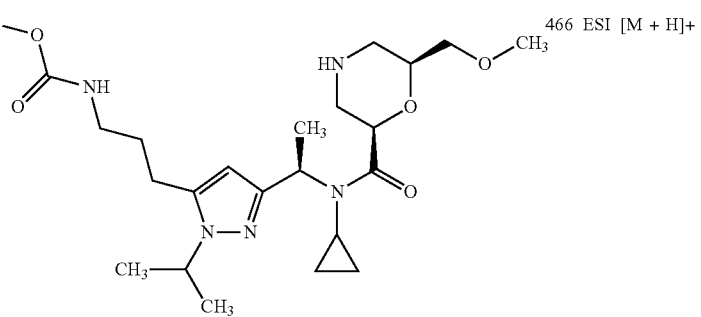 | 466 ESI [M + H]+ |
| Example 302 | 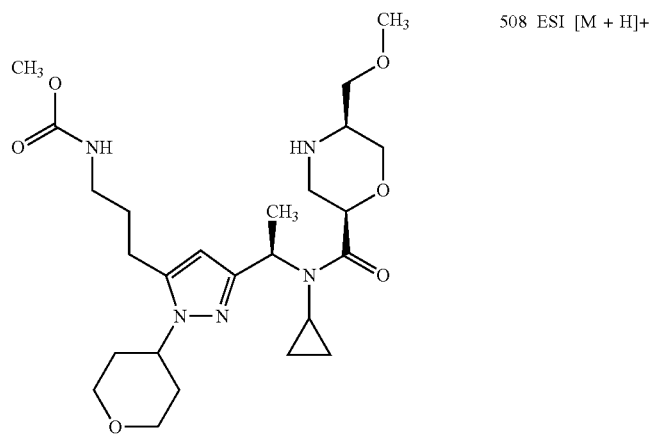 | 508 ESI [M + H]+ |
| Example 303 | 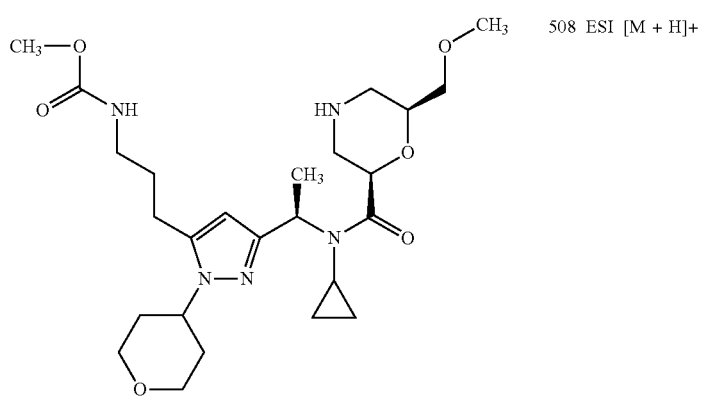 | 508 ESI [M + H]+ |

TABLE 56
| Example 304 | 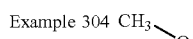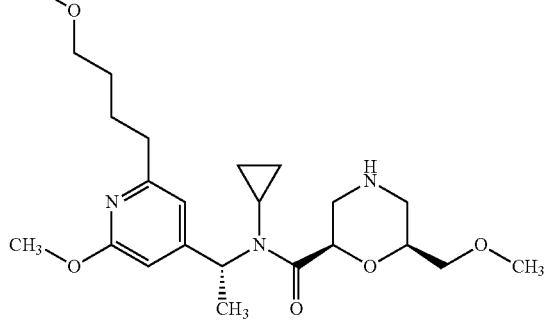 | 436 APCI [M + H]+ |
| Example 305 | 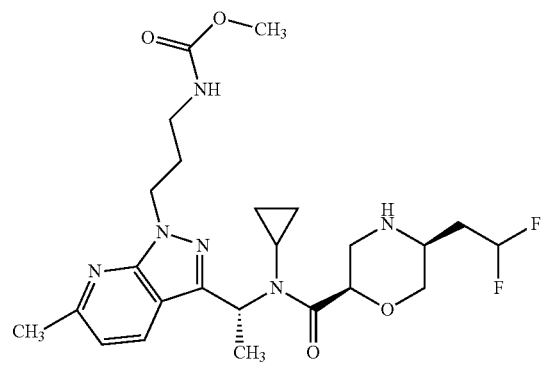 [SMILES: COC(=O)NCCCn1nc([C@@H](C)N(C(=O)[C@H]2CN[C@@H](CC(F)F)CO2)C2CC2)c2ccc(C)nc21] | 509 APCI [M + H]+ |
| Example 306 | 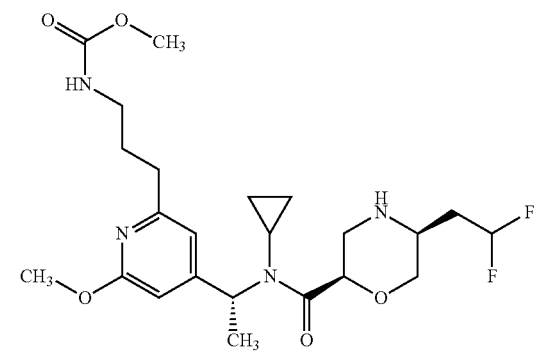 [SMILES: COC(=O)NCCCc1cc([C@@H](C)N(C(=O)[C@H]2CN[C@@H](CC(F)F)CO2)C2CC2)cc(OC)n1] | 485 APCI [M + H]+ |
| Example 307 | 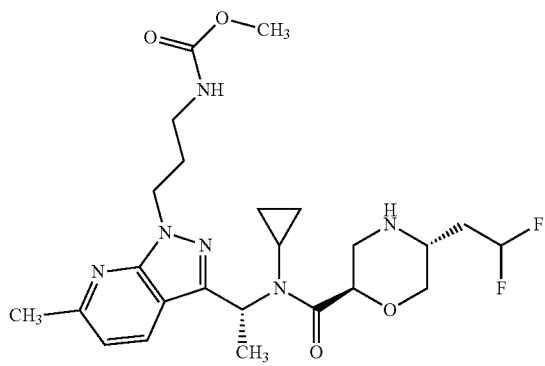 [SMILES: COC(=O)NCCCn1nc([C@@H](C)N(C(=O)[C@H]2CN[C@H](CC(F)F)CO2)C2CC2)c2ccc(C)nc21] | 509 APCI [M + H]+ |

TABLE 56-continued
| Example 308 | 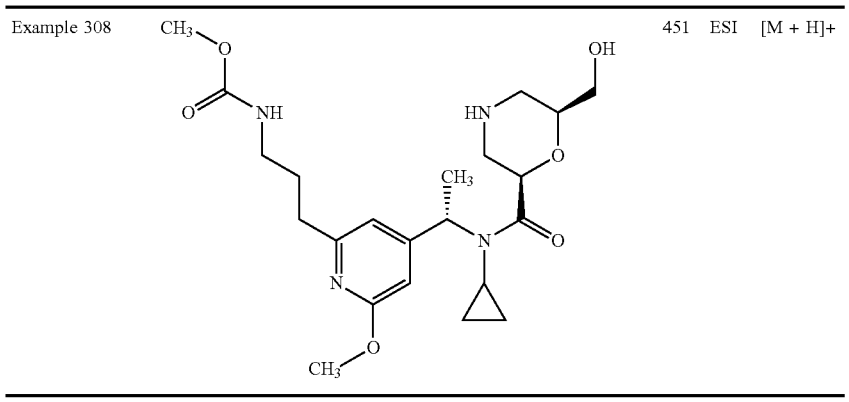 | 451 | ESI | [M + H]+ |
TABLE 57
| Example 309 | 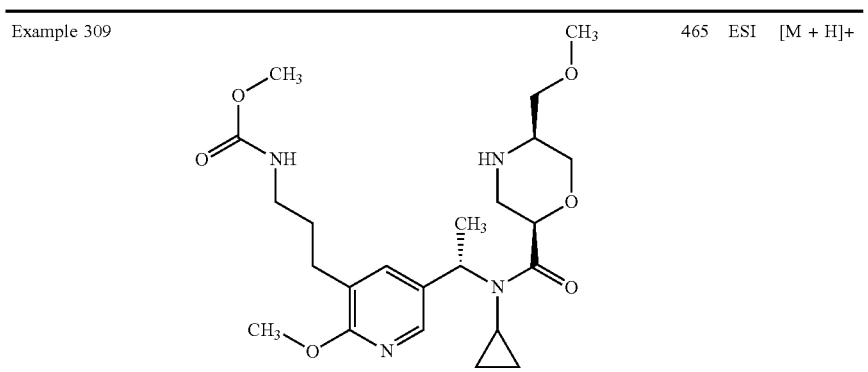 | 465 | ESI | [M + H]+ |
| Example 310 | 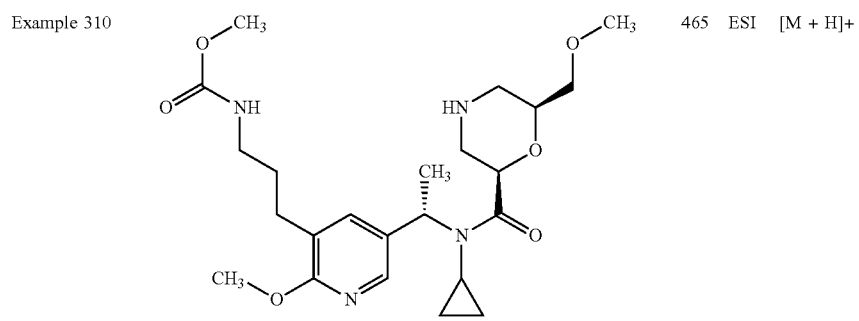 | 465 | ESI | [M + H]+ |
| Example 311 | 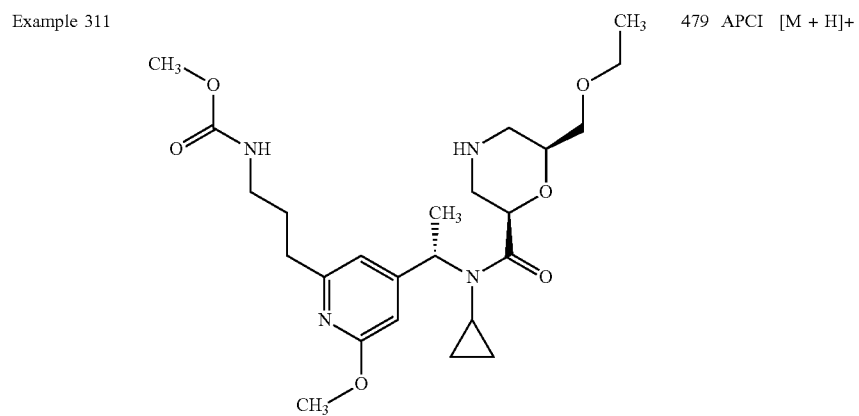 | 479 | APCI | [M + H]+ |

TABLE 57-continued
| Example 312 | 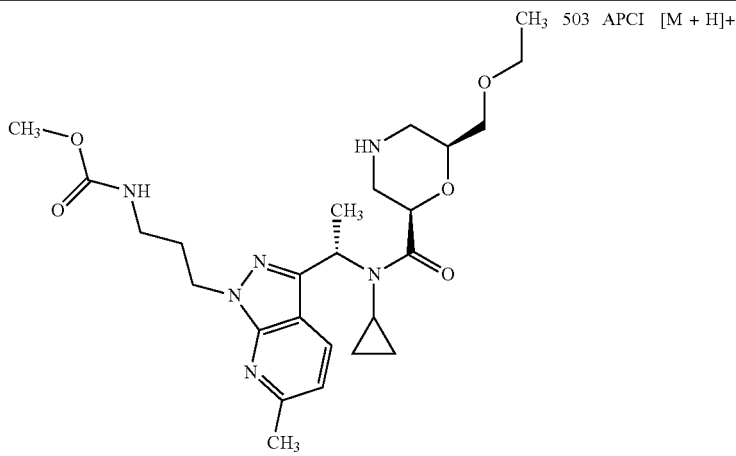 | CH₃ | 503 | APCI [M + H]+ |
| Example 313 | 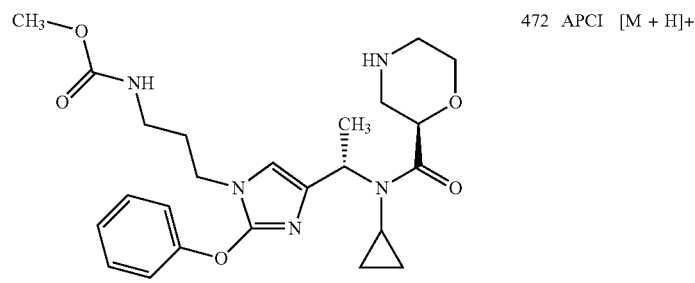 | | 472 | APCI [M + H]+ |
TABLE 58
| Example 314 | 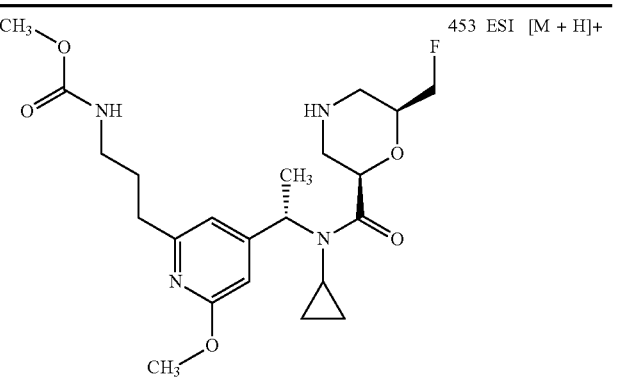 | | 453 | ESI [M + H]+ |
| Example 315 | 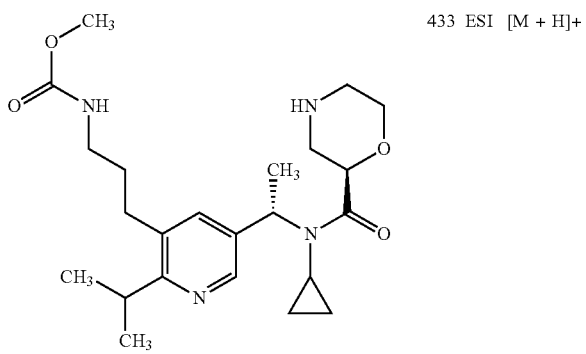 | | 433 | ESI [M + H]+ |

TABLE 58-continued
| Example 316 | 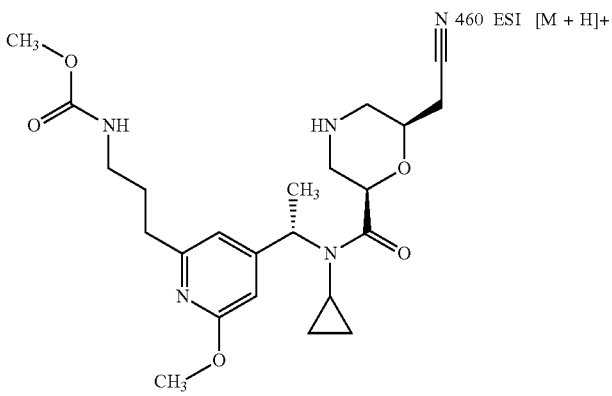 | 460 ESI [M + H]+ |
|---|---|---|
| Example 317 | 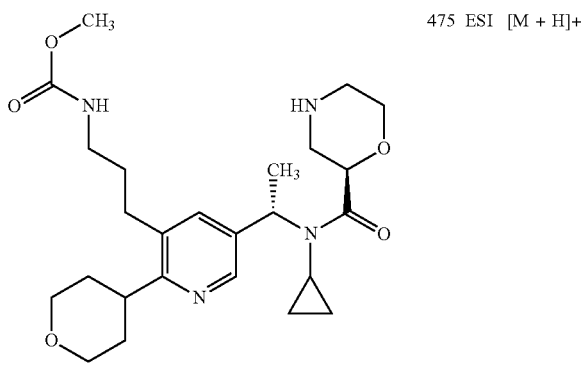 | 475 ESI [M + H]+ |
| Example 318 | 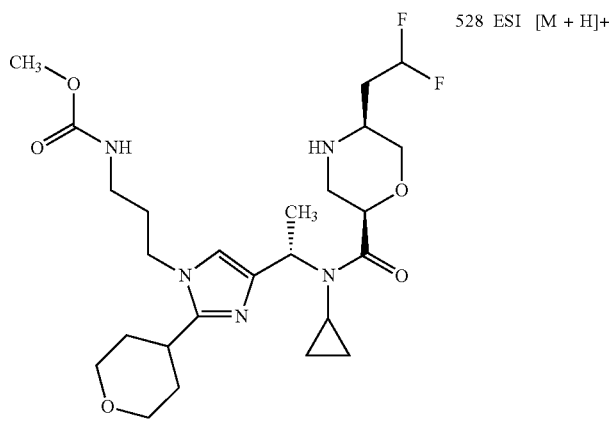 | 528 ESI [M + H]+ |
TABLE 59
| Example 319 | 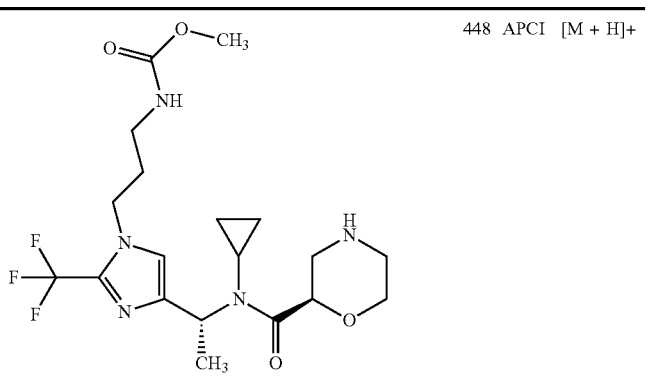 | 448 APCI [M + H]+ |
|---|---|---|

TABLE 59-continued
| Example 320 | 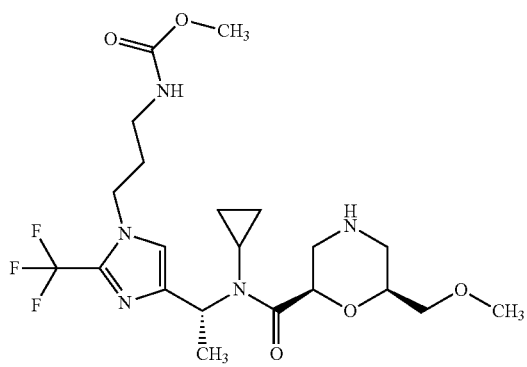 [SMILES: COC[C@@H]1CNC[C@H](C(=O)N(C2CC2)[C@H](C)c2cn(CCCNC(=O)OC)c(C(F)(F)F)n2)O1] | 492 | APCI | [M + H]+ |
| Example 321 | 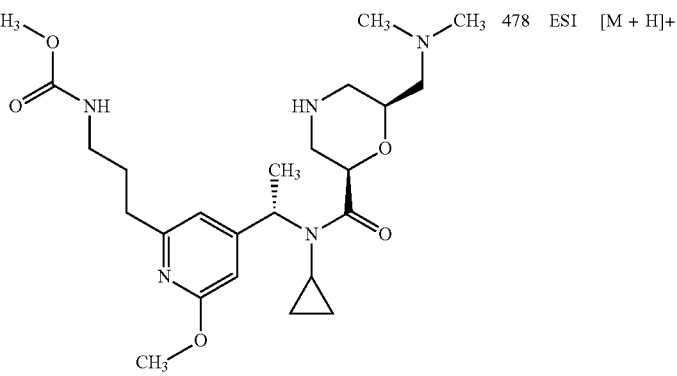 | 478 | ESI | [M + H]+ |
| Example 322 | 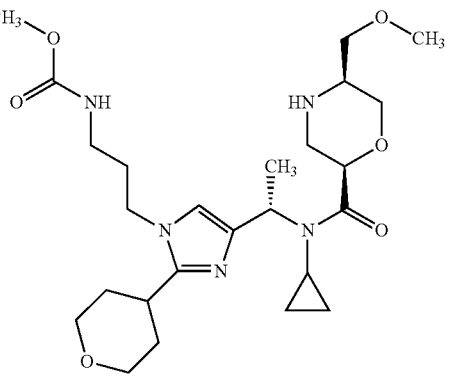 | 508 | ESI | [M + H]+ |
| Example 323 | 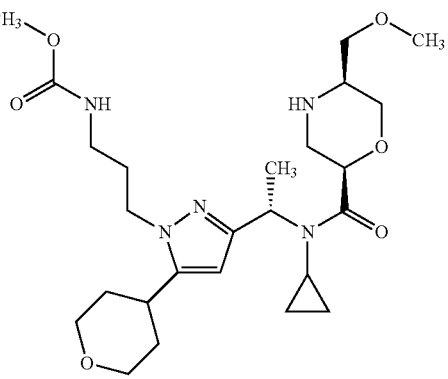 | 508 | ESI | [M + H]+ |

TABLE 60
| Example 324 | 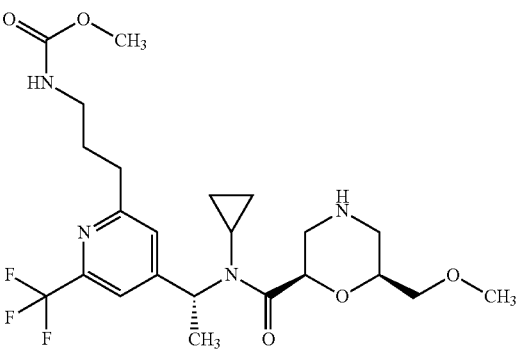 [SMILES: COC[C@@H]1CNC[C@H](C(=O)N(C2CC2)[C@H](C)c2cc(CCCNC(=O)OC)nc(C(F)(F)F)c2)O1] | 503 APCI [M + H]+ |
| Example 325 | 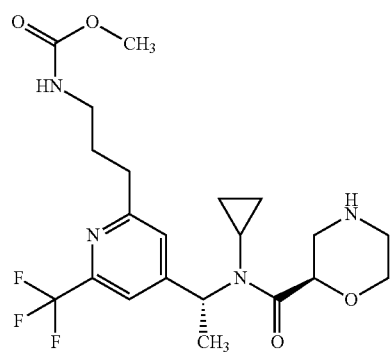 [SMILES: COC(=O)NCCCc1cc([C@@H](C)N(C(=O)[C@H]2CNCCO2)C2CC2)cc(C(F)(F)F)n1] | 459 APCI [M + H]+ |
| Example 326 | 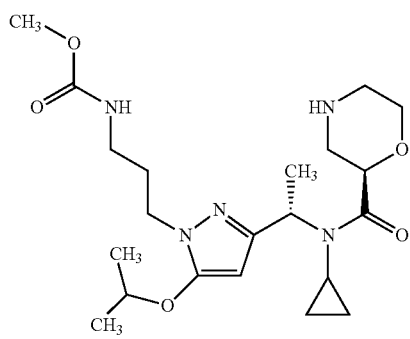 [SMILES: COC(=O)NCCCn1nc([C@H](C)N(C(=O)[C@H]2CNCCO2)C2CC2)cc1OC(C)C] | 438 APCI [M + H]+ |
| Example 327 | 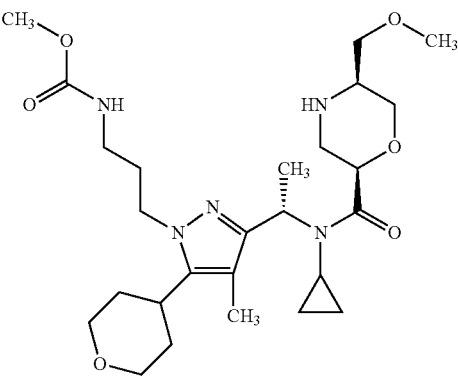 [SMILES: COC[C@H]1CO[C@@H](C(=O)N(C2CC2)[C@@H](C)c2nn(CCCNC(=O)OC)c(C3CCOCC3)c2C)CN1] | 522 ESI [M + H]+ |

TABLE 60-continued
| Example 328 | 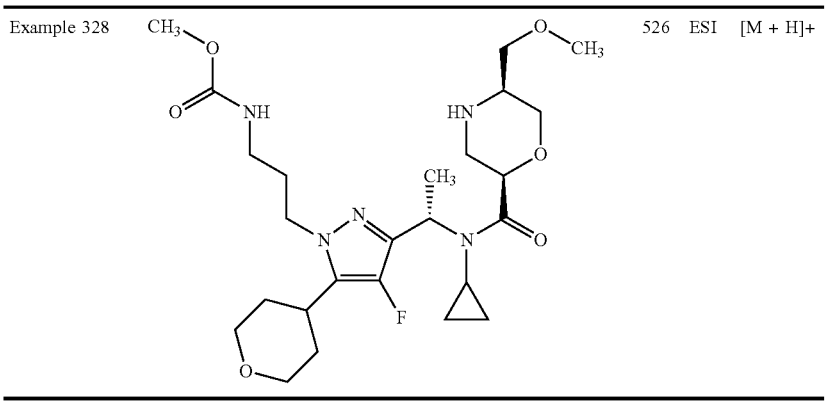 | 526 | ESI | [M + H]+ |
TABLE 61
| Example 329 | 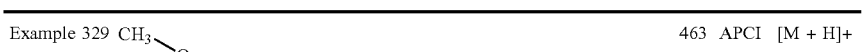 | 463 | APCI | [M + H]+ |
| Example 330 |  | 526 | ESI | [M + H]+ |
| Example 331 | 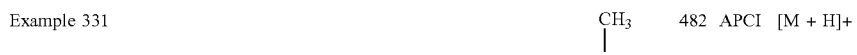 | 482 | APCI | [M + H]+ |

TABLE 61-continued
| Example 332 | 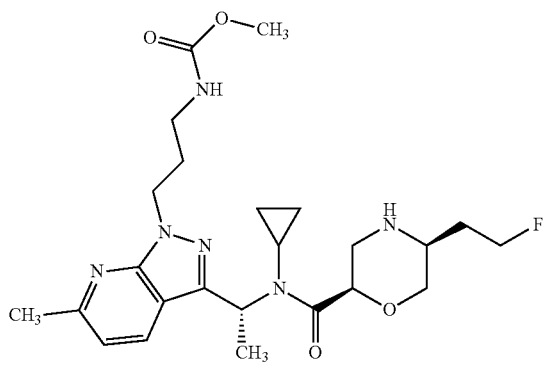 [SMILES: COC(=O)NCCCn1nc([C@@H](C)N(C(=O)[C@H]2CN[C@@H](CCF)CO2)C2CC2)c2ccc(C)nc21] | 491 APCI [M + H]+ |
| Example 333 | 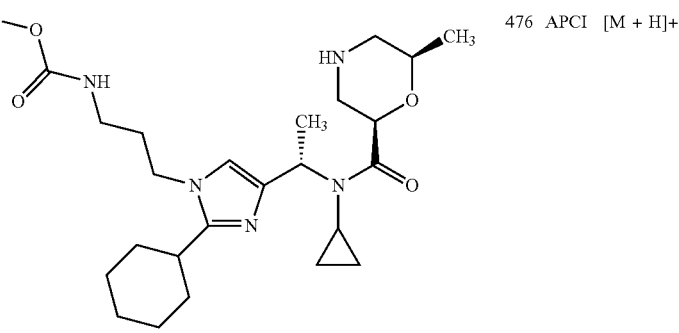 | 476 APCI [M + H]+ |
TABLE 62
| Example 334 | 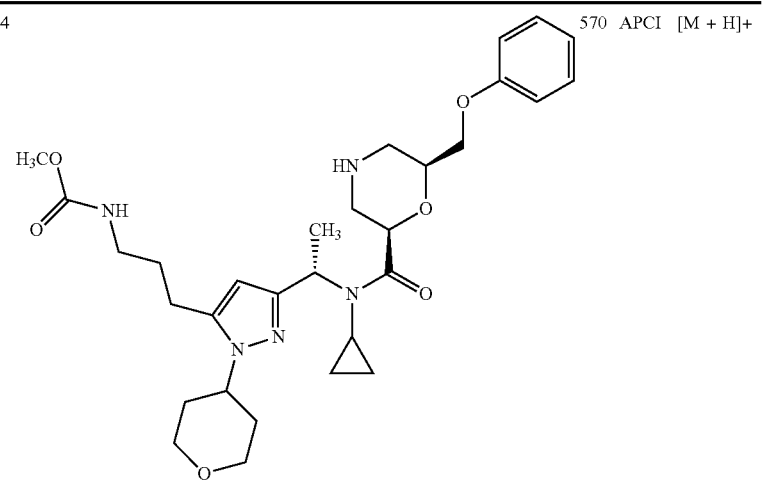 | 570 APCI [M + H]+ |
| Example 335 | 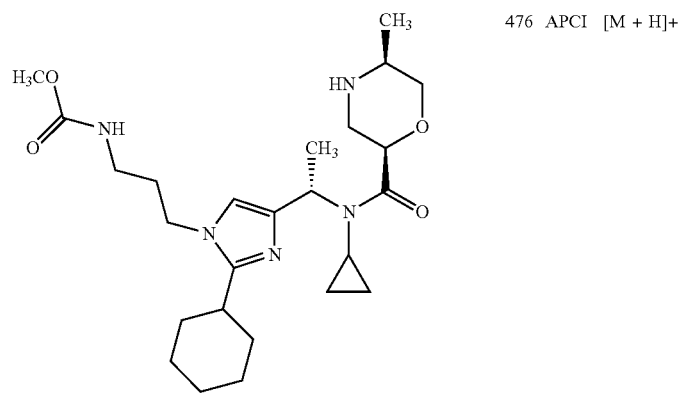 | 476 APCI [M + H]+ |

TABLE 62-continued
Example 336 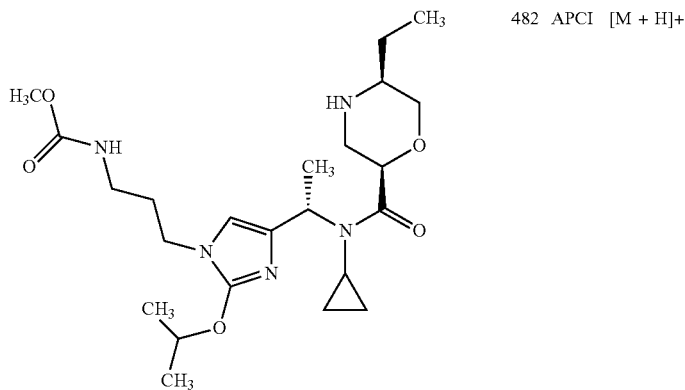 482 APCI [M + H]+
Example 337 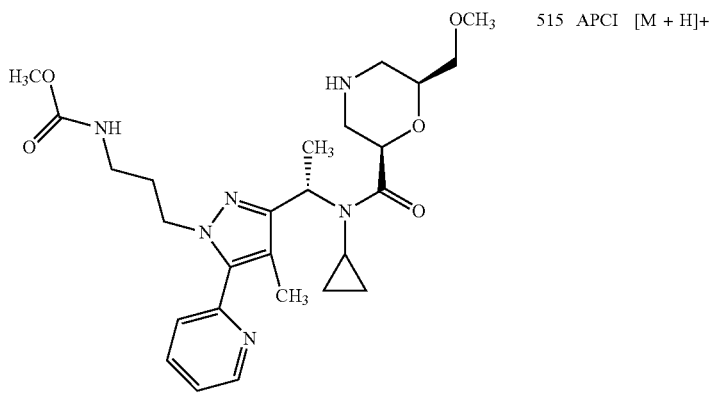 515 APCI [M + H]+
Example 338 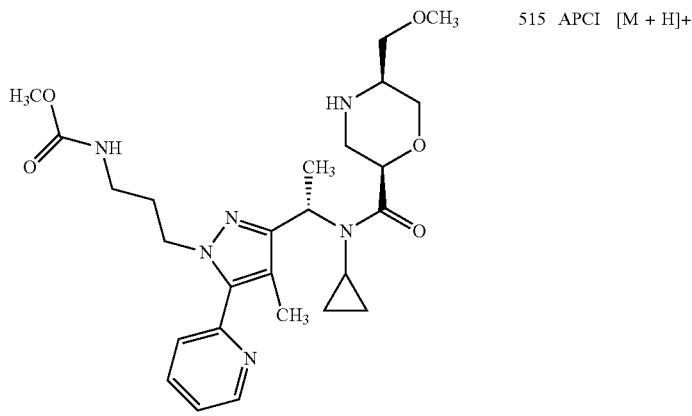 515 APCI [M + H]+

TABLE 63
| Example 339 | | 584 ESI [M + H]+ |
|---|---|---|
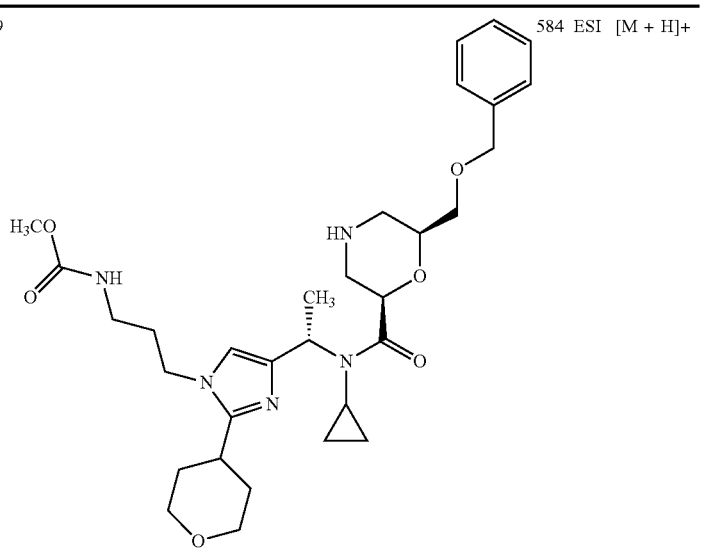
| Example 340 | | 496 ESI [M + H]+ |
|---|---|---|
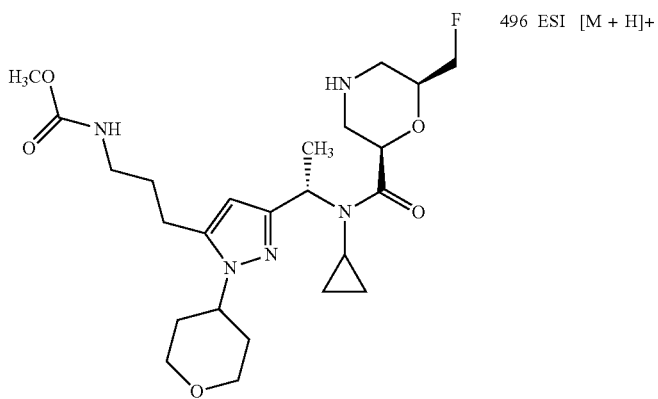
| Example 341 | | 484 ESI [M + H]+ |
|---|---|---|
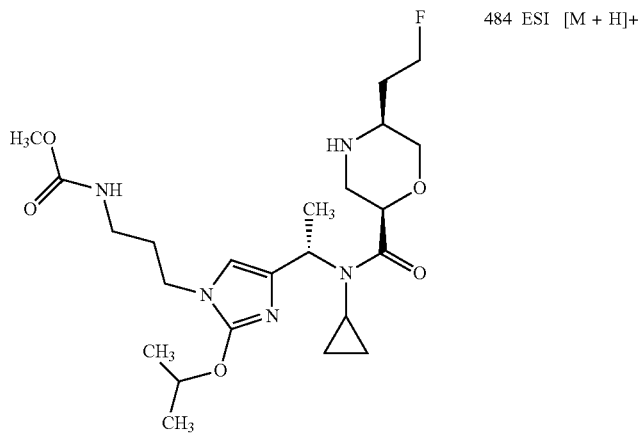

TABLE 64
| Example No. | Chemical Formula | Salt | MS Result ESI | Ion Species |
|---|---|---|---|---|
| Example 342 | 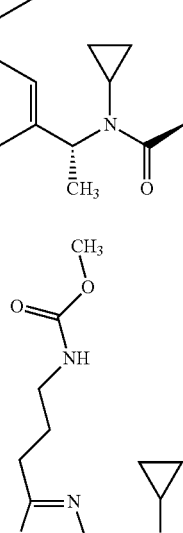 | 2HCl | 445.3 | [M + H]+ |
| Example 343 | 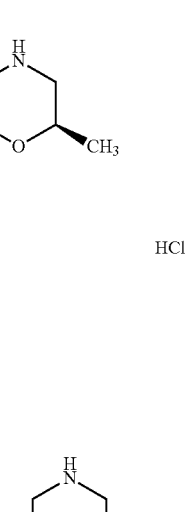 | HCl | 470.3 | [M + H]+ |
| Example 344 | 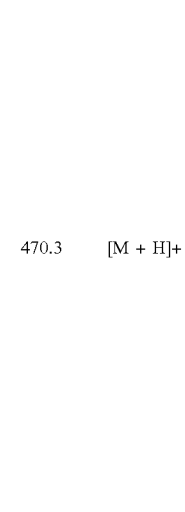 | HCl | 484.3 | [M + H]+ |
| Example 345 |  | HCl | 484.3 | [M + H]+ |

TABLE 65
Example 346 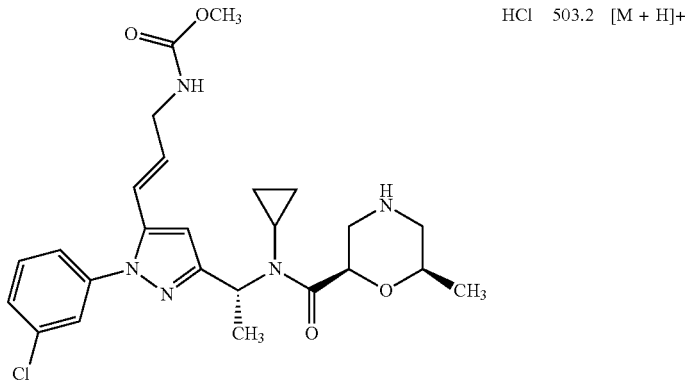 HCl 503.2 [M + H]+
Example 347 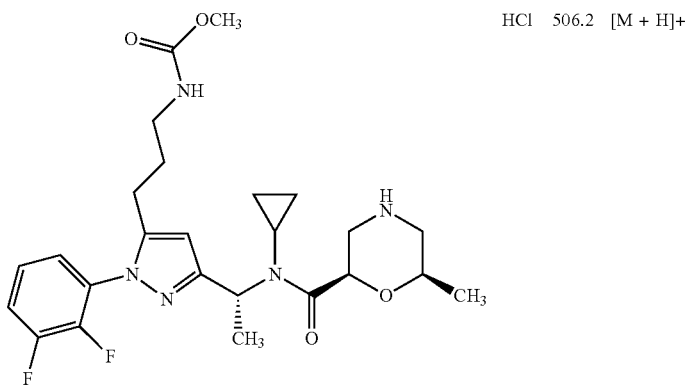 HCl 506.2 [M + H]+
Example 348 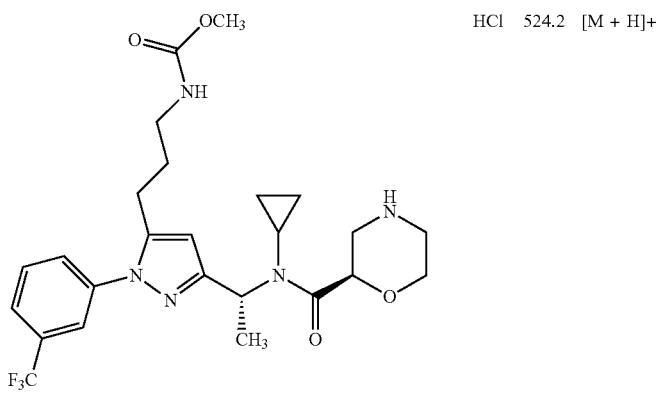 HCl 524.2 [M + H]+
Example 349 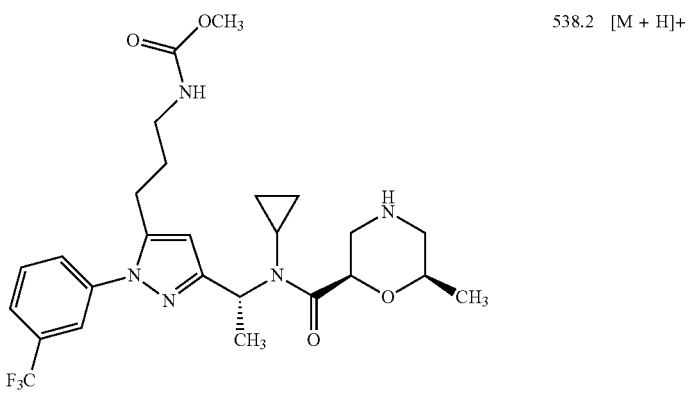 538.2 [M + H]+

TABLE 65-continued
| Example 350 | 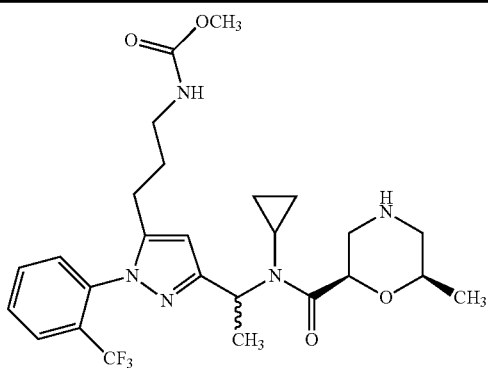 | | 538.3 [M + H]+ |
TABLE 66
| Example 351 | 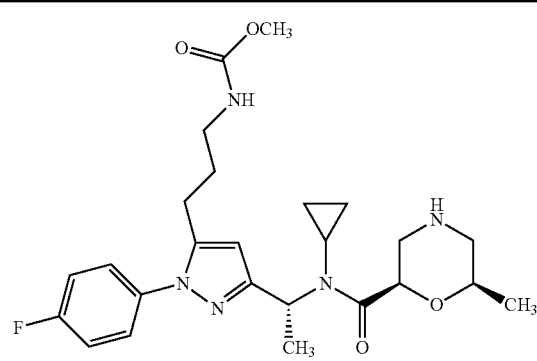 | HCl | 488.3 [M + H]+ |
| Example 352 | 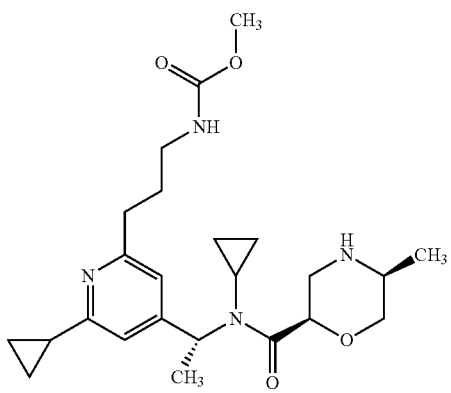 [SMILES: COC(=O)NCCCc1cc([C@@H](C)N(C(=O)[C@H]2CN[C@@H](C)CO2)C2CC2)cc(C2CC2)n1] | 2HCl | 445.3 [M + H]+ |
| Example 353 | 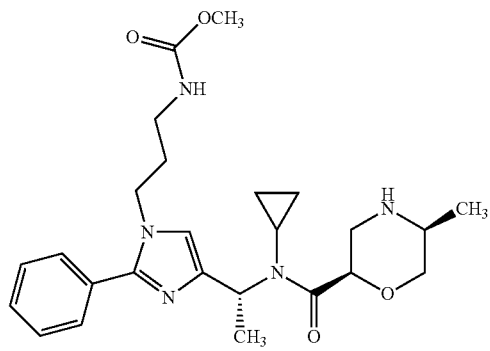 [SMILES: COC(=O)NCCCn1cc([C@@H](C)N(C(=O)[C@H]2CN[C@@H](C)CO2)C2CC2)nc1-c1ccccc1] | HCl | 470.2 [M + H]+ |

TABLE 66-continued
| Example 354 | 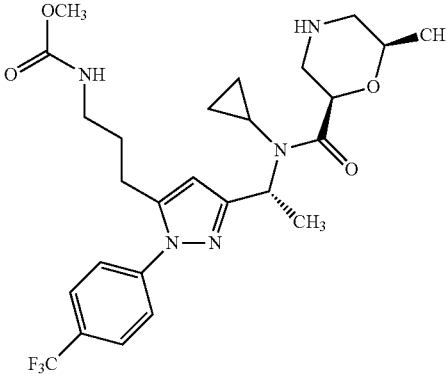 | HCl | 538.2 [M + H]+ |
| Example 355 | 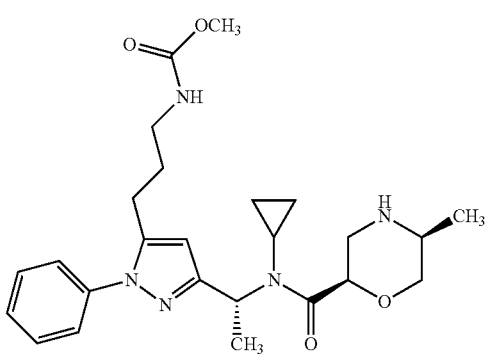 [SMILES: COC(=O)NCCCc1cc([C@@H](C)N(C(=O)[C@H]2CN[C@@H](C)CO2)C2CC2)nn1-c1ccccc1] | HCl | 470.3 [M + H]+ |
TABLE 67
| Example 356 | 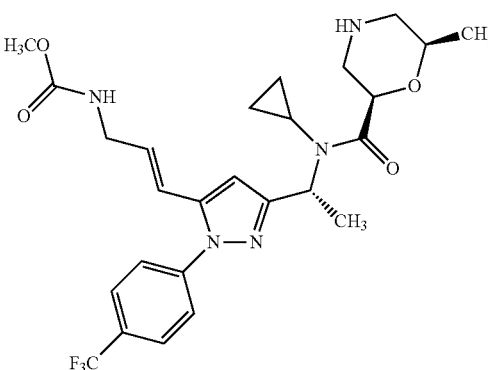 | HCl | 536.2 [M + H]+ |
| Example 357 | 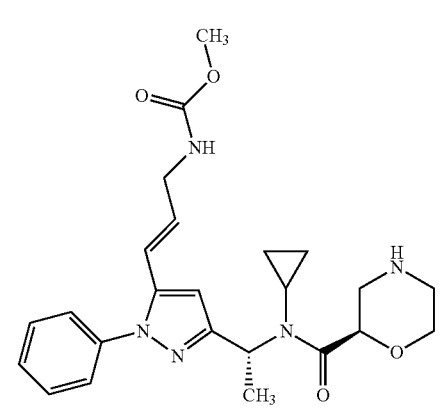 [SMILES: COC(=O)NC/C=C/c1cc([C@@H](C)N(C(=O)[C@H]2CNCCO2)C2CC2)nn1-c1ccccc1] | HCl | 454.2 [M + H]+ |

TABLE 67-continued
| Example 358 | 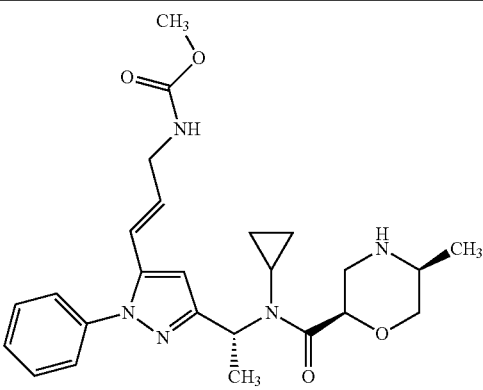 | HCl | 468.2 | [M + H]+ |
| Example 359 | 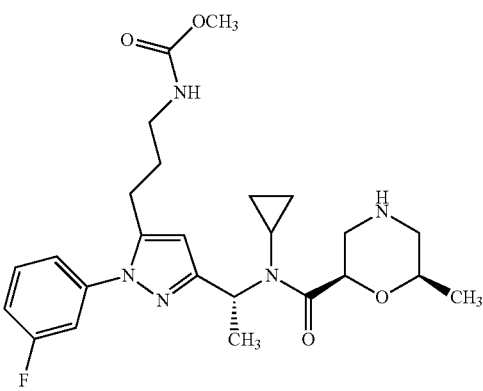 | HCl | 488.2 | [M + H]+ |
TABLE 68
| Example 360 | 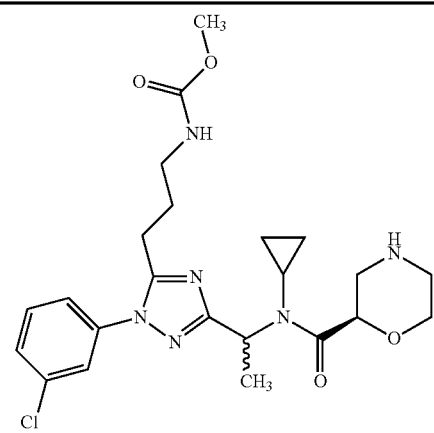 | HCl | 491.2 | [M + H]+ |
| Example 361 | 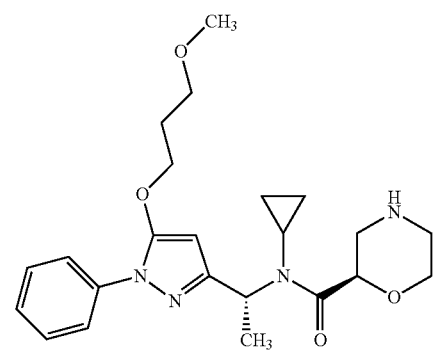 [SMILES: COCCCOc1cc([C@@H](C)N(C(=O)[C@H]2CNCCO2)C2CC2)nn1-c1ccccc1] | HCl | 429.2 | [M + H]+ |

TABLE 68-continued
| Example 362 | 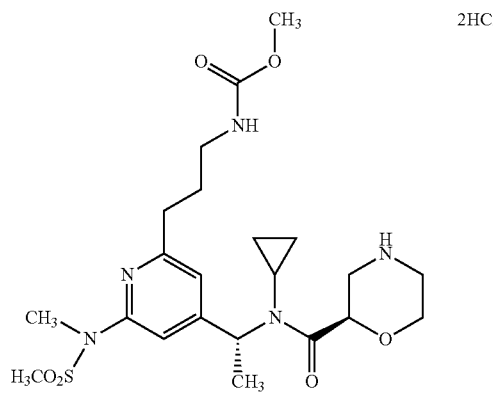 | 2HCl | 498.2 | [M + H]+ |
| Example 363 | 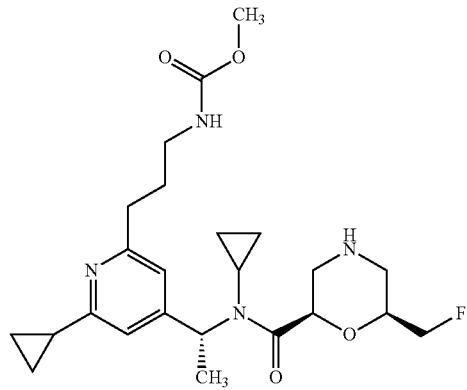 [SMILES: COC(=O)NCCCc1cc([C@@H](C)N(C(=O)[C@H]2CNC[C@@H](CF)O2)C2CC2)cc(C2CC2)n1] | 2HCl | 464.3 | [M + H]+ |
TABLE 69
| Example 364 | 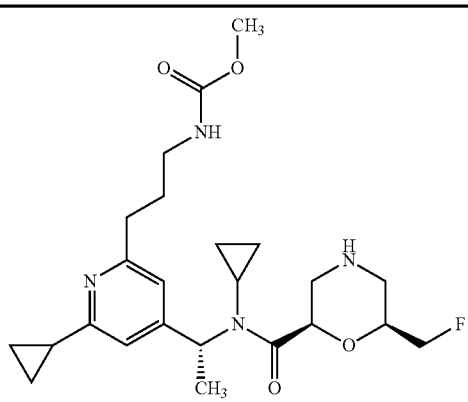 | 2HCl | 464.3 | [M + H]+ |

TABLE 69-continued
| Example 365 | 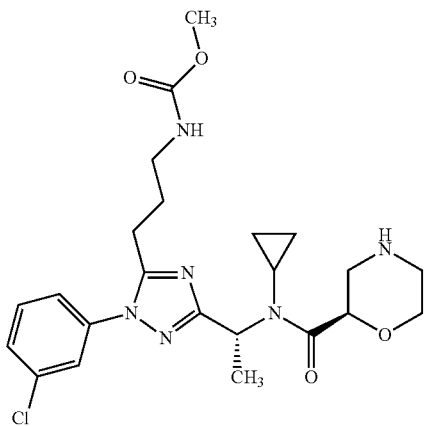 [SMILES: COC(=O)NCCCc1nc([C@@H](C)N(C(=O)[C@H]2CNCCO2)C2CC2)nn1-c1cccc(Cl)c1] | 491.2 [M + H]+ |
| Example 366 | 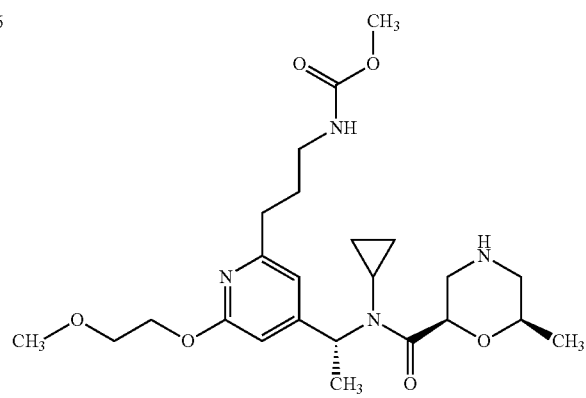 | 2HCl 479.3 [M + H]+ |
| Example 367 | 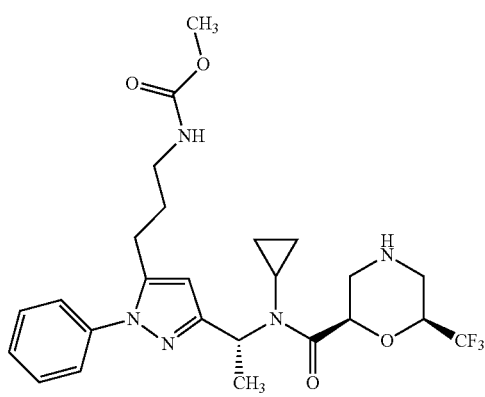 [SMILES: COC(=O)NCCCc1cc([C@@H](C)N(C(=O)[C@H]2CNC[C@@H](C(F)(F)F)O2)C2CC2)nn1-c1ccccc1] | 524.2 [M + H]+ |

TABLE 70
| Example 368 | 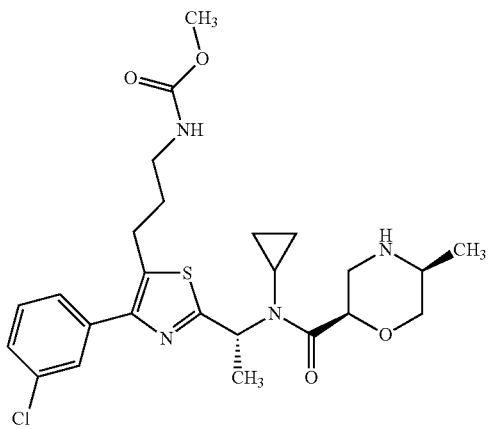 [SMILES: COC(=O)NCCCc1sc([C@@H](C)N(C(=O)[C@H]2CN[C@@H](C)CO2)C2CC2)nc1-c1cccc(Cl)c1] | HCl | 521.2 [M + H]+ |
| Example 369 | 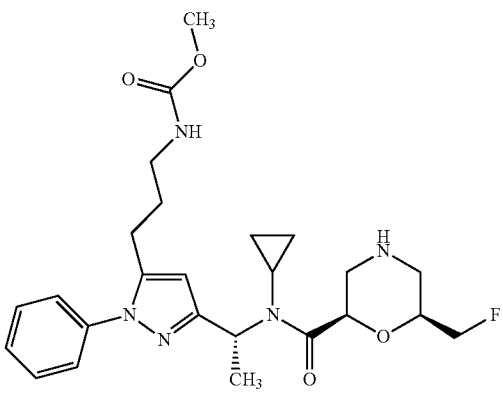 [SMILES: COC(=O)NCCCc1cc([C@@H](C)N(C(=O)[C@H]2CNC[C@@H](CF)O2)C2CC2)nn1-c1ccccc1] | | 488.3 [M + H]+ |
| Example 370 | 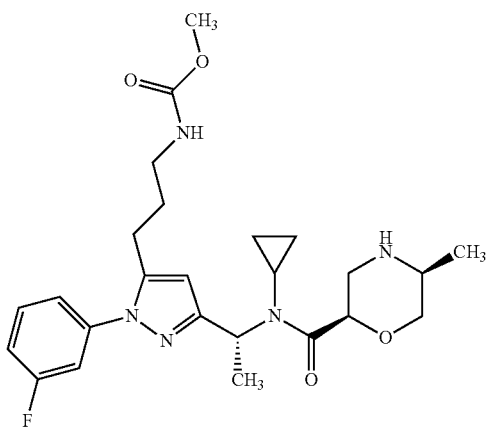 [SMILES: COC(=O)NCCCc1cc([C@@H](C)N(C(=O)[C@H]2CN[C@@H](C)CO2)C2CC2)nn1-c1cccc(F)c1] | | 488.3 [M + H]+ |
| Example 371 | 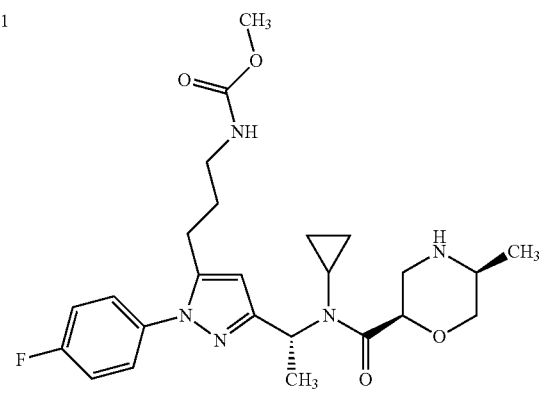 | | 488.2 [M + H]+ |

TABLE 71
| Example 372 | 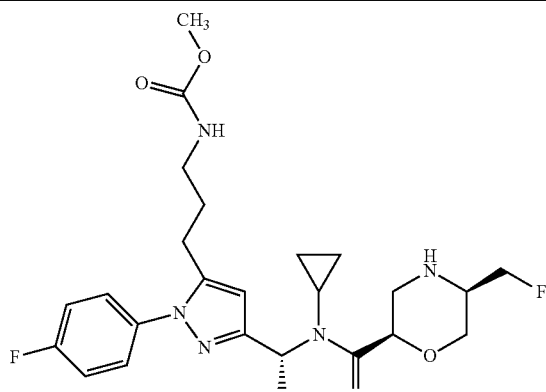 | 506.2 [M + H]+ |
| Example 373 | 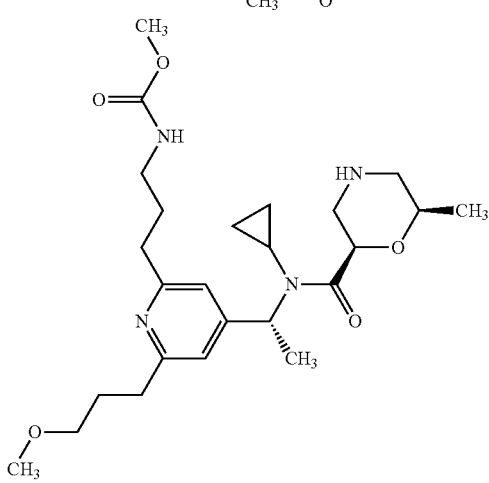 | 2HCl 477.3 [M + H]+ |
| Example 374 | 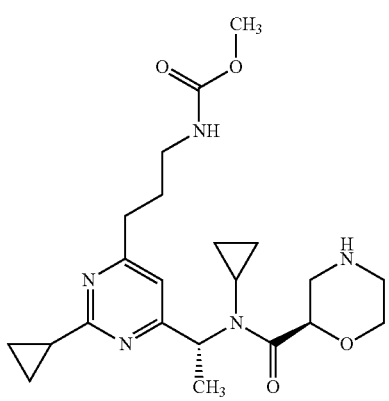 [SMILES: COC(=O)NCCCc1cc([C@@H](C)N(C(=O)[C@H]2CNCCO2)C2CC2)nc(C2CC2)n1] | 432.2 [M + H]+ |
| Example 375 | 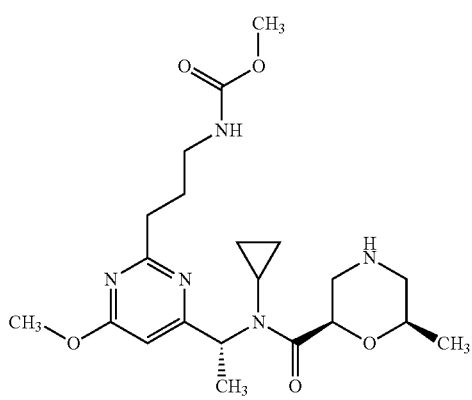 | 435.9 [M + H]+ |

TABLE 72
| Example 376 | 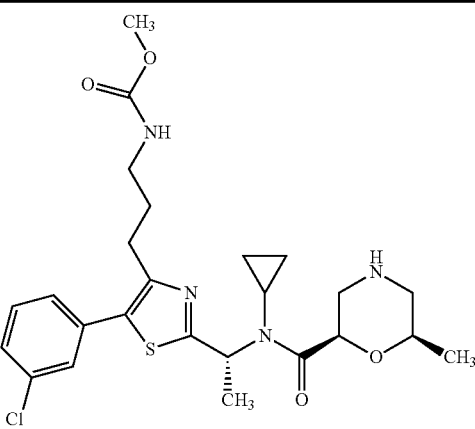 | HCl | 520.8 | [M + H]+ |
| Example 377 | 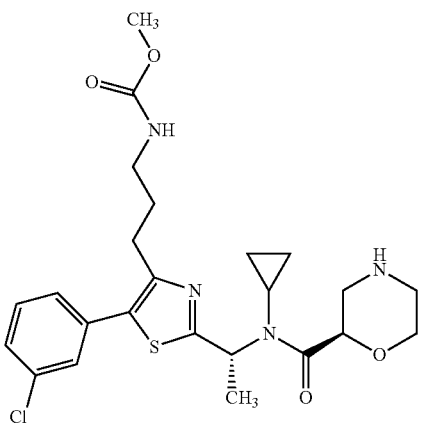 [SMILES: COC(=O)NCCCc1nc([C@@H](C)N(C(=O)[C@H]2CNCCO2)C2CC2)sc1-c1cccc(Cl)c1] | HCl | 506.8 | [M + H]+ |
| Example 378 | 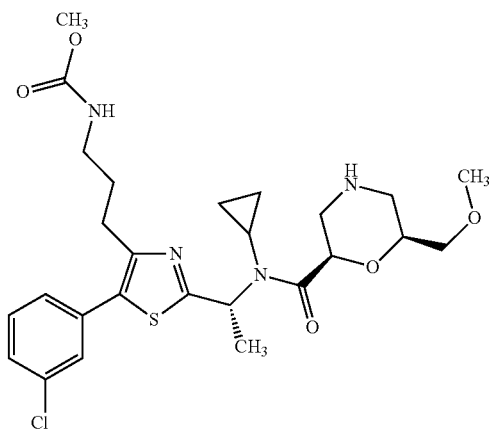 | HCl | 550.8 | [M + H]+ |
| Example 379 | 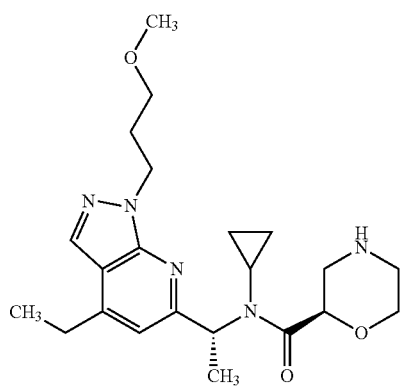 [SMILES: CCc1cc([C@@H](C)N(C(=O)[C@H]2CNCCO2)C2CC2)nc2c1cnn2CCCOC] | 2HCl | 415.9 | [M + H]+ |

TABLE 72-continued
| Example 380 | 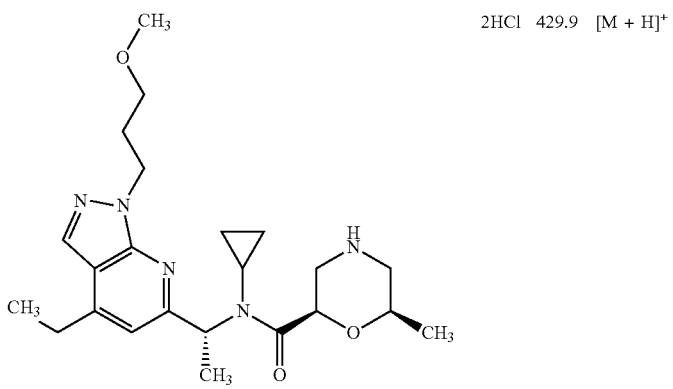 | 2HCl | 429.9 | [M + H]+ |
TABLE 73
| Example 381 | 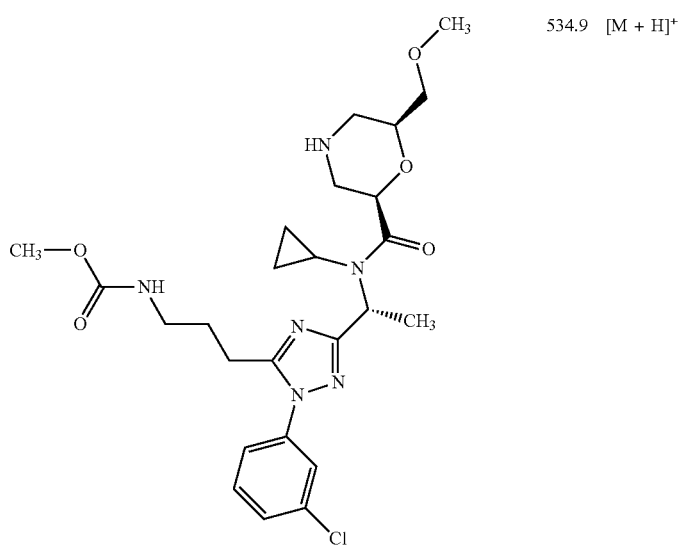 | | 534.9 | [M + H]+ |
| Example 382 | 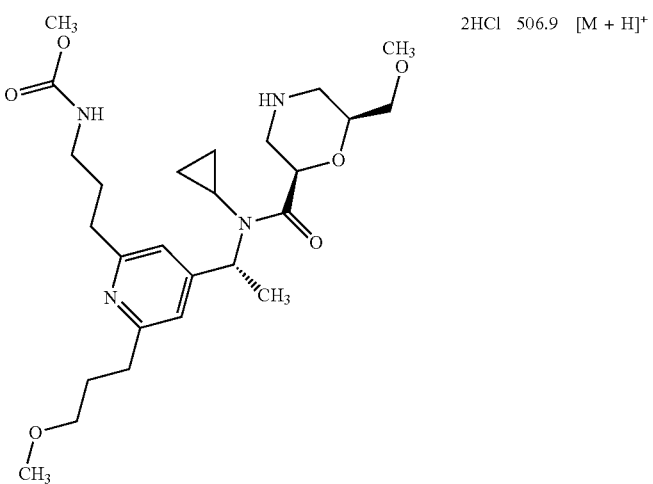 | 2HCl | 506.9 | [M + H]+ |

TABLE 73-continued
| Example 383 |  | 2HCl | 508.9 | [M + H]+ |
| Example 384 | 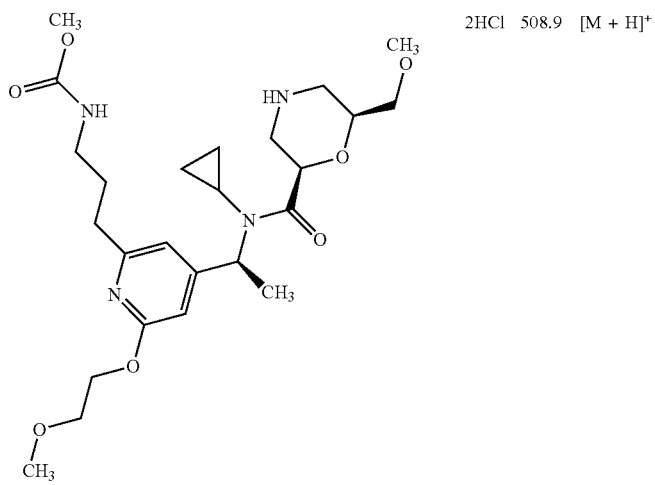 | 2HCl | 508.9 | [M + H]+ |
TABLE 74
| Example 385 | 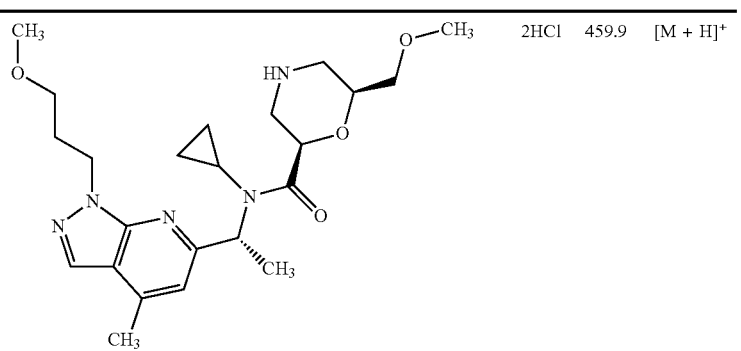 | 2HCl | 459.9 | [M + H]+ |

| | | | |
|---|---|---|---|
| Example 386 | 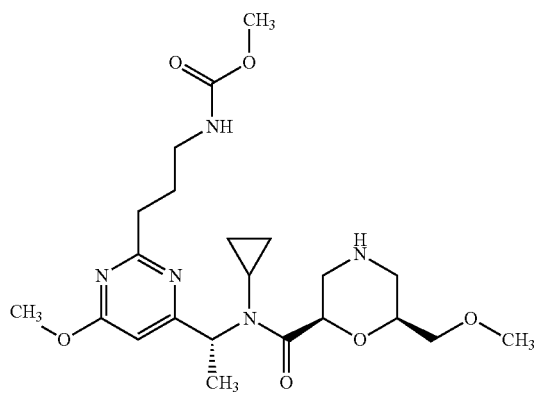 | | 233.5 [M + 2H]²⁺ |
| Example 387 | 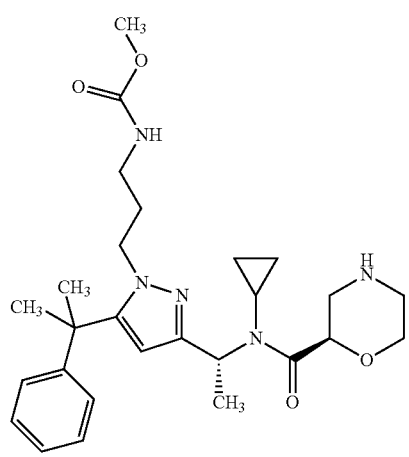 [SMILES: COC(=O)NCCCn1nc([C@@H](C)N(C(=O)[C@H]2CNCCO2)C2CC2)cc1C(C)(C)c1ccccc1] | | 497.9 [M + H]⁺ |
| Example 388 | 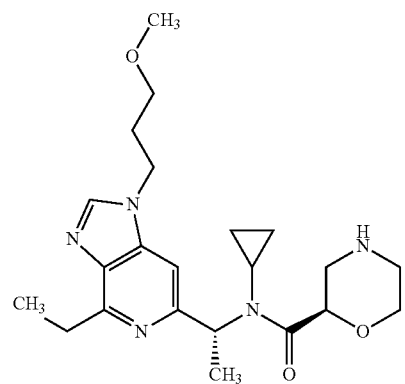 [SMILES: CCc1nc([C@@H](C)N(C(=O)[C@H]2CNCCO2)C2CC2)cc2c1ncn2CCCOC] | 2HCl | 416.0 [M + H]⁺ |
| Example 389 | 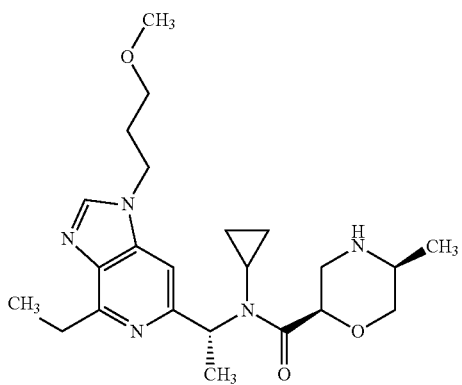 [SMILES: CCc1nc([C@@H](C)N(C(=O)[C@H]2CN[C@@H](C)CO2)C2CC2)cc2c1ncn2CCCOC] | 2HCl | 215.50 [M + 2H]²⁺ |

TABLE 75
| | | | |
|---|---|---|---|
| Example 390 | 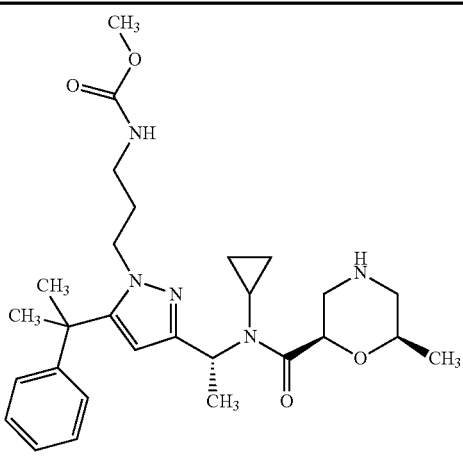 | 511.9 | [M + H]+ |
| Example 391 | 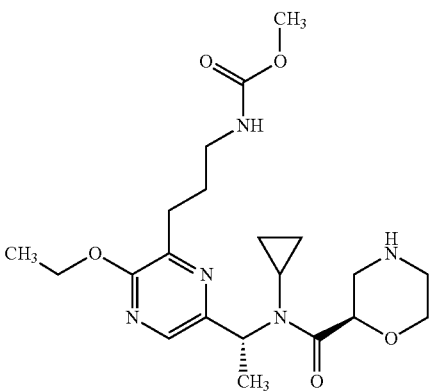 [SMILES: CCOc1ncc([C@@H](C)N(C(=O)[C@H]2CNCCO2)C2CC2)nc1CCCNC(=O)OC] | 435.9 | [M + H]+ |
| Example 392 | 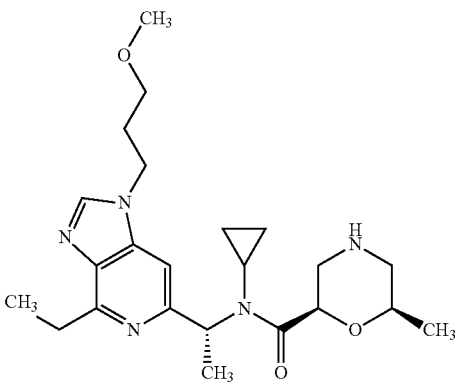 [SMILES: CCc1nc([C@@H](C)N(C(=O)[C@H]2CNC[C@@H](C)O2)C2CC2)cc2c1ncn2CCCOC] | 2HCl 215.50 | [M + 2H]2+ |
| Example 393 | 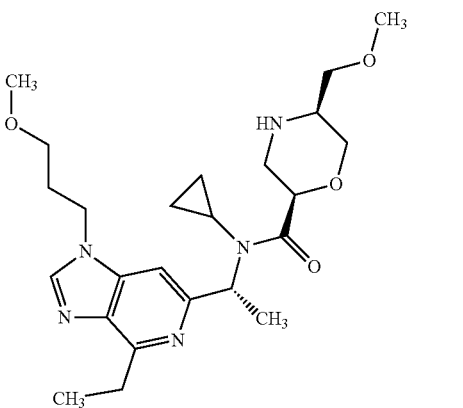 [SMILES: CCc1nc([C@@H](C)N(C(=O)[C@H]2CN[C@@H](COC)CO2)C2CC2)cc2c1ncn2CCCOC] | 2HCl 230.50 | [M + 2H]2+ |

TABLE 75-continued
| Example 394 | 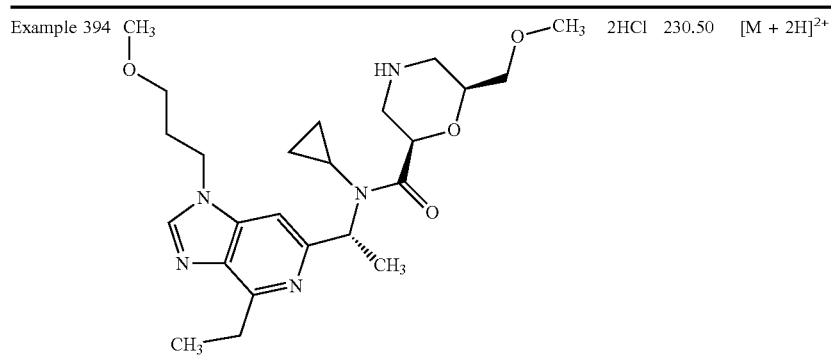 | 2HCl | 230.50 | [M + 2H]²⁺ |
TABLE 76
| Example 395 | 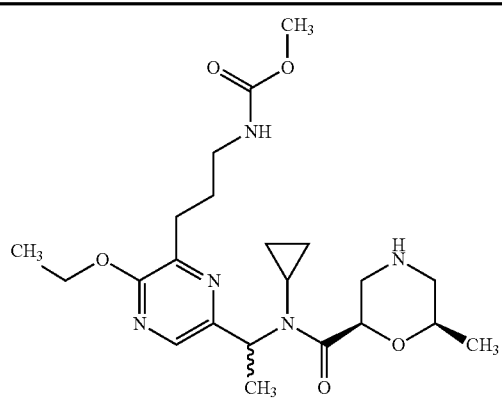 | | 449.9 [M + H]⁺ |
| Example 396 | 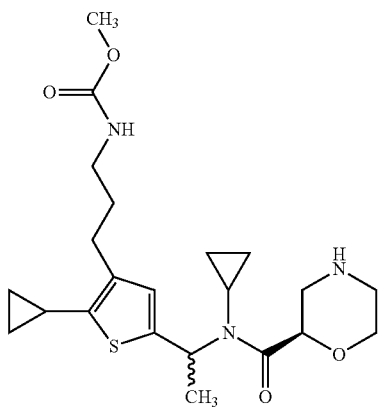 [SMILES: COC(=O)NCCCc1cc(C(C)N(C(=O)[C@H]2CNCCO2)C2CC2)sc1C1CC1] | | 435.9 [M + H]⁺ |
| Example 397 | 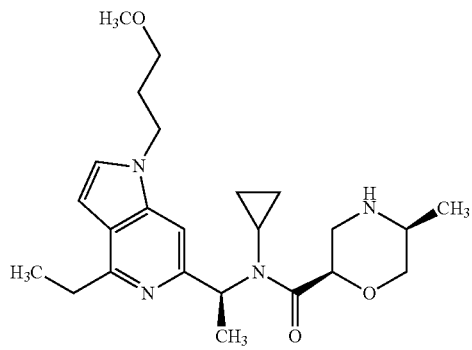 [SMILES: CCc1nc([C@H](C)N(C(=O)[C@H]2CN[C@@H](C)CO2)C2CC2)cc2c1ccn2CCCOC] | 2HCl | 429.3 [M + H]⁺ |

TABLE 76-continued
| Example 398 | 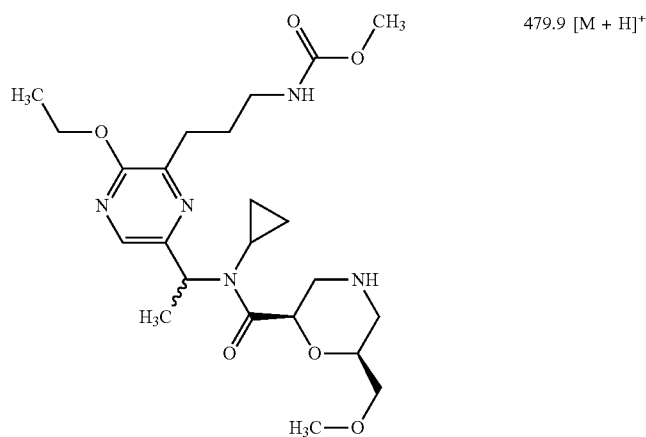 | 479.9 [M + H]+ |
|---|---|---|
| Example 399 | 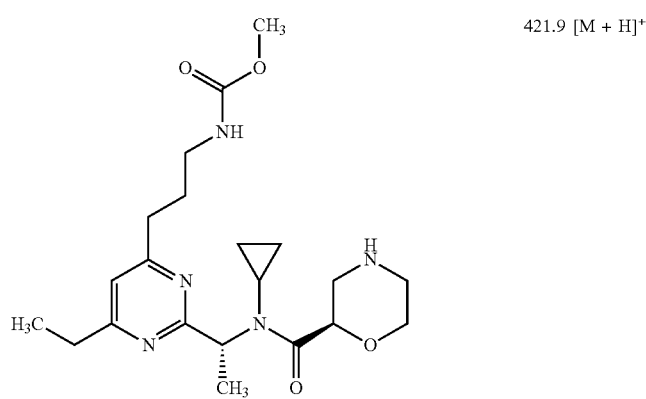 | 421.9 [M + H]+ |
TABLE 77
| Example 400 | 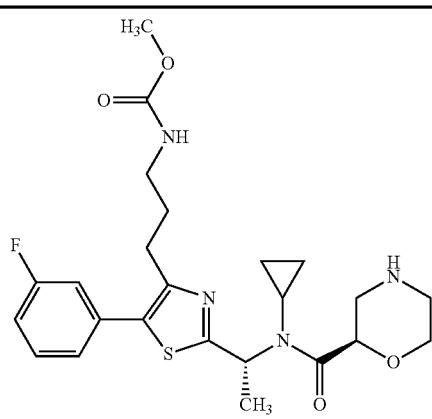 | 2HCl 490.9 [M + H]+ |
|---|---|---|

TABLE 77-continued
Example 401 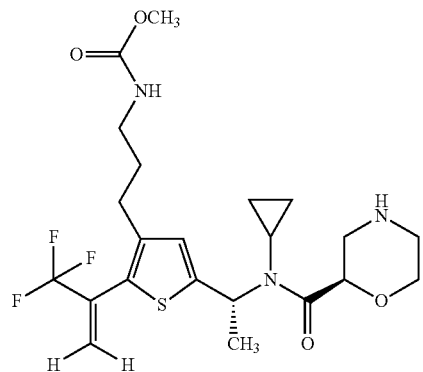 [SMILES: C=C(c1sc([C@@H](C)N(C(=O)[C@H]2CNCCO2)C2CC2)cc1CCCNC(=O)OC)C(F)(F)F] 489.9 [M + H]+
Example 402 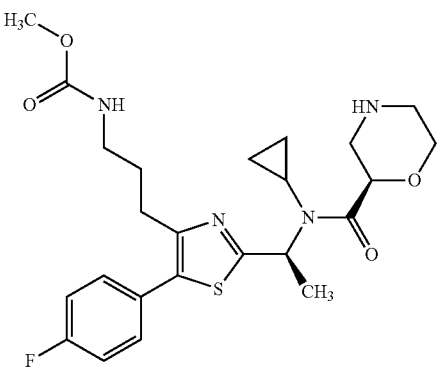 [SMILES: COC(=O)NCCCc1nc([C@H](C)N(C(=O)[C@H]2CNCCO2)C2CC2)sc1-c1ccc(F)cc1] 2HCl 490.9 [M + H]+
Example 403 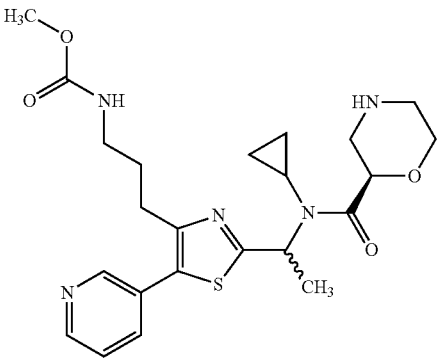 [SMILES: COC(=O)NCCCc1nc(C(C)N(C(=O)[C@H]2CNCCO2)C2CC2)sc1-c1cccnc1] 473.9 [M + H]+

TABLE 78
| Example | Chemical Formula | MS Result | MS Method | Ion Species |
|---|---|---|---|---|
| Example 404 | 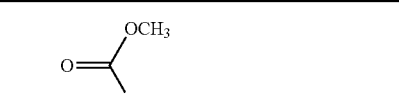 | 496 | ESI | [M + H]+ |
TABLE 79
| Example | Chemical Formula | Salt | MS Result ESI | Ion Species |
|---|---|---|---|---|
| Example 405 | | | 491.9 | [M + H]+ |
| Example 406 | 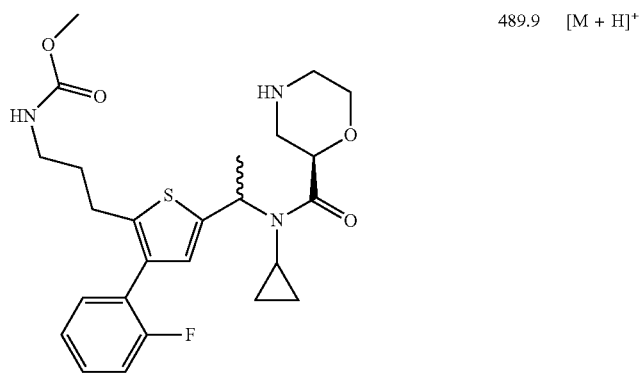 | | 489.9 | [M + H]+ |

TABLE 79-continued
| Example | Chemical Formula | Salt | MS Result ESI | Ion Species |
|---|---|---|---|---|
| Example 407 | 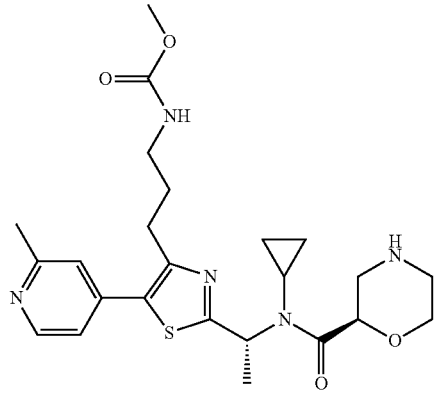 [SMILES: COC(=O)NCCCc1nc([C@@H](C)N(C(=O)[C@H]2CNCCO2)C2CC2)sc1-c1ccnc(C)c1] | | 244.5 | [M + 2H]²⁺ |
| Example 408 | 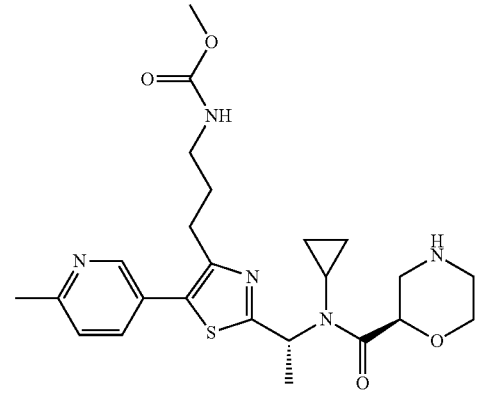 [SMILES: COC(=O)NCCCc1nc([C@@H](C)N(C(=O)[C@H]2CNCCO2)C2CC2)sc1-c1ccc(C)nc1] | | 244.5 | [M + 2H]²⁺ |
TABLE 80
| Example 409 | 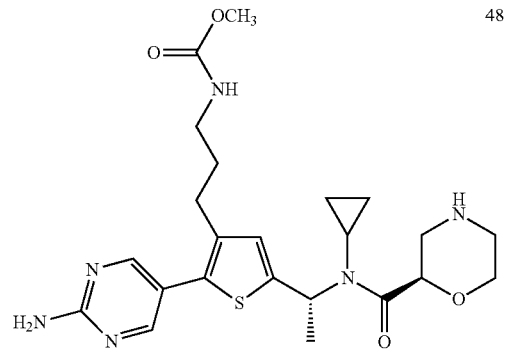 | | 488.9 | [M + H]⁺ |

TABLE 80-continued
| | | |
|---|---|---|
| Example 410 | 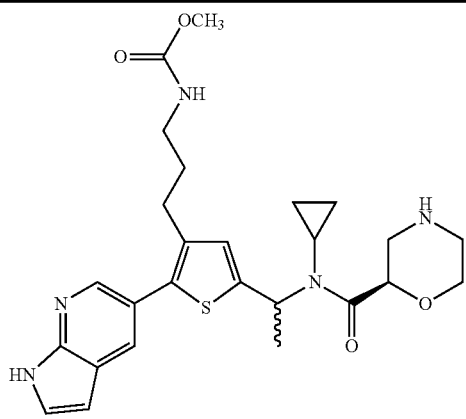 | 256.5 [M + 2H]²⁺ |
| Example 411 | 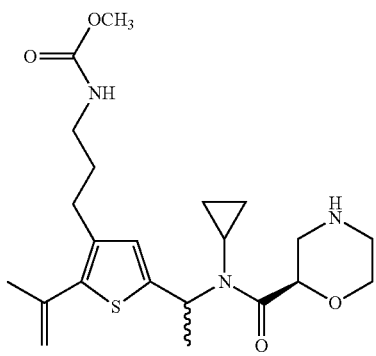 [SMILES: C=C(C)c1sc(C(C)N(C(=O)[C@H]2CNCCO2)C2CC2)cc1CCCNC(=O)OC] | 435.9 [M + H]⁺ |
| Example 412 | 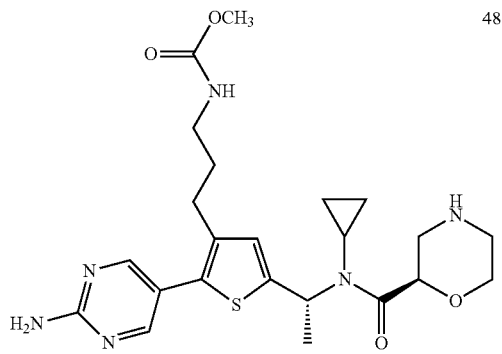 | 488.9 [M + H]⁺ |
TABLE 81
| | | |
|---|---|---|
| Example 413 | 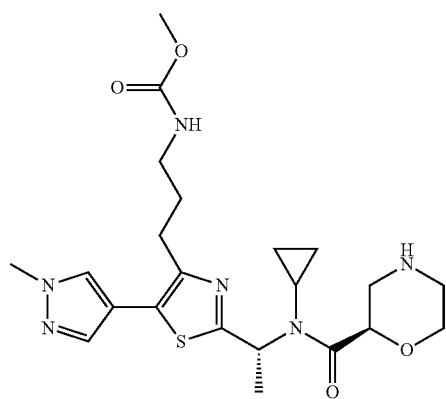 [SMILES: COC(=O)NCCCc1nc([C@@H](C)N(C(=O)[C@H]2CNCCO2)C2CC2)sc1-c1cnn(C)c1] | 476.9 [M + H]⁺ |

TABLE 81-continued
| Example 414 | 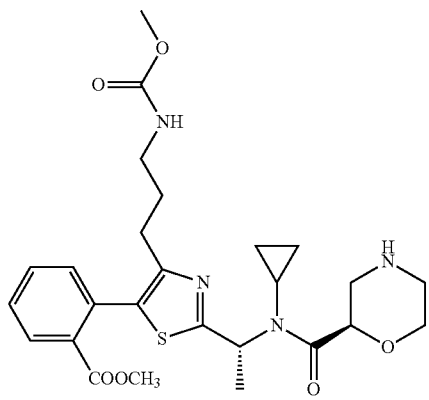 [SMILES: COC(=O)NCCCc1nc([C@@H](C)N(C(=O)[C@H]2CNCCO2)C2CC2)sc1-c1ccccc1C(=O)OC] | 530.9 [M + H]+ |
| --- | --- | --- |
| Example 415 | 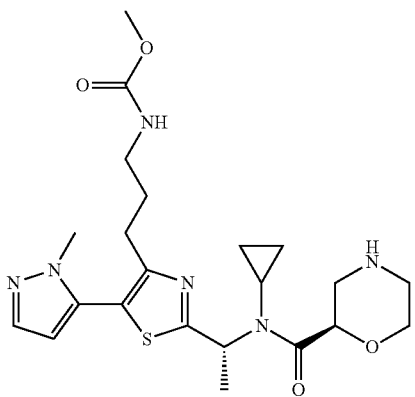 [SMILES: COC(=O)NCCCc1nc([C@@H](C)N(C(=O)[C@H]2CNCCO2)C2CC2)sc1-c1ccnn1C] | 476.9 [M + H]+ |
| Example 416 | 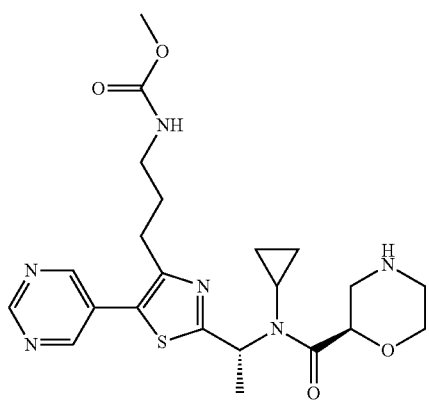 | 490.9 [M + H]+ |

TABLE 82
| Example 417 | 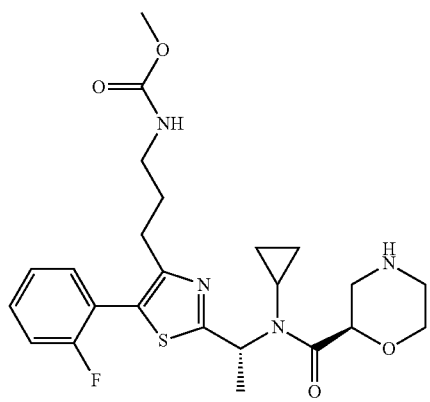 [SMILES: COC(=O)NCCCc1nc([C@@H](C)N(C(=O)[C@H]2CNCCO2)C2CC2)sc1-c1ccccc1F] | | 489.9 [M + H]+ |
| --- | --- | --- | --- |
| Example 418 | 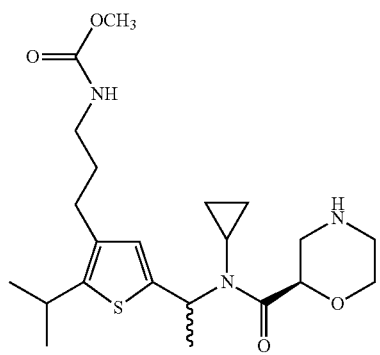 [SMILES: COC(=O)NCCCc1cc(C(C)N(C(=O)[C@H]2CNCCO2)C2CC2)sc1C(C)C] | | 437.9 [M + H]+ |
| Example 419 | 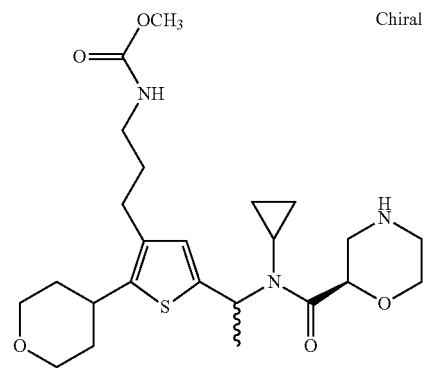 [SMILES: COC(=O)NCCCc1cc(C(C)N(C(=O)[C@H]2CNCCO2)C2CC2)sc1C1CCOCC1] | Chiral | 479.9 [M + H]+ |
| Example 420 | 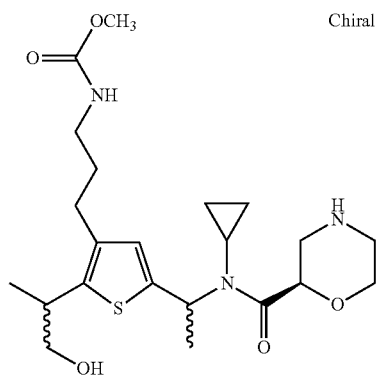 [SMILES: COC(=O)NCCCc1cc(C(C)N(C(=O)[C@H]2CNCCO2)C2CC2)sc1C(C)CO] | Chiral | 453.9 [M + H]+ |

TABLE 83
| | | | |
|---|---|---|---|
| Example 421 | 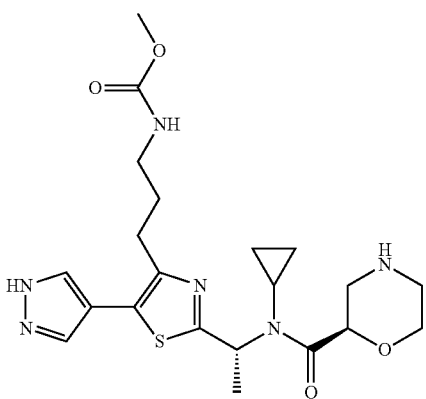 [SMILES: COC(=O)NCCCc1nc([C@@H](C)N(C(=O)[C@H]2CNCCO2)C2CC2)sc1-c1cn[nH]c1] | | 462.9 [M + H]+ |
| Example 422 | 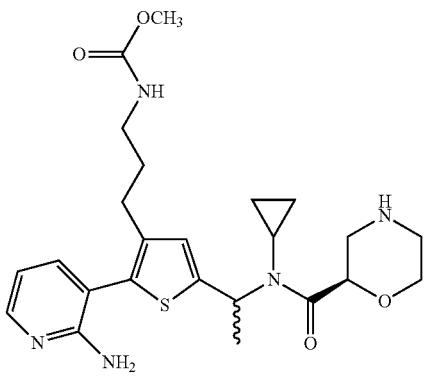 [SMILES: COC(=O)NCCCc1cc(C(C)N(C(=O)[C@H]2CNCCO2)C2CC2)sc1-c1cccnc1N] | | 244.5 [M + 2H]2+ |
| Example 422 | 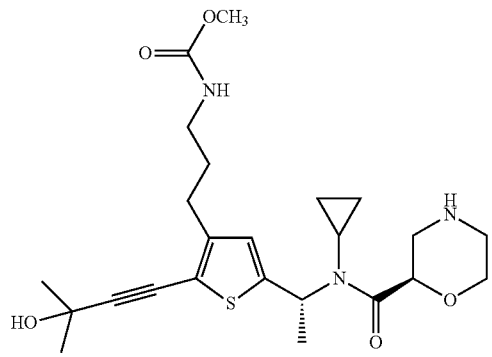 [SMILES: COC(=O)NCCCc1cc([C@@H](C)N(C(=O)[C@H]2CNCCO2)C2CC2)sc1C#CC(C)(C)O] | | 477.9 [M + H]+ |
| Example 424 | 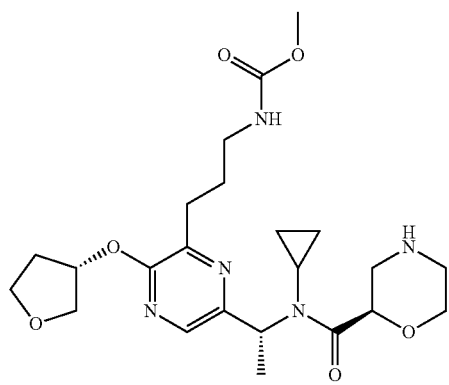 [SMILES: COC(=O)NCCCc1nc([C@@H](C)N(C(=O)[C@H]2CNCCO2)C2CC2)cnc1O[C@H]1CCOC1] | HCl | 478.0 [M + H]+ |

TABLE 84
| Example 425 | 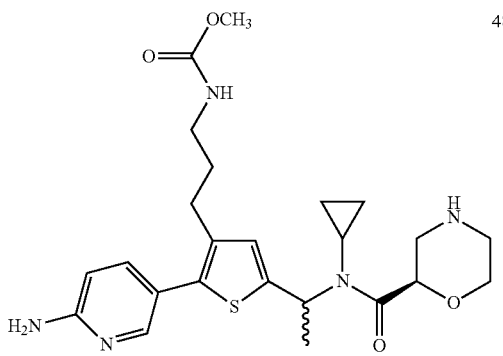 | 487.9 [M + H]+ |
| Example 426 | 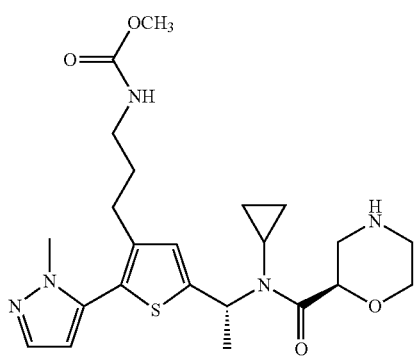 [SMILES: COC(=O)NCCCc1cc([C@@H](C)N(C(=O)[C@H]2CNCCO2)C2CC2)sc1-c1ccnn1C] | 475.9 [M + H]+ |
| Example 427 | 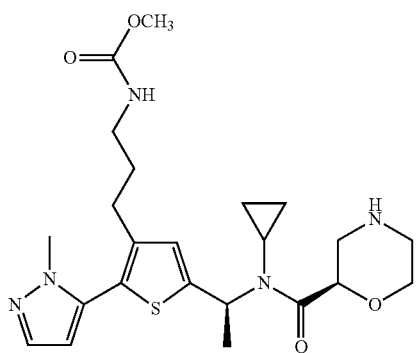 | 515.9 [M + H]+ |
| Example 428 | 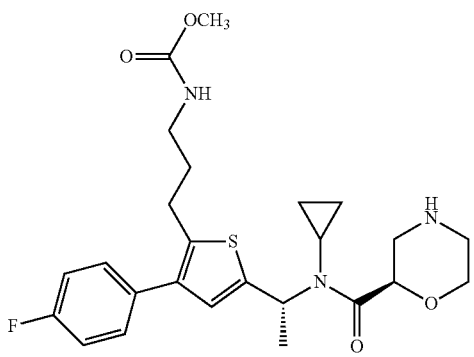 [SMILES: COC(=O)NCCCc1sc([C@@H](C)N(C(=O)[C@H]2CNCCO2)C2CC2)cc1-c1ccc(F)cc1] | 489.9 [M + H]+ |

TABLE 85
| Example 429 | 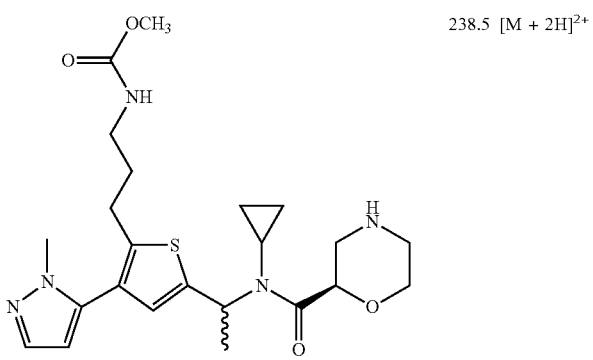 | 238.5 [M + 2H]²⁺ |
| Example 430 | 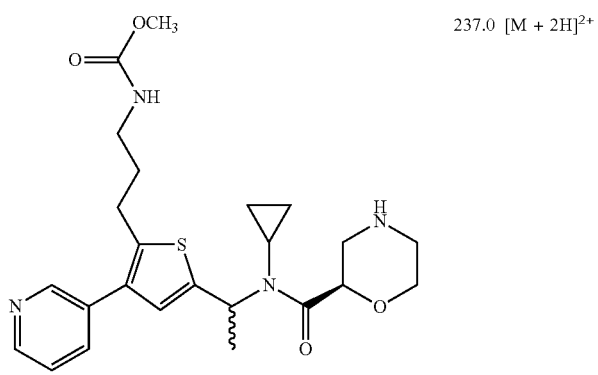 | 237.0 [M + 2H]²⁺ |
| Example 431 | 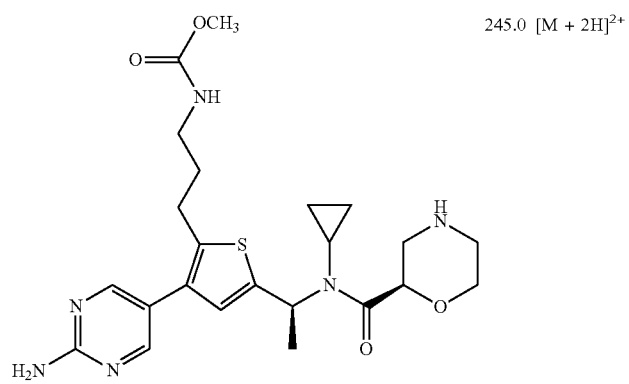 | 245.0 [M + 2H]²⁺ |
| Example 432 | 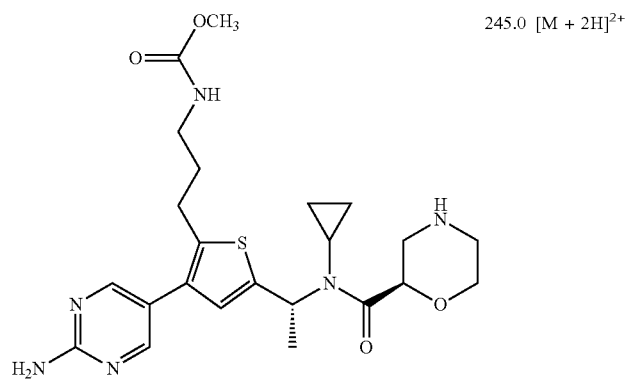 | 245.0 [M + 2H]²⁺ |

TABLE 86
| Example 433 | 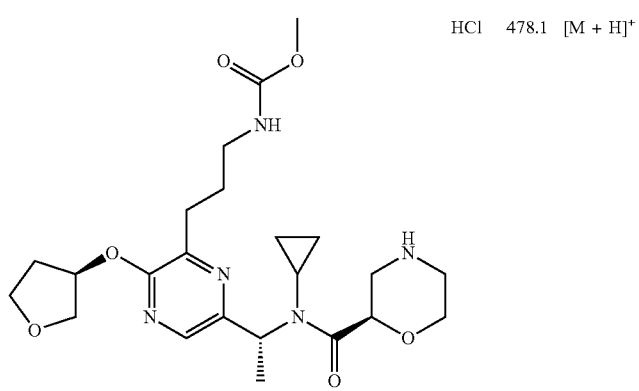 | HCl | 478.1 [M + H]+ |
| Example 434 | 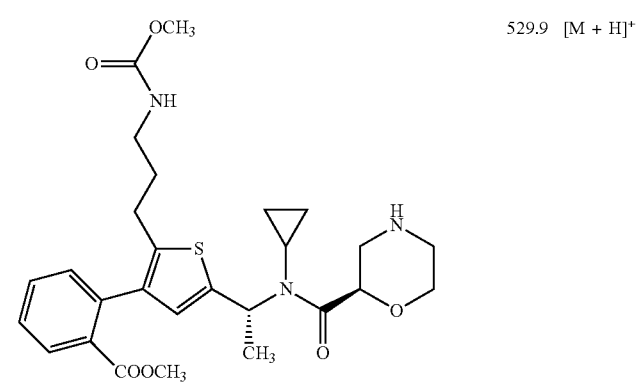 | | 529.9 [M + H]+ |
| Example 435 | 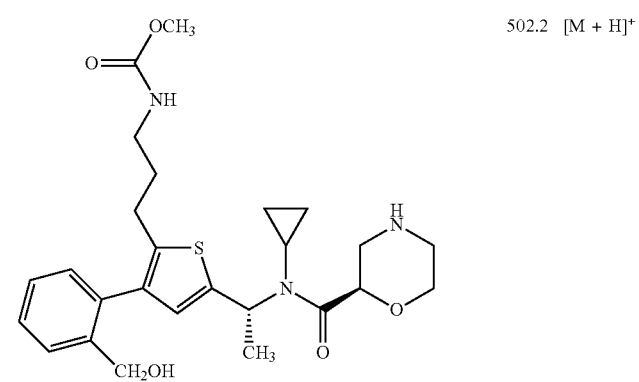 | | 502.2 [M + H]+ |
| Example 436 | 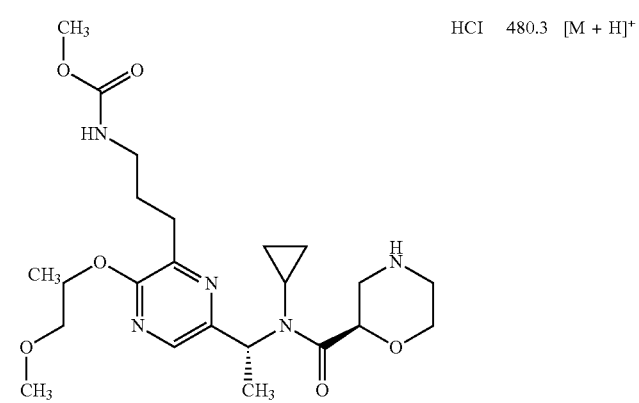 | HCl | 480.3 [M + H]+ |

TABLE 87
| Example 437 | 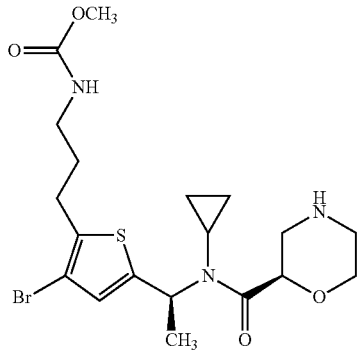 [SMILES: COC(=O)NCCCc1sc([C@H](C)N(C(=O)[C@H]2CNCCO2)C2CC2)cc1Br] | 475.1 [M + H]+ |
| Example 438 | 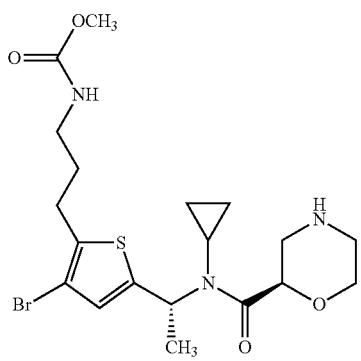 [SMILES: COC(=O)NCCCc1sc([C@@H](C)N(C(=O)[C@H]2CNCCO2)C2CC2)cc1Br] | 475.1 [M + H]+ |
| Example 439 | 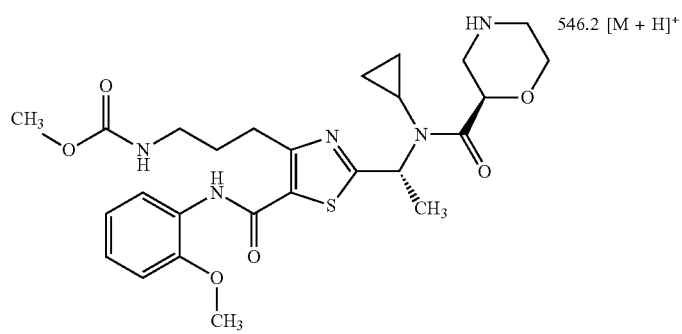 | 546.2 [M + H]+ |
| Example 440 | 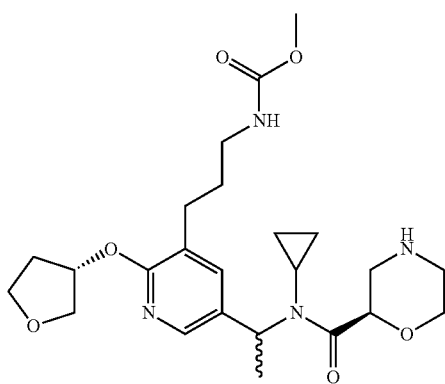 [SMILES: COC(=O)NCCCc1cc(C(C)N(C(=O)[C@H]2CNCCO2)C2CC2)cnc1O[C@H]1CCOC1] | 477.3 [M + H]+ |

TABLE 88
| Example 441 | 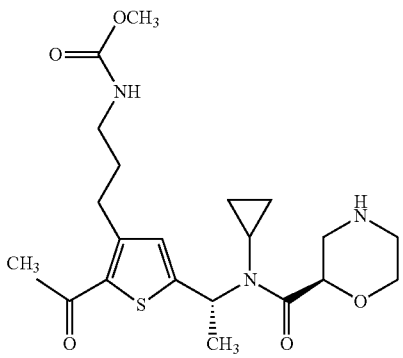 [SMILES: COC(=O)NCCCc1cc([C@@H](C)N(C(=O)[C@H]2CNCCO2)C2CC2)sc1C(C)=O] | 438.2 [M + H]+ |
| Example 442 | 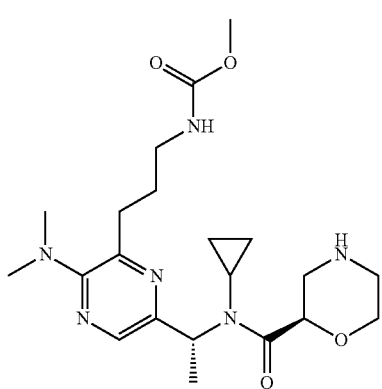 [SMILES: COC(=O)NCCCc1nc([C@@H](C)N(C(=O)[C@H]2CNCCO2)C2CC2)cnc1N(C)C] | 2HCl 435.1 [M + H]+ |
| Example 443 | 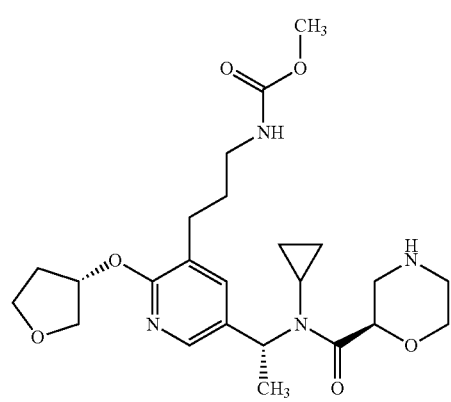 [SMILES: COC(=O)NCCCc1cc([C@@H](C)N(C(=O)[C@H]2CNCCO2)C2CC2)cnc1O[C@H]1CCOC1] | 2HCl 477.1 [M + H]+ |
| Example 444 | 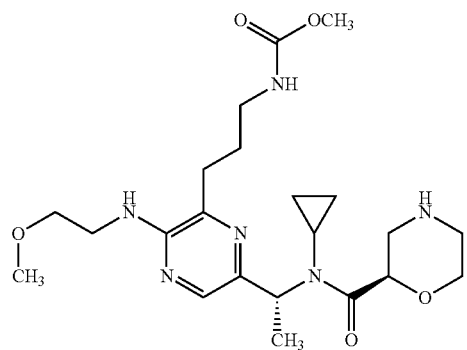 [SMILES: COCCNc1ncc([C@@H](C)N(C(=O)[C@H]2CNCCO2)C2CC2)nc1CCCNC(=O)OC] | 465.1 [M + H]+ |

Reference Example 1

N-[1-(2-naphthyl)ethyl]cyclopropanamine hydrochloride [REx(1-2)]

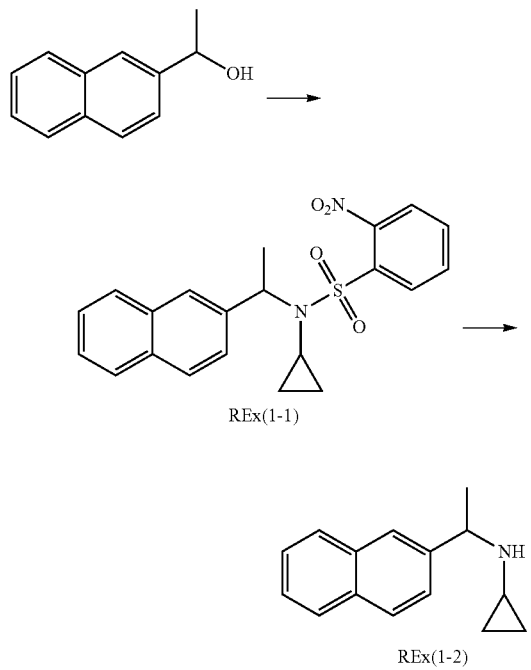

(1) N-Cyclopropyl-N-[1-(2-naphthyl)ethyl]-2-nitrobenzenesulfonamide [REx(1-1)]:

To a solution of 1-(2-naphthyl)ethanol (344 mg). N-cyclopropyl-2-nitrobenzenesulfonamide (581 mg) and triphenylphosphine (787 mg) in tetrahydrofuran (10 mL) was added dropwise diisopropyl azodicarboxylate (590 μL) under ice-cooling, and the mixture was stirred at room temperature for 3 hours. The reaction solution was concentrated, and the resulting residue was purified by silica gel column chromatography (eluent: n-hexane/ethyl acetate=4/1→1/1), and then triturated with diethyl ether—n-hexane (1:1) to give N-cyclopropyl-N-[1-(2-naphthyl)ethyl]-2-nitrobenzenesulfonamide [REx(1-1)] (499 mg) as a colorless powder.

APCI-MS m/z: 397 [M+H]$^+$.

(2) N-[1-(2-Naphthyl)ethyl]cyclopropylamine hydrochloride [REx(1-2)]:

To a solution of the compound obtained in (1) (480 mg) and 4-bromothiophenol (250 mg) in N,N-dimethylformamide (12 mL) was added potassium carbonate (304 mg), and the mixture was stirred at room temperature for 17 hours. To the reaction solution was added water, and the mixture was extracted with ethyl acetate. The organic layer was sequentially washed with water twice and saturated saline, dried over sodium sulfate, and then concentrated under reduced pressure. The resulting residue was dissolved in ethyl acetate (5 mL), and then thereto was added 4-normal hydrogen chloride-ethyl acetate (1 mL). The precipitated solid was filtered to give N-[1-(2-naphthyl)ethyl]cyclopropylamine hydrochloride [REx(1-2)] (211 mg) as a colorless powder.

APCI-MS m/z: 212 [M+H]$^+$.

Reference Example 2

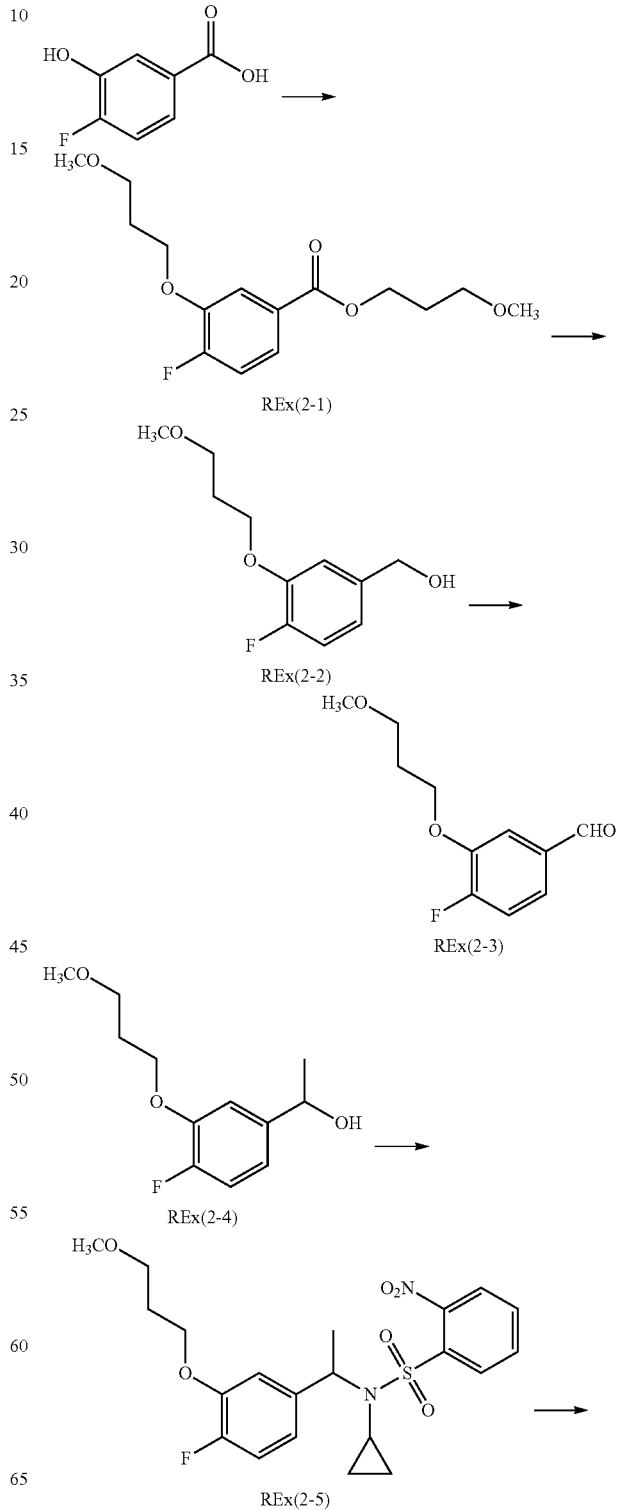

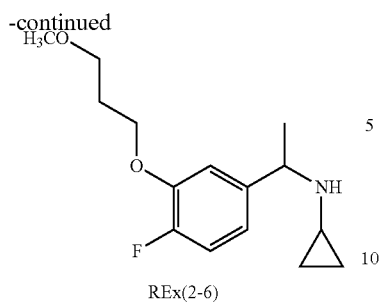

REx(2-6)

(1) 3-Methoxypropyl 4-fluoro-3-(3-methoxypropoxy)benzoate [REx(2-1)]:

To a solution of 4-fluoro-3-hydroxybenzoic acid (2.0 g) in acetonitrile (100 mL)—N,N-dimethylformamide (50 mL)—water (2.0 mL) were added potassium carbonate (5.31 g) and 1-bromo-3-methoxypropane (4.32 g), and the mixture was heated to reflux at 90° C. for 18 hours. To the reaction mixture was added water under ice-cooling, and then the mixture was extracted with ethyl acetate. The organic layer was washed with saturated saline, dried over magnesium sulfate, and then concentrated under reduced pressure. The resulting residue was purified by silica gel column chromatography (eluent: n-hexane/ethyl acetate=4/1→1/2 to give 3-methoxypropyl 4-fluoro-3-(3-methoxypropoxy)benzoate [REx(2-1)] (2.72 g) as a colorless oil.

APCI-MS m/z: 301 [M+H]$^+$.

(2) [Fluoro-3-(3-methoxypropoxy)phenyl]methanol [REx(2-2)]:

To a suspension of lithium aluminum hydride (344 mg) in tetrahydrofuran (20 mL) was added dropwise a solution of the compound obtained in the above (1) (2.72 g) in tetrahydrofuran (8 mL) under ice-cooling, and then the mixture was stirred under the cooling for 1 hour. Under the cooling, to the reaction mixture were sequentially and slowly added water and 2-normal aqueous sodium hydroxide solution (1 mL), and then the mixture was stirred at room temperature for 1 hour. An insoluble was filtered off through Celite, and the filtrate was washed with aqueous saturated sodium hydrogen carbonate solution, and then dried over magnesium sulfate. The resultant was concentrated under reduced pressure, and the resulting residue was purified by silica gel column chromatography (eluent: n-hexane/ethyl acetate=2/1→1/2) to give [fluoro-3-(3-methoxypropoxy)phenyl]methanol [REx(2-2)] (1.78 g) as a colorless oil.

APCI-MS m/z: 232 [M+NH$_4$]$^+$.

(3) 4-Fluoro-3-(3-methoxypropoxy)benzaldehyde [REx(2-3)]:

To a solution of the compound obtained in the above (2) (1.65 g) in dichloromethane (43 mL) was added 85% activated manganese dioxide (7.88 g), and the mixture was stirred at room temperature for 1 hour, and then the mixture was heated to reflux for 2 hours. An insoluble was filtered off through Celite, and then the filtrate was concentrated under reduced pressure to give 4-fluoro-3-(3-methoxypropoxy)benzaldehyde [REx(2-3)] (1.59 g) as a colorless oil.

APCI-MS m/z: 213 [M+H]$^+$.

(4) 1-[4-Fluoro-3-(3-methoxypropoxy)phenyl]ethanol [REx(2-4)]:

To a solution of the compound obtained in the above (3) (1.55 g) in tetrahydrofuran (30 mL) was added dropwise a solution of methylmagnesium bromide in 3M diethyl ether (2.68 mL) under ice-cooling, and the mixture was stirred at the same temperature for 10 minutes. Under ice-cooling, thereto was added aqueous ammonium chloride solution, and the mixture was extracted with ethyl acetate. The organic layer was sequentially washed with water and saturated saline, and then dried over magnesium sulfate and concentrated under reduced pressure to give 1-[4-fluoro-3-(3-methoxypropoxy)phenyl]ethanol [REx(2-4)] (1.43 g) as a yellow oil.

APCI-MS m/z: 246 [M+NH$_4$]$^+$.

(5) Then, an amine compound [REx(2-6)] may be obtained in the similar manner to Reference Example 1.

Reference Example 3

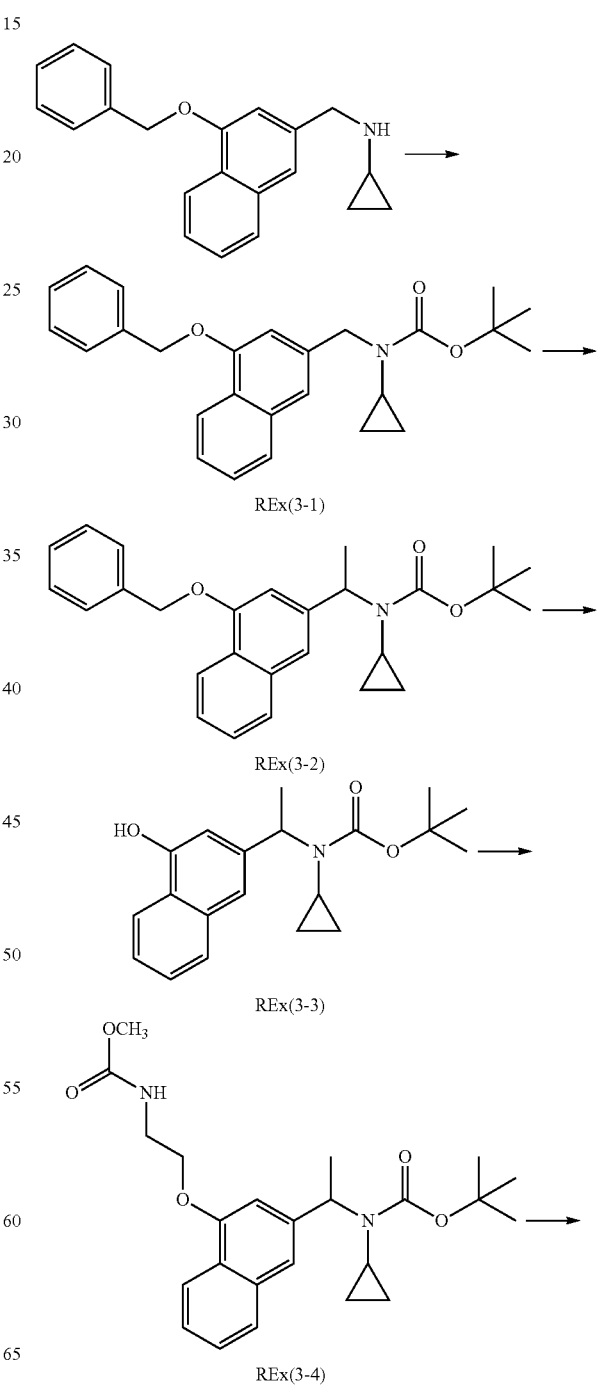

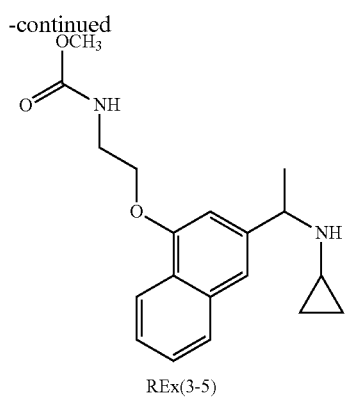

REx(3-5)

(1) tert-Butyl {[4-(benzyloxy)-2-naphthyl]methyl}cyclopropylcarbamate [REx(3-1)]:

To a solution of N-{([4-(benzyloxy)-2-naphthyl]methyl}cyclopropylamine (12.3 g) in dichloromethane (150 mL) were added triethylamine (5.93 mL) and di-t-butyl dicarbonate (9.29 g) under ice-cooling, and the mixture was stirred at room temperature for 3 hours. To the reaction solution was added saturated aqueous ammonium chloride solution under ice-cooling, and the mixture was extracted with chloroform. The organic layer was washed with water and saturated saline, dried over sodium sulfate, and then concentrated under reduced pressure. The resulting residue was purified by silica gel column chromatography (eluent: n-hexane/ethyl acetate=19/1-9/1) to give tert-butyl {[4-(benzyloxy)-2-naphthyl]methyl}cyclopropylcarbamate [REx(3-1)] (15.8 g) as a colorless powder.

APCI-MS m/z: 404 [M+H]$^+$.

(2) tert-Butyl {1-[4-(benzyloxy)-2-naphthyl]ethyl}cyclopropylcarbamate [REx(3-2)]:

To a solution of the compound obtained in the above (1) (807 mg) and tetramethylethylenediamine (0.39 μL) in tetrahydrofuran (10 mL) were added dropwise a solution of 1.55M n-butyllithium in hexane (1.55 mL) at −78° C. under argon over 5 minutes. The mixture was stirred at the same temperature for 1 hour, and then thereto was added iodomethane (0.187 μL) at −78° C. The mixture was stirred at the same temperature for 30 minutes, and then stirred under ice-cooling for 2 hours. To the reaction solution was added saturated aqueous ammonium chloride solution under ice-cooling, and then the mixture was extracted with ethyl acetate. The organic layer was washed with water twice and saturated saline, dried over sodium sulfate, and then concentrated under reduced pressure. The resulting residue was purified by silica gel column chromatography (eluent: n-hexane/ethyl acetate=20/1→6/1) to give tert-butyl {1-[4-(benzyloxy)-2-naphthyl]ethyl}cyclopropylcarbamate [REx(3-2)] (611 mg) as a colorless oil.

APCI-MS m/z: 418 [M+H]$^+$.

(3) tert-Butyl [1-(4-hydroxy2-naphthyl)ethyl]carbamate [REx(3-3)]:

To a solution of the compound obtained in the above (2) (126 mg) in methanol (3 mL) was added 10% palladium on carbon (13 mg), and the mixture was stirred under hydrogen for 3 hours. The reaction solution was diluted with ethyl acetate, and a catalyst was filtered, and then the resultant was concentrated under reduced pressure. The resulting residue was triturated with isopropyl ether/n-hexane (1:1) to give tert-butyl cyclopropyl[1-(4-hydroxy2-naphthyl)ethyl]carbamate [REx(3-3)] (50 mg) as a colorless powder.

ESI-MS m/z: 326[M−H]$^−$ (4) Methyl {2-[(3-{1-[(tert-butoxycarbonyl)(cyclopropyl)amino]ethyl}-1-naphthyl)oxy]ethyl}carbamate [REx(3-4)]:

To a solution of the compound obtained in the above (3) (243 mg) and methyl (2-bromoethyl)carbamate (203 mg) in acetonitrile (10 mL) was added potassium carbonate (205 mg), and the mixture was stirred at 80° C. for 7 hours. After cooling, to the reaction solution was added water, and the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=4/1→1/1) to give methyl {2-[(3-{1-[(tert-butoxycarbonyl)(cyclopropyl)amino]ethyl}-1-naphthyl)oxy]ethyl}carbamate [REx(3-4)] (161 mg) as a pale yellow oil.

APCI-MS m/z: 429 [M+H]$^+$.

(5) Methyl [2-({3-[1-(cyclopropylamino)ethyl]-1-naphthyl}oxy)ethyl]carbamate [REx(3-5)]:

To a solution of the compound obtained in the above (4) (156 mg) in chloroform (2 mL) was added 4-normal hydrogen chloride-dioxane solution (2 mL) under ice-cooling, and the mixture was stirred at room temperature for 1 hour. The mixture was concentrated under reduced pressure, and to the resulting residue was added aqueous saturated sodium hydrogen carbonate solution, and the mixture was extracted with chloroform. The organic layer was dried over sodium sulfate, and then concentrated under reduced pressure. The resulting residue was purified by silica gel column chromatography (eluent: ethyl acetate→ethyl acetate/methanol=10/1) to give methyl [2-({3-[1-(cyclopropylamino)ethyl]-1-naphthyl}oxy)ethyl]carbamate [REx(3-5)] (76 mg) as a pale yellow oil.

APCI-MS m/z: 329 [M+H]$^+$.

Reference Example 4

[1-(4-Methoxy-2-naphthyl)ethyl]cyclopropylamine [REx(4-1)]

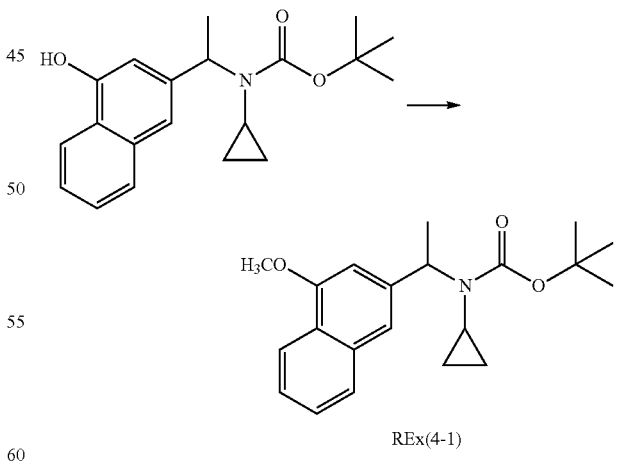

REx(4-1)

To a mixture of tert-butyl cyclopropyl[1-(4-hydroxy2-naphthyl)ethyl]carbamate (43 mg) and potassium carbonate (27 mg) was added N,N-dimethylformamide (2.0 mL), and then thereto added methyl iodide (0.016 mL), and the mixture was stirred at room temperature for 4 hours. After cooling, to the reaction solution was added water, and the mixture was extracted with ethyl acetate. The organic layer was sequentially washed with water twice and saturated saline, dried over sodium sulfate, and then concentrated under reduced pressure. The resulting residue was purified by silica gel column chromatography (eluent: n-hexane/ethyl acetate=10/1→4/1) to give tert-butyl cyclopropyl[1-(4-methoxy-2-naphthyl)ethyl]carbamate [REx(4-1)] (33 mg) as a colorless oil.

APCI-MS m/z: 342 [M+H]⁺.

Then, deprotection of Boc group according to any one of methods of Examples 1 to 5 may give the desired amine compound.

Reference Example 5

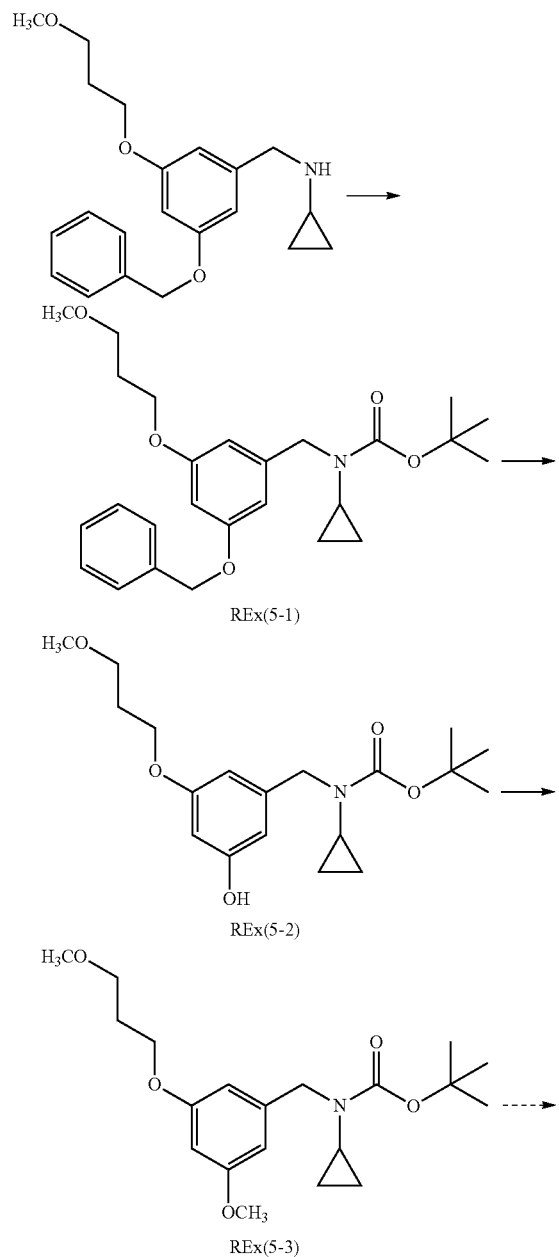

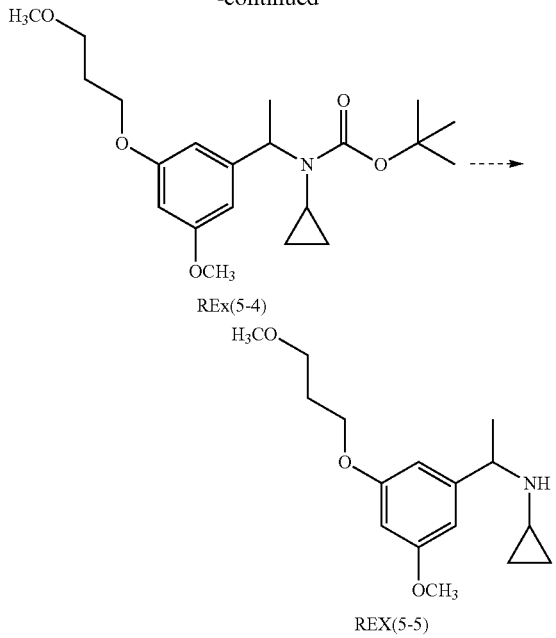

(1) tert-Butyl [3-(benzyloxy)-5-(3-methoxypropoxy)benzyl]cyclopropylcarbamate [REx(5-1)]:

To a solution of N-[3-(benzyloxy)-5-(3-methoxypropoxy)benzyl]cyclopropylamine (15.4 g) in dichloromethane (190 mL) were added triethylamine (6.60 mL) and di-t-butyl dicarbonate (10.3 g) under ice-cooling, and the mixture was stirred at room temperature for 4 hours. To the reaction solution was added saturated aqueous ammonium chloride solution under ice-cooling, and the mixture was extracted with chloroform. The organic layer was washed with water and saturated saline, dried over sodium sulfate, and then concentrated under reduced pressure. The resulting residue was purified by silica gel column chromatography (eluent: n-hexane/ethyl acetate=14/1) to give tert-butyl [3-(benzyloxy)-5-(3-methoxypropoxy)benzyl]cyclopropylcarbamate [REx(5-1)] (20.0 g) as a colorless oil.

APCI-MS m/z: 459 [M+NH₄]⁺.

(2) tert-Butyl cyclopropyl[3-hydroxy5-(3-methoxypropoxy)benzyl]carbamate [REx(5-2)]:

To a solution of the compound obtained in the above (1) (14.0 g) in ethanol (210 mL) was added 20% palladium hydroxide on carbon (2.80 g), and the mixture was stirred under hydrogen for 30 minutes. An insoluble was filtered, and then concentrated under reduced pressure. The resulting residue was purified by silica gel column chromatography (eluent: n-hexane/ethyl acetate=4/1→2/1) to give tert-butyl cyclopropyl[3-hydroxy5-(3-methoxypropoxy)benzyl]carbamate [REx(5-2)] (11.0 g) as a colorless oil.

APCI-MS m/z: 352 [M+H]⁺.

(3) tert-Butyl cyclopropyl[3-methoxy-5-(3-methoxypropoxy)benzyl]carbamate [REx(5-3)]:

To a solution of the compound obtained in the above (2) (3.51 g) in N,N-dimethylformamide (50 mL) was added potassium carbonate (2.07 g), and then thereto was added iodomethane (0.75 mL) under ice-cooling, and the mixture was stirred at room temperature for 23 hours. To the reaction solution was added water, and the mixture was extracted with ethyl acetate. The organic layer was sequentially washed with water twice and saturated saline, dried over sodium sulfate, and then concentrated under reduced pressure. The resulting residue was purified by silica gel column chromatography (eluent: n-hexane/ethyl acetate=3/1) to give tert-butyl cyclopropyl[3-methoxy-5-(3-methoxypropoxy)benzyl]carbamate [REx(5-3)] (3.65 g) as a colorless oil.

APCI-MS m/z: 366 [M+H]+.

(4) Methylation according to the method of Reference Example 3(2), then deprotecting Boc group according to any one of methods of Examples 1 to 5 give the desired amine compound [REx(5-5)]:

Reference Example 6

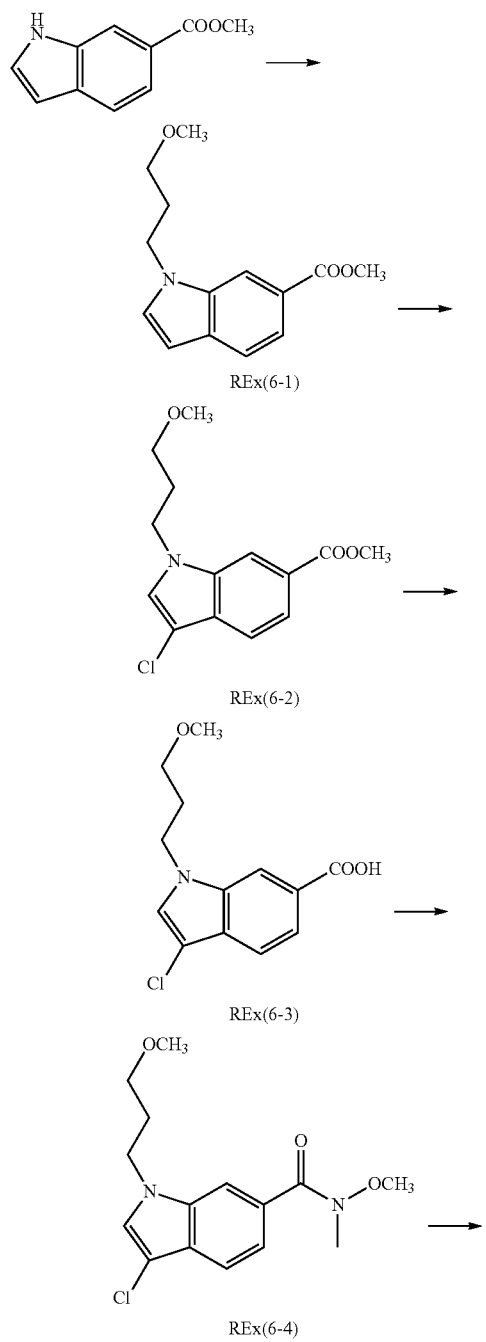

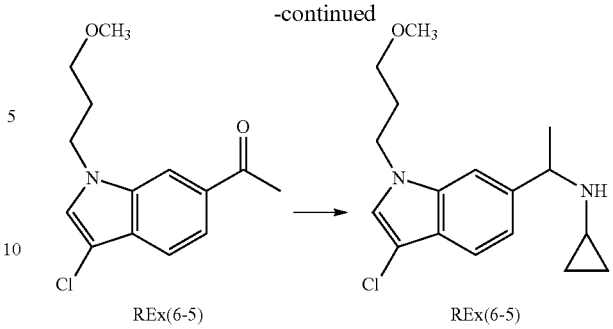

(1) Methyl 1-(3-methoxypropyl)-1H-indole-6-carboxylate [REx(6-1)]:

To a solution of methyl 1H-indole-6-carboxylate (5.0 g) in N,N-dimethylformamide (40 mL) was added drop by drop 60% oil-based sodium hydride (1.37 g) under ice-cooling, and then the mixture was stirred at room temperature for 15 minutes. Then, thereto was added dropwise a solution of 1-bromo-3-methoxypropane (5.24 g) in N,N-dimethylformamide (10 mL) under ice-cooling, and then thereto was added potassium iodide (948 mg), and the mixture was stirred at room temperature for 3 hours. To the reaction mixture was sequentially added ethyl acetate and water under ice-cooling, and the organic layer was separated. The organic layer was washed with water twice and saturated saline, dried over sodium sulfate, and then concentrated under reduced pressure. The resulting residue was purified by silica gel column chromatography (eluent: n-hexane/ethyl acetate=9/1→4/1) to give methyl 1-(3-methoxypropyl)-1H-indole-6-carboxylate [REx(6-1)] (5.8 g) as a colorless oil.

APCI-MS m/z: 248 [M+H]+.

(2) Methyl 3-chloro-1-(3-methoxypropyl)-1H-indole-6-carboxylate [REx(6-2)]:

To a solution of the compound obtained in the above (1) (2.78 g) in dichloromethane (35 mL) was added N-chlorosuccinimide (1.65 g) under ice-cooling, and the mixture was stirred at room temperature for 18 hours. To the reaction mixture was added water, and the mixture was extracted with chloroform. The organic layer was washed with saturated saline, dried over sodium sulfate, and then concentrated under reduced pressure. The resulting residue was purified by silica gel column chromatography (eluent: n-hexane→n-hexane/ethyl acetate=2/1) to give methyl 3-chloro-1-(3-methoxypropyl)-1H-indole-6-carboxylate [REx(6-2)] (3.10 g) as a yellow oil.

APCI-MS m/z: 282/284 [M+H]+.

(3) 3-Chloro-1-(3-methoxypropyl)-1H-Indol-6-carboxylic acid [REx(6-3)]:

To a solution of the compound obtained in the above (2) (1.20 g) in ethanol (10 mL) was added 2-normal aqueous sodium hydroxide solution (4.26 mL) under ice-cooling, and the mixture was stirred at room temperature for 20 hours. The reaction mixture was concentrated, and then the mixture was acidified by adding 2-normal hydrochloric acid under ice-cooling, and then thereto was added water, and the mixture was extracted with ethyl acetate. The organic layer was washed with saturated saline, and then concentrated under reduced pressure to give 3-chloro-1-(3-methoxypropyl)-1H-indole-6-carboxylic acid [REx(6-3)] (1.14 g) as a colorless powder.

ESI-MS m/z: 266/268[M−H]−

(4) 3-Chloro-N-methoxy-1-(3-methoxypropyl)-N-methyl-1H-indol-6-carboxamide [REx(6-4)]:

To a solution of the compound obtained in the above (3) (1.14 g), N,O-dimethylhydroxyamine hydrochloride (831 mg), 1-ethyl-3-(3-dimethylaminopropyl)carbodiimide hydrochloride (1.25 g) and 1-hydroxybenzotriazole (863 mg) in chloroform (12 mL) was added diisopropylethylamine (1.85 mL) under ice-cooling, and then the mixture was stirred at room temperature for 24 hours. To the reaction mixture was added aqueous saturated sodium hydrogen carbonate solution under ice-cooling, and the mixture was extracted with chloroform. The organic layer was sequentially washed with water and saturated saline, dried over magnesium sulfate, and then concentrated under reduced pressure. The resulting residue was purified by silica gel column chromatography (eluent: n-hexane/ethyl acetate=1/1→1/3) to give 3-chloro-N-methoxy-1-(3-methoxypropyl)-N-methyl-1 1-indole-6-carboxamide [REx(6-4)] (1.20 g) as a pale yellow oil APCI-MS m/z: 311/313 [M+H]$^+$.

(5) 1-[3-Chloro-1-(3-methoxypropyl)-1H-Indol-6-yl]ethanone [REx(6-5)]:

To a solution of the compound obtained in the above (4) (1.20 g) in tetrahydrofuran (15 mL) was added dropwise a 3M solution of methylmagnesium bromide in diethyl ether (2.56 mL) under ice-cooling, and the mixture was stirred at the same temperature for 1 hour. To the reaction solution was added 1-normal hydrochloric acid under ice-cooling, and the mixture was extracted with ethyl acetate. The organic layer was washed with saturated saline, and then dried over magnesium sulfate and concentrated under reduced pressure. The resulting residue was purified by silica gel column chromatography (eluent: n-hexane/ethyl acetate=4/1→1/1) to give 1-[3-chloro-1-(3-methoxypropyl)-1H-indol-6-yl]ethanone [REx(6-5)] (945 mg) as a pale yellow oil.

APCI-MS m/z: 266/268 [M+H]$^+$.

(6) N-{1-[3-Chloro-1-(3-methoxypropyl)-1H-Indol-6-yl]ethyl}cyclopropanamine [REx(6-6)]:

To a solution of the compound obtained in the above (5) (155 mg) and cyclopropylamine (99.9 mg) in dichloroethane (3.0 mL) were added magnesium sulfate (351 mg), sodium triacetoxyborohydride (371 mg) and acetic acid (105 mg), and then the mixture was stirred at room temperature for 17 hours. To the reaction mixture was added aqueous saturated sodium hydrogen carbonate solution under ice-cooling, and the mixture was extracted with chloroform. The organic layer was washed with saturated saline, dried over magnesium sulfate, and then concentrated under reduced pressure. The resulting residue was purified by silica gel column chromatography (eluent: ethyl acetate→ethyl acetate/methanol=20/1) to give N-{1-[3-chloro-1-(3-methoxypropyl)-H-indol-6-yl]ethyl}cyclopropanamine [REx(6-6)] (111 mg) as a pale yellow oil.

APCI-MS m/z: 307/309 [M+H]$^+$.

Reference Example 7

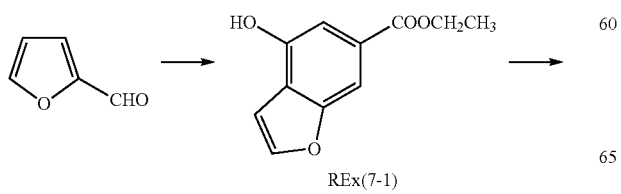

REx(7-1)

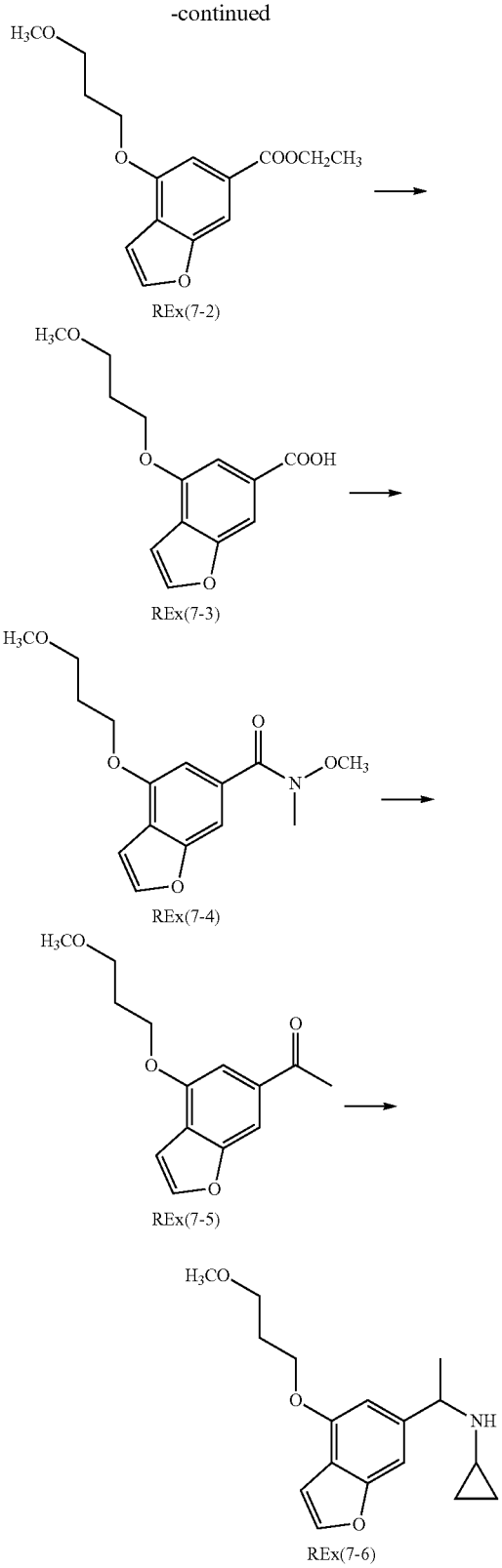

(1) Ethyl 4-(acetyloxy)benzofuran-6-carboxylate:

To a suspension of 60% oil-based sodium hydride (6.50 g) in tetrahydrofuran (400 mL) was added dropwise a solution of 4-tert-butyl 1-ethyl 2-(diethoxyphosphoryl)succinate (55.0 g) in tetrahydrofuran (100 mL) under ice-cooling over 30 minutes, and then the mixture was stirred under the cooling for 1 hour. Then, thereto was added a solution of 2-furaldehyde (12.8 mL) in tetrahydrofuran (40 mL) under ice-cooling over 15 minutes, and the mixture was stirred at room temperature for 1 hour. Ice water was poured into the reaction mixture under ice-cooling, and the mixture was extracted with ethyl acetate. The organic layer was sequentially washed with water and saturated saline, dried over sodium sulfate, and then concentrated under reduced pressure to give 4-tert-butyl 1-ethyl (2E)-2-(2-furylmethylene)succinate (47.0 g) as a brown oil crude. Then, the oil (47.0 g) was stirred in trifluoroacetic acid (100 mL) at room temperature for 1 hour, and then concentrated under reduced pressure. The resulting residue was treated azeotropically with toluene several times to give (3E)-3-(ethoxycarbonyl)-4-(2-furyl)-but-3-enoic acid (39.2 g) as a brown oil crude. Then, the oil (39.2 g) was dissolved in acetic anhydride (100 mL), and thereto was added potassium acetate (19.8 g), and then the mixture was heated to reflux for 45 minutes. The reaction mixture was let stand to be cooled, and then thereto was added water (100 mL), and then the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=5/1) to give ethyl 4-(acetyloxy)benzofuran-6-carboxylate (24.7 g) as a pale orange solid.

APCI-MS m/z: 266 [M+NH$_4$]$^+$.

(2) Ethyl 4-hydroxy-1-benzofuran-6-carboxylate [REx(7-1)]:

To a solution of the compound obtained in the above (1) (24.7 g) in ethanol (150 mL) was added potassium carbonate (42.0 g), and the mixture was heated to reflux for 30 minutes. The reaction mixture was ice-cooled, and then acidified by 10% hydrochloric acid, and then extracted with ethyl acetate. The organic layer was washed with saturated saline, dried over sodium sulfate, and then concentrated under reduced pressure. The resulting residue was triturated with n-hexane-dichloromethane (5:1) to give ethyl 4-hydroxy-1-benzofuran-6-carboxylate [REx(7-1)] (19.6 g) as a pale yellow powder.

APCI-MS m/z: 207 [M+H]$^+$.

(3) Ethyl 4-(3-methoxypropoxy)-1-benzofuran-6-carboxylate [REx(7-2)]:

To a solution of the compound obtained in the above (2) (5.0 g) in acetonitrile (50 mL) were added potassium carbonate (5.0 g) and 1-bromo-3-methoxypropane (4.54 g), and the mixture was heated to reflux for 1.5 hours. To the reaction mixture was added water under ice-cooling, and then the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=5/1→2/1) to give ethyl 4-(3-methoxypropoxy)-1-benzofuran-6-carboxylate [REx(7-2)] (6.61 g) as a colorless oil.

APCI-MS m/z: 279 [M+H]$^+$.

(4) 4-(3-Methoxypropoxy)-1-benzofuran-6-carboxylic acid [REx(7-3)]:

To a solution of the compound obtained in the above (3) (2.64 g) in ethanol (20 mL) was added 2-normal aqueous sodium hydroxide solution (9.5 mL), and the mixture was stirred at room temperature for 3 hours. Then, thereto was added 2-normal hydrochloric acid under ice-cooling, and the mixture was extracted with ethyl acetate. The organic layer was washed with saturated saline, dried over magnesium sulfate, and then concentrated under reduced pressure to give 4-(3-methoxypropoxy)-1-benzofuran-6-carboxylic acid [REx(7-3)] (2.40 g) as a colorless powder.

APCI-MS m/z: 265 [M+H+MeOH—H$_2$O]$^+$.

(5) N-Methoxy-4-(3-methoxypropoxy)-N-methyl-1-benzofuran-6-carboxamide [REx(7-4)]:

To a solution of the compound obtained in the above (4) (2.39 g), N,O-dimethylhydroxyamine hydrochloride (1.86 g), 1-ethyl-3-(3-dimethylaminopropyl)carbodiimide hydrochloride (2.74 g) and 1-hydroxybenzotriazole (1.93 g) in chloroform (30 mL) was added diisopropylethylamine (4.2 mL) under ice-cooling, and the mixture was stirred at room temperature for 4 hours. Under ice-cooling, to the reaction mixture was added aqueous saturated sodium hydrogen carbonate solution, and the mixture was extracted with chloroform. The organic layer was sequentially washed with water and saturated saline, dried over magnesium sulfate, and then concentrated under reduced pressure. The resulting residue was purified by silica gel column chromatography (eluent: n-hexane/ethyl acetate=1/1→1/3) to give N-methoxy-4-(3-methoxypropoxy)-N-methyl-1-benzofuran-6-carboxamide [REx(7-4)] (2.67 g) as a pale yellow oil.

APCI-MS m/z: 294 [M+H]$^+$.

(6) 1-[4-((3-Methoxypropoxy)-1-benzofuran-6-yl]ethanone [REx(7-5)]:

To a solution of the compound obtained in the above (5) (2.67 g) in tetrahydrofuran (30 mL) was added dropwise a 3M solution of methylmagnesium bromide in diethyl ether (6.1 mL) under ice-cooling, and the mixture was stirred at the same temperature for 15 minutes. Under ice-cooling, 10% hydrochloric acid was poured into the mixture, and then the mixture was extracted with ethyl acetate. The organic layer was washed with saturated saline, and then dried over magnesium sulfate and concentrated under reduced pressure. The resulting residue was purified by silica gel column chromatography (eluent: n-hexane/ethyl acetate=4/1→1/1) to give 1-[4-((3-methoxypropoxy)-1-benzofuran-6-yl]ethanone [REx(7-5)] (2.15 g) as a colorless powder.

APCI-MS m/z: 249 [M+H]$^+$.

(7) N-{1-[4-(3-Methoxypropoxy)-1-benzofuran-6-yl]ethyl}cyclopropanamine [REx(7-6)]:

To a solution of the compound obtained in the above (6) (2.15 g) and cyclopropylamine (2.10 mL) in dichloroethane (150 mL) were added sodium triacetoxyborohydride (5.50 g), acetic acid (1.48 mL) and magnesium sulfate (5.20 g), and then the mixture was stirred at room temperature for 23 hours. Thereto was added aqueous saturated sodium hydrogen carbonate solution under ice-cooling, and the mixture was extracted with chloroform. The organic layer was washed with saturated saline, dried over magnesium sulfate, and then concentrated under reduced pressure. The resulting residue was purified by silica gel column chromatography (eluent: chloroform/methanol=20/1→13/1) to give N-{1-[4-(3-methoxypropoxy)-1-benzofuran-6-yl]ethyl}cyclopropanamine [REx(7-6)] (2.47 g) as a pale yellow oil.

APCI-MS m/z: 290 [M+H]$^+$.

Reference Example 8

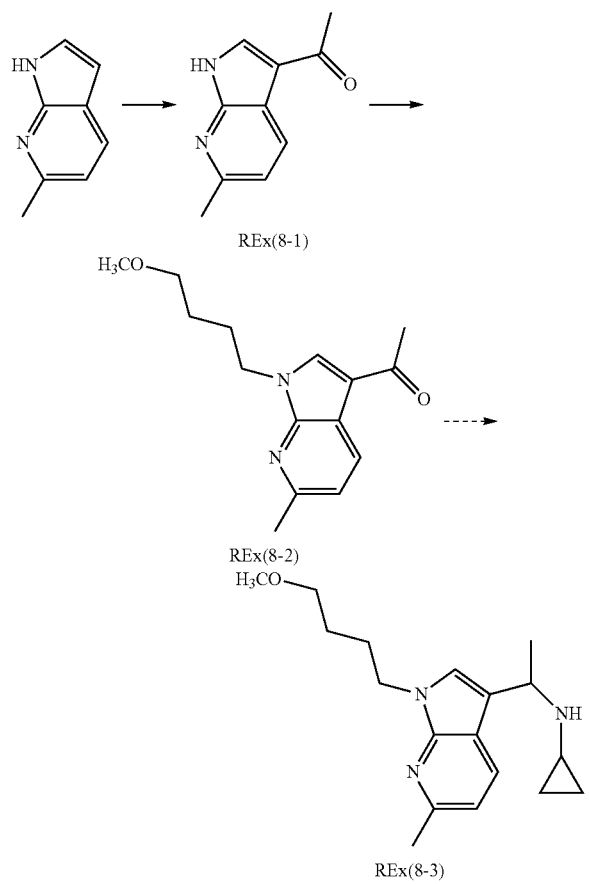

(1) 1-(6-Methyl-1H-pyrrolo[2,3-b]pyridin-3-yl)ethanone [REx(8-1)]:

To a solution of 6-methyl-1H-pyrrolo[2,3-b]pyridine (500 mg) in dichloroethane (6 mL) were added aluminum chloride (1.09 g) and acetyl chloride (0.40 mL), and then the mixture was stirred at room temperature for 1.5 hours. The reaction solution was poured into aqueous saturated sodium hydrogen carbonate solution, and extracted with chloroform. The organic layer was washed with saturated saline, dried over magnesium sulfate, and then concentrated under reduced pressure. The resulting residue was triturated with isopropyl ether to give 1-(6-methyl-1H-pyrrolo[2,3-b]pyridin-3-yl)ethanone [REx(8-1)] (481 mg) as a yellow powder.

APCI-MS m/z: 175 [M+H]$^+$.

(2) 1-[1-(4-Methoxybutyl)-6-methyl-1H-pyrrolo[2,3-b]pyridin-3-yl]ethanone [REx(8-2)]:

To a solution of the compound obtained in the above (1) (280 mg) in N,N-dimethylformamide (6 mL) was added 60% oil-based sodium hydride (83.6 mg), and then the mixture was stirred at room temperature for 30 minutes. Thereto was added dropwise a solution of 4-methoxybutyl 4-methylbenzenesulfonate in N,N-dimethylformamide (1 mL), and then thereto was added potassium iodide (267 mg), and the mixture was stirred at 50° C. for 1 hour. The reaction mixture was poured into water, and extracted with ethyl acetate. The organic layer was washed with water twice and saturated saline, dried over magnesium sulfate, and then concentrated under reduced pressure. The resulting residue was purified by silica gel column chromatography (eluent: n-hexane/ethyl acetate=2/1→1/9) to give 1-[1-(4-methoxybutyl)-6-methyl-1H-pyrrolo[2,3-b]pyridin-3-yl]ethanone [REx(8-2)] (366 mg) as a yellow oil.

APCI-MS m/z: 261 [M+H]$^+$.

(3) An amine compound [REx(8-3)] is obtained in the similar manner to Reference Example 7(7).

Reference Example 9

1-[1-(3-Methoxypropyl)-3-methyl-1H-indol-6-yl]ethanone [REx(9-1)]

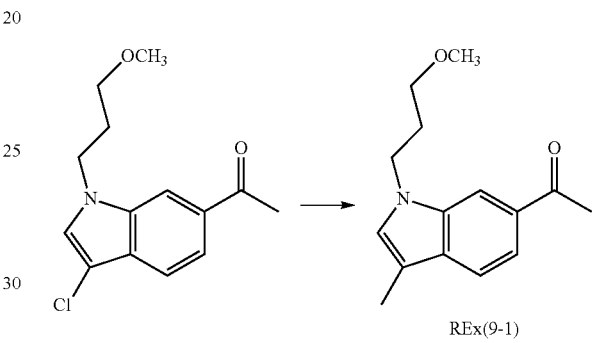

To a solution of 1-[3-chloro-1-(3-methoxypropyl)-1H-indol-6-yl]ethanone (843 mg) in 1,4-dioxane (15 mL) were added potassium phosphate (1.35 g), trimethylboroxine (883 mg), tris(dibenzylideneacetone)dipalladium (290 mg) and 2-dicyclohexylphosphino-2',4',6'-triisopropyl-1,1'-biphenyl (X-Phos) (605 mg) under argon, and the mixture was heated to stir at 110° C. for 4 hours. Thereto was added water under ice-cooling, and the mixture was extracted with ethyl acetate. The organic layer was washed with saturated saline, dried over magnesium sulfate, and then concentrated under reduced pressure. The resulting residue was purified by silica gel column chromatography (eluent: n-hexane/ethyl acetate=3/1→3/2) to give 1-[1-(3-methoxypropyl)-3-methyl-1H-indol-6-yl]ethanone [REx(9-1)] (663 mg) as a yellow oil.

APCI-MS m/z: 246 [M+H]$^+$.

Reference Example 10

Methyl 1-(3-methoxypropyl)indoline-6-carboxylate [REx(10-1)]

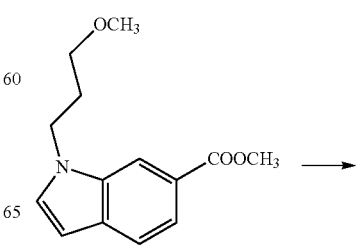

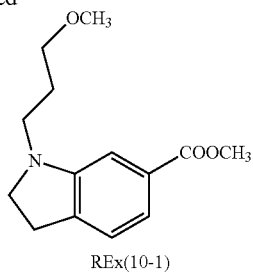

REx(10-1)

To a mixture of methyl 1-(3-methoxypropyl)-1H-indole-6-carboxylate (1.5 g) and sodium cyanohydroborate (1.61 g) was added acetic acid (15 mL) under ice-cooling, and the mixture was stirred at room temperature for 3 hours. To the reaction solution was added aqueous saturated sodium hydrogen carbonate solution under ice-cooling, and the mixture was neutralized by adding sodium hydrogen carbonate, and then extracted with ethyl acetate.

The organic layer was washed with saturated saline, dried over sodium sulfate, and then concentrated under reduced pressure. The resulting residue was purified by silica gel column chromatography (eluent: n-hexane→n-hexane/ethyl acetate=2/1) to give methyl 1-(3-methoxypropyl)indoline-6-carboxylate [REx(10-1)] (1.20) as a pale yellow oil.

APCI-MS m/z: 250 [M+H]$^+$.

Reference Example 14

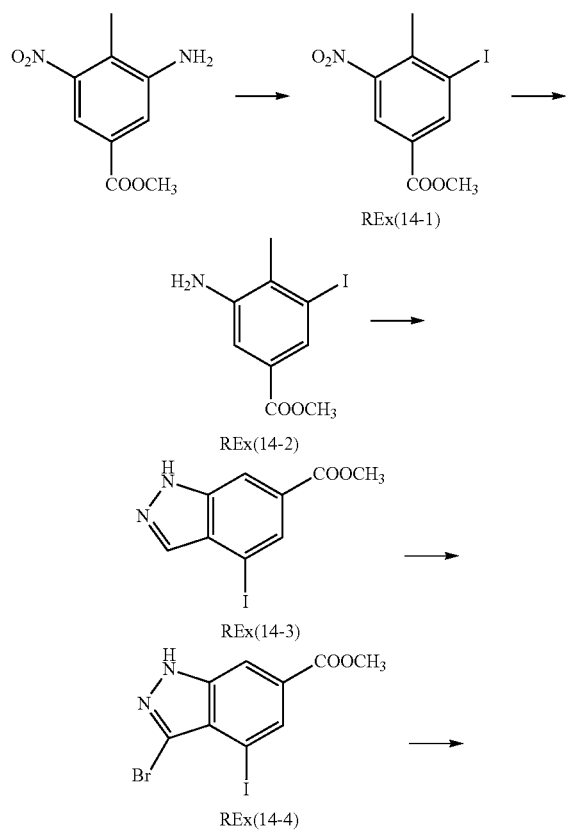

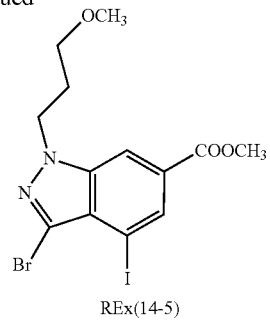

REx(14-5)

(1) Methyl 3-iodo-4-methyl-5-nitrobenzoate [REx(14-1)]:

To a suspension of methyl 3-amino-4-methyl-5-nitrobenzoate (36.0 g) in 6-normal hydrochloric acid (276 mL) was added dropwise a solution of sodium nitrite (13.0 g) in water (35 mL) under ice-salt-cooling over 20 minutes, and the mixture was stired under ice-cooling for 1 hour. Then, thereto was added dropwise a solution of potassium iodide (34.1 g) in water (280 mL) under ice-cooling over 20 minutes, and the mixture was stirred at room temperature for 2 hours. To the reaction solution was added water under ice-cooling, and the mixture was extracted with chloroform. The organic layer was sequentially washed with aqueous saturated sodium thiosulfate solution and saturated saline, dried over sodium sulfate, and then concentrated under reduced pressure. The resulting residue was purified by silica gel column chromatography (eluent: n-hexane/ethyl acetate=50/1) to give methyl 3-iodo-4-methyl-5-nitrobenzoate [REx(14-1)] (40.5 g) as a yellow powder.

(2) Methyl 3-amino-5-iodo-4-methylbenzoate [REx(14-2)]:

To a solution of the compound obtained in the above (1) (40.5 g) in ethyl acetate (500 mL) was added tin (II) chloride dihydrate (142 g), and the mixture was heated to stir at 60° C. for 1 hour. Aqueous sodium hydrogen carbonate solution was poured into the reaction mixture under ice-cooling, and then an insoluble was filtered through Celite. The organic layer was separated, and then washed with saturated saline, dried over sodium sulfate, and then concentrated under reduced pressure to give methyl 3-amino-5-iodo-4-methylbenzoate [REx(14-2)] (35.3 g) as a pale yellow powder.

APCI-MS m/z: 292 [M+H]$^+$.

(3) Methyl 4-iodo-1H-indazole-6-carboxylate [REx(14-3)]:

To a suspension of the compound obtained in the above (2) (35.3 g) in water (615 mL) were added concentrated hydrochloric acid (102 mL) and ammonium tetrafluoroborate (16.5 g), and the mixture was cooled to −3° C. Under the cooling, thereto was added dropwise a solution of sodium nitrite (9.20 g) in water (34 mL) over 20 minutes. The mixture was stirred at −3° C. for 1 hour, and then the precipitated crystal was filtered, sequentially washed with water (100 mL) and diethyl ether (100 mL), and then dried under reduced pressure. The resulting solid was suspended in chloroform (420 mL), and then thereto were added potassium acetate (13.1 g) and 18-crown-6 (801 mg), and the mixture was stirred at room temperature for 15 hours. To the reaction mixture was added water under ice-cooling, and then the mixture was extracted with chloroform. The organic layer was washed with saturated saline, dried over sodium sulfate, and then concentrated under reduced pressure. The resulting residue was triturated with chloroform to give methyl 4-iodo-1H-indazole-6-carboxylate [REx(14-3)] (18.9 g) as a pale orange powder.

APCI-MS m/z: 303 [M+H]$^+$.

(4) Methyl 3-bromo-4-iodo-1H-indazole-6-carboxylate [REx(14-4)]:

The compound obtained in the above (3) (24.5 g) was dissolved in acetic acid (720 mL), and after blocking out light, bromine (8.30 mL) was added dropwise to the mixture at room temperature. After stirring at room temperature for 40 hours, bromine (4.15 mL) was added thereto, and the mixture was stirred for additional 24 hours at room temperature. Then, thereto were added acetic acid (100 mL) and bromine (4.15 mL), and the mixture was stirred at room temperature for 6 hours. The reaction mixture was poured into ice water, and then thereto was added sodium thiosulfate, and the mixture was stirred at room temperature for 20 minutes, and then the precipitated solid was filtered. The solid was washed with water, and then dissolved in ethyl acetate and washed with saturated saline. The organic layer was dried over sodium sulfate, and then concentrated under reduced pressure. The resulting residue was triturated with isopropyl ether to give methyl 3-bromo-4-iodo-1H-indazole-6-carboxylate [REx(14-4)] (27.3 g) as a pale yellow powder.

APCI-MS m/z: 381/383 [M+H]$^+$.

(5) Methyl 3-bromo-4-iodo-1-(3-methoxypropyl)-1H-indazole-6-carboxylate [REx(14-5)]:

To a solution of the compound obtained in the above (4) (22.3 g) in N,N-dimethylformamide (200 mL) was added 60% oil-based sodium hydride (2.81 g) under ice-cooling, and the mixture was stirred at room temperature for 15 minutes. To the mixture was added a solution of 1-bromo-3-methoxypropane (10.8 g) in N,N-dimethylformamide (40 mL) under ice-cooling, and the mixture was stirred at room temperature for 18 hours. 10% Hydrochloric acid was poured into the reaction solution under ice-cooling, and then the mixture was extracted with ethyl acetate. The organic layer was sequentially washed with water and saturated saline, dried over sodium sulfate, and then concentrated under reduced pressure. The resulting residue was purified by silica gel column chromatography (eluent: n-hexane/ethyl acetate=9/1) to give methyl 3-bromo-4-iodo-1-(3-methoxypropyl)-1H-indazole-6-carboxylate [REx(14-5)] (23.5 g) as a pale orange powder.

APCI-MS m/z: 453/455 [M+H]$^+$.

Reference Example 15

1-[4-Chloro-1-(3-methoxypropyl)-3-methyl-1H-indazol-6-yl]ethanone [REx(15-1)]

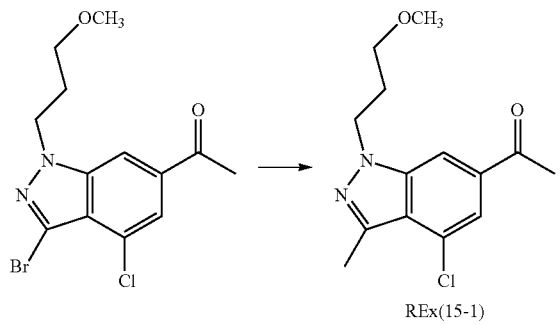 [SMILES: COCCCn1nc(Br)c2c(Cl)cc(C(C)=O)cc21 ; COCCCn1nc(C)c2c(Cl)cc(C(C)=O)cc21]

REx(15-1)

To a solution of 1-[3-bromo-4-chloro-1-(3-methoxypropyl)-1H-indazol-6-yl]ethanone (1.0 g) in 1,4-dioxane (20 mL) were added potassium carbonate (1.2 g), trimethylboroxine (0.41 mL) and 1,1'-bis(diphenylphosphino)ferrocene dichloropalladium (II) (212 mg) under argon, and the mixture was heated to stir at 80° C. for 24 hours. Then, thereto was added water under ice-cooling, and the mixture was extracted with ethyl acetate. The organic layer was washed with saturated saline, dried over magnesium sulfate, and then concentrated under reduced pressure. The resulting residue was purified by NH-silica gel column chromatography (eluent: n-hexane/ethyl acetate=4/1→3/2) to give 1-[4-chloro-1-(3-methoxypropyl)-3-methyl-1H-indazol-6-yl]ethanone [REx(15-1)] (392 mg) as a pale yellow oil.

APCI-MS m/z: 281/283 [M+H]$^+$.

Reference Example 16

1-[1-(3-Methoxypropyl)-3,4-dimethyl-1H-indazol-6-yl]ethanone [REx(16-1)]

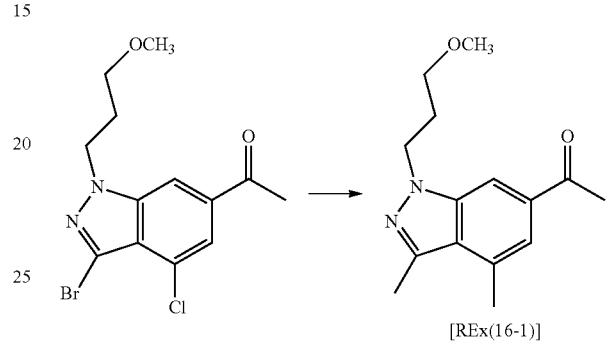

To a solution of 1-[3-bromo-4-chloro-1-(3-methoxypropyl)-1H-indazol-6-yl]ethanone (1.0 g) in 1,4-dioxane (7.5 mL) were added potassium carbonate (1.2 g), trimethylboroxine (1.0 mL) and 1,1'-bis(diphenylphosphino)ferrocene dichloropalladium (II) (212 mg) under argon, and the mixture was heated to stir at 110° C. for 24 hours. Then, thereto was added water under ice-cooling, and the mixture was extracted with ethyl acetate.

The organic layer was washed with saturated saline, dried over magnesium sulfate, and then concentrated under reduced pressure. The resulting residue was purified by NH-silica gel column chromatography (eluent: n-hexane/ethyl acetate=3/1→1/1) to give 1-[1-(3-methoxypropyl)-3,4-dimethyl-1H-indazol-6-yl]ethanone [REx(16-1)] (689 mg) as an orange oil.

APCI-MS m/z: 261 [M+H]$^+$.

Reference Example 17

1-[3-Bromo-1-(3-methoxypropyl)-4-(trifluoromethyl)-1H-indazol-6-yl]ethanone [REx(17-1)]

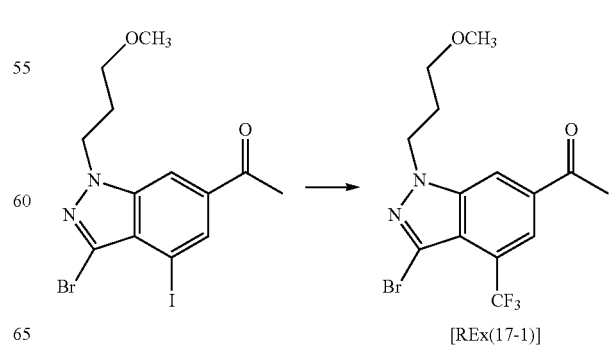

A mixture of 1-[3-bromo-4-iodo-1-(3-methoxypropyl)-1H-indazol-6-yl]ethanone (500 mg), methyl fluorosulfonyldifluoroacetate (1.36 g), hexamethylphosphorylamide (1.27 g) and copper (I) iodide (337 mg) was heated to stir in N,N-dimethylformamide (7.0 mL) under argon at 75° C. for 15 hours. Water and ethyl acetate were poured into the reaction mixture under ice-cooling, and then an insoluble was filtered through Celite. The organic layer was separated, and then sequentially washed with water and saturated saline, dried over sodium sulfate, and then concentrated under reduced pressure. The resulting residue was purified by silica gel column chromatography (eluent: n-hexane→n-hexane/ethyl acetate=1/1) to give 1-[3-bromo-1-(3-methoxypropyl)-4-(trifluoromethyl)-1H-indazol-6-yl]ethanone [REx(17-1)] (87 mg) as a yellow oil.

APCI-MS m/z: 379/381 [M+H]$^+$.

Reference Example 18

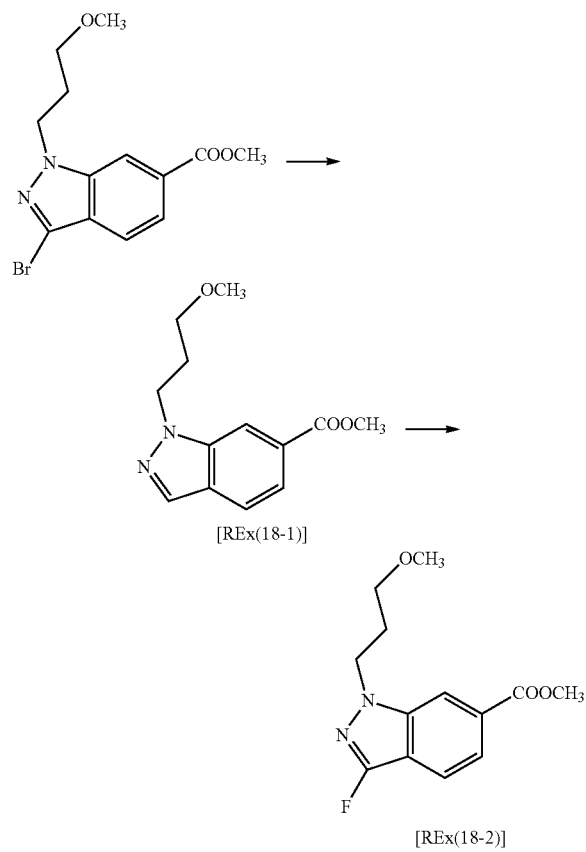

[REx(18-1)]

[REx(18-2)]

(1) Methyl 1-(3-methoxypropyl)-1H-indazole-6-carboxylate [REx(18-1)]:

To a solution of methyl 3-bromo-1-(3-methoxypropyl)-1H-indazole-6-carboxylate (3.0 g) and diisopropylethylamine (2.4 mL) in methanol (60 mL) was added 10% palladium on carbon catalyst (600 mg), and the mixture was stirred under hydrogen for 1 hour. An insoluble was filtered, and then the filtrate was concentrated under reduced pressure. The residue was dissolved in chloroform, sequentially washed with 10% hydrochloric acid water and saturated saline, and then concentrated under reduced pressure to give methyl 1-(3-methoxypropyl)-1H-indazole-6-carboxylate [REx(18-1)] (2.40 g) as a pale yellow oil.

(2) Methyl 3-fluoro-1-(3-methoxypropyl)-1H-indazole-6-carboxylate [REx(18-2)]:

To a solution of the compound obtained in the above (1) (2.20 g) in acetonitrile (30 mL) was added Selectfluor (Registered trademark) (3.45 g), and the mixture was stirred at 80° C. for 15 hours. Then, thereto was added aqueous sodium hydrogen carbonate solution under ice-cooling, and the mixture was extracted with ethyl acetate. The organic layer was washed with saturated saline, dried over sodium sulfate, and then concentrated under reduced pressure. The resulting residue was purified by silica gel column chromatography (eluent: n-hexane→n-hexane/ethyl acetate=5/1) to give methyl 3-fluoro-1-(3-methoxypropyl)-1H-indazole-6-carboxylate [REx(18-2)] (1.01 g) as a colorless oil.

APCI-MS m/z: 267 [M+H]$^+$.

Reference Example 19

1-[3-Fluoro-5-(3-methoxypropoxy)phenyl]ethanone [REx(19-2)]

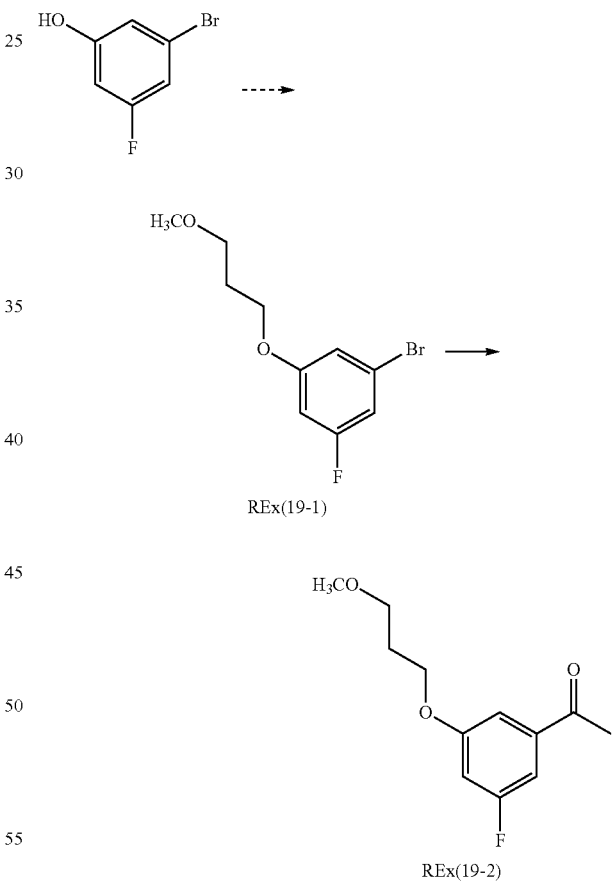

REx(19-1)

REx(19-2)

1-Bromo-3-fluoro-5-(3-methoxypropoxy)benzene (4.0 g) was added to water (30.4 mL), and then thereto were added ethylene glycol monovinyl ether (6.8 mL), potassium carbonate (2.52 g), 1,3-bis(diphenylphosphino)propane (125 mg) and palladium acetate (34 mg), and the mixture was heated to stir at 90° C. for 22 hours. After cooling, thereto was added concentrated hydrochloric acid (7.2 mL), and the mixture was stirred at room temperature for 20 minutes. The reaction solution was extracted with ethyl acetate, washed with saturated saline, and then dried over magnesium sulfate. After concentrating under reduced pressure, the resulting residue was purified by silica gel column chromatography (eluent: n-hexane/ethyl acetate=20/1→2/1) to give 1-[3-fluoro-5-(3-methoxypropoxy)phenyl]ethanone [REx(19-2)] (1.03 g) as a yellow oil.

APCI-MS m/z: 227 [M+H]$^+$.

A starting material [REx(19-1)] is prepared from, for example, 1-bromo-3-fluoro-phenol according to the conventional manner (such as the method of Reference Example 7 (3)).

Reference Example 20

1-[3-hydroxy-5-(3-methoxypropoxy)phenyl]ethanone [REx(20-1)]

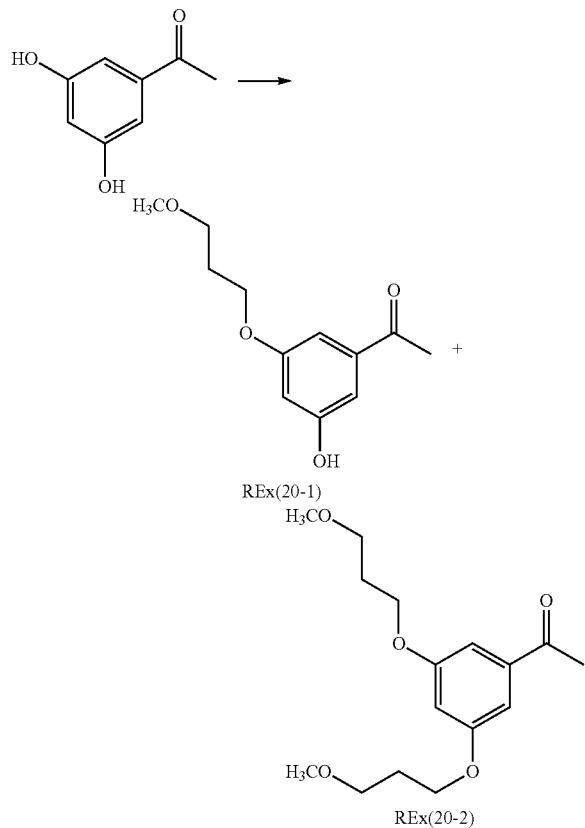

To a solution of 1-(3,5-dihydroxyphenyl)ethanone (10 g) in N,N-dimethylformamide (164 mL)—water (5 mL) were added potassium carbonate (13.6 g) and 3-methoxypropyl 4-methylbenzene sulfonate (16.1 g), and the mixture was heated to stir at 80° C. for 2 hours. The reaction solution was concentrated under reduced pressure, and then thereto was added water, and then the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=3/1→1/1) to give 1-[3-hydroxy-5-(3-methoxypropoxy)phenyl]ethanone [REx(20-1)] (4.65 g) as a colorless powder and 1-[3,5-bis(3-methoxypropoxy)phenyl]ethanone [REx(20-2)] (4.98 g) as a colorless oil.

REx(20-1): APCI-MS m/z: 225 [M+H]$^+$.
REx(20-2): APCI-MS m/z: 297 [M+H]$^+$.

Reference Example 21

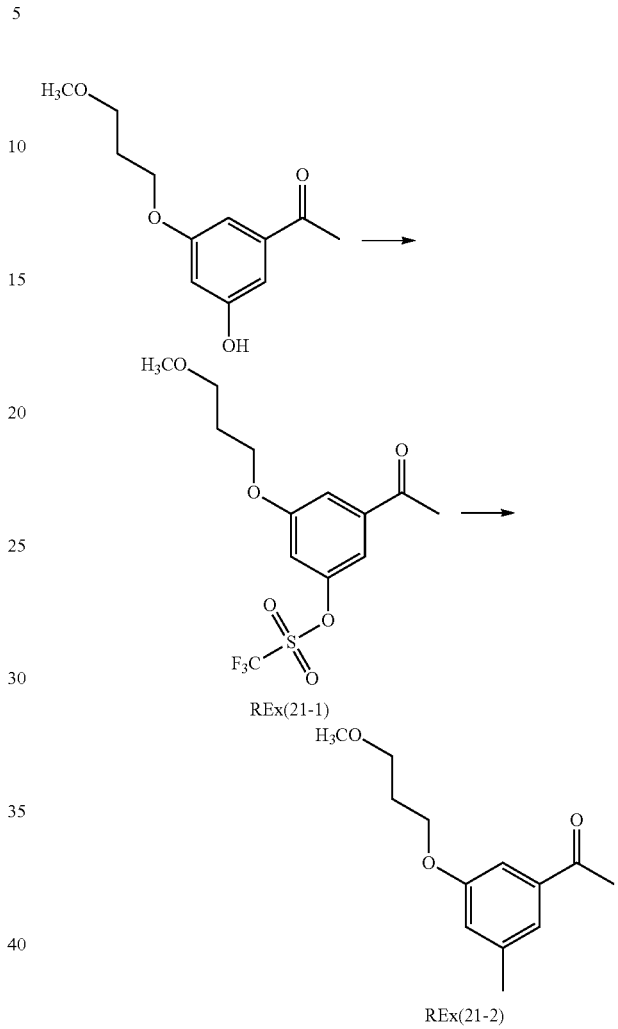

(1) 3-Acetyl-5-(3-methoxypropoxy)phenyltrifluoromethanesulfonate [REx(21-1)]:

To a solution of 1-[3-hydroxy-5-(3-methoxypropoxy)phenyl]ethanone (4.65 g) in chloroform (100 mL) was added pyridine (5.02 mL) under ice-cooling, and then thereto was added dropwise trifluoromethanesulfonic anhydride (3.67 mL) under the ice-cooling, and then the mixture was stirred at the same temperature for 20 minutes. Then, thereto was added 1-normal hydrochloric acid, and the mixture was extracted with chloroform, and then the organic layer was sequentially washed with water and saturated saline, dried over magnesium sulfate, and then concentrated under reduced pressure to give a crude product of 3-acetyl-5-(3-methoxypropoxy)phenyltrifluoromethanesulfonate [REx(21-1)] (8.22 g) as a yellow oil.

APCI-MS m/z: 374 [M+NH$_4$]$^+$.

(2) 1-[3-(3-Methoxypropoxy)-5-methylphenyl]ethanone [REx(21-2)]:

To a solution of the compound obtained in the (1) (8.22 g) in 1,4-dioxane (100 mL) were added potassium carbonate (8.6 g), trimethylboroxine (3.5 mL) and 1,1'-bis(diphenylphosphino)ferrocene dichloropalladium (II) (1.51 g), and the mixture was heated to stir at 110° C. for 2 hours. After cooling to room temperature, thereto was added water, and the mixture was extracted with ethyl acetate. The organic layer was washed with saturated saline, dried over magnesium sulfate, and then concentrated under reduced pressure. The resulting residue was purified by silica gel column chromatography (eluent: n-hexane→n-hexane/ethyl acetate=5/1) to give 1-[3-(3-methoxypropoxy)-5-methylphenyl]ethanone [REx(21-2)] (4.15 g) as a brown oil.

APCI-MS m/z: 223 [M+H]$^+$.

Reference Example 22

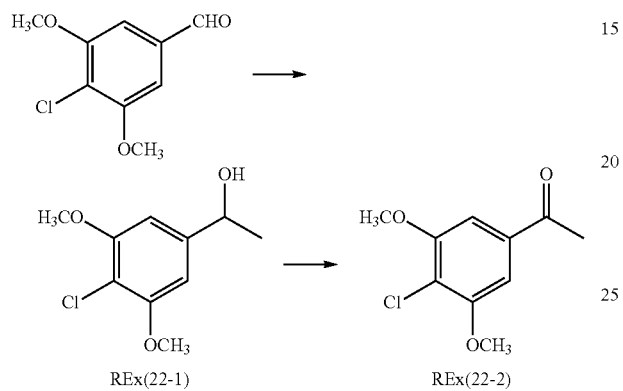

(1) 1-(4-Chloro-3,5-dimethoxyphenyl)ethanol [REx(22-1)]:

To a solution of 4-chloro-3,5-dimethoxybenzaldehyde (1.0 g) in tetrahydrofuran (20 mL) was added dropwise a 3M solution of methylmagnesium bromide in diethyl ether (1.83 mL) under ice-cooling, and the mixture was stirred at the same temperature for 1 hour. Then, thereto was added aqueous ammonium chloride solution under ice-cooling, and the mixture was extracted with ethyl acetate. The organic layer was sequentially washed with water and saturated saline, and then dried over magnesium sulfate and concentrated under reduced pressure to give a crude product of 1-(4-chloro-3,5-dimethoxyphenyl)ethanol [REx(22-1)] (1.23 g) as a colorless powder.

APCI-MS m/z: 200 [M+H—H$_2$O]$^+$.

(2) 1-(4-Chloro-3,5-dimethoxyphenyl)ethanone [REx(22-2)]:

To a solution of the compound obtained in the above (1) (1.23 g) in dichloromethane (28 mL) was added 85% activated manganese dioxide (5.81 g), and the mixture was stirred at 40° C. for 4 hours. The reaction solution was cooled to room temperature, and then thereto was added water-chloroform, and an insoluble was filtered off through Celite, and then the organic layer was separated. The organic layer was concentrated under reduced pressure, and the resulting residue was purified by silica gel column chromatography (eluent: n-hexane/ethyl acetate=10/1→1/1) to give 1-(4-chloro-3,5-dimethoxyphenyl)ethanone [REx(22-2)] (723 mg) as a colorless powder.

APCI-MS m/z: 215 [M+H]$^+$.

Reference Example 23

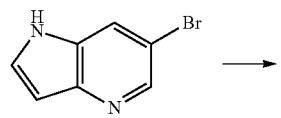

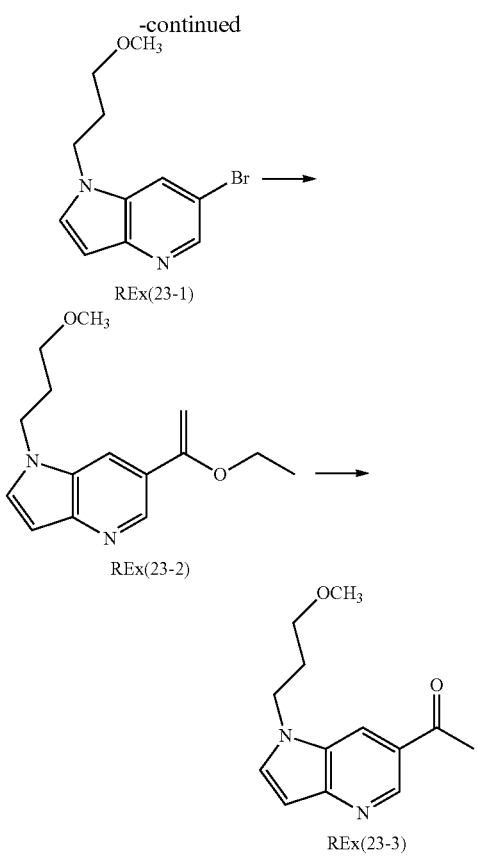

(1) 6-(1-Ethoxyvinyl)-1-(3-methoxypropyl)-1H-pyrrolo[3,2-b]pyridine [REx(23-2)]:

To a solution of 6-bromo-1-(3-methoxypropyl)-1H-pyrrolo[3,2-b]pyridine (1.5 g) in toluene (30 mL) were added tri-n-butyltin-1-ethoxyvinyl (5.65 mL) and dichlorobis(triphenylphosphine)palladium (II) (782 mg), and the mixture was heated to stir at 110° C. for 30 minutes. The reaction solution was cooled to room temperature, and then thereto was added water-ethyl acetate, and an insoluble was filtered through Celite. The organic layer was separated, and then washed with saturated saline, dried over magnesium sulfate, and then concentrated under reduced pressure. The resulting residue was purified by NH-silica gel column chromatography (eluent: n-hexane/ethyl acetate=4/1→1/1) to give 6-(1-ethoxyvinyl)-1-(3-methoxypropyl)-1H-pyrrolo[3,2-b]pyridine [REx(23-2)] (1.69 g) as a yellow oil.

A starting compound [REx(23-1)] is obtained by 3-methoxypropylation at N of 6-bromo-1-1H-pyrrolo[3,2-b]pyridine.

APCI-MS m/z: 261 [M+H]$^+$.

(2) 1-[1-(3-Methoxypropyl)-1H-pyrrolo[3,2-b]pyridin-6-yl]ethanone [REx(23-3)]:

The compound obtained in the above (1) (1.69 g) was dissolved in chloroform (20 mL), and then thereto was added 4-normal hydrogen chloride/1,4-dioxane under ice-cooling, and the mixture was stirred at the same temperature for 2 hours. Then, thereto was added aqueous saturated sodium hydrogen carbonate solution under ice-cooling, and the mixture was extracted with chloroform. The organic layer was washed with saturated saline, dried over magnesium sulfate, and then concentrated under reduced pressure. The resulting residue was purified by NH-silica gel column chromatography (eluent: n-hexane/ethyl acetate=2/1→1/1)

to give 1-[1-(3-methoxypropyl)-1H-pyrrolo[3,2-b]pyridin-6-yl]ethanone [REx(23-3)] (766 mg) as a yellow oil.

APCI-MS m/z: 233 [M+H]$^+$.

Reference Example 24

1-[4-Methoxy-3-(4-methoxybutyl)phenyl]ethanone [REx(24-1)]

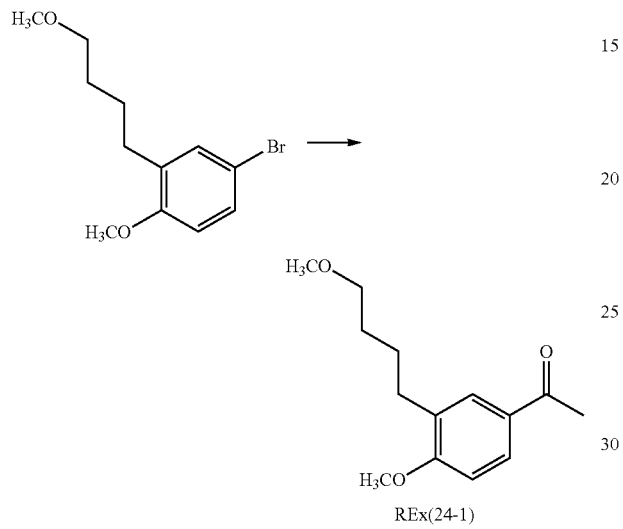

REx(24-1)

To a solution of 4-bromo-1-methoxy-2-(4-methoxybutyl)benzene (523 mg) in tetrahydrofuran (10 mL) were added lithium chloride (326 mg), tetrakis(triphenylphosphine)palladium (0) (381 mg) and tri-n-butyltin-1-ethoxyvinyl (1.11 mL), and the mixture was heated to stir at 80° C. for 20 hours. The reaction solution was cooled to room temperature, and then thereto was added aqueous potassium fluoride solution, and the mixture was stirred for 30 minutes. The mixture was extracted with diethyl ether, and then thereto was added 10% hydrochloric acid, and the mixture was stirred for 1 hour. The organic layer was separated, dried over magnesium sulfate, and then concentrated under reduced pressure. The resulting residue was purified by silica gel column chromatography (eluent: n-hexane/ethyl acetate=9/1→1/1) to give 1-[4-methoxy-3-(4-methoxybutyl)phenyl]ethanone [REx(24-1)] (195 mg) as a yellow oil.

APCI-MS m/z: 237 [M+H]$^+$.

Reference Example 25

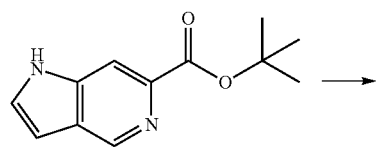

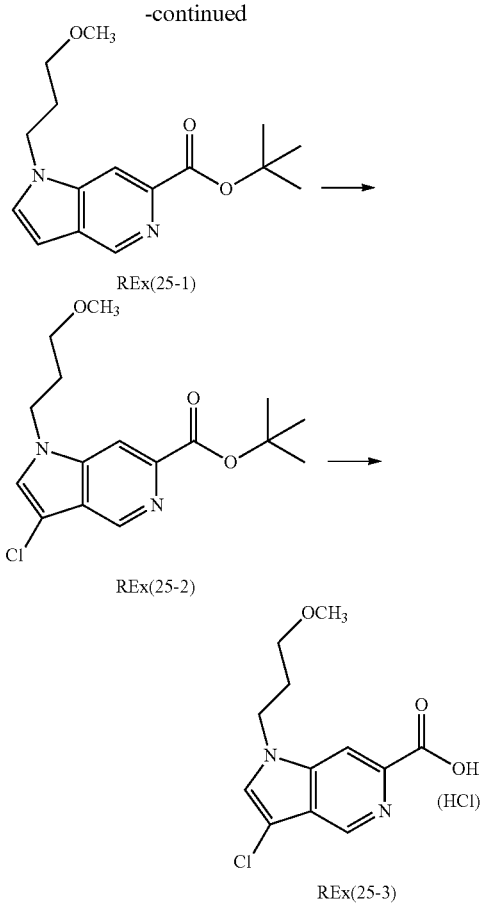

REx(25-1)

REx(25-2)

REx(25-3)

(1) tert-Butyl 1-(3-methoxypropyl)-1H-pyrrolo[3,2-c]pyridine-6-carboxylate [REx(25-1)]:

To a solution of tert-butyl 1H-pyrrolo[3,2-c]pyridine-6-carboxylate (2.0 g) in N,N-dimethylformamide (15 mL) was added drop by drop 60% oil-based sodium hydride (385 mg) under ice-cooling, and then the mixture was stirred at room temperature for 15 minutes. Then, thereto was added dropwise a solution of 1-bromo-3-methoxypropane (1.47 g) in N,N-dimethylformamide (5 mL) under ice-cooling, and then the mixture was stirred at room temperature for 18 hours. To the reaction mixture was added water under ice-cooling, and the mixture was extracted with ethyl acetate. The organic layer was sequentially washed with water and saturated saline, dried over sodium sulfate, and then concentrated under reduced pressure. The resulting residue was purified by silica gel column chromatography (eluent: n-hexane/ethyl acetate=1/1) to give tert-butyl 1-(3-methoxypropyl)-1H-pyrrolo[3,2-c]pyridine-6-carboxylate [REx(25-1)] (2.52 g) as a yellow oil.

APCI-MS m/z: 291 [M+H]$^+$.

(2) tert-Butyl 3-chloro-1-(3-methoxypropyl)-1H-pyrrolo[3,2-c]pyridine-6-carboxylate [REx(25-2)]:

To a solution of the compound obtained in the above (1) (2.52 g) in dichloromethane (50 mL) was added N-chlorosuccinimide (1.50 g) under ice-cooling, and the mixture was stirred at room temperature for 72 hours. To the reaction mixture was added water under ice-cooling, and the mixture was extracted with chloroform. The organic layer was washed with saturated saline, dried over sodium sulfate, and then concentrated under reduced pressure. The resulting residue was purified by NH-silica gel column chromatography (eluent: n-hexane/ethyl acetate=9/1) to give tert-butyl 3-chloro-1-(3-methoxypropyl)-1H-pyrrolo[3,2-c]pyridine-6-carboxylate [REx(25-2)] (2.45 g) as a colorless powder.

APCI-MS m/z: 325/327 [M+H]$^+$.

(3) 3-Chloro-1-(3-methoxypropyl)-1H-pyrrolo[3,2-c]pyridine-6-carboxylic acid hydrochloride [REx(25-3)]:

The compound obtained in the above (2) (2.42 g) was added to tritfluoroacetic acid (24 mL), and the mixture was stirred at room temperature for 2 hours. To the reaction solution was added 1-normal hydrochloric acid water (15 mL) under ice-cooling, and then the mixture was concentrated under reduced pressure. The resulting residue was triturated with isopropyl ether to give 3-chloro-1-(3-methoxypropyl)-1H-pyrrolo[3,2-c]pyridine-6-carboxylic acid hydrochloride [REx(25-3)] (2.20 g) as a brown powder.

ESI-MS m/z: 267/269[M−H]$^-$

Reference Example 26

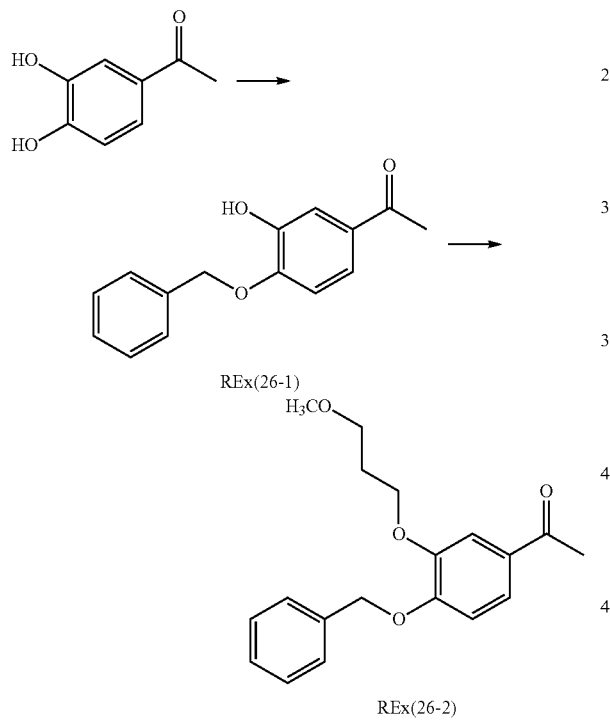

(1) 1-[4-(Benzyloxy)-3-hydroxyphenyl]ethanone [REx(26-1)]:

To a solution of 3',4'-dihydroxyacetophenone (25.4 g) in N,N-dimethylacetamide (420 mL) were added potassium carbonate (23.1 g) and benzyl bromide (19.9 mL) under ice-cooling, and the mixture was stirred at room temperature for 90 minutes. An insoluble was filtered, and then diluted with ethyl acetate. The organic layer was sequentially washed with water and saturated saline, dried over magnesium sulfate, and then concentrated under reduced pressure. The resulting residue was purified by silica gel column chromatography (eluent: n-hexane-n-hexane/ethyl acetate=20/1), and then triturated with ethyl acetate to give 1-[4-(benzyloxy)-3-hydroxyphenyl]ethanone [REx(26-1)] (11.0 g) as a colorless powder.

APCI-MS m/z: 243 [M+H]$^+$.

(2) 1-[4-(Benzyloxy)-3-(3-methoxypropyl)phenyl]ethanone [REx(26-2)]:

To a solution of the compound obtained in the above (1) (11.0 g) in acetonitrile (113 mL) were added potassium carbonate (9.37 g) and 3-methoxypropyl 4-methylbenzene sulfonate (13.2 g), and the mixture was heated to reflux for 20 hours. The reaction solution was cooled to room temperature, and then thereto was added water, and the mixture was extracted with ethyl acetate. The organic layer was dried over magnesium sulfate, and then concentrated under reduced pressure. The resulting residue was triturated with diisopropyl ether to give 1-[4-(benzyloxy)-3-(3-methoxypropyl)phenyl]ethanone [REx(26-2)] (8.75 g) as a colorless powder.

APCI-MS m/z: 315 [M+H]$^+$.

Reference Example 27

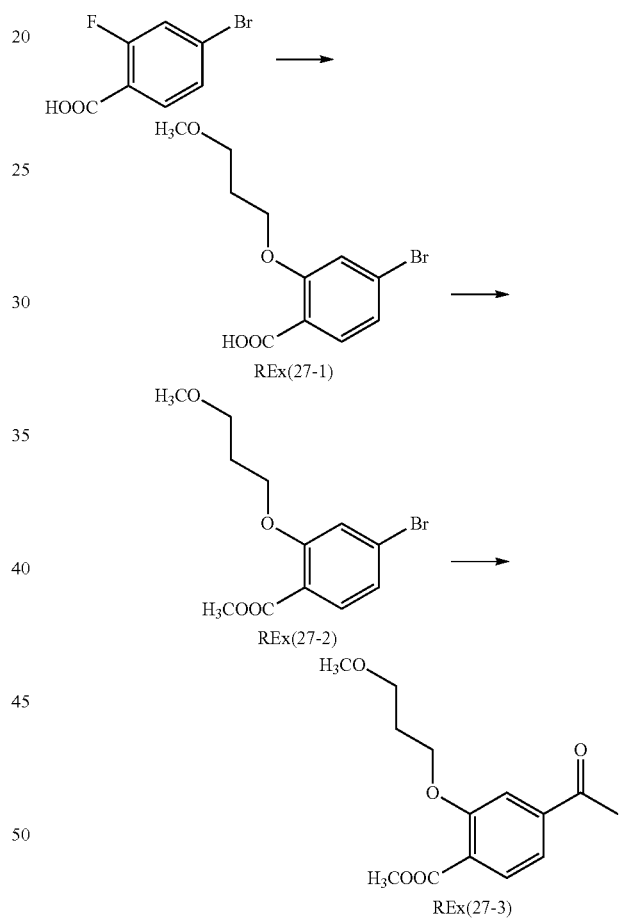

(1) 4-Bromo-2-(3-methoxypropoxy)benzoic acid [REx(27-1)]:

To a solution of 3-methoxy-1-propanol (5.02 g) in N,N-dimethylformamide (37 mL) was added 60% oil-based sodium hydride (2.05 g), and the mixture was stirred at room temperature for 30 minutes. Then, thereto was added dropwise a solution of 4-bromo-2-fluorobenzoic acid (300 mg) in N,N-dimethylformamide (60 mL), and the mixture was stirred at room temperature for 20 hours. To the reaction solution was added water and n-hexane, and then the mixed solution was acidified by concentrated hydrochloric acid. The resulting colorless powder was filtered to give 4-bromo-2-(3-methoxypropoxy)benzoic acid [REx(27-1)] (4.43 g).

ESI-MS m/z: 289[M−H]$^-$ (2) Methyl 4-bromo-2-(3-methoxypropoxy)benzoate [REx (27-2)]:

To a mixture of the compound obtained in the above (1) (4.42 g) and potassium carbonate (4.22 g) was added N,N-dimethylformamide (20 mL), and then thereto was added methyl iodide (1.43 mL), and the mixture was stirred at room temperature for 30 minutes. After cooling, to the reaction solution was added water, and the mixture was extracted with ethyl acetate. The organic layer was sequentially washed with water twice and saturated saline, dried over magnesium sulfate, and then concentrated under reduced pressure. The resulting residue was purified by silica gel column chromatography (eluent: n-hexane/ethyl acetate=20/1-3/1) to give methyl 4-bromo-2-(3-methoxypropoxy)benzoate [REx(27-2)] (4.01 g) as a colorless oil.

APCI-MS m/z: 343/305 [M+H]$^+$.

(3) Methyl 4-acetyl-2-(3-methoxypropoxy)benzoate [REx (27-3)]:

To a solution of the compound obtained in the above (2) (4.0 g) in toluene (44 mL) were added tri-n-butyltin-1-ethoxyvinyl (8.90 mL) and dichlorobis(triphenylphosphine) palladium (II) (1.85 g), and the mixture was heated to stir at 100° C. for 17 hours. The reaction solution was cooled to room temperature, and then thereto was added 4-normal hydrogen chloride-1,4-dioxane (24 mL), and the mixture was stirred at room temperature for 1 hour. To the reaction solution was added water, and the mixture was extracted with ethyl acetate. The organic layer was washed with saturated saline, and then thereto were added magnesium sulfate and NH-silica gel, and an insoluble was filtered. The filtrate was concentrated under reduced pressure. The resulting residue was purified by silica gel column chromatography (eluent: n-hexane/ethyl acetate=20/1) to give methyl 4-acetyl-2-(3-methoxypropoxy)benzoate [REx(27-3)] (1.02 g) as a yellow oil.

APCI-MS m/z: 267 [M+H]$^+$.

Reference Example 28

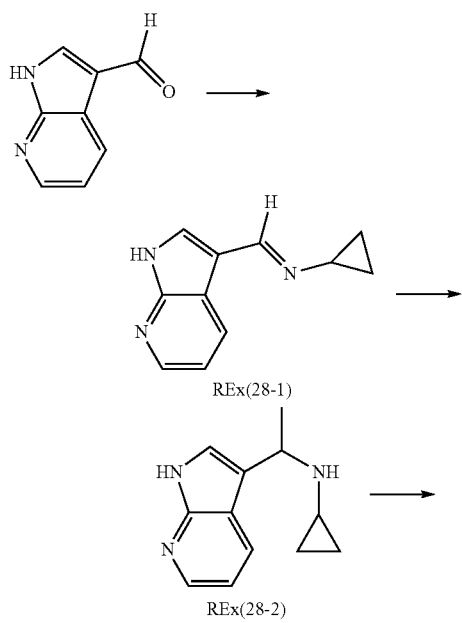

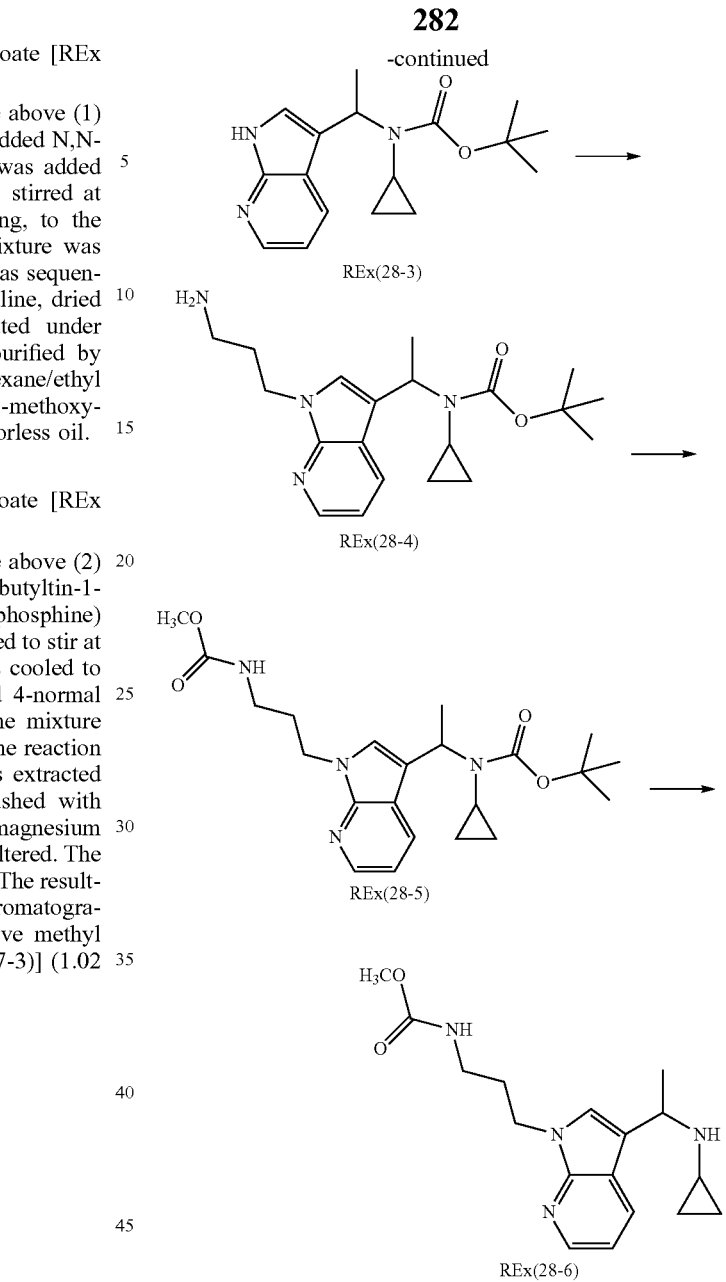

(1) N-[(1E)-1H-Pyrrolo[2,3-b]pyridin-3-ylmethylene]cyloprolylamine [REx(28-1)]:

To a suspension of 1H-pyrrolo[2,3-b]pyridin-3-carbaldehyde (1.46 g) in ethanol (30 mL) was added cyclopropylamine (1.41 mL), and the mixture was stirred at 50° C. for 19 hours. The reaction solution was concentrated under reduced pressure, and then treated azeotropically with toluene. The resulting residue was triturated with isopropyl ether/n-hexane (3:1) to give N-[(1E)-1H-pyrrolo[2,3-b]pyridin-3-ylmethylene]cyclopropylamine [REx(28-1)] (1.75 g) as a colorless powder.

APCI-MS m/z: 186 [M+H]$^+$.

(2) N-[1-(1H-Pyrrolo[2,3-b]pyridin-3-yl)ethyl]cylopro-lylamine [REx(28-2)]:

To a suspension of the compound obtained in the above (1) (1.11 g) and 1-(trimethylsilyl)-1H-benzotriazole (2.20 mL) in toluene (50 mL) was added dropwise a 3M solution of methylmagnesium bromide in diethyl ether (10 mL) under ice-cooling over 10 minutes, and the mixture was stirred at 110° C. for 6 hours. The reaction solution was poured into ice-cooled ammonium chloride solution, and extracted with ethyl acetate. An insoluble was filtered, and then the organic layer was separated, and the aqueous layer was extracted with chloroform. The organic layers were collected, dried over sodium sulfate, and then concentrated under reduced pressure. The resulting residue was dissolved in ethyl acetate, and extracted with 10% aqueous citric acid solution. The aqueous layer was alkalified by aqueous potassium carbonate solution, and then extracted with chloroform. The organic layer was dried over sodium sulfate, and then concentrated under reduced pressure to give a crude product of N-[1-(1H-pyrrolo[2,3-b]pyridin-3-yl)ethyl]cyclopropylamine [REx(28-2)] (800 mg) as a yellow oil.

(3) tert-Butyl cyclopropyl[1-(1H-pyrrolo[2,3-b]pyridin-3-yl)ethyl]carbamate [REx(28-3)]:

To a solution of the compound obtained in the above (2) (800 mg) and potassium carbonate (1.10 g) in tetrahydrofuran (10 mL)—water (10 mL) was added a solution of di-t-butyl dicarbonate (786 mg) in tetrahydrofuran (1 mL), and the mixture was stirred at room temperature for 6 hours. To the reaction solution was added water, and the mixture was extracted with ethyl acetate. The organic layer was sequentially washed with water and saturated saline, dried over sodium sulfate, and then concentrated under reduced pressure. The resulting residue was dissolved in acetonitrile (20 mL), and then thereto were added sodium hydroxide (320 mg) and tetrabutylammonium hydrogen sulfate (68 mg), and the mixture was stirred at 50° C. for 30 minutes. The reaction solution was cooled, and then an insoluble was filtered, and the filtrate was concentrated under reduced pressure. The resulting residue was dissolved in ethyl acetate, and washed with water. The organic layer was dried over sodium sulfate, and then concentrated under reduced pressure. The resulting residue was purified by silica gel column chromatography (eluent: n-hexane/ethyl acetate=3/1→1/3) to give tert-butyl cyclopropyl[1-(1H-pyrrolo[2,3-b]pyridin-3-yl)ethyl]carbamate [REx(28-3)] (338 mg) as a pale yellow oil.

APCI-MS m/z: 302 [M+H]$^+$.

(4) tert-Butyl {1-[1-(3-aminopropyl)-1H-pyrrolo[2,3-b]pyridin-3-yl]ethyl}cyclopropylcarbamate [REx(28-4)]:

To a solution of the compound obtained in the above (3) (301 mg) in acetonitrile (10 mL) were added sodium hydroxide (300 mg) and tetrabutylammonium hydrogen sulfate (17 mg), and the mixture was stirred at room temperature for 15 minutes. Then, thereto was added 3-chloropropylamine hydrochloride (650 mg), and the mixture was stirred at 70° C. for 4 hours. The reaction solution was cooled, and then an insoluble was filtered, and the filtrate was concentrated under reduced pressure. The resulting residue was dissolved in ethyl acetate, and sequentially washed with water and saturated saline. The organic layer was dried over sodium sulfate, and then concentrated under reduced pressure to give a crude product of tert-butyl {1-[1-(3-aminopropyl)-1H-pyrrolo[2,3-b]pyridin-3-yl]ethyl}cyclopropylcarbamate [REx(28-4)] (378 mg) as a yellow oil.

APCI-MS m/z: 359 [M+H]$^+$.

(5) Methyl [3-(3-{1-[(tert-butoxycarbonyl)(cyclopropyl)amino]ethyl}-1H-pyrrolo[2,3-b]pyridin-1-yl)propyl]carbamate [REx(28-5)]:

To a solution of the compound obtained in the above (4) (370 mg) in chloroform (10 mL) were added pyridine (0.25 mL) and methyl chloroformate (0.16 mL) under ice-cooling, and the mixture was stirred at room temperature for 2 hours. The reaction solution was concentrated, and then treated azeotropically with toluene. The resulting residue was dissolved in chloroform, and washed with 1-normal aqueous sodium hydrogen carbonate solution. The organic layer was dried over sodium sulfate, and then concentrated under reduced pressure. The resulting residue was purified by silica gel column chromatography (eluent: n-hexane/ethyl acetate=1/1→ethyl acetate) to give methyl [3-(3-{1-[(tert-butoxycarbonyl)(cyclopropyl)amino]ethyl}-1H-pyrrolo[2,3-b]pyridin-1-yl)propyl]carbamate [REx(28-5)] (203 mg) as a colorless oil.

APCI-MS m/z: 417 [M+H]$^+$.

(6) Methyl (3-{3-[1-(cyclopropylamino)ethyl]-1H-pyrrolo[2,3-b]pyridin-1-yl}propyl)carbamate [REx(28-6)]:

To a solution of the compound obtained in the above (5) (187 mg) and 2,6-lutidine (0.157 mL) in dichloromethane (4 mL) was added trimethylsilyltriflate (0.180 μL) under ice-cooling, and the mixture was stirred at the same temperature for 1 hour. Then, thereto were added aqueous saturated sodium hydrogen carbonate solution and methanol (2 mL) under ice-cooling, and the mixture was extracted with chloroform. The organic layer was dried over magnesium sulfate, and then concentrated under reduced pressure. The resulting residue was purified by silica gel column chromatography (eluent: chloroform→chloroform/methanol=5/1→chloroform/methanol/ammonia water=50/10/1) to give methyl (3-{3-[1-(cyclopropylamino)ethyl]-1H-pyrrolo[2,3-b]pyridin-1-yl}propyl)carbamate [REx(28-6)] (89 mg) as a colorless oil.

Reference Example 29

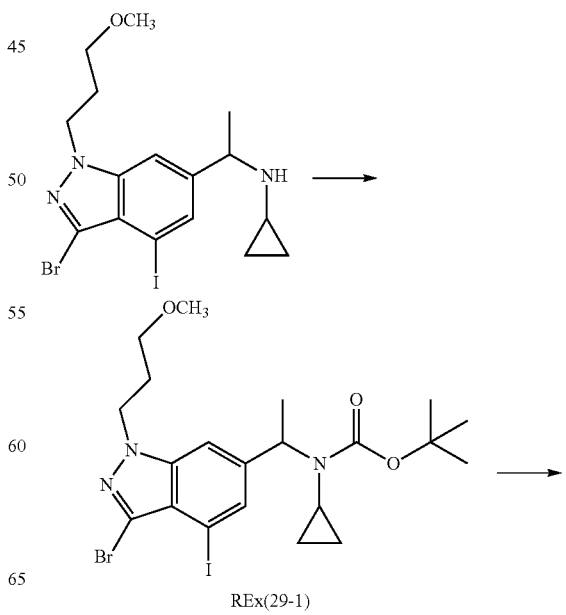

REx(29-1)

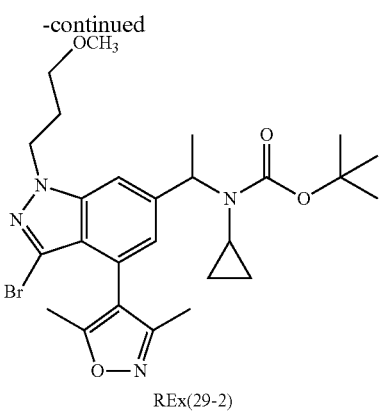

REx(29-2)

(1) tert-Butyl N-{1-[3-bromo-4-iodo-1-(3-methoxypropyl)-1H-indazol-6-yl]ethyl}cyclopropylcarbamate [REx(29-1)]:

To a solution of N-{1-[3-bromo-4-iodo-1-(3-methoxypropyl)-1H-indazol-6-yl]ethyl}cyclopropanamine (10.2 g) in dichloromethane (200 mL) was added di-t-butyl dicarbonate (5.12 g) under ice-cooling, and the mixture was stirred at room temperature for 21 hours. Then, thereto was added dimethylaminopyridine (261 mg), and the mixture was stirred for additional 6 hours at room temperature. To the reaction solution was added water under ice-cooling, and the mixture was extracted with chloroform. The organic layer was washed with saturated saline, dried over sodium sulfate, and then concentrated under reduced pressure. The resulting residue was purified by silica gel column chromatography (eluent: n-hexane/ethyl acetate=9/1→4/1) to give tert-butyl N-{1-[3-bromo-4-iodo-1-(3-methoxypropyl)-1H-indazol-6-yl]ethyl}cyclopropylcarbamate [REx(29-1)] (7.62 g) as a yellow oil.

(2) tert-Butyl {-[3-bromo-4-(3,5-dimethylisoxazol-4-yl)-1-(3-methoxypropyl)-1H-indazol-6-yl]ethyl}cyclopropylcarbamate [REx(29-2)]:

To a solution of the compound obtained in the above (1) (300 mg) and 3,5-dimethylisoxazol-4-boronic acid (146 mg) in dimethoxyethane (5.0 mL) was added 2M aqueous sodium carbonate solution (2.6 mL) under argon, and then thereto was added tetrakis(triphenylphosphine)palladium (0) (30 mg), and the mixture was stirred at 105° C. for 22 hours. Then, thereto was added water under ice-cooling, and the mixture was extracted with ethyl acetate. The organic layer was washed with saturated saline, dried over sodium sulfate, and then concentrated under reduced pressure. The resulting residue was purified by silica gel column chromatography (eluent: n-hexane→+n-hexane/ethyl acetate=3/2) to give tert-butyl {(1-[3-bromo-4-(3,5-dimethylisoxazol-4-yl)-1-(3-methoxypropyl)-1H-indazol-6-yl]ethyl}cyclopropylcarbamate [REx(29-2)] (154 mg) as a colorless oil.

APCI-MS m/z: 547/549 [M+H]⁺.

Deprotection of Boc group is done according to the above method.

Reference Example 30 tert-Butyl cyclopropyl{1-[1-(3-methoxypropyl)-1H-indazol-6-yl]ethyl}carbamate [REx(30-1)]

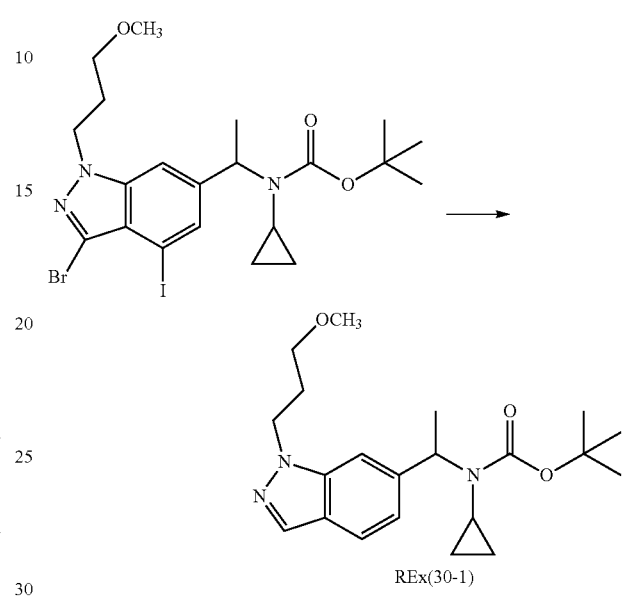

REx(30-1)

To a solution of tert-butyl N-{1-[3-bromo-4-iodo-1-(3-methoxypropyl)-1H-indazol-6-yl]ethyl}cyclopropylcarbamate (1.0 g) in 1,4-dioxane (20 mL) were added diisopropylethylamine (0.90 mL) and 10% palladium on carbon catalyst (200 mg), and the mixture was stirred under hydrogen for 42 hours. An insoluble was filtered, and then the filtrate was sequentially washed with aqueous saturated sodium hydrogen carbonate solution and saturated saline, dried over sodium sulfate, and then concentrated under reduced pressure. The resulting residue was purified by silica gel column chromatography (eluent: n-hexane/ethyl acetate=9/1→4/1) to give tert-butyl cyclopropyl{-[1-(3-methoxypropyl)-1H-indazol-6-yl]ethyl}carbamate [REx(30-1)] (167 mg) as a colorless oil.

APCI-MS m/z: 374 [M+H]⁺.

Reference Example 31

N-{1-[3-(3-Methoxypropyl)-5-(trifluoromethyl)phenyl]ethyl}cyloprolylamine [REx(31-1)]

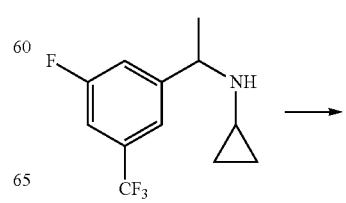

-continued

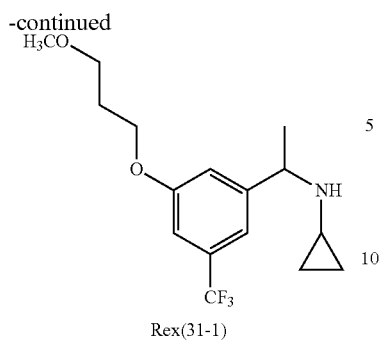
Rex(31-1)

-continued

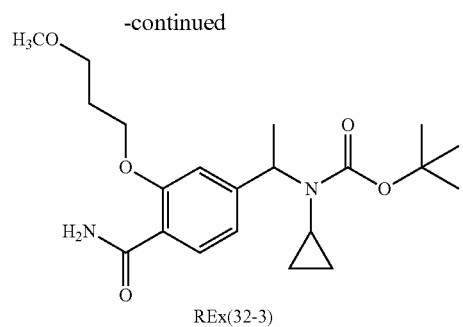
REx(32-3)

To a solution of 3-methoxy-1-propanol (0.14 mL) in N,N-dimethylformamide (3.0 mL) was added 60% oil-based sodium hydride (97 mg), and the mixture was stirred at room temperature for 10 minutes. Then, thereto was added dropwise a solution of N-{1-[3-fluoro-5-(trifluoromethyl)phenyl]ethyl}cyclopropylamine (300 mg) in N,N-dimethylformamide (1.0 mL), and the mixture was heated to stir at 40° C. for 4 hours. After cooling to room temperature, thereto was added water, and the mixture was extracted with ethyl acetate. The organic layer was sequentially washed with water and saturated saline, dried over magnesium sulfate, and then concentrated under reduced pressure. The resulting residue was purified by silica gel column chromatography (eluent: n-hexane/ethyl acetate=10/1→2/3) to give N-{1-[3-(3-methoxypropyl)-5-(trifluoromethyl)phenyl]ethyl}cyclopropanamine [REx(31-1)] (227 mg) as a colorless oil.

APCI-MS m/z: 318 [M+H]$^+$.

Reference Example 32

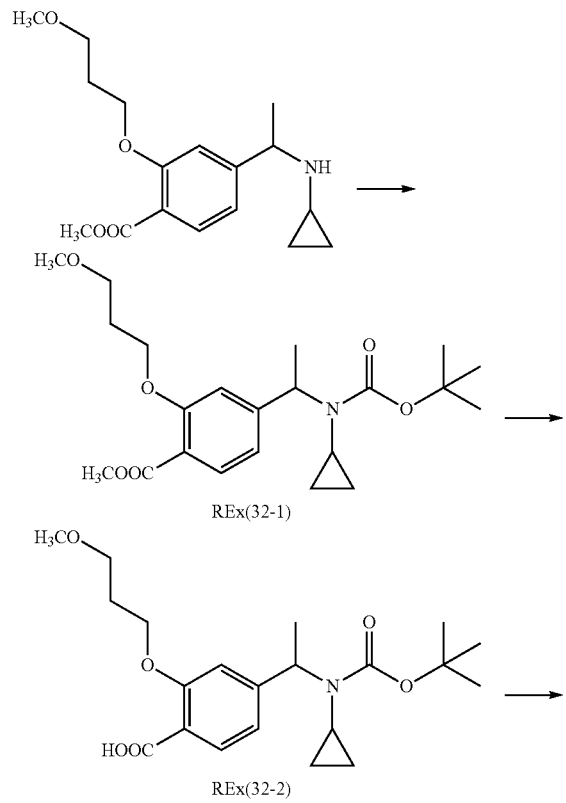

(1) Methyl 4-{1-[(tert-butoxycarbonyl)(cyclopropyl)amino]ethyl}-2-(3methoxypropoxy)benzoate [REx(32-1)]:

To a solution of methyl 4-[1-(cyclopropylamino)ethyl]-2-(3-methoxypropoxy)benzoate (1.20 g) in chloroform (9.6 mL) were added di-t-butyl dicarbonate (2.00 g) and triethylamine (2.34 mL) under ice-cooling, and the mixture was stirred at room temperature for 20 hours. To the reaction solution was added water under ice-cooling, and the mixture was extracted with chloroform. The organic layer was dried over magnesium sulfate, and then concentrated under reduced pressure. The resulting residue was purified by silica gel column chromatography (eluent: n-hexane/ethyl acetate=10/1→2/1) to give methyl 4-{1-[(tert-butoxycarbonyl)(cyclopropyl)amino]ethyl}-2-(3-methoxypropoxy)benzoate (7.62 g) as a colorless oil.

APCI-MS m/z: 408 [M+H]$^+$.

(2) 4-{1-[(tert-Butoxycarbonyl)(cyclopropyl)amino]ethyl}-2-(3-methoxypropoxy)benzoic acid [REx(32-2)]:

To a solution of the compound obtained in the above (1) (1.10 g) in methanol (13.5 mL) was added 2-normal aqueous sodium hydroxide solution (13.5 mL), and the mixture was stirred at room temperature for 2 hours. To the reaction solution was added chloroform, and then thereto was added 2-normal hydrochloric acid (13.5 mL) under ice-cooling. The organic layer was separated, and then washed with water, dried over magnesium sulfate, and then concentrated under reduced pressure. The resulting residue was purified by silica gel column chromatography (eluent: chloroform-→chloroform/methanol=20/1) to give 4-{1-[(tert-butoxycarbonyl)(cyclopropyl)amino]ethyl}-2-(3-methoxypropoxy)benzoic acid (1.14 g) as a colorless oil.

ESI-MS m/z: 392[M−H]$^-$ (3) tert-butyl {1-[4-(aminocarbonyl)-3-(3-methoxypropoxy)phenyl]ethyl}cyclopropylcarbamate [REx(32-3)]:

To a solution of the compound obtained in the above (2) (250 mg) in N,N-dimethylformamide (3.2 mL) were added ammonium chloride (40.8 mg), diisopropylethylamine (0.133 mL), 1-ethyl-3-(3-dimethylaminopropyl)carbodiimide hydrochloride (146 mg) and 1-hydroxybenzotriazole (103 mg), and then the mixture was stirred at room temperature for 30 minutes. To the reaction mixture was added water, and the mixture was extracted with ethyl acetate. The organic layer was sequentially washed with water and saturated saline, and then concentrated under reduced pressure. The resulting residue was purified by silica gel column chromatography (eluent: n-hexane/ethyl acetate=3/2→1/6) to give tert-butyl {1-[4-(aminocarbonyl)-3-(3-methoxypropoxy)phenyl]ethyl}cyclopropylcarbamate (164 mg) as a colorless oil.

APCI-MS m/z: 393 [M+H]$^+$.

Similarly, deprotection of Boc group is done according to the above method.

Reference Example 33

2-[1-(Cyclopropylamino)ethyl]quinazolin-4(3H)-one [REx(33-1)]

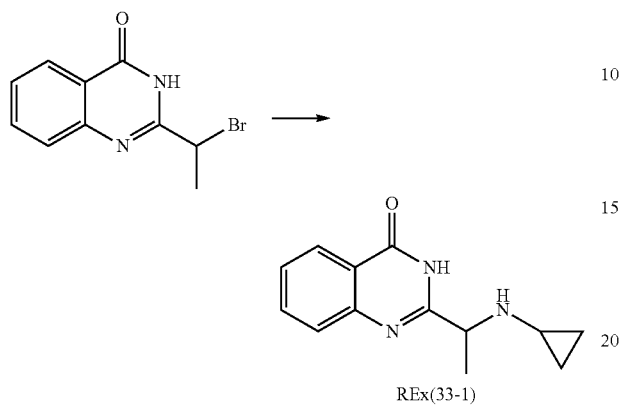

REx(33-1)

To a suspension of 2-(1-bromoethyl)quinazolin-4(3H)-one (2.53 g) in N,N-dimethylformamide (30 mL) was added cyclopropylamine (3.46 mL), and the mixture was diluted with N,N-dimethylformamide (20 mL) and water (1 mL), and then stirred for 18 hours. The reaction solution was concentrated under reduced pressure, and to the residue was added aqueous sodium hydrogen carbonate solution, and then the mixture was extracted with chloroform. The organic layer was dried over sodium sulfate, and then concentrated under reduced pressure. The resulting residue was triturated with diisopropyl ether/ethyl acetate (20:1) to give 2-[1-(cyclopropylamino)ethyl]quinazolin-4(3H)-one [REx(33-1)] (1.71 g) as a colorless powder.

APCI-MS m/z: 230 [M+H]$^+$.

Reference Examples 34 to 100

The following compounds of Reference Examples 34 to 100 were prepared according to the methods of the above Reference Examples. Each symbol of Methods A-1 to F refers to each method according to the following methods of Reference Examples.

| Method A-1 | Reference Example 1 |
| Method A-2 | Reference Example 2 |
| Method B | Reference Example 3 |
| Method C-1 | Reference Example 6 |
| Method C-2 | Reference Example 7 |
| Method C-3 | Reference Example 8 |
| Method D | Reference Example 28 |
| Method E-1 | Reference Example 29 |
| Method E-2 | Reference Example 30 |
| Method E-3 | Reference Example 31 |
| Method E-4 | Reference Example 32 |
| Method F | Reference Example 33 |

TABLE 89

| Ref. | Chemical Formula | Salt | MS Result (APCI) | Ion Species | Method |
|---|---|---|---|---|---|
| 34 | (structure) | HCl | 280 | [M + H]+ | B |
| 35 | (structure) | HCl | 222 | [M + H]+ | C-2 |
| 36 | (structure) |  | 288 | [M + H]+ | C-3 |

TABLE 89-continued
| Ref. | Chemical Formula | Salt | MS Result (APCI) | Ion Species | Method |
|---|---|---|---|---|---|
| 37 | 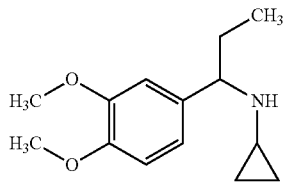 | | 222 | [M + H]+ | C-2 |
| 38 | 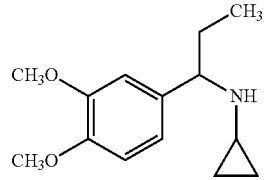 | | 236 | [M + H]+ | C-2 |
| 39 | 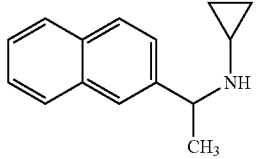 [SMILES: CC(NC1CC1)c1ccc2ccccc2c1] | HCl | 212 | [M + H]+ | A |
| 41 | 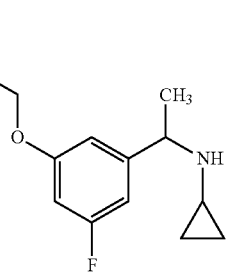 | | 268 | [M + H]+ | C-2 |
| 42 | 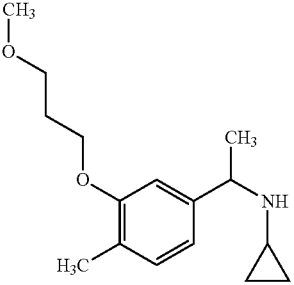 | | 267 | [M + H]+ | A-2 |
TABLE 90
| 43 | 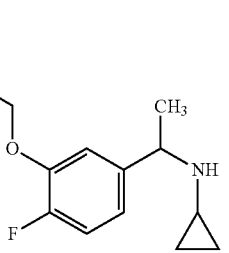 | | 268 | [M + H]+ | A-2 |

TABLE 90-continued
| | | | | |
|---|---|---|---|---|
| 44 | 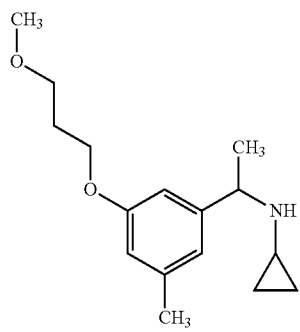 [SMILES: COCCCOc1cc(C)cc(C(C)NC2CC2)c1] | 264 | [M + H]+ | C-2 |
| 45 | 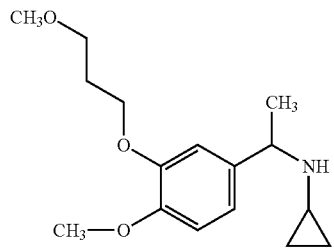 | 280 | [M + H]+ | C-2 |
| 46 | 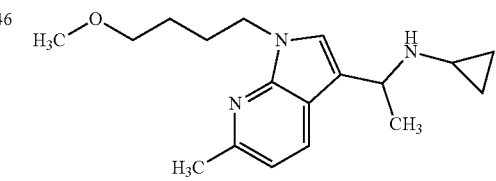 | 302 | [M + H]+ | C-3 |
| 47 | 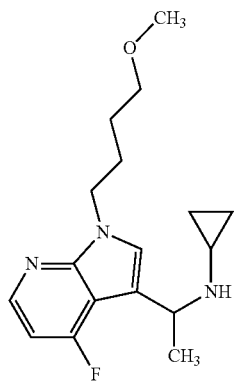 [SMILES: COCCCCn1cc(C(C)NC2CC2)c2c(F)ccnc21] | 306 | [M + H]+ | C-3 |
| 48 | 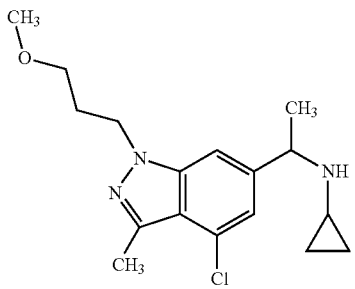 [SMILES: COCCCn1nc(C)c2c(Cl)cc(C(C)NC3CC3)cc21] | 322/324 | [M + H]+ | C-1 |

TABLE 90-continued

| 49 | [structure: 1-(3-methoxypropyl)-3,4-dimethyl-6-[1-(cyclopropylamino)ethyl]-1H-pyrazolo-indazole] | | 302 | [M + H]+ | C-1 |

TABLE 91

| 50 | [structure: 4-methoxyquinolin-2-yl with 1-(cyclopropylamino)ethyl] | | 243 | [M + H]+ | C-2 |
| 51 | [structure: 3-(3-methoxypropoxy)-4-cyanophenyl with 1-(cyclopropylamino)ethyl] | | 275 | [M + H]+ | C-2 |
| 52 | [structure: 3,5-bis(trifluoromethyl)phenyl with 1-(cyclopropylamino)ethyl] | HCl | 298 | [M + H]+ | C-2 |
| 53 | [structure: methyl N-[3-(3-{1-(cyclopropylamino)ethyl}-1H-pyrrolo[2,3-b]pyridin-1-yl)propyl]carbamate] | | 317 | [M + H]+ | D |
| 54 | [structure: 4-methoxynaphthalen-2-yl with 1-(cyclopropylamino)ethyl] | | 242 | [M + H]+ | B |

TABLE 91-continued
| | | | | |
|---|---|---|---|---|
| 55 | 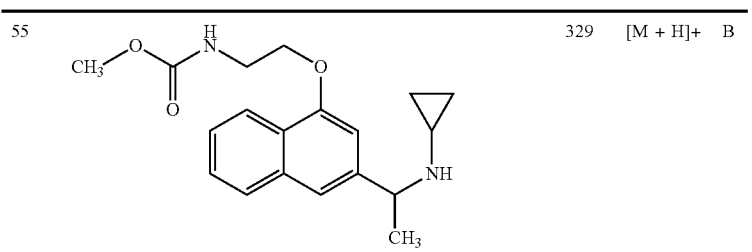 | 329 | [M + H]+ | B |
| 56 | 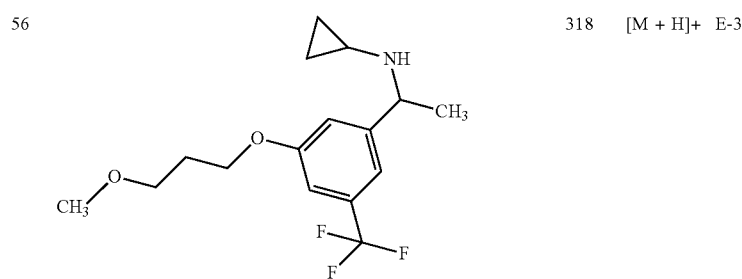 | 318 | [M + H]+ | E-3 |
| 57 | 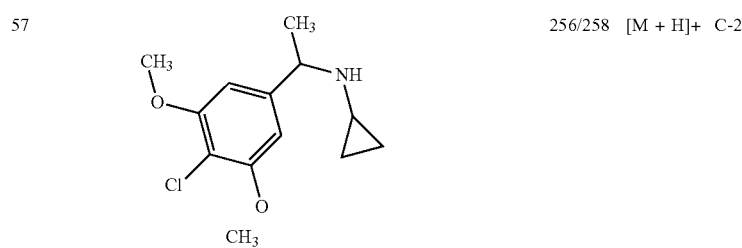 | 256/258 | [M + H]+ | C-2 |
| 58 | 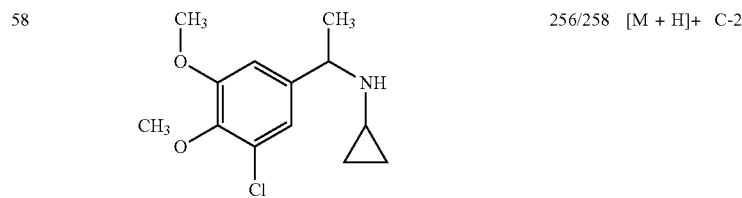 | 256/258 | [M + H]+ | C-2 |
TABLE 92
| | | | | |
|---|---|---|---|---|
| 59 | 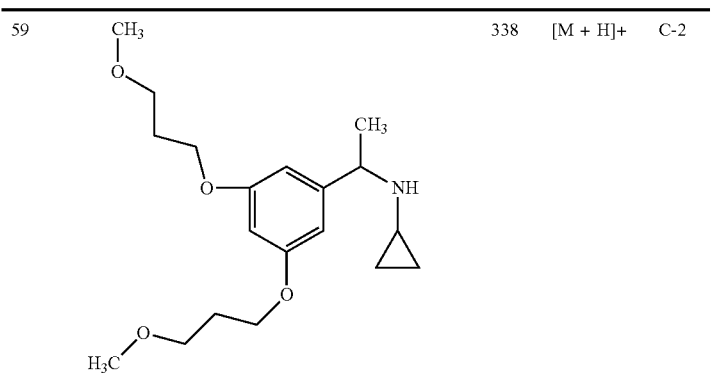 | 338 | [M + H]+ | C-2 |

TABLE 92-continued
| | | | | |
|---|---|---|---|---|
| 61 | 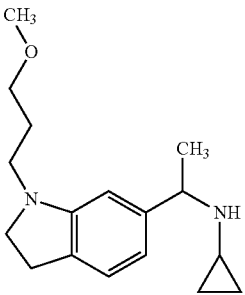 [SMILES: COCCCN1CCc2ccc(C(C)NC3CC3)cc21] | 275 | [M + H]+ | C-1 |
| | 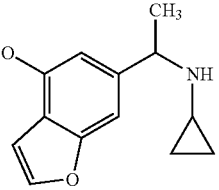 | | | |
| 63 | 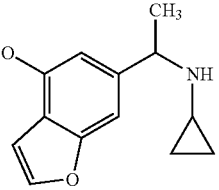 | 290 | [M + H]+ | C-2 |
| 64 | 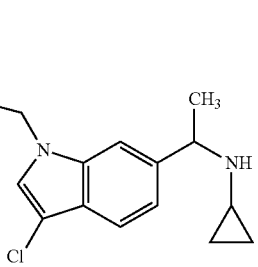 | 307/309 | [M + H]+ | C-1 |
| 65 | 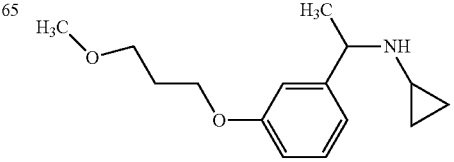 | 250 | [M + H]+ | C-2 |
| 66 | 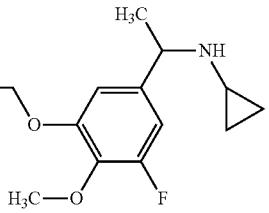 | 298 | [M + H]+ | B |
| 67 | 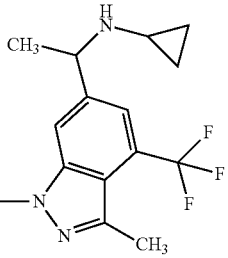 | 356 | [M + H]+ | C-1 |

TABLE 92-continued
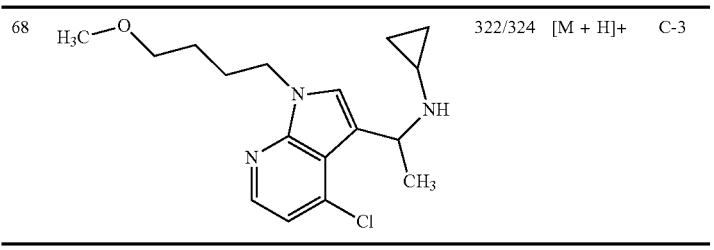
| 68 | | 322/324 | [M + H]+ | C-3 |
TABLE 93
| 69 | | 288 | [M + H]+ | C-3 |
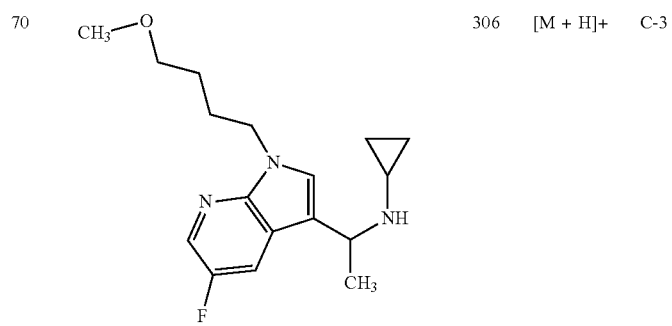
| 70 | | 306 | [M + H]+ | C-3 |
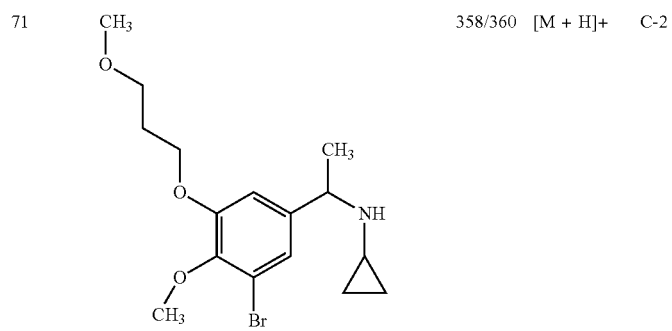
| 71 | | 358/360 | [M + H]+ | C-2 |
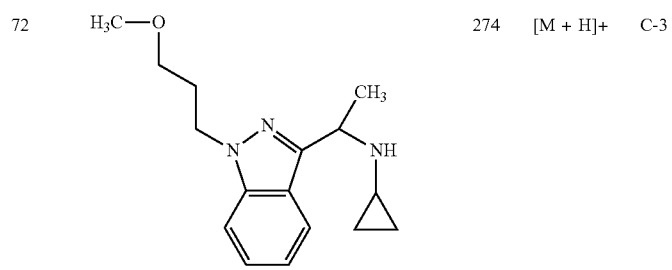
| 72 | | 274 | [M + H]+ | C-3 |

TABLE 93-continued
| 73 | 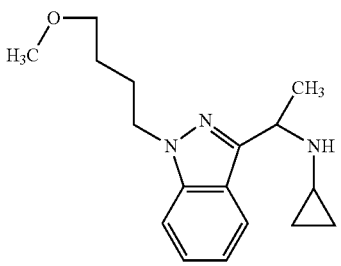 [SMILES: COCCCCn1nc(C(C)NC2CC2)c2ccccc21] | 288 | [M + H]+ | C-3 |
| 74 | 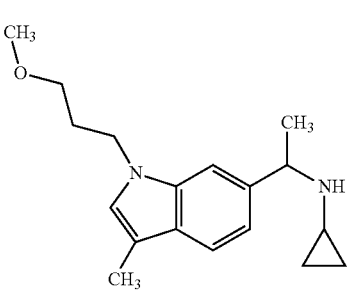 [SMILES: COCCCn1cc(C)c2ccc(C(C)NC3CC3)cc21] | 287 | [M + H]+ | C-1 |
| 75 | 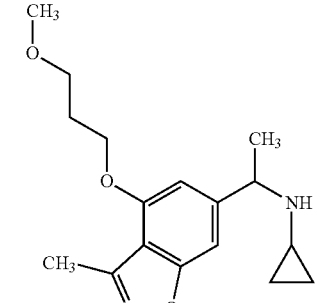 | 305 | [M + H]+ | C-2 |
TABLE 94
| 76 | 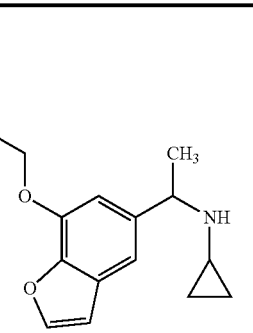 | 290 | [M + H]+ | C-2 |
| 77 | 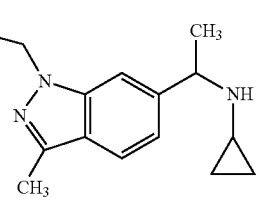 | 288 | [M + H]+ | C-1 |

TABLE 94-continued

| # | Structure | MS | Method |
|---|---|---|---|
| 78 | 3-methoxy-propoxy, methoxy, chloro substituted phenyl with CH(CH₃)NH-cyclopropyl | 314/316 [M + H]+ | C-2 |
| 79 | 1-(4-methoxybutyl)-pyrazolo[3,4-b]pyridin-3-yl with CH(CH₃)NH-cyclopropyl | 289 [M + H]+ | C-3 |
| 80 | 1-(4-methoxybutyl)-7-methyl-pyrrolo[3,2-b]pyridin-3-yl with CH(CH₃)NH-cyclopropyl | 302 [M + H]+ | C-3 |
| 82 | 2-(3-methoxypropoxy)-3-benzyloxy phenyl with CH(CH₃)NH-cyclopropyl | 356 [M + H]+ | C-2 |
| 83 | 2-(3-methoxypropoxy)-3-(N,N-dimethylcarbamoyl) phenyl with CH(CH₃)NH-cyclopropyl | 321 [M + H]+ | E-4 |

TABLE 95
| 84 | 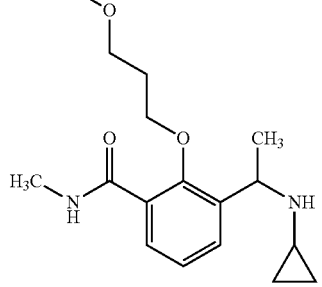 | 307 | [M + H]+ | E-4 |
| 85 | 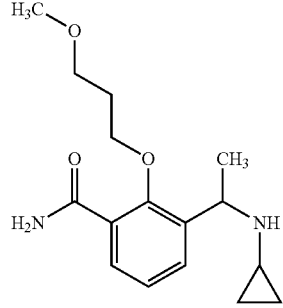 [SMILES: COCCCOc1c(C(N)=O)cccc1C(C)NC1CC1] | 293 | [M + H]+ | E-4 |
| 86 | 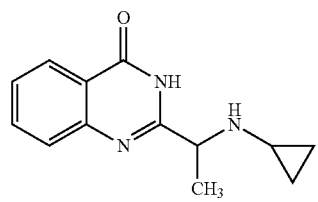 [SMILES: CC(NC1CC1)c1nc2ccccc2c(=O)[nH]1] | 230 | [M + H]+ | F |
| 87 | 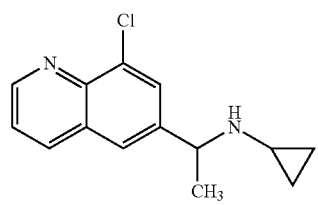 [SMILES: CC(NC1CC1)c1cc(Cl)c2ncccc2c1] | 247/249 | [M + H]+ | C-2 |
| 88 | 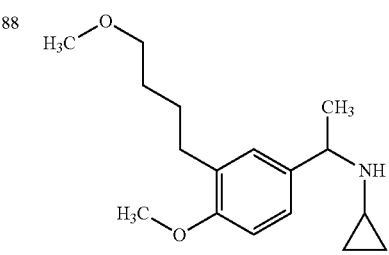 | 278 | [M + H]+ | C-2 |

TABLE 95-continued
| 89 | 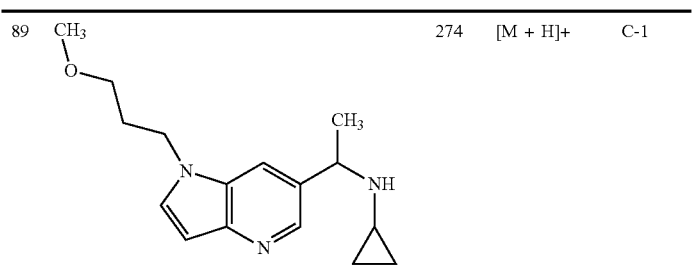 | 274 | [M + H]+ | C-1 |
| 90 | 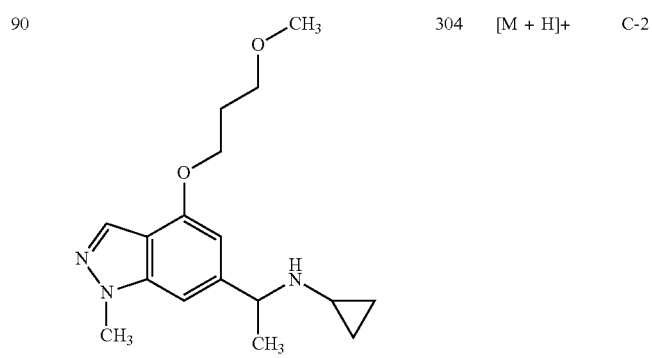 | 304 | [M + H]+ | C-2 |
TABLE 96
| 91 | 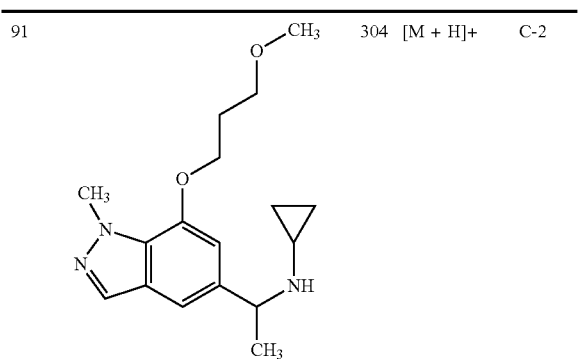 | 304 | [M + H]+ | C-2 |
| 92 | 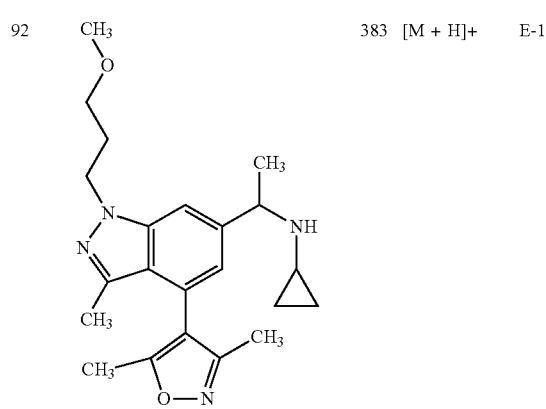 | 383 | [M + H]+ | E-1 |
TABLE 96-continued
| 93 | 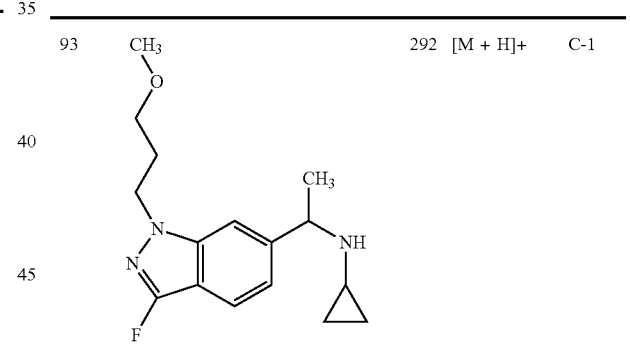 | 292 | [M + H]+ | C-1 |
| 94 | 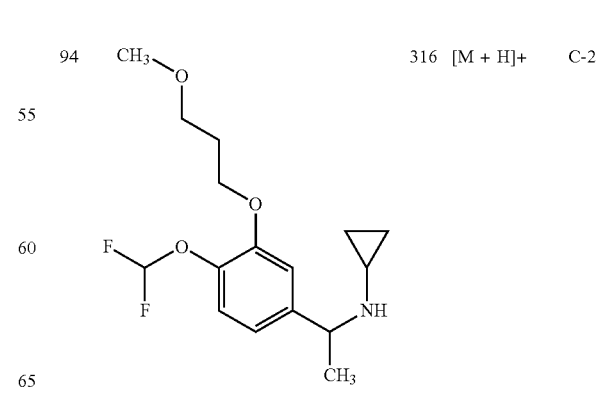 | 316 | [M + H]+ | C-2 |

TABLE 96-continued

| 95 | [structure] | 288 [M + H]+ | C-1 |

TABLE 97

| 96 | [structure] | 308/310 [M + H]+ | C-1 |
| 97 | [structure] | 274 [M + H]+ | E-2 |
| 98 | [structure] | 306 [M + H]+ | C-1 |
| 99 | [structure] | 260 [M + H]+ | C-1 |

TABLE 97-continued

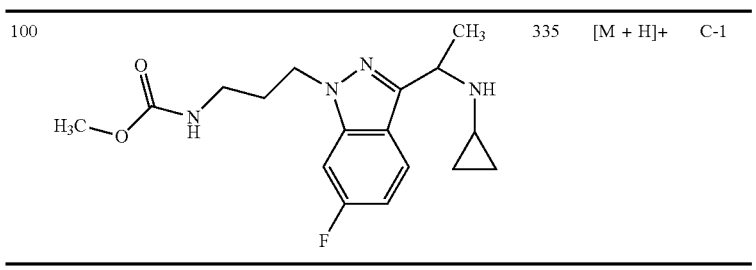

| 100 | | CH₃ | 335 | [M + H]+ | C-1 |

Reference Example 101

Methyl 3-acetyl-1H-indazole-1-carboxylate

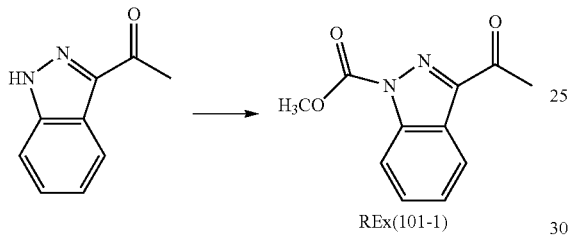

REx(101-1)

To a solution of 1-(1H-indazol-3-yl)ethanone (5.0 g) and triethylamine (6.53 mL) in chloroform (80 mL) was added dropwise a solution of methyl chlorocarbonate (3.24 g) in chloroform (20 mL) under ice-cooling over 1 hour, and the mixture was stirred at room temperature for 14 hours. The reaction solution was washed with aqueous saturated sodium chloride solution, dried over magnesium sulfate, and then concentrated under reduced pressure. The resulting residue was triturated with n-hexane to give methyl 3-acetyl-1H-indazole-1-carboxylate) [REx(101-1)] (6.67 g) as a colorless powder.

APCI-MS m/z: 219 [M+H]⁺.

Reference Example 102

Methyl [3-(3-acetyl-6-fluoro-1H-indazol-1-yl)pro-pyl]carbamate [REx(102-2)]

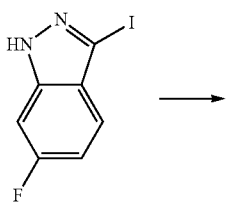

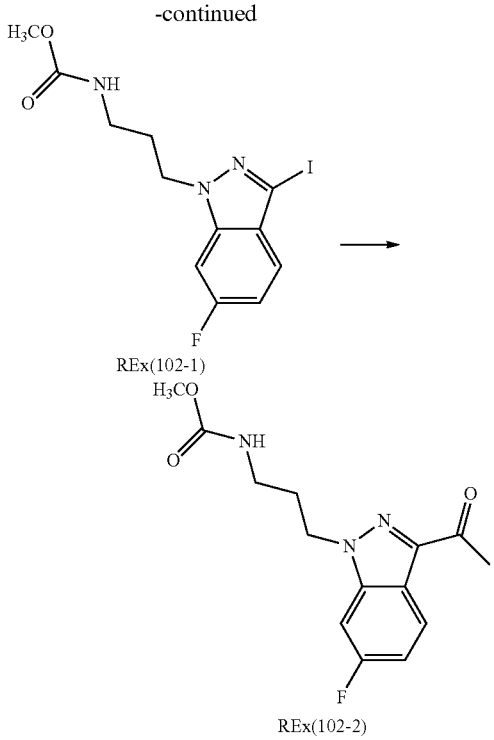

REx(102-1)

REx(102-2)

(1) To a solution of 6-fluoro-3-iodo-1H-indazole (1.5 g) and methyl (3-bromopropyl)carbamate (1.68 g) in N,N-dimethylformamide (5 mL) was added potassium carbonate (1.58 g), and the mixture was stirred at room temperature for 3 days. To the reaction solution was added ethyl acetate, and the mixture was washed with aqueous saturated sodium chloride solution, dried over magnesium sulfate, and then concentrated under reduced pressure. The resulting residue was purified by silica gel column chromatography (eluent: n-hexane/ethyl acetate=1/20→3/2) to give methyl [3-(6-fluoro-3-iodo-1H-indazol-1-yl)propyl]carbamate [REx(102-1)] (836 mg) as a red oil.

APCI-MS m/z: 378 [M+H]⁺.

(2) To a solution of the compound obtained in (1) (830 mg) in 1,4-dioxane (10 mL) were added tri-n-butyltin-1-ethoxyvinyl (1.03 g) and dichlorobis(triphenylphosphine) palladium (II) (155 mg), and the mixture was heated to reflux for 17 hours. The reaction solution was cooled to room temperature, and then thereto was added a solution of potassium fluoride (250 mg) in water (3 mL), and the mixture was stirred at room temperature for 15 minutes. Then, thereto was added 1-normal hydrochloric acid (5 mL), and the mixture was stirred at room temperature for 1 hour, and then an insoluble was filtered. To the filtrate was added ethyl acetate, and the mixture was washed with aqueous saturated sodium chloride solution, dried over magnesium sulfate, and then concentrated under reduced pressure. The resulting residue was purified by silica gel column chromatography (eluent: n-hexane/ethyl acetate=20/1→1/1) to give methyl [3-(3-acetyl-6-fluoro-1H-indazol-1-yl)propyl]carbamate [REx(102-2)] (437 mg) as a red oil.
APCI-MS m/z: 294 [M+H]+.

Reference Example 103

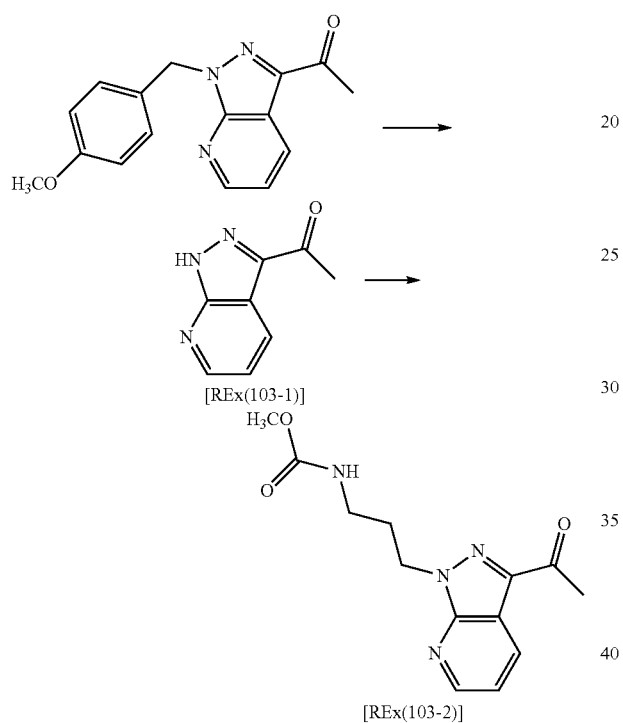

[REx(103-1)]

[REx(103-2)]

1) To 1-[1-(4-methoxybenzyl)-1H-pyrazolo[3,4-b]pyridin-3-yl]ethanone (3.14 g) was added trifluoroacetic acid (20 mL), and the mixture was heated to reflux for 2 days. The reaction solution was concentrated under reduced pressure. The resulting residue was diluted with ethyl acetate, and then sequentially washed with aqueous saturated sodium hydrogen carbonate solution and saturated saline, dried over magnesium sulfate, and then concentrated under reduced pressure. The resulting residue was purified by silica gel column chromatography (eluent: n-hexane/ethyl acetate=95/5→7/3) to give 1-(1H-pyrazolo[3,4-b]pyridin-3-yl)ethanone) [REx(103-1)] (1.73 g) as a pale yellow powder.
APCI-MS m/z: 162 [M+H]+.

2) To a solution of 1-(1H-pyrazolo[3,4-b]pyridin-3-yl)ethanone (500 mg) and methyl (3-bromopropyl)carbamate (912 mg) in N,N-dimethylformamide (5 mL) was added potassium carbonate (864 mg), and the mixture was stirred at room temperature for 3 days. To the reaction solution was added ethyl acetate, and the mixture was washed with saturated saline, dried over magnesium sulfate, and then concentrated under reduced pressure. The resulting residue was purified by silica gel column chromatography (eluent: n-hexane/ethyl acetate=95/5→1/1) to give methyl [3-(3-acetyl-1H-pyrazolo[3,4-b]pyridin-1-yl)propyl]carbamate) [REx(103-2)] (308 mg) as a red oil.
APCI-MS m/z: 277 [M+H]+.

Reference Example 104

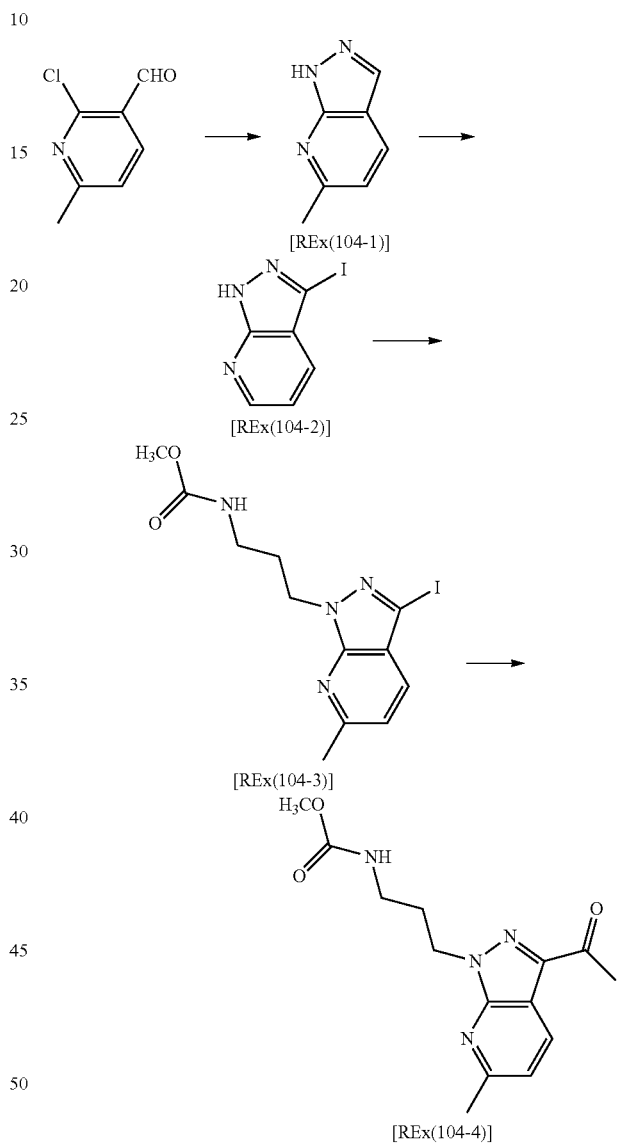

[REx(104-1)]

[REx(104-2)]

[REx(104-3)]

[REx(104-4)]

1) To a mixture of 2-chloro-6-methylnicotinaldehyde (5.0 g) and hydrazine monohydrate (6.24 mL) was added para-toluenesulfonic acid monohydrate (3.67 g), and the mixture was stirred at 130° C. for 18 hours. The reaction solution was cooled, and then thereto was added 10% aqueous citric acid solution, and the mixture was stirred at room temperature for 30 minutes. The reaction solution was extracted with ethyl acetate, and washed with saturated saline. The organic layer was dried over sodium sulfate, and then concentrated under reduced pressure to give 6-methyl-1H-pyrazolo[3,4-b]pyridine [REx(104-1)] (3.61 g) as a brown powder.
APCI-MS m/z: 134 [M+H]+.

2) To a solution of 6-methyl-1H-pyrazolo[3,4-b]pyridine (4.44 g) and iodine (16.9 g) in N,N-dimethylformamide (100 mL) was added potassium hydroxide (7.48 g) under ice-cooling, and the mixture was stirred at room temperature for 4 hours. The reaction solution was poured into ice water, and the precipitate was filtered. The filtrate was extracted with ethyl acetate, washed with saturated saline, and then dried over sodium sulfate and concentrated under reduced pressure. The resulting residue was combined with the above-mentioned precipitate and purified by silica gel column chromatography (eluent: chloroform-cchloroform/methanol=19/1) to give 3-iodo-6-methyl-1H-pyrazolo[3,4-b]pyridine [REx(104-2)] (6.48 g) as a brown powder.

APCI-MS m/z: 260 [M+H]+.

3) 3-Iodo-6-methyl-1H-pyrazolo[3,4-b]pyridine and methyl (3-bromopropyl)carbamate were treated in the similar manner to Reference Example 102(1) to give methyl [3-(3-iodo-6-methyl-1H-pyrazolo[3,4-b]pyridin-1-yl)propyl]carbamate [REx(104-3)] as a colorless powder.

APCI-MS m/z: 375 [M+H]+.

4) Methyl [3-(3-iodo-6-methyl-1H-pyrazolo[3,4-b]pyridin-1-yl)propyl]carbamate and tri-n-butyltin-ethoxyvinyl were treated in the similar manner to Reference Example 102(2) to give methyl [3-(3-acetyl-6-methyl-1H-pyrazolo[3,4-b]pyridin-1-yl)propyl]carbamate [REx(104-4)] as a colorless powder.

APCI-MS m/z: 291 [M+H]+.

Reference Example 105

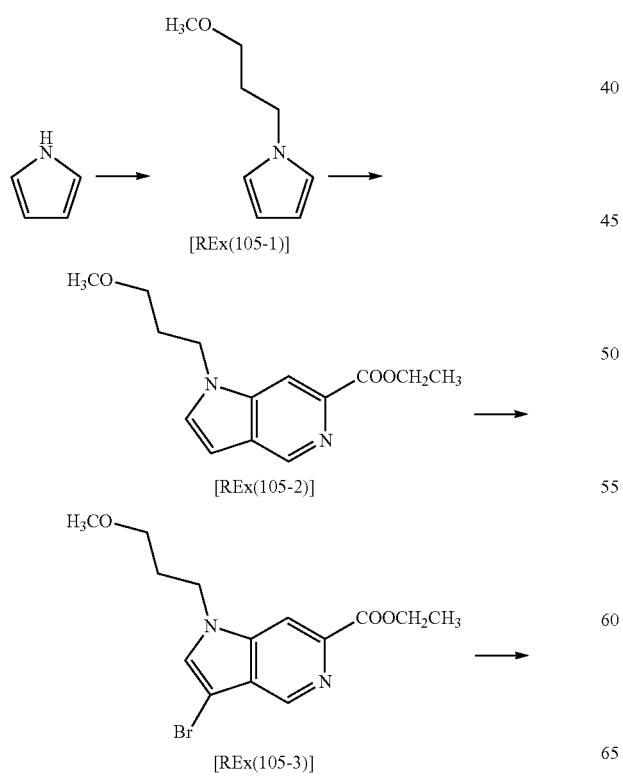

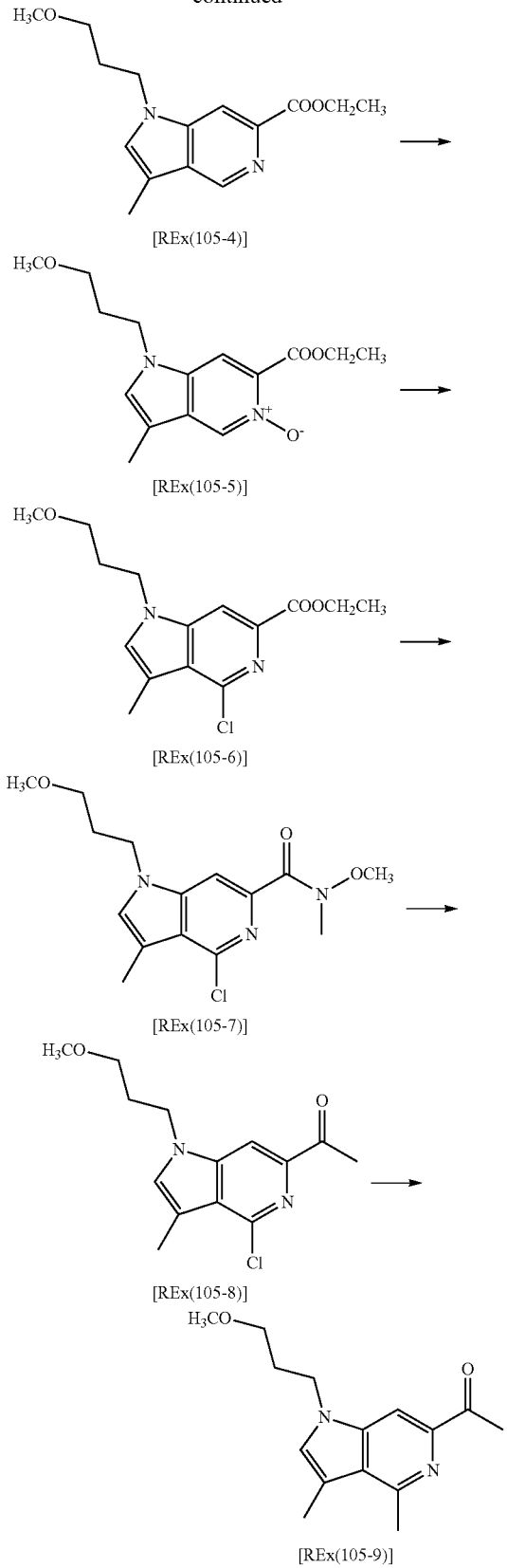

1) To a solution of 1 1-pyrrole (5.0 g) in N,N-dimethylformamide (40 mL) was added drop by drop sodium hydride (3.58 g) under ice-cooling, and then the mixture was stirred at room temperature for 20 minutes. Then, thereto was added dropwise a solution of 1-bromo-3-methoxypropane (2.74 g) in N,N-dimethylformamide (2 mL) under ice-cooling, and the mixture was stirred at room temperature for 2 hours. To the reaction mixture was added water under ice-cooling, and then the mixture was extracted with diethyl ether. The organic layer was washed with saturated saline, dried over sodium sulfate, and then concentrated under reduced pressure. The resulting residue was purified by silica gel column chromatography (eluent: n-hexane/ethyl acetate=100/1→20/1) to give 1-(3-methoxypropyl)-1H-pyrrole [REx(105-1)] (9.07 g) as a colorless oil.

2) A solution of 1-(3-methoxypropyl)-1H-pyrrole (3.92 g), ethyl 3-dimethylamino-2-(dimethylaminomethyleneamino)acrylate (7.20 g) (ref. Liebigs Ann. Chem. 1980, 344-357) and trifluoroacetic acid (8.33 mL) in acetic acid (32 mL) was stirred at room temperature for 18 hours, and then heated to reflux for 3 hours. After cooling, the reaction solution was concentrated under reduced pressure. To the resulting residue was added aqueous saturated sodium hydrogen carbonate solution under ice-cooling, and the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=1/1→AcOEt) to give ethyl 1-(3-methoxypropyl)-1H-pyrrolo[3,2-c]pyridine-6-carboxylate [REx(105-2)] (4.79 g) as a brown oil.
APCI-MS m/z: 263 [M+H]$^+$.

3) To a solution of ethyl 1-(3-methoxypropyl)-1H-pyrrolo[3,2-c]pyridine-6-carboxylate (2.00 g) in dichloromethane (40 mL) was added N-bromosuccinimide (1.49 g) under ice-cooling, and the mixture was stirred at room temperature for 3 hours. To the reaction solution was added water, and the mixture was extracted with chloroform. The organic layer was washed with saturated saline, dried over sodium sulfate, and then concentrated under reduced pressure. The resulting residue was purified by NH-silica gel column chromatography (eluent: n-hexane/ethyl acetate=9/1→4/1) to give ethyl 3-bromo-1-(3-methoxypropyl)-1H-pyrrolo[3,2-c]pyridine-6-carboxylate [REx(105-3)] (2.12 g) as a yellow oil.
APCI-MS m/z: 341/343 [M+H]$^+$.

4) To a solution of ethyl 3-bromo-1-(3-methoxypropyl)-1H-pyrrolo[3,2-c]pyridine-6-carboxylate (1.70 g) in 1,4-dioxane (25 mL) were added trimethylboroxine (2.09 mL), cesium carbonate (4.87 g), 2-dicyclohexylphosphino-2',4',6'-triisopropyl-1,1'-biphenyl (X-Phos) (297 mg) and tris(dibenzylideneacetone)dipalladium (228 mg) under argon, and the mixture was stirred at 110° C. for 15 hours. The reaction solution was cooled, and then thereto was added water, and the mixture was extracted with ethyl acetate. The organic layer was washed with saturated saline, dried over sodium sulfate, and then concentrated under reduced pressure. The resulting residue was purified by silica gel column chromatography (eluent: n-hexane→ethyl acetate) to give ethyl 1-(3-methoxypropyl)-3-methyl-1H-pyrrolo[3,2-c]pyridine-6-carboxylate [REx(105-4)] (831 mg) as a yellow oil.
APCI-MS m/z: 277 [M+H]$^+$.

5) To a solution of ethyl 1-(3-methoxypropyl)-3-methyl-1H-pyrrolo[3,2-c]pyridine-6-carboxylate (100 mg) in chloroform (2 mL) was added meta-chloroperoxybenzoic acid (250 mg) under ice-cooling, and then the mixture was stirred at room temperature for 2 hours. The reaction solution was concentrated, and then the resulting residue was purified by NH-silica gel column chromatography (eluent: ethyl acetate→ethyl acetate/methanol=10/1) to give ethyl 1-(3-methoxypropyl)-3-methyl-1H-pyrrolo[3,2-c]pyridine-6-carboxylate 5-oxide [REx(105-5)] (41 mg) as a pale yellow oil.
APCI-MS m/z: 293 [M+H]$^+$.

6) A solution of ethyl 1-(3-methoxypropyl)-3-methyl-1H-pyrrolo[3,2-c]pyridine-6-carboxylate 5-oxide (40 mg) in phosphorus oxychloride (2 mL) was stirred at 100° C. for 1 hour. The reaction solution was concentrated, and the resulting residue was dissolved in ethyl acetate. It was sequentially washed with aqueous saturated sodium hydrogen carbonate solution and saturated saline, and dried over sodium sulfate, and then concentrated under reduced pressure. The resulting residue was purified by silica gel column chromatography (eluent: n-hexane→n-hexane/ethyl acetate=1/1) to give ethyl 4-chloro-1-(3-methoxypropyl)-3-methyl-1H-pyrrolo[3,2-c]pyridine-6-carboxylate [REx(105-6)] (23 mg) as a colorless powder.
APCI-MS m/z: 311/313 [M+H]$^+$.

7) To a solution of ethyl 4-chloro-1-(3-methoxypropyl)-3-methyl-1H-pyrrolo[3,2-c]pyridine-6-carboxylate (290 mg) in ethanol (6 mL) was added 2-normal aqueous sodium hydroxide solution (0.95 mL) under ice-cooling, and the mixture was stirred at room temperature for 90 minutes. Then, thereto was added 2-normal hydrochloric acid (0.95 mL) under ice-cooling, and then the reaction solution was concentrated. To a solution of the residue in chloroform (6 mL) were added N,O-dimethylhydroxyamine hydrochloride (137 mg), 1-ethyl-3-(3-dimethylaminopropyl)carbodiimide hydrochloride (268 mg), 1-hydroxybenzotriazole (189 mg) and diisopropylethylamine (325 µL) under ice-cooling, and then the mixture was stirred at room temperature for 15 hours. To the reaction mixture was added aqueous saturated sodium hydrogen carbonate solution under ice-cooling, and the mixture was extracted with chloroform. The organic layer was sequentially washed with water and saturated saline, dried over sodium sulfate, and then concentrated under reduced pressure. The resulting residue was purified by silica gel column chromatography (eluent: n-hexane-1-ethyl acetate) to give 4-chloro-N-methoxy-1-(3-methoxypropyl)-N,3-dimethyl-1H-pyrrolo[3,2-c]pyridine-6-carboxamide [REx(105-7)] (277 mg) as a colorless oil.
APCI-MS m/z: 326/328 [M+H]$^+$.

8) 4-Chloro-N-methoxy-1-(3-methoxypropyl)-N,3-dimethyl-1H-pyrrolo[3,2-c]pyridine-6-carboxamide and methylmagnesium bromide were treated in the similar manner to Reference Example 6(5) to give 1-[4-chloro-1-(3-methoxypropyl)-3-methyl-1H-pyrrolo[3,2-c]pyridin-6-yl]ethanone [REx(105-8)] as a colorless powder.
APCI-MS m/z: 281/283 [M+H]$^+$.

9) To a solution of 1-[4-chloro-1-(3-methoxypropyl)-3-methyl-1H-pyrrolo[3,2-c]pyridin-6-yl]ethanone (50 mg) in 1,4-dioxane (2 mL) were added trimethylboroxine (50 µL), cesium carbonate (174 mg), 2-dicyclohexylphosphino-2',4',6'-triisopropyl-1,1'-biphenyl (X-Phos) (17 mg) and tris(dibenzylideneacetone)dipalladium (8 mg) under argon, and the mixture was stirred at 80° C. for 2 hours. The reaction solution was cooled, and then thereto was added water, and the mixture was extracted with ethyl acetate. The organic layer was washed with saturated saline, dried over sodium sulfate, and then concentrated under reduced pressure. The resulting residue was purified by silica gel column chromatography (eluent: n-hexane-n-hexane/ethyl acetate=1/1) to give 1-[1-(3- methoxypropyl)-3,4-dimethyl-1H-pyrrolo[3,2-c]pyridin-6-yl]ethanone [REx(105-9)] (105 mg) as a colorless oil. APCI-MS m/z: 261 [M+H]⁺.

Reference Example 106

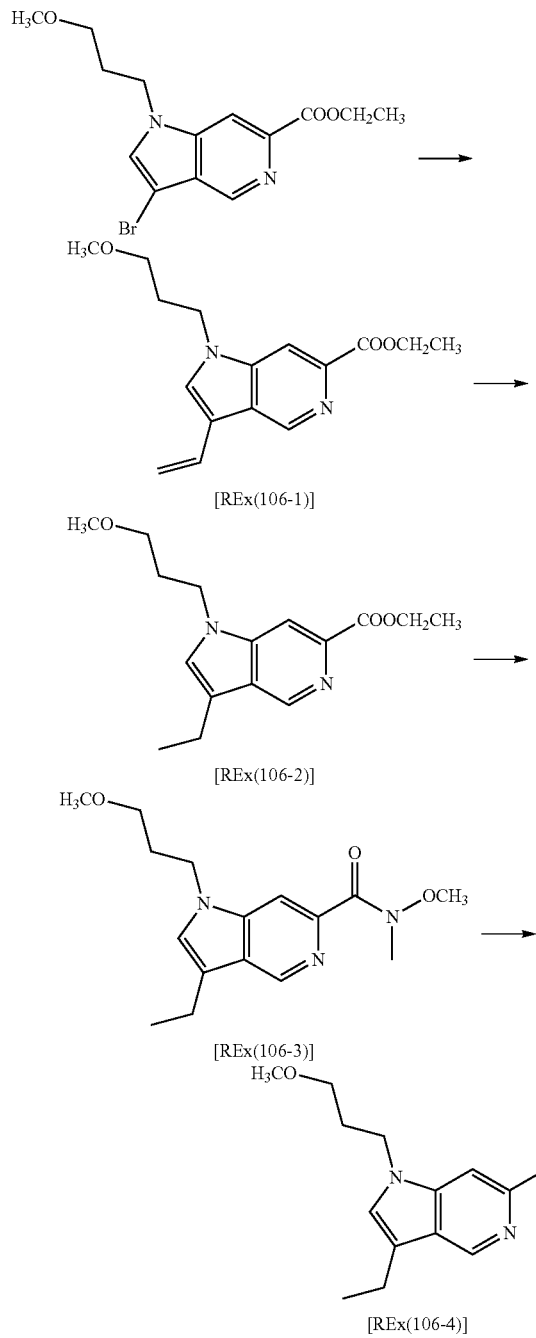

1) To a solution of ethyl 3-bromo-1-(3-methoxypropyl)-1H-pyrrolo[3,2-c]pyridine-6-carboxylate (200 mg) in 1,4-dioxane (2 mL) were added trivinylboroxine pyridine complex (141 mg), cesium carbonate (573 mg), 2-dicyclohexylphosphino-2',4',6'-triisopropyl-1,1'-biphenyl (X-Phos) (56 mg) and tris(dibenzylideneacetone)dipalladium (27 mg) under argon, and the mixture was stirred at 100° C. for 1 hour. The reaction solution was cooled, and then thereto was added water, and the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=9/1-4/1) to give ethyl 1-(3-methoxypropyl)-3-vinyl-1H-pyrrolo[3,2-c]pyridine-6-carboxylate [REx(106-1)] (118 mg) as a yellow oil.
APCI-MS m/z: 289 [M+H]⁺.

2) To a solution of ethyl 1-(3-methoxypropyl)-3-vinyl-1H-pyrrolo[3,2-c]pyridine-6-carboxylate (460 mg) in ethanol (9 mL) was added 10% palladium on carbon (92 mg), and the mixture was stirred under hydrogen for 1 hour. An insoluble was filtered off, and then the filtrate was concentrated under reduced pressure. The resulting residue was purified by silica gel column chromatography (eluent: n-hexane/ethyl acetate=9/1→1/1) to give ethyl 3-ethyl-1-(3-methoxypropyl)-1H-pyrrolo[3,2-c]pyridine-6-carboxylate [REx(106-2)] (294 mg) as a yellow oil.
APCI-MS m/z: 291 [M+H]⁺.

3) Ethyl 3-ethyl-1-(3-methoxypropyl)-1H-pyrrolo[3,2-c]pyridine-6-carboxylate was treated with aqueous sodium hydroxide solution and N,O-dimethylhydroxyamine hydrochloride in the similar manner to Reference Example 105(7) to give 3-ethyl-N-methoxy-1-(3-methoxypropyl)-N-methyl-1H-pyrrolo[3,2-c]pyridine-6-carboxamide [REx(106-3)] as a pale yellow oil.
APCI-MS m/z: 306 [M+H]⁺.

4) 3-Ethyl-N-methoxy-1-(3-methoxypropyl)-N-methyl-1H-pyrrolo[3,2-c]pyridine-6-carboxamide and methylmagnesium bromide were treated in the similar manner to Reference Example 6(5) to give 1-[3-ethyl-1-(3-methoxypropyl)-1H-pyrrolo[3,2-c]pyridin-6-yl]ethanone [REx(106-4)] as a pale yellow oil.
APCI-MS m/z: 261 [M+H]⁺.

Reference Example 107

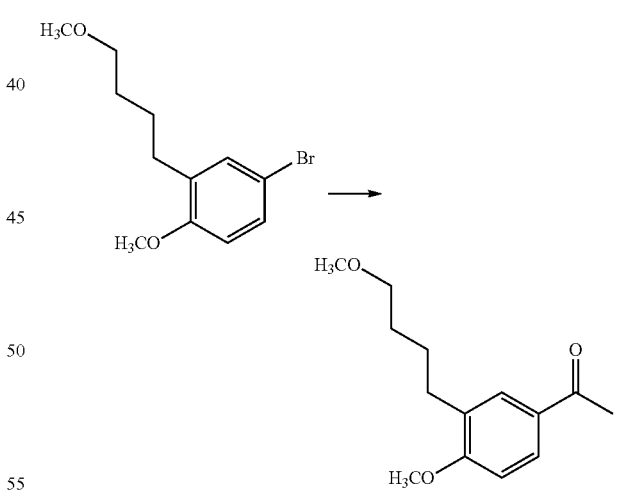

4-Bromo-1-methoxy-2-(4-methoxybutyl)benzene and tri-n-butyltin-1-ethoxyvinyl were treated in the similar manner to Reference Example 27(3) to give 1-[4-methoxy-3-(4-methoxybutyl)phenyl]ethanone as a yellow oil.
APCI-MS m/z: 237 [M+H]⁺.

Reference Example 108 to 112

Compounds of Reference Examples 103 to 107 were treated in the similar manner to Reference Example 6-(6) to give the following compounds.

TABLE 98

| Ref. No. | Chemical Formula | Salt | Molecular Weight | Form | MS Result APCI | Ion Species |
|---|---|---|---|---|---|---|
| 108 | | | 317.3861 | Oil | 318 | [M + H]⁺ |
| 109 | | | 331.4127 | Oil | 332 | [M + H]⁺ |
| 110 | | | 301.4265 | Oil | 302 | [M + H]⁺ |
| 111 | | | 301.4265 | Oil | 302 | [M + H]⁺ |
| 112 | | | 277.4018 | Oil | 278 | [M + H]⁺ |

Reference Example 113

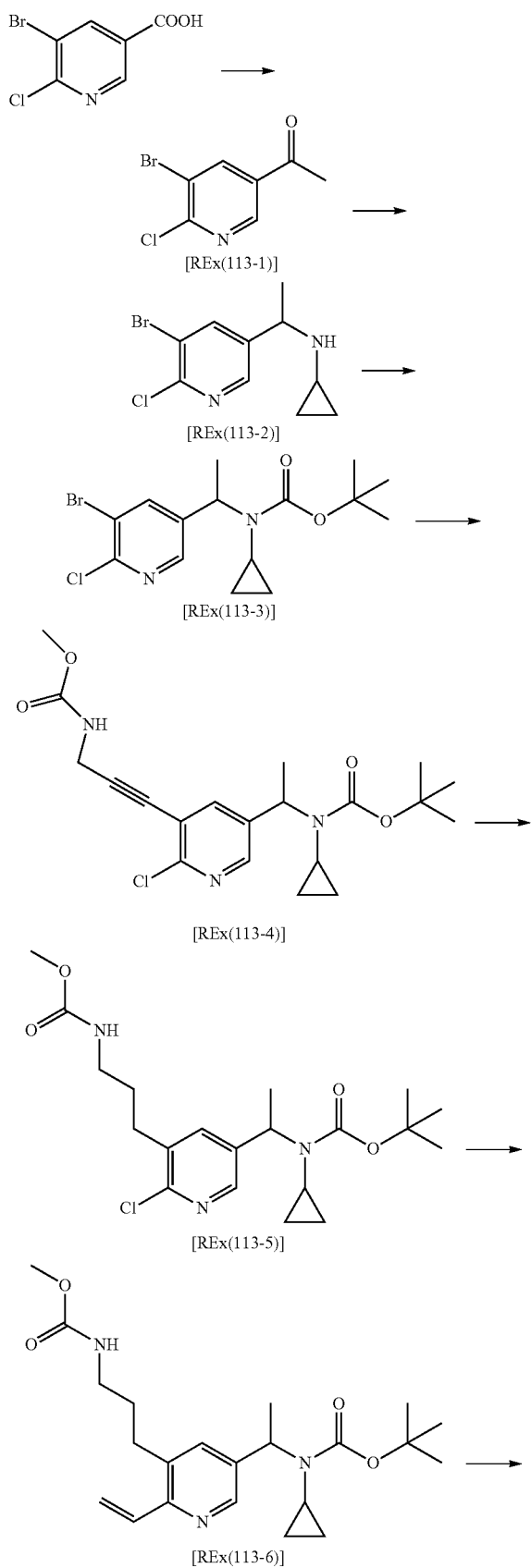
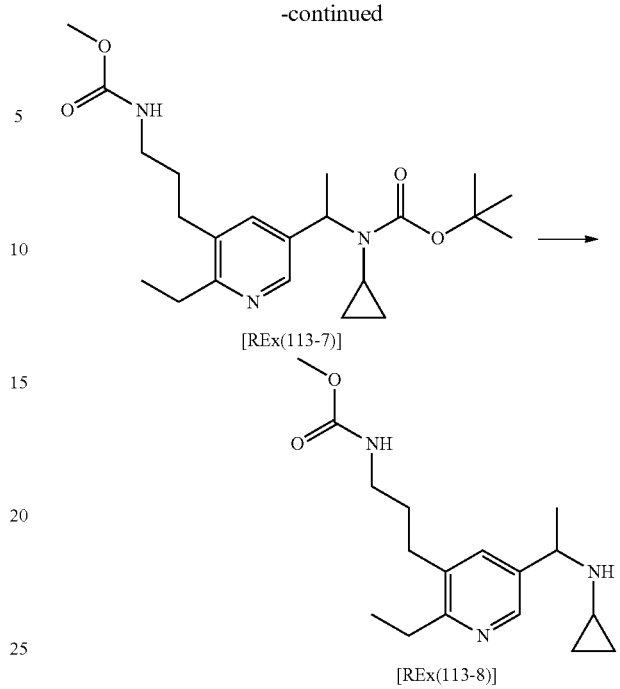

1) 5-Bromo-6-chloronicotinic acid and N,O-dimethylhydroxyamine hydrochloride were treated in the similar manner to Reference Example 7(5), and then the resulting compound and methylmagnesium bromide were treated in the similar manner to Reference Example 7(6) to give 1-(5-bromo-6-chloropyridin-3-yl)ethanone [REx(113-1)] as a colorless powder.
APCI-MS m/z: 234/236 [M+H]$^+$.

2) 1-(5-Bromo-6-chloropyridin-3-yl)ethanone and cyclopropylamine were treated in the similar manner to Reference Example 6(6) to give N-[1-(5-bromo-6-chloropyridin-3-yl)ethyl]cyclopropylamine [REx(113-2)] as a pale yellow oil.
APCI-MS m/z: 275/277 [M+H]$^+$.

3) To a solution of N-[1-(5-bromo-6-chloropyridin-3-yl)ethyl]cyclopropylamine (2.47 g) in ethyl acetate (15 mL)—tetrahydrofuran (15 mL)—water (15 mL) were added sodium hydrogen carbonate (3.78 g) and di-tert-butyl dicarbonate (3.94 g), and the mixture was stirred at room temperature for 41 hours. To the reaction solution was added water, and then the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=4/1→1/1) to give tert-butyl [1-(5-bromo-6-chloropyridin-3-yl)ethyl]cyclopropylcarbamate [REx(113-3)] (2.6 g) as a pale yellow oil.

4) To a solution of t-butyl [1-(5-bromo-6-chloropyridin-3-yl)ethyl]cyclopropylcarbamate (530 mg) in N,N-dimethylformamide (8 mL) were added methyl prop-2-yn-1-ylcarbamate (384 mg), triethylamine (1.96 mL), dichlorobis(triphenylphosphine)palladium (II) (69 mg) and copper (I) iodide (40 mg), and the mixture was stirred at 60° C. for 2 hours. The reaction solution was cooled, and then diluted with ethyl acetate, and an insoluble was filtered off. The filtrate was sequentially washed with water and saturated saline, dried over sodium sulfate, and then concentrated under reduced pressure. The resulting residue was purified by silica gel column chromatography (eluent: n-hexane/ethyl acetate=4/1→1/1) to give methyl [3-(5-{1-[(tert-butoxycarbonyl)(cyclopropyl)amino]ethyl}-2-chloropyridin-3-yl)prop-2-yn-1-yl]carbamate [REx(113-4)] (362 mg) as a pale yellow oil.
APCI-MS m/z: 408/410 [M+H]$^+$.

5) Methyl [3-(5-{1-[(tert-butoxycarbonyl)(cyclopropyl)amino]ethyl}-2-chloropyridin-3-yl)prop-2-yn-1-yl]carbamate was reduced in the similar manner to Example 296(5) to give methyl [3-(5-{1-[(tert-butoxycarbonyl)(cyclopropyl)amino]ethyl}-2-chloropyridin-3-yl)propyl]carbamate [REx(113-5)] as a pale yellow oil.
APCI-MS m/z: 412/414 [M+H]$^+$.

6) To a solution of methyl [3-(5-{1-[(tert-butoxycarbonyl)(cyclopropyl)amino]ethyl}-2-chloropyridin-3-yl)propyl]carbamate (380 mg) in dimethoxyethane (8 mL) were added vinyl boronic acid pinacol ester (235 µL), 2M sodium carbonate (1.38 mL) and dichlorobis(triphenylphosphine)palladium (II) (65 mg), and the mixture was stirred at 85° C. for 17 hours. The reaction solution was cooled, and then an insoluble was filtered off through Celite, and to the filtrate was added water, and the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=3/1→1/4) to give methyl [3-(5-{1-[(tert-butoxycarbonyl)(cyclopropyl)amino]ethyl}-2-vinylpyridin-3-yl)propyl]carbamate [REx(113-6)] (282 mg) as a pale yellow oil.
APCI-MS m/z: 404 [M+H]$^+$.

7) To a solution of methyl [3-(5-{1-[(tert-butoxycarbonyl)(cyclopropyl)amino]ethyl}-2-vinylpyridin-3-yl)propyl]carbamate (280 mg) in methanol (10 mL) was added 10% palladium on carbon (140 mg), and the mixture was stirred under hydrogen for 2 hours. An insoluble was filtered off, and then the filtrate was concentrated under reduced pressure. The resulting residue was purified by silica gel column chromatography (eluent: chloroform-→chloroform/methanol=4/1) to give methyl [3-(5-{1-[(tert-butoxycarbonyl)(cyclopropyl)amino]ethyl}-2-ethylpyridin-3-yl)propyl]carbamate [REx(113-7)] (210 mg) as a pale yellow oil.
APCI-MS m/z: 406 [M+H]$^+$.

8) To a solution of methyl [3-(5-{1-[(tert-butoxycarbonyl)(cyclopropyl)amino]ethyl}-2-ethylpyridin-3-yl)propyl]carbamate (204 mg) in dichloromethane (1.5 mL) was added trifluoroacetic acid (1.5 mL) under ice-cooling, and the mixture was stirred at room temperature for 1 hour. The reaction solution was poured into ice-cooled aqueous saturated sodium hydrogen carbonate solution, and extracted with chloroform. The organic layer was washed with saturated saline, dried over sodium sulfate, and then concentrated under reduced pressure. The resulting residue was purified by NH-silica gel column chromatography (eluent: chloroform→chloroform/methanol=20/1) to give methyl (3-{5-[1-(cyclopropylamino)ethyl]-2-ethylpyridin-3-yl}propyl)carbamate [REx(113-8)] (142 mg) as a pale yellow oil.
APCI-MS m/z: 306 [M+H]$^+$.

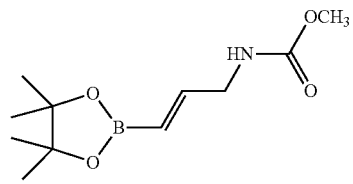

Reference Example 114

To a solution of (−)-α-pinene (3.64 mL) in tetrahydrofuran (5 mL) was added dropwise borane-dimethyl sulfide complex (1.09 mL) under ice-cooling, and the mixture was stirred at room temperature for 15 hours. To the reaction solution was added dropwise a solution of methyl prop-2-yn-1-ylcarbamate (1.0 g) in tetrahydrofuran (3 mL) under ice-cooling, and then the mixture was stirred at room temperature for 17 hours. To the reaction solution was added dropwise acetaldehyde (5 mL) under ice-cooling, and the mixture was stirred at room temperature for 3 hours. The reaction solution was concentrated under reduced pressure, and the resulting residue was dissolved in diethyl ether (15 mL). To the solution was added pinacol (1.56 g), and the mixture was stirred at room temperature for 2 hours. The reaction solution was washed with water, and then dried over magnesium sulfate and concentrated under reduced pressure. The resulting residue was purified by silica gel column chromatography (eluent: n-hexane/ethyl acetate=10/1→3/2) to give methyl [(2E)-3-(4,4,5,5-tetramethyl-1,3,2-dioxaboran-2-yl)prop-2-en-1-yl]carbamate (1.18 g) as a pale yellow oil.

APCI-MS m/z: 242 [M+H]$^+$.

Reference Example 115

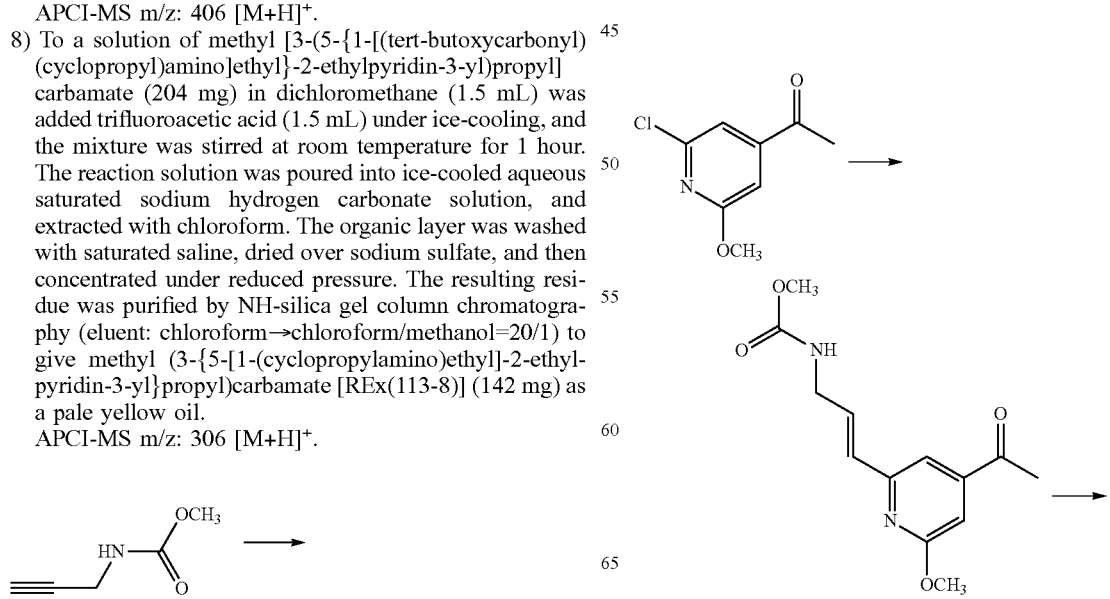

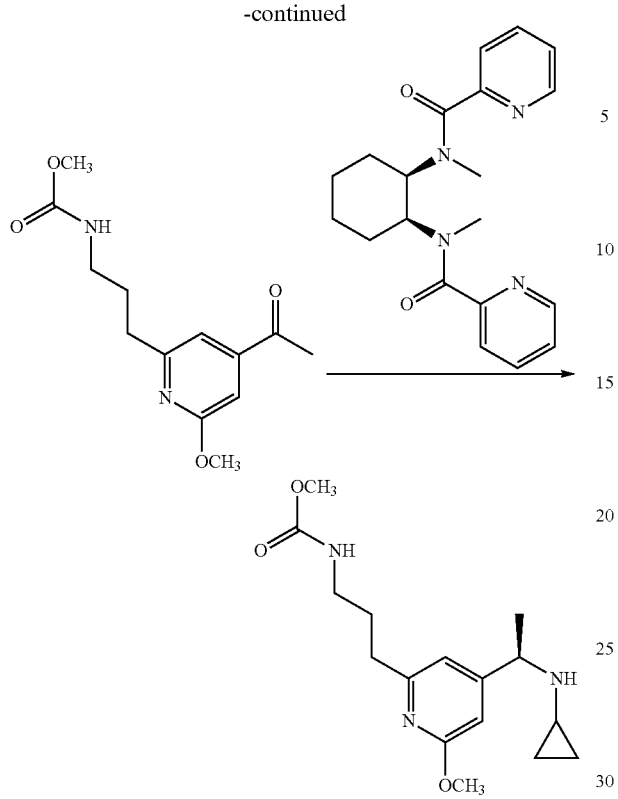

(1) To a solution of 1-(2-chloro-6-methoxypyridin-4-yl)ethanone (12.3 g) in dimethoxyethane (490 mL) were added [(2E)-3-(4,4,5,5-tetramethyl-1,3,2-dioxaborane-2-yl)prop-2-en-1-yl]carbamic acid methyl ester (16.0 g), 2M potassium carbonate (69 mL) and tetrakis(triphenylphosphine)palladium (0) (3.84 g), and the mixture was heated to reflux for 3 hours. After cooling the reaction solution, water was added thereto, and the mixture was extracted with ethyl acetate. The organic layer was sequentially washed with water and saturated saline, dried over sodium sulfate, and then concentrated under reduced pressure. The resulting residue was purified by silica gel column chromatography (eluent: n-hexane/ethyl acetate=7/1→1/1) to give methyl [(2E)-3-(4-acetyl-6-methoxypyridin-2-yl)prop-2-en-1-yl]carbamate (11.8 g).
APCI-MS m/z: 265 [M+H]⁻.

(2) To a solution of methyl [(2E)-3-(4-acetyl-6-methoxypyridin-2-yl)prop-2-en-1-yl]carbamate (2.70 g) in ethyl acetate (140 mL) was added 10% palladium on carbon (270 mg), and the mixture was stirred under hydrogen for 10 minutes. An insoluble was filtered off through Celite, and the resulting residue obtained by concentrate the filtrate under reduced pressure was purified by silica gel column chromatography (eluent: n-hexane/ethyl acetate=6/1→1/2) and (eluent: chloroform→chloroform/methanol=20/1) to give [3-(4-acetyl-6-methoxypyridin-2-yl)propyl]carbamic acid methyl ester (1.68 g).
APCI-MS m/z: 267 [M+H]⁺.

(3) To a solution of [3-(4-acetyl-6-methoxypyridin-2-yl)propyl]carbamic acid methyl ester (5.49 g) in ethanol (110 mL) were added cyclopropylamine (5.71 mL) and acetic acid (1.77 mL), and the mixture was stirred at 60° C. for 18 hours. After the reaction solution was concentrated, ethyl acetate was added to the resulting residue under ice-cooling, and aqueous saturated sodium hydrogen carbonate solution was added to make the solution alkaline After an extruciton with ethyl acetate, the organic layer was washed with saturated saline, dried over sodium sulfate, and then concentrated under reduced pressure to give methyl {3-[4-(N-cyclopropylethanimidoyl)-6-methoxypyridin-2-yl]propyl}carbamate (6.78 g).
APCI-MS m/z: 306 [M+H]⁺.

(4) To a solution of methyl {3-[4-(N-cyclopropylethanimidoyl)-6-methoxypyridin-2-yl]propyl}carbamate (6.30 g) and N,N'-(1S,2S)-cyclohexane-1,2-diylbis(N-methylpyridin-2-carboxamide) (727 mg) in dichloromethane (120 mL) was added acetic acid (1.42 mL) under ice-cooling, and then trichlorosilane (8.32 mL) was added dropwise, and the mixture was stirred under ice-cooling for 4 hours. To the reaction solution were added aqueous saturated sodium hydrogen carbonate solution and methanol under ice-cooling, and then potassium carbonate was added until the mixture was basic, and then stirred for 30 minutes at the same temperature. An insoluble was removed by Celite, and washed with chloroform. After the filtrate was extracted with chloroform, the organic layer was washed with saturated saline, dried over sodium sulfate, and then concentrated under reduced pressure. The resulting residue was purified by NH-silica gel column chromatography (eluent: n-hexane/ethyl acetate=2/1→1/1) to give methyl (3-{4-[(1R)-1-(cyclopropylamino)ethyl]-6-methoxypyridin-2-yl}propyl)carbamate (5.65 g).
APCI-MS m/z: 308 [M+H]⁺.

Reference Example 116

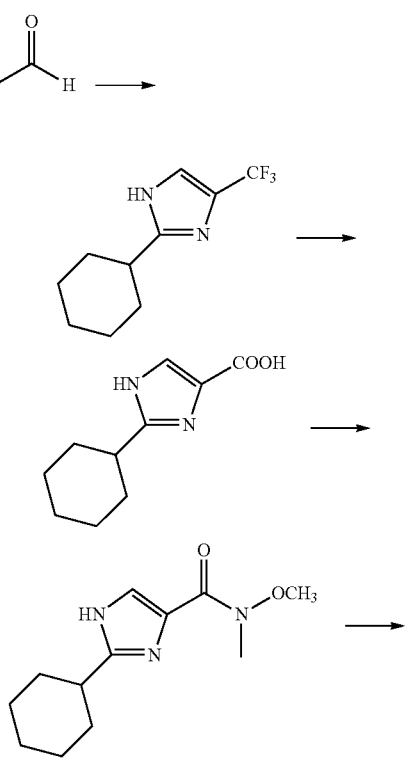

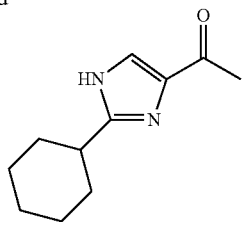

(1) To a solution of 3,3-dibromo-1,1,1-trifluoroacetone (5.76 g) in water (20 mL) was added acetic acidpotassium (3.84 g), and the mixture was stirred at 90° C. for 0.5 hours. After the reaction solution was return to the room temperature, methanol (20 mL), tetrahydrofuran (20 mL), ammonia water (40 mL), and cyclohexanal (2.0 g) were added thereto, and the mixture was stirred at room temperature for 17 hours. Ethyl acetate was added to the reaction mixture for extruciton. The organic layer was washed with saturated saline, dried over sodium sulfate, and then concentrated under reduced pressure. The resulting residue was suspended in n-hexane (10 mL), and then filtrate to give 2-cyclohexyl-4-(trifluoromethyl)-1H-imidazole (2.1 g).
APCI-MS m/z: 219 [M+H]$^+$.

(2) To 2-cyclohexyl-4-(trifluoromethyl)-1H-imidazole (2.0 g) was added 5-normal aqueous sodium hydroxide solution (12 mL), and then the mixture was stirred at 60° C. for 0.5 hours, and further at 100° C. for 2 hours. The reaction solution was return to the room temperature, and then an insoluble was filtered through Celite. The resulting filtrate was concentrated under reduced pressure to give 2-cyclohexyl-1H-imidazol-4-carboxylic acid (4.0 g).
APCI-MS m/z: 195 [M+H]$^+$.

(3) To 2-cyclohexyl-1H-imidazol-4-carboxylic acid (2.0 g) was added thionyl chloride (20 mL), and the mixture was stirred under reflux for 2 hours. After the reaction solution was return to the room temperature, and concentrated under reduced pressure. A solution of the resulting residue in chloroform (20 mL) was added dropwise to a solution of N,O-dimethylhydroxylamine hydrochloride in chloroform (20 mL)-saturated sodium hydrogen carbonate water (50 mL) under ice-cooling, and the mixture was stirred at room temperature for 17 hours. Chloroform was added to the reaction mixture for extrucion. The organic layer was dried over sodium sulfate, and then concentrated under reduced pressure. The resulting residue was suspended in n-hexane (10 mL), and then filtrate to give 2-cyclohexyl-N-methoxy-N-methyl-1H-imidazol-4-carboxamide (650 mg).
APCI-MS m/z: 238 [M+H]$^+$.

(4) To a solution of 2-cyclohexyl-N-methoxy-N-methyl-1H-imidazol-4-carboxamide (640 mg) in tetrahydrofuran (10 mL) was added dropwise diethyl ether solution of methylmagnesium bromide (3.6 mL) under ice-cooling, and then the mixture was stirred for 2 hours at the same temperature. Further diethyl ether solution of methylmagnesium bromide (3.6 mL) was added dropwise, and the mixture was stirred at room temperature for 17 hours To the reaction solution were added aqueous saturated sodium hydrogen carbonate solution, and the mixture was extracted with ethyl acetate. The organic layer was washed with saturated saline, dried over sodium sulfate, and concentrated under reduced pressure. The resulting residue was purified by silica gel column chromatography (eluent: ethyl acetate/methanol=1/0→19/1) to give 1-(2-cyclohexyl-1H-imidazol-4-yl)ethanone (330 mg).
APCI-MS m/z: 193 [M+H]$^+$.

(5) 1-(2-Cyclohexyl-1H-imidazol-4-yl)ethanone was treated in analogously with Reference Example 115-(4) to give N-[(1R)-1-(2-cyclohexyl-1H-imidazol-4-yl)ethyl]cyloprolylamine.

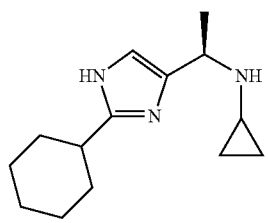 [SMILES: C[C@@H](NC1CC1)c1c[nH]c(C2CCCCC2)n1]

APCI-MS m/z: 234 [M+H]$^+$.

(6) N-[(1R)-1-(2-cyclohexyl-1H-imidazol-4-yl)ethyl]cyloprolylamine was treated in analogously with Example 1-(1) to give tert-butyl (2R)-2-{[(1R)-1-(2-cyclohexyl-1H-imidazol-4-yl)ethyl](cyclopropyl)carbamoyl}morpholine-4-carboxylate.

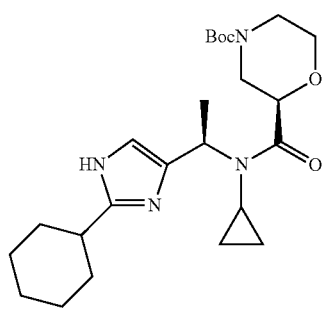 [SMILES: C[C@H](c1c[nH]c(C2CCCCC2)n1)N(C(=O)[C@H]1CN(C(=O)OC(C)(C)C)CCO1)C1CC1]

APCI-MS m/z: 447 [M+H]$^+$.

Reference Example 117

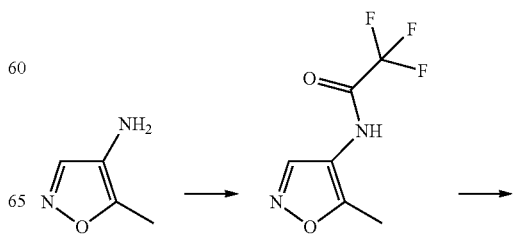

333

-continued

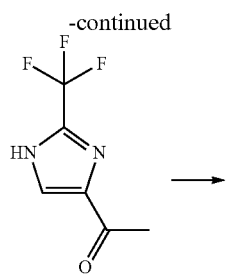

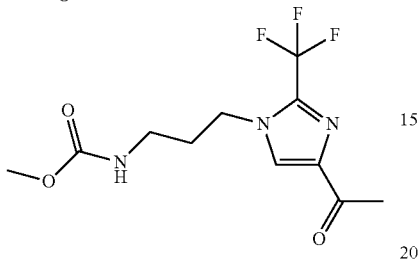

(1) To 5-methyl-1,2-oxazol-4-amine (1.78 g) was added anhydrous trifluoroacetic acid (18 mL), and the mixture was stirred at room temperature for 40 minutes. The reaction solution was treated azeotropically with toluene, and the resulting residue was purified by silica gel column chromatography (eluent: n-hexane/ethyl acetate=87/13→67/33) to give 2,2,2-trifluoro-N-(5-methyl-1,2-oxazol-4-yl)acetamide (2.48 g).
APCI-MS m/z: 195 [M+H]$^+$.

(2) To a solution of 2,2,2-trifluoro-N-(5-methyl-1,2-oxazol-4-yl)acetamide (2.48 g) in ethanol (18 mL) was added 10% palladium on carbon (1.0 g) under hydrogen atmosphere, and the mixture was stirred at room temperature for 1 hours. An insoluble was filtered through Celite, and the filtrate was concentrated under reduced pressure. To a solution of the resulting residue in ethanol (150 mL) was added sodium hydroxide (562 mg), and the mixture was stirred at 95° C. for 30 minutes. After the reaction solution was return to the room temperature, ammonium chloride (820 mg) was there and the mixture was stirred at room temperature for 15 minutes. The reaction solution was concentrated under reduced pressure, and the resulting residue was suspended in acetone (30 mL), and an insoluble was filtered off through Celite. The filtrate was concentrated under reduced pressure, and the resulting residue was suspended in diisopropyl ether (30 mL), and then filtrate to give 1-[2-(trifluoromethyl)-1H-imidazol-4-yl]ethanone (1.97 g).
APCI-MS m/z: 179 [M+H]$^+$.

(3) To a solution of 1-[2-(trifluoromethyl)-1H-imidazol-4-yl]ethanone (1.80 g) in N,N-dimethylformamide (50 mL) were added potassium carbonate (4.19 g), methyl (3-bromopropyl)carbamate (2.97 g) in N,N-dimethylformamide solution (16 mL) at room temperature, and the mixture was stirred, under nitrogen stream, at room temperature for 2 days. The reaction solution was diluted with an excess of ethyl acetate, and washed with water and saturated saline, dried over anhydrous magnesium sulfate, and then the solvent was distilled under reduced pressure. The resulting residue was purified by silica gel column chromatography (eluent: n-hexane/ethyl acetate=60/40→37/63). The powder obtained after evaporation of a

334 solvent was suspended in diisopropyl ether, and the precipitate was filtered, and washed with diisopropyl ether to give {3-[4-acetyl-2-(trifluoromethyl)-1H-imidazol-1-yl]propyl}carbamic acid methyl ester (1.36 g) as colorless powder.
APCI-MS m/z: 294 [M+H]$^+$.

Reference Example 118

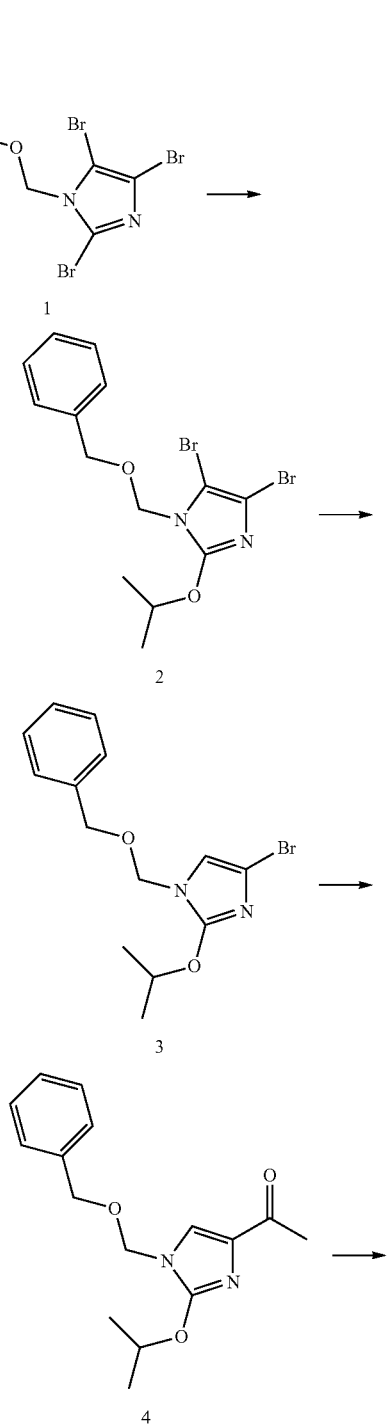

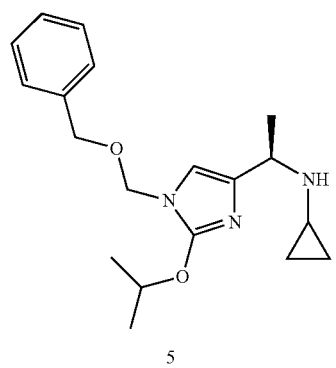

(1) To a solution of 2-propanol (3.6 mL) in N,N-dimethylformamide (80 mL), under ice-cooling, 60% sodium hydride (1.88 g) was added in small-portions, and then the mixture was stirred at room temperature for 30 minutes. To the reaction solution was added 1-[(benzyloxy)methyl]-2,4,5-tribromo-1H-imidazole (10.0 g) in N,N-dimethylformamide (30 mL) dropwise under ice-cooling, and the mixture was stirred under ice-cooling for 30 minutes and further at room temperature for 3 hours. To the reaction solution was added water under ice-cooling, and the mixture was extracted with ethyl acetate. The organic layer was sequentially washed with water and saturated saline, dried over sodium sulfate, and then concentrated under reduced pressure. The resulting residue was purified by silica gel column chromatography (eluent: n-hexane/ethyl acetate=30/1→20/1) to give 1-[(benzyloxy)methyl]-4,5-dibromo-2-(propan-2-yloxy)-1H-imidazole (6.78 g).
APCI-MS m/z: 403/405/407 [M+H]$^+$.

(2) To a solution of 1-[(benzyloxy)methyl]-4,5-dibromo-2-(propan-2-yloxy)-1H-imidazole (5.0 g) in tetrahydrofuran (20 mL)-diethyl ether (140 mL) was added dropwise, at −78° C., 1.63 M n-butyl lithium solution in hexane (7.59 mL), and the mixture was stirred at −78° C. for 30 minutes. At −78° C., 1.63 M n-butyl lithium solution in hexane (1.52 mL) was added dropwise, and the mixture was stirred at −78° C. for 15 minutes. To the reaction solution was added water, and extructed with diethyl ether. The organic layer was washed with saturated saline, dried over sodium sulfate, and then concentrated under reduced pressure. The resulting residue was purified by silica gel column chromatography (eluent: n-hexane/ethyl acetate=100/1→20/1) to give 1-[(benzyloxy)methyl]-4-bromo-2-(propan-2-yloxy)-1H-imidazole (3.44 g).
APCI-MS m/z: 325/327 [M+H]$^+$.

(3) Under nitrogen atmosphere, to a solution of 1-[(benzyloxy)methyl]-4-bromo-2-(propan-2-yloxy)-1H-imidazole (2.25 g) in 1,4-dioxane (70 mL) was added tri-n-butyltin-1-ethoxyvinyl (3.00 g) and tetrakis(triphenylphosphine)palladium (0) (800 mg), and the mixture was stirred at 100° C. for 4 hours. Tri-n-butyltin-1-ethoxyvinyl (1.50 g) and tetrakis(triphenylphosphine)palladium (0) (200 mg) was added thereto, and the mixture was stirred at 100° C. for 4 hours. After the reaction solution was return to the room temperature, 2-normal hydrochloric acid aqueous (70 mL) was added thereto, and the mixture was stirred at room temperature for 1 hour. Under ice-cooling, 2-normal aqueous sodium hydroxide solution (70 mL) and aqueous saturated sodium hydrogen carbonate solution were added thereto, and the mixture was extracted with ethyl acetate. An insoluble was filtrated through Celite, and the organic layer was washed with saturated saline, dried over sodium sulfate, and then concentrated under reduced pressure. The resulting residue was purified by silica gel column chromatography (eluent: n-hexane/ethyl acetate=20/1→1/1) to give 1-{1-[(benzyloxy)methyl]-2-(propan-2-yloxy)-1H-imidazol-4-yl}ethanone (960 mg).
APCI-MS m/z: 289 [M+H]$^+$.

(4) 1-{1-[(Benzyloxy)methyl]-2-(propan-2-yloxy)-1H-imidazol-4-yl}ethanone was treated in analogously with Reference Example 115-(4) to give N-[(1R)-1-{1-[(benzyloxy)methyl]-2-(propan-2-yloxy)-1H-imidazol-4-yl}ethyl]cyloprolylamine.
APCI-MS m/z: 330 [M+H]$^+$.

Reference Example 119

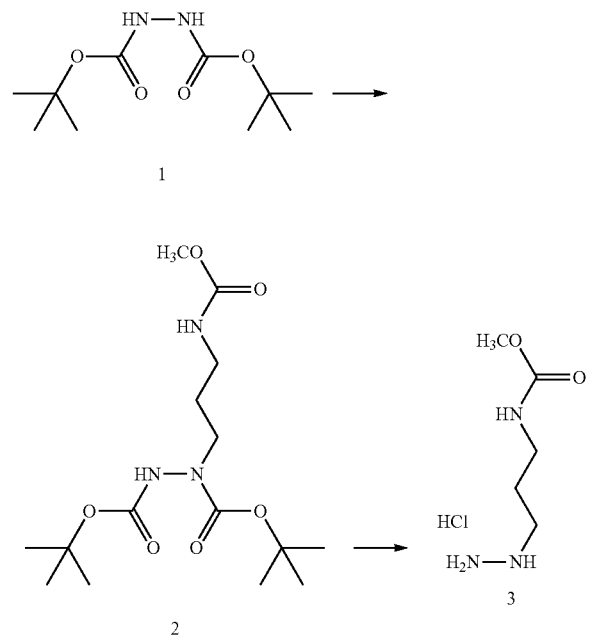

(1) To a solution of a di-tert-butyl hydrazine-1,2-dicarboxylate (50.0 g) in N,N-dimethylformamide (200 mL), under ice-cooling, 60% sodium hydride (9.47 g) was added in small-portions, and the mixture was stirred under ice-cooling for 30 minutes. Under ice-cooling, methyl (3-bromopropyl)carbamate (50.6 g) in N,N-dimethylformamide (50 mL) was added dropwise, and then the mixture was stirred at room temperature for 20 hours. To the reaction solution was added water under ice-cooling, and the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=7/1→3/1) to give di-tert-butyl 1-{3-[(methoxycarbonyl)amino]propyl}hydrazine-1,2-dicarboxylate (35.0 g).
APCI-MS m/z: 365 [M+NH$_4$]$^+$.

(2) To a solution of di-tert-butyl 1-{3-[(methoxycarbonyl)amino]propyl}hydrazine-1,2-dicarboxylate (35.0 g) in chloroform (210 mL) was added dropwise 4-normal hydrogen chloride-1,4-dioxane solution (210 mL) under ice-cooling, and the mixture was stirred at room temperature for 3 hours, then concentrated under reduced pressure. The resulting residue was suspended in isopropyl ether, and then filtrate to give methyl (3-hydradinylpropyl)carbamate hydrochloride (18.1 g).
ESI-MS m/z: 148 [M+H]$^+$.

Reference Example 120

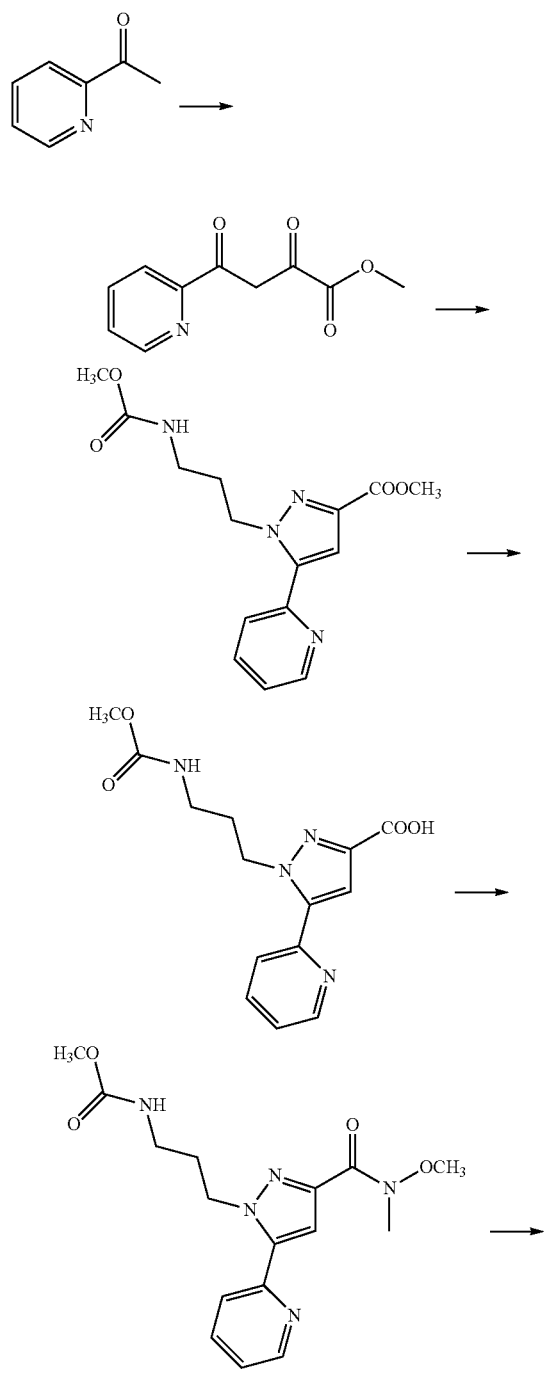

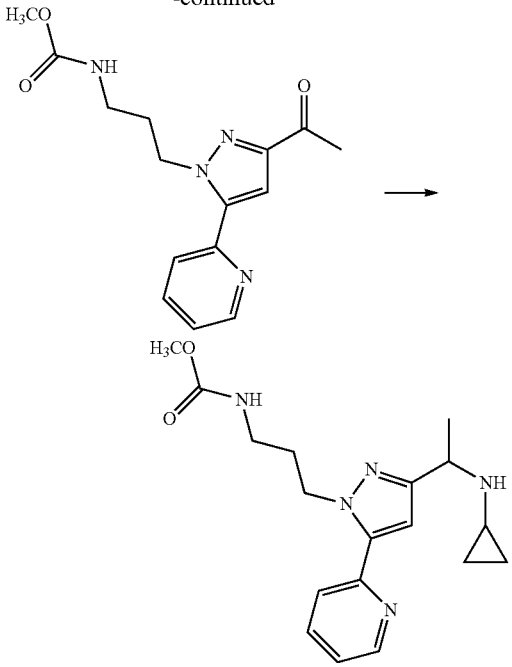

-continued (1) To a solution of 1-(pyridin-2-yl)ethanone (23.38 g) and dimethyl oxalate (27.35 g) in methanol (40 mL) was added dropwise 28% sodium methoxide solution in methanol (74.47 g) under ice-cooling, and the mixture was stirred at room temperature for 90 hours. To the reaction solution was added 10% aqueous citric acid solution until acidic, and the mixture was extracted with ethyl acetate. The organic layer was washed with saturated saline, dried over sodium sulfate, and concentrated under reduced pressure. The resulting residue was suspended in n-hexane/ethyl acetate (=30/1), and then filtrate to give 2,4-dioxo-4-(pyridin-2-yl)butaneacidmethyl (35.75 g).
APCI-MS m/z: 208 [M+H]$^+$.

(2) To 2,4-dioxo-4-(pyridin-2-yl)butaneacidmethyl (6.0 g) and methyl (3-hydradinopropyl)carbamate hydrochloride (5.32 g) was added methanol (120 mL), and the mixture was stirred at 60° C. for 3 hours. The mixture was concentrated under reduced pressure, and to the resulting residue saturated sodium hydrogen carbonate solution was added thereto, and the mixture was extracted with ethyl acetate. The organic layer was washed with saturated saline, dried over sodium sulfate, and concentrated under reduced pressure. The resulting residue was purified by silica gel column chromatography (eluent: n-hexane/ethyl acetate=1/1→1/4) to give methyl 1-{3-[(methoxycarbonyl)amino]propyl}-5-(pyridin-2-yl)-1H-pyrazol-3-carboxylate (6.68 g).
APCI-MS m/z: 319 [M+H]$^+$.

(3) To methyl 1-{3-[(methoxycarbonyl)amino]propyl}-5-(pyridin-2-yl)-1H-pyrazol-3-carboxylate (300 mg) was added 1-normal aqueous sodium hydroxide solution (1.88 mL), and the mixture was stirred at room temperature for 1 hour. To the reaction solution 10% aqueous citric acid solution was added until acidic, and the mixture was extracted with ethyl acetate. The organic layer was washed with saturated saline, dried over sodium sulfate, concentrated under reduced pressure to give 1-{3-

[(methoxycarbonyl)amino]propyl}-5-(pyridin-2-yl)-1H-pyrazol-3-carboxylic acid (299 mg).

APCI-MS m/z: 305 [M+H]+.

(4) To a solution of 1-{3-[(methoxycarbonyl)amino]propyl}-5-(pyridin-2-yl)-1H-pyrazol-3-carboxylic acid (295 mg) and N,O-dimethylhydroxylamine hydrochloride (142 mg) in dichloromethane were added diphenyl chlorophosphate (313 mg) and diisopropylethylamine (675 µL) under ice-cooling, and the mixture was stirred at room temperature for 18 hours. The mixture was concentrated under reduced pressure, and the resulting residue was purified by silica gel column chromatography (eluent: n-hexane/ethyl acetate=1/0→1/3) to give methyl (3-{3-[methoxy(methyl)carbamoyl]-5-(pyridin-2-yl)-1H-pyrazol-1-yl}propyl)carbamicacid (211 mg).

APCI-MS m/z: 348 [M+H]+.

(5) To a solution of (3-{3-[methoxy(methyl)carbamoyl]-5-(pyridin-2-yl)-1H-pyrazol-1-yl}propyl)carbamic acid methyl ester (205 mg) in tetrahydrofuran (10 mL), at −78° C. diethyl ether solution of methylmagnesium bromide (590 µL) was added dropwise, and the mixture was stirred for 1 hour with temperature raising to 0° C. To the reaction solution was added saturated aqueous ammonium chloride solution (4 mL) at 0° C., and the mixture was extracted with ethyl acetate. The organic layer was washed with saturated saline, dried over magnesium sulfate, and concentrated under reduced pressure. The resulting residue was purified by silica gel column chromatography (eluent: n-hexane/ethyl acetate=1/0→1/1) to give {3-[3-acetyl5-(pyridin-2-yl)-1H-pyrazol-1-yl]propyl}carbamic acid methyl ester (138 mg).

APCI-MS m/z: 303 [M+H]+.

(6) To a solution of {3-[3-acetyl-5-(pyridin-2-yl)-1H-pyrazole1-yl]propyl}carbamic acid methyl ester (134 mg) and cyclopropylamine (92 µL) in dichloromethane (10 mL) were added acetic acid (76 µL) and sodium triacetoxyborohydride (282 mg) at room temperature, and the mixture was stirred for 17 hours at the same temperature. To the reaction solution was added saturated sodium hydrogen carbonate solution, and the mixture was extracted with ethyl acetate. The organic layer was washed with saturated saline, dried over magnesium sulfate, and concentrated under reduced pressure. The resulting residue was purified by silica gel column chromatography (eluent: n-hexane/ethyl acetate=1/0→1/1) to give methyl (3-{3-[1-(cyclopropylamino)ethyl]-5-(pyridin-2-yl)-1H-pyrazol-1-yl}propyl)carbamate (146 mg).

APCI-MS m/z: 344 [M+H]+.

Reference Example 121

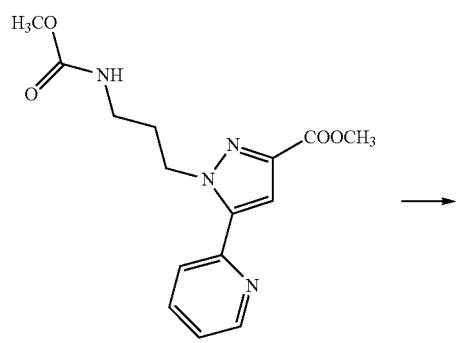

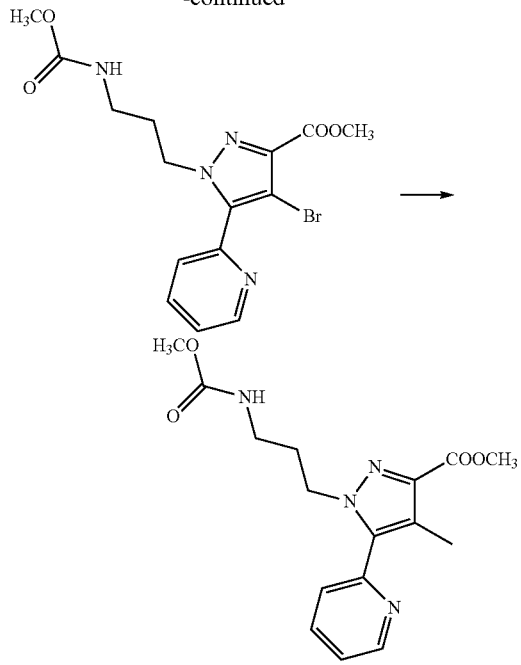

(1) To a solution of methyl 1-{3-[(methoxycarbonyl)amino]propyl}-5-(pyridin-2-yl)-1H-pyrazol-3-carboxylate (5.16 g) in N,N-dimethylformamide (100 mL) was added N-bromosuccinimide (5.77 g) in small-portions under ice-cooling, and the mixture was stirred at room temperature for 20 hours. To the reaction solution was added water under ice-cooling, and then the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=3/1→1/1), and suspended in isopropyl ether, then filtrate to give methyl 4-bromo-1-{3-[(methoxycarbonyl)amino]propyl}-5-(pyridin-2-yl)-1H-pyrazol-3-carboxylate (5.93 g).

APCI-MS m/z: 397/399 [M+H]+.

(2) Under nitrogen atmosphere, to a solution of methyl 4-bromo-1-{3-[(methoxycarbonyl)amino]propyl}-5-(pyridin-2-yl)-1H-pyrazol-3-carboxylate (382 mg) in 1,4-dioxane (5.0 mL) were added trimethylboroxine (262 µL), potassium (408 mg), 2-dicyclohexylphosphino-2',4',6'-triisopropyl-1,1'-biphenyl (X-Phos) (183 mg), tris(dibenzylideneacetone)dipalladium (88 mg), and the mixture was stirred at 110° C. for 20 hours. After cooling the reaction solution, water was added thereto, and the mixture was extracted with ethyl acetate. The organic layer was washed with saturated saline, dried over magnesium sulfate, and then concentrated under reduced pressure. The resulting residue was purified by silica gel column chromatography (eluent: n-hexane/ethyl acetate=1/1→1/2) to give methyl 1-{3-[(methoxycarbonyl)amino]propyl}-4-methyl5-(pyridin-2-yl)-1H-pyrazol-3-carboxylate (177 mg).

APCI-MS m/z: 333 [M+H]+.

Reference Example 122

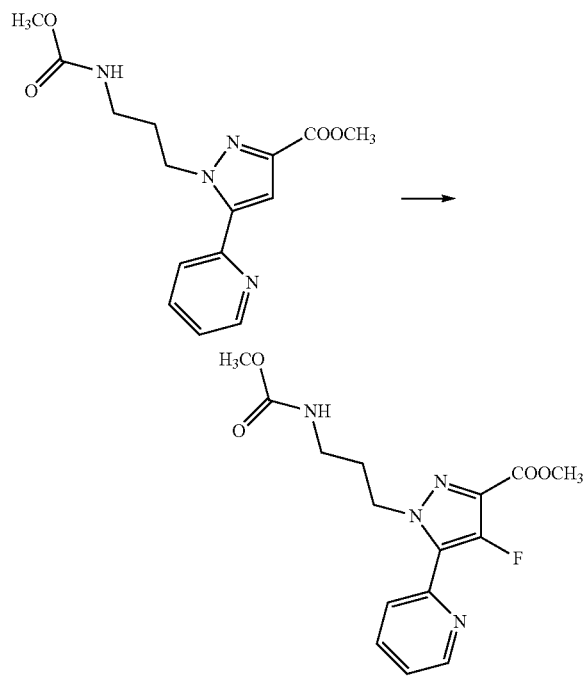

To a solution of methyl 1-{3-[(methoxycarbonyl)amino]propyl}-5-(pyridin-2-yl)-1H-pyrazol-3-carboxylate (465 mg) in acetonitrile (5.0 mL) was added Selectfluor® (1.03 g), and the mixture was stirred at 60° C. for 17 hours. After cooling the reaction solution, it is dissolved in ethyl acetate, washed with saturated saline, dried over magnesium sulfate, and then concentrated under reduced pressure. The resulting residue was purified by silica gel column chromatography (eluent: n-hexane/ethyl acetate=9/1→1/1) to give methyl 4-fluoro-1-{3-[(methoxycarbonyl)amino]propyl}-5-(pyridin-2-yl)-1H-pyrazol-3-carboxylate (183 mg).

APCI-MS m/z: 337 [M+H]+.

Reference Example 123

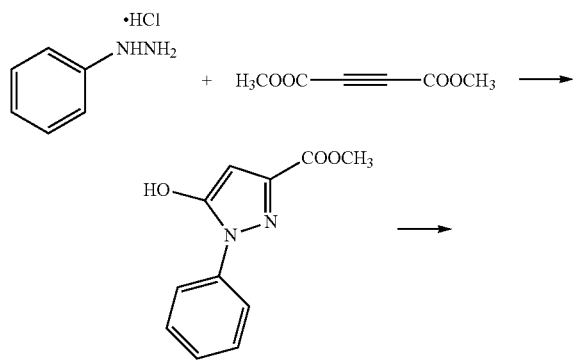

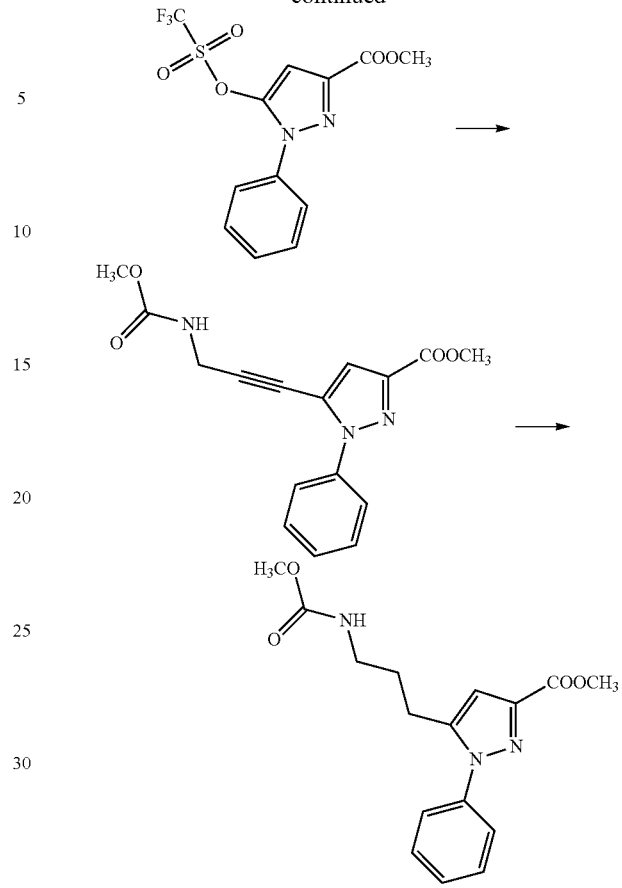

(1) To a solution of dimethyl acetylenedicarboxylate (20.0 g) in methanol (400 mL) was added phenylhydrazine hydrochloride (20.4 g), and further potassium carbonate (38.9 g) were added thereto, and then the mixture was stirred under reflux for 3 hours. After cooling the reaction solution, water (300 mL) was added thereto, and the reaction solution made acidic by 10% hydrochroric acid, and the mixture was stirred for 20 minutes. It was extructed with ethyl acetate, the organic layer was washed with saturated saline, dried over sodium sulfate, and then concentrated under reduced pressure. The resulting residue was suspended in diethyl ether, then filtrate to give methyl 5-hydroxyl-phenyl-1H-pyrazol-3-carboxylate (19.0 g).

APCI-MS m/z: 219 [M+H]+.

(2) To a solution of methyl 5-hydroxyl-phenyl-1H-pyrazol-3-carboxylate (10.0 g) in tetrahydrofuran (100 mL) was added N-phenyl bis(trifluoromethane sulfoneimide) (17.2 g) and triethylamine (8.3 mL), and then the mixture was stirred at room temperature for 30 minutes. The resulting reaction solution was concentrated under reduced pressure and the resulting residue was purified by silica gel column chromatography (eluent: n-hexane/ethyl acetate=100/1→7/1) to give 1-phenyl5-{[(trifluoromethyl)sulfonyl]oxy}-1H-pyrazol-3-carboxylic acidmethyl (11.9 g).

APCI-MS m/z: 351 [M+H]+.

(3) To a solution of 1-phenyl5-{[(trifluoromethyl)sulfonyl]oxy}-1H-pyrazol-3-carboxylic acidmethyl (11.9 g) in N,N-dimethylformamide (80 mL) were added methyl prop-2-yn-1-ylcarbamate (5.74 g) in N,N-dimethylformamide (40 mL), copper(I) iodide (966 mg), dichlorobis(triphenylphosphine)palladium (II) (1.66 g), triethylamine (47.1 mL), and the mixture was stirred at 60° C. for 1 hour. After cooling the reaction solution, water was added thereto, and the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=7/1→1/1) to give methyl 5-{3-[(methoxycarbonyl)amino]prop-1-yn-1-yl}-1-phenyl-1H-pyrazol-3-carboxylate (7.50 g).
APCI-MS m/z: 314 [M+H]+.

(4) To a solution of methyl 5-{3-[(methoxycarbonyl)aminoprop-1-yn-1-yl}-1-phenyl-1H-pyrazol-3-carboxylate (7.50 g) in methanol (150 mL) was added 10% palladium on carbon (1.50 g) under hydrogen atmosphere, and the mixture was stirred for 5 hours. An insoluble was filtered off through Celite, and washed with methanol. To a solution of a residue obtained by concentrate the filtrate under reduced pressure in methanol (100 mL) was added 10% palladium on carbon (1.50 g) and the mixture was stirred under hydrogen atmosphere for 17 hours. An insoluble was filtered off through Celite, and washed with methanol. The resulting residue obtained by concentrate the filtrate under reduced pressure was purified by silica gel column chromatography (eluent: n-hexane/ethyl acetate=3/1→1/1) to give methyl 5-{3-[(methoxycarbonyl)amino]propyl}-1-phenyl-1H-pyrazol-3-carboxylate (6.84 g).
APCI-MS m/z: 318 [M+H]+.

Reference Example 124

Methyl 4-fluoro-5-{3-[(methoxycarbonyl)amino]propyl}-1-phenyl-1H-pyrazol-3-carboxylate

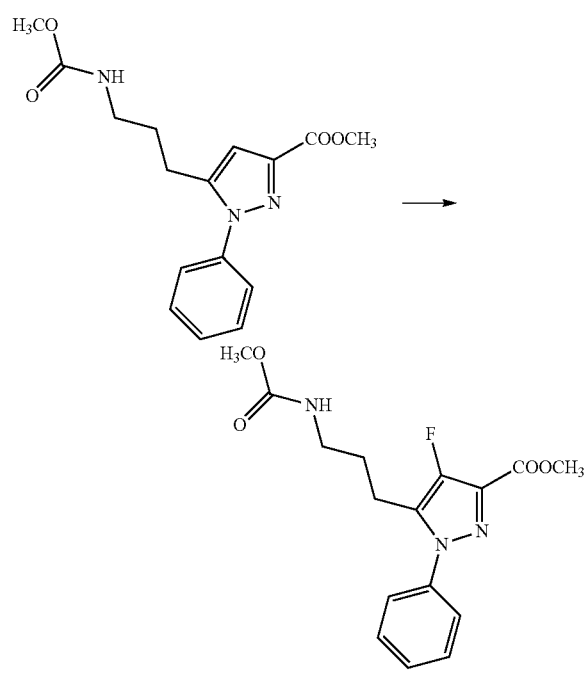

To a solution of methyl 5-{3-[(methoxycarbonyl)amino]propyl}-1-phenyl-1H-pyrazol-3-carboxylate (981 mg) in acetonitrile (10 mL) was added Selectfluor® (2.19 g), and the mixture was stirred at 60° C. for 20 hours. After cooling the reaction solution, water was added thereto, and the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=5/1→1/1) to give (330 mg).
APCI-MS m/z: 336 [M+H]+.

Reference Example 125

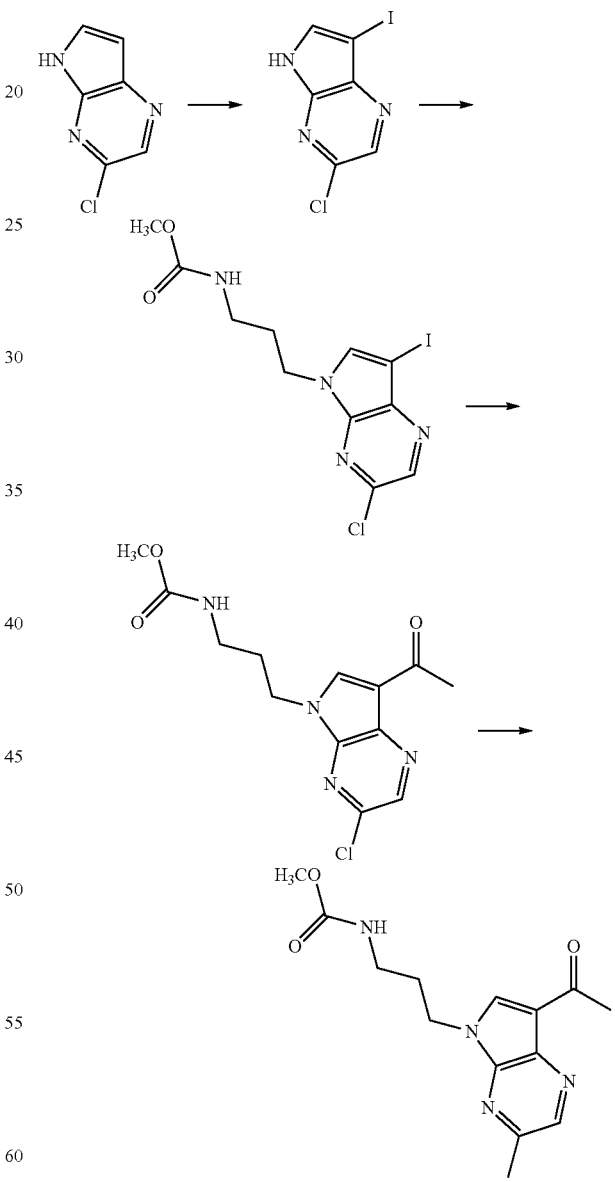

(1) To a solution of 3-chloro-5H-pyrrolo[2,3-b]pyrazin (4.69 g) in N,N-dimethylformamide (70 mL) were added potassium hydroxide (6.85 g) and iodine (15.5 g) under ice-cooling, and the mixture was stirred at room temperature for 3 hours. Under ice-cooling, an aqueous sodium thiosulfate solution and ethyl acetate were added mm and after mixing, a solid is then filtrate to give 2 (3.96 g). The organic layer of the filtrate was separated, and the organic layer was sequentially washed with water and saturated saline, dried over sodium sulfate, and then concentrated under reduced pressure to give 3-chloro-7-iodo-5H-pyrrolo[2,3-b]pyrazin (4.29 g).

APCI-MS m/z: 280/282 [M+H]⁺.

(2) To a solution of 3-chloro-7-iodo-5H-pyrrolo[2,3-b]pyrazin (2.0 g) and potassium carbonate (1.98 g) in N,N-dimethylformamide (30 mL) was added methyl (3-bromopropyl)carbamate (1.68 g) under ice-cooling, and then the mixture was stirred at room temperature for 15 hours. To the reaction solution was added water under ice-cooling, and then the mixture was extracted with ethyl acetate. The organic layer was sequentially washed with water and saturated saline, dried over sodium sulfate, and then concentrated under reduced pressure. The resulting residue was suspended in diethyl ether-n-hexane (1:1), then filtrate to give methyl [3-(3-chloro-7-iodo-5H-pyrrolo[2,3-b]pyrazin-5-yl)propyl]carbamate (2.53 g).

APCI-MS m/z: 395 [M+H]⁺.

(3) Under nitrogen atmosphere, to a solution of methyl [3-(3-chloro-7-iodo-5H-pyrrolo[2,3-b]pyrazin-5-yl)propyl]carbamate (2.52 g) in 1,4-dioxane (45 mL) were added tri-n-butyltin-1-ethoxyvinyl (3.00 g) and tetrakis(triphenylphosphine)palladium (0) (449 mg), and the mixture was stirred at 80° C. for 4 hours. After cooling the reaction solution, 6-normal hydrochloric acid (10 mL) was added thereto, and then the mixture was stirred at room temperature for 30 minutes. Under ice-cooling, 5-normal aqueous sodium hydroxide solution (12 mL) and aqueous saturated sodium hydrogen carbonate solution were added thereto, and the mixture was extracted with ethyl acetate. To the organic layer was added 20% potassium fluoride aqueous solution (100 mL), and the mixture was stirred at room temperature for 15 hours. An insoluble was filtrated through Celite, the organic layer was washed with saturated saline, dried over sodium sulfate, and then concentrated under reduced pressure. The resulting residue was purified by silica gel column chromatography (eluent: n-hexane/ethyl acetate=10/1→1/3) to give [3-(7-acetyl-3-chloro-5H-pyrrolo[2,3-b]pyrazin-5-yl)propyl]carbamic acid methyl ester (1.35 g).

APCI-MS m/z: 311/313 [M+H]⁺.

(4) Under nitrogen atmosphere, to a solution of [3-(7-acetyl-3-chloro-5H-pyrrolo[2,3-b]pyrazin-5-yl)propyl]carbamic acid methyl ester (400 mg) in 1,4-dioxane (8.0 mL) were added trimethylboroxine (361 μL), charcoalacidcesium (1.26 g), 2-dicyclohexylphosphino-2',4',6'-triisopropyl-1,1'-biphenyl (X-Phos) (123 mg) and tris(dibenzylideneacetone)dipalladium (59 mg), and the mixture was stirred at 80° C. for 5 hours. After cooling the reaction solution, water was added thereto, and the mixture was extracted with ethyl acetate. The organic layer was washed with saturated saline, dried over sodium sulfate, and then concentrated under reduced pressure. The resulting residue was purified by silica gel column chromatography (eluent: n-hexane/ethyl acetate=10/1→ethyl acetate) to give methyl [3-(7-acetyl-3-methyl-5H-pyrrolo[2,3-b]pyrazin-5-yl)propyl]carbamate (182 mg).

APCI-MS m/z: 291 [M+H]⁺.

Reference Example 126

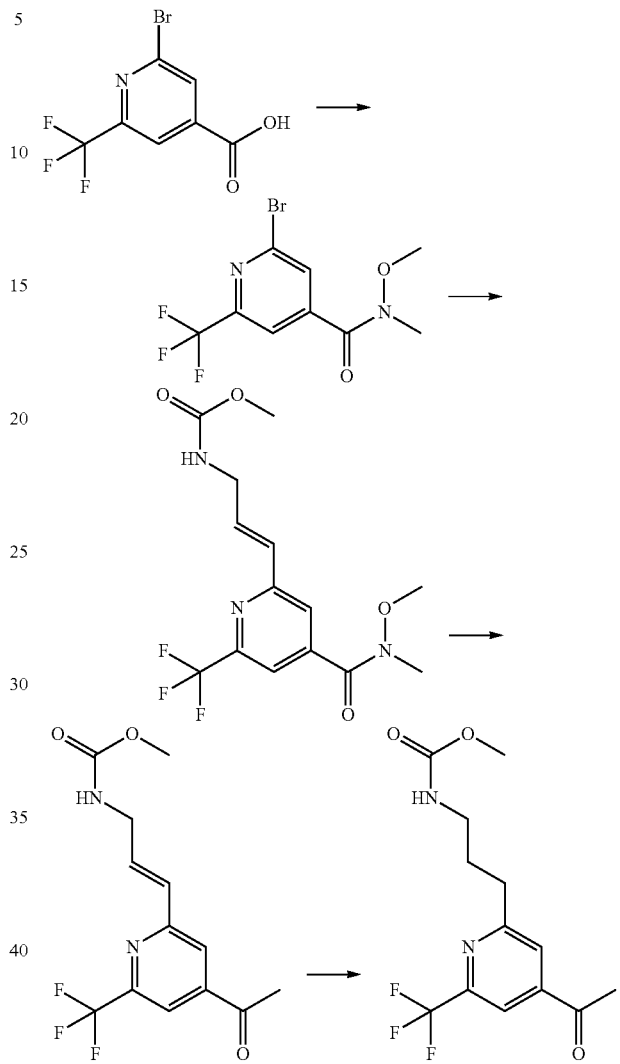

(1) To a solution of 2-bromo-6-(trifluoromethyl)pyridin-4-carboxylic acid (5.91 g) in chloroform (70 mL) were added N,O-dimethylhydroxylamine hydrochloride (2.78 g), 1-ethyl-3-(3-dimethylaminopropyl)carbodiimide hydrochloride (6.30 g) and diisopropylethylamine (7.63 mL) at room temperature, and the mixture was stirred under nitrogen stream, at room temperature for 2 hours. The reaction solution was diluted with chloroform, and washed with aqueous saturated sodium hydrogen carbonate solution, water and saturated saline, then dried over anhydrous magnesium sulfate, and the solvent was distilled under reduced pressure. The resulting residue was purified by silica gel column chromatography (eluent: N-hexane/ethyl acetate=85/15→60/40) to give 2-bromo-N-methoxy-N-methyl-6-(trifluoromethyl)pyridin-4-carboxamide (5.59 g).

APCI-MS m/z: 313/315 [M+H]⁺.

(2) To a solution of 2-bromo-N-methoxy-N-methyl-6-(trifluoromethyl)pyridin-4-carboxamide (3.14 g) in 1,2-dimethoxyethane (58 mL) were added methyl [(2E)-3-(4,4,5,5-tetramethyl-1,3,2-dioxaborolan-2-yl)prop-2-en-1-yl]

carbamate (3.13 g), 2-normal potassium carbonate aqueous solution (12.5 mL), tetrakis(triphenylphosphine) palladium (0) (578 mg) at room temperature, and the mixture was heated to reflux under nitrogen stream for 3 hours. The reaction solution was cooled to room temperature, and then diluted with an excess of ethyl acetate, washed with saturated saline, dried over anhydrous magnesium sulfate, and then the solvent was distilled under reduced pressure. The resulting residue was purified by silica gel column chromatography (eluent: N-hexane/ethyl acetate=50/50→28/72) to give methyl [(2E)-3-{4-[methoxy(methyl)carbamoyl]-6-(trifluoromethyl)pyridin-2-yl}prop-2-en-1-yl]carbamate (3.23 g).
APCI-MS m/z: 348 [M+H]+.

(3) To a solution of methyl [(2E)-3-{4-[methoxy(methyl)carbamoyl]-6-(trifluoromethyl)pyridin-2-yl}prop-2-en-1-yl]carbamate (3.16 g) in tetrahydrofuran solution (85 mL), under nitrogen stream, at −70° C., 3.0-normal methylmagnesium bromide-ether solution (15.2 mL) was added dropwise. Then, and the mixture was stirred for 1 hour under ice-cooling with rising temperature. To the reaction solution was added 1-normal hydrochloric acid solution to adjust pH of the mixture to about 3 to 4, and the mixture was extracted with ethyl acetate. The organic layer was washed with aqueous saturated sodium hydrogen carbonate solution and saturated saline, and then dried over anhydrous magnesium sulfate, and the solvent was distilled under reduced pressure. The resulting residue was purified by silica gel column chromatography (eluent: N-hexane/ethyl acetate=62/38→41/59) to give methyl {(2E)-3-[4-acetyl-6-(trifluoromethyl)pyridin-2-yl]prop-2-en-1-yl}carbamate (2.18 g).
APCI-MS m/z: 303 [M+H]+.

(4) To a solution of methyl {(2E)-3-[4-acetyl-6-(trifluoromethyl)pyridin-2-yl]prop-2-en-1-yl}carbamate (2.17 g) in ethyl acetate (400 mL) was added 10% palladium on carbon (540 mg) at room temperature, and the mixture was stirred vigorously at room temperature for 30 minutes under hydrogen stream. An insoluble was filtrated, and the solvent was distilled under reduced pressure. The resulting residue was purified by silica gel column chromatography (eluent: N-hexane/ethyl acetate=70/30→49/51) to give {3-[4-acetyl-6-(trifluoromethyl)pyridin-2-yl]propyl}carbamic acid methyl ester (1.83 g).
APCI-MS m/z: 305 [M+H]+.

Reference Example 127

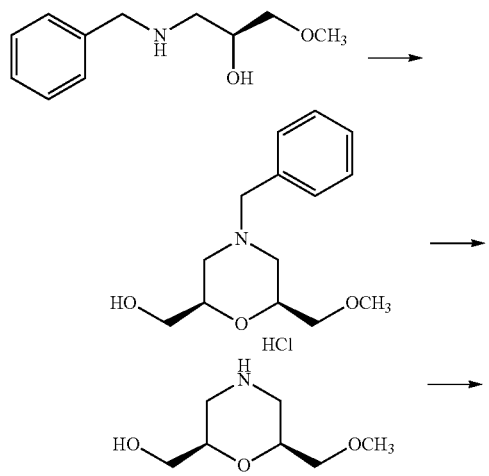

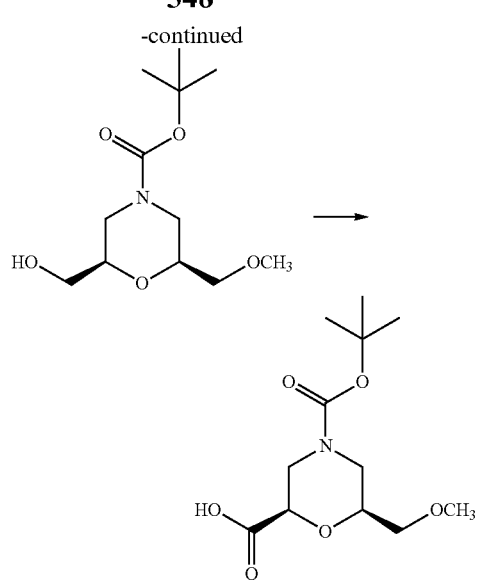

(1) To a solution of (2S)-1-(benzylamino)-3-methoxypropan-2-ol (44.5 g) in toluene (1100 mL) was added (S)-(+)-epichlorohydrin (23.1 mL) and lithium perchlorate (31.5 g) under argon, and the mixture was stirred at 50° C. for 2.5 hours. After the reaction solution was return to the room temperature, 28% sodium methoxide solution in methanol (220 mL) was added dropwise, and the mixture was stirred at 50° C. for 2 hours. The reaction solution was cooled, and poured into ammonium chloride aqueous solution (800 mL), and the mixture was extracted with ethyl acetate. The organic layer was sequentially washed with water and saline, dried over sodium sulfate, and then concentrated under reduced pressure. The resulting residue was purified by silica gel column chromatography (eluent: n-hexane/ethyl acetate=3/1→ethyl acetate group, further ethyl acetate/methanol=20/1) to give [(2R,6S)-4-benzyl-6-(methoxymethyl)morpholin-2-yl]methanol (44.6 g).
APCI-MS m/z: 252 [M+H]+.

(2) To a solution of [(2R,6S)-4-benzyl-6-(methoxymethyl)morpholin-2-yl]methanol (44.6 g) in methanol (880 mL) were added 20% palladium hydroxide on carbon (8.91 g) and 2-normal hydrogen chloride-methanol solution (89 mL) under hydrogen atmosphere, and the mixture was stirred for 1.5 hours. An insoluble was filtered off through Celite, and washed with methanol and ethyl acetate. The filtrate was concentrated under reduced pressure to give [(2R,6S)-6-(methoxymethyl)morpholin-2-yl]methanol hydrochloride (36.1 g).
APCI-MS m/z: 162 [M+H]+.

(3) To a solution of [(2R,6S)-6-(methoxymethyl)morpholin-2-yl]methanol hydrochloride (35.1 g) in tetrahydrofuran (400 mL)-water (400 mL) were added sodium hydrogen carbonate (74.5 g) and di-t-butyl dicarbonate (40.6 g) under ice-cooling, and the mixture was stirred at room temperature for 18 hours. Under ice-cooling, to the reaction solution was added water, and the mixture was extracted with ethyl acetate. The organic layer was washed with saline, dried over sodium sulfate, and then concentrated under reduced pressure. The resulting residue was purified by silica gel column chromatography (eluent: n-hexane/ethyl acetate=1/1→1/2) to give tert-butyl (2R,6S)-2-(hydroxymethyl)-6-(methoxymethyl)morpholine-4-carboxylate (35.4 g).
APCI-MS m/z: 262 [M+H]+.

(4) To a solution of tert-butyl (2R,6S)-2-(hydroxymethyl)-6-(methoxymethyl)morpholine-4-carboxylate (35.4 g) in dichloromethane (400 mL)-water (200 mL) were added iodobenzene diacetate (87.3 g) and 2,2,6,6-tetramethyl-piperidin 1-oxyl (4.24 g) under ice-cooling, and the mixture was stirred vigorously under ice-cooling for 6 hours. Under ice-cooling, methanol (600 mL) was added dropwise, and the mixture was stirred for 10 minutes, and concentrated under reduced pressure. It was concentrated azeotropically with toruene, and the resulting residue was suspended in isopropyl ether-n-hexane (1:1), and then filtrate to give (2R,6S)-4-(tert-butoxycarbonyl)-6-(methoxymethyl)morpholine-2-carboxylic acid (32.6 g).

ESI-MS m/z 274[M−H]−

Reference Example 128

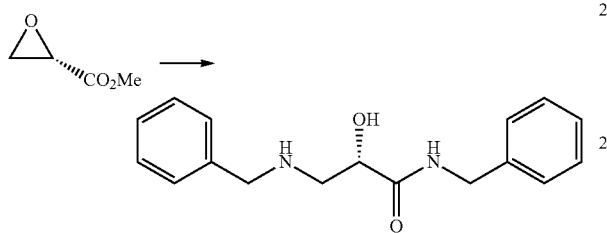

To methyl (2S)-glycidate (A) (3.0 g) was added benzylamine (22.3 mL), and the mixture was stirred for 1 hours at room temperature. Then, dichloromethane (20 mL) was added thereto, and further stirred at room temperature for two nights. The reaction solvent was distilled under reduced pressure, and the resulting residue was suspended in n-hexane, the precipitate was filtered, washed with hexane, and then dried at room temperature for under reduced pressure to give (2S)—N-benzyl-3-(benzylamino)-2-hydroxypropanamide (8.2 g).

APCI-MS m/z: 285 [M+H]+.

Reference Example 129

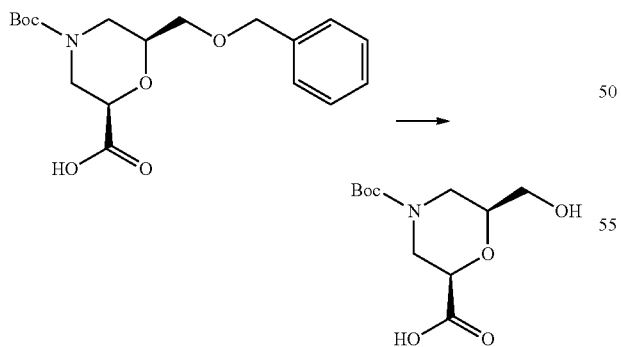

To a solution of (2R,6S)-6-[(benzyloxy)methyl]-4-(tert-butoxycarbonyl)morpholine-2-carboxylic acid (3.51 g) in ethanol (50 mL) was added 10% palladium on carbon (3.5 g) under hydrogen atmosphere, and the mixture was stirred at room temperature for 8 hours. An insoluble was filtered through Celite, and the filtrate was concentrated under reduced pressure to give (2R,6S)-4-(tert-butoxycarbonyl)-6-(hydroxymethyl)morpholine-2-carboxylic acid (2.65 g).

ESI-MS m/z: 261[M−H]−

Reference Example 130

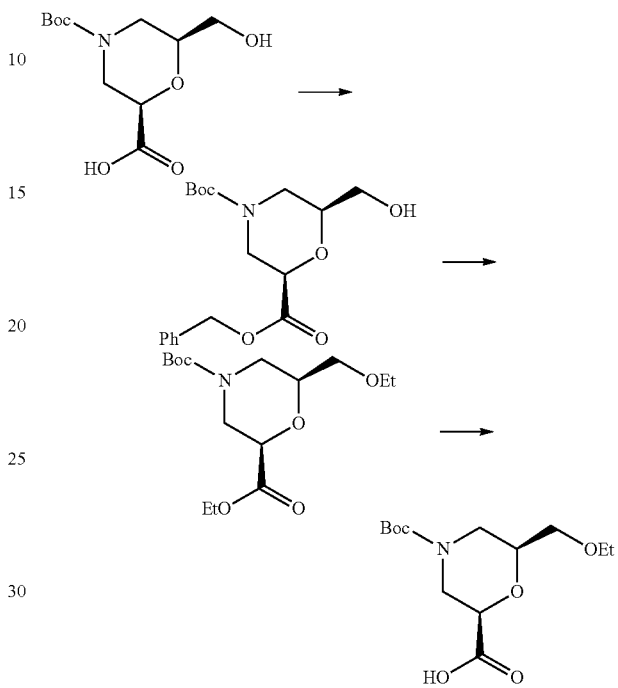

(1) To a solution of (2R,6S)-4-(tert-butoxycarbonyl)-6-(hydroxymethyl)morpholine-2-carboxylic acid (2.65 g) in N,N-dimethylformamide (15 mL) were added sodium hydrogen carbonate (1 g) and benzyl bromide (1.78 mL) at room temperature, and the mixture was stirred at room temperature for 25 hours. To the reaction solution was added saturated aqueous ammonium chloride solution, and the mixture was extracted with ethyl acetate. The organic layer was washed with water and saturated saline, dried over anhydrous sodium sulfate, and then the solvent was distilled under reduced pressure. The resulting residue was purified by silica gel column chromatography (eluent: n-hexane/ethyl acetate=75/25→50/50) to give 2-benzyl 4-tert-butyl (2R,6S)-6-(hydroxymethyl)morpholin-2,4-dicarboxylate (2.96 g).

ESI-MS m/z: 352 [M+H]+.

(2) To a solution of 2-benzyl 4-tert-butyl (2R,6S)-6-(hydroxymethyl)morpholin-2,4-dicarboxylate (1 g) in dimethylsulfoxide (2.7 mL) were added ethyl iodide (2.19 mL) and silver oxide (3.16 g) at room temperature, and the mixture was stirred under nitrogen stream, at room temperature for 24 hours. The reaction solution was diluted with ethyl acetate, and then activated carbon was added. An insoluble was filtrated, and the filtrate was washed with water and saturated saline, dried over anhydrous sodium sulfate, and then the solvent was distilled under reduced pressure. The resulting residue was purified by silica gel column chromatography (eluent: n-hexane/ethyl acetate=90/10→70/30) to give 4-tert-butyl 2-ethyl (2R,6S)-6-(ethoxymethyl)morpholin-2,4-dicarboxylate (658 mg).

ESI-MS m/z: 318 [M+H]+.

(3) To a solution of 4-tert-butyl 2-ethyl (2R,6S)-6-(ethoxymethyl)morpholin-2,4-dicarboxylate (655 mg) in methanol (8.3 mL) was added 1-normal aqueous sodium hydroxide solution (8.3 mL), and the mixture was stirred at room temperature for 1 hour. To the reaction solution was added saturated aqueous ammonium chloride solution, and then, and the mixture was extracted with ethyl acetate. The organic layer was dried over anhydrous sodium sulfate, and the solvent was distilled under reduced pressure. The resulting residue was purified by silica gel column chromatography (eluent: chloroform→chloroform/methanol/acetic acid=95/5/0.25) to give (2R,6S)-4-(tert-butoxycarbonyl)-6-(ethoxymethyl)morpholine-2-carboxylic acid (466 mg).

ESI-MS m/z: 288[M−H]⁻

Reference Example 131

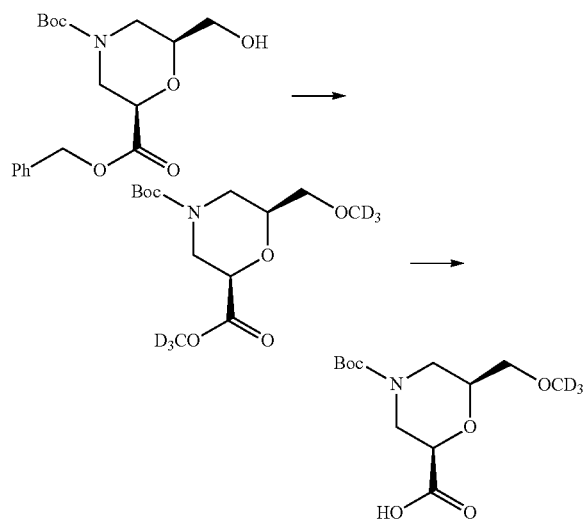

(1) 4-tert-Butyl 2-ethyl (2R,6S)-6-(hydroxymethyl)morpholin-2,4-dicarboxylate (1.0 g) was treated according to the procedure for the synthesis of 4-tert-butyl 2-ethyl (2R,6S)-6-(ethoxymethyl)morpholine-2,4-dicarboxylate, but using methyl-d₃ instead of ethyl iodide to give 4-tert-butyl 2-(methyl-d₃) (2R,6S)-6-{[(methyl-d₃)methyloxy]methyl}morpholine-2,4-dicarboxylate (393 mg).

APCI-MS m/z: 296 [M+H]⁺.

(2) 4-tert-Butyl 2-(methyl-d₃) (2R,6S)-6-{[(methyl-d₃)methyloxy]methyl}morpholine-2,4-dicarboxylate (390 mg) was treated in analogous with the synthetic processes in Reference Example 130-(3) to give (2R,6S)-4-(tert-butoxycarbonyl)-6-{[(methyl-d₃)methyloxy]methyl}morpholine-2-carboxylic acid (371 mg).

APCI-MS m/z: 277 [M+H]⁺.

Reference Example 132

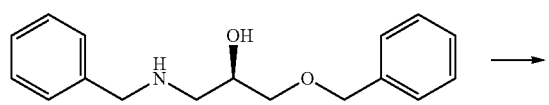

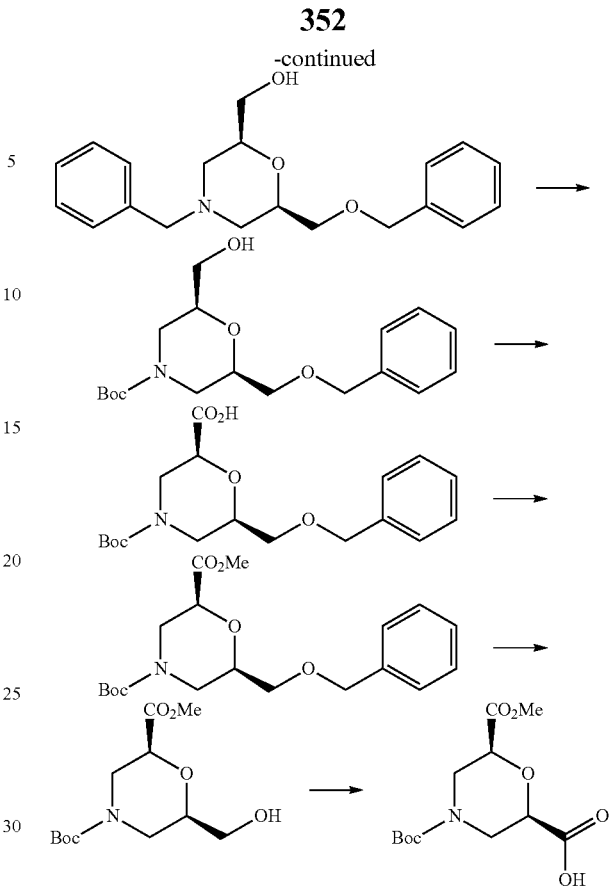

(1) Starting with (2R)-1-(benzylamino)-3-(benzyloxy)propan-2-ol (6.09 g) and (R)-(−)-epichlorohydrin and the process similar to Reference Example 127-(1) was used to give {(2S,6R)-4-benzyl-6-[(benzyloxy)methyl]morpholin-2-yl}methanol (3.92 g).

APCI-MS m/z: 328 [M+H]⁺.

(2) {(2S,6R)-4-Benzyl-6-[(benzyloxy)methyl]morpholin-2-yl}methanol (3.59 g) was treated in analogous with Reference Example 127-(2) (3) to give tert-butyl (2R,6S)-2-[(benzyloxy)methyl]-6-(hydroxymethyl)morpholine-4-carboxylate (2.47 g).

APCI-MS m/z: 338 [M+H]⁺.

(3) tert-Butyl (2R,6S)-2-[(benzyloxy)methyl]-6-(hydroxymethyl)morpholine-4-carboxylate (2.46 g) was treated in analogous with Reference Example 127-(4) to give (2S,6R)-6-[(benzyloxy)methyl]-4-(tert-butoxycarbonyl)morpholine-2-carboxylic acid (2.14 g).

APCI-MS m/z: 369 [M+NH₄]⁺.

(4) To a solution of (2S,6R)-6-[(benzyloxy)methyl]-4-(tert-butoxycarbonyl)morpholine-2-carboxylic acid (2.13 g) in N,N-dimethylformamide (35 mL) were added potassium carbonate (2.51 g) and methyl iodide (0.41 mL) at room temperature, and the mixture was stirred under nitrogen stream at room temperature for 6 hours. The reaction solution was diluted with an excess of ethyl acetate, and an insoluble was filtrated. The filtrate was washed with water and saturated saline, dried over anhydrous magnesium sulfate, and then the solvent was distilled under reduced pressure. The resulting residue was purified by silica gel column chromatography (eluent: n-hexane/ethyl acetate=75/25→40/60) to give 4-tert-butyl 2-methyl (2S,6R)-6-[(benzyloxy)methyl]morpholine-2,4-dicarboxylate (2.20 g).

APCI-MS m/z: 383 [M+NH₄]⁺.

(5) To a solution of 4-tert-butyl 2-methyl (2S,6R)-6-[(benzyloxy)methyl]morpholine-2,4-dicarboxylate (2.18 g) in methanol (200 mL) was added 7.5% palladium hydroxide on carbon (750 mg), and the mixture was stirred under hydrogen stream at room temperature for 9 hours. The reaction solution was diluted with ethyl acetate, an insoluble was filtrated, and then the solvent was distilled under reduced pressure. The resulting residue was purified by silica gel column chromatography (eluent: N-hexane/ethyl acetate=50/50→20/80) to give 4-tert-butyl 2-methyl (2S,6R)-6-(hydroxymethyl)morpholine-2,4-dicarboxylate (1.52 g).
APCI-MS m/z: 293 [M+NH$_4$]$^+$.

(6) 4-tert-Butyl-2-methyl (2S,6R)-6-(hydroxymethyl)morpholine-2,4-dicarboxylate (1.51 g) was treated in analogous with Reference Example 127-(4) to give (2S,6R)-4-(tert-butoxycarbonyl)-6-(methoxycarbonyl)morpholine-2-carboxylic acid (1.31 g).
APCI-MS m/z: 307 [M+NH$_4$]$^+$.

(2) To a solution of tert-butyl (2R,6S)-2-[(benzyloxy)methyl]-6-(dimethylcarbamoyl)morpholine-4-carboxylate (480 mg) in methanol (50 mL) was added 20% palladium hydroxide on carbon (250 mg), and the mixture was stirred vigorously under hydrogen stream at room temperature for 1 hour. An insoluble was filtrated, the filtrate was concentrated under reduced pressure, and the resulting residue was purified by silica gel column chromatography (eluent: ethyl acetate/methanol=85/15→40/60) to give (2S,6R)-2-(dimethylcarbamoyl)-6-(hydroxymethyl)morpholine-4-carboxylic acid tert-butyl (295 mg).
APCI-MS m/z: 389 [M+H]$^+$.

(3) tert-Butyl (2S,6R)-2-(dimethylcarbamoyl)-6-(hydroxymethyl)morpholine-4-carboxylate (290 mg) was treated in analogous with Reference Example 127-(4) to give (2R,6S)-4-(tert-butoxycarbonyl)-6-(dimethylcarbamoyl)morpholine-2-carboxylic acid (271 mg).
APCI-MS m/z: 303 [M+H]$^+$.

Reference Example 133

Reference Example 134

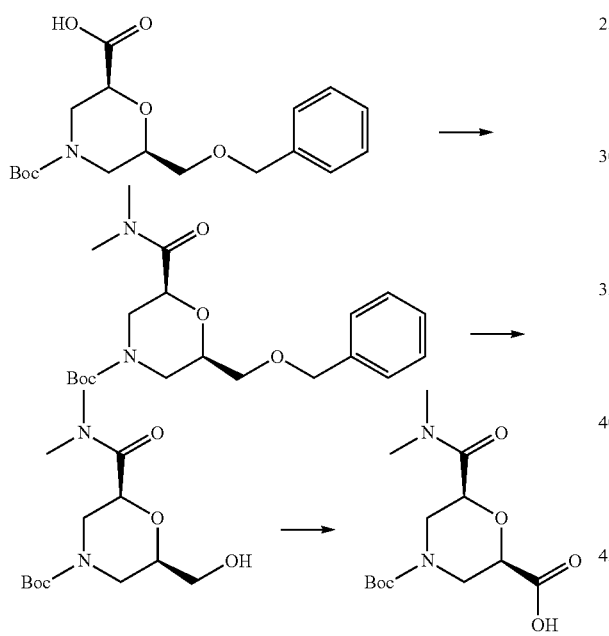

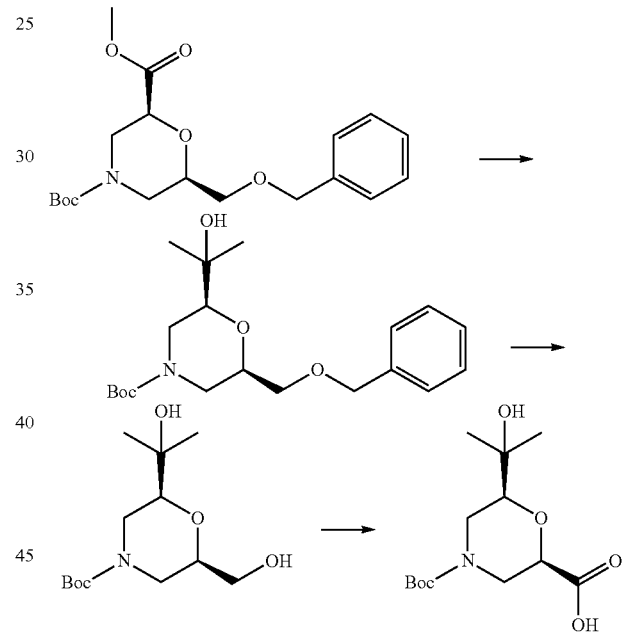

(1) To a solution of (2S,6R)-6-[(benzyloxy)methyl]-4-(tert-butoxycarbonyl)morpholine-2-carboxylic acid (880 mg) in N,N-dimethylformamide (20 mL) were added 1-hydroxybenzotriazole (338 mg), 1-ethyl-3-(3-dimethylaminopropyl)carbodiimide hydrochloride (720 mg), dimethylamine hydrochloride (613 mg) and triethylamine (1.4 mL) at room temperature, and the mixture was stirred under nitrogen stream at room temperature for 16 hours. The reaction solution was diluted with an excess of ethyl acetate, and washed with water, saturated sodium hydrogen carbonate solution and saturated saline, dried over anhydrous magnesium sulfate, and then the solvent was distilled under reduced pressure. The resulting residue was purified by silica gel column chromatography (eluent: n-hexane/ethyl acetate=80/20→40/60) to give tert-butyl (2R,6S)-2-[(benzyloxy)methyl]-6-(dimethylcarbamoyl)morpholine-4-carboxylate (480 mg).
APCI-MS m/z: 379 [M+H]$^+$.

(1) A solution of 4-tert-butyl 2-methyl (2S,6R)-6-[(benzyloxy)methyl]morpholine-2,4-dicarboxylate (450 mg) in tetrahydrofuran (5 mL) was cooled to −10° C., and under nitrogen stream, 3-normal methylmagnesium bromide-diethyl ether solution (1.65 mL) was added dropwise, and the mixture was stirred under ice-cooling for 1 hour. To the reaction solution, saturated aqueous ammonium chloride solution was added thereto, and then the mixture was extracted with ethyl acetate. The organic layer was dried over anhydrous sodium sulfate, and then the solvent was distilled under reduced pressure. The resulting residue was purified by silica gel column chromatography (eluent: chloroform/methanol/acetic acid=90/10→50/50) to give tert-butyl (2R,6S)-2-[(benzyloxy)methyl]-6-(2-hydroxypropan-2-yl)morpholine-4-carboxylate (0.52 g).
ESI-MS m/z: 366 [M+H]$^+$.

(2) tert-Butyl (2R,6S)-2-[(benzyloxy)methyl]-6-(2-hydroxypropan-2-yl)morpholine-4-carboxylate (0.52 g) was treated in analogous with Reference Example 133-(2) to give tert-butyl (2R,6S)-2-(hydroxymethyl)-6-(2-hydroxypropan-2-yl)morpholine-4-carboxylate (0.50 g).
ESI-MS m/z: 276 [M+H]+.

(3) To a solution of (2R,6S)-2-(hydroxymethyl)-6-(2-hydroxypropan-2-yl)morpholine-4-carboxylic acid tert-butyl (0.50 g) in dichloromethane (14 mL)-water (7 mL) were added iodobenzene diacetate (1.37 g) and 2,2,6,6-tetramethylpiperidine 1-oxyl (70 mg) under ice-cooling, and the mixture was stirred vigorously under ice-cooling for 10 hours. To the reaction solution was added dropwise methanol (14 mL) under ice-cooling, and then the reaction solution was concentrated under reduced pressure. The resulting residue was concentrated azeotropically with ethanol, the resulting residue was dissolved in diethyl ether, and extracted with 0.2-normal aqueous sodium hydroxide solution. The aqueous layer was adjusted to pH 3 with 10% potassium hydrogen sulfate aqueous solution, and it was extructed with a solvent mixture of chloroform-methanol (10:1). The organic layer was washed with saturated saline, and then dried over anhydrous magnesium sulfate, and the solvent was distilled under reduced pressure to give (2R,6S)-4-(tert-butoxycarbonyl)-6-(2-hydroxypropan-2-yl)morpholine-2-carboxylic acid (0.16 g).
ESI-MS m/z: 288[M−H]−

Reference Example 135

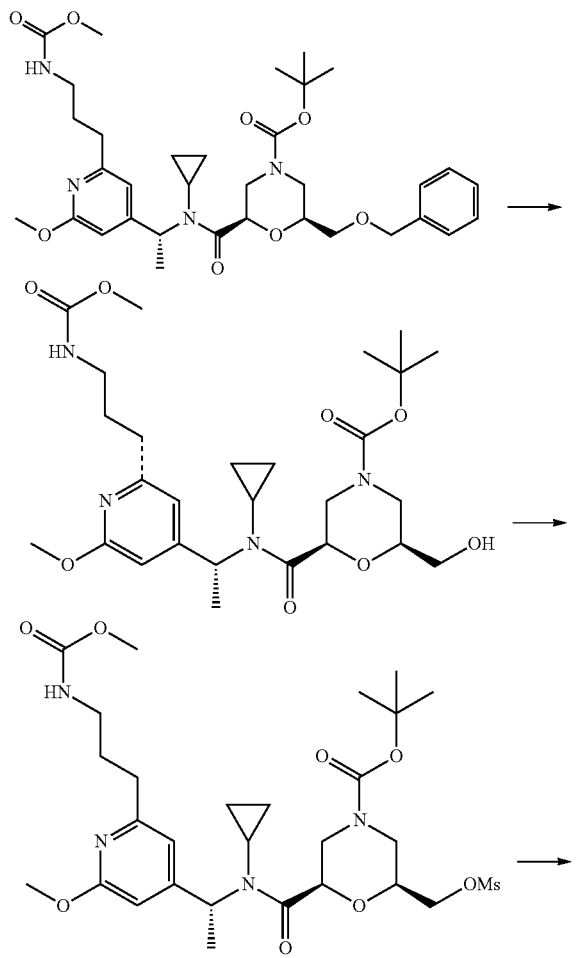

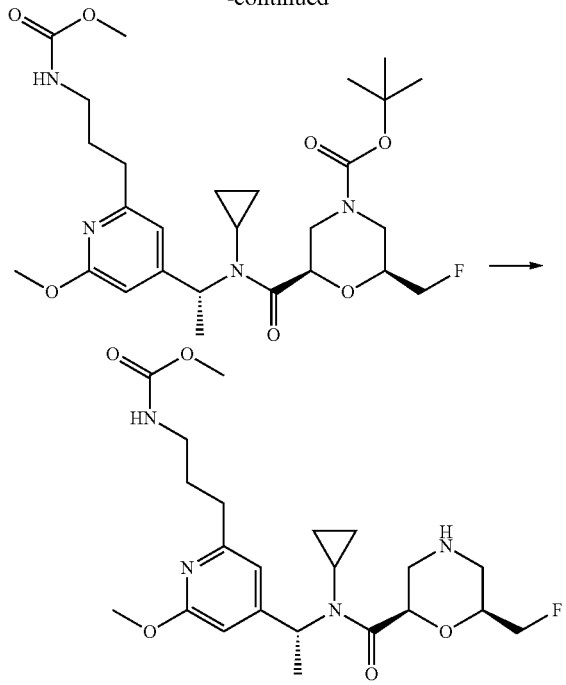

(1) To a solution of tert-butyl (2S,6R)-2-[(benzyloxy)methyl]-6-{cyclopropyl[(1R)-1-(2-methoxy-6-{3-[(methoxycarbonyl)amino]propyl}pyridin-4-yl)ethyl]carbamoyl}morpholine-4-carboxylate (1.12 g) in ethanol (9 mL) was added 7.5% palladium on carbon (500 mg) at room temperature, and the mixture was stirred vigorously under hydrogen stream at room temperature for 30 hours. An insoluble was filtrated, and the solvent was distilled. The resulting residue was purified by silica gel column chromatography (eluent: chloroform/methanol=100/0→97/3) to give tert-butyl (2R,6S)-2-{cyclopropyl[(1R)-1-(2-methoxy-6-{3-[(methoxycarbonyl)amino]propyl}pyridin-4-yl)ethyl]carbamoyl}-6-(hydroxymethyl)morpholine-4-carboxylate (847 mg).
ESI-MS m/z: 551 [M+H]+.

(2) To a solution of tert-butyl (2R,6S)-2-{cyclopropyl[(1R)-1-(2-methoxy-6-{3-[(methoxycarbonyl)amino]propyl}pyridin-4-yl)ethyl]carbamoyl}-6-(hydroxymethyl)morpholine-4-carboxylate (300 mg) in toluene (1.1 mL)-dichloromethane (1.1 mL) were added triethylamine (150 µL) and trimethylamine hydrochloride (5 mg) to dissolve the material, and methanesulfonyl chloride (63 µL) was added thereto under nitrogen stream and under ice-cooling, and then the mixture was stirred for 2 hours. To the reaction solution was added 10% potassium hydrogen sulfate aqueous solution, and the mixture was extracted with ethyl acetate. The organic layer was dried over anhydrous sodium sulfate, and the solvent was distilled under reduced pressure to give tert-butyl (2R,6S)-2-{cyclopropyl[(1R)-1-(2-methoxy-6-{3-[(methoxycarbonyl)amino]propyl}pyridin-4-yl)ethyl]carbamoyl}-6-{[(methylsulfonyl)oxy]methyl}morpholine-4-carboxylate (385 mg).
ESI-MS m/z: 629 [M+H]+.

(3) tert-Butyl (2R,6S)-2-{cyclopropyl[(1R)-1-(2-methoxy-6-{3-[(methoxycarbonyl)amino]propyl}pyridin-4-yl)ethyl]carbamoyl}-6-{[(methylsulfonyl)oxy]methyl}morpholine-4-carboxylate (100 mg) was dissolved in 1-normal tributylammonium fluoride-tetrahydrofuran solution (8 mL), and the mixture was stirred with heating at 60° C. for 5 hours, and further at 80° C. for 1.5 hours. To the reaction solution were added ethyl acetate and 10% potassium hydrogen sulfate aqueous solution, and the mixture was extracted with ethyl acetate. The organic layer was washed with saturated saline, dried over anhydrous sodium sulfate, and then the solvent was distilled under reduced pressure. The resulting residue was purified by silica gel column chromatography (eluent: n-hexane/ethyl acetate=70/30→50/50) and then further by Waters, PolaPak™ Rxn CX (strong cation exchange packing material) cartridge (purification solvent: water-→methanol, eluent: 1-normal ammonia-methanol) to give tert-butyl (2R,6S)-2-{cyclopropyl[(1R)-1-(2-methoxy-6-{(3-[(methoxycarbonyl)amino]propyl}pyridin-4-yl)ethyl]carbamoyl}-6-(fluoromethyl)morpholine-4-carboxylate (31 mg).
ESI-MS m/z: 553 [M+H]$^+$.

(4) To a solution of tert-butyl (2R,6S)-2-{cyclopropyl[(1R)-1-(2-methoxy-6-(3-[(methoxycarbonyl)amino]propyl}pyridin-4-yl)ethyl]carbamoyl)-6-(fluoromethyl)morpholine-4-carboxylate (30 mg) in dichloromethane (2 mL) was added trifluoroacetic acid (1 mL) at room temperature, and the mixture was stirred at room temperature for 1 hour. To the reaction solution was added aqueous saturated sodium hydrogen carbonate solution, and the mixture was extracted with chloroform. The organic layer was washed with saturated saline, and then dried over anhydrous sodium sulfate, and the solvent was distilled under reduced pressure to give methyl (3-{4-[(1R)-1-(cyclopropyl{[(2R,6S)-6-(fluoromethyl)morpholin-2-yl]carbonyl}amino)ethyl]-6-methoxypyridin-2-yl}propyl)carbamate (25 mg).
ESI-MS m/z: 453 [M+H]$^+$.

Reference Example 136

To a solution of tert-butyl (2R,6S)-2-{cyclopropyl[(1R)-1-(2-methoxy-6-{3-[(methoxycarbonyl)amino]propyl}pyridin-4-yl)ethyl]carbamoyl}-6-{([(methylsulfonyl)oxy]methyl}morpholine-4-carboxylate (129 mg) in dimethylsulfoxide (2 mL) was added sodium cyanide (22 mg) at room temperature, and the mixture was stirred under nitrogen stream at 50° C. for 22 hours and further at 70° C. for 4 hours. The reaction solution was poured into saturated sodium hydrogen carbonate solution, and the mixture was extracted with ethyl acetate. The organic layer was washed with saturated saline, and then dried over anhydrous sodium sulfate, and then the solvent was distilled under reduced pressure. The resulting residue was purified by silica gel column chromatography (eluent: n-hexane/ethyl acetate=50/50→33/67) to give (2R,6R)-2-(cyanomethyl)-6-{cyclopropyl[(1R)-1-(2-methoxy-6-{3-[(methoxycarbonyl)amino]propyl}pyridin-4-yl)ethyl]carbamoyl}morpholine-4-carboxylic acid tert-butyl (62 mg).
APCI-MS m/z: 560 [M+H]$^+$.

Reference Example 137

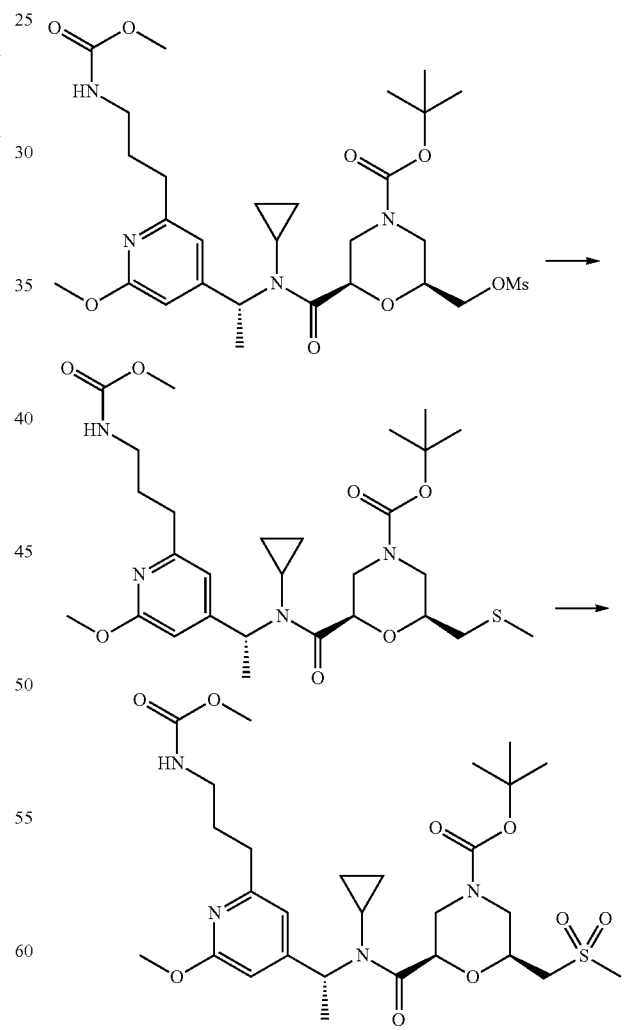

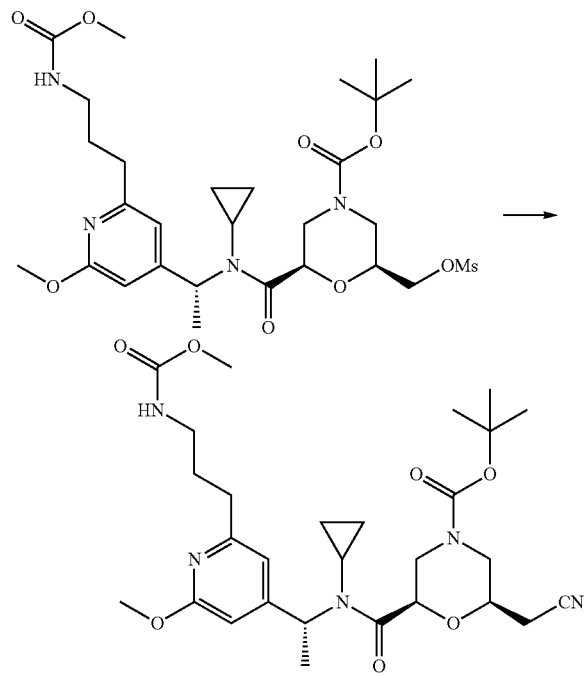

(1) To a solution of tert-butyl (2R,6S)-2-{cyclopropyl[(1R)-1-(2-methoxy-6-{3-[(methoxycarbonyl)amino]propyl}pyridin-4-yl)ethyl]carbamoyl}-6-{[(methylsulfonyl)oxy]methyl}morpholine-4-carboxylate (100 mg) in N,N-dimethylformamide (1 mL) was added sodium thiomethoxide (20 mg) at room temperature, and the mixture was stirred at room temperature for 16 hours. To the reaction solution was added an additional sodium thiomethoxide (10 mg), and the mixture was stirred further at room temperature for 30 minutes. To the reaction solution was added water, and the mixture was extracted with ethyl acetate. The organic layer was washed with aqueous saturated sodium hydrogen carbonate solution and saturated saline, and then dried over anhydrous sodium sulfate, and then the solvent was distilled under reduced pressure. The resulting residue was purified by silica gel column chromatography (eluent: n-hexane/ethyl acetate=70/30→50/50) to give tert-butyl (2R,6S)-2-{cyclopropyl[(1R)-1-(2-methoxy-6-{3-[(methoxycarbonyl)amino]propyl}pyridin-4-yl)ethyl]carbamoyl}-6-[(methylsulfonyl)methyl]morpholine-4-carboxylate (99 mg).
ESI-MS m/z: 581 [M+H]$^+$.

(2) To a solution of (2R,6S)-2-{cyclopropyl[(1R)-1-(2-methoxy-6-{3-[(methoxycarbonyl)amino]propyl}pyridin-4-yl)ethyl]carbamoyl}-6-[(methylsulfanyl)methyl]morpholine-4-carboxylic acid tert-butyl (99 mg) in dichloromethane (1.4 mL) was added m-chloroperbenzoic acid (>65%, 115 mg) under ice-cooling, and the mixture was stirred for 30 minutes. To the reaction solution was added aqueous saturated sodium hydrogen carbonate solution, and the mixture was extracted with chloroform. The organic layer was washed with saturated saline, dried over anhydrous sodium sulfate, and then the solvent was distilled under reduced pressure. The resulting residue was purified by NH-silica gel column chromatography (eluent: n-hexane/ethyl acetate=50/50→25/75) to give tert-butyl (2R,6S)-2-{cyclopropyl[(1R)-1-(2-methoxy-6-{3-[(methoxycarbonyl)amino]propyl}pyridin-4-yl)ethyl]carbamoyl}-6-[(methylsulfonyl)methyl]morpholine-4-carboxylate (62 mg).
ESI-MS m/z: 613 [M+H]$^+$.

Reference Example 138

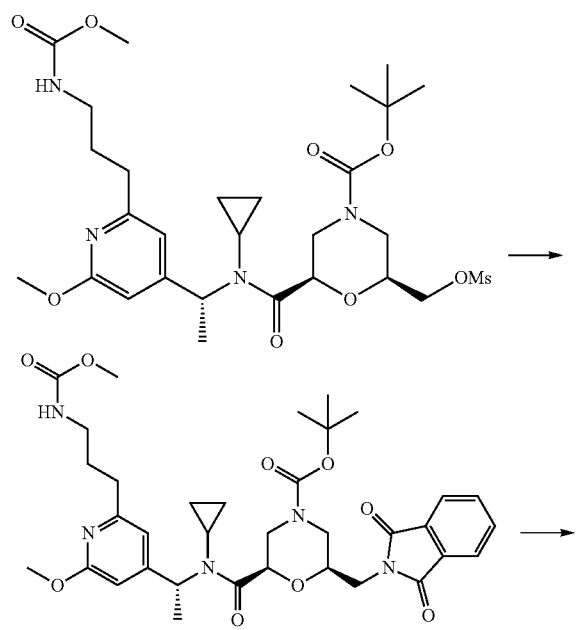

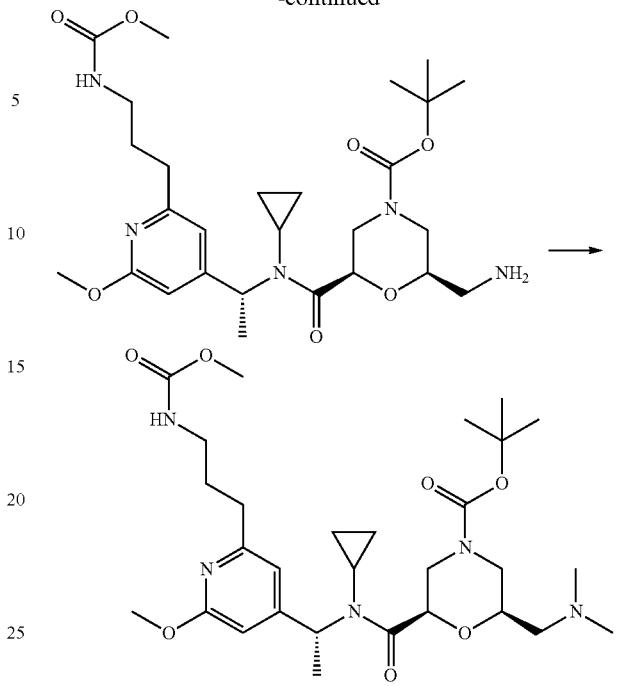

(1) To a solution of tert-butyl (2R,6S)-2-{cyclopropyl[(1R)-1-(2-methoxy-6-{3-[(methoxycarbonyl)amino]propyl}pyridin-4-yl)ethyl]carbamoyl}-6-{[(methylsulfonyl)oxy]methyl}morpholine-4-carboxylate (194 mg) in N,N-dimethylformamide (1.54 mL) was added phthalimide potassium (171 mg) at room temperature, and the mixture was stirred under nitrogen stream at 70° C. for 19 hours. To the reaction solution was added water, and the mixture was extracted with ethyl acetate. The organic layer was washed with saturated saline, and then dried over anhydrous sodium sulfate, the solvent was distilled under reduced pressure. The resulting residue was purified by NH-silica gel column chromatography (eluent: n-hexane/ethyl acetate=50/50→40/60→chloroform/methanol=95/5) to give tert-butyl (2R,6R)-2-{cyclopropyl[(1R)-1-(2-methoxy-6-{3-[(methoxycarbonyl)amino]propyl}pyridin-4-yl)ethyl]carbamoyl}-6-[(1,3-dioxo-1,3-dihydro-2H-isoindol-2-yl)methyl]morpholine-4-carboxylate (92 mg).
ESI-MS m/z: 680 [M+H]$^+$.

(2) tert-Butyl (2R,6R)-2-{cyclopropyl[(1R)-1-(2-methoxy-6-{3-[(methoxycarbonyl)amino]propyl}pyridin-4-yl)ethyl]carbamoyl}-6-[(1,3-dioxo-1,3-dihydro-2H-isoindol-2-yl)methyl]morpholine-4-carboxylate (90 mg) was mixed with ethanolamine (3 mL), and the mixture was stirred at room temperature for 16 hours. To the reaction solution was added water, and the mixture was extracted with ethyl acetate. The organic layer was washed with saturated saline, dried over anhydrous sodium sulfate, and then the solvent was distilled under reduced pressure. The resulting residue was purified by NH-silica gel column chromatography (eluent: chloroform/methanol=100/0→95/5) to give tert-butyl (2R,6R)-2-(aminomethyl)-6-{cyclopropyl[(1R)-1-(2-methoxy-6-{3-[(methoxycarbonyl)amino]propyl}pyridin-4-yl)ethyl]carbamoyl}morpholine-4-carboxylate (67 mg).
ESI-MS m/z: 550 [M+H]$^+$.

(3) To a solution of tert-butyl (2R,6R)-2-(aminomethyl)-6-{cyclopropyl[(1R)-1-(2-methoxy-6-{3-[(methoxycarbonyl)amino]propyl}pyridin-4-yl)ethyl]carbamoyl}morpholine-4-carboxylate (21 mg) in methanol (3 mL) was added 37% folmaldehyde aqueous solution (31 mg) at room temperature, and the mixture was stirred at room temperature for 3 hours. Then, to the reaction solution, 10% palladium on carbon (26 mg) was added thereto, and the mixture was stirred vigorously under hydrogen stream at room temperature for 1.5 hours. An insoluble was filtered through Celite, and then the solvent was distilled under reduced pressure. The resulting residue was purified by NH-silica gel column chromatography (eluent: chloroform) to give tert-butyl (2R,6R)-2-{cyclopropyl[(1R)-1-(2-methoxy-6-{3-[(methoxycarbonyl)amino]propyl}pyridin-4-yl)ethyl]carbamoyl}-6-[(dimethylamino)methyl]morpholine-4-carboxylate (21 mg).

ESI-MS m/z: 578 [M+H]⁺.

Reference Example 139

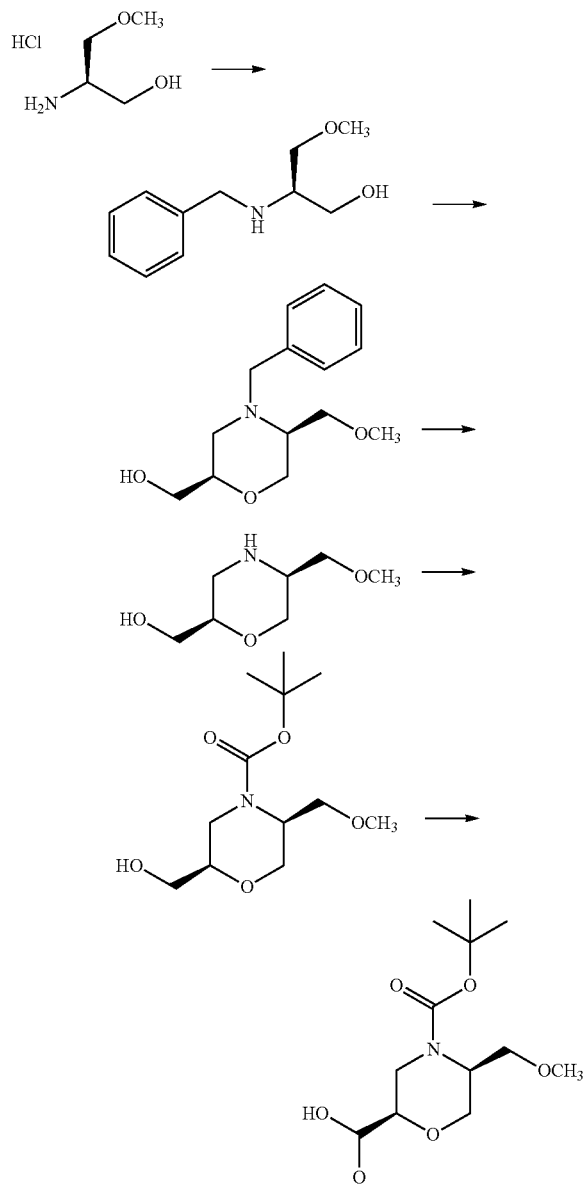

(1) To a solution of (2R)-2-amino-3-methoxypropan-1-ol hydrochloride (13.4 g) in methanol (260 mL) were added dropwise diisopropylethylamine (19.8 mL) and benzaldehyde (9.60 mL) under ice-cooling, and the mixture was stirred at room temperature for 4 hours. Under ice-cooling, sodium borohydride (3.57 g) was added thereto in small-portions, and the mixture was stirred at room temperature for 1 hour. To the reaction solution was added water under ice-cooling, and the mixture was extracted with ethyl acetate. The organic layer was washed sequentially with aqueous saturated sodium hydrogen carbonate solution and saline, dried over sodium sulfate, and then concentrated under reduced pressure. The resulting residue was purified by silica gel column chromatography (eluent: n-hexane/ethyl acetate=1/1→ethyl acetate group, further ethyl acetate/methanol=9/1) to give (2R)-2-(benzylamino)-3-methoxypropan-1-ol (12.0 g).

APCI-MS m/z: 196 [M+H]⁺.

(2) To a solution of (2R)-2-(benzylamino)-3-methoxypropan-1-ol (14.2 g) in toluene (420 mL) was added (S)-(+)-epichlorohydrin (7.4 mL) and lithium perchlorate (10.1 g), and the mixture was stirred under argon atmosphere at 50° C. for 3.5 hours. After the reaction solution was return to the room temperature, 28% sodium methoxide solution in methanol (35.2 g) which was diluted with methanol (86 mL), was added dropwise thereto, and the mixture was stirred at 50° C. for 2 hours. The reaction solution was cooled, and it was poured into ammonium chloride aqueous solution (500 mL), and the mixture was extracted with ethyl acetate. The organic layer was sequentially washed with water and saline, dried over sodium sulfate, and then concentrated under reduced pressure. The resulting residue was purified by silica gel column chromatography (eluent: n-hexane/ethyl acetate=4/1→1/1) to give [(2R,5S)-4-benzyl-5-(methoxymethyl)morpholin-2-yl]methanol (9.40 g).

APCI-MS m/z: 252 [M+H]⁺.

(3) To a solution of [(2R,5S)-4-benzyl-5-(methoxymethyl)morpholin-2-yl]methanol (9.40 g) in methanol (180 mL) was added 20% palladium hydroxide on carbon (940 mg), and the mixture was stirred under hydrogen atmosphere for 4 hours. An insoluble was filtered through Celite, washed with methanol, and the filtrate was concentrated under reduced pressure to give [(2R,5S)-5-(methoxymethyl)morpholin-2-yl]methanol (6.10 g).

APCI-MS m/z: 162 [M+H]⁺.

(4) To a solution of [(2R,5S)-5-(methoxymethyl)morpholin-2-yl]methanol (6.03 g) in tetrahydrofuran (90 mL)-water (90 mL) were added sodium hydrogen carbonate (15.7 g) and di-t-butyl dicarbonate (8.57 g) under ice-cooling, and the mixture was stirred at room temperature for 18 hours. Under ice-cooling, to the reaction solution water was added thereto, and the mixture was extracted with ethyl acetate. The organic layer was sequentially washed with water and saline, dried over sodium sulfate, and then concentrated under reduced pressure. The resulting residue was purified by silica gel column chromatography (eluent: n-hexane/ethyl acetate=4/1→1/1) to give tert-butyl (2R,5S)-2-(hydroxymethyl)-5-(methoxymethyl)morpholine-4-carboxylate (8.45 g).

APCI-MS m/z: 262 [M+H]⁺.

(5) To a solution of tert-butyl (2R,5S)-2-(hydroxymethyl)-5-(methoxymethyl)morpholine-4-carboxylate (8.45 g) in dichloromethane (130 mL)-water (65 mL) were added iodobenzene diacetate (20.8 g) and 2,2,6,6-tetramethylpiperidine 1-oxyl (1.01 g) under ice-cooling, and the mixture was stirred vigorously under ice-cooling for 6 hours. Under ice-cooling, methanol (150 mL) was added dropwise thereto, and the mixture was stirred for 10 minutes, and then concentrated under reduced pressure. It was concentrated azeotropically with toruene, and the resulting residue was purified by silica gel column chromatography (eluent: n-hexane/ethyl acetate=1/1→ethyl acetate) to give (2R,5S)-4-(tert-butoxycarbonyl)-5-(methoxymethyl)morpholine-2-carboxylic acid (6.62 g).

ESI-MS m/z: 274[M−H]⁻

Reference Example 140

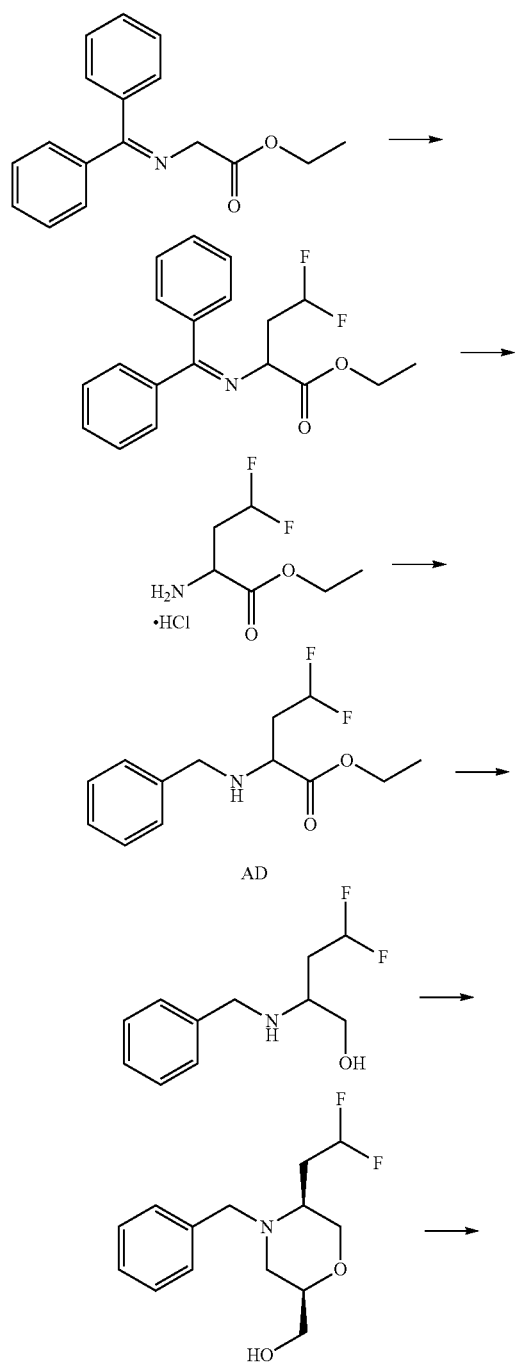

AD

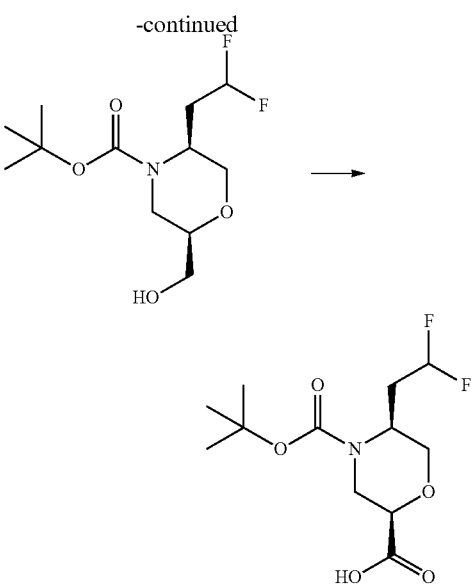

1) To N,N-dimethylformamide (30 mL) was added potassium tert-butoxide (2.36 g) under ice-cooling, and the mixture was stirred under ice-cooling for 15 minutes to dissolve the material. N-(Diphenylmethylidene)glycineethyl (5.35 g) was added thereto, and then, under ice-cooling, the mixture was further stirred for 35 minutes. Then 1-difluoro-2-iodoethane (4.87 g) was added dripwise thereto and the mixture was further stirred under ice-cooling for 3 hours and 30 minutes. The reaction solution was slowly pored into saturated aqueous ammonium chloride solution, and the mixture was extracted with ethyl acetate. The organic layer was washed with water and saturated saline, dried over anhydrous magnesium sulfate, and then the solvent was distilled under reduced pressure. The resulting residue was purified by silica gel column chromatography (eluent: N-hexane/ethyl acetate=94/6→73/26) to give ethyl 2-[(diphenylmethylidene)amino]-4,4-difluorobutanoate.

(2) The resulting ethyl 2-[(diphenylmethylidene)amino]4,4-difluorobutanoate was dissolved into ethyl acetate (120 mL), and 3-normal hydrochloric acid aqueous (21 mL) was added thereto, and then the mixture was stirred at room temperature for 21 hours. The reaction solvent was distilled off under reduced pressure, and the resulting residue was suspended in ethyl acetate, the precipitate was filtered, and then washed with ethyl acetate to give ethyl 2-amino-4,4-difluorobutanoate hydrochloride (2.72 g).

APCI-MS m/z: 168 [M+H]⁺.

(2) To a solution of ethyl 2-amino-4,4-difluorobutanoate hydrochloride (2.72 g) in dichloromethane (50 mL) were added diisopropylamine (3.48 mL), benzaldehyde (1.48 mL) and sodium triacetoxyborohydride (4.24 g), and the mixture was stirred under nitrogen stream at room temperature for 21 hours. To the reaction solution was added saturated sodium hydrogen carbonate, and the mixture was stirred at room temperature for 15 minutes, and the mixture was extracted with chloroform. The organic layer was washed with saturated saline, dried over anhydrous magnesium sulfate, and then the solvent was distilled under reduced pressure. The resulting residue was purified by silica gel column chromatography (eluent: N-hexane/ethyl acetate=100/0→94/6) to give ethyl 2-(benzylamino)-4,4-difluorobutanoate (1.44 g).

APCI-MS m/z: 258 [M+H]⁺.

(3) Lithium aluminium hydride (516 mg) was suspended in tetrahydrofuran (50 mL), and a solution of ethyl 2-(benzylamino)-4,4-difluorobutanoate (1.40 g) in tetrahydrofuran (30 mL) was added dropwise thereto over 8 minutes under nitrogen stream and under ice-cooling, and then the mixture was stirred for 40 minutes. To the reaction solution was added drop by drop water and 12-normal aqueous sodium hydroxide solution, and then an insoluble was filtrated, and the insoluble was washed with tetrahydrofuran and diethyl ether. The organic layer was washed with saturated saline, dried over anhydrous magnesium sulfate, and then the solvent was distilled under reduced pressure. The resulting residue was purified by silica gel column chromatography (eluent: N-hexane/ethyl acetate=46/54→25/75) to give 2-(benzylamino)-4,4-difluorobutane-1-ol (1.17 g).
APCI-MS m/z: 216 [M+H]+.

4) To a solution of 2-(benzylamino)-4,4-difluorobutane-1-ol (1.17 g) in toluene (30 mL) were added (S)-(+)-epichlorohydrin (587 μL) and lithium perchlorate (797 mg), and the mixture was stirred under nitrogen stream, at 50° C. for 2 hours. To the reaction solution was added methanol (2.5 mL) and 5-normal sodium methoxide-methanol solution (3.5 mL), and the mixture was stirred further at 50° C. for 2 hours. The reaction solution was poured into saturated aqueous ammonium chloride solution, and the mixture was extracted with ethyl acetate. The organic layer was washed with saturated saline, dried over anhydrous magnesium sulfate, and then the solvent was distilled under reduced pressure. The resulting residue was purified by silica gel column chromatography (eluent: N-hexane/ethyl acetate) to give [(2R,5S)-4-benzyl-5-(2,2-difluoroethyl)morpholin-2-yl]methanol (325 mg).
APCI-MS m/z: 272 [M+H]+.

5) To a solution of [(2R,5S)-4-benzyl-5-(2,2-difluoroethyl)morpholin-2-yl]methanol (320 mg) in methanol (50 mL) was added 20% palladium hydroxide on carbon (150 mg), and the mixture was stirred vigorously under hydrogen stream at room temperature for 1 hour. The reaction solution was diluted with ethyl acetate, an insoluble was filtrated, and then the solvent was distilled under reduced pressure. The resulting residue was dissolved into ethyl acetate (40 mL), water (10 mL), sodium carbonate (626 mg) and di-tert-butyl dicarbonate (309 mg) were added thereto, and the mixture was stirred vigorously at room temperature for 2 hours. The reaction solution was extrucited with ethyl acetate, and the organic layer was washed with saturated saline, and dried over anhydrous magnesium sulfate, and then the solvent was distilled under reduced pressure. The resulting residue was purified by silica gel column chromatography (eluent: N-hexane/ethyl acetate=62/38→41/59) to give tert-butyl (2R,5S)-5-(2,2-difluoroethyl)-2-(hydroxymethyl)morpholine-4-carboxylate (255 mg).
APCI-MS m/z: 282 [M+H]+.

(6) To a solution of tert-butyl (2R,5S)-5-(2,2-difluoroethyl)-2-(hydroxymethyl)morpholine-4-carboxylate (394 mg) in dichloromethane (11 mL)-water (5.5 mL) were added iodobenzene diacetate (902 mg) and 2,2,6,6-tetramethylpiperidine 1-oxyl (44 mg) under ice-cooling, and the mixture was stirred vigorously under ice-cooling for 6 hours. To the reaction solution was added dropwise methanol under ice-cooling, and then the reaction solution was concentrated under reduced pressure. The resulting residue was purified by silica gel column chromatography (eluent: chloroform/methanol=97/3→80/20) to give (2R,5S)-4-(tert-butoxycarbonyl)-5-(2,2-difluoroethyl)morpholine-2-carboxylic acid (245 mg).
APCI-MS m/z: 296 [M+H]+.

Reference Example 141

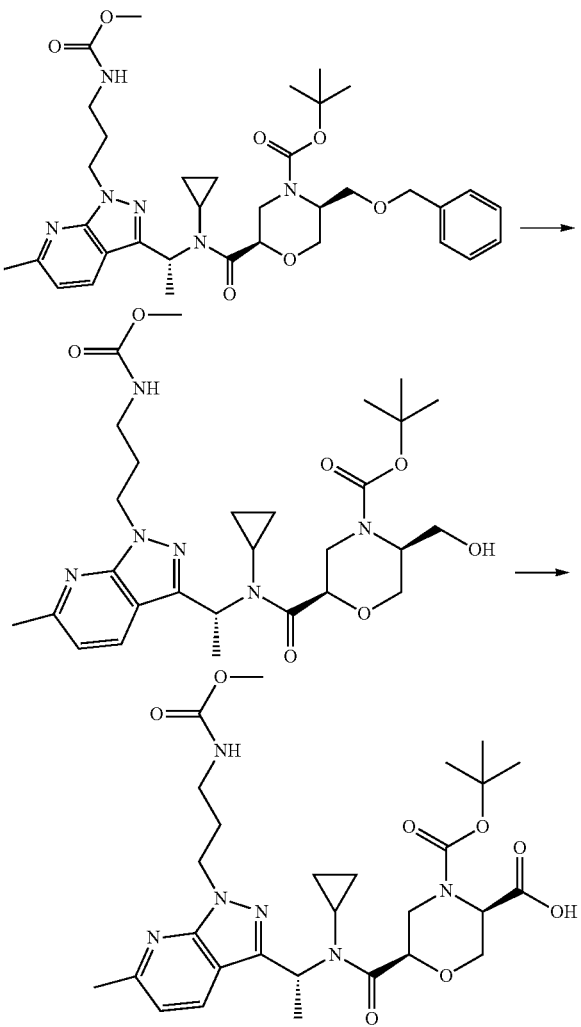

(1) To a solution of tert-butyl (2R,5S)-5-[(benzyloxy)methyl]-2-{cyclopropyl[(1R)-1-(1-{3-[(methoxycarbonyl)amino]propyl}-6-methyl-1H-pyrazolo[3,4-b]pyridin-3-yl)ethyl]carbamoyl}morpholine-4-carboxylate (1.19 g) in methanol (100 mL) was added 20% palladium hydroxide on carbon (500 mg) at room temperature, and the mixture was stirred, under hydrogen stream, at room temperature for 4 hours An insoluble was filtrated, and the solvent in filtrate was distilled. The resulting residue was purified by silica gel column chromatography (eluent: chloroform/methanol=100/0→, 95/5) to give tert-butyl (2R,5S)-2-{cyclopropyl[(1R)-1-(1-{3-[(methoxycarbonyl)amino]propyl}-6-methyl-1H-pyrazolo[3,4-b]pyridin-3-yl)ethyl]carbamoyl}-5-(hydroxymethyl)morpholine-4-carboxylate (869 mg).
APCI-MS m/z: 575 [M+H]+.

(2) To a solution of tert-butyl (2R,5S)-2-{cyclopropyl[(1R)-1-(1-{3-[(methoxycarbonyl)amino]propyl}-6-methyl-1H-pyrazolo[3,4-b]pyridin-3-yl)ethyl]carbamoyl}-5-(hydroxymethyl)morpholine-4-carboxylate (250 mg) in dichloromethane (5 mL)-water (2.5 mL) were added iodobenzene diacetate (560 mg) and 2,2,6,6-tetramethyl-piperidin-1-oxyl (27 mg) under ice-cooling, and the mixture was stirred vigorously under ice-cooling for 6 hours. To the reaction solution, under ice-cooling, methanol was added dropwise, and the reaction solution was concentrated under reduced pressure. To the resulting residue was added water, and then the mixture was extracted with chloroform. The organic layer was washed with saturated saline, and then dried over anhydrous magnesium sulfate, the solvent was distilled under reduced pressure. The resulting residue was purified by silica gel column chromatography (eluent: chloroform/methanol=100/0→, 88/12) to give (3R,6R)-4-(tert-butoxycarbonyl)-6-{cyclopropyl[(1R)-1-(1-{3-[(methoxycarbonyl)amino]propyl}-6-methyl-1H-pyrazolo[3,4-b]pyridin-3-yl)ethyl]carbamoyl}morpholin-3-carboxylic acid (85 mg).
APCI-MS m/z: 589 [M+H]$^+$.

Reference Example 142

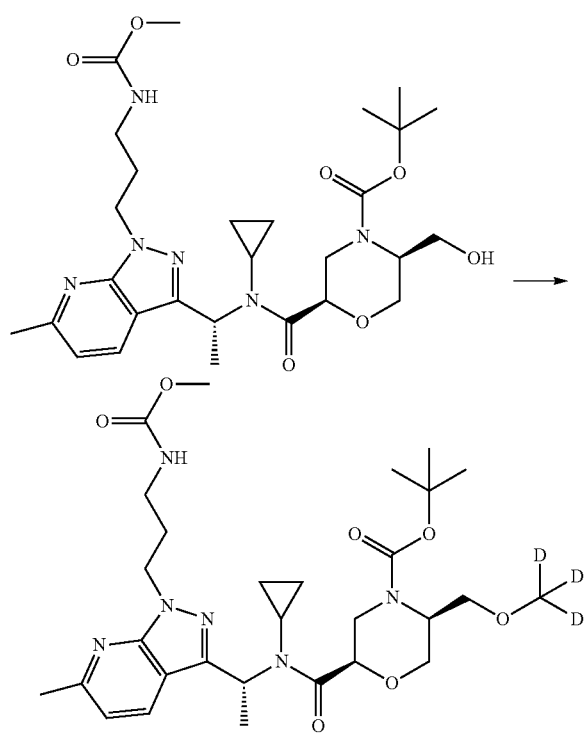

(1) To a solution of tert-butyl (2R,5S)-2-{cyclopropyl[(1R)-1-(1-{3-[(methoxycarbonyl)amino]propyl}-6-methyl-1H-pyrazolo[3,4-b]pyridin-3-yl)ethyl]carbamoyl}-5-(hydroxymethyl)morpholine-4-carboxylate (430 mg) in methyl iodide-d$_3$ (3 mL) was added silver oxide (867 mg) at room temperature, and the mixture was stirred under nitrogen stream at 35° C. for 17 hours. Then, methyl iodide-d$_3$ solution (2 mL) was added thereto, and further stirred for 5 hours. An insoluble in the reaction solution was filtrated, and the solvent was distilled under reduced pressure. The resulting residue was purified by silica gel column chromatography (eluent: chloroform/methanol=100/0→93/7) to give tert-butyl (2R,5S)-2-{cyclopropyl[(1R)-1-(1-{3-[(methoxycarbonyl)amino]propyl}-6-methyl-1H-pyrazolo[3,4-b]pyridin-3-yl)ethyl]carbamoyl}-5-{[(methyl-d$_3$)oxy]methyl}morpholine-4-carboxylate (385 mg).
ESI-MS m/z: 592 [M+H]$^+$.

Reference Example 143

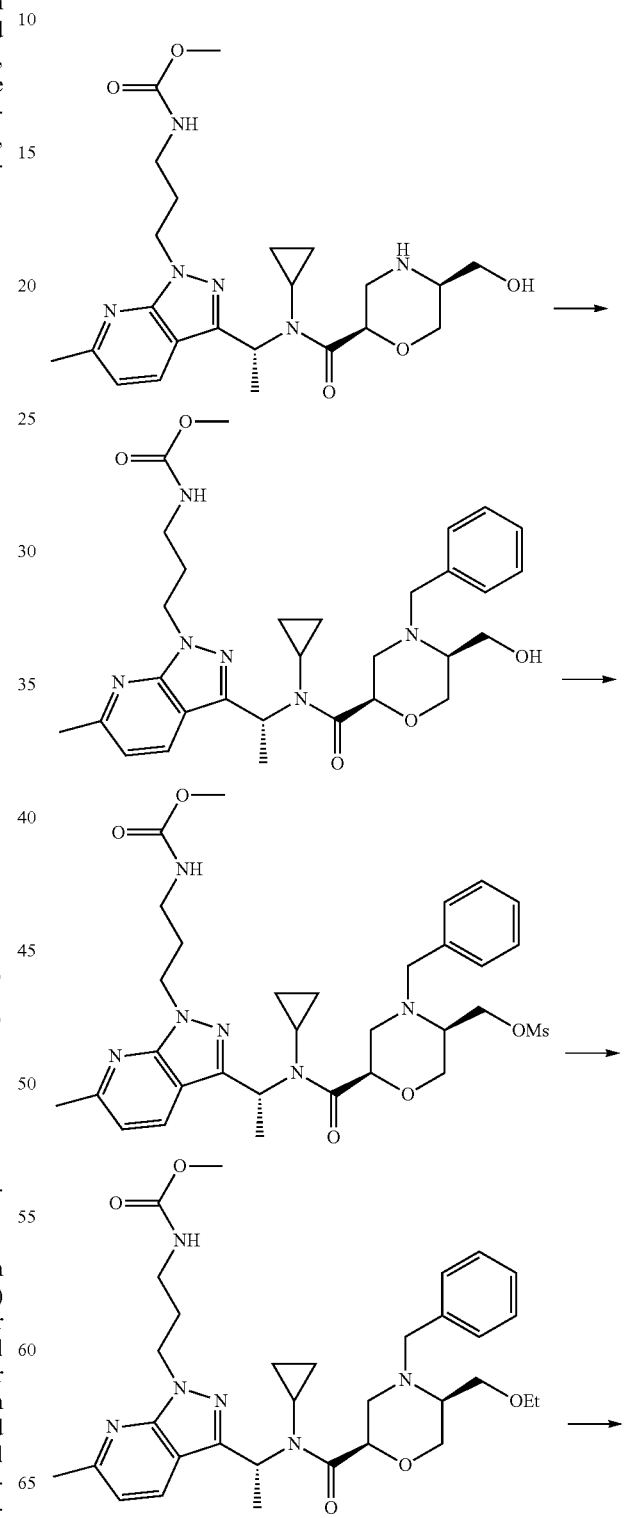

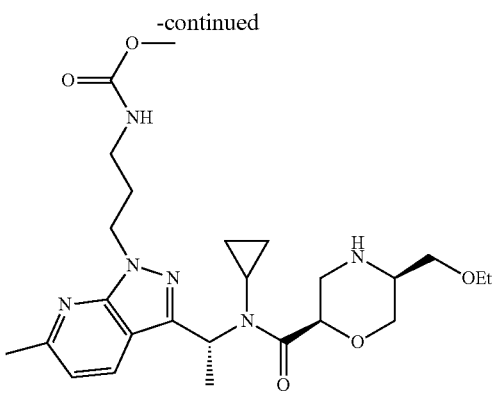

(1) To a solution of methyl (3-{3-[(1R)-1-(cyclopropyl{[(2R,5S)-5-(hydroxymethyl)morpholin-2-yl]carbonyl}amino)ethyl]-6-methyl-1H-pyrazolo[3,4-b]pyridin-1-yl}propyl)carbamate (1.01 g) in dichloromethane (20 mL) were added benzaldehyde (271 mg) and sodium triacetoxyborohydride (677 mg) under ice-cooling, and the mixture was stirred under nitrogen stream at room temperature for 2 hours. To the reaction solution was added aqueous saturated sodium hydrogen carbonate solution under ice-cooling, and then the mixture was extracted with chloroform. The organic layer was washed with saturated saline, dried over anhydrous sodium sulfate, and then the solvent was distilled under reduced pressure. The resulting residue was purified by silica gel column chromatography (eluent: (eluent: n-hexane/ethyl acetate=91/9→0/100→ethyl acetate/methanol=83/7) to give methyl [3-(3-{(1R)-1-[{[(2R,5S)-4-benzyl-5-(hydroxymethyl)morpholin-2-yl]carbonyl}(cyclopropyl)amino]ethyl}-6-methyl-1H-pyrazolo[3,4-b]pyridin-1-yl)propyl]carbamate (1.03 g).
APCI-MS m/z: 589 [M+H]⁺.

(2) To a solution of methyl [3-(3-{(1R)-1-[{[(2R,5S)-4-benzyl-5-(hydroxymethyl)morpholin-2-yl]carbonyl}(cyclopropyl)amino]ethyl}-6-methyl-1H-pyrazolo[3,4-b]pyridin-1-yl)propyl]carbamate (150 mg) in dichloromethane (4.5 mL) were added triethylamine (148 μL) and methanesulfonyl chloride (78 μL) under ice-cooling, and the mixture was stirred for 2 hours with raising the temperature slowly from ice-cooling to room temperature. The reaction solution was poured into aqueous saturated sodium hydrogen carbonate solution, and the mixture was extracted with chloroform. The organic layer was aqueous saturated sodium hydrogen carbonate solution, washed with water and saturated saline, dried over anhydrous magnesium sulfate, and the solvent was evaporated off under reduced pressure to give a crude [(3R,6R)-4-benzyl-6-{cyclopropyl[(1R)-1-(1-{3-[(methoxycarbonyl)amino]propyl}-6-methyl-1H-pyrazolo[3,4-b]pyridin-3-yl)ethyl]carbamoyl}morpholin-3-yl]methyl methanesulfonate (188 mg).
APCI-MS m/z: 643 [M+H]⁺.

(3) To ethanol (5 mL) was added sodium hydride (60%, 50 mg) at room temperature, and then the solution of the crude [(3R,6R)-4-benzyl-6-{cyclopropyl[(1R)-1-(1-{3-[(methoxycarbonyl)amino]propyl}-6-methyl-1H-pyrazolo[3,4-b]pyridin-3-yl)ethyl]carbamoyl}morpholin-3-yl]methyl methanesulfonate (188 mg) in ethanol (4 mL) was added thereto, and the mixture was stirred at room temperature for 20 hours and then at 50° C. for 23 hours. To the reaction solution was added 10% potassium hydrogen sulfate aqueous solution, and adjust the pH of the solution to about 6. Water, and then chloroform were added thereto, and the mixture was extracted with ethyl acetate. The organic layer was washed with saturated saline, and then dried over anhydrous magnesium sulfate, the solvent was distilled under reduced pressure. The resulting residue was purified by silica gel column chromatography (eluent: n-hexane/ethyl acetate=50/50→10/90) to give methyl [3-(3-{(1R)-1-[{[(2R,5S)-4-benzyl-5-(ethoxymethyl)morpholin-2-yl]carbonyl}(cyclopropyl)amino]ethyl}-6-methyl-1H-pyrazolo[3,4-b]pyridin-1-yl)propyl]carbamate (80 mg).
APCI-MS m/z: 593 [M+H]⁺.

(4) To a solution of methyl [3-(3-{(1R)-1-[{[(2R,5S)-4-benzyl-5-(ethoxymethyl)morpholin-2-yl]carbonyl}(cyclopropyl)amino]ethyl}-6-methyl-1H-pyrazolo[3,4-b]pyridin-1-yl)propyl]carbamate (77 mg) in methanol (10 mL) was added at room temperature, palladium hydroxide on carbon (50 mg), and the mixture was stirred vigorously under hydrogen stream, at room temperature for 4 hours. An insoluble in the reaction solution was filtrated, and the solvent was distilled under reduced pressure. The resulting residue was purified by silica gel column chromatography (eluent: chloroform/methanol=99/1→, 90/10) to give methyl (3-{3-[(1R)-1-(cyclopropyl{[(2R,5S)-5-(ethoxymethyl)morpholin-2-yl]carbonyl}amino)ethyl]-6-methyl-1H-pyrazolo[3,4-b]pyridin-1-yl}propyl)carbamate (43 mg).
APCI-MS m/z: 503 [M+H]⁺.

Reference Example 144

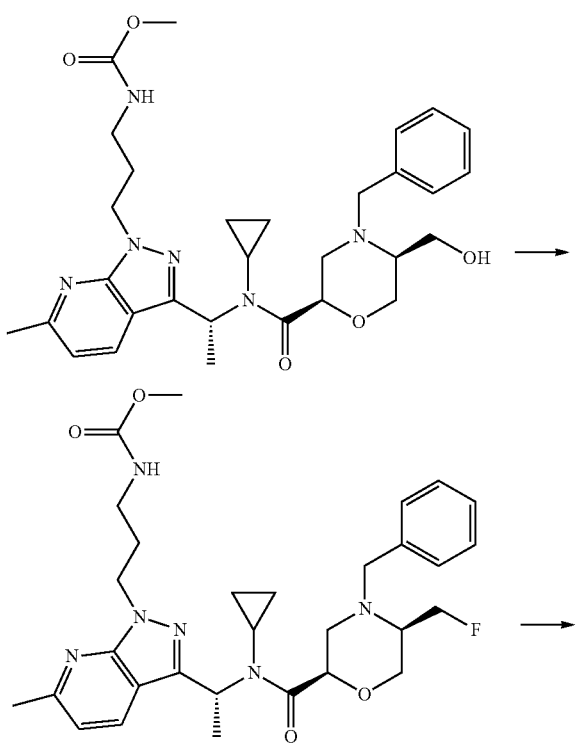

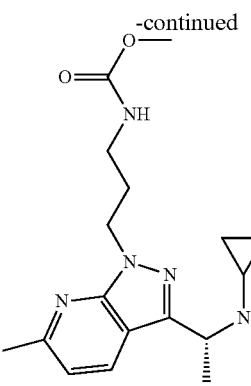

(1) To a solution of N,N-diethylaminosulfur trifluoride (DAST, 70 μL) in dichloromethane (3 mL) was added methyl [3-(3-{(1R)-1-[{[(2R,5S)-4-benzyl-5-(hydroxymethyl)morpholin-2-yl]carbonyl}(cyclopropyl)amino]ethyl}-6-methyl-1H-pyrazolo[3,4-b]pyridin-1-yl)propyl]carbamate (250 mg) in dichloromethane (3 mL), under nitrogen stream, at −78° C., and the mixture was stirred at −78° C. for 5 minutes, and under ice-cooling for 3 hours, and then at room temperature for 15 hours. The reaction solution was ice-cooled again, and under nitrogen stream, N,N-diethylaminosulfur trifluoride (DAST, 35 μL) was added thereto, and then the mixture was stirred at room temperature for 5 hours. To the reaction solution was added aqueous saturated sodium hydrogen carbonate solution under ice-cooling, and the mixture was extracted with chloroform. The organic layer was washed with saturated saline, and then dried over anhydrous sodium sulfate, the solvent was distilled under reduced pressure. The resulting residue was purified by silica gel column chromatography (eluent: n-hexane/ethyl acetate=100/0→40/60) and then reverse phase column chromatography (Capcellpak C18 UG80, eluent: 0.05% trifluoroacetic acid/water=30/70→40/70) to give methyl [3-(3-{(1R)-1-[{[(2R,5R)-4-benzyl-5-(fluoromethyl)morpholin-2-yl]carbonyl}(cyclopropyl)amino]ethyl}-6-methyl-1H-pyrazolo[3,4-b]pyridin-1-yl)propyl]carbamate (49 mg).

APCI-MS m/z: 567 [M+H]+.

(2) To a solution of methyl [3-(3-{(1R)-1-[{[(2R,5R)-4-benzyl-5-(fluoromethyl)morpholin-2-yl]carbonyl}(cyclopropyl)amino]ethyl}-6-methyl-1H-pyrazolo[3,4-b]pyridin-1-yl)propyl]carbamate (75 mg) in methanol (3.0 mL), palladium hydroxide on carbon (25 mg) was added and the mixture was stirred vigorously under hydrogen atmosphere, at room temperature for 3 hours. An insoluble in the reaction solution was filtrated, the solvent was distilled under reduced pressure. The resulting residue was purified by silica gel column chromatography (eluent: chloroform→chloroform/methanol=10/1) to give, methyl (3-{3-[(1R)-1-(cyclopropyl{[(2R,5S)-5-(ethoxymethyl)morpholin-2-yl]carbonyl}amino)ethyl]-6-methyl-1H-pyrazolo[3,4-b]pyridin-1-yl}propyl)carbamate (55 mg).

APCI-MS m/z: 477 [M+H]+.

Reference Example 145

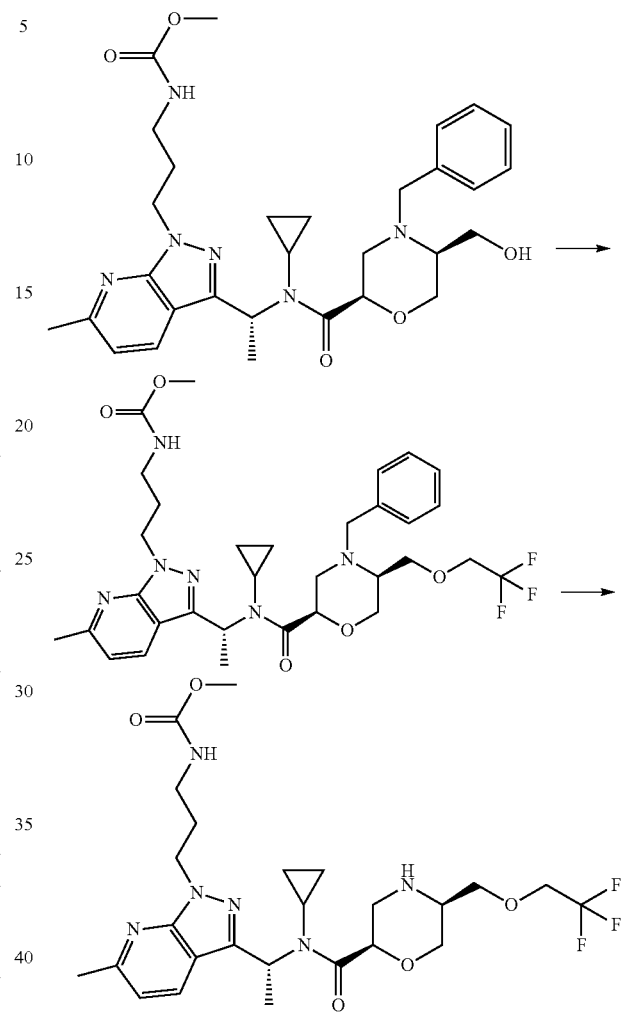

(1) To a solution of methyl [3-(3-{(1R)-1-[{[(2R,5S)-4-benzyl-5-(hydroxymethyl)morpholin-2-yl]carbonyl}(cyclopropyl)amino]ethyl}-6-methyl-1H-pyrazolo[3,4-b]pyridin-1-yl)propyl]carbamate (436 mg) in tetrahydrofuran (15.4 mL) was added sodium hydride (60%, 124 mg) under ice-cooling, and the mixture was stirred under nitrogen stream, at room temperature for 30 minutes. The reaction solution was ice-cooled, 2,2,2-trifluoroethyl perfluorobutylsulfonate (722 μL) was added thereto, and the mixture was stirred at room temperature for 40 minutes. Under ice-cooling, to the reaction solution was added saturated saline, and the mixture was extracted with ethyl acetate. The organic layer was dried over anhydrous sodium sulfate, and the solvent was distilled under reduced pressure. The resulting residue was purified by silica gel column chromatography (eluent: chloroform/methanol=100/0→95/5) to give methyl [3-(3-{(1R)-1-[({(2R,5S)-4-benzyl-5-[(2,2,2-trifluoroethoxy)methyl]morpholin-2-yl}carbonyl)(cyclopropyl)amino]ethyl}-6-methyl-1H-pyrazolo[3,4-b]pyridin-1-yl)propyl]carbamate (280 mg).

ESI-MS m/z: 647 [M+H]+.

(2) Methyl [3-(3-{(1R)-1-[({(2R,5S)-4-benzyl-5-[(2,2,2-trifluoroethoxy)methyl]morpholin-2-yl}carbonyl)(cyclopropyl)amino]ethyl}-6-methyl-1H-pyrazolo[3,4-b]pyridin-1-yl)propyl]carbamate (287 mg) was prepared by using analogous processes for synthesizing methyl [3-(3-{(1R)-1-[({(2R,5S)-4-benzyl-5-[(2,2,2-trifluoroethoxy)methyl]morpholin-2-yl}carbonyl)(cyclopropyl)amino]ethyl}-6-methyl-1H-pyrazolo[3,4-b]pyridin-1-yl)propyl]carbamate to give methyl [3-(3-{(1R)-1-[cyclopropyl({2R,5S)-5-[(2,2,2-trifluoroethoxy)methyl]morpholin-2-yl}carbonyl)amino]ethyl}-6-methyl-1H-pyrazolo[3,4-b]pyridin-1-yl)propyl]carbamater (136 mg).
ESI-MS m/z: 557 [M+H]$^+$.

Reference Example 146

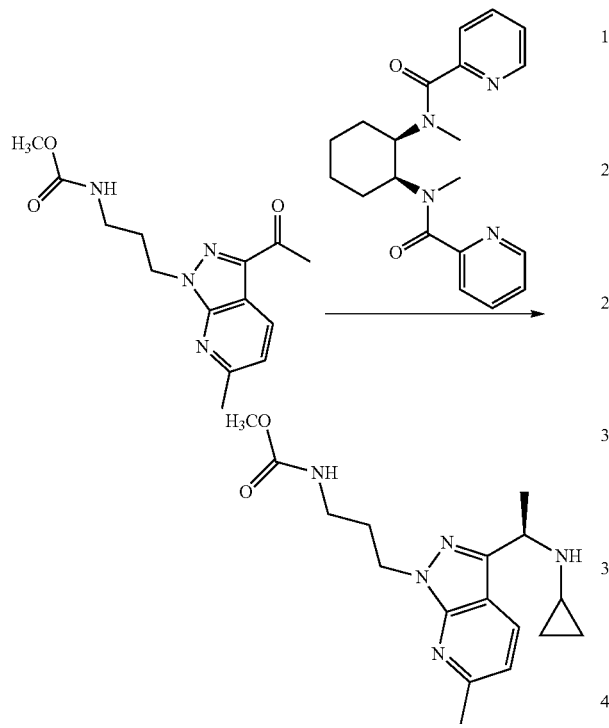

(1) To a solution of [3-(3-acetyl-6-methyl-1H-pyrazolo[3,4-b]pyridin-1-yl)propyl]carbamic acid methyl ester (6.91 g) in ethanol (270 mL) were added cyclopropylamine (6.60 mL) and acetic acid (2.04 mL), and the mixture was stirred at 60° C. for 3 hours. The reaction solution was concentrated, and ethyl acetate was added to the resulting residue, under ice-cooling, and aqueous saturated sodium hydrogen carbonate solution was added to make the solution alkaline After an extruciton with ethyl acetate, the organic layer was washed with saturated saline, dried over sodium sulfate, and then concentrated under reduced pressure to give methyl {3-[3-(N-cyclopropylethanimidoyl)-6-methyl-1H-pyrazolo[3,4-b]pyridin-1-yl]propyl}carbamate (8.01 g).

APCI-MS m/z: 330 [M+H]$^+$.

(2) To a solution of methyl {3-[3-(N-cyclopropylethanimidoyl)-6-methyl-1H-pyrazolo[3,4-b]pyridin-1-yl]propyl}) carbamate (8.01 g) and N,N'-(1S,2S)-cyclohexane-1,2-diylbis(N-methylpyridin-2-carboxamide) (839 mg) in dichloromethane (160 mL), under ice-cooling, was added acetic acid (2.04 mL), and then trichlorosilane (7.21 mL) was added dropwise, and the mixture was stirred under ice-cooling, for 6 hours. To the reaction solution was added aqueous saturated sodium hydrogen carbonate solution and methanol under ice-cooling, and then stirred for 30 minutes at the same temperature. An insoluble was removed with Celite, and washed with chloroform. The filtrate was extracted with chloroform, and the organic layer was washed with saturated saline, dried over sodium sulfate, and then concentrated under reduced pressure. The resulting residue was purified by NH-silica gel column chromatography (eluent: n-hexane/ethyl acetate=4/1→1/1) and silica gel column chromatography (eluent: n-hexane/ethyl acetate=1/1→ethyl acetate/methanol=9/1) to give methyl (3-{3-[(1R)-1-(cyclopropylamino)ethyl]-6-methyl-1H-pyrazolo[3,4-b]pyridin-1-yl)propyl]carbamate (6.81 g).

APCI-MS m/z: 332 [M+H]$^+$.

The following compounds were prepared according to the methods disclosed in the specification.

TABLE 99

| Ref. | Chemical Formula | MS Result | MS Method | Ion Species |
|---|---|---|---|---|
| Ref. 147 | | 243 | APCI | [M + H]+ |
| Ref. 148 | | 278 | APCI | [M + H]+ |

TABLE 99-continued
| Ref. | Chemical Formula | MS Result | MS Method | Ion Species |
|------|------------------|-----------|-----------|-------------|
| Ref. 149 | 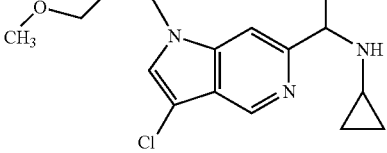 | 308/310 | APCI | [M + H]+ |
| Ref. 150 | 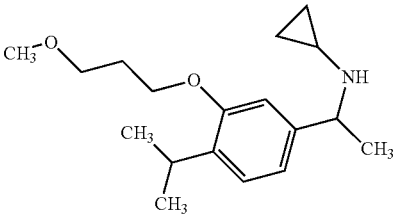 [SMILES: COCCCOc1cc(C(C)NC2CC2)ccc1C(C)C] | 292 | APCI | [M + H]+ |
| Ref. 151 | 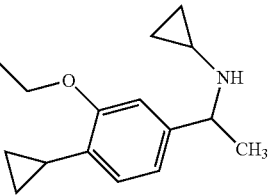 | 290 | APCI | [M + H]+ |
| Ref. 152 | 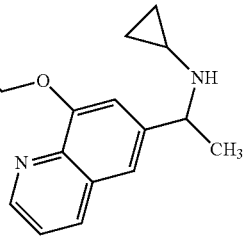 | 301 | APCI | [M + H]+ |
| Ref. 153 | 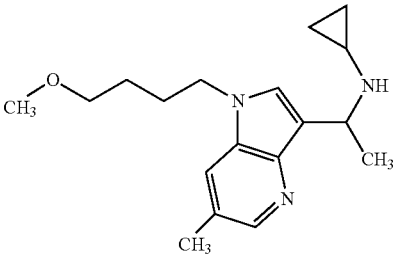 [SMILES: COCCCCn1cc(C(C)NC2CC2)c2ncc(C)cc21] | 302 | APCI | [M + H]+ |
| Ref. 154 | 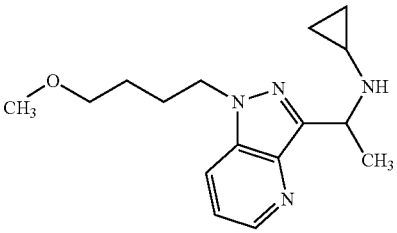 [SMILES: COCCCCn1nc(C(C)NC2CC2)c2ncccc21] | 289 | APCI | [M + H]+ |

TABLE 100
| Ref. 155 | 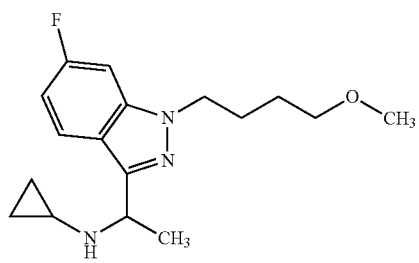 [SMILES: COCCCCn1nc(C(C)NC2CC2)c2ccc(F)cc21] | 306 APCI [M + H]+ |
| Ref. 156 | 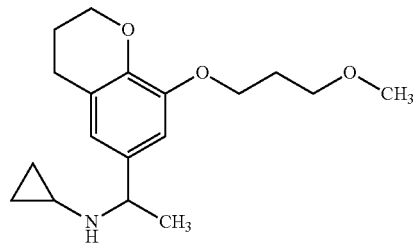 [SMILES: COCCCOc1cc(C(C)NC2CC2)cc2c1OCCC2] | 306 APCI [M + H]+ |
| Ref. 157 | 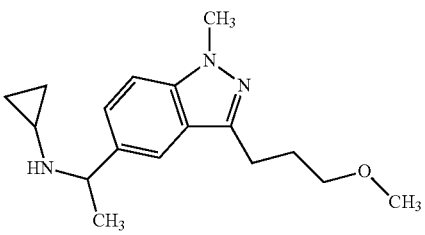 [SMILES: COCCCc1nn(C)c2ccc(C(C)NC3CC3)cc12] | 288 APCI [M + H]+ |
| Ref. 158 | 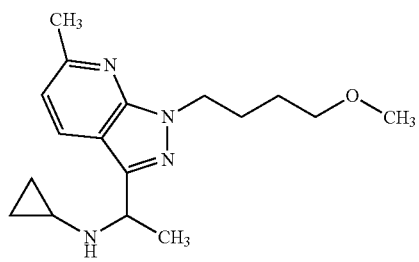 [SMILES: COCCCCn1nc(C(C)NC2CC2)c2ccc(C)nc21] | 303 APCI [M + H]+ |
| Ref. 159 | 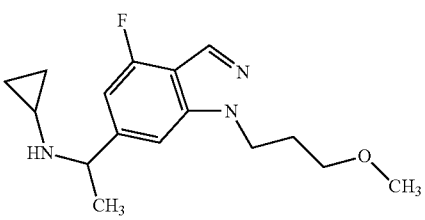 [SMILES: COCCCNc1cc(C(C)NC2CC2)cc(F)c1C=N] | 292 APCI [M + H]+ |
| Ref. 160 | 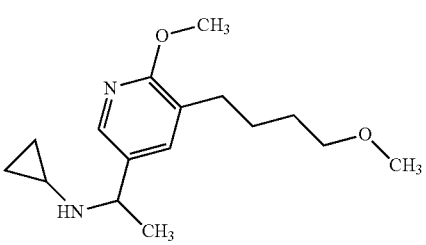 [SMILES: COCCCCc1cc(C(C)NC2CC2)cnc1OC] | 279 APCI [M + H]+ |

TABLE 100-continued
| Ref. 161 | 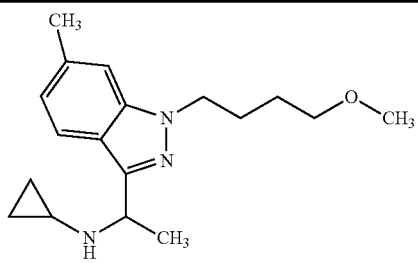 | 302 APCI [M + H]+ |
| Ref. 162 | 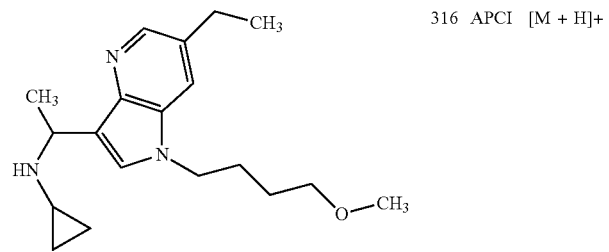 | 316 APCI [M + H]+ |
TABLE 101
| Ref. 163 | 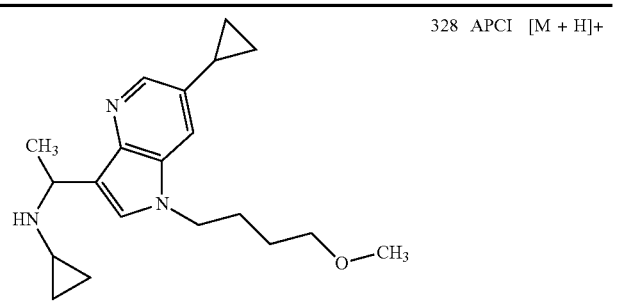 | 328 APCI [M + H]+ |
| Ref. 164 | 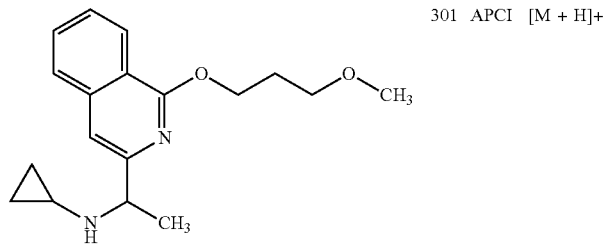 | 301 APCI [M + H]+ |
| Ref. 165 | 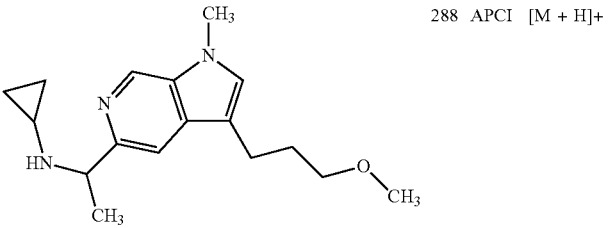 | 288 APCI [M + H]+ |
| Ref. 166 | 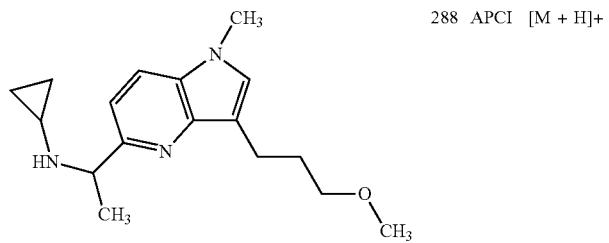 | 288 APCI [M + H]+ |

TABLE 101-continued
| Ref. 167 | 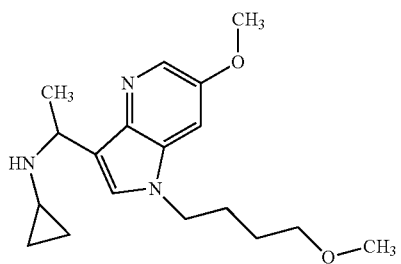 [SMILES: COCCCCn1cc(C(C)NC2CC2)c2ncc(OC)cc21] | 318 APCI [M + H]+ |
| Ref. 168 | 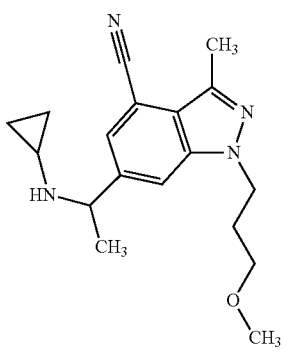 [SMILES: COCCCn1nc(C)c2c(C#N)cc(C(C)NC3CC3)cc21] | 313 APCI [M + H]+ |
| Ref. 169 | 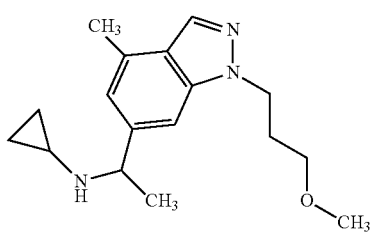 [SMILES: COCCCn1ncc2c(C)cc(C(C)NC3CC3)cc21] | 288 APCI [M + H]+ |
TABLE 102
| Ref. 170 | 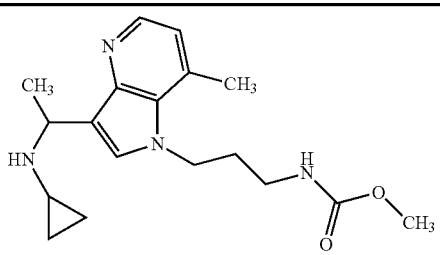 | 331 APCI [M + H]+ |
| Ref. 171 | 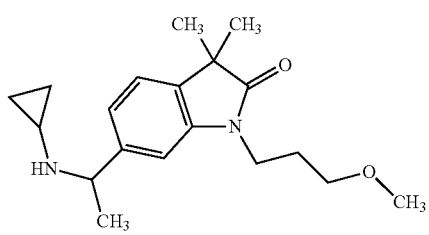 [SMILES: COCCCN1C(=O)C(C)(C)c2ccc(C(C)NC3CC3)cc21] | 317 APCI [M + H]+ |

TABLE 102-continued
| Ref. 172 | 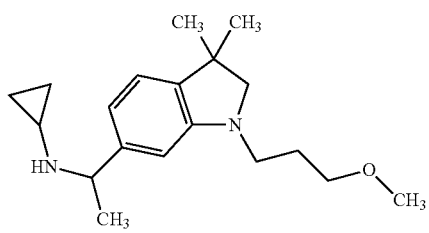 [SMILES: COCCCN1CC(C)(C)c2ccc(C(C)NC3CC3)cc21] | 303 | APCI [M + H]+ |
| Ref. 173 | 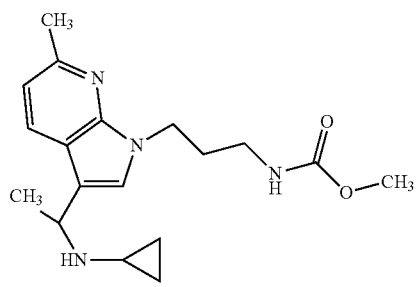 [SMILES: COC(=O)NCCCn1cc(C(C)NC2CC2)c2ccc(C)nc21] | 331 | APCI [M + H]+ |
| Ref. 174 | 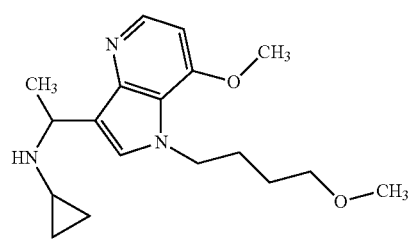 [SMILES: COCCCCn1cc(C(C)NC2CC2)c2nccc(OC)c21] | 318 | APCI [M + H]+ |
| Ref. 175 | 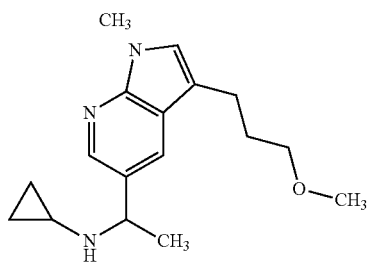 | 288 | APCI [M + H]+ |
| Ref. 176 | 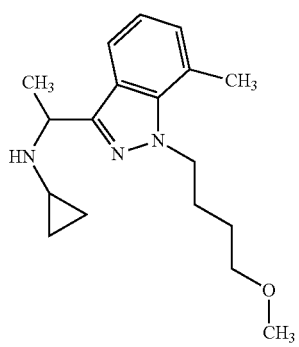 [SMILES: COCCCCn1nc(C(C)NC2CC2)c2cccc(C)c21] | 302 | APCI [M + H]+ |

TABLE 103
| Ref. 177 | 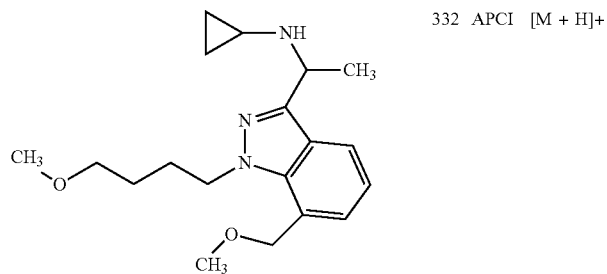 | 332 APCI [M + H]+ |
|---|---|---|
| Ref. 178 | 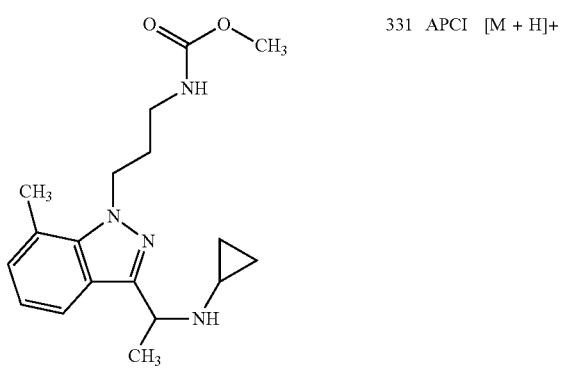 | 331 APCI [M + H]+ |
| Ref. 179 | 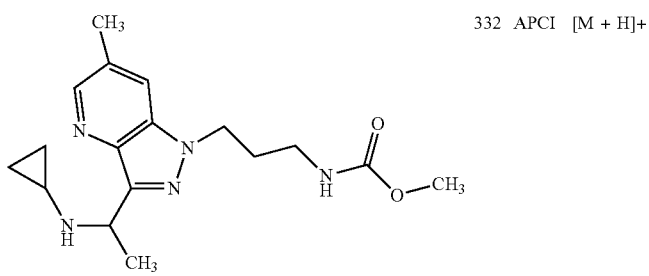 | 332 APCI [M + H]+ |
| Ref. 180 | 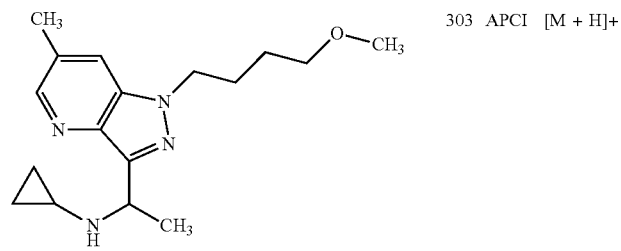 | 303 APCI [M + H]+ |
| Ref. 181 | 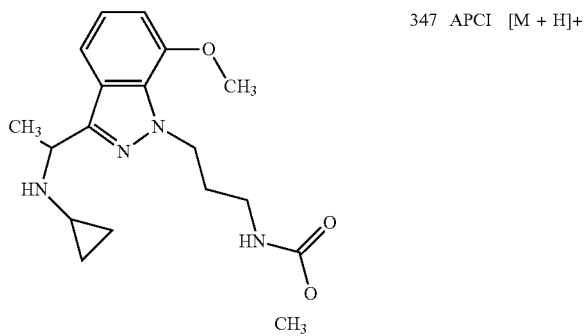 | 347 APCI [M + H]+ |

TABLE 103-continued
| Ref. 182 | 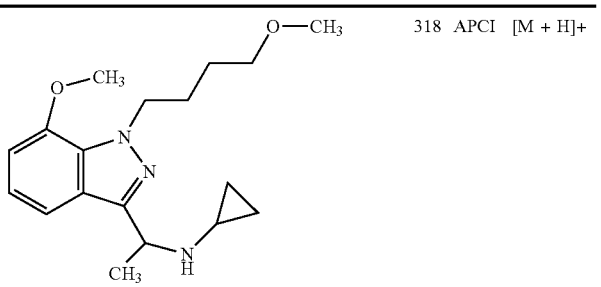 | 318 APCI [M + H]+ |
| Ref. 183 | 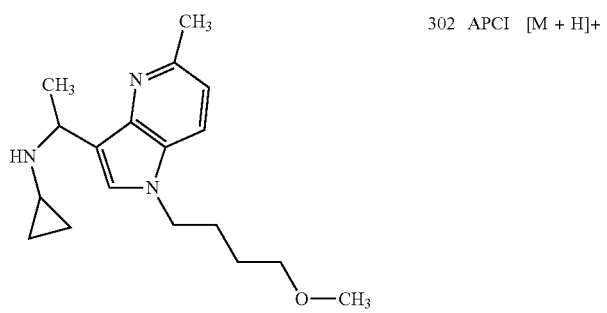 | 302 APCI [M + H]+ |
TABLE 104
| Ref. 184 | 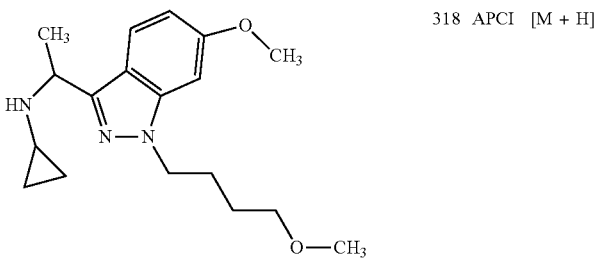 | 318 APCI [M + H]+ |
| Ref. 185 | 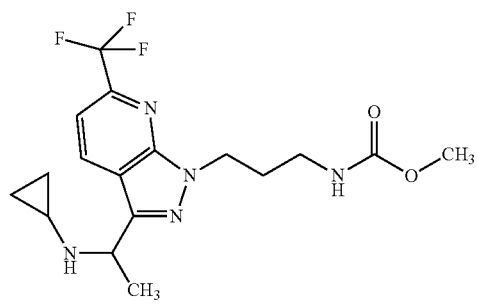 [SMILES: COC(=O)NCCCn1nc(C(C)NC2CC2)c2ccc(C(F)(F)F)nc21] | 386 APCI [M + H]+ |
| Ref. 186 | 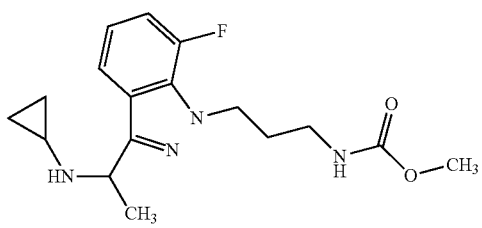 [SMILES: COC(=O)NCCCNc1c(F)cccc1C(=N)C(C)NC1CC1] | 335 APCI [M + H]+ |

TABLE 104-continued
| Ref. 187 | 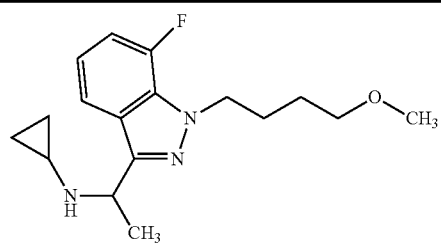 | 306 APCI [M + H]+ |
| Ref. 188 | 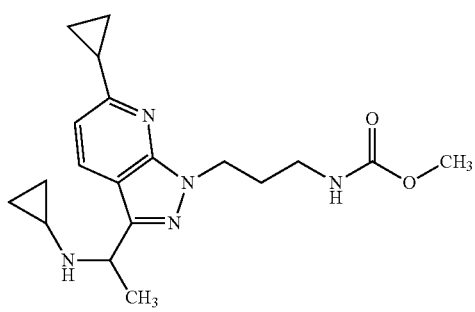 [SMILES: COC(=O)NCCCn1nc(C(C)NC2CC2)c2ccc(C3CC3)nc21] | 358 APCI [M + H]+ |
| Ref. 189 | 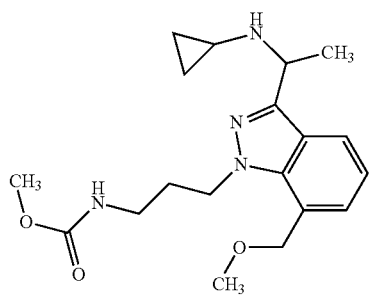 [SMILES: COCc1cccc2c(C(C)NC3CC3)nn(CCCNC(=O)OC)c12] | 361 APCI [M + H]+ |
| Ref. 190 | 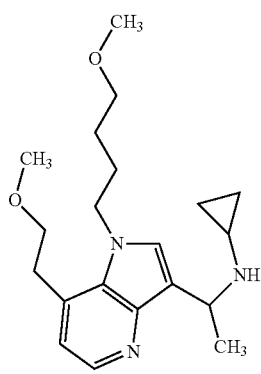 [SMILES: COCCCCn1cc(C(C)NC2CC2)c2nccc(CCOC)c21] | 346 APCI [M + H]+ |
TABLE 105
| Ref. 191 | 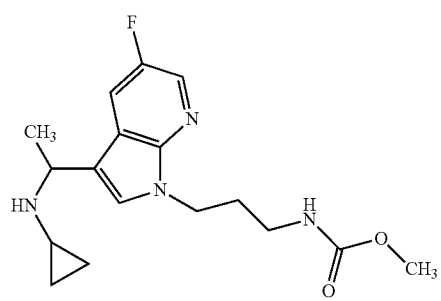 [SMILES: COC(=O)NCCCn1cc(C(C)NC2CC2)c2cc(F)cnc21] | 335 APCI [M + H]+ |

TABLE 105-continued
| Ref. | Structure | MS | Method |
|---|---|---|---|
| Ref. 192 | 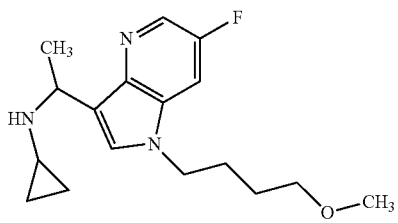 [SMILES: COCCCCn1cc(C(C)NC2CC2)c2ncc(F)cc21] | 306 | APCI [M + H]+ |
| Ref. 193 | 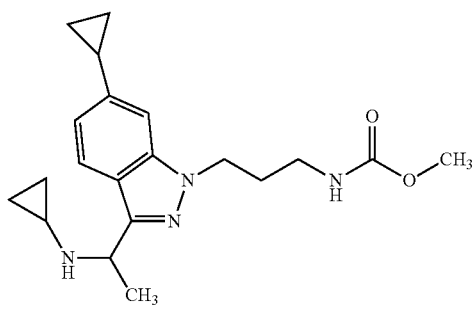 [SMILES: COC(=O)NCCCn1nc(C(C)NC2CC2)c2ccc(C3CC3)cc21] | 357 | APCI [M + H]+ |
| Ref. 194 | 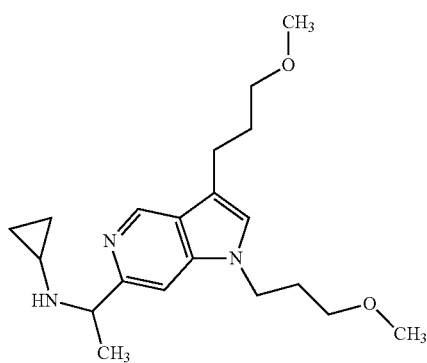 [SMILES: COCCCc1cn(CCCOC)c2cc(C(C)NC3CC3)ncc12] | 346 | APCI [M + H]+ |
| Ref. 195 | 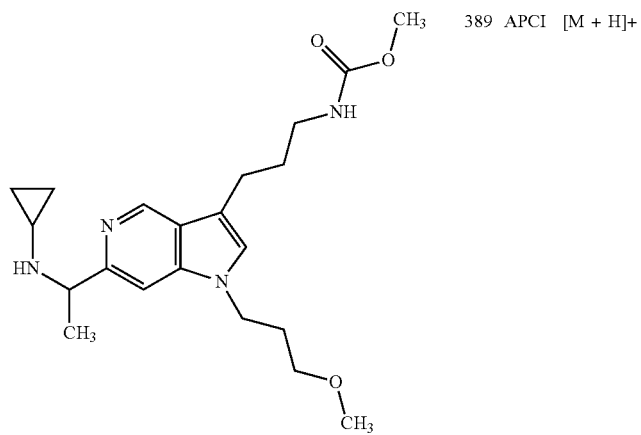 | 389 | APCI [M + H]+ |

TABLE 105-continued
| Ref. 196 | 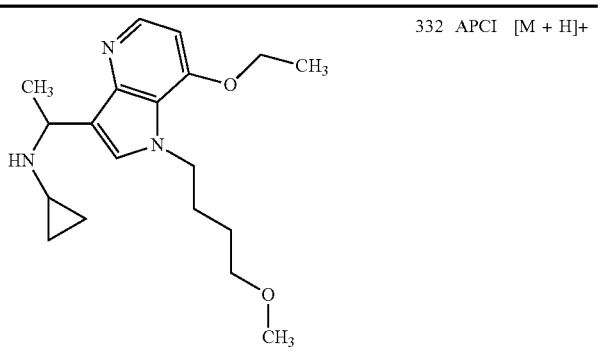 | 332 | APCI | [M + H]+ |
TABLE 106
| Ref. 197 | 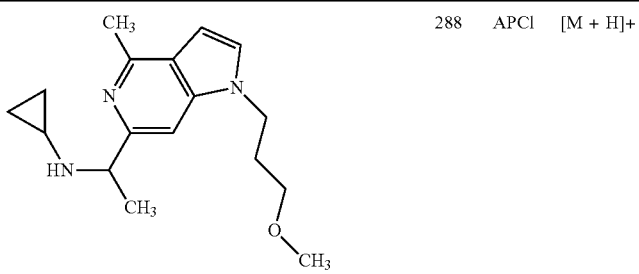 | 288 | APCI | [M + H]+ |
| Ref. 198 | 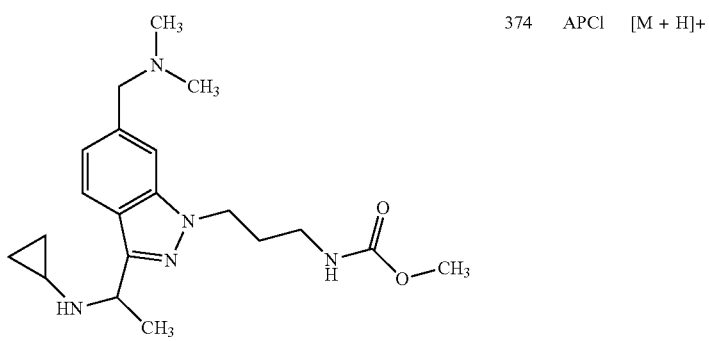 | 374 | APCI | [M + H]+ |
| Ref. 199 | 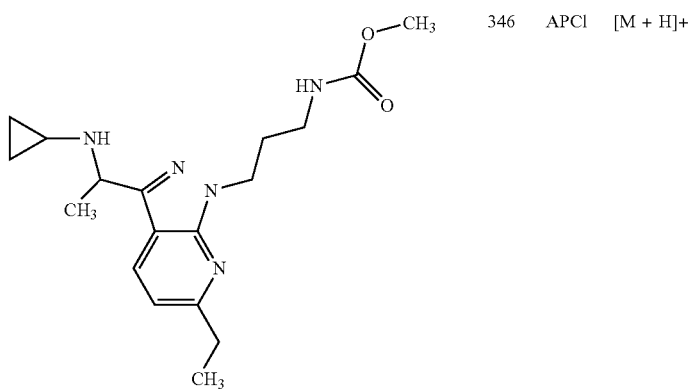 | 346 | APCI | [M + H]+ |

TABLE 106-continued
| Ref. 200 | 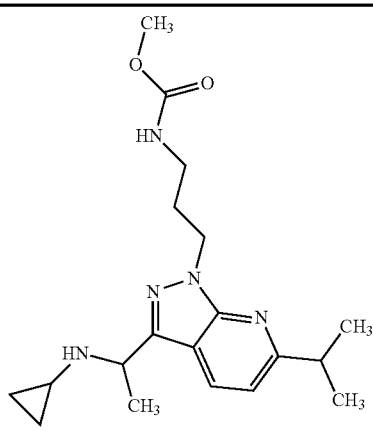 | 360 | APCI | [M + H]+ |
| Ref. 201 | 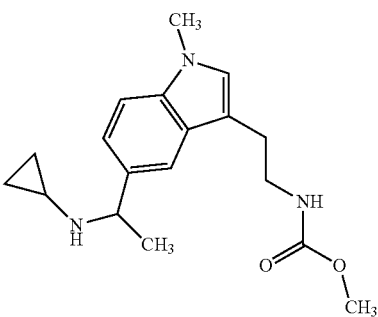 [SMILES: COC(=O)NCCc1cn(C)c2ccc(C(C)NC3CC3)cc12] | 316 | APCI | [M + H]+ |
| Ref. 202 | 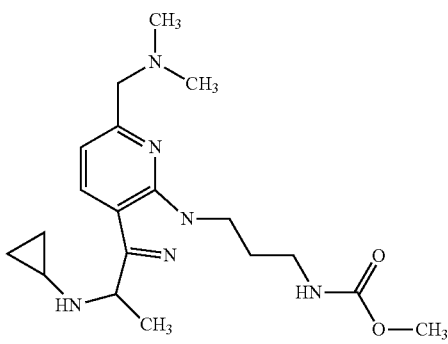 [SMILES: COC(=O)NCCCNc1nc(CN(C)C)ccc1C(=N)C(C)NC1CC1] | 375 | APCI | [M + H]+ |
TABLE 107
| Ref. 203 | 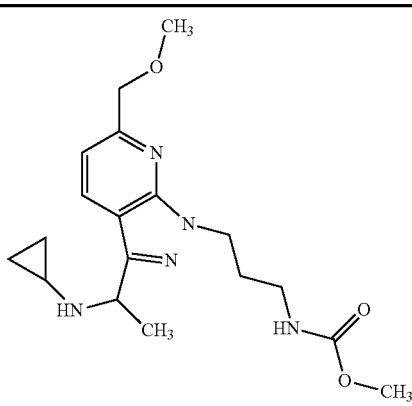 | 362 | APCI | [M + H]+ |

TABLE 107-continued
| Ref. 204 | 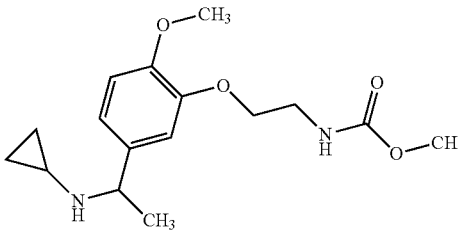 | 309 | APCl | [M + H]+ |
| --- | --- | --- | --- | --- |
| Ref. 205 | 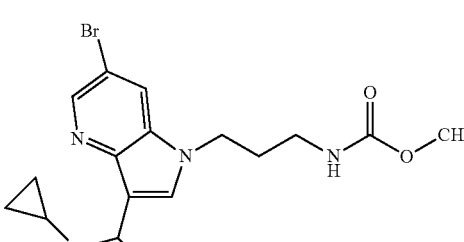 | 395/387 | APCl | [M + H]+ |
| Ref. 206 | 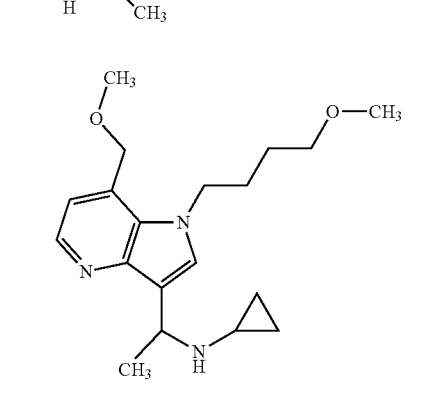 | 332 | APCl | [M + H]+ |
| Ref. 207 | 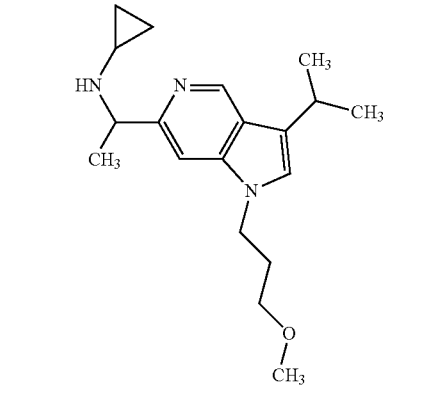 [SMILES: COCCCn1cc(C(C)C)c2cnc(C(C)NC3CC3)cc21] | 316 | APCl | |
| Ref. 208 | 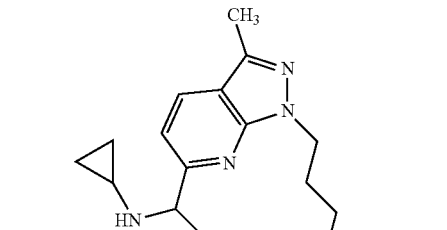 | 289 | APCl | [M + H]+ |

TABLE 108
| Ref. 209 | 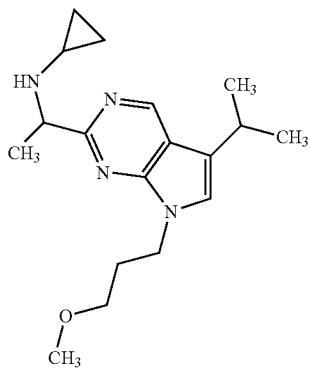 [SMILES: COCCCn1cc(C(C)C)c2cnc(C(C)NC3CC3)nc21] | 317 | APCl | [M + H]+ |
| Ref. 210 | 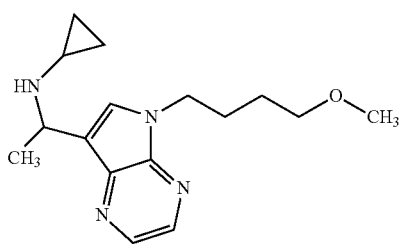 [SMILES: COCCCCn1cc(C(C)NC2CC2)c2nccnc21] | 289 | APCl | [M + H]+ |
| Ref. 211 | 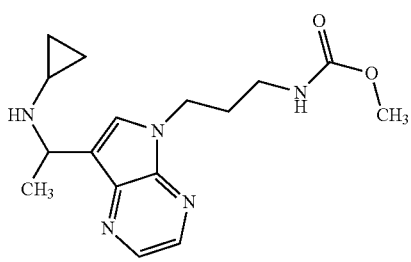 [SMILES: COC(=O)NCCCn1cc(C(C)NC2CC2)c2nccnc21] | 318 | APCl | [M + H]+ |
| Ref. 212 | 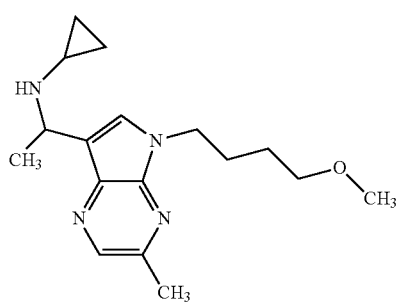 [SMILES: COCCCCn1cc(C(C)NC2CC2)c2ncc(C)nc21] | 303 | APCl | [M + H]+ |
| Ref. 213 | 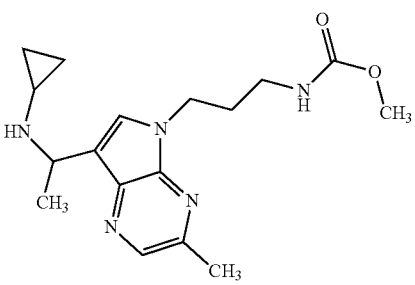 [SMILES: COC(=O)NCCCn1cc(C(C)NC2CC2)c2ncc(C)nc21] | 332 | APCl | [M + H]+ |

TABLE 108-continued
| Ref. 214 | 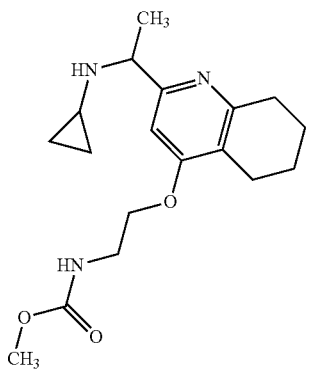 [SMILES: COC(=O)NCCOc1cc(C(C)NC2CC2)nc2c1CCCC2] | 334 | APCl | [M + H]+ |
TABLE 109
| Ref. 215 | 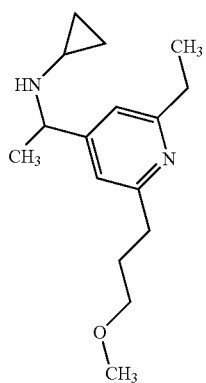 [SMILES: CCc1cc(C(C)NC2CC2)cc(CCCOC)n1] | 263 | APCl | [M + H]+ |
| Ref. 216 | 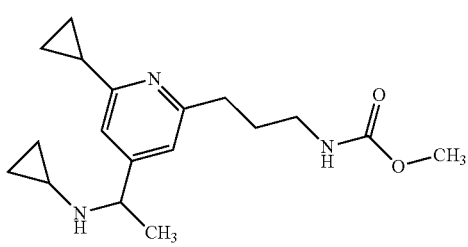 [SMILES: COC(=O)NCCCc1cc(C(C)NC2CC2)cc(C2CC2)n1] | 318 | APCl | [M + H]+ |
| Ref. 217 | 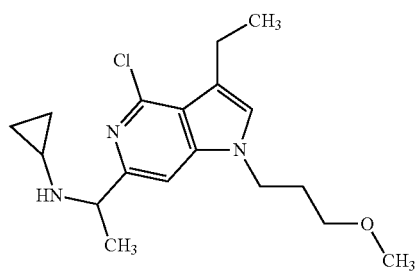 [SMILES: CCc1cn(CCCOC)c2cc(C(C)NC3CC3)nc(Cl)c12] | 336/338 | APCl | [M + H]+ |

TABLE 109-continued
| Ref. 218 | 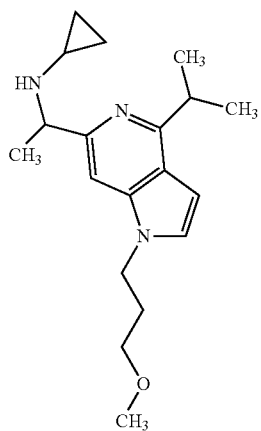 [SMILES: COCCCn1ccc2c(C(C)C)nc(C(C)NC3CC3)cc21] | 316 | APCl | [M + H]+ |
| --- | --- | --- | --- | --- |
| Ref. 219 | 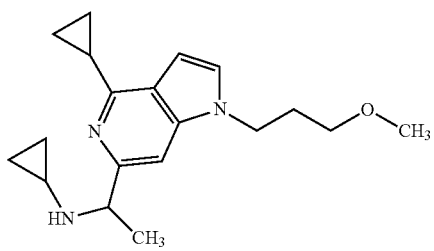 [SMILES: COCCCn1ccc2c(C3CC3)nc(C(C)NC3CC3)cc21] | 314 | APCl | [M + H]+ |
| Ref. 220 | 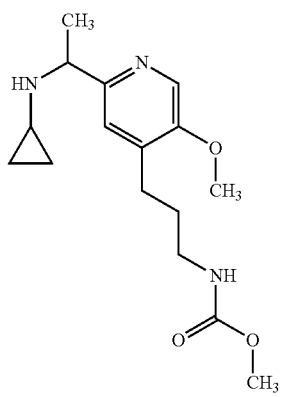 [SMILES: COC(=O)NCCCc1cc(C(C)NC2CC2)ncc1OC] | 308 | APCl | [M + H]+ |
TABLE 110
| Ref. 221 | 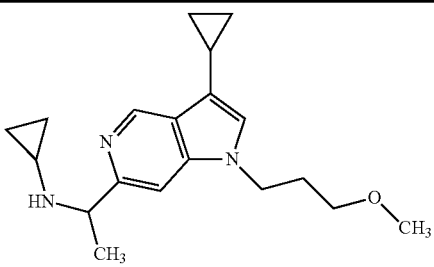 | 314 | APCl | [M + H]+ |
| --- | --- | --- | --- | --- |

TABLE 110-continued
| Ref. 222 | 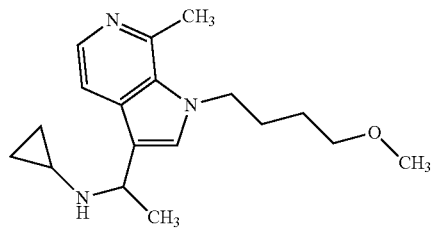 [SMILES: COCCCCn1cc(C(C)NC2CC2)c2ccnc(C)c21] | 302 | APCI | [M + H]+ |
| Ref. 223 | 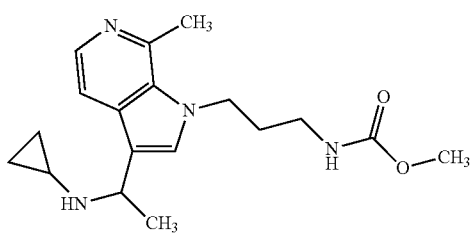 [SMILES: COC(=O)NCCCn1cc(C(C)NC2CC2)c2ccnc(C)c21] | 331 | APCI | [M + H]+ |
| Ref. 224 | 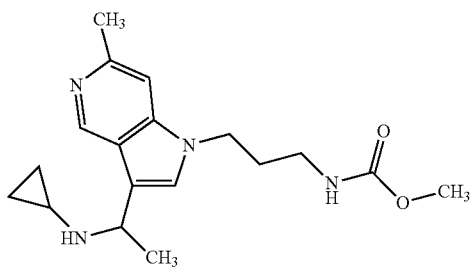 [SMILES: COC(=O)NCCCn1cc(C(C)NC2CC2)c2cnc(C)cc21] | 331 | APCI | [M + H]+ |
| Ref. 225 | 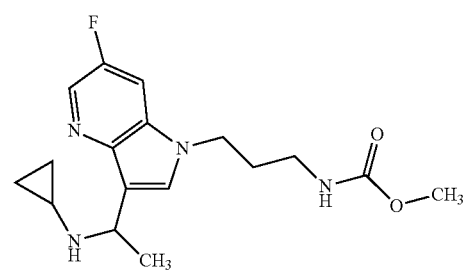 [SMILES: COC(=O)NCCCn1cc(C(C)NC2CC2)c2ncc(F)cc21] | 335 | APCI | [M + H]+ |
| Ref. 226 | 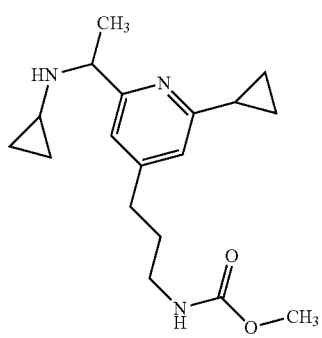 [SMILES: COC(=O)NCCCc1cc(C2CC2)nc(C(C)NC2CC2)c1] | 318 | APCI | [M + H]+ |

TABLE 110-continued
| Ref. 227 | 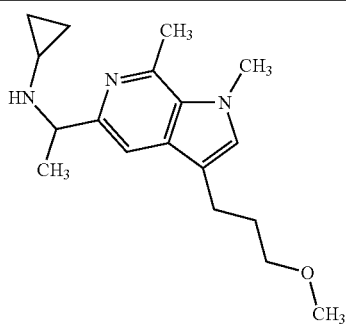 | 302 | APCl | [M + H]+ |
TABLE 111
| Ref. 228 | 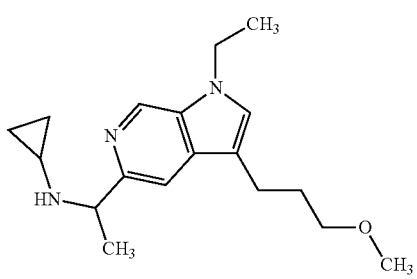 [SMILES: CCn1cc(CCCOC)c2cc(C(C)NC3CC3)ncc21] | 302 | APCl | [M + H]+ |
| Ref. 229 | 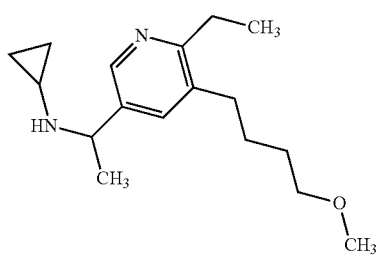 [SMILES: CCc1ncc(C(C)NC2CC2)cc1CCCCOC] | 277 | APCl | [M + H]+ |
| Ref. 230 | 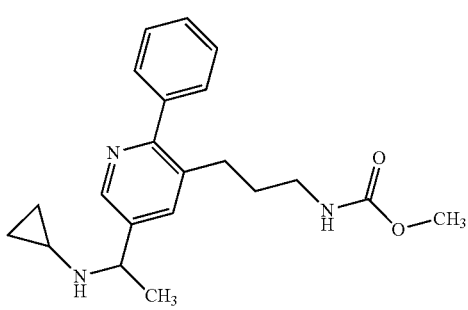 [SMILES: COC(=O)NCCCc1cc(C(C)NC2CC2)cnc1-c1ccccc1] | 354 | APCl | [M + H]+ |
| Ref. 231 | 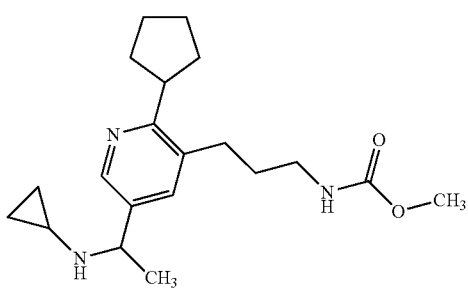 [SMILES: COC(=O)NCCCc1cc(C(C)NC2CC2)cnc1C1CCCC1] | 346 | APCl | [M + H]+ |

TABLE 111-continued
| Ref. 232 | 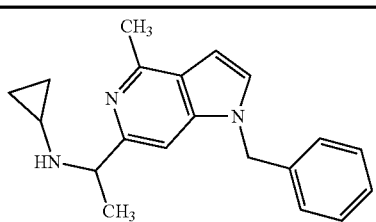 | 306 | APCI | [M + H]+ |
| Ref. 233 | 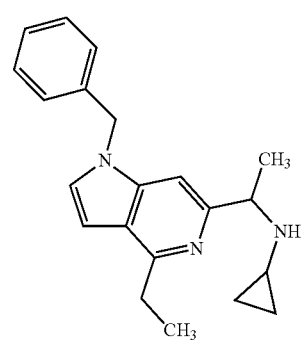 [SMILES: CCc1nc(C(C)NC2CC2)cc2c1ccn2Cc1ccccc1] | 320 | APCI | [M + H]+ |
| Ref. 234 | 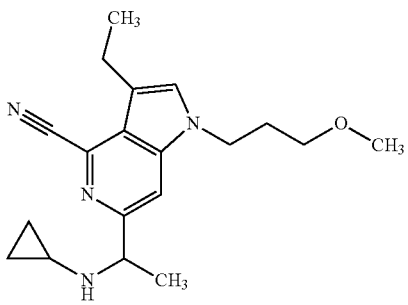 [SMILES: CCc1cn(CCCOC)c2cc(C(C)NC3CC3)nc(C#N)c12] | 327 | APCI | [M + H]+ |
TABLE 112
| Ref. 235 | 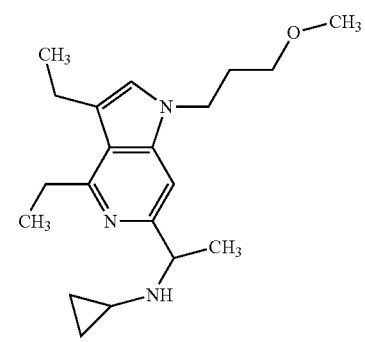 [SMILES: CCc1cn(CCCOC)c2cc(C(C)NC3CC3)nc(CC)c12] | 330 | APCI | [M + H]+ |
| Ref. 236 | 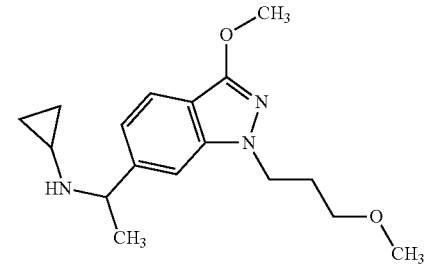 [SMILES: COCCCn1nc(OC)c2ccc(C(C)NC3CC3)cc21] | 304 | APCI | [M + H]+ |

TABLE 112-continued
| Ref. 237 | 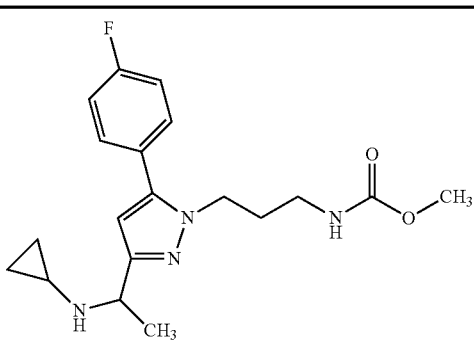 | 361 | APCl | [M + H]+ |
| Ref. 238 | 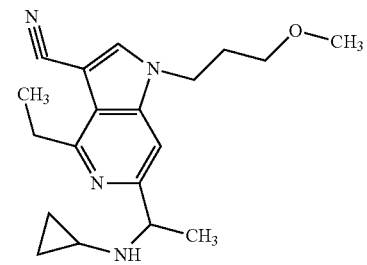 [SMILES: CCc1nc(C(C)NC2CC2)cc2c1c(C#N)cn2CCCOC] | 327 | APCl | [M + H]+ |
| Ref. 239 | 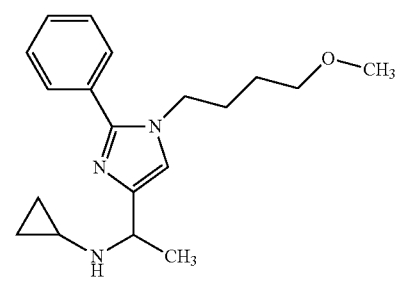 [SMILES: COCCCCn1cc(C(C)NC2CC2)nc1-c1ccccc1] | 314 | APCl | [M + H]+ |
| Ref. 240 | 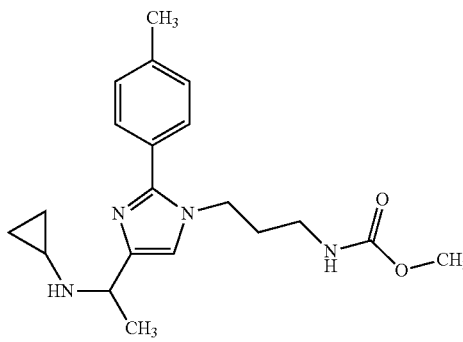 | 357 | APCl | [M + H]+ |
TABLE 113
| Ref. 241 | 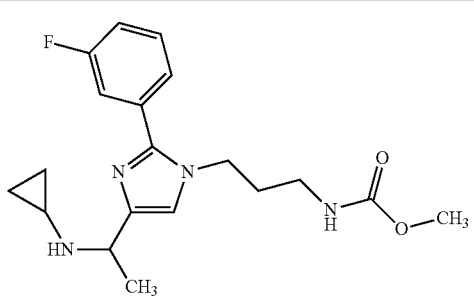 [SMILES: COC(=O)NCCCn1cc(C(C)NC2CC2)nc1-c1cccc(F)c1] | 361 | APCl | [M + H]+ |

TABLE 113-continued
| Ref. 242 | 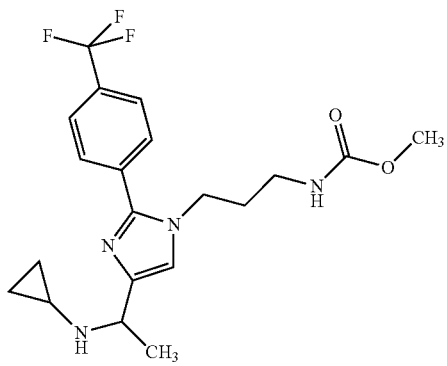 [SMILES: COC(=O)NCCCn1cc(C(C)NC2CC2)nc1-c1ccc(C(F)(F)F)cc1] | 411 | APCl | [M + H]+ |
| --- | --- | --- | --- | --- |
| Ref. 243 | 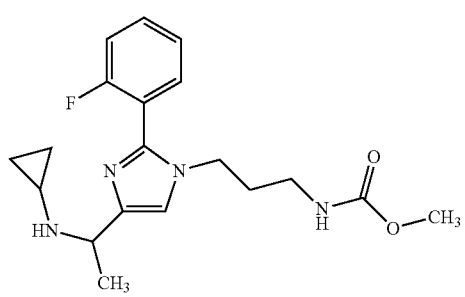 [SMILES: COC(=O)NCCCn1cc(C(C)NC2CC2)nc1-c1ccccc1F] | 361 | APCl | [M + H]+ |
| Ref. 244 | 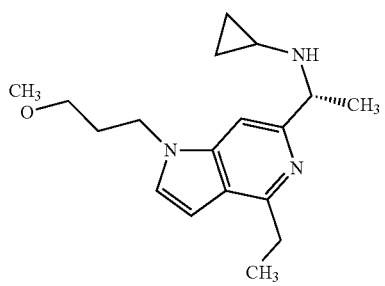 | 302 | APCl | [M + H]+ |
| Ref. 245 | 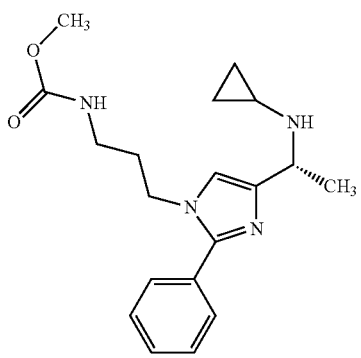 [SMILES: COC(=O)NCCCn1cc([C@@H](C)NC2CC2)nc1-c1ccccc1] | 343 | APCl | [M + H]+ |
| Ref. 246 | 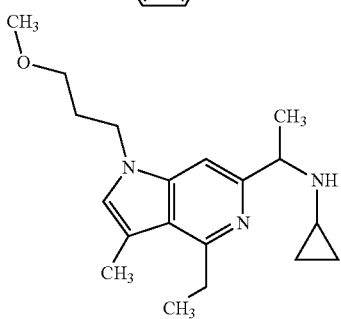 | 316 | APCl | [M + H]+ |

TABLE 114
| Ref. 247 | 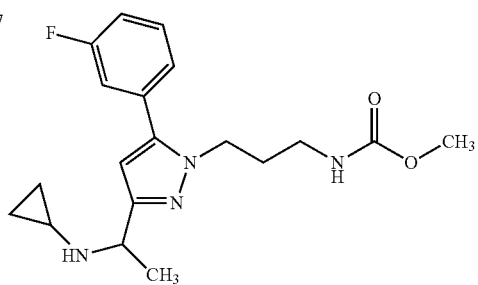 | 361 APCI [M + H]+ |
| Ref. 248 | 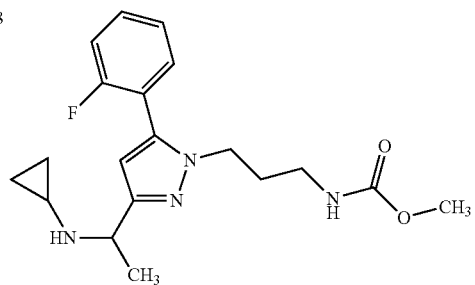 | 361 APCI [M + H]+ |
| Ref. 249 | 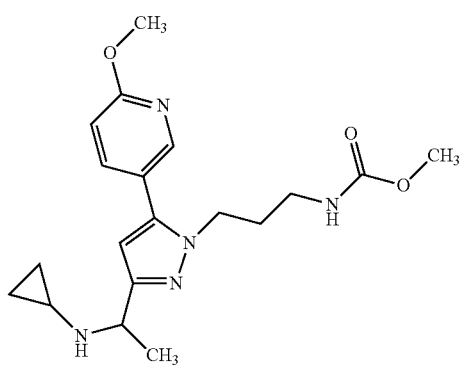 [SMILES: COC(=O)NCCCn1nc(C(C)NC2CC2)cc1-c1ccc(OC)nc1] | 374 APCI [M + H]+ |
| Ref. 250 | 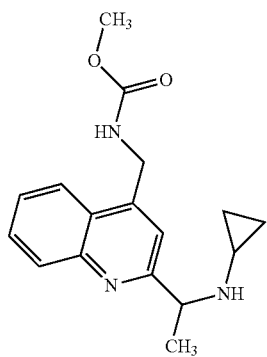 [SMILES: COC(=O)NCc1cc(C(C)NC2CC2)nc2ccccc12] | 300 APCI [M + H]+ |

TABLE 114-continued
| Ref. 251 | 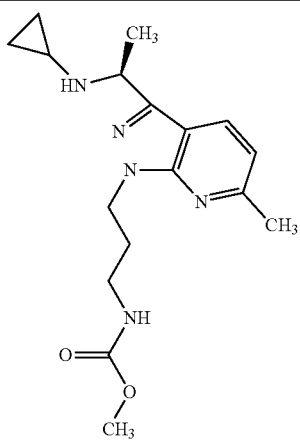 | 332 APCI [M + H]+ |
TABLE 115
| Ref. 252 | 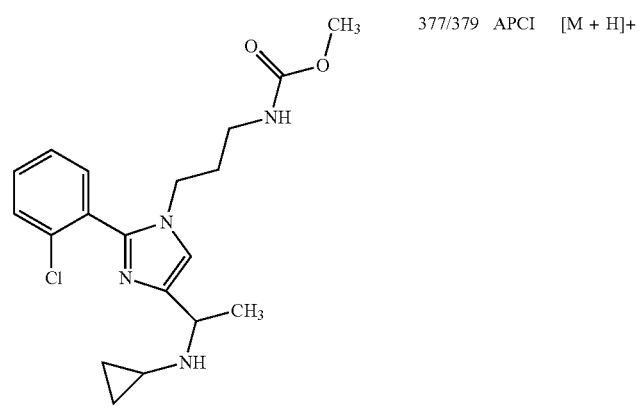 | 377/379 APCI [M + H]+ |
| Ref. 253 | 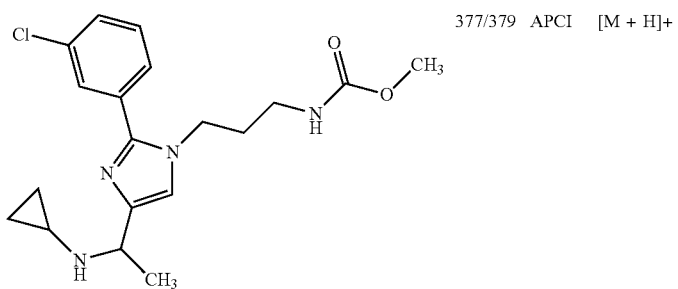 | 377/379 APCI [M + H]+ |
| Ref. 254 | 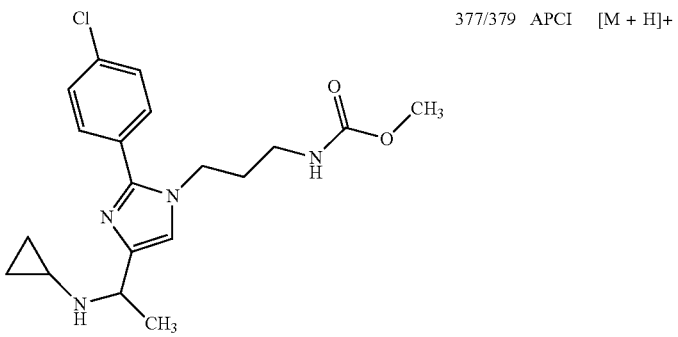 | 377/379 APCI [M + H]+ |

TABLE 115-continued
| Ref. 255 | 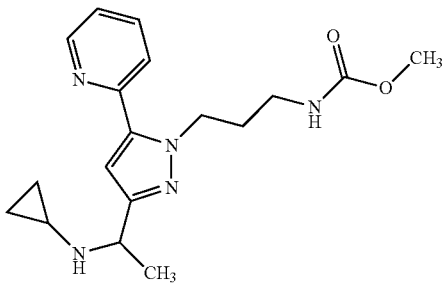 [SMILES: COC(=O)NCCCn1nc(C(C)NC2CC2)cc1-c1ccccn1] | 344 | APCI | [M + H]+ |
| Ref. 256 | 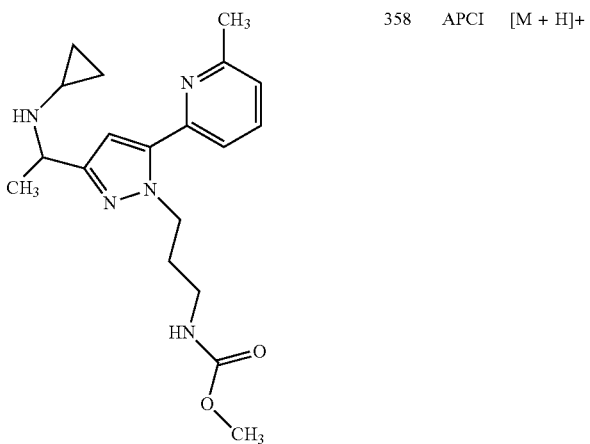 | 358 | APCI | [M + H]+ |
| Ref. 257 | 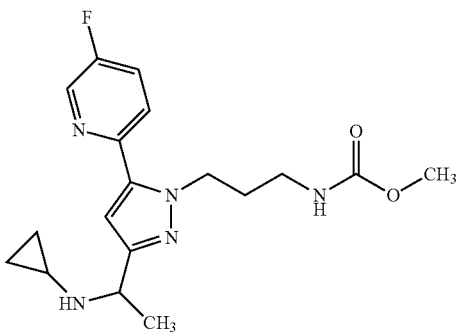 [SMILES: COC(=O)NCCCn1nc(C(C)NC2CC2)cc1-c1ccc(F)cn1] | 362 | APCI | [M + H]+ |
TABLE 116
| Ref. 258 | 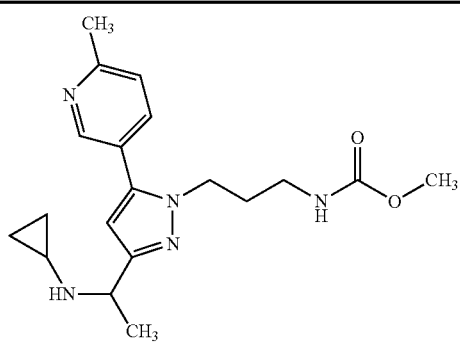 | 358 | APCI | [M + H]+ |

TABLE 116-continued
| Ref. 259 | 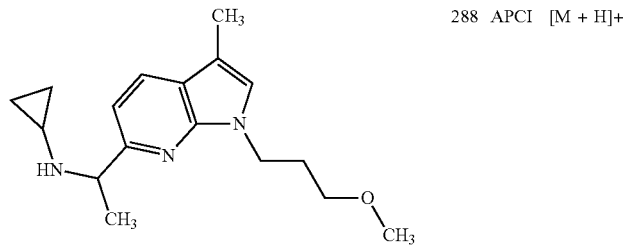 | 288 APCI [M + H]+ |
| Ref. 260 | 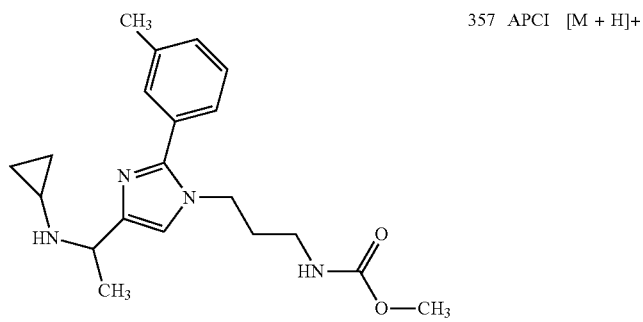 | 357 APCI [M + H]+ |
| Ref. 261 | 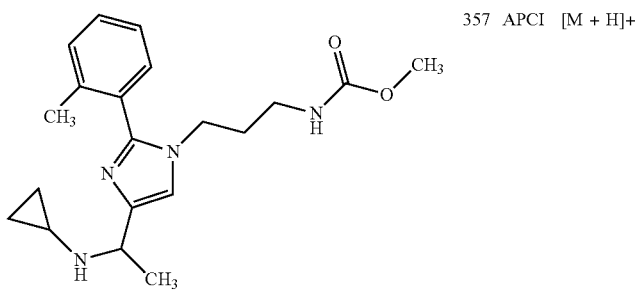 | 357 APCI [M + H]+ |
| Ref. 262 | 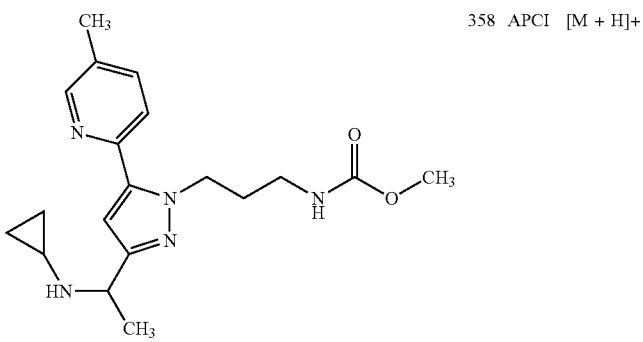 | 358 APCI [M + H]+ |
| Ref. 263 | 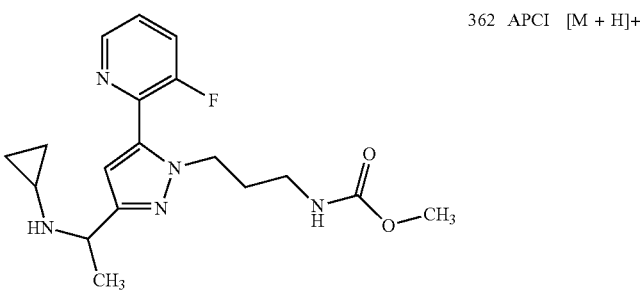 | 362 APCI [M + H]+ |

TABLE 117
| Ref. 264 | 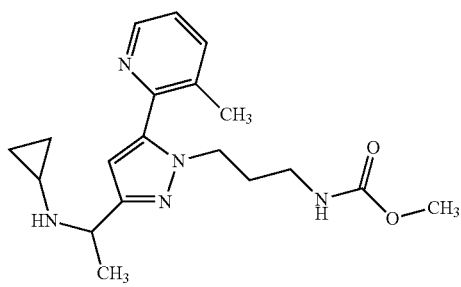 [SMILES: COC(=O)NCCCn1nc(C(C)NC2CC2)cc1-c1ncccc1C] | 358 APCI [M + H]+ |
| Ref. 265 | 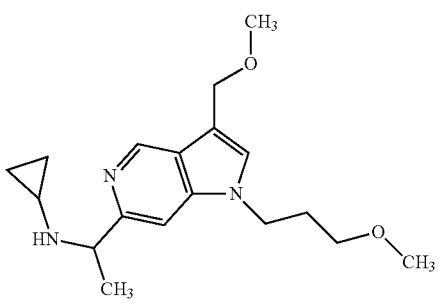 [SMILES: COCCCn1cc(COC)c2cnc(C(C)NC3CC3)cc21] | 318 APCI [M + H]+ |
| Ref. 266 | 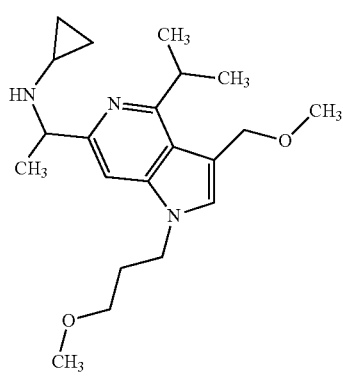 [SMILES: COCCCn1cc(COC)c2c(C(C)C)nc(C(C)NC3CC3)cc21] | 360 APCI [M + H]+ |
| Ref. 267 | 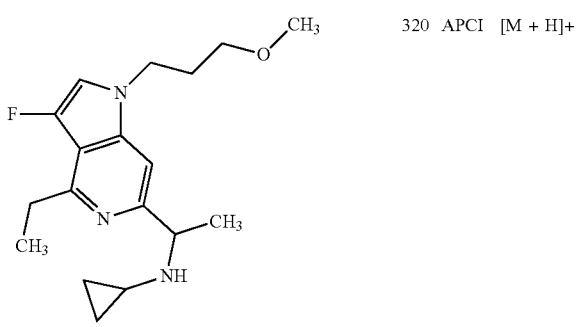 | 320 APCI [M + H]+ |
| Ref. 268 | 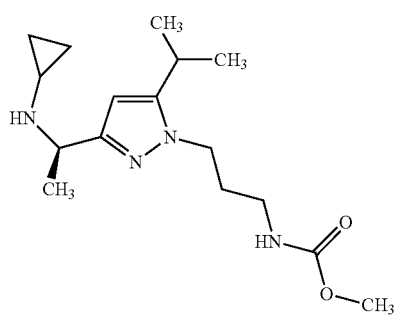 [SMILES: COC(=O)NCCCn1nc([C@@H](C)NC2CC2)cc1C(C)C] | 309 APCI [M + H]+ |

TABLE 117-continued
| Ref. 269 | 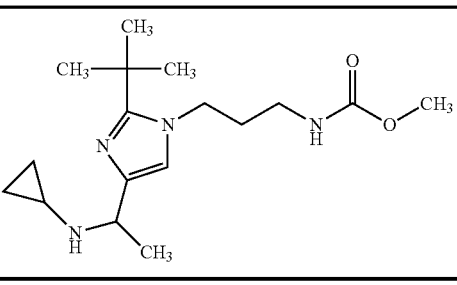 | 323 APCI [M + H]+ |
TABLE 118
| Ref. 270 | 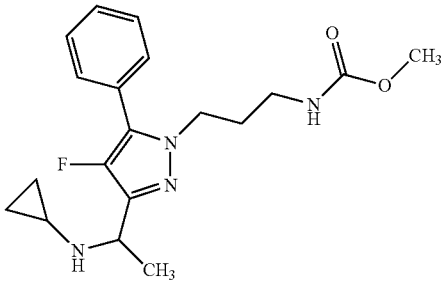 [SMILES: COC(=O)NCCCn1nc(C(C)NC2CC2)c(F)c1-c1ccccc1] | 361 APCI [M + H]+ |
| Ref. 271 | 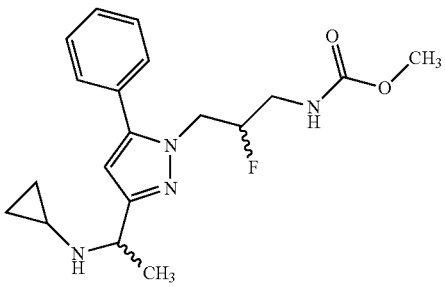 [SMILES: COC(=O)NCC(F)Cn1nc(C(C)NC2CC2)cc1-c1ccccc1] | 361 APCI [M + H]+ |
| Ref. 272 | 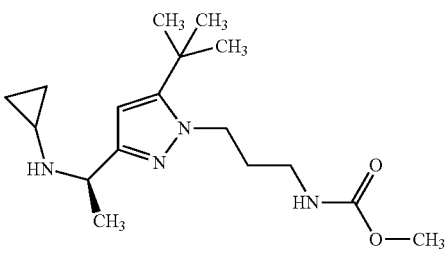 [SMILES: COC(=O)NCCCn1nc([C@@H](C)NC2CC2)cc1C(C)(C)C] | 323 APCI [M + H]+ |
| Ref. 273 | 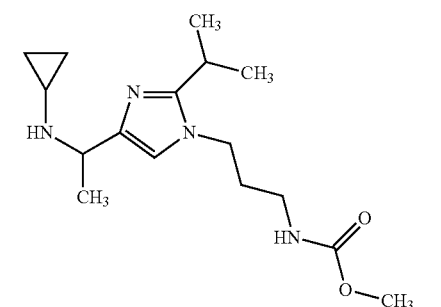 | 309 APCI [M + H]+ |

TABLE 118-continued
| Ref. 274 | 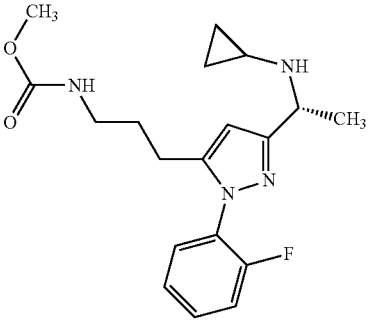 [SMILES: COC(=O)NCCCc1cc([C@@H](C)NC2CC2)nn1-c1ccccc1F] | 361 APCI [M + H]+ |
| Ref. 275 | 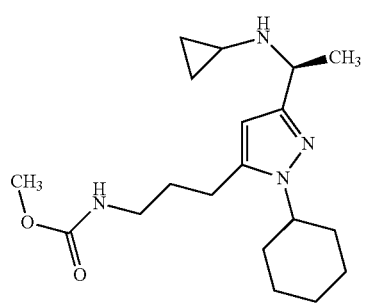 [SMILES: COC(=O)NCCCc1cc([C@H](C)NC2CC2)nn1C1CCCCC1] | 349 APCI [M + H]+ |
TABLE 119
| Ref. 276 | 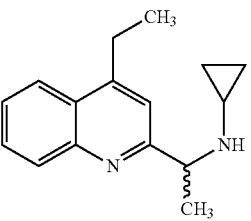 | 241 APCI [M + H]+ |
| Ref. 277 | 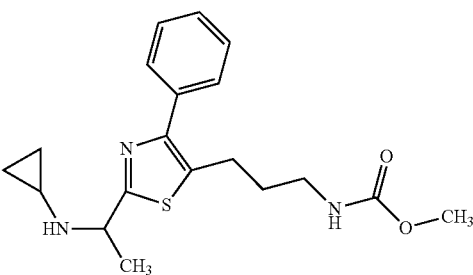 [SMILES: COC(=O)NCCCc1sc(C(C)NC2CC2)nc1-c1ccccc1] | 360 APCI [M + H]+ |
| Ref. 278 | 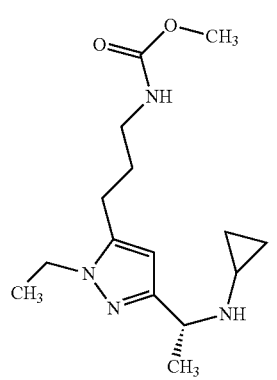 [SMILES: CCn1nc([C@@H](C)NC2CC2)cc1CCCNC(=O)OC] | 295 APCI [M + H]+ |

TABLE 119-continued
| Ref. 279 | 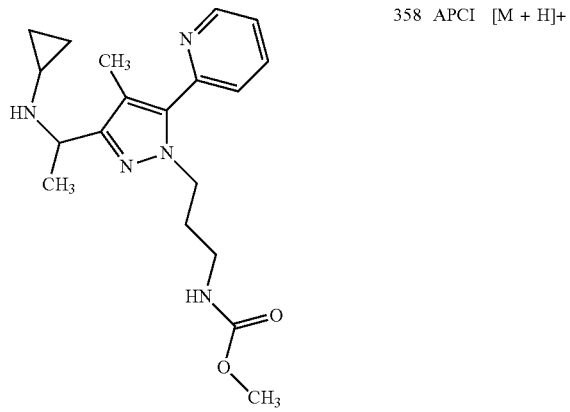 | 358 APCI [M + H]+ |
| Ref. 280 | 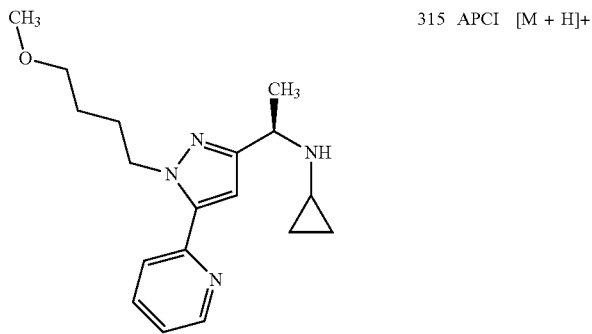 | 315 APCI [M + H]+ |
| Ref. 281 | 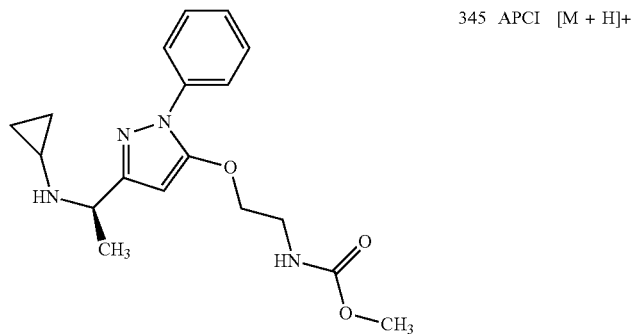 | 345 APCI [M + H]+ |
TABLE 120
| Ref. 282 | 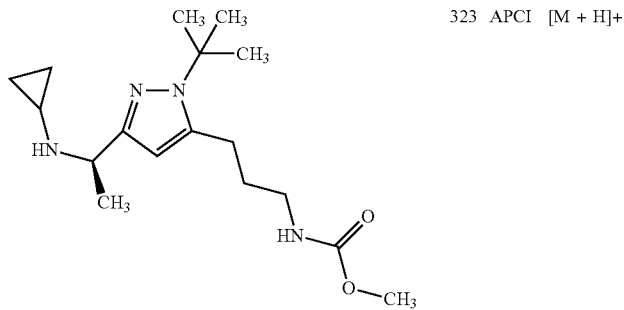 | 323 APCI [M + H]+ |

| | | |
|---|---|---|
| Ref. 283 | 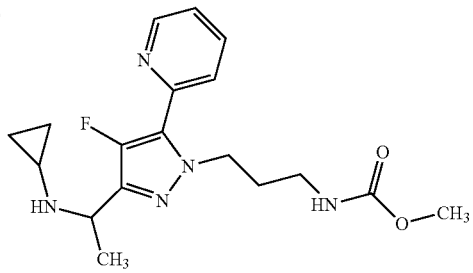 [SMILES: COC(=O)NCCCn1nc(C(C)NC2CC2)c(F)c1-c1ccccn1] | 362 APCI [M + H]+ |
| Ref. 284 | 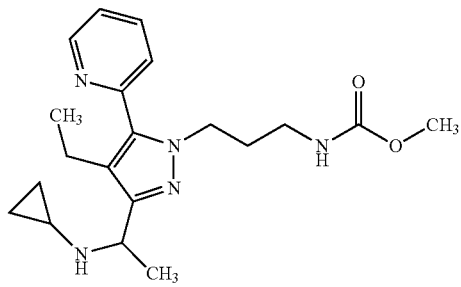 [SMILES: CCc1c(C(C)NC2CC2)nn(CCCNC(=O)OC)c1-c1ccccn1] | 372 APCI [M + H]+ |
| Ref. 285 | 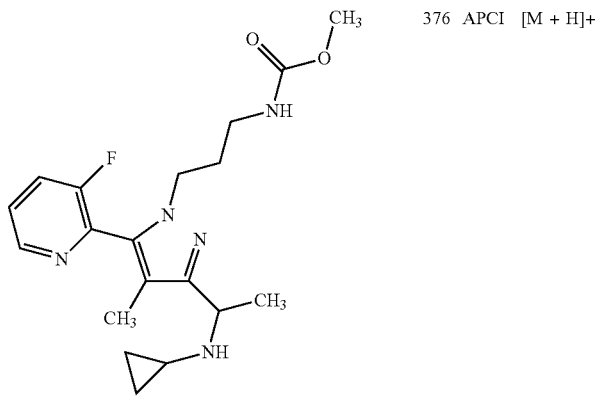 | 376 APCI [M + H]+ |
| Ref. 286 | 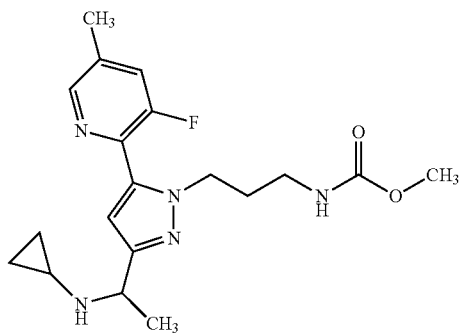 [SMILES: COC(=O)NCCCn1nc(C(C)NC2CC2)cc1-c1ncc(C)cc1F] | 376 APCI [M + H]+ |

TABLE 121
| Ref. 287 | 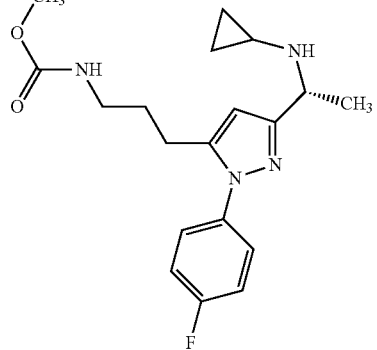 | 361 APCI [M + H]+ |
| Ref. 288 | 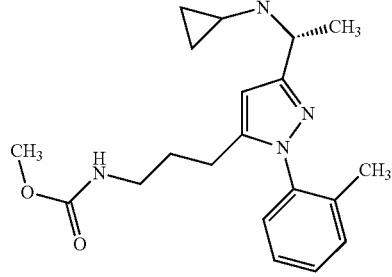 | 357 APCI [M + H]+ |
| Ref. 289 | 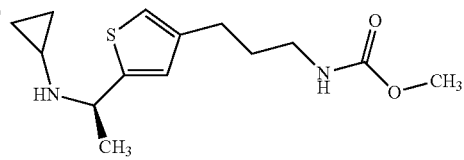 [SMILES: COC(=O)NCCCc1csc([C@@H](C)NC2CC2)c1] | 283 APCI [M + H]+ |
| Ref. 290 | 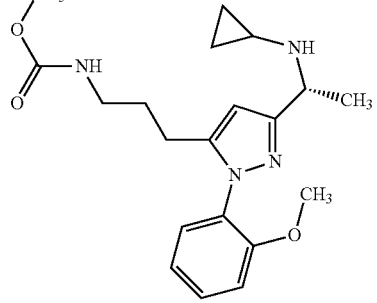 | 373 APCI [M + H]+ |
| Ref. 291 | 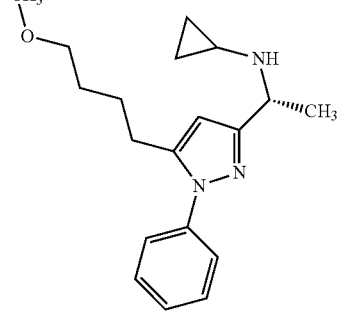 | 314 APCI [M + H]+ |

TABLE 121-continued
| Ref. 292 | 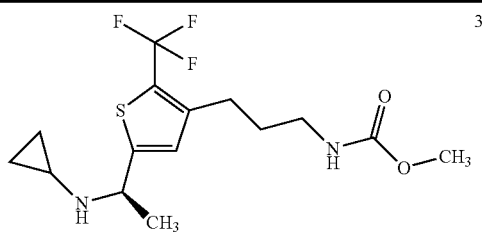 | 351 APCI [M + H]+ |
TABLE 122
| Ref. 293 | 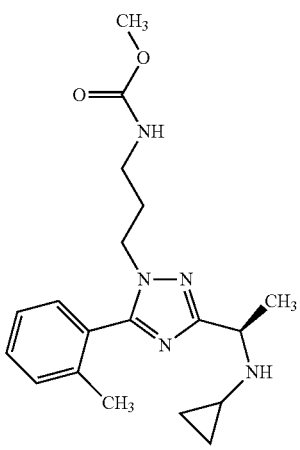 [SMILES: COC(=O)NCCCn1nc([C@@H](C)NC2CC2)nc1-c1ccccc1C] | 358 APCI [M + H]+ |
| Ref. 294 | 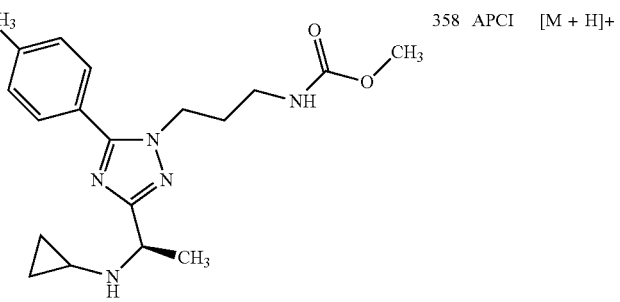 | 358 APCI [M + H]+ |
| Ref. 295 | 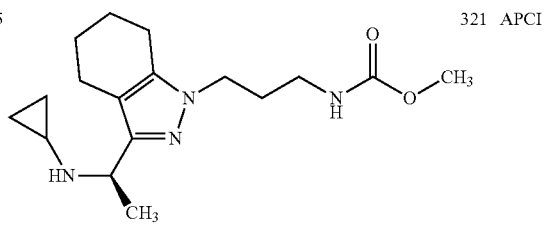 | 321 APCI [M + H]+ |
| Ref. 296 | 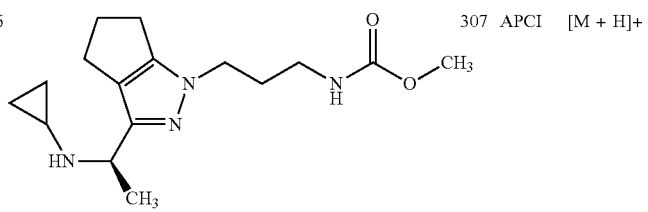 | 307 APCI [M + H]+ |

TABLE 122-continued

| Ref. 297 | (structure) | 357 | APCI | [M + H]+ |
| Ref. 298 | (structure) | 335 | APCI | [M + H]+ |

TABLE 123

| Ref. 299 | (structure) | 322 | APCI | [M + H]+ |
| Ref. 300 | (structure) | 317 | APCI | [M + H]+ |
| Ref. 301 | (structure) | 361 | APCI | [M + H]+ |

TABLE 123-continued
| Ref. 302 | 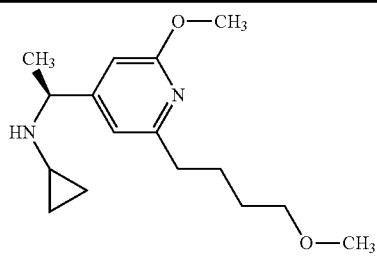 | 279 | APCI | [M + H]+ |
| Ref. 303 | 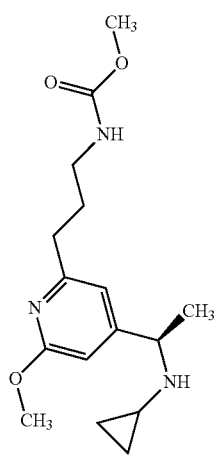 [SMILES: COC(=O)NCCCc1cc([C@@H](C)NC2CC2)cc(OC)n1] | 308 | ESI | [M + H]+ |
| Ref. 304 | 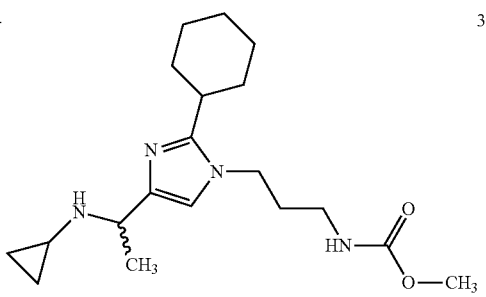 | 349 | ESI | [M + H]+ |
TABLE 124
| Ref. 305 | 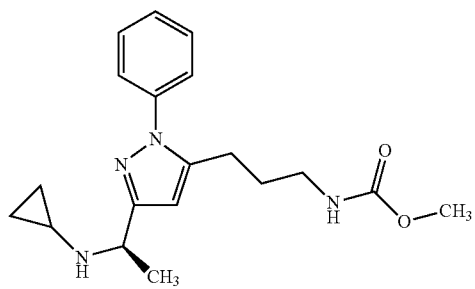 [SMILES: COC(=O)NCCCc1cc([C@@H](C)NC2CC2)nn1-c1ccccc1] | 343 | ESI | [M + H]+ |

TABLE 124-continued
| Ref. 306 | 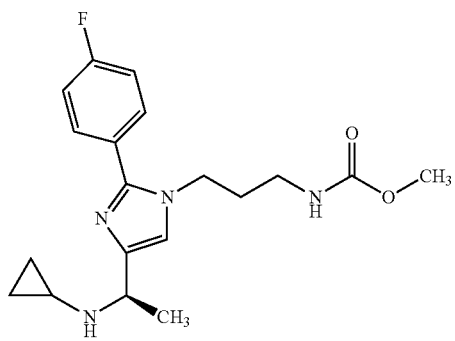 [SMILES: COC(=O)NCCCn1cc([C@@H](C)NC2CC2)nc1-c1ccc(F)cc1] | 361 | ESI | [M + H]+ |
| Ref. 307 | 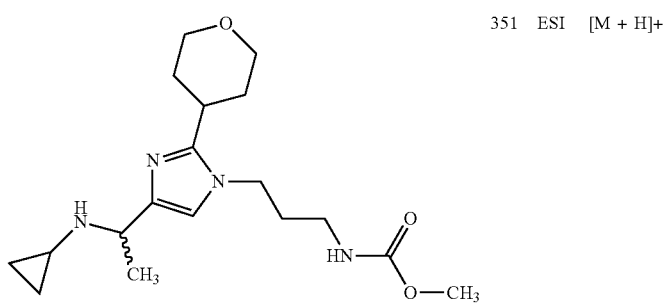 | 351 | ESI | [M + H]+ |
| Ref. 308 | 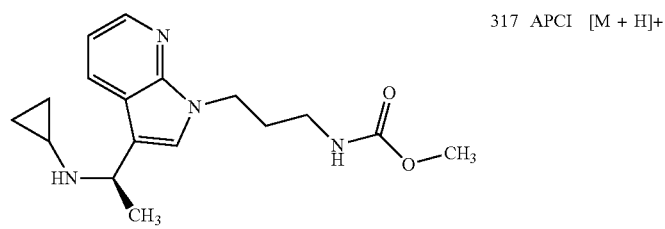 | 317 | APCI | [M + H]+ |
| Ref. 309 | 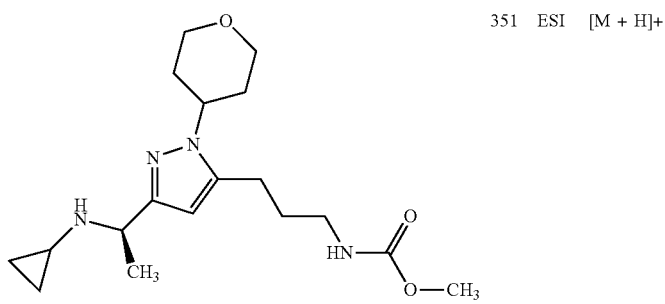 | 351 | ESI | [M + H]+ |
| Ref. 310 | 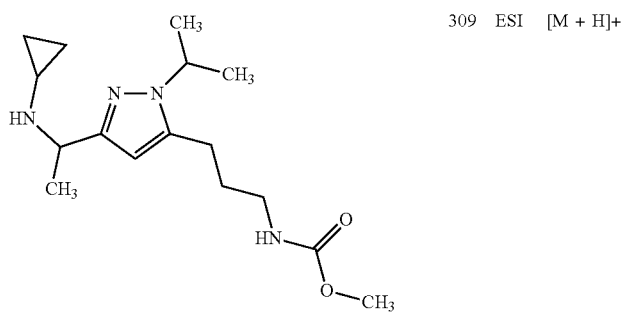 | 309 | ESI | [M + H]+ |

TABLE 125
| | | | | |
|---|---|---|---|---|
| Ref. 311 | 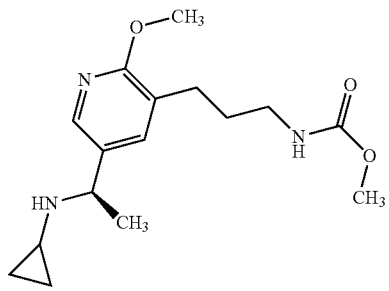 [SMILES: COC(=O)NCCCc1cc([C@@H](C)NC2CC2)cnc1OC] | 308 | ESI | [M + H]+ |
| Ref. 312 | 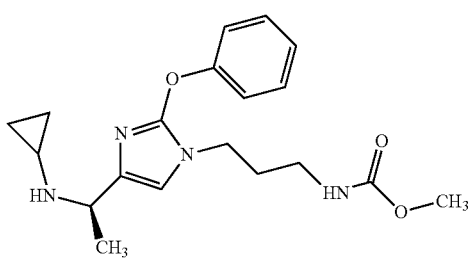 [SMILES: COC(=O)NCCCn1cc([C@@H](C)NC2CC2)nc1Oc1ccccc1] | 359 | APCI | [M + H]+ |
| Ref. 313 | 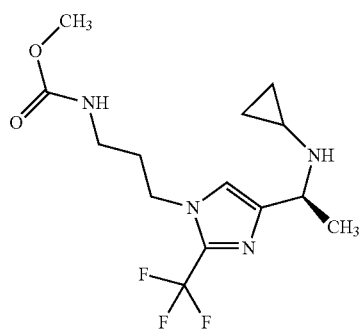 [SMILES: COC(=O)NCCCn1cc([C@H](C)NC2CC2)nc1C(F)(F)F] | 335 | APCI | [M + H]+ |
| Ref. 314 | 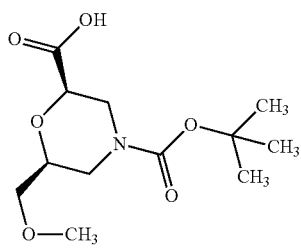 [SMILES: COC[C@@H]1CN(C(=O)OC(C)(C)C)C[C@H](C(=O)O)O1] | 274 | ESI | [M − H]− |
| Ref. 315 | 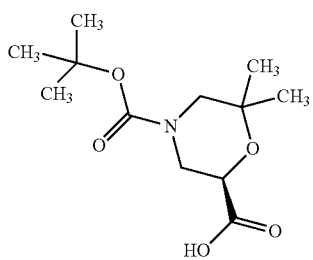 [SMILES: CC(C)(C)OC(=O)N1C[C@H](C(=O)O)OC(C)(C)C1] | 258 | ESI | [M − H]− |

TABLE 125-continued
| Ref. 316 | 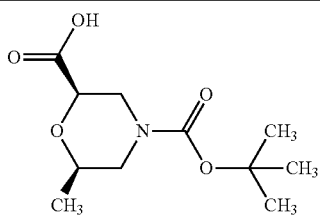 | 244 | ESI | [M − H]− |
| Ref. 317 | 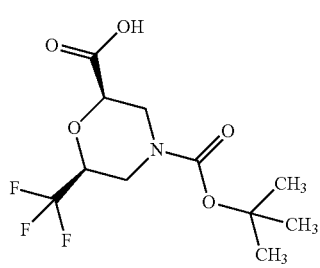 [SMILES: CC(C)(C)OC(=O)N1C[C@@H](C(F)(F)F)O[C@@H](C(=O)O)C1] | 298 | ESI | [M − H]− |
TABLE 126
| Ref. 318 | 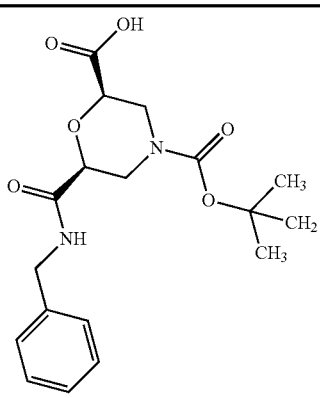 | 365 | APCI | [M + H]+ |
| Ref. 319 | 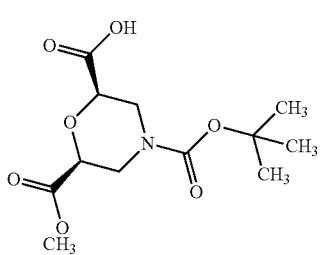 | 307 | APCI | [M + NH4]+ |
TABLE 126-continued
| Ref. 320 | 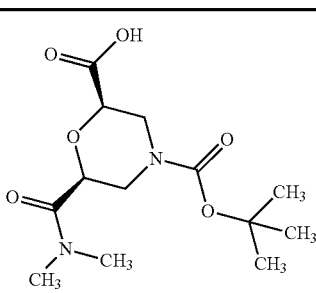 | 303 | APCI | [M + H]+ |
| Ref. 321 | 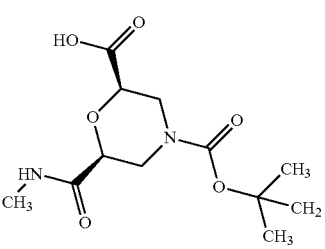 [SMILES: CNC(=O)[C@@H]1CN(C(=O)OC(C)(C)C)C[C@H](C(=O)O)O1] | 289 | APCI | [M + H]+ |
| Ref. 322 | 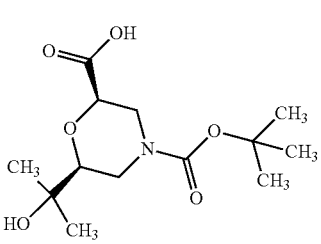 [SMILES: CC(C)(C)OC(=O)N1C[C@@H](C(C)(C)O)O[C@@H](C(=O)O)C1] | 288 | ESI | [M − H]− |

TABLE 126-continued
| Ref. 323 | 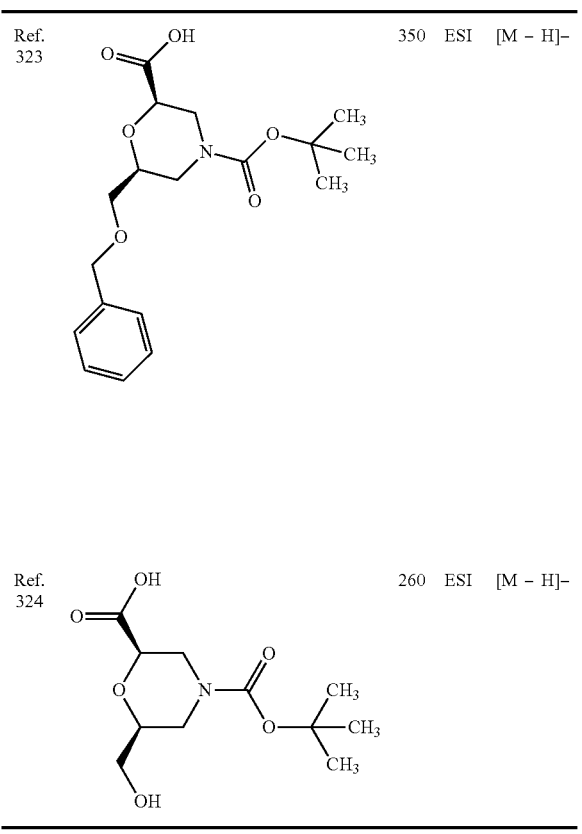 | 350 ESI [M − H]− |
|---|---|---|
| Ref. 324 | 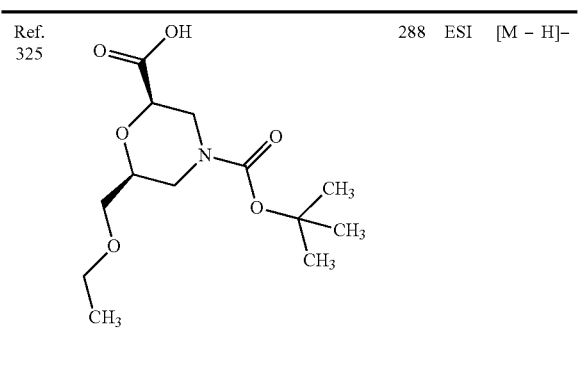 | 260 ESI [M − H]− |
TABLE 127
| Ref. 325 | | 288 ESI [M − H]− |
|---|---|---|
| Ref. 326 | 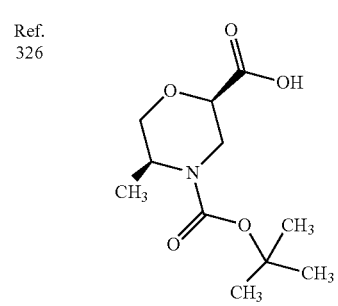 | 244 ESI [M − H]− |
TABLE 127-continued
| Ref. 327 | 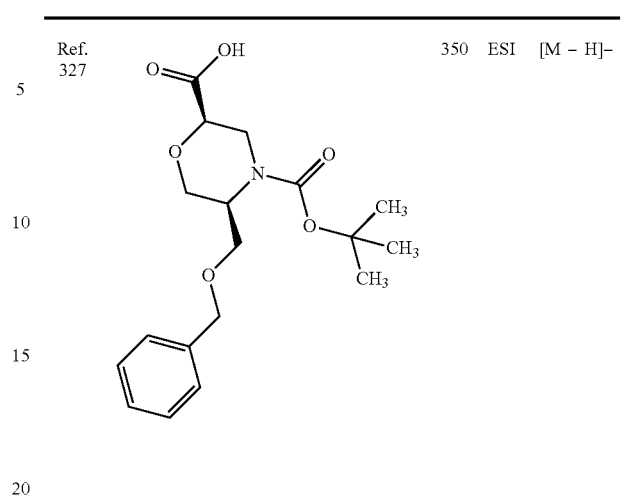 | 350 ESI [M − H]− |
|---|---|---|
| Ref. 329 | | 274 ESI [M − H]− |
| Ref. 331 | 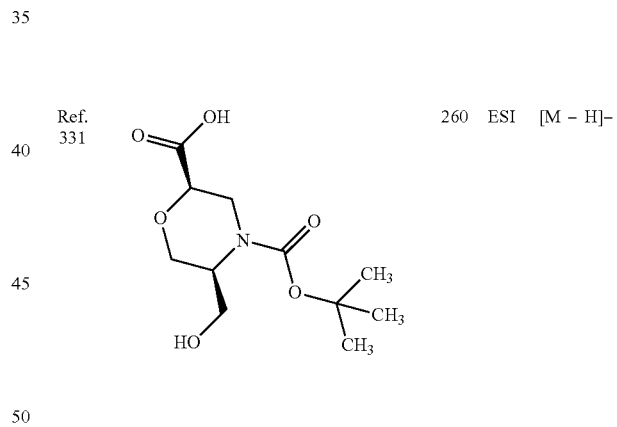 | 260 ESI [M − H]− |
| Ref. 332 | 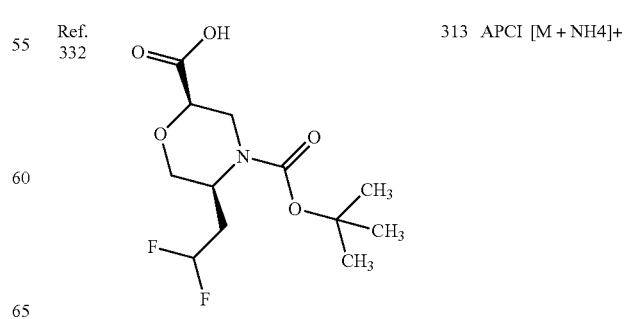 | 313 APCI [M + NH4]+ |

TABLE 128
| | | | | |
|---|---|---|---|---|
| Ref. 333 | 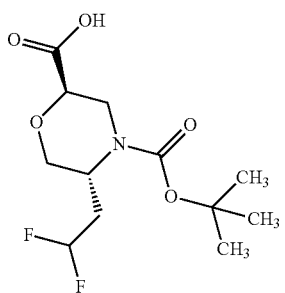 [SMILES: CC(C)(C)OC(=O)N1C[C@H](C(=O)O)OC[C@H]1CC(F)F] | 313 | APCI | [M + NH4]+ |
| Ref. 334 | 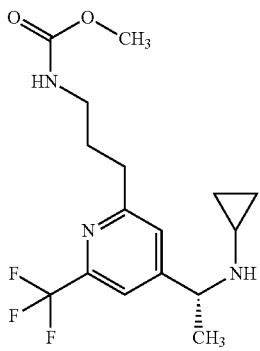 [SMILES: COC(=O)NCCCc1cc([C@@H](C)NC2CC2)cc(C(F)(F)F)n1] | 346 | APCI | [M + H]+ |
| Ref. 335 | 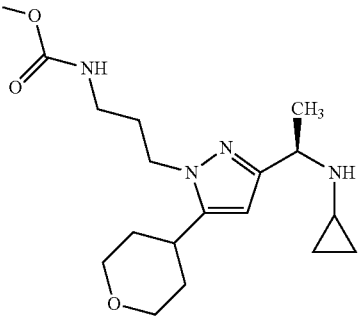 | 351 | ESI | [M + H]+ |
| Ref. 336 | 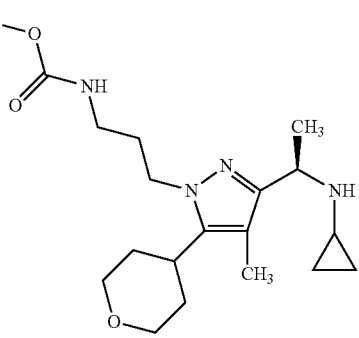 | 365 | ESI | [M + H]+ |
| Ref. 337 | 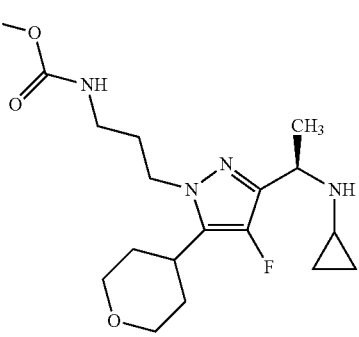 | 369 | ESI | [M + H]+ |

TABLE 128-continued

| | | | |
|---|---|---|---|
| Ref. 338 | 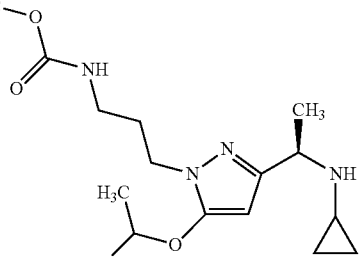 | 325 ESI | [M + H]+ |

Test Example

Inhibitory Activity Against Human Renin

A substrate of synthetic peptide (Nma-KHPFH LVIHK (Dnp)-$NH_2$) and test compound were mixed, and fluorescence intensity was assayed using a fluorophotometer before starting an enzymatic reaction (exciting wavelength: 340 nm, measuring wavelength: 460 nm). Recombinant human renin was added and the mixture was incubated at 37° C. for 1 hour, and the fluorescence intensity was measured after the reaction using a fluorophotometer (exciting wavelength: 340 nm, measuring wavelength: 460 nm). Renin activity was evaluated on the ground of fluorescence intensity which was obtained by deduction of the intensity before the reaction from the intensity after the reaction, and 50%/a inhibitory concentration ($IC_{50}$) was calculated from renin activities under the existence of various concentration of the test compound. Example compounds herein showed the following values.

TABLE 129

| Example No. | $IC_{50}$ (nM) |
|---|---|
| 1 | 0.3 |
| 2 | 0.3 |
| 3 | 0.6 |
| 4 | 0.4 |
| 5 | 0.7 |
| 6 | 0.3 |
| 7 | 3.1 |
| 8 | 4.4 |
| 9 | 7.3 |
| 10 | 3.7 |
| 11 | 4.4 |
| 12 | 3.6 |
| 13 | 3.9 |
| 14 | 5.2 |
| 15 | 2.6 |
| 16 | 0.8 |
| 17 | 4.4 |
| 18 | 2.3 |
| 19 | 2.4 |
| 20 | 0.5 |
| 21 | 1.2 |
| 22 | 6.5 |
| 23 | 2.4 |
| 24 | 8.1 |
| 25 | 6.3 |
| 26 | 3.4 |
| 27 | 8.3 |
| 28 | 7.1 |

TABLE 129-continued

| Example No. | $IC_{50}$ (nM) |
|---|---|
| 29 | 0.6 |
| 30 | 0.7 |
| 31 | 2.0 |
| 32 | 3.3 |
| 33 | 5.3 |
| 34 | 3.8 |
| 35 | 0.4 |
| 36 | 0.5 |
| 37 | 0.9 |
| 38 | 1.2 |
| 39 | 2.0 |
| 40 | 0.7 |
| 41 | 0.7 |
| 42 | 0.5 |
| 43 | 0.6 |
| 44 | 3.0 |
| 45 | 3.4 |
| 46 | 1.5 |
| 47 | 4.8 |
| 48 | 1.5 |
| 49 | 0.5 |
| 50 | 1.0 |
| 51 | 8.8 |
| 52 | 1.8 |
| 53 | 0.9 |
| 54 | 2.3 |
| 55 | 0.3 |
| 56 | 4.2 |
| 57 | 0.3 |
| 58 | 1.6 |
| 59 | 0.9 |
| 60 | 2.9 |
| 61 | 4.0 |
| 62 | 0.6 |
| 63 | 1.3 |
| 64 | 0.7 |
| 65 | 0.2 |
| 66 | 7.2 |
| 67 | 8.9 |
| 68 | 4.5 |
| 69 | 2.6 |
| 70 | 1.0 |
| 71 | 1.4 |
| 72 | 0.7 |
| 73 | 1.4 |
| 74 | 4.6 |
| 75 | 0.3 |
| 76 | 0.6 |
| 77 | 0.6 |
| 78 | 0.9 |
| 79 | 0.9 |
| 80 | 5.7 |
| 81 | 0.4 |
| 82 | 0.5 |
| 83 | 2.1 |
| 84 | 1.7 |
| 85 | 1.0 |
| 86 | 1.1 |

TABLE 129-continued

| Example No. | IC$_{50}$ (nM) |
|---|---|
| 87 | 4.8 |
| 88 | 3.2 |
| 89 | 1.0 |
| 90 | 0.8 |
| 91 | 2.1 |
| 92 | 1.9 |
| 93 | 1.6 |
| 94 | 2.6 |
| 95 | 7.2 |
| 96 | 0.8 |
| 97 | 8.2 |
| 98 | 2.8 |
| 99 | 1.8 |
| 100 | 9.0 |
| 101 | 2.5 |
| 102 | 0.4 |
| 103 | 2.1 |
| 104 | 8.2 |
| 105 | 1.2 |
| 106 | 0.7 |
| 107 | 0.7 |
| 108 | 1.1 |
| 109 | 3.4 |
| 110 | 0.9 |
| 111 | 3.5 |
| 112 | 2.0 |

TABLE 130

| | |
|---|---|
| 113 | 1.4 |
| 114 | 1.1 |
| 115 | 1.8 |
| 116 | 1.2 |
| 117 | 2.0 |
| 118 | 2.5 |
| 119 | 0.5 |
| 120 | 1.7 |
| 121 | 5.4 |
| 122 | 0.2 |
| 123 | 0.8 |
| 124 | 1.8 |
| 125 | 1.3 |
| 126 | 6.0 |
| 127 | 1.8 |
| 128 | 1.4 |
| 129 | 1.3 |
| 130 | 1.5 |
| 131 | 0.8 |
| 132 | 1.3 |
| 133 | 1.6 |
| 134 | 6.3 |
| 135 | 6.3 |
| 136 | 0.3 |
| 137 | 0.4 |
| 138 | 6.1 |
| 139 | 2.1 |
| 140 | 0.8 |
| 141 | 0.5 |
| 142 | 0.5 |
| 143 | 1.5 |
| 144 | 0.7 |
| 145 | 0.5 |
| 146 | 1.0 |
| 147 | 2.5 |
| 148 | 5.1 |
| 149 | 0.8 |
| 150 | 2.6 |
| 151 | 1.0 |
| 152 | 1.1 |
| 153 | 2.2 |
| 154 | 2.4 |
| 155 | 0.8 |
| 156 | 2.1 |
| 157 | 3.4 |
| 158 | 0.3 |

TABLE 130-continued

| | |
|---|---|
| 159 | 0.2 |
| 160 | 0.8 |
| 161 | 0.7 |
| 162 | 0.6 |
| 163 | 0.4 |
| 164 | 0.6 |
| 165 | 0.6 |
| 166 | 7.0 |
| 167 | 4.1 |
| 168 | 0.3 |
| 169 | 0.3 |
| 170 | 0.4 |
| 171 | 0.4 |
| 172 | 0.4 |
| 173 | 0.3 |
| 174 | 0.4 |
| 175 | 0.3 |
| 176 | 0.4 |
| 177 | 1.0 |
| 178 | 0.3 |
| 179 | 0.3 |
| 180 | 0.6 |
| 181 | 0.7 |
| 182 | 0.7 |
| 183 | 0.3 |
| 184 | 0.5 |
| 185 | 0.3 |
| 186 | 0.4 |
| 187 | 0.5 |
| 188 | 0.5 |
| 189 | 0.9 |
| 190 | 1.2 |
| 191 | 0.7 |
| 192 | 0.2 |
| 193 | 0.4 |
| 194 | 3.0 |
| 195 | 3.6 |
| 196 | 0.7 |
| 197 | 0.2 |
| 198 | 0.2 |
| 199 | 0.2 |
| 200 | 4.5 |
| 201 | 4.1 |
| 202 | 0.2 |
| 203 | 0.5 |
| 204 | 7.1 |
| 205 | 1.4 |
| 206 | 1.5 |
| 207 | 6.9 |
| 208 | 2.3 |
| 209 | 2.1 |
| 210 | 0.2 |
| 211 | 0.5 |
| 212 | 4.6 |
| 213 | 0.3 |
| 214 | 2.8 |
| 215 | 0.5 |
| 216 | 0.1 |
| 217 | 1.5 |
| 218 | 1.1 |
| 219 | 0.4 |
| 220 | 0.4 |
| 221 | 0.3 |
| 222 | 0.5 |
| 223 | 0.4 |
| 224 | 3.1 |
| 225 | 0.5 |
| 226 | 0.3 |

TABLE 131

| | |
|---|---|
| 227 | 0.2 |
| 228 | 0.4 |
| 229 | 0.5 |
| 230 | 0.5 |
| 231 | 1.2 |
| 232 | 0.6 |

TABLE 131-continued

| | |
|---|---|
| 233 | 0.3 |
| 234 | 0.4 |
| 235 | 0.1 |
| 236 | 0.2 |
| 237 | 0.5 |
| 238 | 0.6 |
| 239 | 3.1 |
| 240 | 0.2 |
| 241 | 0.3 |
| 242 | 0.8 |
| 243 | 0.7 |
| 244 | 1.0 |
| 245 | 0.3 |
| 246 | 0.4 |
| 247 | 1.3 |
| 248 | 0.9 |
| 249 | 0.5 |
| 250 | 0.3 |
| 251 | 0.8 |
| 252 | 6.4 |
| 253 | 0.4 |
| 254 | 0.5 |
| 255 | 0.4 |
| 256 | 3.1 |
| 257 | 1.3 |
| 258 | 3.2 |
| 259 | 1.2 |
| 260 | 2.6 |
| 261 | 0.7 |
| 262 | 3.9 |
| 263 | 0.2 |
| 264 | 1.1 |
| 265 | 6.8 |
| 266 | 2.7 |
| 267 | 0.4 |
| 268 | 0.5 |
| 269 | 0.3 |
| 270 | 0.5 |
| 271 | 3.0 |
| 272 | 6.1 |
| 273 | 1.0 |
| 274 | 0.5 |
| 275 | 0.9 |
| 276 | 0.5 |
| 277 | 0.6 |
| 278 | 1.2 |
| 279 | 0.5 |
| 280 | 0.3 |
| 281 | 0.4 |
| 282 | 0.6 |
| 283 | 0.9 |
| 284 | 1.3 |
| 285 | 0.6 |
| 286 | 0.4 |
| 287 | 0.8 |
| 288 | 0.4 |
| 289 | 0.5 |
| 290 | 0.4 |
| 291 | 0.6 |
| 292 | 0.4 |
| 293 | 7.7 |
| 294 | 6.0 |
| 295 | 1.5 |
| 296 | 7.0 |
| 297 | 0.5 |
| 298 | 3.5 |
| 299 | 0.9 |
| 300 | 2.8 |
| 301 | 0.6 |
| 302 | 1.6 |
| 303 | 0.8 |
| 304 | 0.7 |
| 305 | 1.2 |
| 306 | 1.6 |
| 307 | 6.6 |
| 308 | 0.5 |
| 309 | 7.1 |
| 310 | 0.4 |
| 311 | 0.4 |
| 312 | 0.7 |

TABLE 131-continued

| | |
|---|---|
| 313 | 2.5 |
| 314 | 0.5 |
| 315 | 1.0 |
| 316 | 1.4 |
| 317 | 0.6 |
| 318 | 1.3 |
| 319 | 3.5 |
| 320 | 3.2 |
| 321 | 5.6 |
| 322 | 1.5 |
| 323 | 2.0 |
| 324 | 0.6 |
| 325 | 0.7 |
| 326 | 0.4 |
| 327 | 2.9 |
| 328 | 1.1 |
| 329 | 0.8 |
| 330 | 0.3 |
| 331 | 2.3 |
| 332 | 0.4 |
| 333 | 0.3 |
| 334 | 0.3 |
| 335 | 0.9 |
| 336 | 1.6 |
| 337 | 1.2 |
| 338 | 5.3 |
| 339 | 0.4 |
| 340 | 0.7 |

TABLE 132

| | |
|---|---|
| 341 | 0.3 |
| 342 | 0.4 |
| 343 | 5.3 |
| 344 | 0.4 |
| 345 | 0.4 |
| 346 | 1.3 |
| 347 | 0.7 |
| 348 | 0.7 |
| 349 | 1.1 |
| 350 | 1.9 |
| 351 | 0.4 |
| 352 | 7.6 |
| 353 | 0.4 |
| 354 | 1.4 |
| 355 | 0.8 |
| 356 | 5.1 |
| 357 | 3.5 |
| 358 | 5.7 |
| 359 | 0.3 |
| 360 | 7.6 |
| 361 | 0.8 |
| 362 | 5.0 |
| 363 | 0.7 |
| 364 | 5.5 |
| 365 | 3.5 |
| 366 | 0.7 |
| 367 | 1.7 |
| 368 | 8.4 |
| 369 | 1.5 |
| 370 | 1.7 |
| 371 | 1.0 |
| 372 | 6.0 |
| 373 | 0.8 |
| 374 | 5.4 |
| 375 | 1.3 |
| 376 | 4.7 |
| 377 | 2.4 |
| 378 | 3.5 |
| 379 | 8.9 |
| 380 | 2.6 |
| 381 | 1.7 |
| 382 | 3.6 |
| 383 | 1.3 |
| 384 | 3.2 |
| 385 | 4.3 |
| 386 | 3.2 |

TABLE 132-continued

| | |
|---|---|
| 387 | 4.4 |
| 388 | 1.8 |
| 389 | 6.1 |
| 390 | 3.5 |
| 391 | 2.0 |
| 392 | 0.7 |
| 393 | 3.7 |
| 394 | 0.6 |
| 395 | 3.5 |
| 396 | 4.8 |
| 397 | 1.3 |
| 398 | 5.1 |
| 399 | 4.0 |
| 400 | 2.3 |
| 401 | 2.7 |
| 402 | 2.3 |
| 403 | 3.1 |
| 404 | 0.7 |
| 405 | 3.9 |
| 406 | 3.4 |
| 407 | 1.7 |
| 408 | 1.1 |
| 409 | 1.0 |
| 410 | 6.7 |
| 411 | 2.2 |
| 412 | 0.6 |
| 413 | 2.0 |
| 414 | 2.8 |
| 415 | 0.6 |
| 416 | 3.0 |
| 417 | 3.4 |
| 418 | 3.9 |
| 419 | 1.4 |
| 420 | 2.7 |
| 421 | 2.2 |
| 422 | 1.7 |
| 423 | 1.0 |
| 424 | 5.0 |
| 425 | 8.8 |
| 426 | 1.7 |
| 427 | 3.5 |
| 428 | 8.1 |
| 429 | 2.0 |
| 430 | 2.4 |
| 431 | 3.8 |
| 432 | 3.3 |
| 433 | 5.3 |
| 434 | 2.0 |
| 435 | 1.3 |
| 436 | 2.2 |
| 437 | 2.7 |
| 438 | 2.4 |
| 439 | 8.0 |
| 440 | 1.9 |
| 441 | 0.8 |
| 442 | 9.5 |
| 443 | 2.0 |
| 444 | 4.2 |

INDUSTRIAL APPLICABILITY

The compound [I] of the present invention or a pharmaceutically acceptable salt thereof has renin inhibitory activity and may be useful for treatment and/or prophylaxis of hypertension, cardiac failure, diabetic nephropathy and the like. Furthermore, the compound [II] is useful as a synthetic intermediate for preparing the compound [I].

The invention claimed is:

1. A compound of the formula [I];

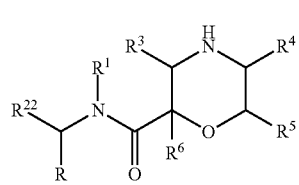

wherein $R^1$ is a cycloalkyl or an alkyl,
$R^{22}$ is 2) an optionally substituted pyridyl, 3) an optionally substituted pyrazolopyridyl, 7) an optionally substituted chromanyl, 13) an optionally quinazolinyl, 14) an optionally substituted dihydroquinazolinyl, 15) an optionally substituted furopyridyl, or 29) an optionally substituted imidazopyridinyl,
R is a lower alkyl group,
$R^3$ and $R^6$ are the same or different, a hydrogen atom, an optionally substituted carbamoyl, an optionally substituted alkyl, or alkoxycarbonyl,
one of $R^4$ and $R^5$ is a hydrogen atom, and
the other is a group selected from
1) a carbamoyl optionally substituted with an alkyl which is optionally substituted with 1 or 2 phenyl,
2) an alkyl optionally substituted with an alkoxy optionally substituted with a halogen or a phenyl; a halogen; a hydroxyl; an amino optionally substituted with 1 or 2 alkyls; or cyano; and
3) an alkoxycarbonyl,
or a pharmaceutically acceptable salt thereof.

2. The compound according to claim 1, wherein $R^3$ and $R^6$ are both hydrogen atoms, or a pharmaceutically acceptable salt thereof.

3. The compound according to claim 1 or 2, wherein the substituents of 2) the optionally substituted pyridyl, 3) the optionally substituted pyrazolopyridyl, 7) the optionally substituted chromanyl, 13) the optionally substituted quinazolinyl, 14) the optionally substituted dihydroquinazolinyl, 15) the optionally substituted furopyridyl, or 29) the optionally substituted imidazopyridinyl in $R^{22}$ are 1 to 3 groups selected from
1) an alkyl optionally substituted with same or different 1 or 2 groups selected from an alkanoylamino optionally substituted with a halogen, an alkoxycarbonylamino, an alkoxy, an aminocarbonylamino optionally substituted with 1 or 2 alkyl, an aryl optionally substituted with a halogen, an alkoxy or a haloalkoxy, a hydroxyl, an heteroaryl, a halogen atom, and an amino group optionally substituted with 1 or 2 alkyl,
2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl, and a halogen,
3) an alkoxy optionally substituted with an alkoxy or an alkoxycarbonylamino,
4) a cycloalkyl,
5) a halogen,
6) a cyano,
7) an aliphatic heterocyclic group,
8) an aryl optionally substituted with same or different 1 or 2 groups selected from an alkyl optionally substituted with an alkylsulfonylamino optionally substituted with a halogen and a halogen; a halogen; an alkoxycarbonyl; a methanesulfonylamino; a halomethanesulfonylamino; a methanesulfonylaminocarbonyl; a benzoylaminocarbonyl; a benzenesulfonylaminocarbonyl; a hydroxyoxazolyl; a hydroxyoxadiazolyl; a tetrazolyl; a hydroxyl and an alkoxy optionally substituted with an alkoxy,
9) a heteroaryl optionally substituted with same or different 1 or 2 groups selected from an alkyl, an amino, a halogen and an alkoxy,
10) an aryloxy, and
11) an amino optionally substituted with 1 to 2 groups selected from an alkyl optionally substituted with an alkoxy and alkylsulfonyl,
12) an alkynyl optionally substituted with a hydroxyl,
13) an aliphatic heterocyclic oxy,
14) an arylcarbamoyl optionally substituted with an alkoxy, and
15) an alkanoyl,
or a pharmaceutically acceptable salt thereof.

4. The compound according to claim 3, wherein the substituents of 2) the optionally substituted pyridyl, 3) the optionally substituted pyrazolopyridyl, 7) the optionally substituted chromanyl, 13) the optionally substituted quinazolinyl, 14) the optionally substituted dihydroquinazolinyl, 15) the optionally substituted furopyridyl, or 29) the optionally substituted imidazopyridinyl as $R^{22}$ are a group selected from
1) an alkyl optionally substituted with same or different 1 or 2 groups selected from an alkanoylamino optionally substituted with a halogen, an alkoxycarbonylamino, an alkoxy, an aminocarbonylamino optionally substituted with 1 or 2 alkyl, an aryl optionally substituted with a halogen, an alkoxy or a haloalkoxy, a hydroxyl, an heteroaryl, a halogen and an amino optionally substituted with 1 or 2 alkyl,
2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl, and a halogen, and
3) an alkoxy optionally substituted with an alkoxy or an alkoxycarbonylamino, or a group selected from
1) an alkyl optionally substituted with same or different 1 or 2 groups selected from an alkanoylamino optionally substituted with a halogen, an alkoxycarbonylamino, an alkoxy, an aminocarbonylamino optionally substituted with 1 or 2 alkyl, an aryl optionally substituted with a halogen, an alkoxy or a haloalkoxy, a hydroxyl, an heteroaryl, a halogen and an amino optionally substituted with 1 or 2 alkyl,
2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl, and a halogen, and
3) an alkoxy optionally substituted with an alkoxy or an alkoxycarbonylamino, and 1 to 2 groups selected from
1) an alkyl optionally substituted with same or different 1 or 2 groups selected from an alkanoylamino optionally substituted with a halogen, an alkoxycarbonylamino, an alkoxy, an aminocarbonylamino optionally substituted with 1 or 2 alkyl, an aryl optionally substituted with a halogen, an alkoxy or a haloalkoxy, a hydroxyl, an heteroaryl, a halogen and an amino optionally substituted with 1 or 2 alkyl,
2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl, and a halogen,
3) an alkoxy optionally substituted with an alkoxy or an alkoxycarbonylamino,
4) a cycloalkyl,
5) a halogen,
6) a cyano,
7) an aliphatic heterocyclic group,
8) an aryl optionally substituted with same or different 1 or 2 groups selected from an alkyl optionally substituted with an alkylsulfonylamino optionally substituted with a halogen, and a halogen; a halogen; an alkoxycarbonyl; a methanesulfonylamino; a halomethanesulfonylamino; a methanesulfonylaminocarbonyl; a benzoylaminocarbonyl; a benzenesulfonylaminocarbonyl; a hydroxyoxazolyl; a hydroxyoxadiazolyl; a tetrazolyl; a hydroxyl; and an alkoxy optionally substituted with an alkoxy,
9) a heteroaryl group optionally substituted with same or different 1 or 2 groups selected from an alkyl group, an amino group, and an alkoxy group,
10) an aryloxy,
11) an amino optionally substituted with 1 to 2 groups selected from an alkyl optionally substituted with an alkoxy, and alkylsulfonyl,
12) an alkynyl optionally substituted with a hydroxyl,
13) an aliphatic heterocyclic-oxy,
14) an arylcarbamoyl optionally substituted with an alkoxy, and
15) an alkanoyl,
or a pharmaceutically acceptable salt thereof.

5. The compound according to claim 1, wherein the substituents of 2) the optionally substituted pyridyl, 3) the optionally substituted pyrazolopyridyl, 7) the optionally substituted chromanyl, 13) the optionally substituted quinazolinyl, 14) the optionally substituted dihydroquinazolinyl, 15) the optionally substituted furopyridyl, or 29) the optionally substituted imidazopyridinyl, as $R^{22}$ are one group selected from
1) an alkyl optionally substituted with same or different 1 or 2 groups selected from an alkanoylamino optionally substituted with a halogen, an alkoxycarbonylamino, an alkoxy, an aminocarbonylamino optionally substituted with 1 or 2 alkyl, an aryl optionally substituted with a halogen, an alkoxy or a haloalkoxy, a hydroxyl, an heteroaryl, a halogen and an amino optionally substituted with 1 or 2 alkyl,
2) an alkenyl optionally substituted with same or different 1 or 2 groups selected from an alkanoylamino, an alkoxycarbonylamino, an alkoxy, an aminocarbonylamino optionally substituted with 1 or 2 alkyl, an aryl, a hydroxyl, and a halogen, and
3) an alkoxy optionally substituted with an alkoxy or an alkoxycarbonylamino, and one group selected from
1) an aryl optionally substituted with same or different 1 or 2 groups selected from an alkyl optionally substituted with an alkylsulfonylamino optionally substituted with a halogen, and a halogen; a halogen; an alkoxycarbonyl; a methanesulfonylamino; a halomethanesulfonylamino; a methanesulfonylaminocarbonyl; a benzoylaminocarbonyl; a benzenesulfonylaminocarbonyl; a hydroxyoxazolyl; a hydroxyoxadiazolyl; a tetrazolyl; a hydroxyl; and an alkoxy optionally substituted with an alkoxy; and 2) a heteroaryl optionally substituted with same or different 1 or 2 groups selected from an alkyl, an amino, a halogen and an alkoxy, or a pharmaceutically acceptable salt thereof.

6. The compound according to claim 5, wherein $R^{22}$ is a group selected from 2) an optionally substituted pyridyl, or a pharmaceutically acceptable salt thereof.

7. A compound that is methyl (3- {3-[(1R)-1-(cyclopropyl{[(2R,6S)-6-(methoxymethyl)morpholin-2-yl]carbonyl}amino)ethyl]-6-methyl-1H-pyrazolo[3,4-b]pyridin-1-yl}propyl)carbamate or a pharmaceutically acceptable salt thereof.

8. A renin inhibitor comprising the compound according to claim 1 or a pharmaceutically acceptable salt thereof.

9. A medicine for the treatment of hypertension, cardiac failure, or diabetic nephropathy, comprising the compound according to claim 1 or a pharmaceutically acceptable salt thereof.

10. A method of treating hypertension, cardiac failure, or diabetic nephropathy, comprising the step of:
administering a therapeutically effective amount of the medicine of claim 9 to a patient in need thereof.

* * * * *